United States Patent
Shirasaki et al.

(10) Patent No.: US 11,765,972 B2
(45) Date of Patent: Sep. 19, 2023

(54) COMPOUND AND ORGANIC ELECTROLUMINESCENCE DEVICE USING THE SAME

(71) Applicant: IDEMITSU KOSAN CO.,LTD., Tokyo (JP)

(72) Inventors: Yoshinao Shirasaki, Sodegaura (JP); Tetsuya Masuda, Sodegaura (JP); Takushi Shiomi, Sodegaura (JP); Masatoshi Saito, Sodegaura (JP); Kei Yoshida, Sodegaura (JP); Masato Nakamura, Sodegaura (JP)

(73) Assignee: IDEMITSU KOSAN CO., LTD., Tokyo (JP)

( * ) Notice: Subject to any disclaimer, the term of this patent is extended or adjusted under 35 U.S.C. 154(b) by 26 days.

(21) Appl. No.: 16/971,260

(22) PCT Filed: Feb. 20, 2019

(86) PCT No.: PCT/JP2019/006323
§ 371 (c)(1),
(2) Date: Aug. 19, 2020

(87) PCT Pub. No.: WO2019/163826
PCT Pub. Date: Aug. 29, 2019

(65) Prior Publication Data
US 2021/0009527 A1  Jan. 14, 2021

(30) Foreign Application Priority Data

Feb. 20, 2018  (JP) ................................. 2018-027695
Oct. 26, 2018  (JP) ................................. 2018-202293

(51) Int. Cl.
| | |
|---|---|
| H10K 85/60 | (2023.01) |
| C09K 11/06 | (2006.01) |
| C07D 405/04 | (2006.01) |
| C07D 409/04 | (2006.01) |
| H10K 50/15 | (2023.01) |
| H10K 50/16 | (2023.01) |
| H10K 101/00 | (2023.01) |
| C07C 15/27 | (2006.01) |
| C07D 233/02 | (2006.01) |
| C07D 251/04 | (2006.01) |

(52) U.S. Cl.
CPC ........... *H10K 85/654* (2023.02); *C07C 15/27* (2013.01); *C07D 233/02* (2013.01); *C07D 251/04* (2013.01); *C07D 405/04* (2013.01); *C07D 409/04* (2013.01); *C09K 11/06* (2013.01); *H10K 85/653* (2023.02); *H10K 85/657* (2023.02); *H10K 85/6574* (2023.02); *H10K 85/6576* (2023.02); *C09K 2211/1007* (2013.01); *C09K 2211/1011* (2013.01); *C09K 2211/1018* (2013.01); *H10K 50/15* (2023.02); *H10K 50/16* (2023.02); *H10K 50/166* (2023.02); *H10K 2101/27* (2023.02)

(58) Field of Classification Search
CPC . C07D 405/04; C07D 409/04; H01L 51/0067; H01L 51/0068
See application file for complete search history.

(56) References Cited

U.S. PATENT DOCUMENTS

| | | | |
|---|---|---|---|
| 2007/0247063 A1 | 10/2007 | Murase et al. | |
| 2012/0138907 A1 | 6/2012 | Murase et al. | |
| 2014/0001456 A1 | 1/2014 | Mizutani et al. | |
| 2014/0073784 A1 | 3/2014 | Mizutani et al. | |
| 2015/0025239 A1 | 1/2015 | Ahn et al. | |
| 2015/0171340 A1* | 6/2015 | Lee ..................... | H01L 51/0073 544/333 |
| 2016/0020405 A1 | 1/2016 | Ito et al. | |

(Continued)

FOREIGN PATENT DOCUMENTS

| | | |
|---|---|---|
| CN | 104245686 A | 12/2014 |
| CN | 104812750 A | 7/2015 |

(Continued)

OTHER PUBLICATIONS

International Preliminary Search Report on Patentability and Written Opinion dated Aug. 27, 2020 for corresponding International Patent Application No. PCT/JP2019/006321.
International Preliminary Search Report on Patentability and Written Opinion dated Aug. 27, 2020 for corresponding International Patent Application No. PCT/JP2019/006322.
International Preliminary Search Report on Patentability and Written Opinion dated Aug. 27, 2020 for corresponding International Patent Application No. PCT/JP2019/006323.
International Search Report dated May 21, 2019 for corresponding International Patent Application No. PCT/JP2019/006321.
International Search Report dated May 21, 2019 for corresponding International Patent Application No. PCT/JP2019/006322.

(Continued)

*Primary Examiner* — Noble E Jarrell
(74) *Attorney, Agent, or Firm* — Foley & Lardner LLP

(57) ABSTRACT

A compound represented by the following formula (1), wherein $X_1$ is O or S, and two or more of $Y_1$, $Y_2$ and $Y_3$ are N, provided that the case where one or both of —$Ar_1$-$Ar_2$ and —$Ar_3$-$Ar_4$ is a p-terphenyl-3-*yl* group is excluded.

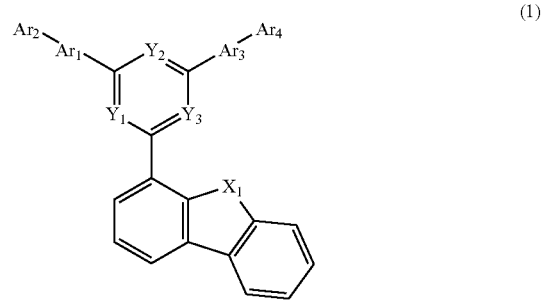

(1)

31 Claims, 1 Drawing Sheet

(56) References Cited

U.S. PATENT DOCUMENTS

| | | |
|---|---|---|
| 2016/0111655 A1 | 4/2016 | Mizutani et al. |
| 2016/0197285 A1* | 7/2016 | Zeng .................. H01L 51/0074 |
| | | 544/216 |
| 2016/0225992 A1 | 8/2016 | Ito et al. |
| 2016/0276596 A1 | 9/2016 | Jang et al. |
| 2016/0329502 A1 | 11/2016 | Dyatkin et al. |
| 2017/0018723 A1 | 1/2017 | Cha et al. |
| 2017/0104167 A1 | 4/2017 | Sim et al. |
| 2017/0250353 A1 | 8/2017 | Koenen et al. |
| 2018/0013071 A1 | 1/2018 | Cha et al. |
| 2018/0102485 A1 | 4/2018 | Mizutani et al. |
| 2018/0331299 A1 | 11/2018 | Mizutani et al. |
| 2018/0337348 A1* | 11/2018 | Jung .................. C07F 7/0812 |
| 2019/0348615 A1 | 11/2019 | Mizutani et al. |

FOREIGN PATENT DOCUMENTS

| | | |
|---|---|---|
| CN | 106573947 A | 4/2017 |
| CN | 106946859 A | 7/2017 |
| CN | 107021926 A | 8/2017 |
| CN | 107056783 A | 8/2017 |
| CN | 108383842 | 8/2018 |
| EP | 1 962 354 A1 | 8/2008 |
| JP | 2005-314239 A | 11/2005 |
| JP | 2015-512875 A | 4/2015 |
| JP | 2017-529320 A | 10/2017 |
| KR | 10-2011-0079401 A | 7/2011 |
| KR | 10-2017-0134264 A | 12/2017 |
| KR | 10-2018-0128181 A | 12/2018 |
| WO | WO-2005/113531 A1 | 12/2005 |
| WO | WO-2007/069569 A1 | 6/2007 |
| WO | WO-2013/077352 A1 | 5/2013 |
| WO | WO-2014054912 A1 * | 4/2014 ........... C07D 209/82 |
| WO | WO-2016/126022 A1 | 8/2016 |
| WO | WO-2017/111036 A1 | 6/2017 |
| WO | WO-2018/103749 A1 | 6/2018 |
| WO | WO-2018/139662 A1 | 8/2018 |

OTHER PUBLICATIONS

International Search Report dated May 28, 2019 for corresponding International Patent Application No. PCT/JP2019/006323.
Notice of References Cited in Office Action dated Apr. 18, 2023 in U.S. Appl. No. 16/971,244.
Office Action issued in corresponding Chinese Patent Application No. 201980014408.5, dated Apr. 28, 2023.

* cited by examiner

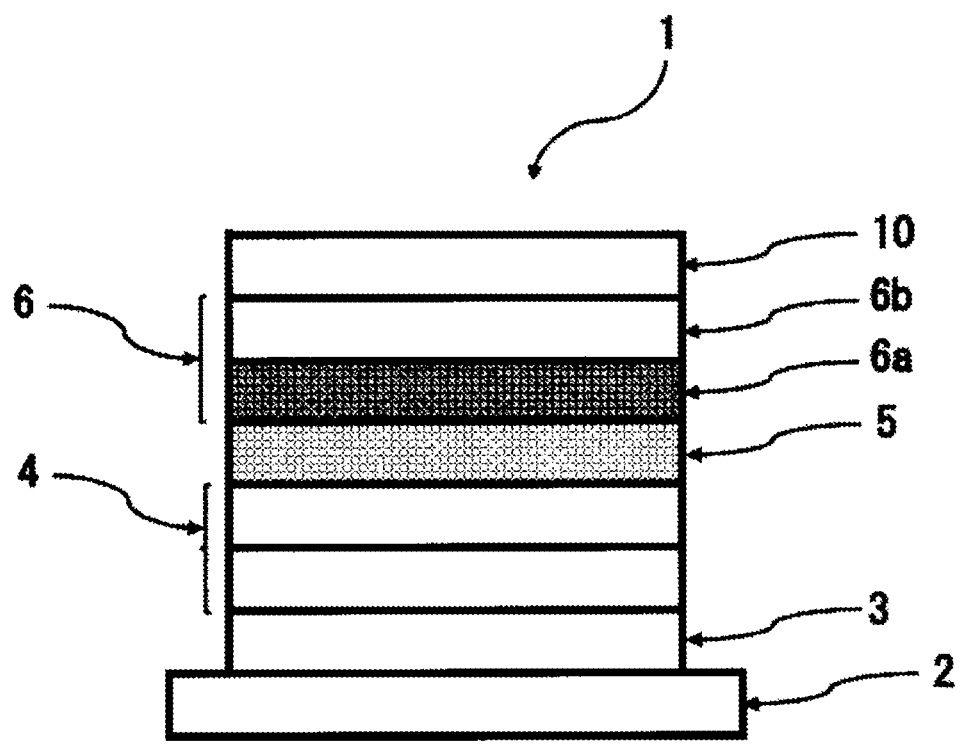

COMPOUND AND ORGANIC ELECTROLUMINESCENCE DEVICE USING THE SAME

CROSS-REFERENCE TO RELATED APPLICATIONS

The present application claims priority under 35 U.S.C. § 371 to International Patent Application No. PCT/JP2019/006323, filed Feb. 20, 2019, which claims priority to and the benefit of Japanese Patent Application Nos. 2018-027695, filed on Feb. 20, 2018, and 2018-202293, filed on Oct. 26, 2018. The contents of these applications are hereby incorporated by reference in their entireties.

TECHNICAL FIELD

The invention relates to a novel compound and an organic electroluminescence device using the same.

BACKGROUND ART

When voltage is applied to an organic electroluminescence device (hereinafter, referred to as an organic EL device in several cases), holes and electrons are injected into an emitting layer from an anode and a cathode, respectively. Then, thus injected holes and electrons are recombined in the emitting layer, and excitons are formed therein.

Patent Documents 1 and 2 disclose a compound in which an azine ring and a dibenzothiophene ring are bonded with or without a linking group, as a material for an organic EL device, and an organic EL device using the same.

RELATED ART DOCUMENT

Patent Document

[Patent Document 1] WO2007/069569
[Patent Document 2] WO2013/077352

SUMMARY OF THE INVENTION

It is an object of the invention to provide a novel compound which can be used as a material for an organic electroluminescence device, that makes the device to have high luminous efficiency, as well as an organic electroluminescence device which exhibits high luminous efficiency using the same.

According to the invention, the following novel compound, an electron transporting material for an organic electroluminescence device, an organic electroluminescence device, and an electronic apparatus:

1. A compound represented by the following formula (1).

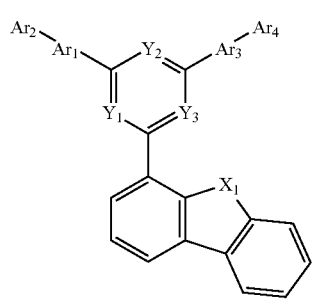

wherein in the formula (1),
$X_1$ is O or S;
$Y_1$, $Y_2$ and $Y_3$ are independently CH or N;
provided that two or more of $Y_1$, $Y_2$ and $Y_3$ are N;

$Ar_1$ and $Ar_3$ are independently
a single bond,
a substituted or unsubstituted phenylene group,
a substituted or unsubstituted naphthylene group,
a substituted or unsubstituted phenanthrene group, or
a substituted or unsubstituted anthrylene group;
$Ar_2$ and $Ar_4$ are independently
a substituted or unsubstituted phenyl group,
a substituted or unsubstituted naphthyl group,
a substituted or unsubstituted phenanthryl group, or
a substituted or unsubstituted anthryl group;
$Ar_1$ and $Ar_2$, and $Ar_3$ and $Ar_4$ independently form a substituted or unsubstituted, saturated or unsaturated ring constituted only by a 6-membered ring by bonding with each other, or do not form a ring; and
provided that the case where either one or both of —$Ar_1$-$Ar_2$ and —$Ar_3$-$Ar_4$ is the following group is excluded.

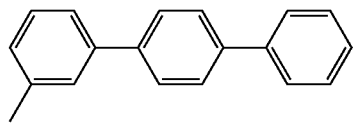

2. An electron-transporting material for an organic electroluminescence device, which comprises the compound represented by the formula (1).
3. An organic electroluminescence device comprising an anode, an organic layer, and a cathode in this order, wherein
the organic layer comprises the compound represented by the formula (1).
4. An organic electroluminescence device comprising an anode, an emitting layer, an electron-transporting region, and a cathode in this order, wherein
the electron transporting region comprises the compound represented by the formula (1).
5. An electronic apparatus comprising the above-mentioned organic electroluminescence device.

According to the present disclosure, a novel compound which can be used as a material for an organic electroluminescence device, that makes the device to have high luminous efficiency, as well as an organic electroluminescence device which exhibits high luminous efficiency using the same can be provided.

BRIEF DESCRIPTION OF THE DRAWINGS

The FIGURE is a schematic diagram of the organic EL device according to an aspect of the invention.

MODE FOR CARRYING OUT THE INVENTION

Definition

In this specification, unless otherwise noted, a hydrogen atom means an atom including isotopes different in the number of neutrons, namely, a protium, a deuterium and a tritium.

In this specification, a term "ring carbon atoms" represents the number of carbon atoms among atoms forming a subject ring itself of a compound having a structure in which atoms are bonded in a ring form (for example, a monocyclic compound, a fused ring compound, a cross-linked compound, a carbocyclic compound or a heterocyclic compound). When the subject ring is substituted by a substituent, the carbon contained in the substituent is not included in the number of ring carbon atoms. The same shall apply to the "ring carbon atoms" described below, unless otherwise noted. For example, a benzene ring has 6 ring carbon atoms, a naphthalene ring has 10 ring carbon atoms, a pyridine ring has 5 ring carbon atoms, and a furan ring has 4 ring carbon atoms. Further, for example, a 9,9-diphenylfluorenyl group has 13 ring carbon atoms, and a 9,9'-spirobifluorenyl group has 25 ring carbon atoms.

Further, when the benzene ring or the naphthalene ring is substituted by an alkyl group as a substituent, for example, the number of carbon atoms of the alkyl group is not included in the ring carbon atoms.

In this specification, a term "ring atoms" represents the number of atoms forming a subject ring itself of a compound having a structure in which atoms are bonded in a ring form (for example, a monocycle, a fused ring and a ring assembly) (for example, a monocyclic compound, a fused ring compound, a cross-linked compound, a carbocyclic compound or a heterocyclic compound). The term "ring atoms" does not include atoms which do not form the ring (for example, a hydrogen atom which terminates a bond of the atoms forming the ring) or atoms contained in a substituent when the ring is substituted by the substituent. The same shall apply to the "ring atoms" described below, unless otherwise noted. For example, a pyridine ring has 6 ring atoms, a quinazoline ring has 10 ring atoms, and a furan ring has 5 ring atoms. A hydrogen atom bonded with a carbon atom of the pyridine ring or the quinazoline ring or an atom forming the substituent is not included in the number of the ring atoms.

In this specification, a term "XX to YY carbon atoms" in an expression of "substituted or unsubstituted ZZ group having XX to YY carbon atoms" represents the number of carbon atoms when the ZZ group is unsubstituted. The number of carbon atoms of a substituent when the ZZ group is substituted is not included. Here, "YY" is larger than "XX", and "XX" and "YY" each mean an integer of 1 or more.

In this specification, a term "XX to YY atoms" in an expression of "substituted or unsubstituted ZZ group having XX to YY atoms" represents the number of atoms when the ZZ group is unsubstituted. The number of atoms of a substituent when the group is substituted is not included. Here, "YY" is larger than "XX", and "XX" and "YY" each mean an integer of 1 or more.

A term "unsubstituted" in the case of "substituted or unsubstituted ZZ group" means that the ZZ group is not substituted by a substituent, and a hydrogen atom is bonded therewith. Alternatively, a term "substituted" in the case of "substituted or unsubstituted ZZ group" means that one or more hydrogen atoms in the ZZ group are substituted by a substituent. Similarly, a term "substituted" in the case of "BB group substituted by an M group" means that one or more hydrogen atoms in the BB group are substituted by the AA group.

Hereinafter, the substituent described in this specification will be described.

The number of the ring carbon atoms of the "unsubstituted aryl group" described in this specification is 6 to 50, preferably 6 to 30, and more preferably 6 to 18, unless otherwise specified.

The number of the ring carbon atoms of the "unsubstituted heterocyclic group" described in this specification is 5 to 50, preferably 5 to 30, and more preferably 5 to 18, unless otherwise specified.

The number of the carbon atoms of the "unsubstituted alkyl group" described in this specification is 1 to 50, preferably 1 to 20, and more preferably 1 to 6, unless otherwise specified.

The number of the carbon atoms of the "unsubstituted alkenyl group" described in this specification is 2 to 50, preferably 2 to 20, and more preferably 2 to 6, unless otherwise specified.

The number of the carbon atoms of the "unsubstituted alkynyl group" described in this specification is 2 to 50, preferably 2 to 20, and more preferably 2 to 6, unless otherwise specified.

The number of the ring carbon atoms of the "unsubstituted cycloalkyl group" described in this specification is 3 to 50, preferably 3 to 20, and more preferably 3 to 6, unless otherwise specified.

The number of the ring carbon atoms of the "unsubstituted arylene group" described in this specification is 6 to 50, preferably 6 to 30, and more preferably 6 to 18, unless otherwise specified.

The number of the ring atoms of the "unsubstituted divalent heterocyclic group" described in this specification is 5 to 50, preferably 5 to 30, and more preferably 5 to 18, unless otherwise specified.

The number of the carbon atoms of the "unsubstituted alkylene group" described in this specification is 1 to 50, preferably 1 to 20, and more preferrably 1 to 6, unless otherwise specified.

Specific examples (specific example group G1) of the "substituted or unsubstituted aryl group" described in this specification include an unsubstituted aryl group and a substituted aryl group described below. (Here, a term "unsubstituted aryl group" refers to a case where the "substituted or unsubstituted aryl group" is the "unsubstituted aryl group," and a term "substituted aryl group" refers to a case where the "substituted or unsubstituted aryl group" is the "substituted aryl group". Hereinafter, a case of merely "aryl group" includes both the "unsubstituted aryl group" and the "substituted aryl group".

The "substituted aryl group" refers to a case where the "unsubstituted aryl group" has a substituent, and specific examples thereof include a group in which the "unsubstituted aryl group" has the substituent, and a substituted aryl group described below. It should be noted that examples of the "unsubstituted aryl group" and examples of the "substituted aryl group" listed in this specification are only one example, and the "substituted aryl group" described in this specification also includes a group in which a group in which "unsubstituted aryl group" has a substituent further has a substituent, and the like, and a group in which "substituted aryl group" further has a substituent.

An unsubstituted aryl group:
a phenyl group,
a p-biphenyl group,
a m-biphenyl group,
an o-biphenyl group,
a p-terphenyl-4-yl group,
a p-terphenyl-3-yl group,
a p-terphenyl-2-yl group,
a m-terphenyl-4-yl group,
a m-terphenyl-3-yl group,
a m-terphenyl-2-yl group,
an o-terphenyl-4-yl group, an o-terphenyl-3-yl group,
an o-terphenyl-2-yl group,
a 1-naphthyl group,
a 2-naphthyl group,
an anthryl group,
a benzanthryl group,
a phenanthryl group,
a benzophenanthryl group,
a phenalenyl group,
a pyrenyl group,
a chrysenyl group,
a benzochrysenyl group,
a triphenylenyl group,
a benzotriphenylenyl group,
a tetracenyl group,
a pentacenyl group,
a fluorenyl group,
a 9,9'-spirobifluorenyl group,
a benzofluorenyl group,
a dibenzofluorenyl group,
a fluoranthenyl group,
a benzofluoranthenyl group, and
a perylenyl group.

A substituted aryl group:
an o-tolyl group,
a m-tolyl group,
a p-tolyl group,
a p-xylyl group,
a m-xylyl group,
an o-xylyl group,
a p-isopropyl phenyl group,
a m-isopropyl phenyl group,
an o-isopropyl phenyl group,
a p-t-butylphenyl group,
a m-t-butylphenyl group,
an o-t-butylphenyl group,
a 3,4,5-trimethylphenyl group,
a 9,9-dimethylfluorenyl group,
a 9,9-diphenylfluorenyl group
a 9,9-di(4-methylphenyl)fluorenyl group,
a 9,9-di(4-isopropylphenyl)fluorenyl group,
a 9,9-di(4-t-butylphenyl)fluorenyl group,
a cyanophenyl group,
a triphenylsilylphenyl group,
a trimethylsilylphenyl group,
a phenylnaphthyl group, and
a naphthylphenyl group.

The "heterocyclic group" described in this specification is a ring group having at least one hetero atom in the ring atom. Specific examples of the hetero atom include a nitrogen atom, an oxygen atom, a sulfur atom, a silicon atom, a phosphorus atom and a boron atom.

The "heterocyclic group" described in this specification may be a monocyclic group, or a fused ring group.

The "heterocyclic group" described in this specification may be an aromatic heterocyclic group, or an aliphatic heterocyclic group.

Specific examples (specific example group G2) of the "substituted or unsubstituted heterocyclic group" include an unsubstituted heterocyclic group and a substituted heterocyclic group described below. (Here, the unsubstituted heterocyclic group refers to a case where the "substituted or unsubstituted heterocyclic group" is the "unsubstituted heterocyclic group," and the substituted heterocyclic group refers to a case where the "substituted or unsubstituted heterocyclic group" is the "substituted heterocyclic group". Hereinafter, the case of merely "heterocyclic group" includes both the "unsubstituted heterocyclic group" and the "substituted heterocyclic group".

The "substituted heterocyclic group" refers to a case where the "unsubstituted heterocyclic group" has a substituent, and specific examples thereof include a group in which the "unsubstituted heterocyclic group" has a substituent, and a substituted heterocyclic group described below. It should be noted that examples of the "unsubstituted heterocyclic group" and examples of the "substituted heterocyclic group" listed in this specification are merely one example, and the "substituted heterocyclic group" described in this specification also includes a group in which "unsubstituted heterocyclic group" which has a substituent further has a substituent, and the like, and a group in which "substituted heterocyclic group" further has a substituent.

An unsubstituted heterocyclic group having a nitrogen atom:
a pyrrolyl group,
an imidazolyl group,
a pyrazolyl group,
a triazolyl group,
a tetrazolyl group,
an oxazolyl group,
an isoxazolyl group,
an oxadiazolyl group,
a thiazolyl group,
an isothiazolyl group,
a thiadiazolyl group,
a pyridyl group,
a pyridazinyl group,
a pyrimidinyl group,
a pyrazinyl group,
a triazinyl group,
an indolyl group,
an isoindolyl group,
an indolizinyl group,
a quinolizinyl group,
a quinolyl group,
an isoquinolyl group,
a cinnolyl group,
a phthalazinyl group,
a quinazolinyl group,
a quinoxalinyl group,
a benzimidazolyl group,
an indazolyl group,
a phenanthrolinyl group,
a phenanthridinyl group
an acridinyl group,
a phenazinyl group,
a carbazolyl group,
a benzocarbazolyl group,
a morpholino group,
a phenoxazinyl group,
a phenothiazinyl group,
an azacarbazolyl group, and
a diazacarbazolyl group.

An unsubstituted heterocyclic group having an oxygen atom:
a furyl group,
an oxazolyl group,
an isoxazolyl group,
an oxadiazolyl group,
a xanthenyl group,
a benzofuranyl group,
an isobenzofuranyl group,
a dibenzofuranyl group,
a naphthobenzofuranyl group, a benzoxazolyl group,
a benzisoxazolyl group,
a phenoxazinyl group,
a morpholino group,
a dinaphthofuranyl group,
an azadibenzofuranyl group,
a diazadibenzofuranyl group,
an azanaphthobenzofuranyl group, and
a diazanaphthobenzofuranyl group.

An unsubstituted heterocyclic group having a sulfur atom:
a thienyl group,
a thiazolyl group,
an isothiazolyl group,
a thiadiazolyl group,
a benzothiophenyl group,
an isobenzothiophenyl group,
a dibenzothiophenyl group,
a naphthobenzothiophenyl group,
a benzothiazolyl group,
a benzisothiazolyl group,
a phenothiazinyl group,
a dinaphthothiophenyl group,
an azadibenzothiophenyl group,
a diazadibenzothiophenyl group,
an azanaphthobenzothiophenyl group, and
a diazanaphthobenzothiophenyl group.

A substituted heterocyclic group having a nitrogen atom:
a (9-phenyl)carbazolyl group,
a (9-biphenylyl)carbazolyl group,
a (9-phenyl)phenylcarbazolyl group,
a (9-naphthyl)carbazolyl group,
a diphenylcarbazol-9-yl group,
a phenylcarbazol-9-yl group,
a methylbenzimidazolyl group,
an ethylbenzimidazolyl group,
a phenyltriazinyl group,
a biphenylyltriazinyl group,
a diphenyltriazinyl group,
a phenylquinazolinyl group, and
a biphenylylquinazolinyl group.

A substituted heterocyclic group having an oxygen atom:
a phenyldibenzofuranyl group,
a methyldibenzofuranyl group,
a t-butyldibenzofuranyl group, and
a monovalent residue of spiro[9H-xanthene-9,9'-[9H]fluorene].

A substituted heterocyclic group having a sulfur atom:
a phenyldibenzothiophenyl group,
a methyldibenzothiophenyl group,
a t-butyldibenzothiophenyl group, and
a monovalent residue of spiro[9H-thioxantene-9,9'-[9H]fluorene].

A monovalent group derived from the following unsubstituted heterocyclic ring containing at least one of a nitrogen atom, an oxygen atom and a sulfur atom, and a monovalent group in which a monovalent group derived from the following unsubstituted heterocyclic ring has a substituent:

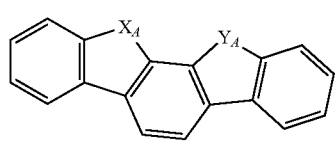
(XY-1)

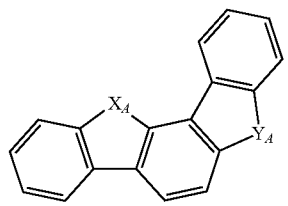
(XY-2)

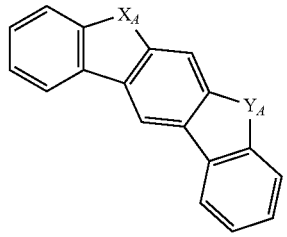
(XY-3)

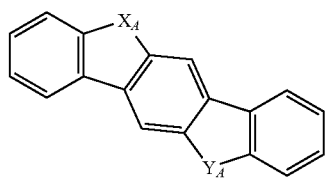
(XY-4)

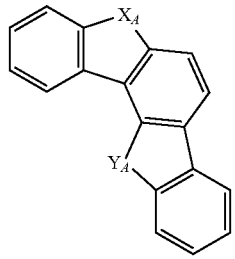
(XY-5)

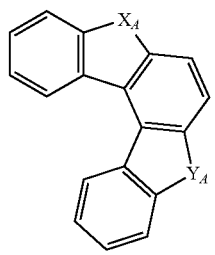
(XY-6)

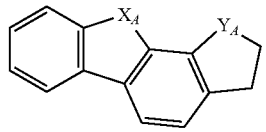
(XY-7)

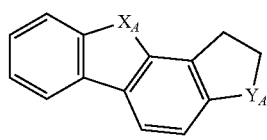
(XY-8)

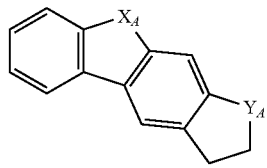
(XY-9)

-continued (XY-10)
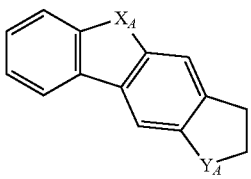

(XY-11)
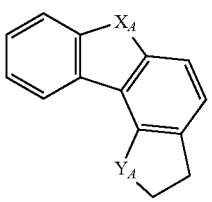

(XY-12)
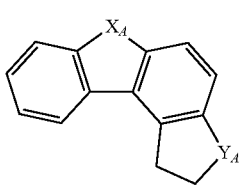

(XY-13)
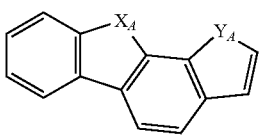

(XY-14)
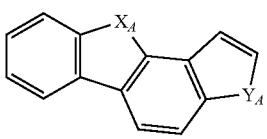

(XY-15)
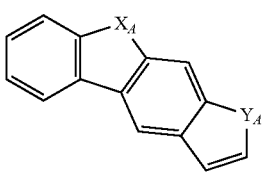

(XY-16)
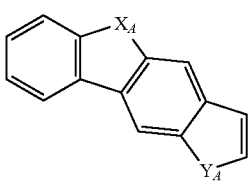

(XY-17)
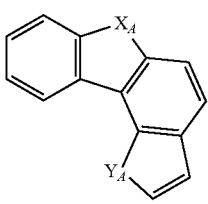

-continued (XY-18)
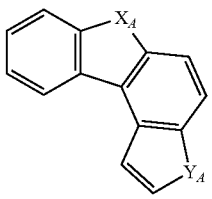

In the formulas (XY-1) to (XY-18), $X_A$ and $Y_A$ are independently an oxygen atom, a sulfur atom, NH or $CH_2$. However, at least one of $X_A$ and $Y_A$ is an oxygen atom, a sulfur atom or NH.

The heterocyclic ring represented by the formulas (XY-1) to (XY-18) becomes a monovalent heterocyclic group having a bond at an arbitrary position.

An expression "the monovalent group derived from the unsubstituted heterocyclic ring represented by the formulas (XY-1) to (XY-18) has a substituent" refers to a case where the hydrogen atom bonded with the carbon atom which constitutes a skeleton of the formulas is substituted by a substituent, or a state in which $X_A$ or $Y_A$ is NH or $CH_2$, and the hydrogen atom in the NH or $CH_2$ is replaced with a substituent.

Specific examples (specific example group G3) of the "substituted or unsubstituted alkyl group" include an unsubstituted alkyl group and a substituted alkyl group described below. (Here, the unsubstituted alkyl group refers to a case where the "substituted or unsubstituted alkyl group" is the "unsubstituted alkyl group," and the substituted alkyl group refers to a case where the "substituted or unsubstituted alkyl group" is the "substituted alkyl group"). Hereinafter, the case of merely "alkyl group" includes both the "unsubstituted alkyl group" and the "substituted alkyl group".

The "substituted alkyl group" refers to a case where the "unsubstituted alkyl group" has a substituent, and specific examples thereof include a group in which the "unsubstituted alkyl group" has a substituent, and a substituted alkyl group described below. It should be noted that examples of the "unsubstituted alkyl group" and examples of the "substituted alkyl group" listed in this specification are merely one example, and the "substituted alkyl group" described in this specification also includes a group in which "unsubstituted alkyl group" has a substituent further has a substituent, and the like, and a group in which "substituted alkyl group" further has a substituent.

An unsubstituted alkyl group:
a methyl group,
an ethyl group,
a n-propyl group,
an isopropyl group,
a n-butyl group,
an isobutyl group,
a s-butyl group, and
a t-butyl group.

A substituted alkyl group:
a heptafluoropropyl group (including an isomer),
a pentafluoroethyl group,
a 2,2,2-trifluoroethyl group, and
a trifluoromethyl group.

Specific examples (specific example group G4) of the "substituted or unsubstituted alkenyl group" include an unsubstituted alkenyl group and a substituted alkenyl group described below. (Here, the unsubstituted alkenyl group refers to a case where the "substituted or unsubstituted alkenyl group" is the "unsubstituted alkenyl group," and the substituted alkenyl group refers to a case where the "substituted or unsubstituted alkenyl group" is the "substituted alkenyl group"). Hereinafter, the case of merely "alkenyl group" includes both the "unsubstituted alkenyl group" and the "substituted alkenyl group".

The "substituted alkenyl group" refers to a case where the "unsubstituted alkenyl group" has a substituent, and specific examples thereof include a group in which the "unsubstituted alkenyl group" has a substituent, and a substituted alkenyl group described below. It should be noted that examples of the "unsubstituted alkenyl group" and examples of the "substituted alkenyl group" listed in this specification are merely one example, and the "substituted alkenyl group" described in this specification also includes a group in which "unsubstituted alkenyl group" has a substituent further has a substituent, and the like, and a group in which "substituted alkenyl group" further has a substituent.

An unsubstituted alkenyl group and a substituted alkenyl group:
a vinyl group,
an allyl group,
a 1-butenyl group,
a 2-butenyl group,
a 3-butenyl group,
a 1,3-butanedienyl group,
a 1-methylvinyl group,
a 1-methylallyl group,
a 1,1-dimethylallyl group,
a 2-methylallyl group, and
a 1,2-dimethylallyl group.

Specific examples (specific example group G5) of the "substituted or unsubstituted alkynyl group" include an unsubstituted alkynyl group described below. (Here, the unsubstituted alkynyl group refers to a case where the "substituted or unsubstituted alkynyl group" is the "unsubstituted alkynyl group"). Hereinafter, a case of merely "alkynyl group" includes both the "unsubstituted alkynyl group" and the "substituted alkynyl group".

The "substituted alkynyl group" refers to a case where the "unsubstituted alkynyl group" has a substituent, and specific examples thereof include a group in which the "unsubstituted alkynyl group" described below has a substituent.

An unsubstituted alkynyl group:
an ethynyl group.

Specific examples (specific example group G6) of the "substituted or unsubstituted cycloalkyl group" described in this specification include an unsubstituted cycloalkyl group and a substituted cycloalkyl group described below. (Here, the unsubstituted cycloalkyl group refers to a case where the "substituted or unsubstituted cycloalkyl group" is the "unsubstituted cycloalkyl group," and the substituted cycloalkyl group refers to a case where the "substituted or unsubstituted cycloalkyl group" is the "substituted cycloalkyl group"). Hereinafter, a case of merely "cycloalkyl group" includes both the "unsubstituted cycloalkyl group" and the "substituted cycloalkyl group".

The "substituted cycloalkyl group" refers to a case where the "unsubstituted cycloalkyl group" a the substituent, and specific examples thereof include a group in which the "unsubstituted cycloalkyl group" has a substituent, and a substituted cycloalkyl group described below. It should be noted that examples of the "unsubstituted cycloalkyl group" and examples of the "substituted cycloalkyl group" listed in this specification are merely one example, and the "substituted cycloalkyl group" described in this specification also includes a group in which "unsubstituted cycloalkyl group" has a substituent further has a substituent, and the like, and a group in which "substituted cycloalkyl group" further has a substituent.

An unsubstituted aliphatic ring group:
a cyclopropyl group,
a cyclobutyl group,
a cyclopentyl group,
a cyclohexyl group,
a 1-adamantyl group,
a 2-adamantyl group,
a 1-norbornyl group, and
a 2-norbornyl group.

A substituted cycloalkyl group:
a 4-methylcyclohexyl group.

Specific examples (specific example group G7) of the group represented by —Si($R_{901}$)($R_{902}$)($R_{903}$) described in this specification include
—Si(G1)(G1)(G1),
—Si(G1)(G2)(G2),
—Si(G1)(G1)(G2),
—Si(G2)(G2)(G2),
—Si(G5)(G5)(G5) and
—Si(G6)(G6)(G6).

In which,
G1 is the "aryl group" described in the specific example group G1.
G2 is the "heterocyclic group" described in the specific example group G2.
G3 is the "alkyl group" described in the specific example group G3.
G6 is the "cycloalkyl group" described in the specific example group G6.

Specific examples (specific example group G8) of the group represented by —O—($R_{904}$) described in this specification include
—O(G1),
—O(G2),
—O(G3) and
—O(G6).

In which,
G1 is the "aryl group" described in the specific example group G1.
G2 is the "heterocyclic group" described in the specific example group G2.
G3 is the "alkyl group" described in the specific example group G3.
G6 is the "cycloalkyl group" described in the specific example group G6.

Specific examples (specific example group G9) of the group represented by —S—($R_{905}$) described in this specification include
—S(G1),
—S(G2),
—S(G3) and
—S(G6).

In which,
G1 is the "aryl group" described in the specific example group G1.
G2 is the "heterocycle group" described in the specific example group G2.
G3 is the "alkyl group" described in the specific example group G3.
G6 is the "cycloalkyl group" described in the specific example group G6.

Specific examples (specific example group G10) of the group represented by —N($R_{906}$)($R_{907}$) described in this specification include —N(G1)(G1),
—N(G2)(G2),
—N(G1)(G2),
—N(G3)(G3) and
—N(G6) (G6).

In which,

G1 is the "aryl group" described in the specific example group G1.

G2 is the "heterocycle group" described in the specific example group G2.

G3 is the "alkyl group" described in the specific example group G3.

G6 is the "cycloalkyl group" described in the specific example group G6.

Specific examples (specific example group G11) of the "halogen atom" described in this specification include a fluorine atom, a chlorine atom, a bromine atom and an iodine atom.

Specific examples of the "alkoxy group" described in this specification include a group represented by —O(G3), where G3 is the "alkyl group" described in the specific example group G3. The number of carbon atoms of the "unsubstituted alkoxy group" are 1 to 50, preferably 1 to 30, and more preferably 1 to 18, unless otherwise specified.

Specific examples of the "alkylthio group" described in this specification include a group represented by —S(G3), where G3 is the "alkyl group" described in the specific example group G3. The number of carbon atoms of the "unsubstituted alkylthio group" are 1 to 50, preferably 1 to 30, and more preferably 1 to 18, unless otherwise specified.

Specific examples of the "aryloxy group" described in this specification include a group represented by —O(G1), where G1 is the "aryl group" described in the specific example group G1. The number of ring carbon atoms of the "unsubstituted aryloxy group" are 6 to 50, preferably 6 to 30, and more preferably 6 to 18, unless otherwise specified.

Specific examples of the "arylthio group" described in this specification include a group represented by —S(G1), where G1 is the "aryl group" described in the specific example group G1. The number of ring carbon atoms of the "unsubstituted arylthio group" are 6 to 50, preferably 6 to 30, and more preferably 6 to 18, unless otherwise specified.

Specific examples of the "aralkyl group" described in this specification include a group represented by -(G3)-(G1), where G3 is the "alkyl group" described in the specific example group G3, and G1 is the "aryl group" described in the specific example group G1. Accordingly, the "aralkyl group" is one aspect of the "substituted alkyl group" substituted by the "aryl group". The number of carbon atoms of the "unsubstituted aralkyl group," which is the "unsubstituted alkyl group" substituted by the "unsubstituted aryl group," are 7 to 50, preferably 7 to 30, and more preferably 7 to 18, unless otherwise specified.

Specific example of the "aralkyl group" include a benzyl group, a 1-phenylethyl group, a 2-phenylethyl group, a 1-phenylisopropyl group, a 2-phenylisopropyl group, a phenyl-t-butyl group, an α-naphthylmethyl group, a 1-α-naphthylethyl group, a 2-α-naphthylethyl group, a 1-α-naphthylisopropyl group, a 2-α-naphthylisopropyl group, a β-naphthylmethyl group, a 1-β-naphthylethyl group, a 2-β-naphthylethyl group, a 1-β-naphthylisopropyl group, and a 2-β-naphthylisopropyl group.

The substituted or unsubstituted aryl group described in this specification is, unless otherwise specified, preferably a phenyl group, a p-biphenyl group, a m-biphenyl group, an o-biphenyl group, a p-terphenyl-4-yl group, a p-terphenyl-3-yl group, a p-terphenyl-2-yl group, a m-terphenyl-4-yl group, a m-terphenyl-3-yl group, a m-terphenyl-2-yl group, an o-terphenyl-4-yl group, an o-terphenyl-3-yl group, an o-terphenyl-2-yl group, a 1-naphthyl group, a 2-naphthyl group, an anthryl group, a phenanthryl group, a pyrenyl group, a chrysenyl group, a triphenylenyl group, a fluorenyl group, a 9,9'-spirobifluorenyl group, a 9,9-diphenylfluorenyl group, or the like.

The substituted or unsubstituted heterocyclic group described in this specification is, unless otherwise specified, preferably a pyridyl group, a pyrimidinyl group, a triazinyl group, a quinolyl group, an isoquinolyl group, a quinazolinyl group, a benzimidazolyl group, a phenanthrolinyl group, a carbazolyl group, a benzocarbazolyl group, an azacarbazolyl group, a diazacarbazolyl group, a dibenzofuranyl group, a naphthobenzofuranyl group, an azadibenzofuranyl group, a diazadibenzofuranyl group, a dibenzothiophenyl group, a naphthobenzothiophenyl group, an azadibenzothiophenyl group, a diazadibenzothiophenyl group, a (9-phenyl)carbazolyl group, a (9-biphenylyl)carbazolyl group, a (9-phenyl)phenylcarbazolyl group, a diphenylcarbazole-9-yl group, a phenylcarbazol-9-yl group, a phenyltriazinyl group, a biphenylyltriazinyl group, diphenyltriazinyl group, a phenyldibenzofuranyl group, a phenyldibenzothiophenyl group, or the like.

The dibenzofuranyl group and the dibenzothiophenyl group as described above are specifically any group described below, unless otherwise specified.

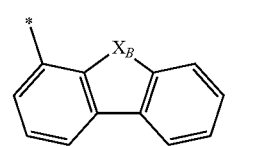
(XY-76)

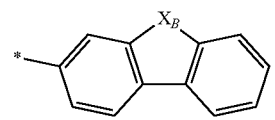
(XY-77)

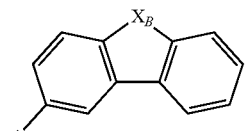
(XY-78)

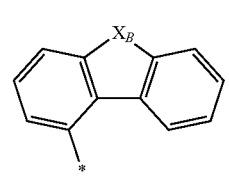
(XY-79)

In the formulas (XY-76) to (XY-79), $X_8$ is an oxygen atom or a sulfur atom.

The substituted or unsubstituted alkyl group described in this specification is, unless otherwise specified, preferably a methyl group, an ethyl group, a propyl group, an isopropyl group, a n-butyl group, an isobutyl group, a t-butyl group, or the like.

The "substituted or unsubstituted arylene group" descried in this specification refers to a group in which the above-described "my group" is converted into divalence, unless otherwise specified. Specific examples (specific example group G12) of the "substituted or unsubstituted arylene group" include a group in which the "aryl group" described in the specific example group G1 is converted into divalence.

Specific examples (specific example group G13) of the "substituted or unsubstituted divalent heterocyclic group" include a group in which the "heterocyclic group" described in the specific example group G2 is converted into divalence.

Specific examples (specific example group G14) of the "substituted or unsubstituted alkylene group" include a group in which the "alkyl group" described in the specific example group G3 is converted into divalence.

The substituted or unsubstituted arylene group described in this specification is any group described below, unless otherwise specified.

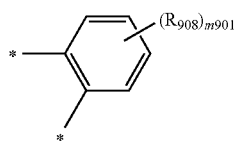
(XY-20)

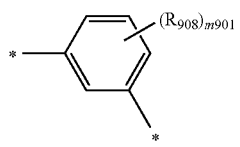
(XY-21)

(XY-22)

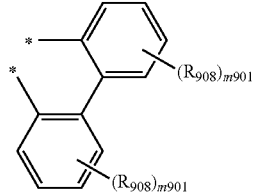
(XY-23)

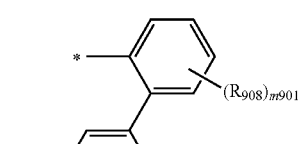
(XY-24)

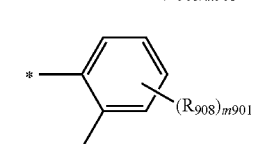
(XY-25)

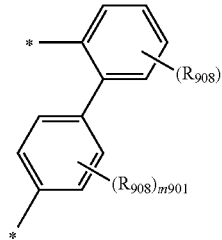

-continued

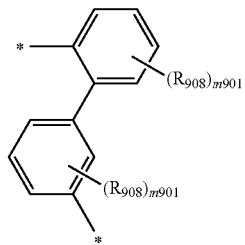
(XY-26)

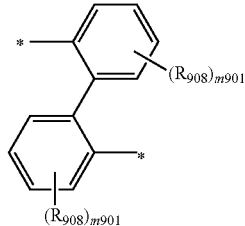
(XY-27)

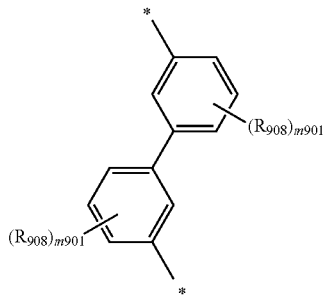
(XY-28)

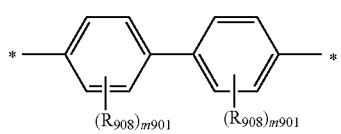
(XY-29)

In the formulas (XY-20) to (XY-29), and $R_{908}$ is a substituent.

Then, m901 is an integer of 0 to 4, and when m901 is 2 or more, a plurality of $R_{908}$ may be the same with or different from each other.

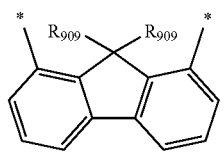
(XY-30)

(XY-31)

(XY-32) 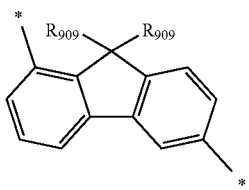

(XY-33) 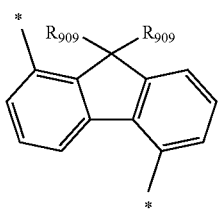

(XY-34) 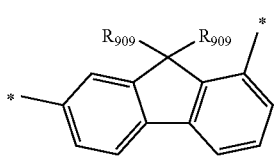

(XY-35) 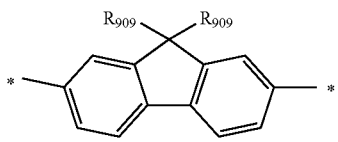

(XY-36) 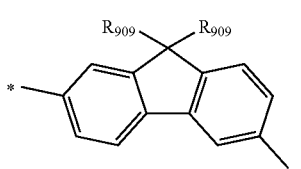

(XY-37) 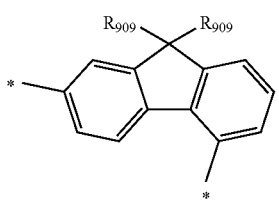

(XY-38) 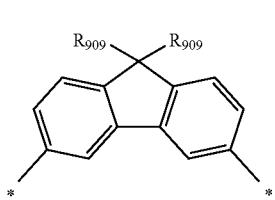

(XY-39) 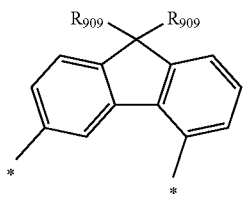

(XY-40) 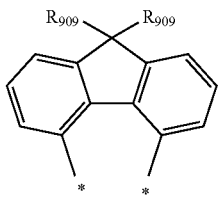

In the formulas (XY-30) to (XY-40), $R_{909}$ is independently a hydrogen atom or a substituent. Two of $R_{909}$ may form a ring by bonding with each other through a single bond.

(XY-41) 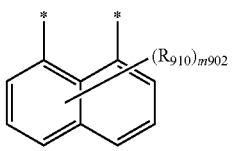

(XY-42) 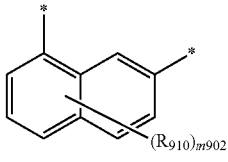

(XY-43) 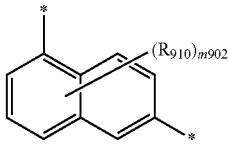

(XY-44) 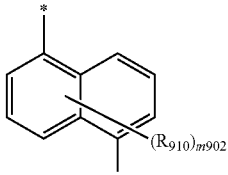

(XY-45) 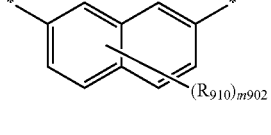

(XY-46) 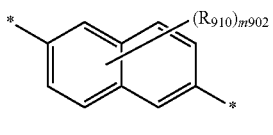

In the formulas (XY-41) to (XY-46), $R_{910}$ is a substituent.

Then, m902 is an integer of 0 to 6. When m902 is 2 or more, a plurality of $R_{910}$ may be the same with or different from each other.

The substituted or unsubstituted divalent heterocyclic group described in this specification is preferably any group described below, unless otherwise specified.

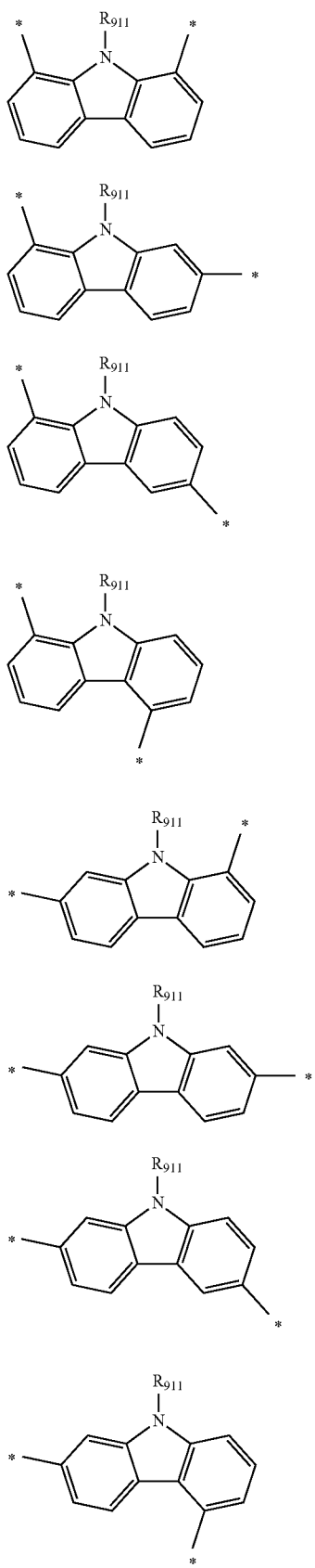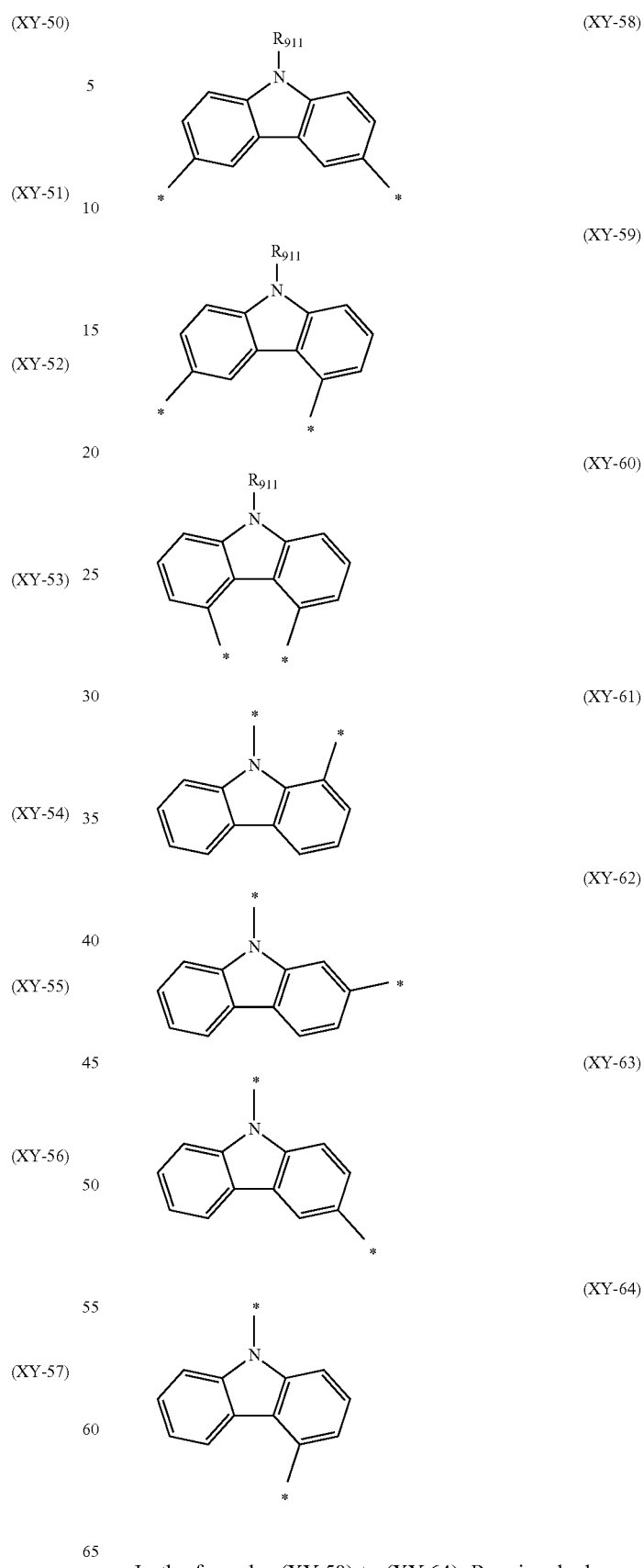
In the formulas (XY-50) to (XY-64), $R_{911}$ is a hydrogen atom or a substituent.

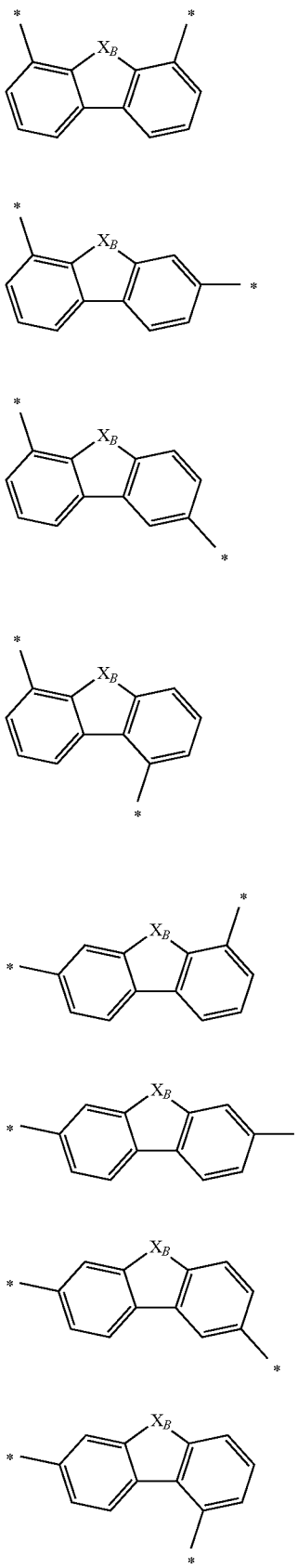

(XY-65)

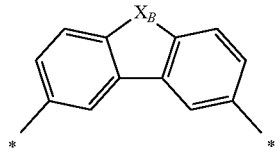

(XY-73)

(XY-66)

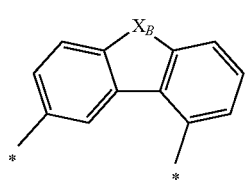

(XY-74)

(XY-67)

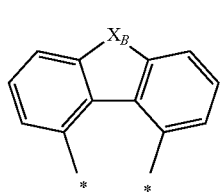

(XY-75)

(XY-68)

In the formulas (XY-65) to (XY-75), $X_B$ is an oxygen atom or a sulfur atom.

Herein, a case where "one or more sets of two or more groups adjacent to each other form a substituted or unsubstituted and saturated or unsaturated ring by bonding with each other" will be described by taking, as an example, a case of an anthracene compound represented by the following formula (XY-80) in which a mother skeleton is an anthracene ring.

(XY-69)

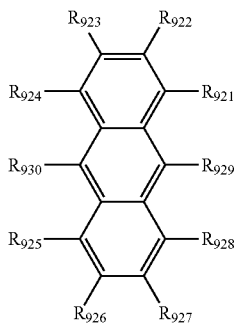

(XY-80)

(XY-70)

(XY-71)

For example, two adjacent to each other into one set when "one or more sets of two or more groups adjacent to each other form the ring by bonding with each other" among $R_{921}$ to $R_{930}$ include $R_{921}$ and $R_{922}$, $R_{922}$ and $R_{923}$, $R_{923}$ and $R_{924}$, $R_{924}$ and $R_{930}$, $R_{930}$ and $R_{925}$, $R_{925}$ and $R_{926}$, $R_{926}$ and $R_{927}$, $R_{927}$ and $R_{928}$, $R_{928}$ and $R_{929}$, and $R_{929}$ and $R_{921}$.

(XY-72)

The above-described "one or more sets" means that two or more sets of two groups adjacent to each other may simultaneously form the ring. For example, a case where $R_{921}$ and $R_{922}$ form a ring A by bonding with each other, and simultaneously $R_{925}$ and $R_{926}$ form a ring B by bonding with each other is represented by the following formula (XY-81).

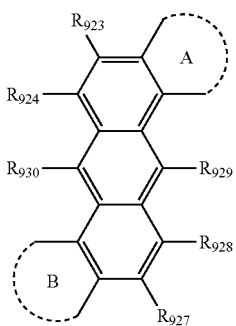

(XY-81)

A case where "two or more groups adjacent to each other" form a ring means that, for example, $R_{921}$ and $R_{922}$ form a ring A by bonding with each other, and $R_{922}$ and $R_{923}$ form a ring C by bonding with each other. A case where the ring A and ring C sharing $R_{922}$ are formed, in which the ring A and the ring C are fused to the anthracene mother skeleton by three of $R_{921}$ to $R_{923}$ adjacent to each other, is represented by the following (XY-82).

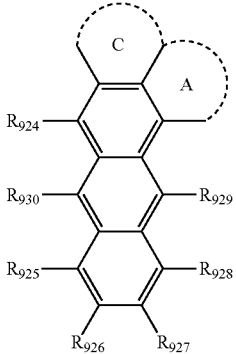

(XY-82)

The rings A to C formed in the formulas (XY-81) and (XY-82) are a saturated or unsaturated ring.

A term "unsaturated ring" means an aromatic hydrocarbon ring or an aromatic heterocyclic ring. A term "saturated ring" means an aliphatic hydrocarbon ring or an aliphatic heterocyclic ring.

For example, the ring A formed by $R_{921}$ and $R_{922}$ being bonded with each other, represented by the formula (XY-81), means a ring formed by a carbon atom of the anthracene skeleton bonded with $R_{921}$, a carbon atom of the anthracene skeleton bonded with $R_{922}$, and one or more arbitrary elements. Specific examples include, when the ring A is formed by $R_{921}$ and $R_{922}$, a case where an unsaturated ring is formed of a carbon atom of an anthracene skeleton bonded with $R_{921}$, a carbon atom of the anthracene skeleton bonded with $R_{922}$, and four carbon atoms, in which a ring formed by $R_{921}$ and $R_{922}$ is formed into a benzene ring. Further, when a saturated ring is formed, the ring is formed into a cyclohexane ring.

Here, "arbitrary elements" are preferably a C element, a N element, an O element and a S element. In the arbitrary elements (for example, a case of the C element or the N element), the bond(s) that does (do) not form the ring may be terminated by a hydrogen atom, or may be substituted by an arbitrary substituent. When the ring contains the arbitrary elements other than the C element, the ring to be formed is a heterocyclic ring.

The number of "one or more arbitrary elements" forming the saturated or unsaturated ring is preferably 2 or more and 15 or less, more preferably 3 or more and 12 or less, and further preferably 3 or more and 5 or less.

When the above-described "saturated or unsaturated ring" has a substituent, the substituent is as described above.

In one embodiment of this specification, the substituent (hereinafter, referred to as an "arbitrary substituent" in several cases) in the case of the "substituted or unsubstituted" is a group selected from the group consisting of an unsubstituted alkyl group having 1 to 50 carbon atoms,
an unsubstituted alkenyl group having 2 to 50 carbon atoms,
an unsubstituted alkynyl group having 2 to 50 carbon atoms,
an unsubstituted cycloalkyl group having 3 to 50 ring carbon atoms,
—Si($R_{901}$)($R_{902}$)($R_{903}$),
—O—($R_{905}$),
—S—($R_{905}$)
—N($R_{906}$)($R_{907}$)
wherein,
$R_{901}$ to $R^{907}$ are independently
a hydrogen atom,
a substituted or unsubstituted alkyl group having 1 to 50 carbon atoms,
a substituted or unsubstituted cycloalkyl group having 3 to 50 ring carbon atoms,
a substituted or unsubstituted aryl group having 6 to 50 ring carbon atoms, or
a substituted or unsubstituted monovalent heterocyclic group having 5 to 50 ring atoms; and when two or more of $R_{901}$ to $R_{907}$ exist, two or more of $R_{901}$ to $R_{907}$ may be the same with or different from each other,
a halogen atom, a cyano group, a nitro group,
an unsubstituted aryl group having 6 to 50 ring carbon atoms, and
an unsubstituted monovalent heterocyclic group having 5 to 50 ring atoms.

In one embodiment, the substituent in the case of "substituted or unsubstituted" is a group selected from the group consisting of an alkyl group having 1 to 50 carbon atoms,
an aryl group having 6 to 50 ring carbon atoms, and
a monovalent heterocyclic group having 5 to 50 ring atoms.

In one embodiment, the substituent in the case of "substituted or unsubstituted" is a group selected from the group consisting of an alkyl group having 1 to 18 carbon atoms,
an aryl group having 6 to 18 ring carbon atoms, and
a monovalent heterocyclic group having 5 to 18 ring atoms.

Specific examples of each group of the arbitrary substituent described above are as described above.

Herein, unless otherwise specified, the saturated or unsaturated ring (preferably substituted or unsubstituted and saturated or unsaturated 5-membered or 6-membered ring, more preferably a benzene ring) may be formed by the arbitrary substituents adjacent to each other.

Herein, unless otherwise specified, the arbitrary substituent may further have the substituent. Specific examples of the substituent that the arbitrary substituent further has include to the ones same as the arbitrary substituent described above.

[Compound Represented by the Formula (1)]

The novel compound according to an aspect of the invention is represented by the following formula (1).

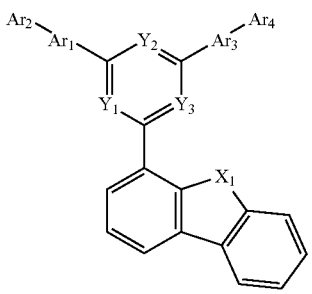

(1)

In the formula (1),
X$_1$ is O or S;
Y$_1$, Y$_2$ and Y$_3$ are independently CH or N;
provided that two or more of Y$_1$, Y$_2$ and Y$_3$ are N;
Ar$_1$ and Ar$_3$ are independently
a single bond,
a substituted or unsubstituted phenylene group,
a substituted or unsubstituted naphthylene group,
a substituted or unsubstituted phenanthrylene group, or
a substituted or unsubstituted anthrylene group;
Ar$_2$ and Ar$_4$ are independently
a substituted or unsubstituted phenyl group,
a substituted or unsubstituted naphthyl group,
a substituted or unsubstituted phenanthryl group, or
a substituted or unsubstituted anthryl group;
Ar$_1$ and Ar$_2$, and Ar$_3$ and Ar$_4$ independently form a substituted or unsubstituted, saturated or unsaturated ring constituted only by a 6-membered ring by bonding with each other, or do not form a ring; and
provided that the case where either one or both of —Ar$_1$-Ar$_2$ and —Ar$_3$-Ar$_4$ is the following group is excluded.

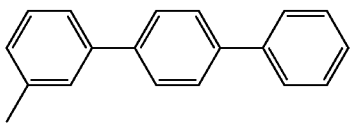 [SMILES: Cc1cccc(-c2ccc(-c3ccccc3)cc2)c1]

Since a compound represented by the formula (1) is excellent in solubility in a solvent and is easy to synthesize and purify, a highly pure compound can be obtained. With a compound having low solubility, it is difficult to sufficiently increase the purity of the material, and an organic EL device using a material having low purity is likely to deteriorate and its efficiency is likely to decrease. On the other hand, if a compound represented by the formula (1) having high solubility is used as a material for an organic EL device, the device is likely to exhibit high efficiency and good device performance.

Here, a term "ring constituted only by a 6-membered ring" means a ring in which the number of ring atoms of one ring is six, and means that a 3 to 5-membered ring and a 7 or more-membered ring is excluded. The saturated 6-membered ring is cyclohexane, and the unsaturated 6-membered ring includes a benzene ring or the like. Specifically, for example, a group derived from a fluorene ring containing a 5-membered ring in addition to a benzene ring or the like is excluded.

The term "ring constituted only by a 6-membered ring" includes a single 6-membered ring and a ring in which two or more 6-membered rings are fused.

Note that an arbitrary substituent may be substituted for a ring constituted only by a 6-membered ring.

In one embodiment,
Ar$_2$ and Ar$_4$ are independently
an unsubstituted phenyl group,
a substituted or unsubstituted naphthyl group,
a substituted or unsubstituted phenanthryl group, or
a substituted or unsubstituted anthryl group.

In one embodiment,
when Ar$_1$ and Ar$_4$ are an unsubstituted phenylene group, Ar$_2$ and Ar$_4$ are independently
an unsubstituted phenyl group,
a substituted or unsubstituted naphthyl group,
a substituted or unsubstituted phenanthryl group, or
a substituted or unsubstituted anthryl group.

In one embodiment,
one of Ar$_1$ and Ar$_4$ is a single bond, and
another is a substituted or unsubstituted phenylene group,
a substituted or unsubstituted naphthylene group,
a substituted or unsubstituted phenanthrylene group, or
a substituted or unsubstituted anthrylene group.

In one embodiment, the compound represented by the formula (1) is a compound represented by the following formula (2). Namely, X$_1$ is S.

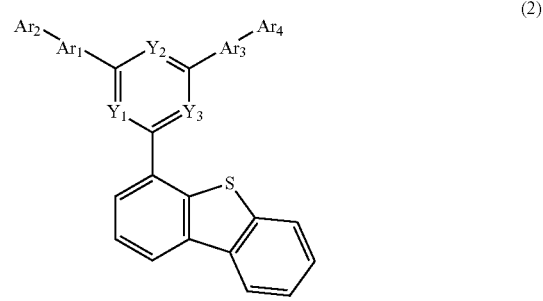

(2)

In formula (2), Y$_1$ to Y$_3$ and Ar$_1$ to Ar$_4$ are as defined in formula (1).

In one embodiment, the compound represented by the formula (1) is one or more compound selected from a compound represented by the following formula (3A) and a compound represented by the following formula (3B), and preferably the compound represented by the following formula (3A). Namely, Y$_1$ to Y$_3$ are Ns.

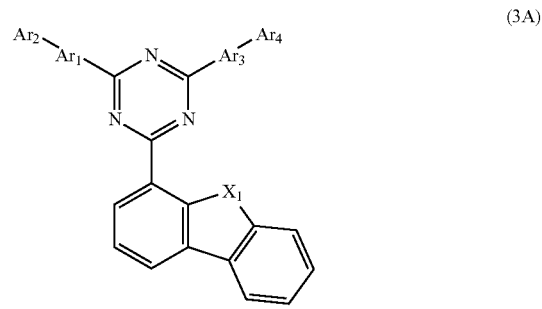

(3A)

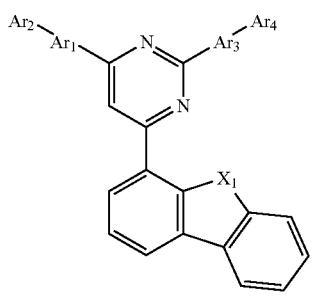
(3B)

In the formulas (3A) and (3B), $X_1$ and $Ar_1$ to $Ar_4$ are as defined in the formula (1).

In the formula (3A), $Y_1$ to $Y_3$ is N; and in the formula (3B), $Y_1$ is CH, and $Y_2$ and $Y_3$ are N.

In one embodiment, the compound represented by the formula (1) is a compound represented by the following formula (4):

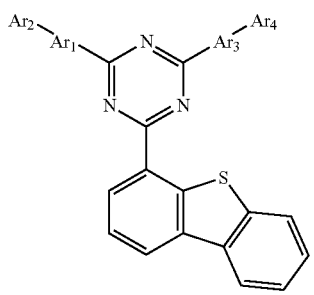
(4)

In the formula (4), $Ar_1$ to $Ar_4$ are as defined in the formula (1).

The formula (4) is a case where in the formula (3A), $X_1$ is S.

In one embodiment, the compound represented by the formula (1) is a compound represented by the following formula (5).

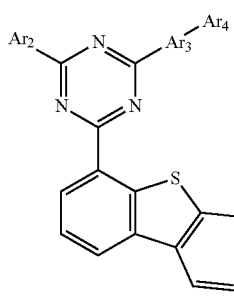
(5)

In the formula (5), $Ar_2$ to $Ar_4$ are as defined in the formula (1).

In one embodiment, $Ar_1$ and $Ar_2$, and $Ar_4$ and $Ar_4$ independently do not form a ring by bonding with each other.

In one embodiment, when $Ar_1$ to $Ar_4$ are substituted by a substituent, the substituent is
an unsubstituted phenyl group,
an unsubstituted naphthyl group,
an unsubstituted phenanthryl group,
an unsubstituted anthryl group,
an unsubstituted biphenyl group,
an unsubstituted alkyl group including 1 to 50 carbon atoms, or
an unsubstituted cycloalkyl group including 3 to 50 ring carbon atoms.

In one embodiment, —$Ar_1$-$Ar_2$ and —$Ar_3$-$Ar_4$ are independently selected from the group consisting of the groups represented by any of the following formulas (a1) to (a11).

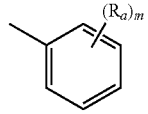
(a1)

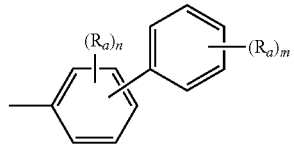
(a2)

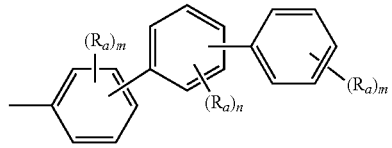
(a3)

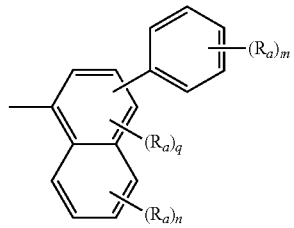
(a4)

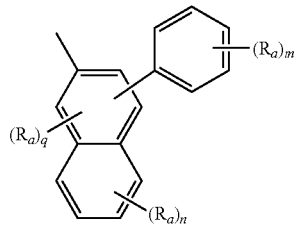
(a5)

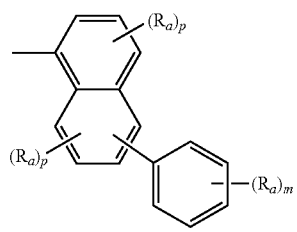
(a6)

-continued

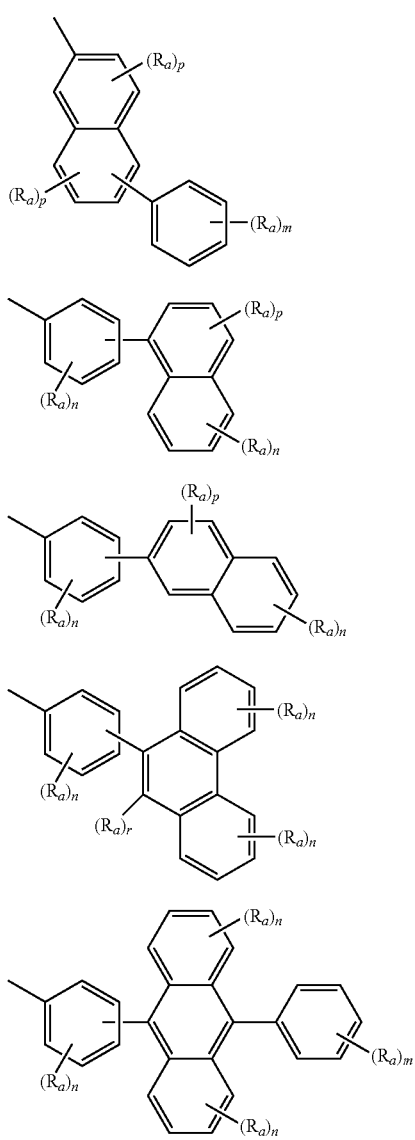

In the formulas (a1) to (a11),
$R_a$ is
a substituted or unsubstituted phenyl group,
a substituted or unsubstituted naphthyl group,
a substituted or unsubstituted phenanthryl group,
a substituted or unsubstituted anthryl group,
a substituted or unsubstituted alkyl group including 1 to 50 carbon atoms, or
a substituted or unsubstituted cycloalkyl group including 3 to 50 ring carbon atoms;
  each m is an integer of 0 to 5;
  each n is an integer of 0 to 4;
  each p is an integer of 0 to 3;
  each q is an integer of 0 to 2;
  r is an integer of 0 or 1;
  when two or more $R_a$'s are present, two or more $R_a$'s may be the same as or different to each other; and
  when two or more $R_a$'s are present, one or more sets of adjacent two or more $R_a$'s form a substituted or unsubstituted, saturated or unsaturated ring by bonding with each other, or do not form a ring.
  Here, when r is 1, $(R_a)_r$ in the formula (a10) denotes $R_a$, and when r is 0, it denotes a hydrogen atom.

In one embodiment, —$Ar_1$-$Ar_2$ and —$Ar_3$-$Ar_4$ are independently selected from the group consisting of the groups represented by any of the following formulas (aa1) to (aa8).

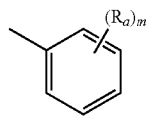
(aa1)

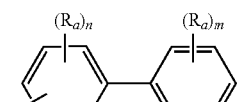
(aa2)

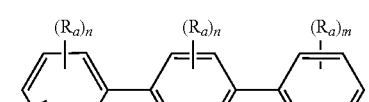
(aa3)

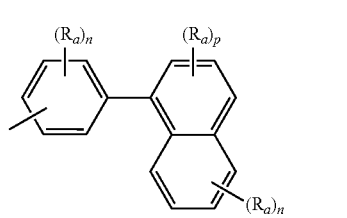
(aa4)

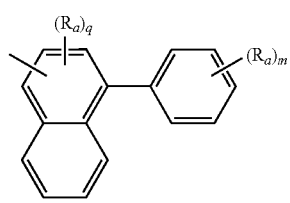
(aa5)

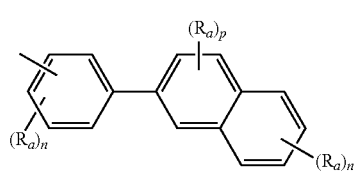
(aa6)

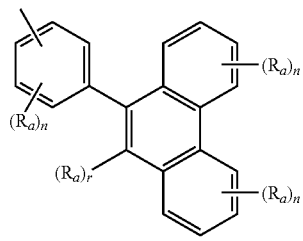
(aa7)

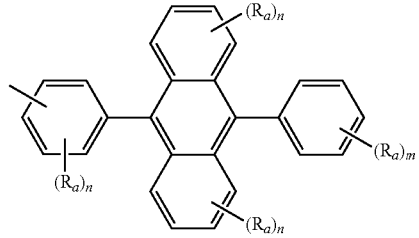
(aa8)

In the formulas (aa1) to (aa8),
$R_a$ is
a substituted or unsubstituted phenyl group,
a substituted or unsubstituted naphthyl group, a substituted or unsubstituted phenanthryl group, a substituted or unsubstituted anthryl group, a substituted or unsubstituted alkyl group including 1 to 50 carbon atoms, or a substituted or unsubstituted cycloalkyl group including 3 to 50 ring carbon atoms;

each m is an integer of 0 to 5;

each n is an integer of 0 to 4;

each p is an integer of 0 to 3;

q is an integer of 0 to 2;

r is an integer of 0 or 1;

when two or more $R_a$'s are present, two or more $R_a$'s may be the same as or different to each other; and when two or more $R_a$'s are present, one or more sets of adjacent two or more $R_a$'s form a substituted or unsubstituted, saturated or unsaturated ring by bonding with each other, or do not form a ring.

Here, when r is 1, $(R_a)_r$ in the formula (aa7) denotes $R_a$, and when r is 0, it denotes a hydrogen atom.

In one embodiment, —$Ar_1$-$Ar_2$ and —$Ar_3$-$Ar_4$ are independently selected from the group consisting of the groups represented by any of the following formulas (ab1) to (ab7).

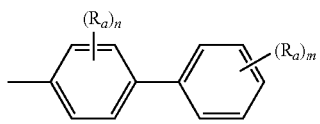
(ab1)

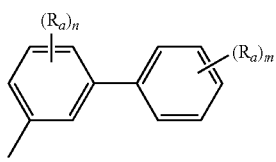
(ab2)

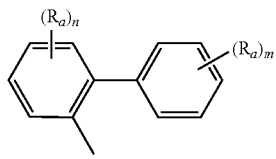
(ab3)

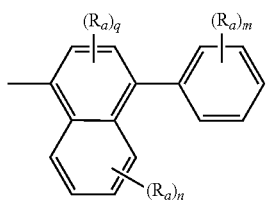
(ab4)

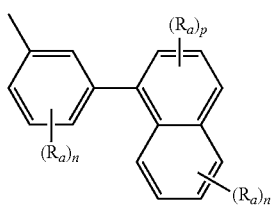
(ab5)

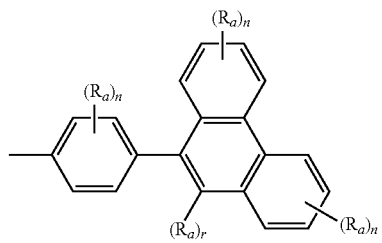
(ab6)

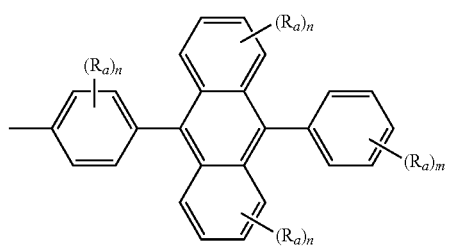
(ab7)

In the formulas (ab1) to (ab7), $R_a$ is a substituted or unsubstituted phenyl group, a substituted or unsubstituted naphthyl group, a substituted or unsubstituted phenanthryl group, a substituted or unsubstituted anthryl group, a substituted or unsubstituted alkyl group including 1 to 50 carbon atoms, or a substituted or unsubstituted cycloalkyl group including 3 to 50 ring carbon atoms;

each m is an integer of 0 to 5;

each n is an integer of 0 to 4;

p is an integer of 0 to 3;

q is an integer of 0 to 2;

r is an integer of 0 or 1;

when two or more $R_a$'s are present, two or more $R_a$'s may be the same as or different to each other; and when two or more $R_a$'s are present, one or more sets of adjacent two or more $R_a$'s independently form a substituted or unsubstituted, saturated or unsaturated ring by bonding with each other, or do not form a ring.

Here, when r is 1, $(R_a)_r$ in the formula (ab6) denotes $R_a$, and when r is 0, it denotes a hydrogen atom.

In one embodiment, —$Ar_1$-$Ar_2$ and —$Ar_3$-$Ar_4$ are independently a group selected from the group consisting of the groups represented by any of the following formulas (ac1) to (ac93).

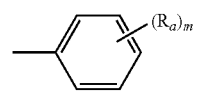
(ac1)

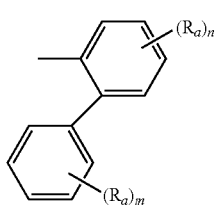
(ac2)

-continued
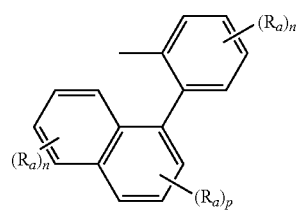
(ac3)
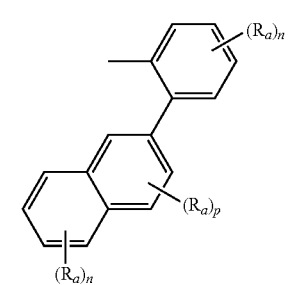
(ac4)
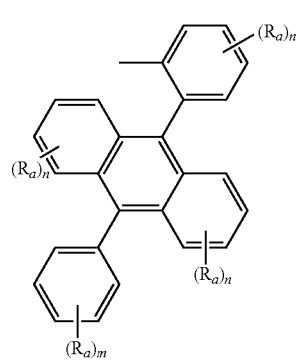
(ac5)
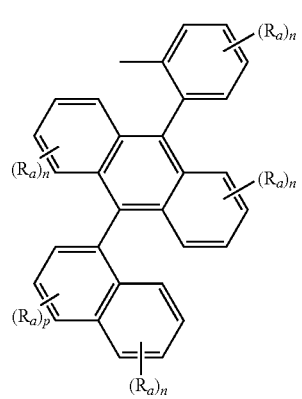
(ac6)
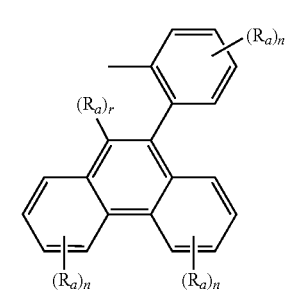
(ac6)
-continued
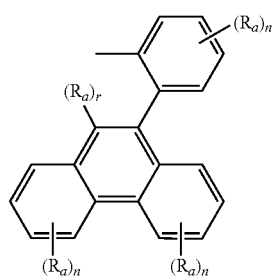
(ac7)
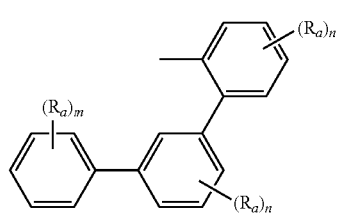
(ac8)
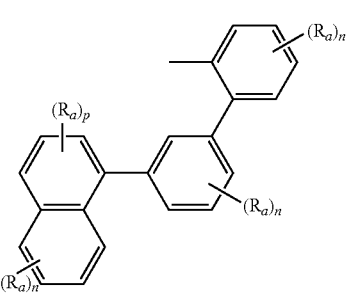
(ac9)
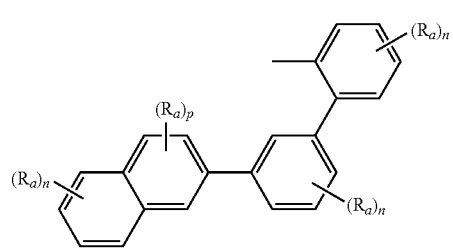
(ac10)
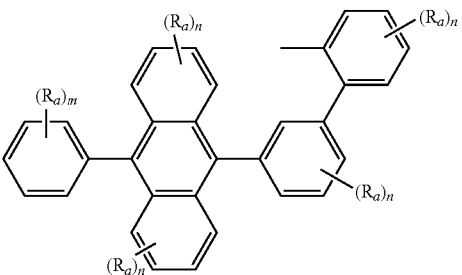
(ac10)
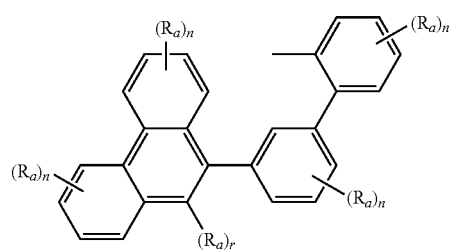
(ac11)

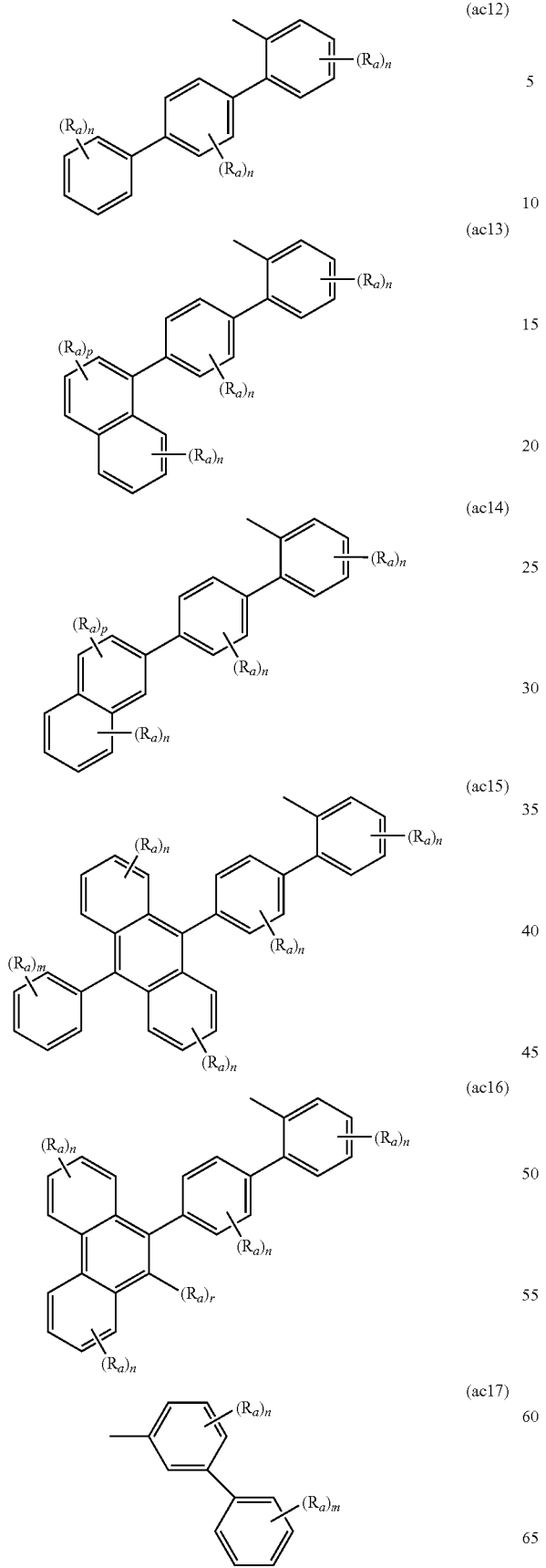
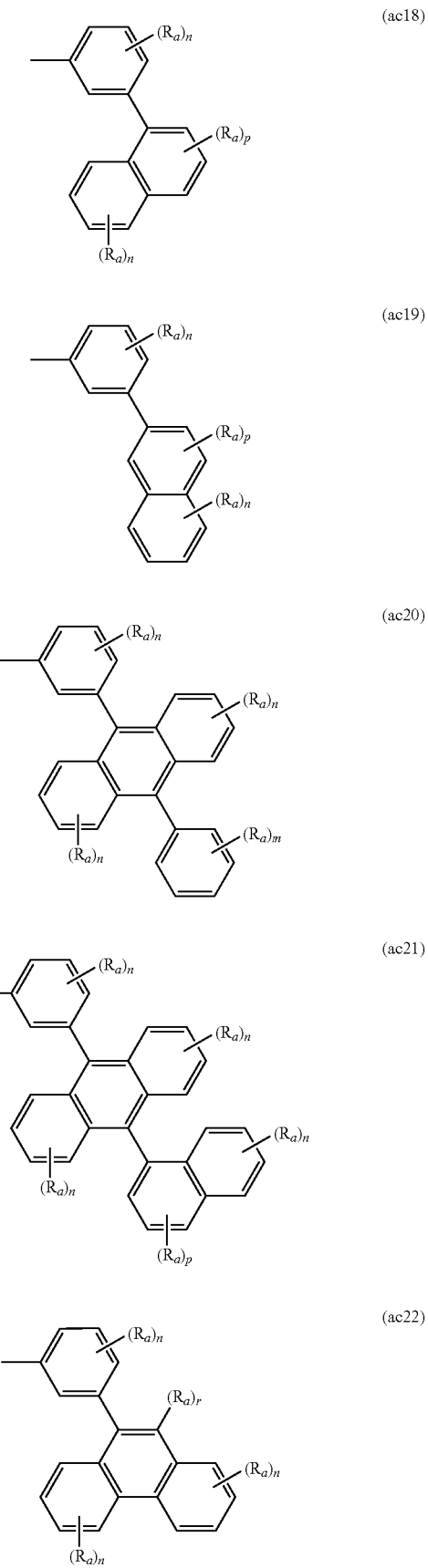

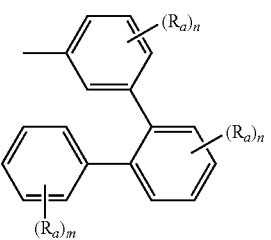 (ac23)
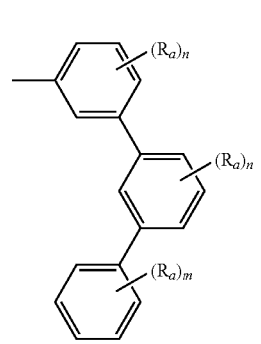 (ac24)
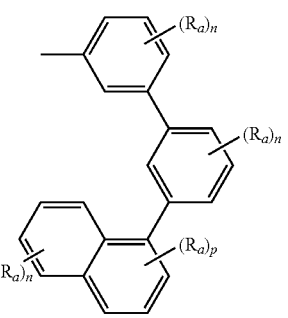 (ac25)
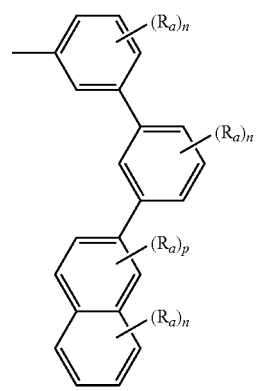 (ac26)
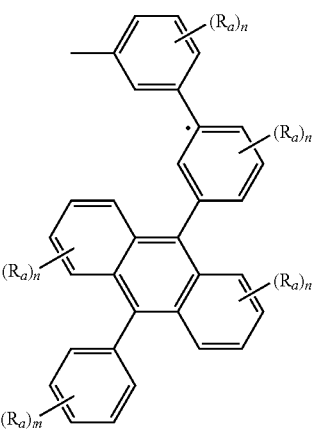 (ac27)
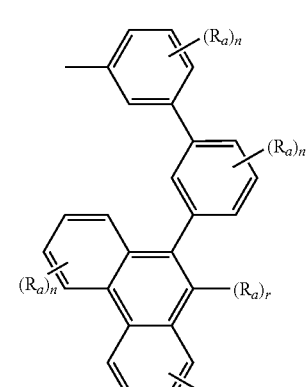 (ac28)
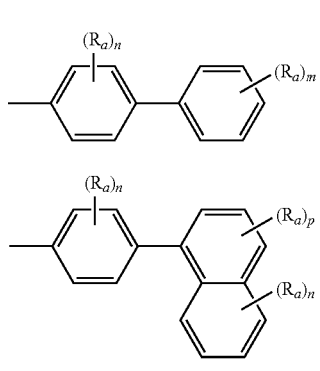 (ac29)
(ac30)
(ac31)
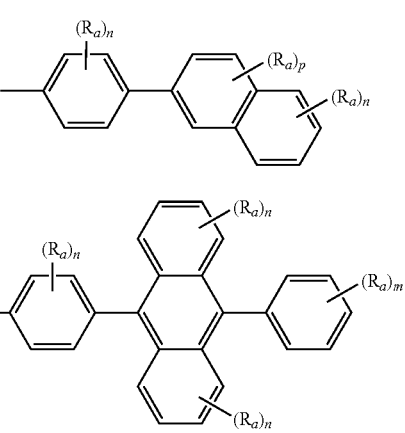 (ac32)

-continued
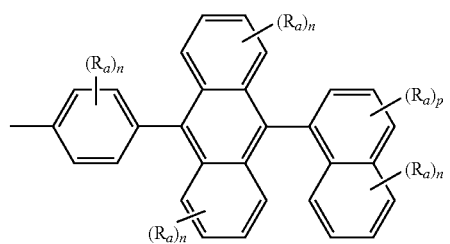
(ac33)
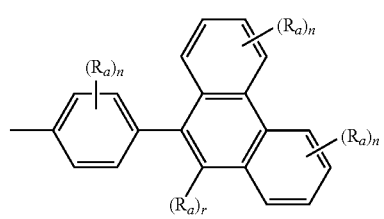
(ac34)
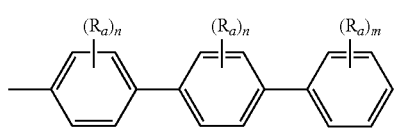
(ac35)
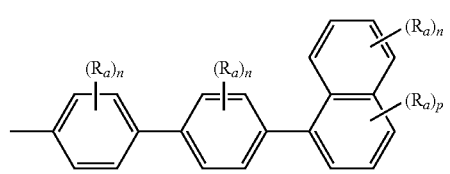
(ac36)
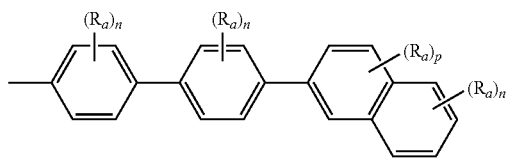
(ac37)
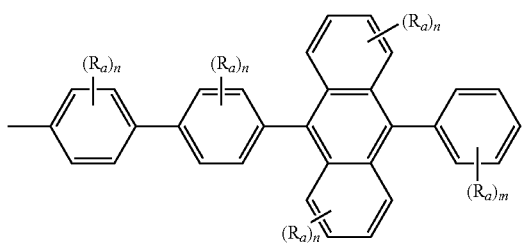
(ac38)
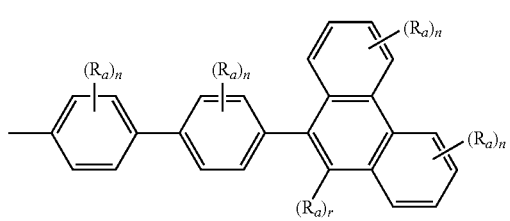
(ac39)
-continued
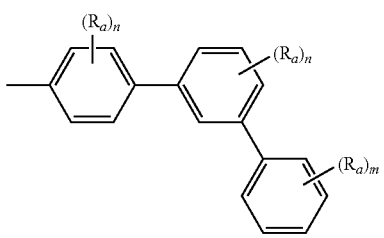
(ac40)
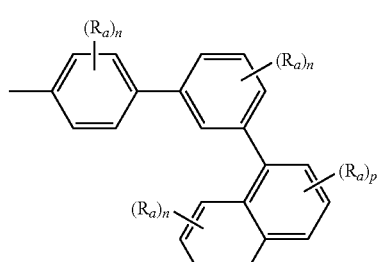
(ac41)
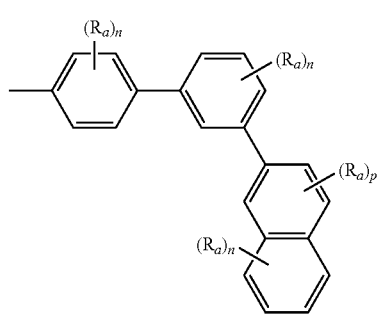
(ac42)
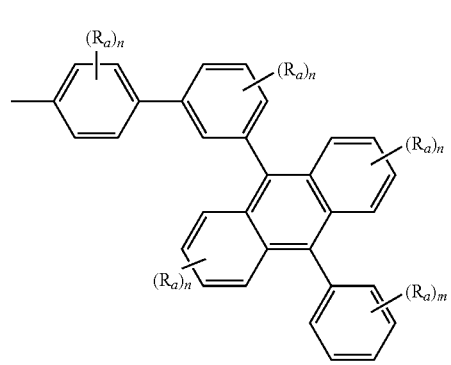
(ac43)
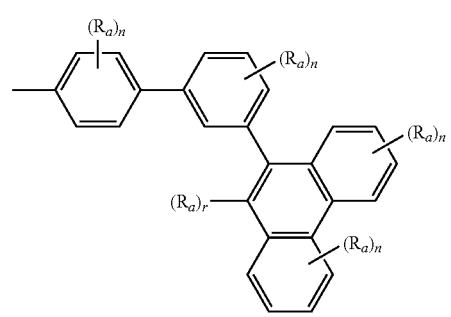
(ac44)

(ac45)
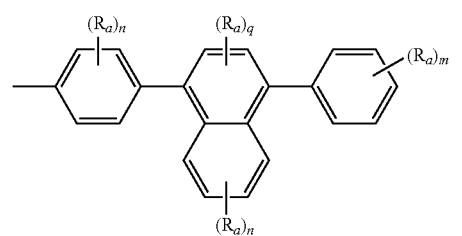
(ac46)
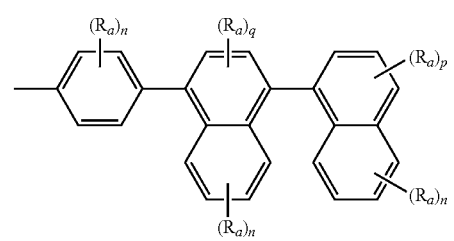
(ac47)
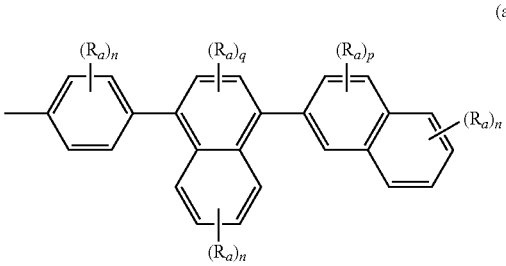
(ac48)
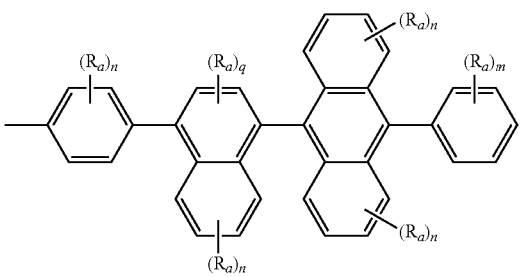
(ac49)
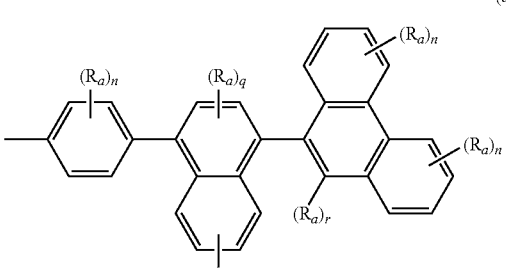
(ac50)
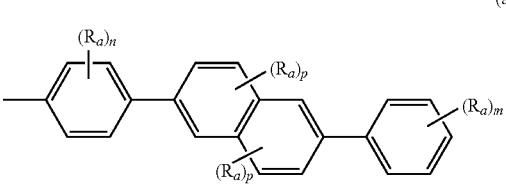
(ac51)
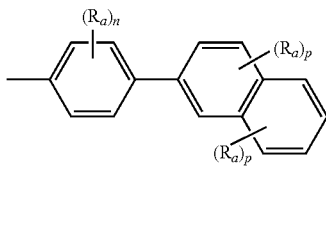
(ac52)
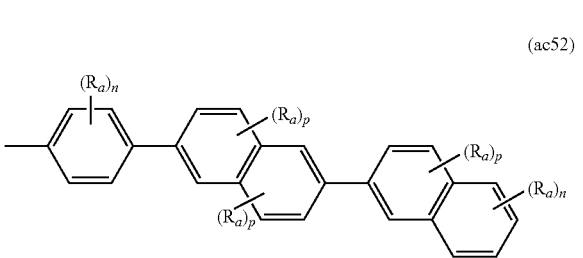
(ac53)
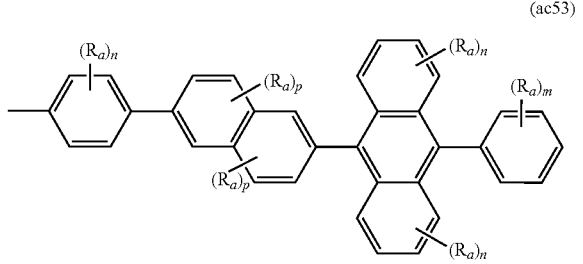
(ac54)
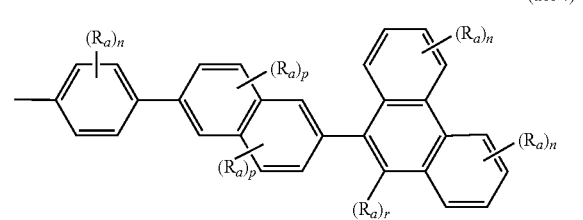
(ac55)
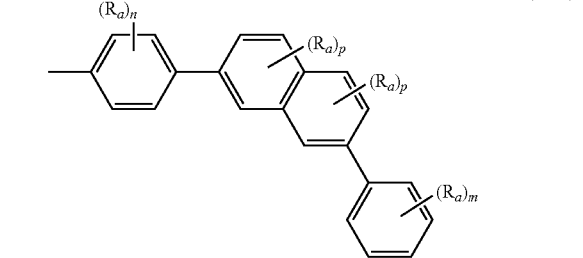
(ac56)
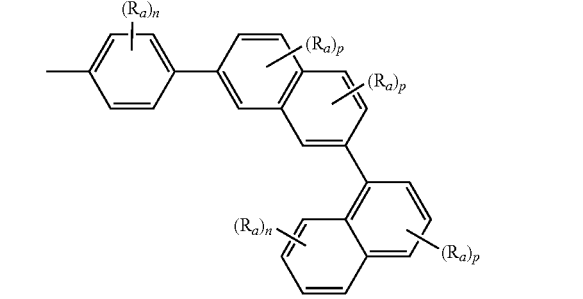

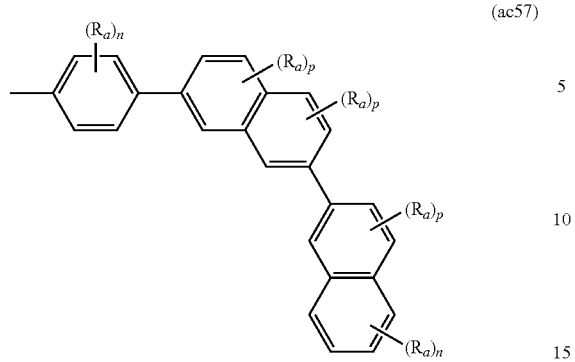
(ac57)
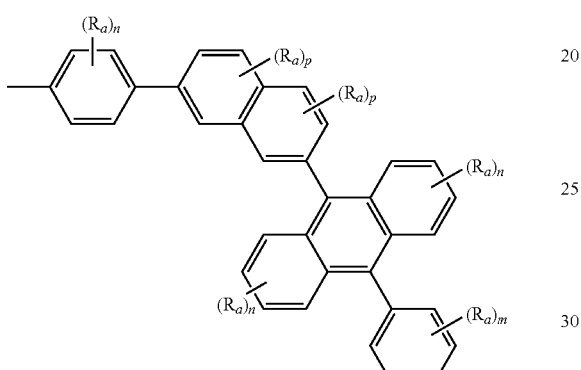
(ac58)
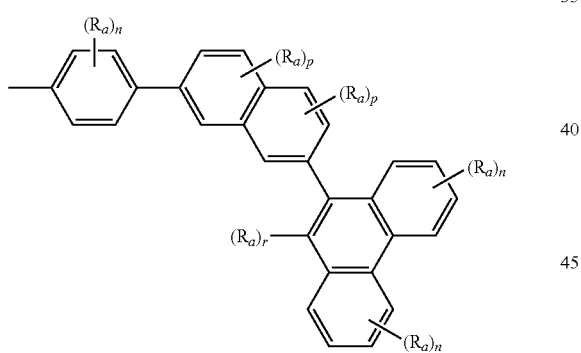
(ac59)
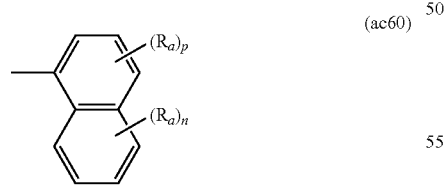
(ac60)
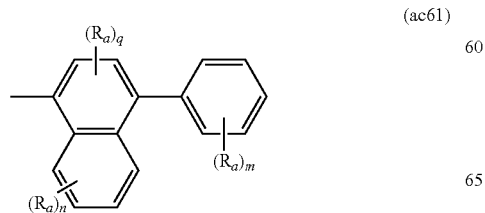
(ac61)
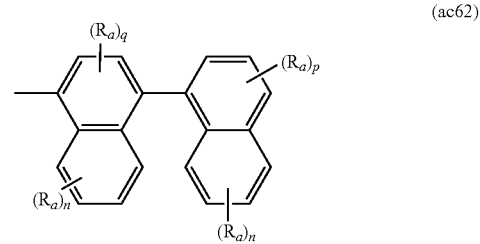
(ac62)
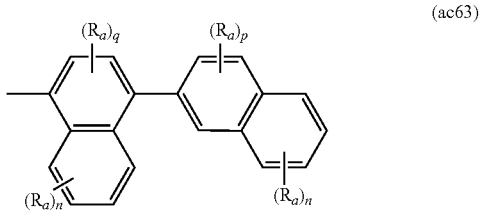
(ac63)
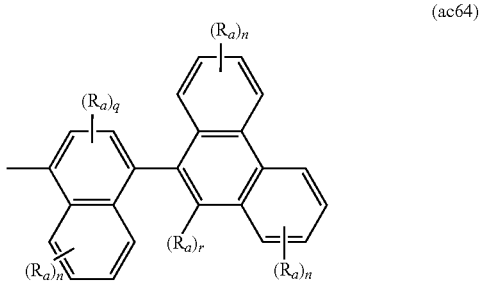
(ac64)
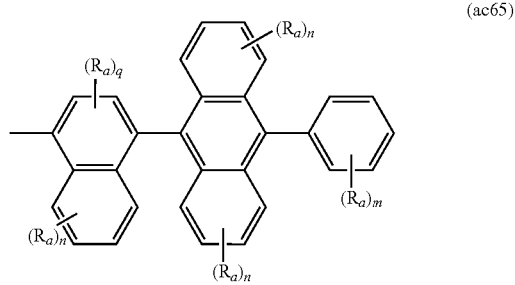
(ac65)
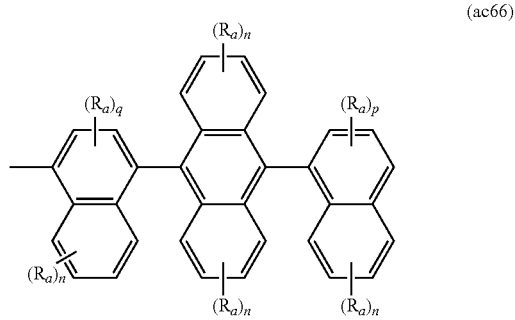
(ac66)
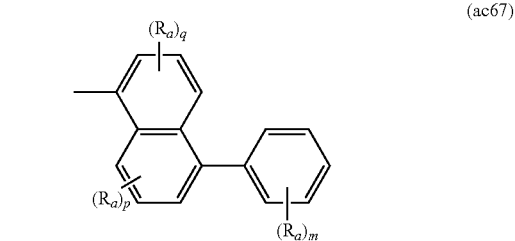
(ac67)

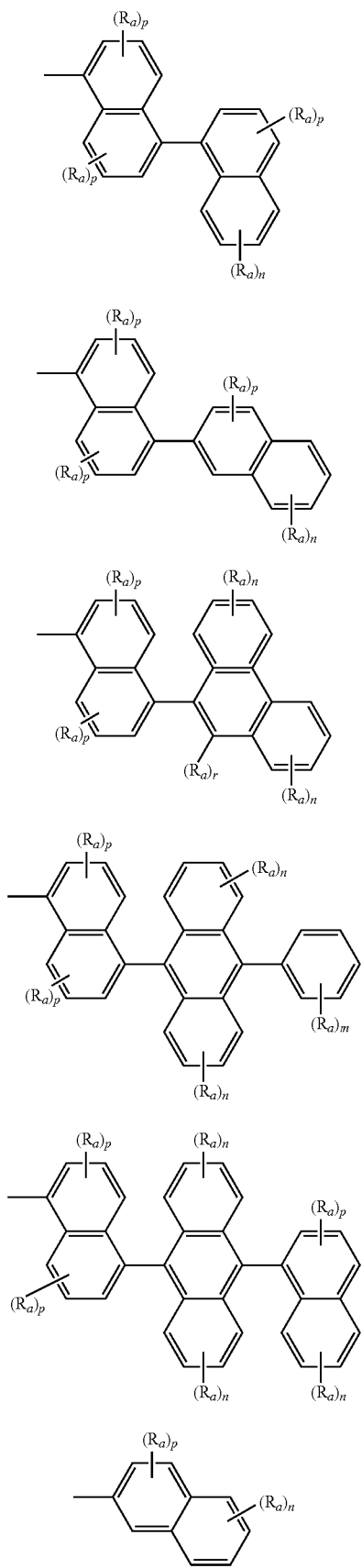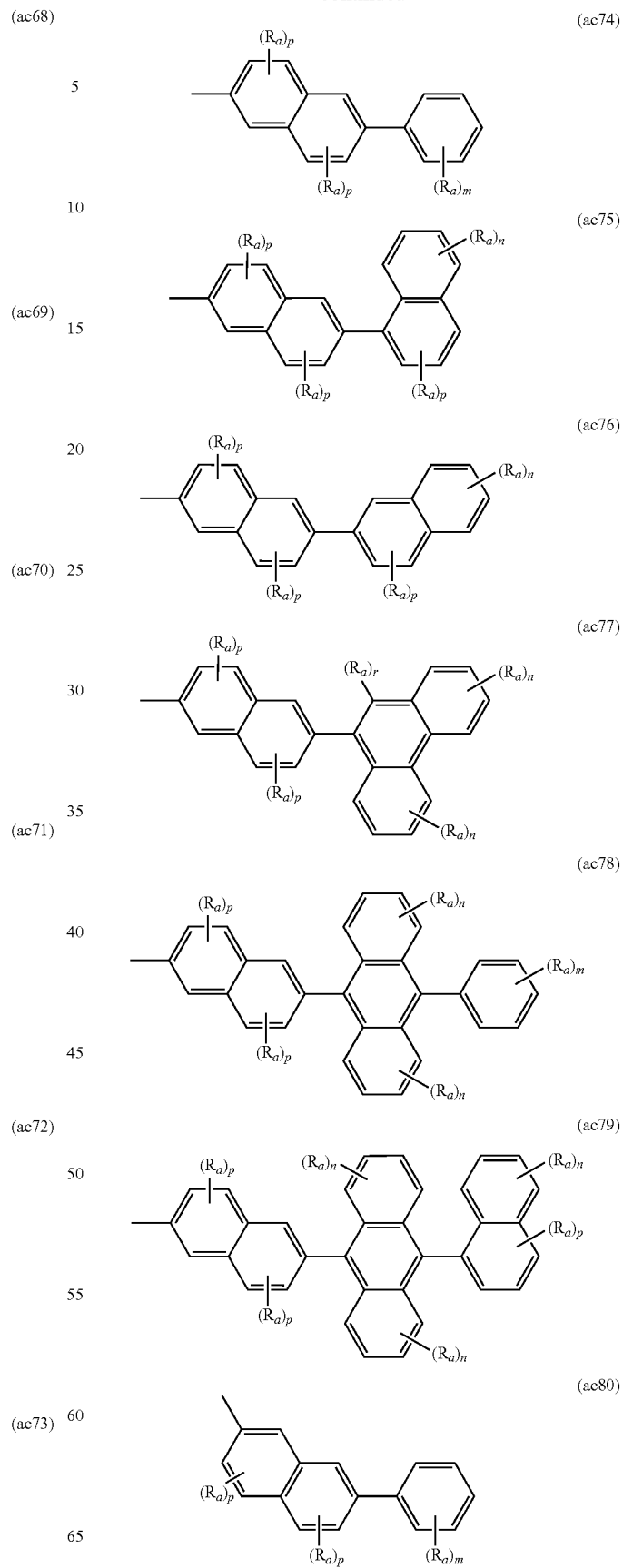

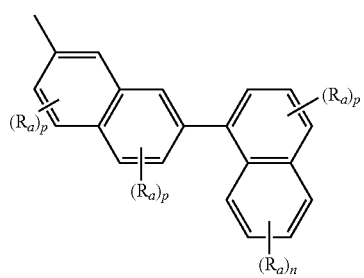
(ac81)
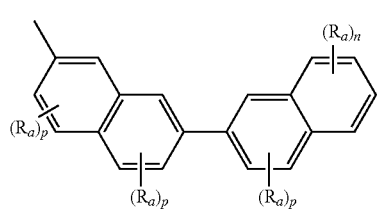
(ac82)
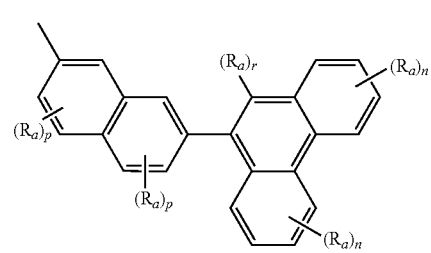
(ac83)
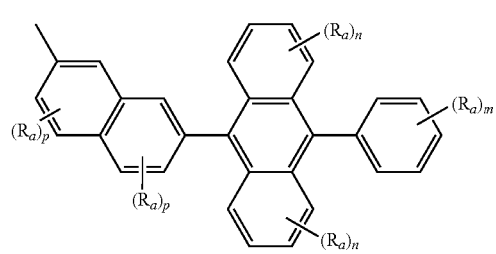
(ac84)
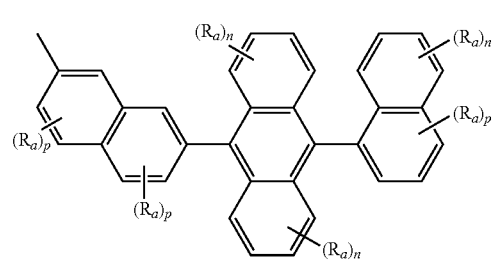
(ac85)
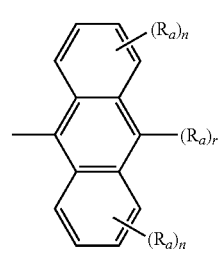
(ac86)
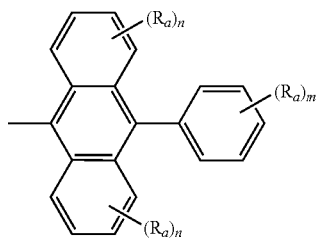
(ac87)
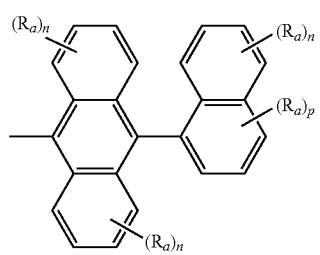
(ac88)
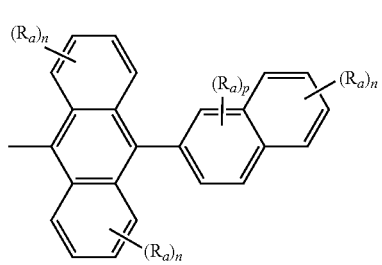
(ac89)
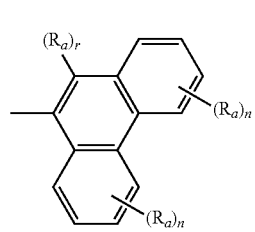
(ac90)
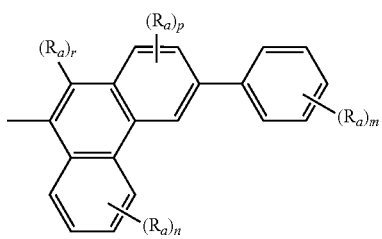
(ac91)
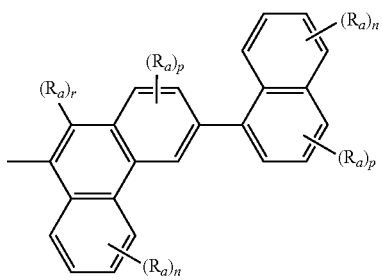
(ac92)

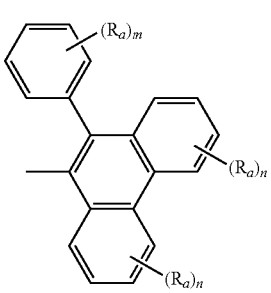

(ac93)

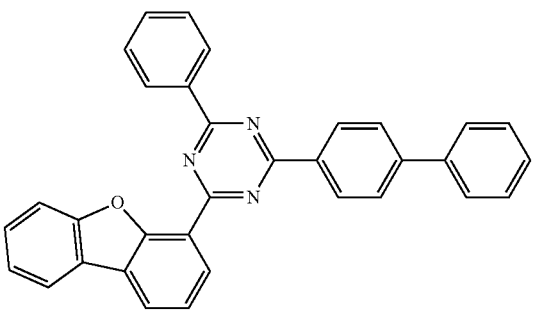

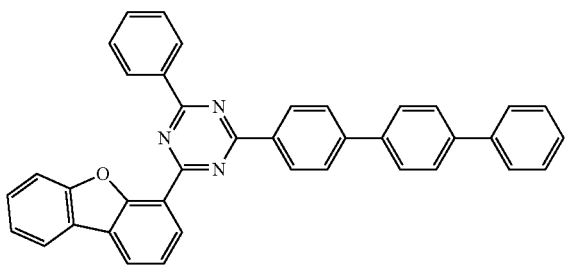

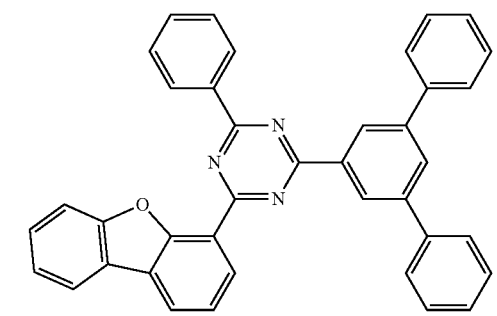

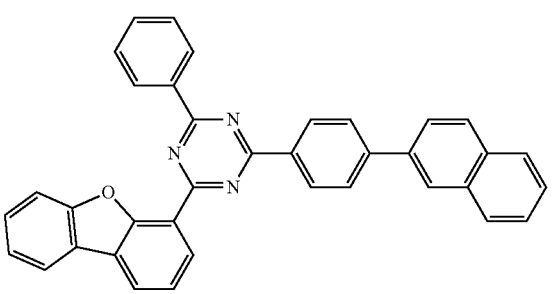

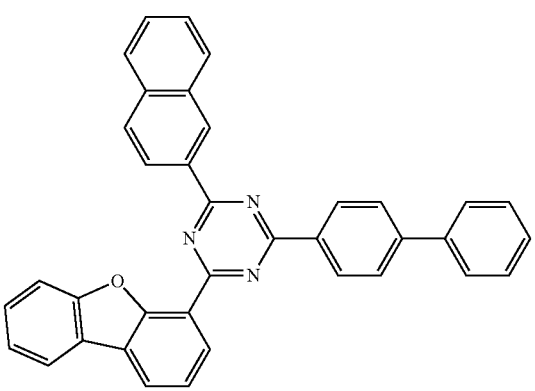

In the formulas (ac1) to (ac93),
$R_a$ is
a substituted or unsubstituted phenyl group,
a substituted or unsubstituted naphthyl group,
a substituted or unsubstituted phenanthryl group,
a substituted or unsubstituted an anthryl group,
a substituted or unsubstituted alkyl group including 1 to 50 carbon atoms, or
a substituted or unsubstituted cycloalkyl group including 3 to 50 ring carbon atoms;
each m is an integer of 0 to 5;
each n is an integer of 0 to 4;
each p is an integer of 0 to 3;
each q is an integer of 0 to 2;
each r is an integer of 0 or 1;
when two or more $R_a$'s are present, two or more $R_a$'s may be the same as or different to each other; and
when two or more $R_a$'s are present, one or more sets of adjacent two or more $R_a$'s form a substituted or unsubstituted, saturated or unsaturated ring by bonding with each other, or do not form a ring.

Here, when r is 1, $(R_a)_r$ in the formula (ac86) denotes $R_a$, and when r is 0, it denotes a hydrogen atom.

In the formulas (a1) to (a11), (aa1) to (aa8), (ab1) to (ab7), and (ac1) to (ac93), $R_a$ is a substituent substituted on $Ar_1$ to $Ar_4$ in the formula (1), or an arbitrary substituent substituted on the substituent. In one embodiment, $R_a$ is preferably an unsubstituted alkyl group including 1 to 50 carbon atoms, or an unsubstituted cycloalkyl group including 3 to 50 ring carbon atoms.

In one embodiment, the one or more sets of adjacent two or more $R_a$'s do not form a ring by bonding with each other.

In one embodiment, m, n, p, q and r are 0. This case means that $Ar_1$ to $Ar_4$ in the formula (1) has no substituent.

In one embodiment, $Ar_2$ and $Ar_4$ are independently
an unsubstituted phenyl group,
an unsubstituted naphthyl group,
an unsubstituted anthryl group, or
an unsubstituted phenanthryl group.

In one embodiment, $Ar_1$ and $Ar_4$ are independently
a single bond,
an unsubstituted p-phenylene group, or
an unsubstituted 1,4-naphthylene group.

Details of each substituent, and each substituent in the case of "a substituted or unsubstituted" in the formulas (1), (2), (3A), (3B), (4), (5), (a1) to (a11), (aa1) to (aa8), and (ab1) to (ab7) are as defined in the [Definition] part of this specification.

In one embodiment, the following compounds are excluded from the compound represented by the formula (1).

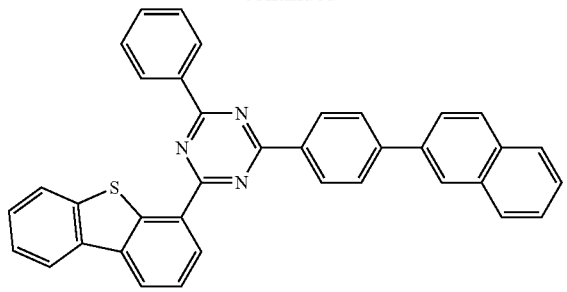

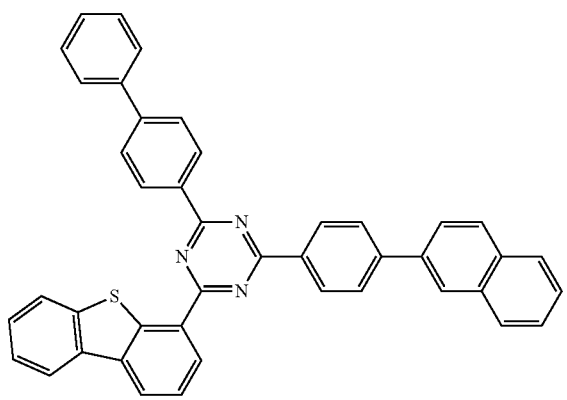

In one embodiment, the compound represented by the formula (1) is the compound represented by the following formula (6).

(6)

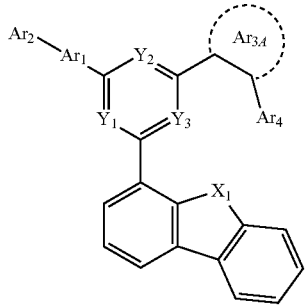

In the formula (6), $X_1$, $Y_1$ to $Y_3$, $Ar_1$, $Ar_2$ and $Ar_4$ are as defined in the formula (1);

$Ar_{3A}$, is a phenylene group, a naphthylene group, a phenanthrylene group, or an anthrylene group, that is constituted with at least inclusion of the benzene ring substituted by $Ar_4$ at an ortho-position thereof, and that may be substituted by one or more substituents in addition to $Ar_4$.

In one embodiment, the compound represented by the formula (1) is the compound represented by the following formula (6-1).

(6-1)

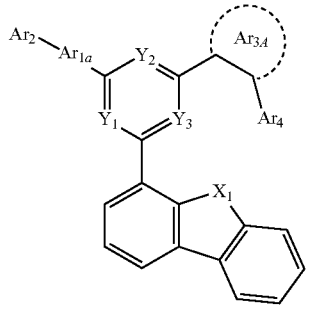

In the formula (6-1), $X_1$, $Y_1$ to $Y_3$, $Ar_2$ and $Ar_4$ are as defined in the formula (1);

$Ar_{3A}$ is as defined in the formula (6);

$Ar_{1a}$ is a divalent group selected from the following group:

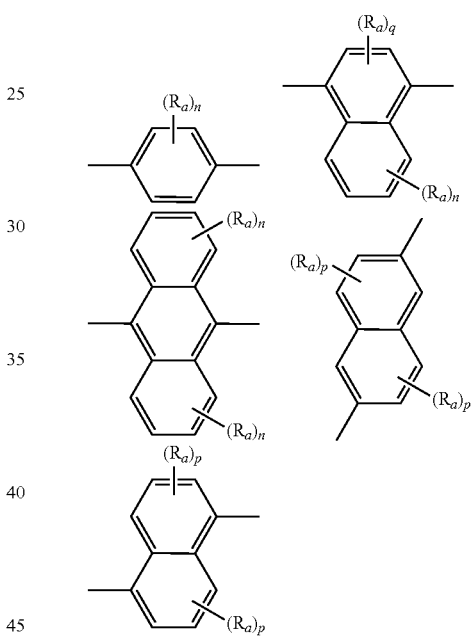

wherein in the formulas, $R_a$ is
a substituted or unsubstituted phenyl group,
a substituted or unsubstituted naphthyl group,
a substituted or unsubstituted phenanthryl group,
a substituted or unsubstituted anthryl group,
a substituted or unsubstituted alkyl group including 1 to 50 carbon atoms, or
a substituted or unsubstituted cycloalkyl group including 3 to 50 ring carbon atoms;
each n is an integer of 0 to 4;
each p is an integer of 0 to 3;
q is an integer of 0 to 2;
when two or more $R_a$'s are present, two or more $R_a$'s may be the same as or different to each other; and
when two or more $R_a$'s are present, one or more sets of adjacent two or more $R_a$'s form a substituted or unsubstituted, saturated or unsaturated ring by bonding with each other, or do not form a ring.

In one embodiment, the compound represented by the formula (1) is a compound represented by the following formula (6-2).

(6-2)

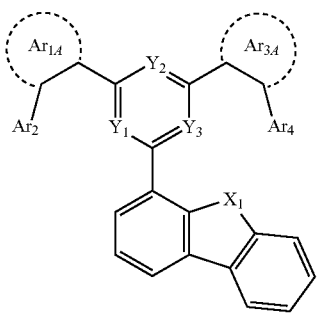

In the formula (6-2), $X_1$, $Y_1$ to $Y_3$, $Ar_2$ and $Ar_4$ are as defined in the formula (1); $Ar_{3A}$ is as defined in the formula (6); and $Ar_{1A}$ is a phenylene group, a naphthylene group, a phenanthrylene group, or an anthrylene group, that is constituted with at least inclusion of the benzene ring substituted by $Ar_2$ at an ortho-position thereof, and that may be substituted by one or more substituents in addition to $Ar_2$.

In one embodiment, the compound represented by the formula (1) is the compound represented by the following formula (7).

(7)

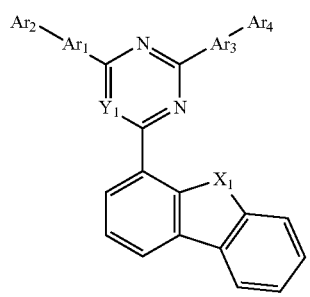

In the formula (7), $X_1$, $Y_1$ and $Ar_1$ to $Ar_4$ are as defined in the formula (1);

provided that at least one of $Ar_1$ to $Ar_4$ is a monovalent or divalent group including a substituted or unsubstituted naphthalene ring or a substituted or unsubstituted phenanthrene ring.

In one embodiment, at least one of $Ar_1$ to $Ar_4$ in the formula (7) is the following monovalent or divalent group constituted from a substituted or unsubstituted naphthalene ring.

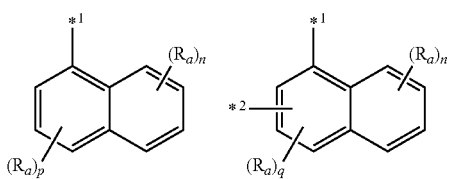

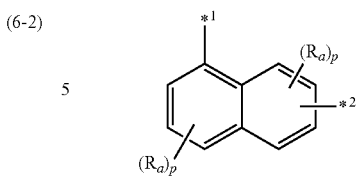

In the formulas, *1 bonds to the nitrogen-containing heterocyclic ring, or $Ar_1$ or $Ar_3$;

*2 bonds to $Ar_2$ or $Ar_4$;

$R_a$ is a substituted or unsubstituted phenyl group,
a substituted or unsubstituted naphthyl group,
a substituted or unsubstituted phenanthryl group,
a substituted or unsubstituted anthryl group,
a substituted or unsubstituted alkyl group including 1 to 50 carbon atoms, or
a substituted or unsubstituted cycloalkyl group including 3 to 50 ring carbon atoms;
    each n is an integer of 0 to 4, respectively;
    each p is an integer of 0 to 3, respectively;
    q is an integer of 0 to 2;
    when two or more $R_a$'s are present, two or more $R_a$'s may be the same as or different to each other; and
    when two or more $R_a$'s are present, one or more sets of adjacent two or more $R_a$'s do not form a substituted or unsubstituted, saturated or unsaturated ring by bonding with each other.

In one embodiment, the compound represented by the formula (1) is a compound represented by the following formula (7-1).

(7-1)

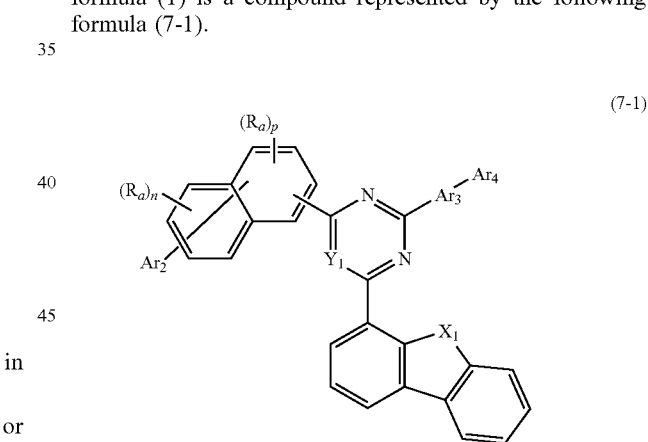

In the formula (7-1), $X_1$, $Y_1$, $Ar_2$, $Ar_3$ and $Ar_4$ are as defined in the formula (1);

$R_a$ is a substituted or unsubstituted phenyl group,
a substituted or unsubstituted naphthyl group,
a substituted or unsubstituted phenanthryl group,
a substituted or unsubstituted anthryl group,
a substituted or unsubstituted alkyl group including 1 to 50 carbon atoms, or
a substituted or unsubstituted cycloalkyl group including 3 to 50 ring carbon atoms;
    n is an integer of 0 to 4;
    p is an integer of 0 to 3;
    provided that n plus p is 6 or less;
    when two or more $R_a$'s are present, two or more $R_a$'s may be the same as or different to each other; and when two or more $R_a$'s are present, one or more sets of adjacent two or more $R_a$'s do not form a substituted or unsubstituted, saturated or unsaturated ring by bonding with each other.

In one embodiment, the compound represented by the formula (1) is a compound represented by the following formula (7-2).

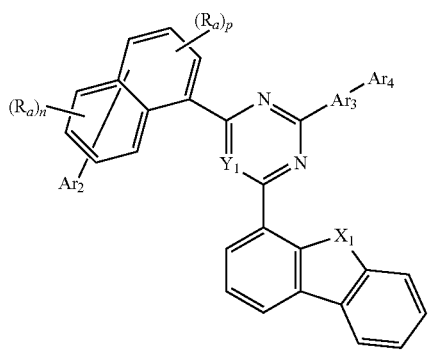

(7-2)

In the formula (7-2), $X_1$, $Y_1$~$Y_3$, $Ar_2$, $Ar_3$ and $Ar_4$ are as defined in the formula (1);

$R_a$ is
a substituted or unsubstituted phenyl group,
a substituted or unsubstituted naphthyl group,
a substituted or unsubstituted phenanthryl group,
a substituted or unsubstituted anthryl group,
a substituted or unsubstituted alkyl group including 1 to 50 carbon atoms, or
a substituted or unsubstituted cycloalkyl group including 3 to 50 ring carbon atoms;
  n is an integer of 0 to 4;
  p is an integer of 0 to 3;
  provided that n plus p is 6 or less;
  when two or more $R_a$'s are present, two or more $R_a$'s may be the same as or different to each other; and
  when two or more $R_a$'s are present, one or more sets of adjacent two or more $R_a$'s do not form a substituted or unsubstituted, saturated or unsaturated ring by bonding with each other.

In one embodiment, the compound represented by the formula (7) is a compound represented by the following formula (7-3).

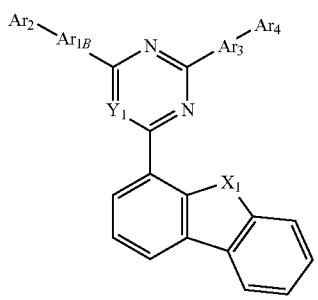

(7-3)

In the formula (7-3), $X_1$, $Y_1$, and $Ar_2$ to $Ar_4$ are as defined in the formula (1); and
$Ar_{1B}$ is a divalent group selected from the following groups;

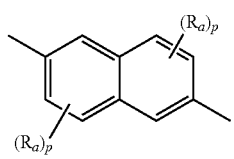

wherein in the formulas, $R_a$ is
a substituted or unsubstituted phenyl group,
a substituted or unsubstituted naphthyl group,
a substituted or unsubstituted phenanthryl group,
a substituted or unsubstituted anthryl group,
a substituted or unsubstituted alkyl group including 1 to 50 carbon atoms, or
a substituted or unsubstituted cycloalkyl group including 3 to 50 ring carbon atoms;
  n is an integer of 0 to 4;
  each p is an integer of 0 to 3;
  r is an integer of 0 or 1;
  when two or more $R_a$'s are present, two or more $R_a$'s may be the same as or different to each other; and
  when two or more $R_a$'s are present, one or more sets of adjacent two or more $R_a$'s do not form a substituted or unsubstituted, saturated or unsaturated ring by bonding with each other.

In one embodiment, the compound represented by the formula (1) is a compound represented by the following formula (7-4).

(7-4)

In the formula (7-4), $X_1$, $Y_1$, $Ar_2$ and $Ar_4$ are as defined in the formula (1); and
$Ar_{1C}$ is a divalent group selected from the following groups.

-continued

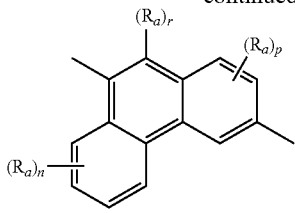

wherein in the formulas, $R_a$ is
a substituted or unsubstituted phenyl group,
a substituted or unsubstituted naphthyl group,
a substituted or unsubstituted phenanthryl group,
a substituted or unsubstituted anthryl group,
a substituted or unsubstituted alkyl group including 1 to 50 carbon atoms, or
a substituted or unsubstituted cycloalkyl group including 3 to 50 ring carbon atoms;

n is an integer of 0 to 4;
each p is an integer of 0 to 3;
r is an integer of 0 or 1;
when two or more $R_a$'s are present, two or more $R_a$'s may be the same as or different to each other; and
when two or more $R_a$'s are present, one or more sets of adjacent two or more $R_a$'s do not form a substituted or unsubstituted, saturated or unsaturated ring by bonding with each other; and $Ar_{3A}$ is a phenylene group, a naphthylene group, a phenanthrylene group, or an anthrylene group, that is constituted with at least inclusion of the benzene ring substituted by $Ar_4$ at an ortho-position thereof, and that may be substituted by one or more substituents in addition to $Ar_4$.

In one embodiment, the compound represented by the formula (1) is the compound represented by the following formula (8).

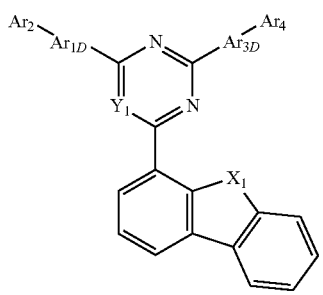

(8)

In the formula (8), $X_1$, $Y_1$, $Ar_2$ and $Ar_4$ are as defined in the formula (1); and
$Ar_{1D}$ and $Ar_{3D}$ are independently a divalent group selected from the following group consisting of:

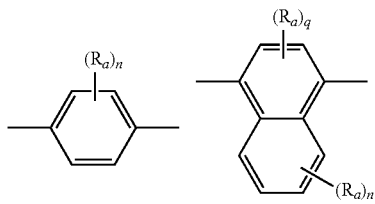

-continued

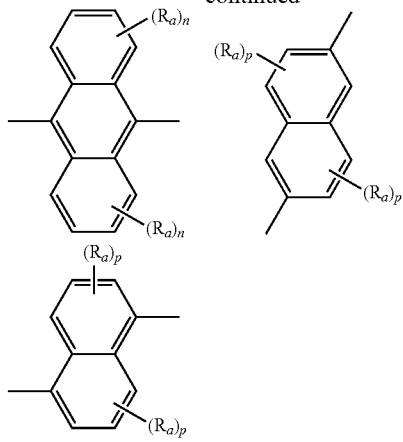

In the formula, $R_a$ is
a substituted or unsubstituted phenyl group,
a substituted or unsubstituted naphthyl group,
a substituted or unsubstituted phenanthryl group,
a substituted or unsubstituted anthryl group,
a substituted or unsubstituted alkyl group including 1 to 50 carbon atoms, or
a substituted or unsubstituted cycloalkyl group including 3 to 50 ring carbon atoms;

each n is an integer of 0 to 4;
each p is an integer of 0 to 3;
q is an integer of 0 to 2;
when two or more $R_a$'s are present, two or more $R_a$'s may be the same as or different to each other; and
when two or more $R_a$'s are present, one or more set of adjacent two or more $R_a$'s do not form a substituted or unsubstituted, saturated or unsaturated ring by bonding with each other.

In one embodiment, the compound represented by the formula (1) is the compound represented by the following formula (9).

(9)

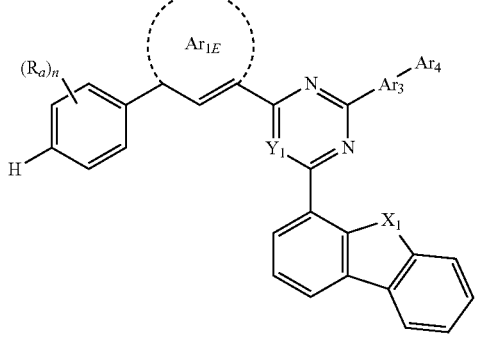

In the formula (9), $X_1$, $Y_1$, $Ar_4$ and $Ar_4$ are as defined in the formula (1);
$Ar_{1E}$ is a phenylene group, a naphthylene group, a phenanthrylene group, or an anthrylene group, that is constituted with at least inclusion of the benzene ring substituted by a phenyl group at a meta-position thereof, and that may be substituted by one or more substituents in addition to the phenyl group;

$R_a$ is a
substituted or unsubstituted phenyl group;
a substituted or unsubstituted naphthyl group;
a substituted or unsubstituted phenanthryl group,
a substituted or unsubstituted anthryl group,
a substituted or unsubstituted alkyl group including 1 to 50 carbon atoms; or
a substituted or unsubstituted cycloalkyl group including 3 to 50 ring carbon atoms;

n is an integer of 0 to 4;

when two or more $R_a$'s are present, two or more $R_a$'s may be the same as or different to each other; and when two or more $R_a$'s are present, one or more sets of adjacent two or more $R_a$'s form a substituted or unsubstituted, saturated or unsaturated ring by bonding with each other, or do not form a ring.

In one embodiment, the compound represented by the formula (9) is a compound represented by the following formula (9-1).

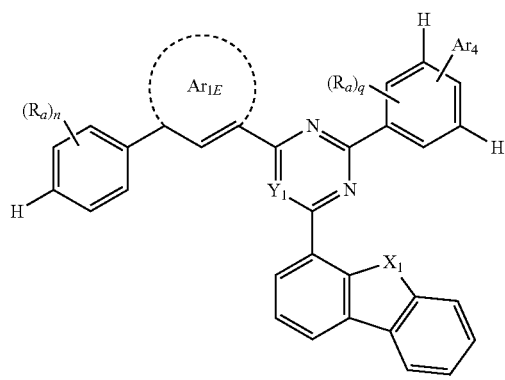

(9-1)

In the formula (9-1), $X_1$, $Y_1$ and $Ar_4$ are as defined in the formula (1);
$Ar_{1E}$, $R_a$ and n are as defined in the formula (9); and
q is an integer of 0 to 2.

In one embodiment, the compound represented by the formula (1) is a compound represented by the following formula (9-2).

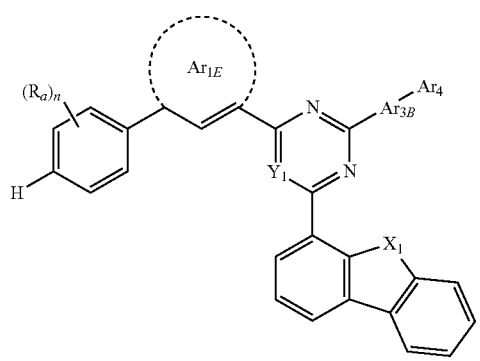

(9-2)

In the formula (9-2), $X_1$, $Y_1$, $Ar_1$ and $Ar_4$ are as defined in the formula (1);

$Ar_{1E}$, $R_a$ and n are as defined in the formula (9);
$Ar_{3B}$ is
a substituted or unsubstituted naphthylene group,
a substituted or unsubstituted phenanthrylene group, or
a substituted or unsubstituted anthrylene group.

In one embodiment, the compound represented by the formula (1) is a compound represented by the following formula (10).

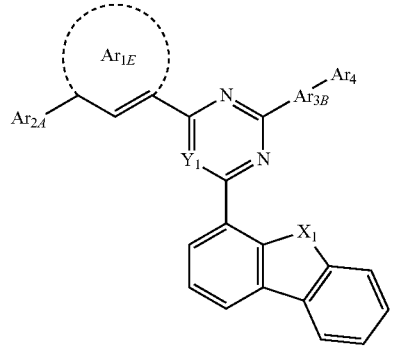

(10)

In the formula (10), $X_1$, $Y_1$ and $Ar_4$ are as defined in the formula (1);

$Ar_{1E}$ is a phenylene group, a naphthylene group, a phenanthrylene group, or an anthrylene group, that is constituted with at least inclusion of the benzene ring substituted by $Ar_{2A}$ at a meta-position thereof, and that may be substituted by one or more substituents in addition to $Ar_{2A}$;

$Ar_{2A}$, is
a substituted or unsubstituted naphthyl group,
a substituted or unsubstituted phenanthryl group, or
a substituted or unsubstituted anthryl group; and $Ar_{3B}$ is
a substituted or unsubstituted naphthylene group,
a substituted or unsubstituted phenanthrylene group, or
a substituted or unsubstituted anthrylene group.

In one embodiment, the compound represented by the formula (1) is a compound represented by the following formula (9-1).

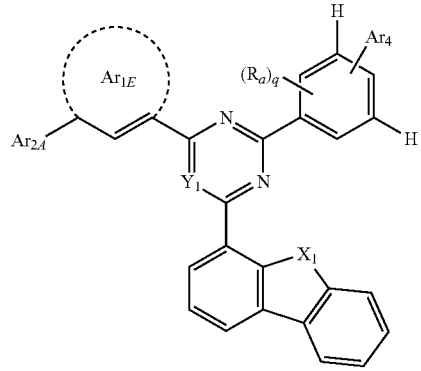

(9-1)

In the formula (9-1), $X_1$, $Y_1$ and $Ar_4$ are as defined in the formula (1);

$Ar_{1E}$ is a phenylene group, a naphthylene group, a phenanthrylene group, or an anthrylene group, that is constituted with at least inclusion of the benzene ring substituted by Ar$_{2A}$ at a meta-position thereof, and that may be substituted by one or more substituents in addition to Ar$_{2A}$;

Ar$_{2A}$ is a substituted or unsubstituted naphthyl group, a substituted or unsubstituted phenanthryl group, or a substituted or unsubstituted anthryl group;

R$_a$ is a substituted or unsubstituted phenyl group, a substituted or unsubstituted naphthyl group, a substituted or unsubstituted phenanthryl group, a substituted or unsubstituted anthryl group, a substituted or unsubstituted alkyl group including 1 to 50 carbon atoms, or a substituted or unsubstituted cycloalkyl group including 3 to 50 ring carbon atoms;

q is an integer of 0 to 2; and when two or more R$_a$'s are pre-sent, the two or more R$_a$'s may be the same as or different to each other.

Specific examples of the compound represented by the formula (1) will be described below, but these are merely examples, and the compound represented by the formula (1) is not limited to the following specific examples.

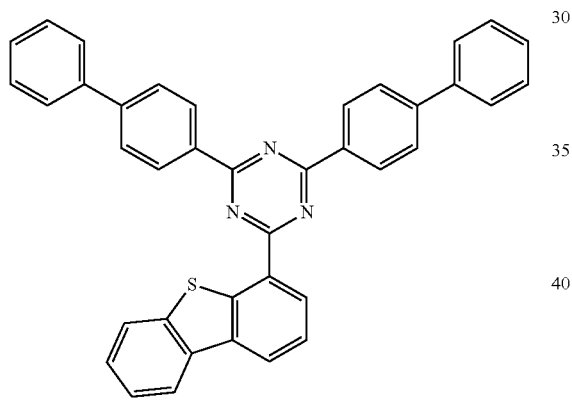

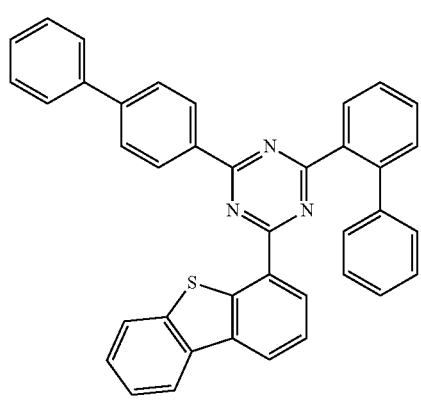

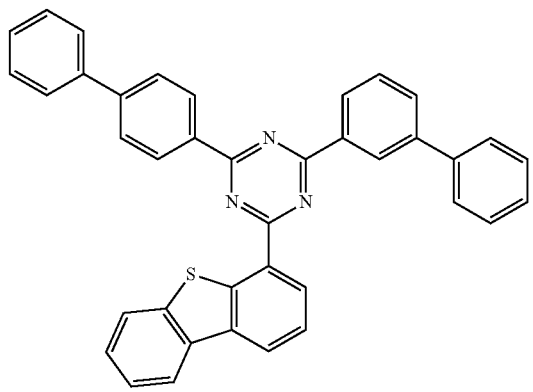

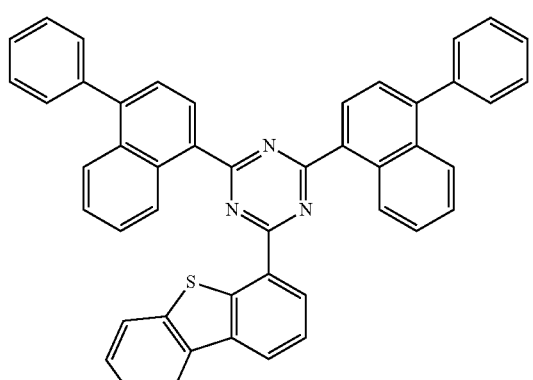

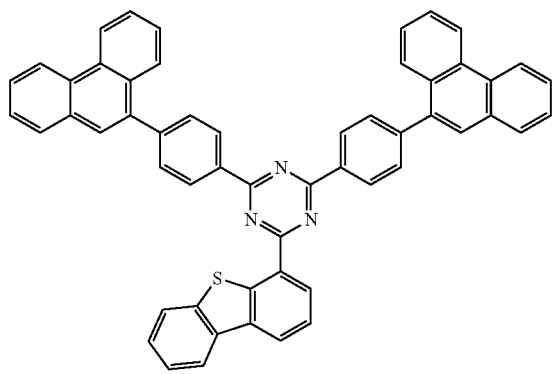

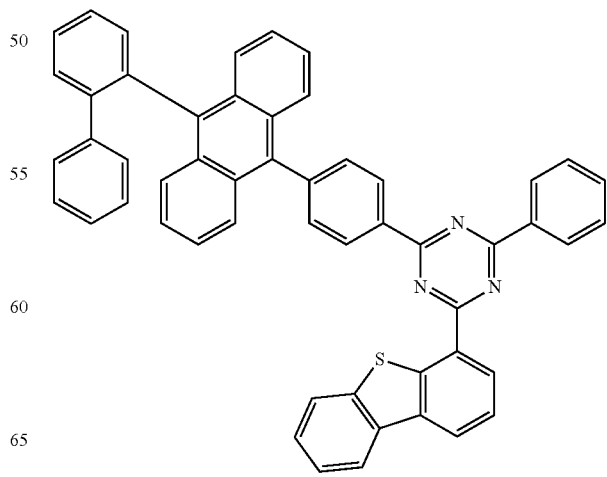

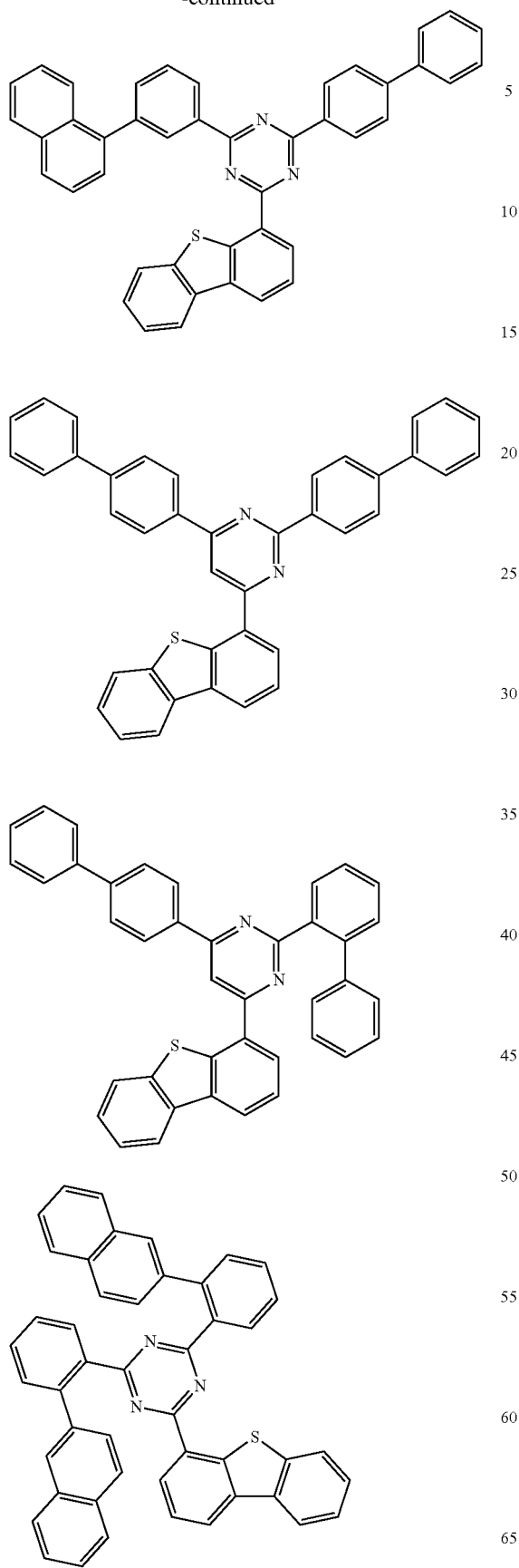
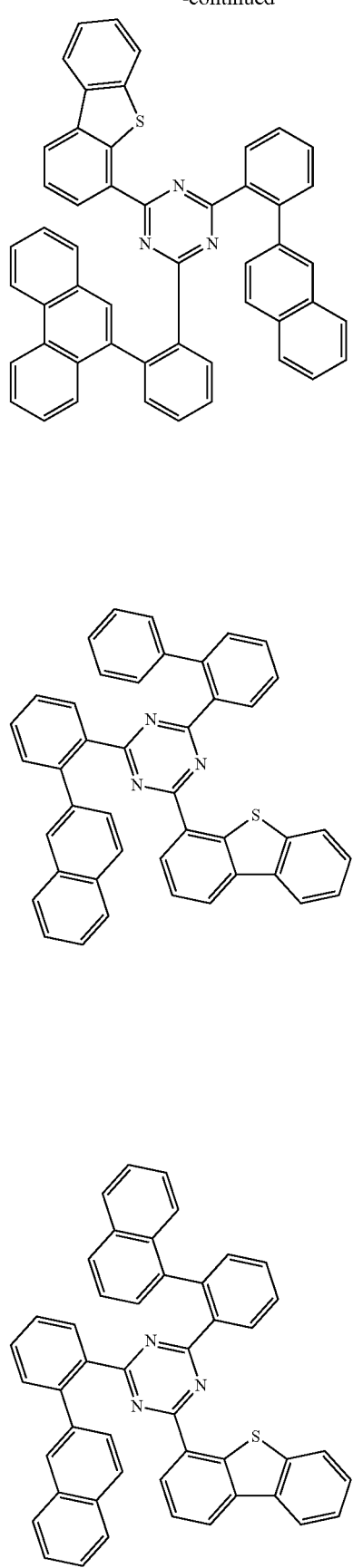

65
-continued
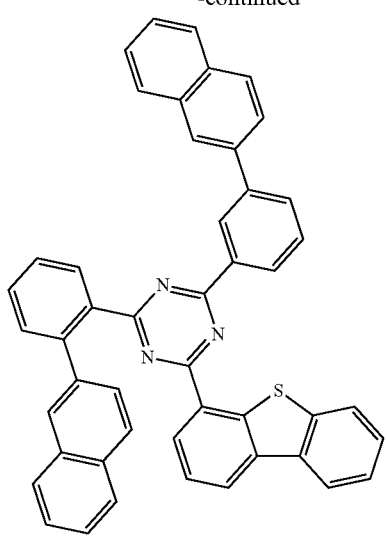
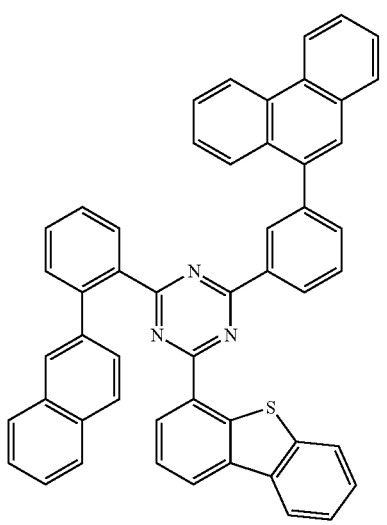
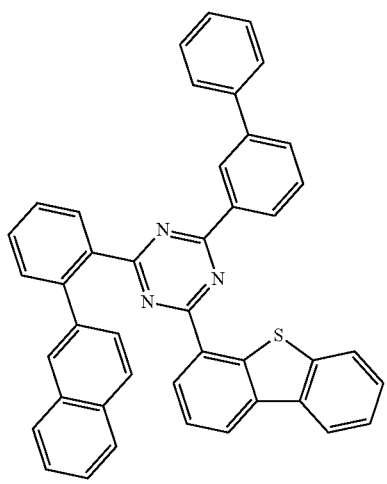
66
-continued
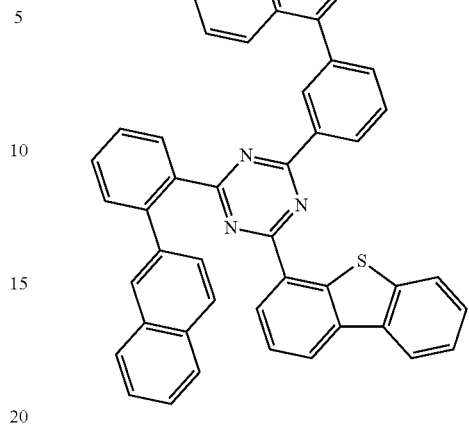
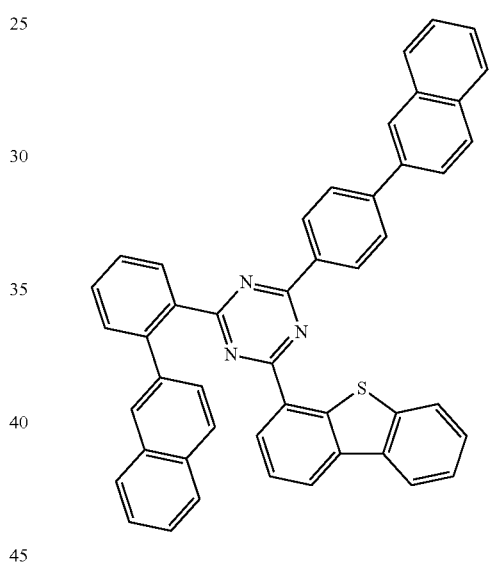
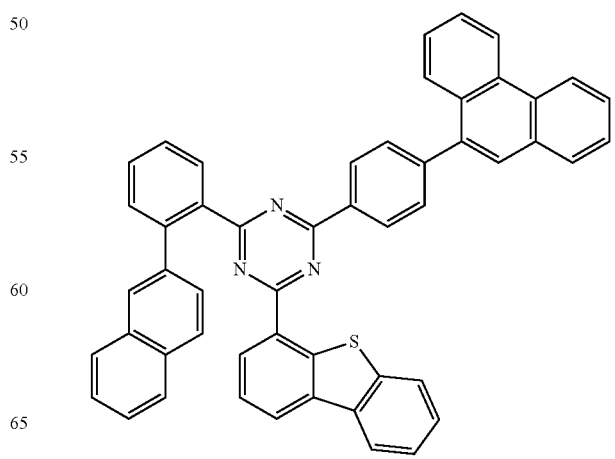

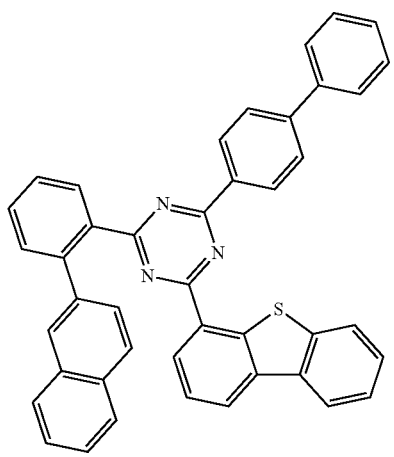
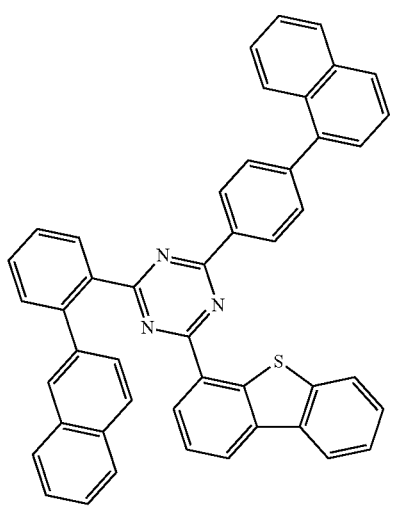
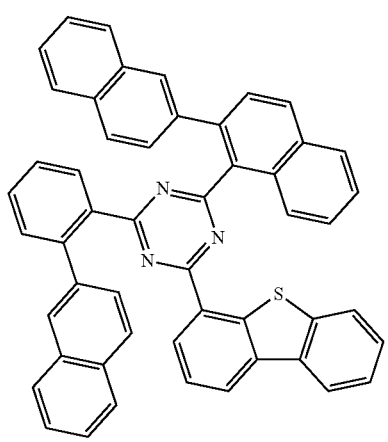
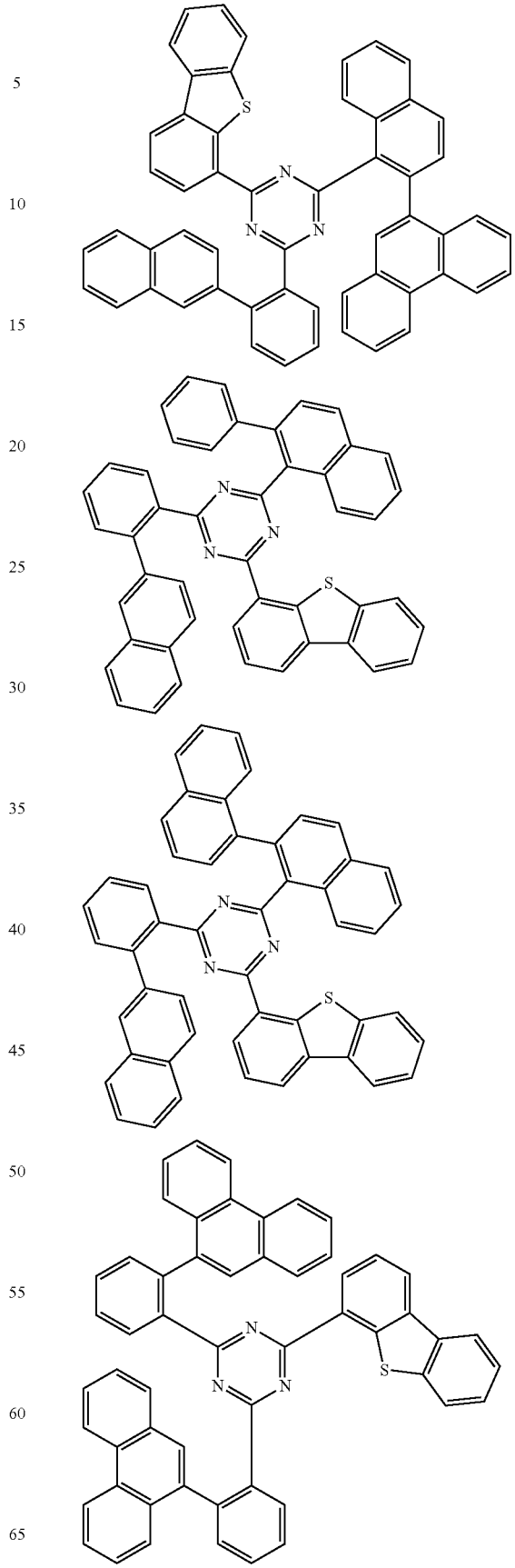

69
-continued
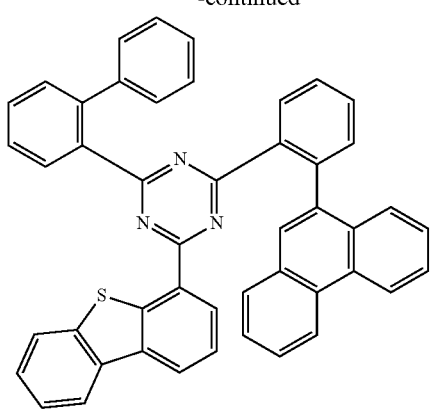
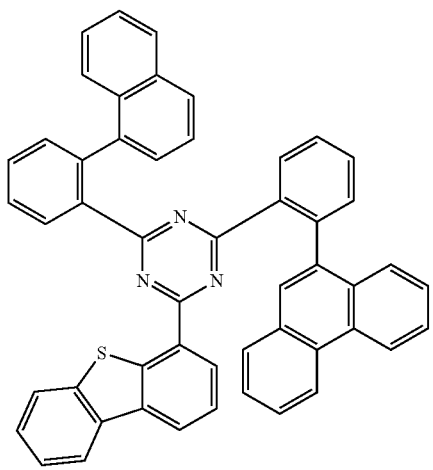
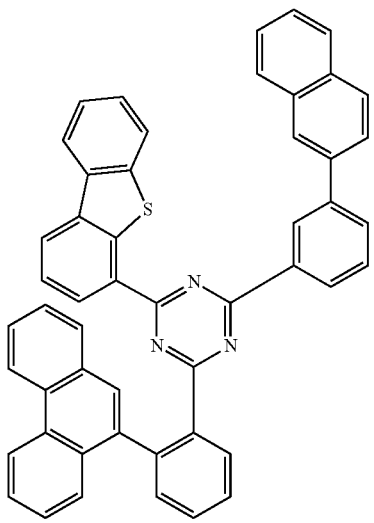
70
-continued
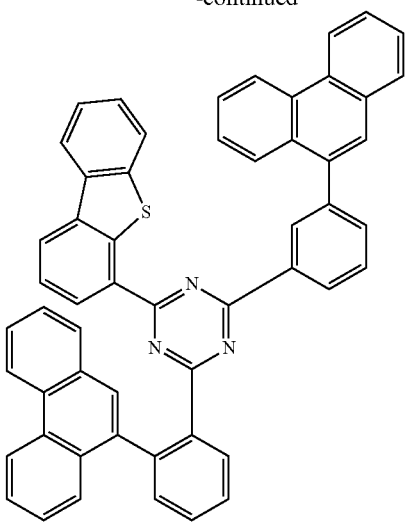
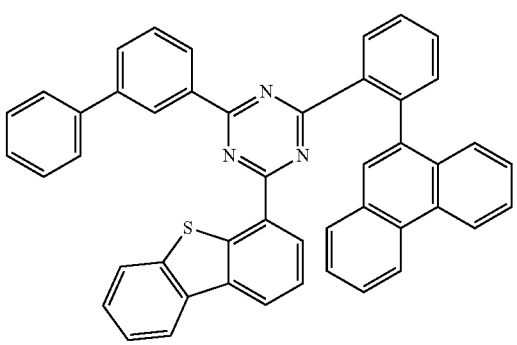
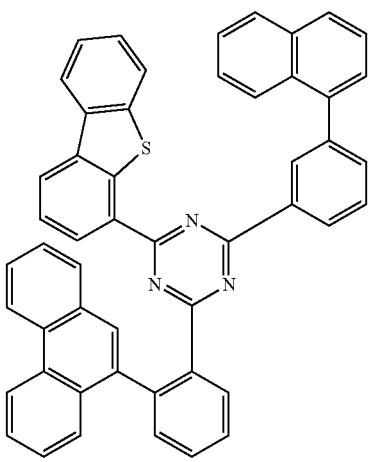

71
-continued
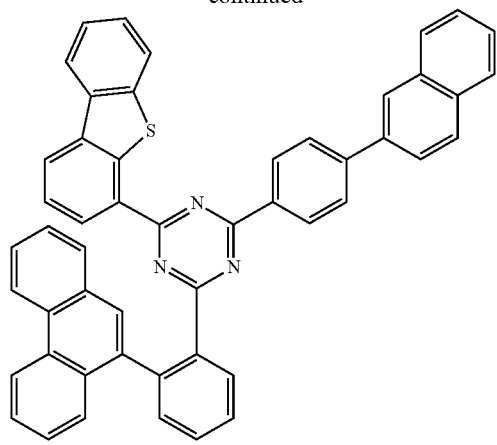
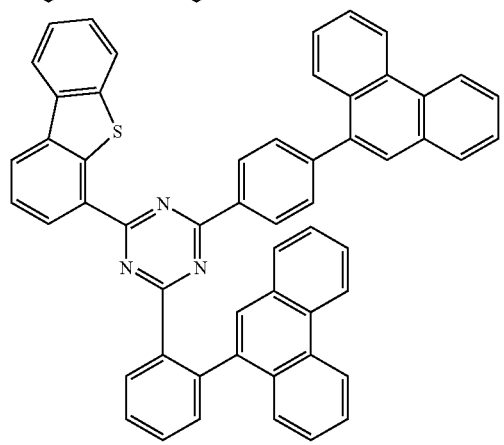
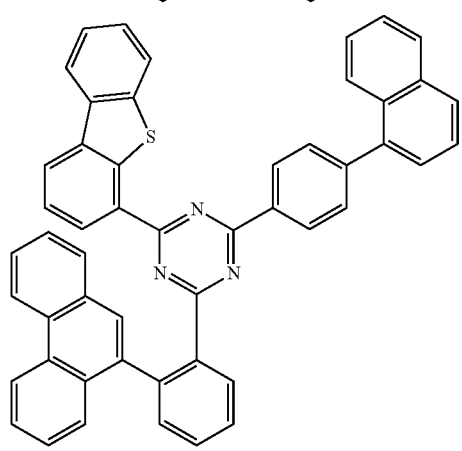
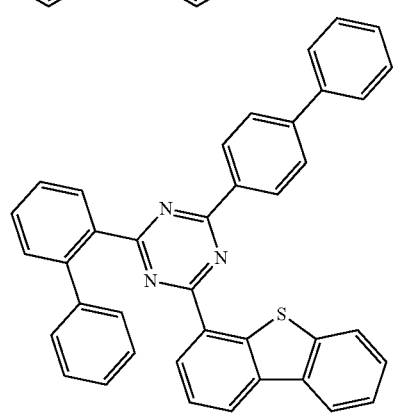
72
-continued
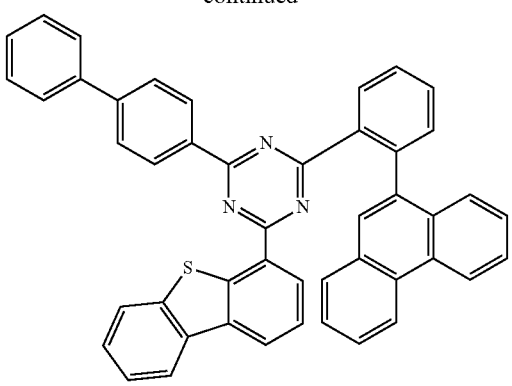
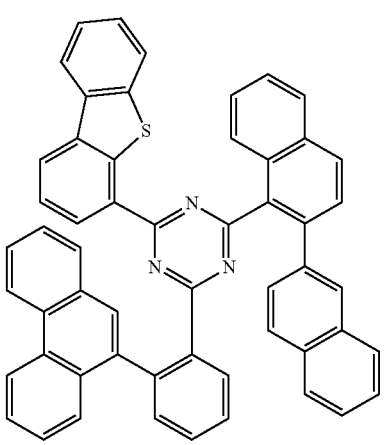
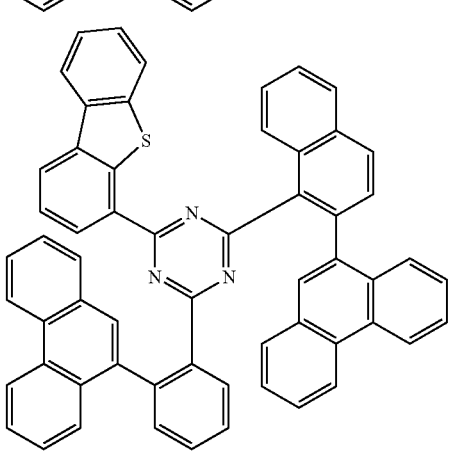
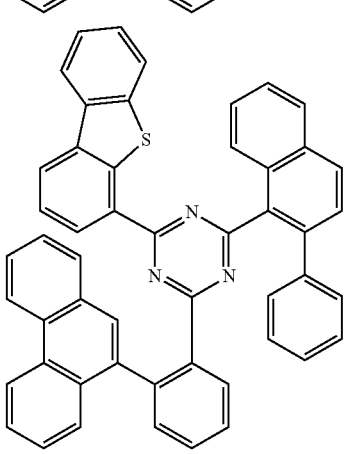

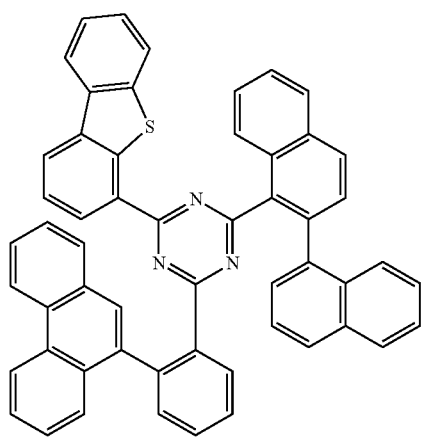
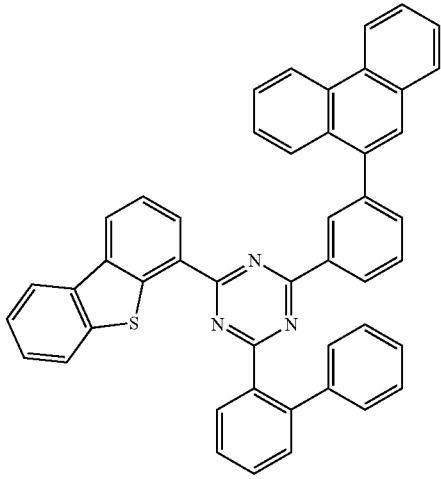
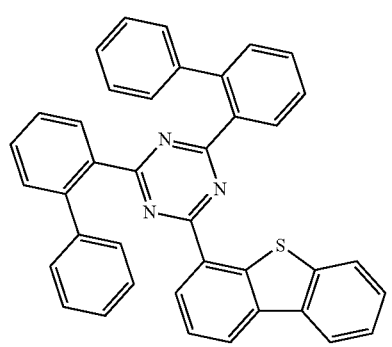
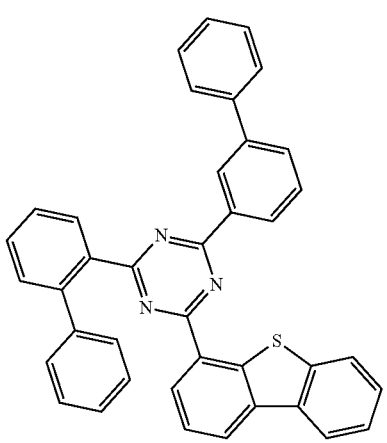
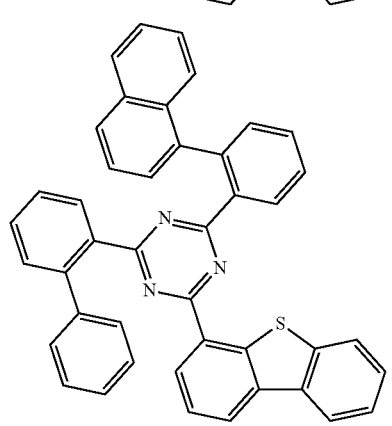
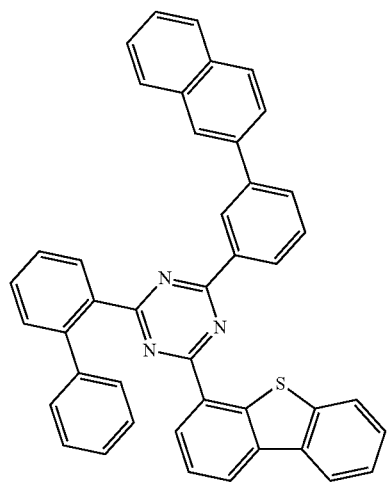
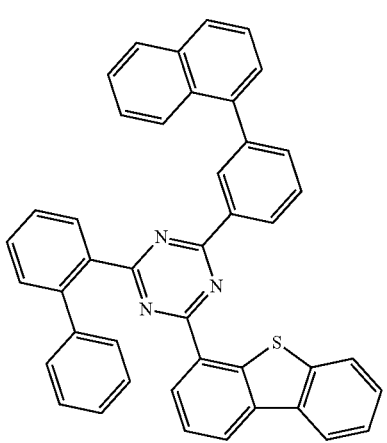

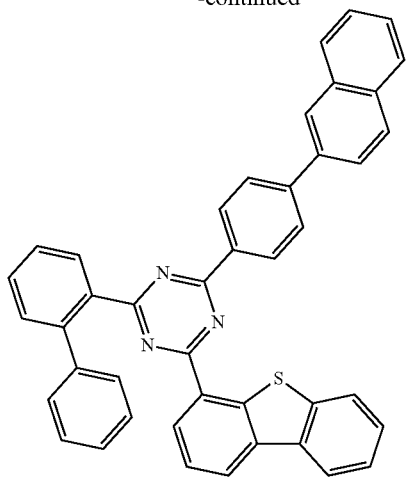
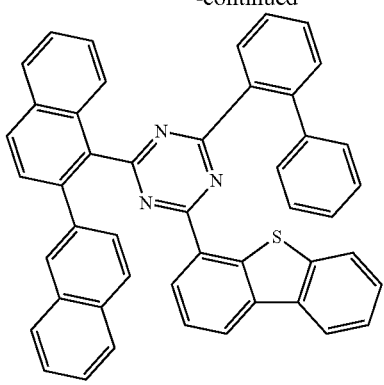
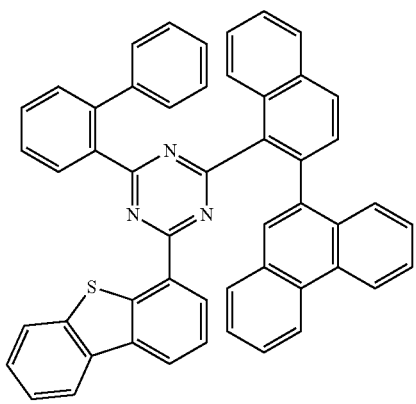
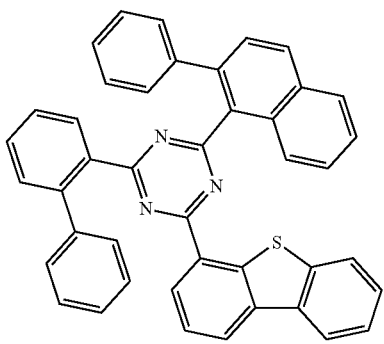
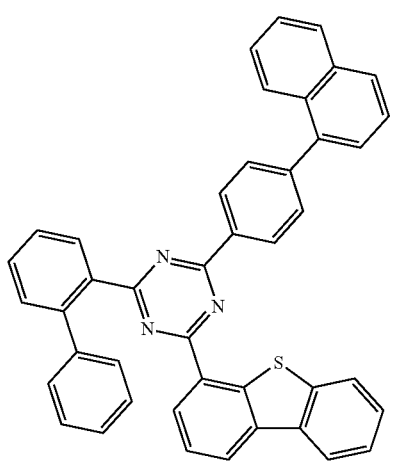
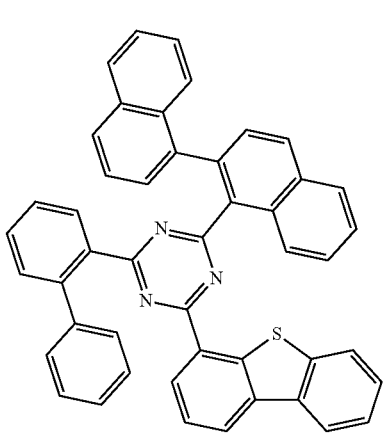

-continued
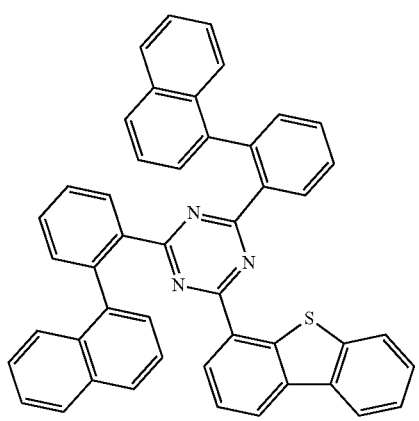
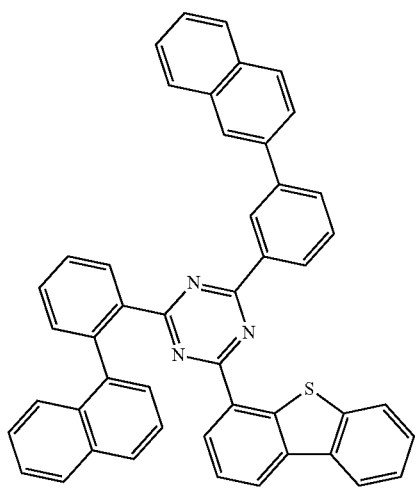
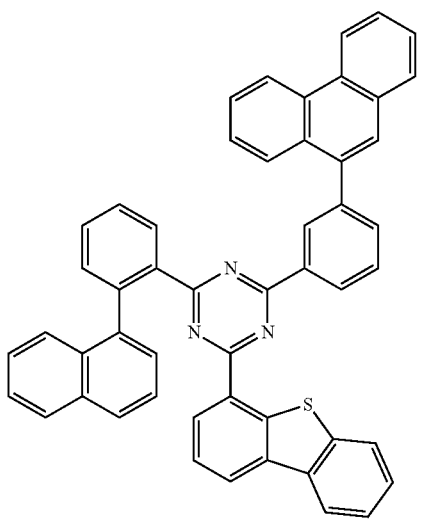
-continued
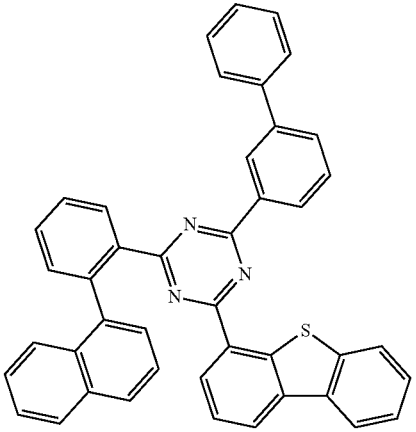
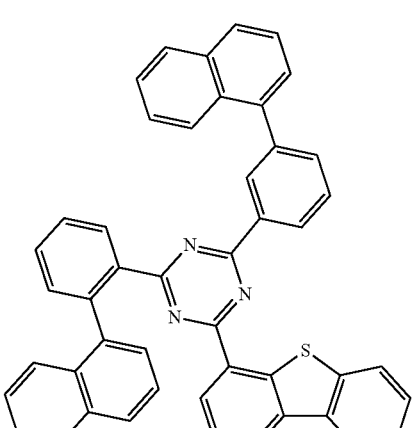
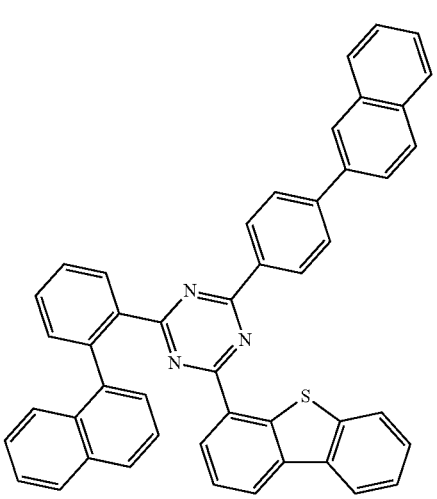

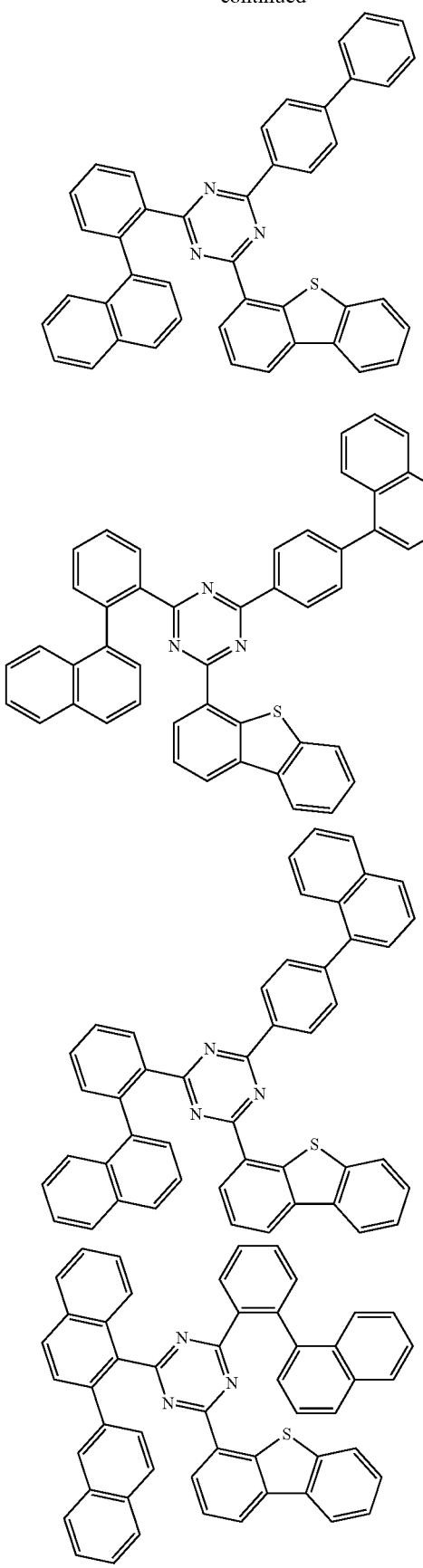
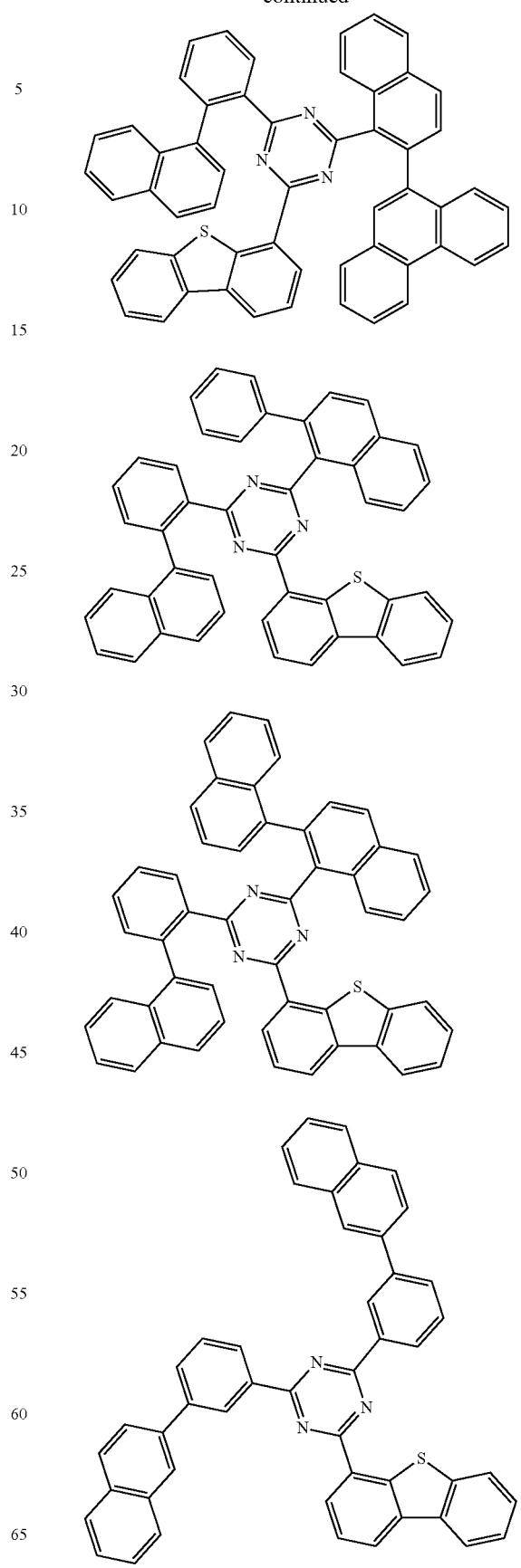

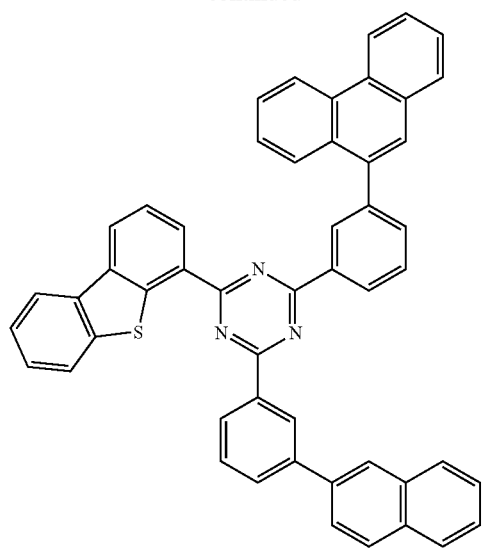
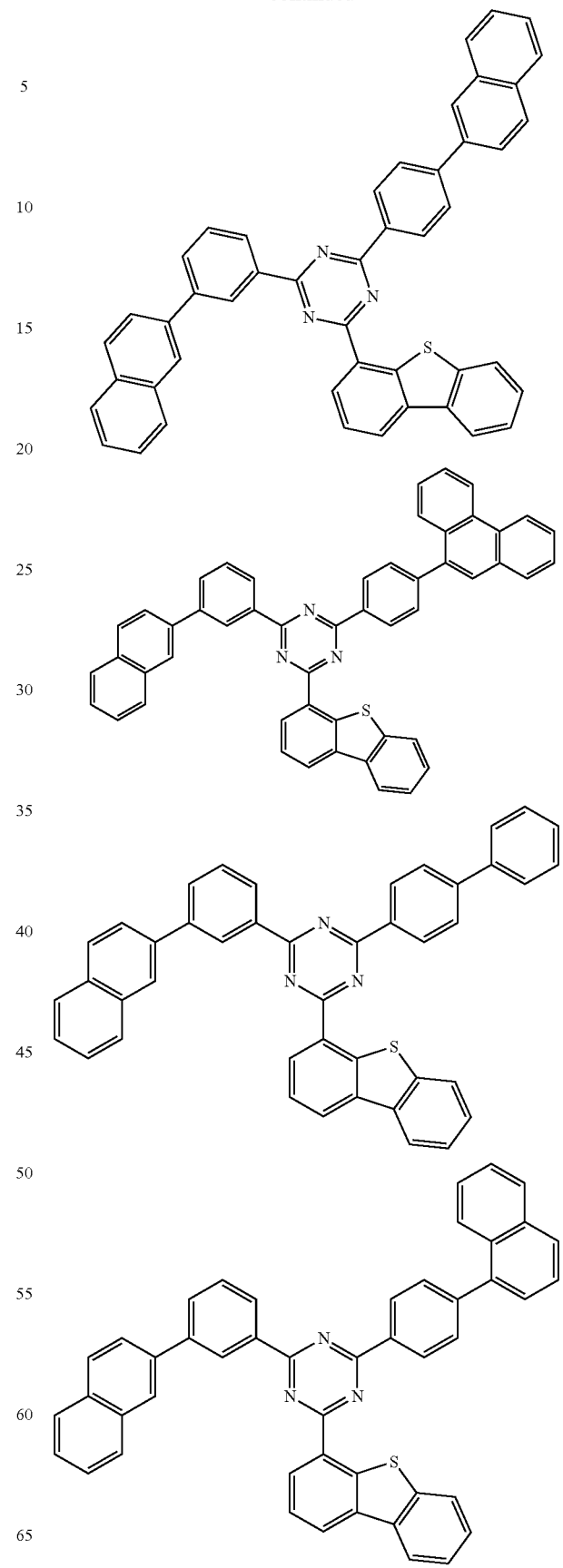

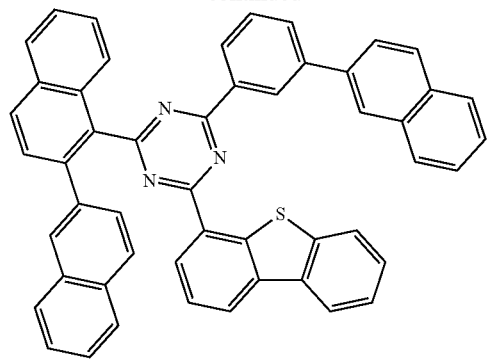
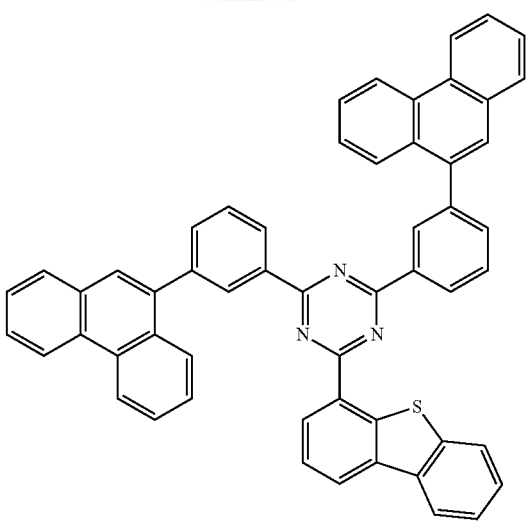
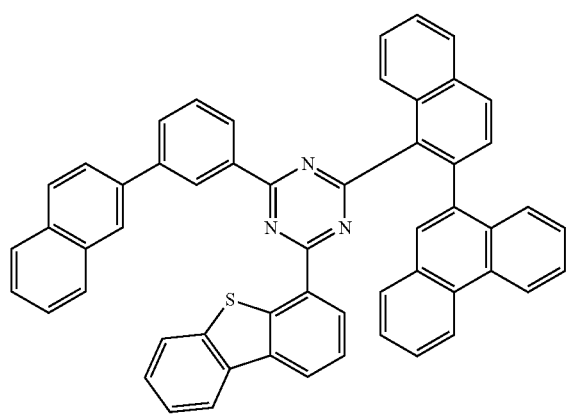
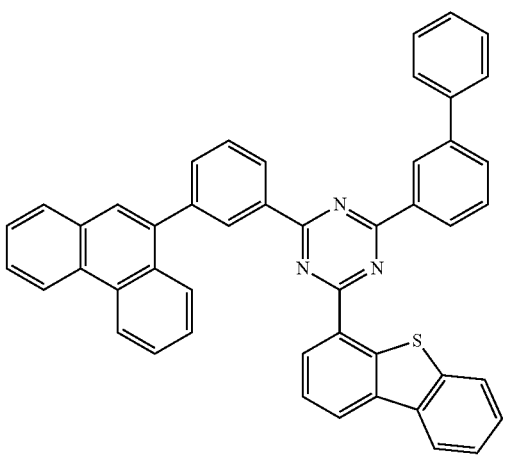
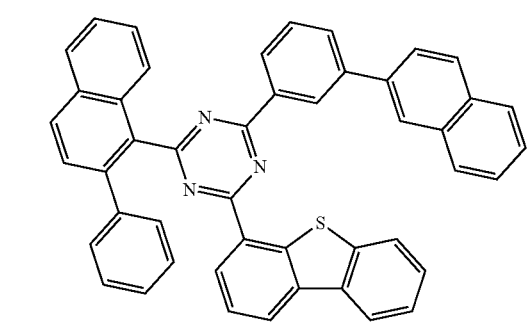
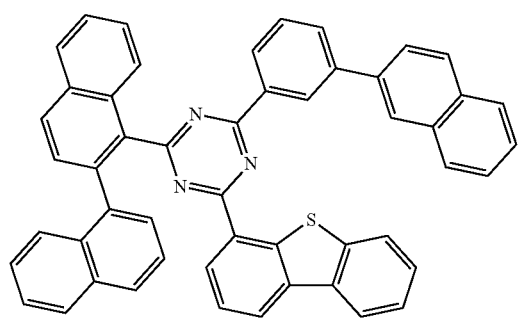
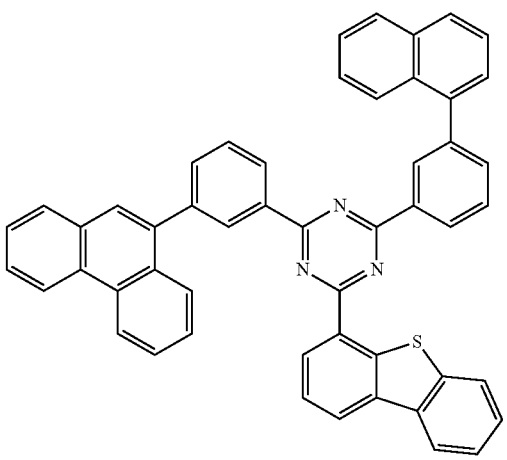

85
-continued
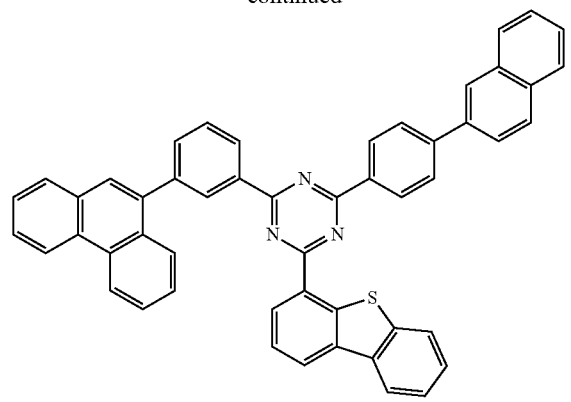
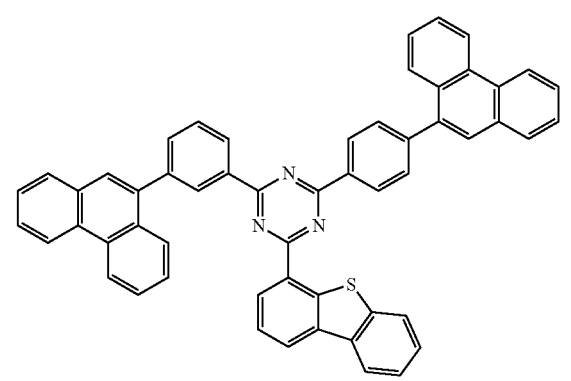
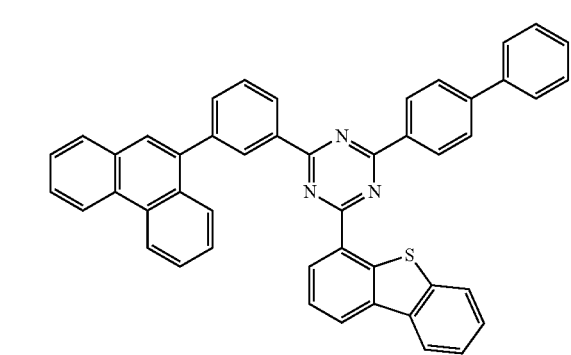
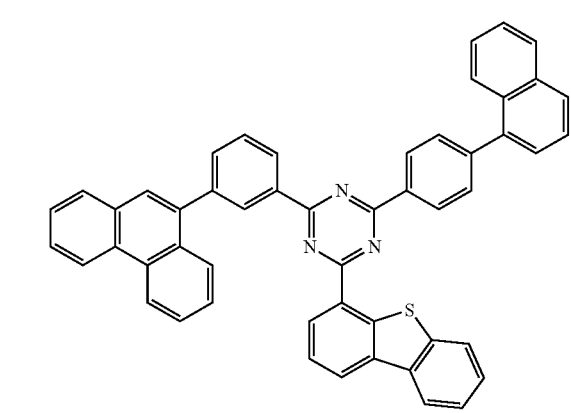
86
-continued
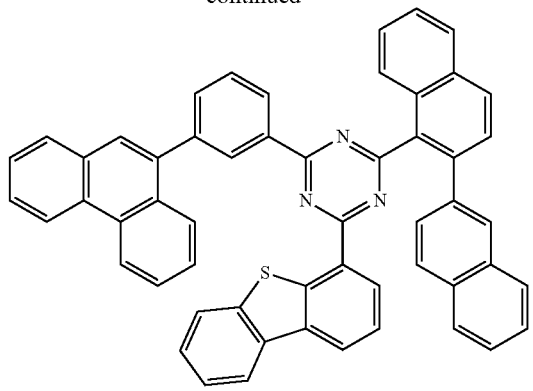
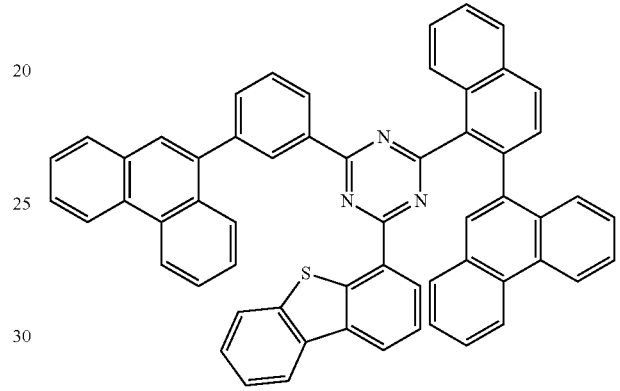
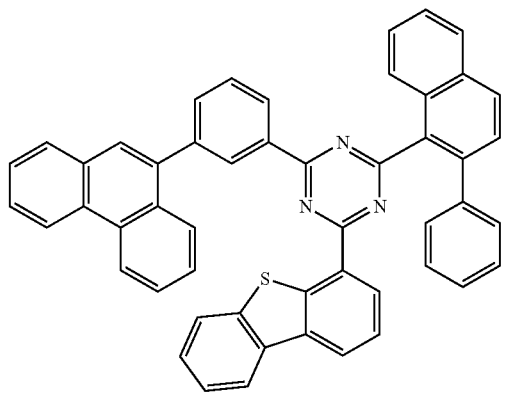
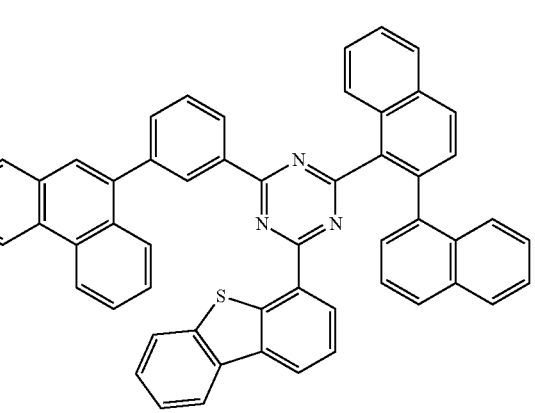

87
-continued
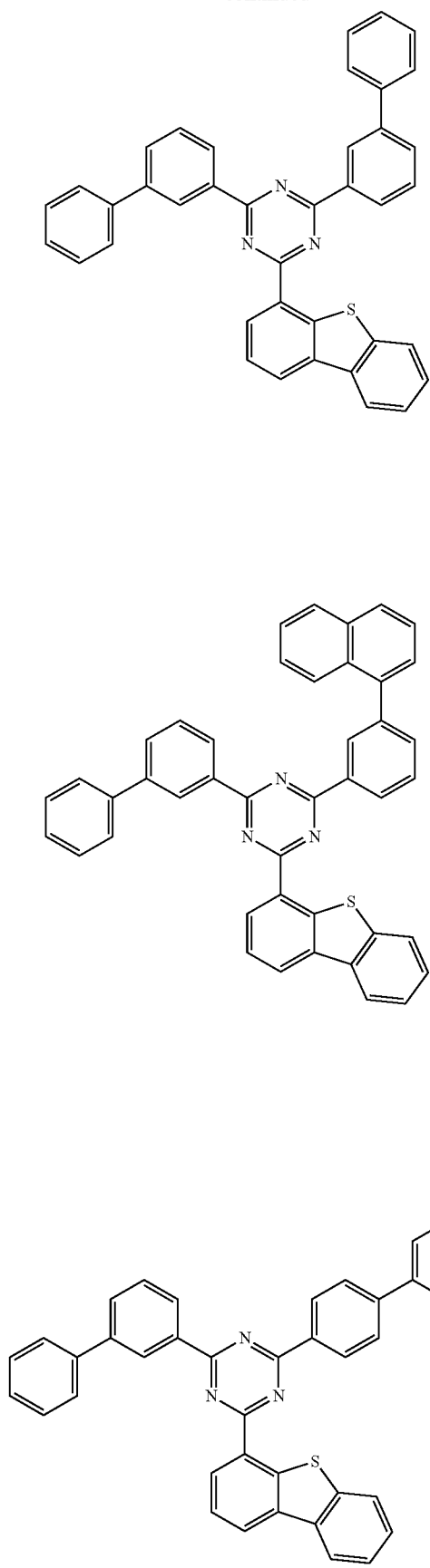
88
-continued
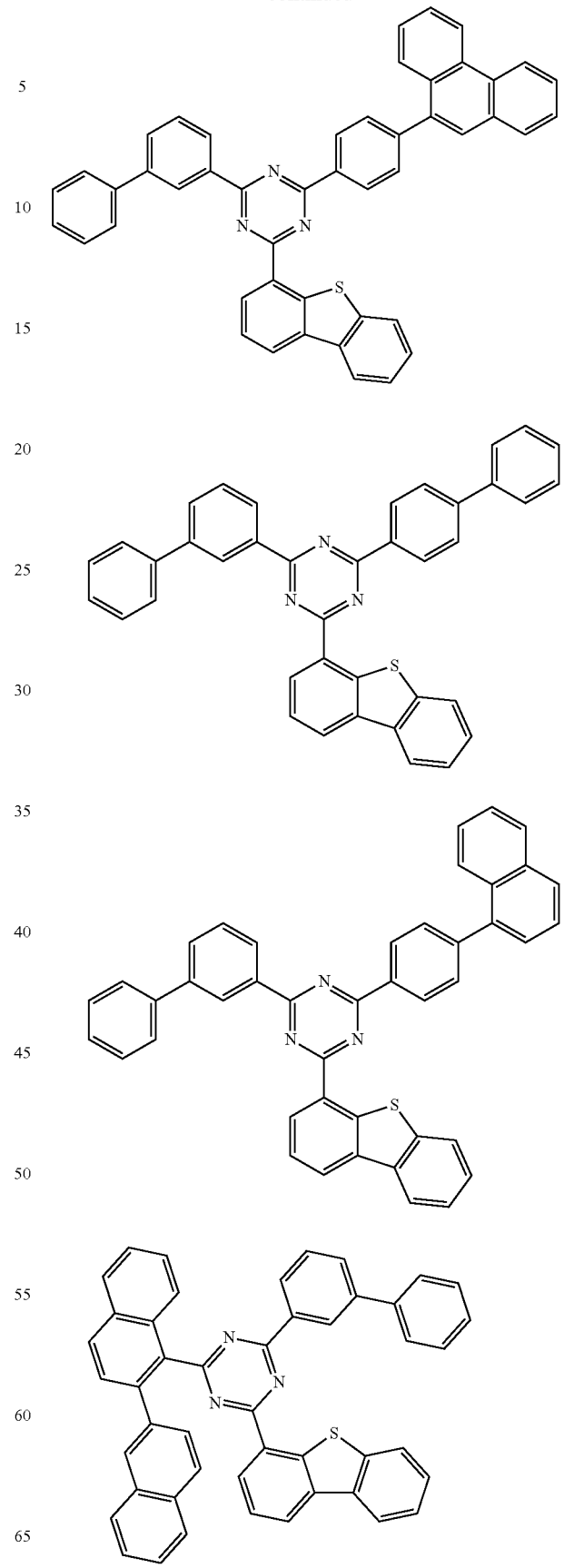

89
-continued
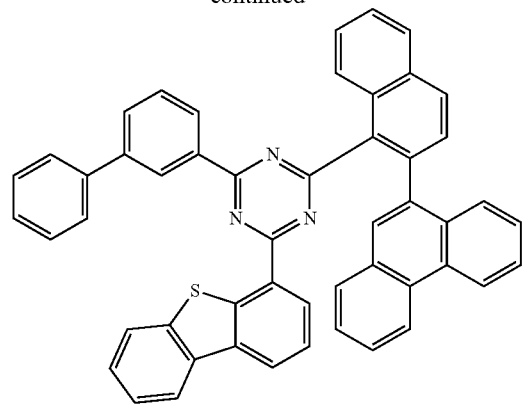
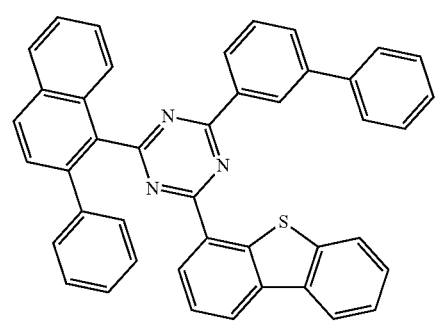
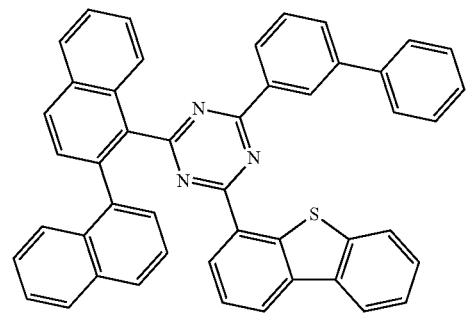
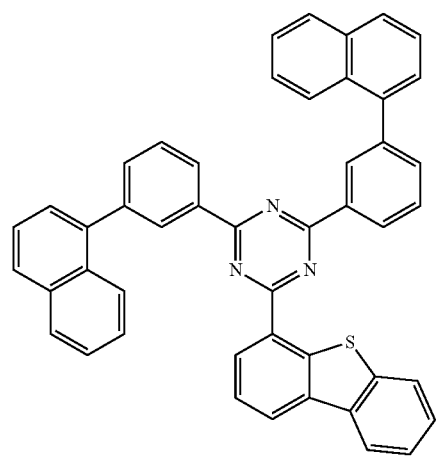
90
-continued
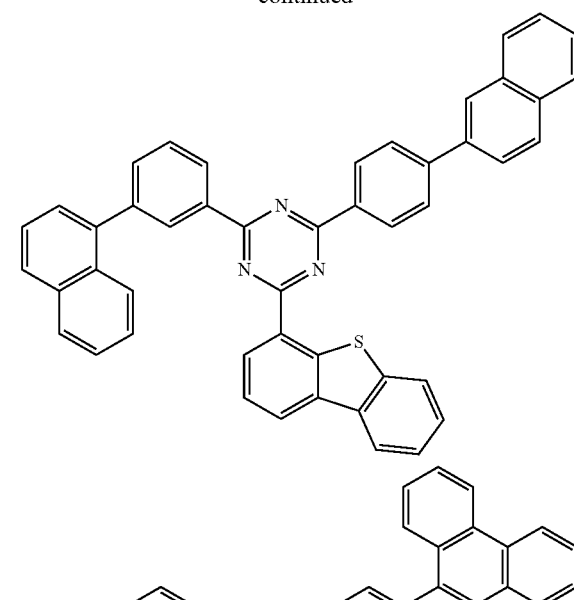
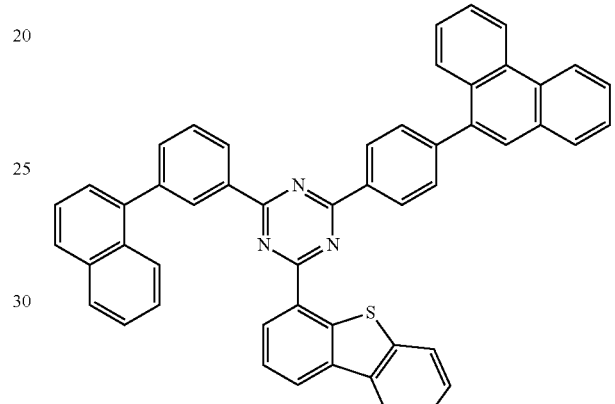
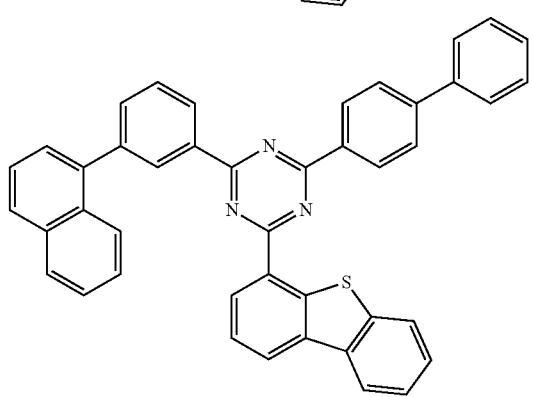
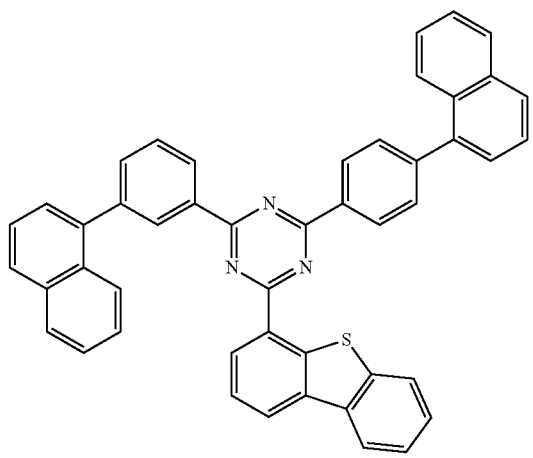

| 91 | 92 |
|---|---|
| 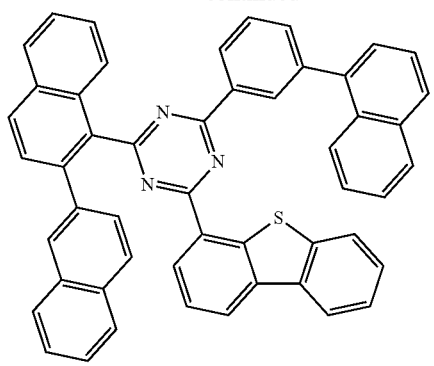 | 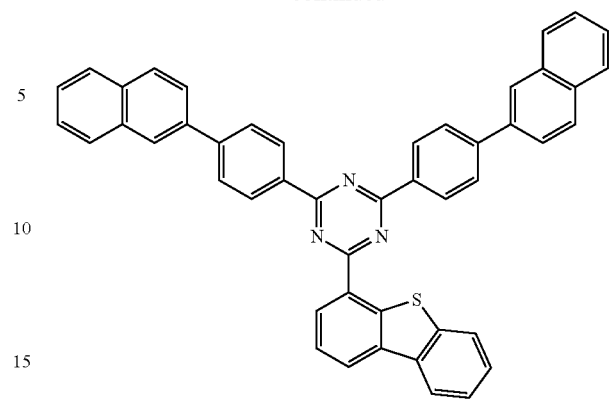 |
| 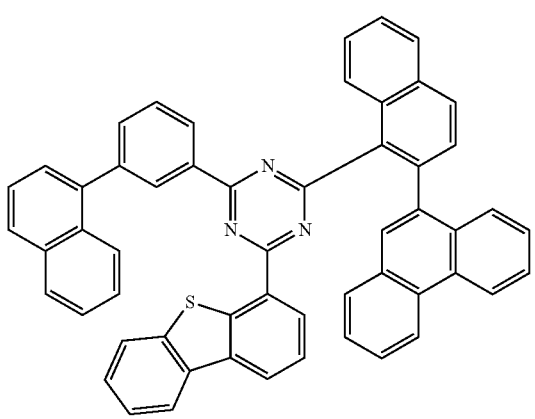 | 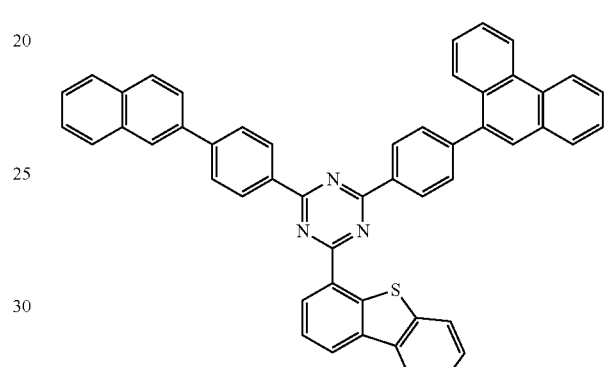 |
| 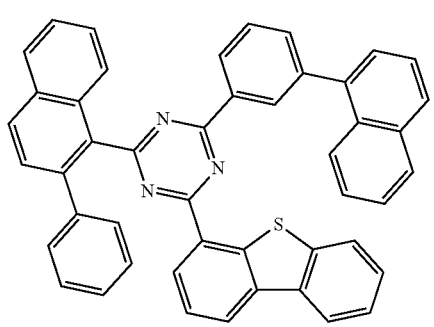 | 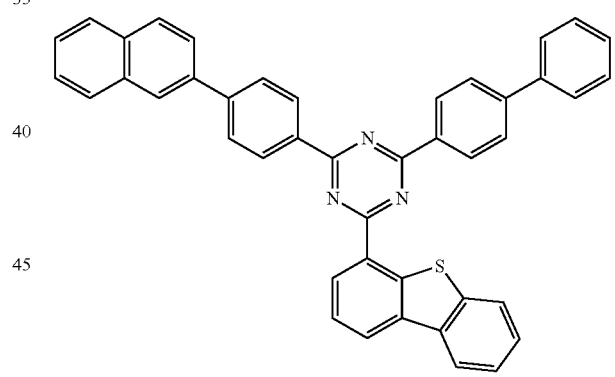 |
| 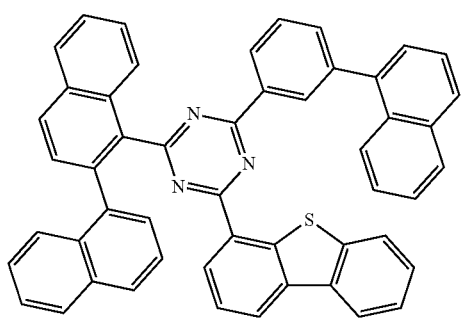 | 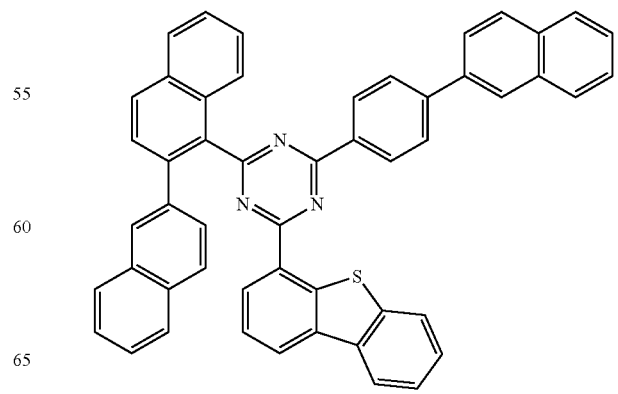 |

93
-continued
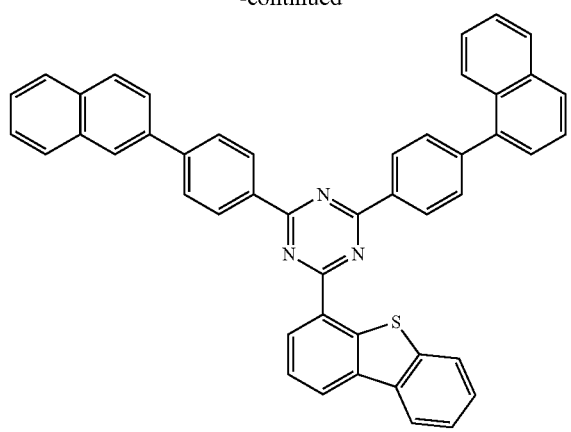
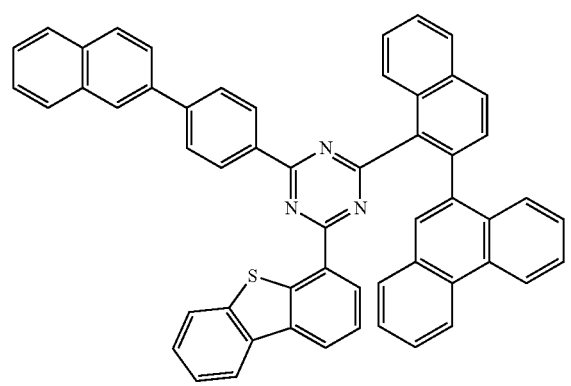
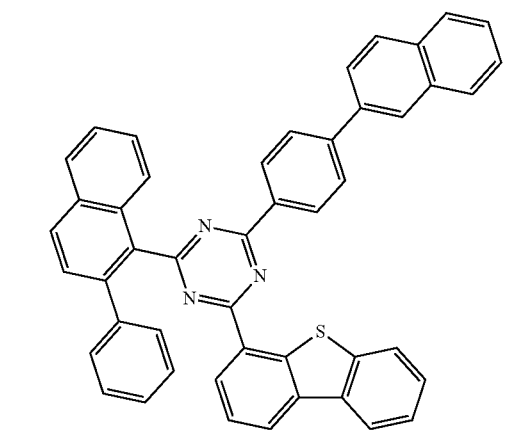
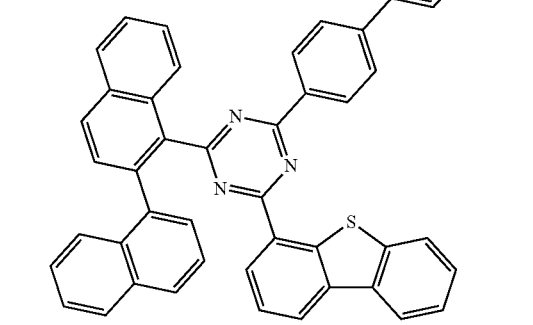
94
-continued
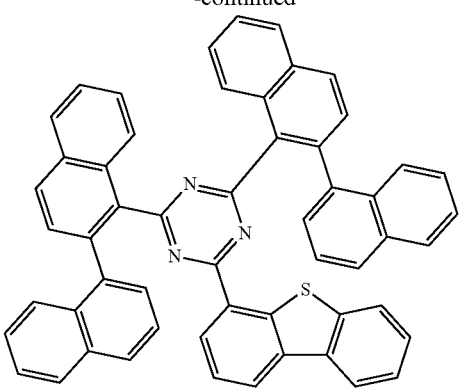
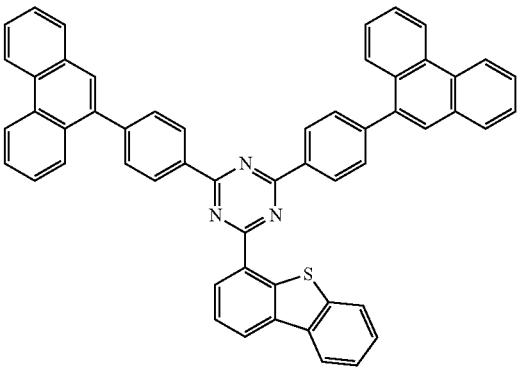
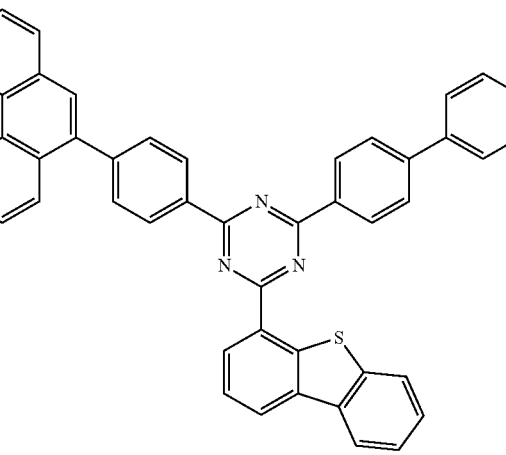
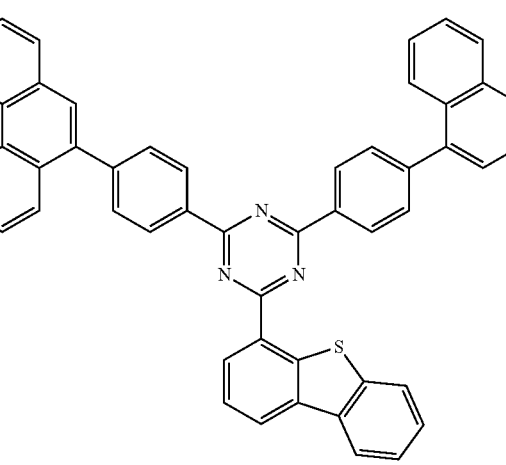

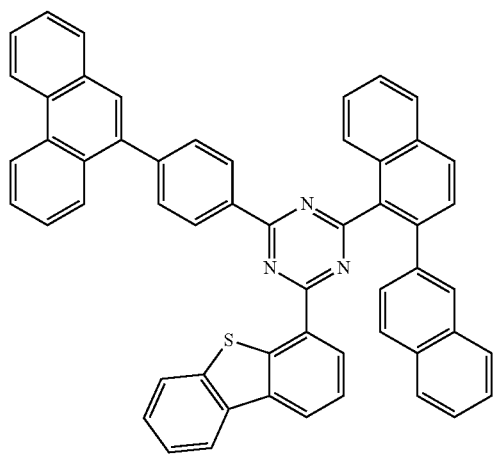
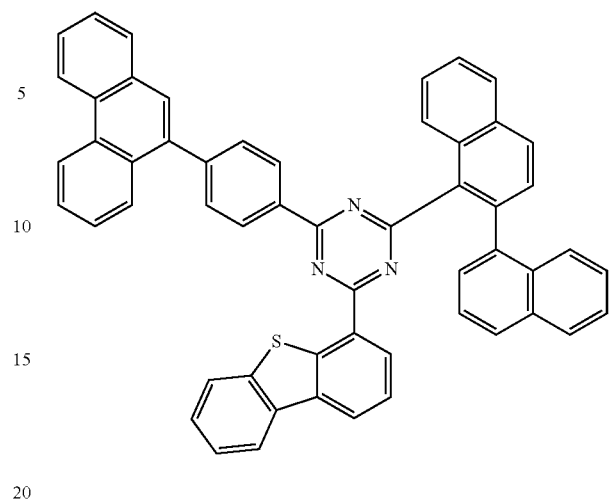
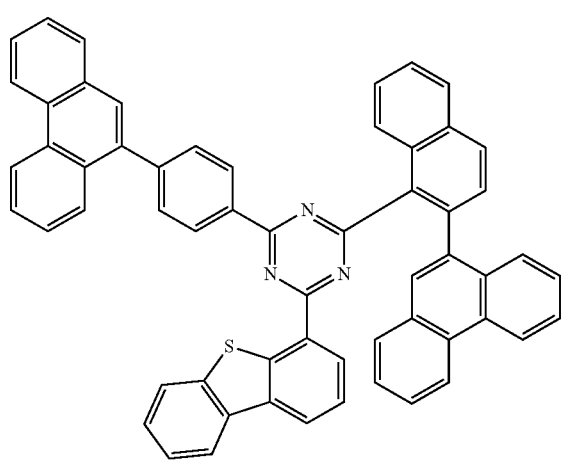
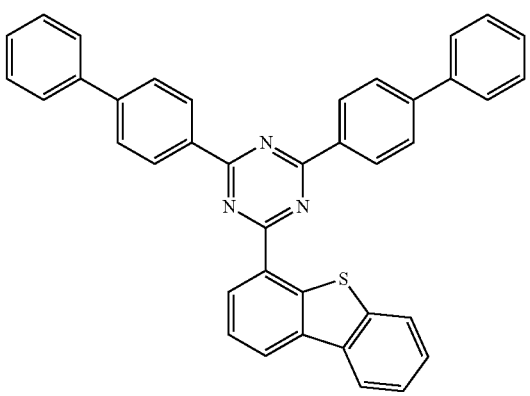
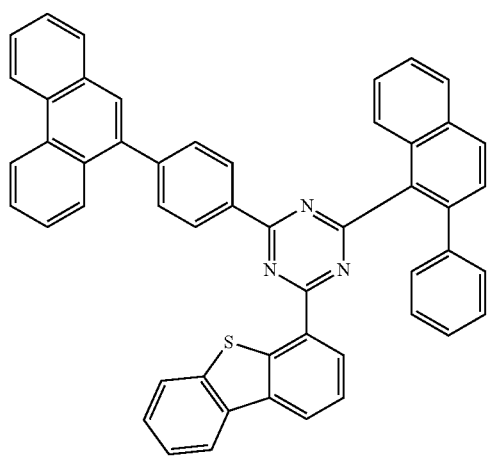
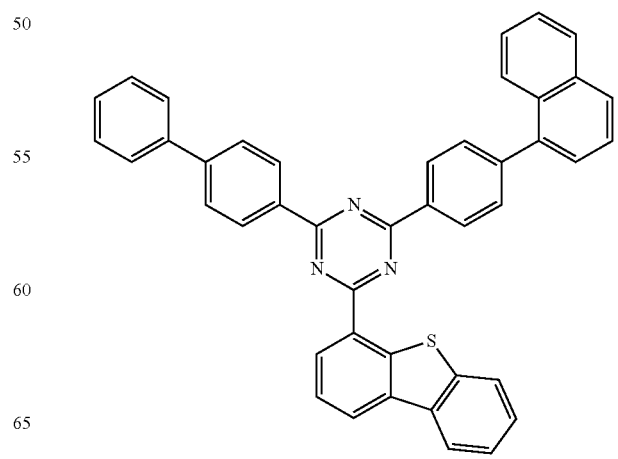

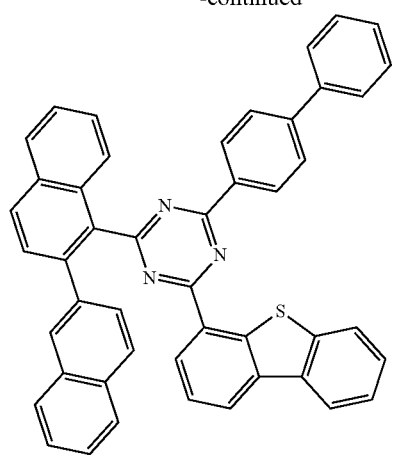
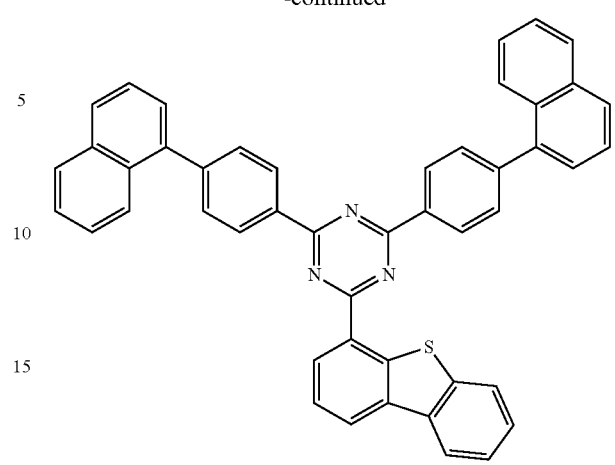
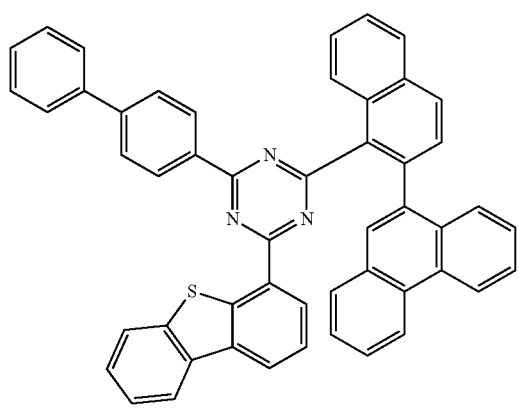
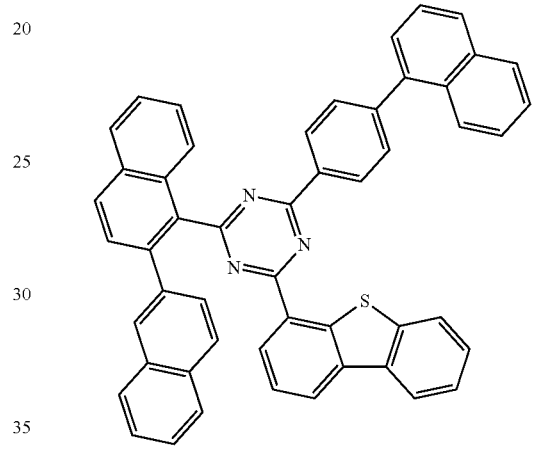
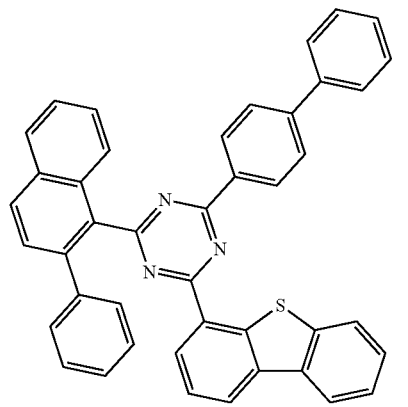
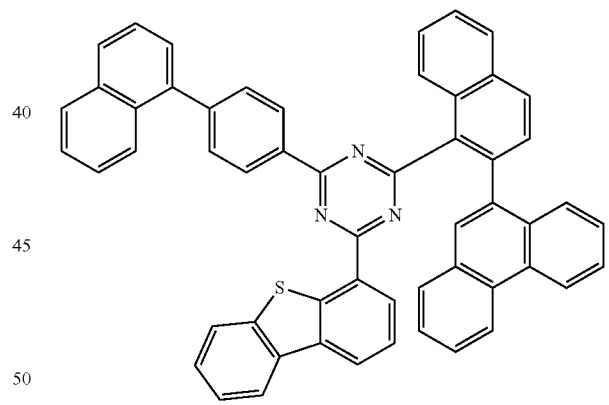
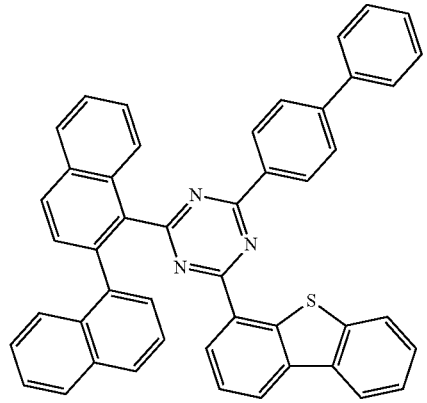
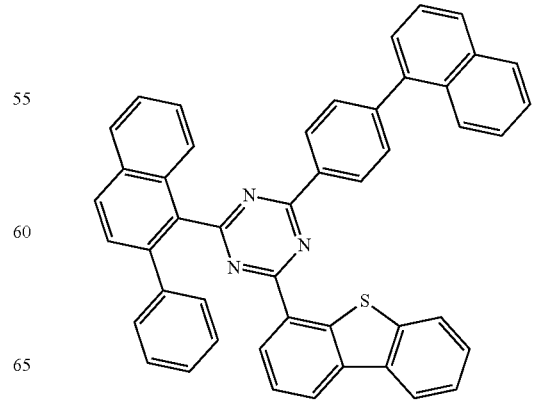

| 99 | 100 |
|---|---|
| 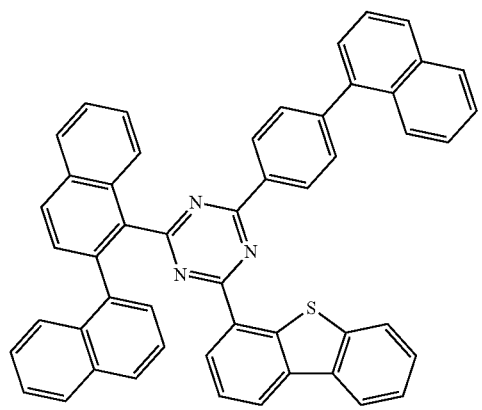 | 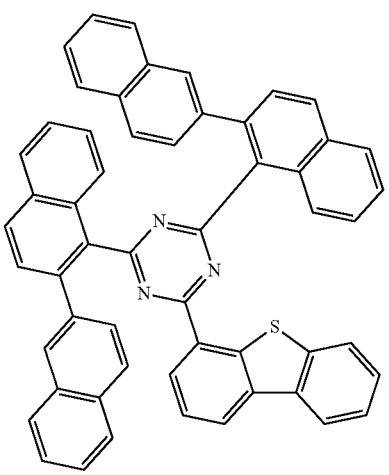 |
| 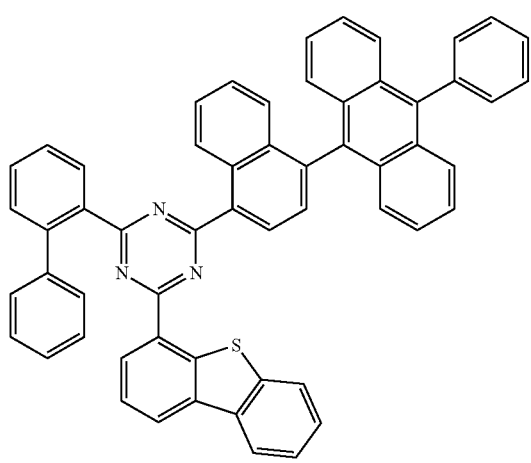 | 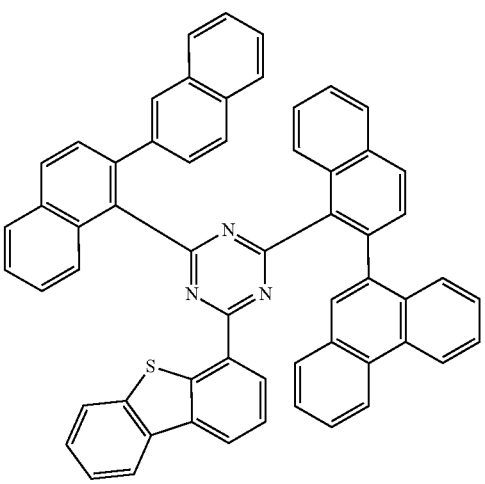 |
| 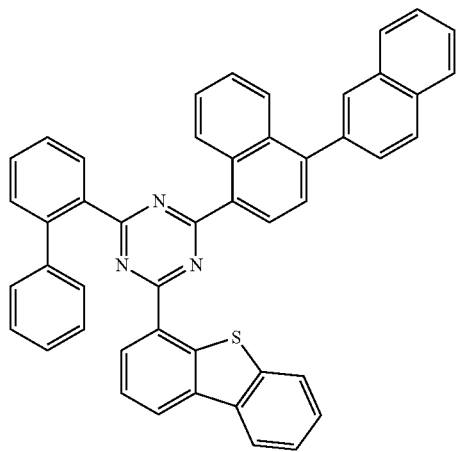 | 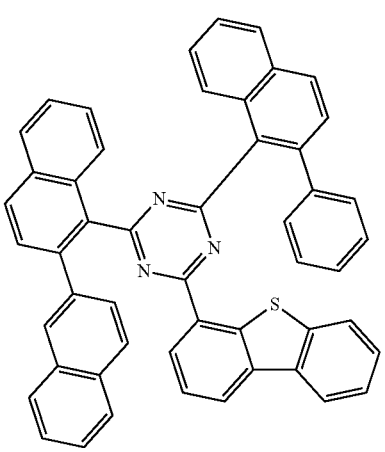 |

101
-continued
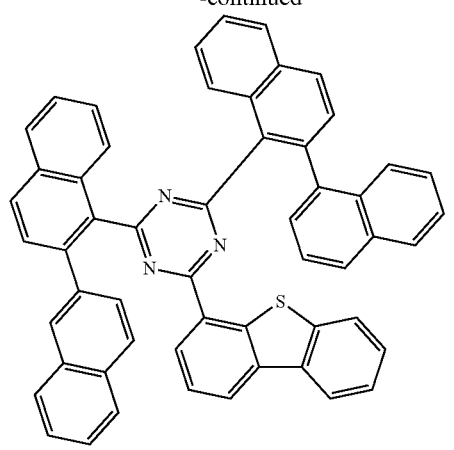
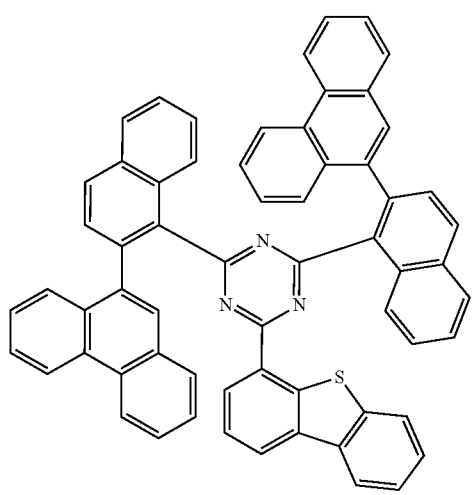
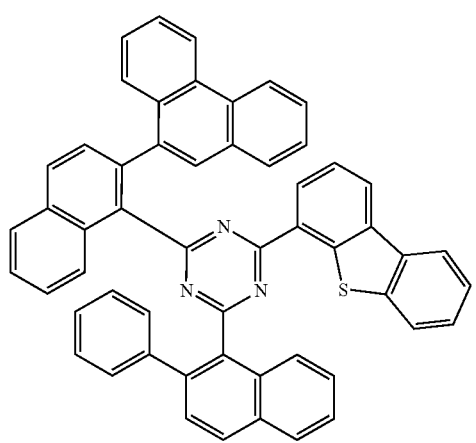
102
-continued
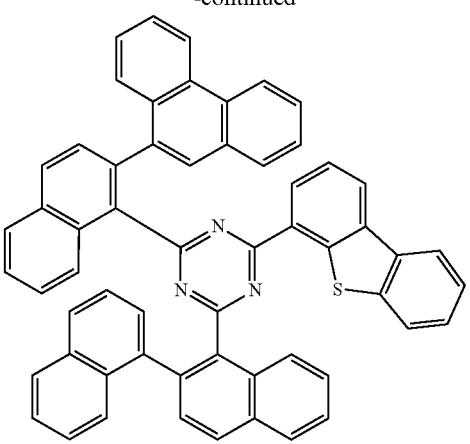
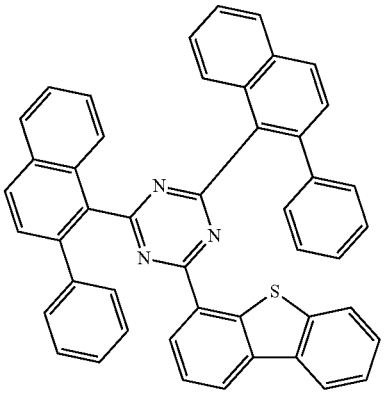
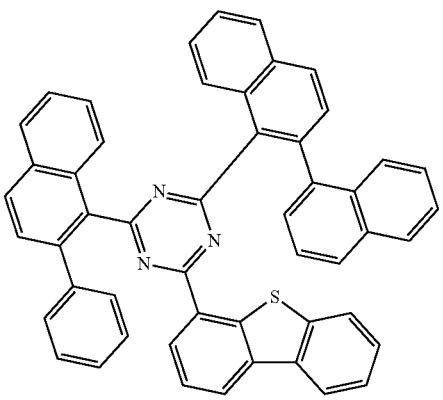
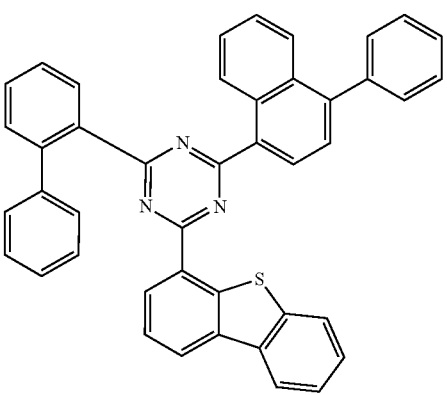

103
-continued
104
-continued
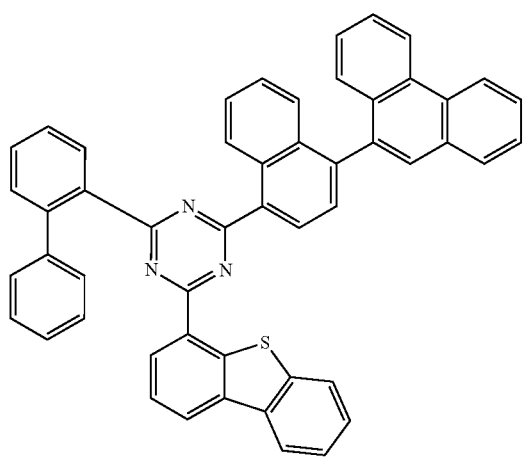
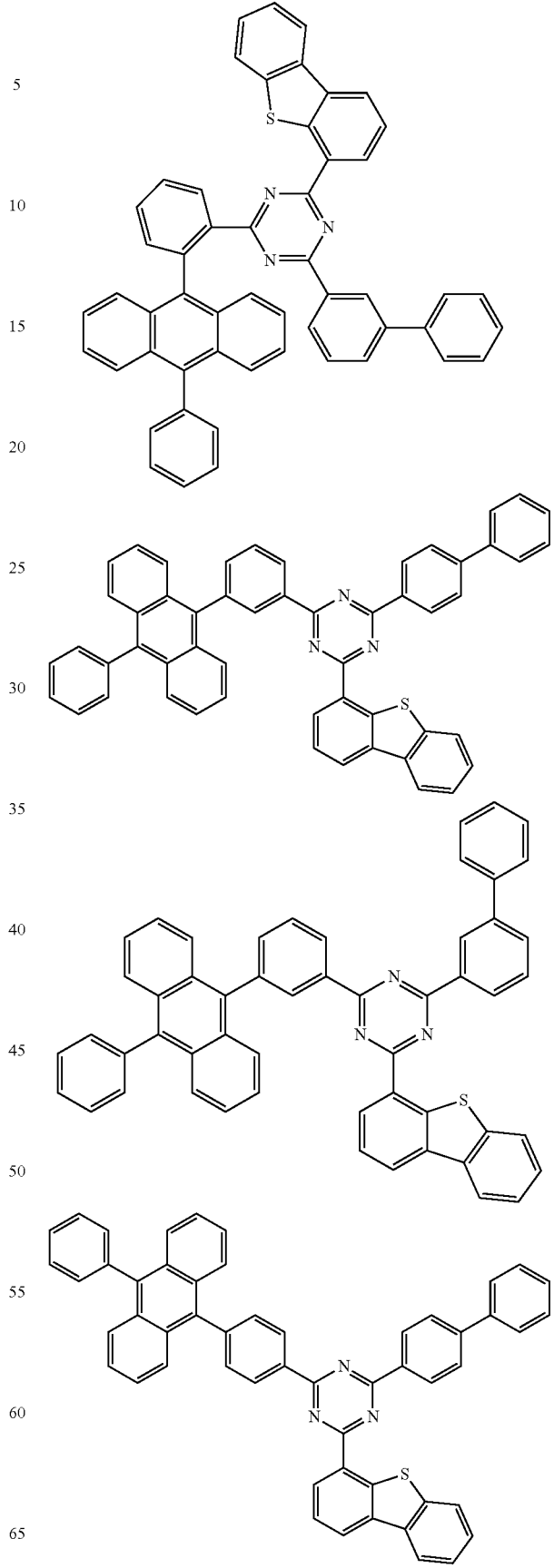

105
-continued
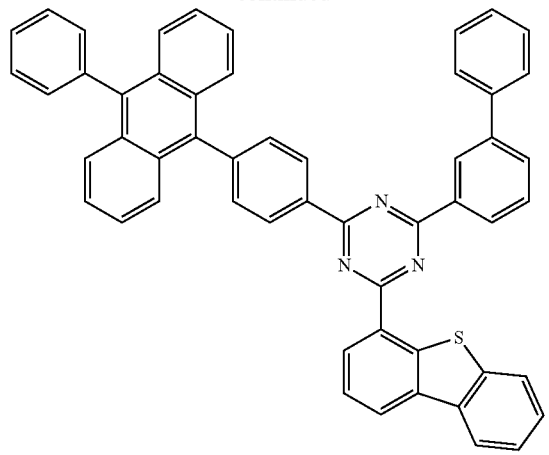
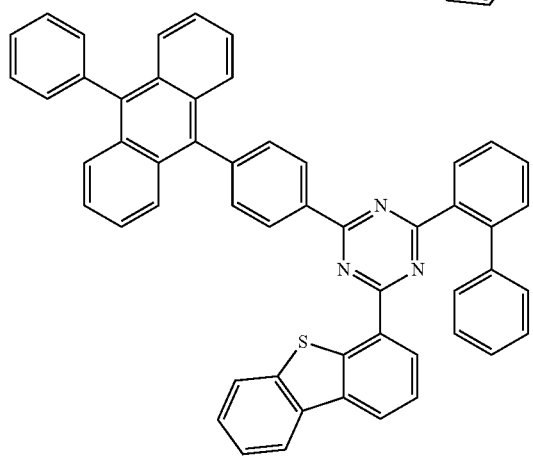
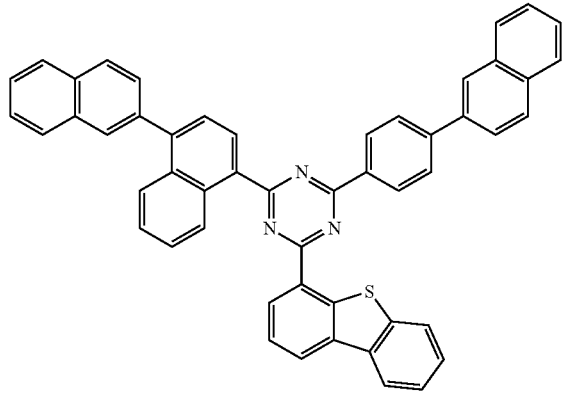
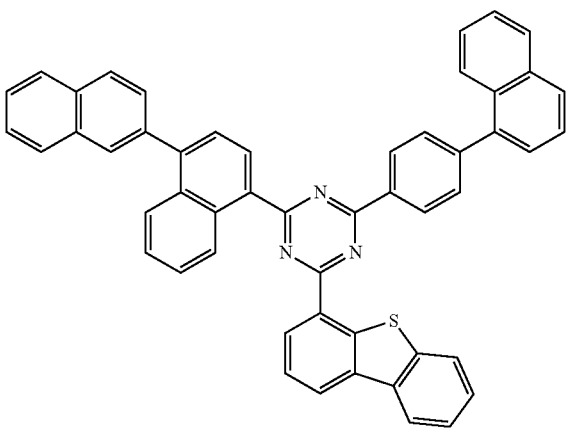
106
-continued
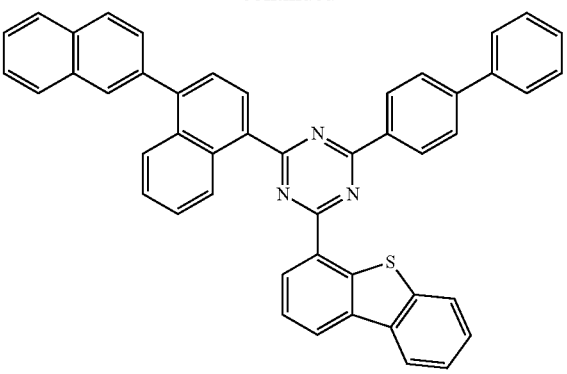
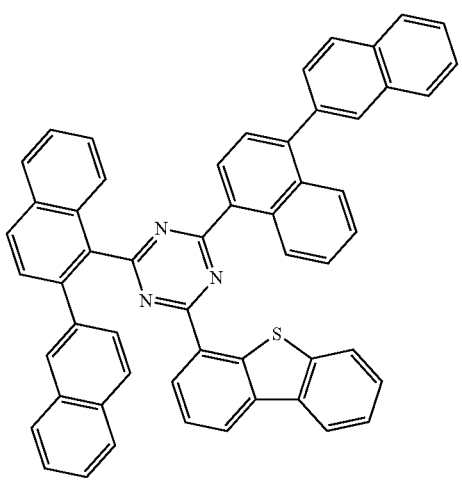
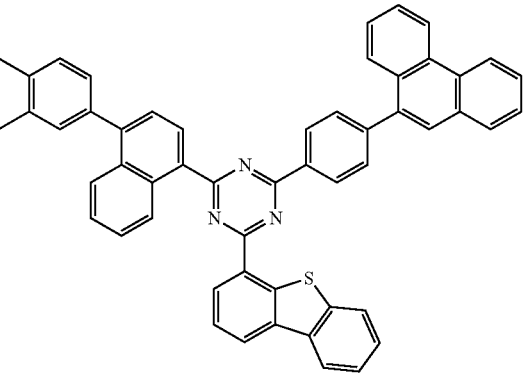
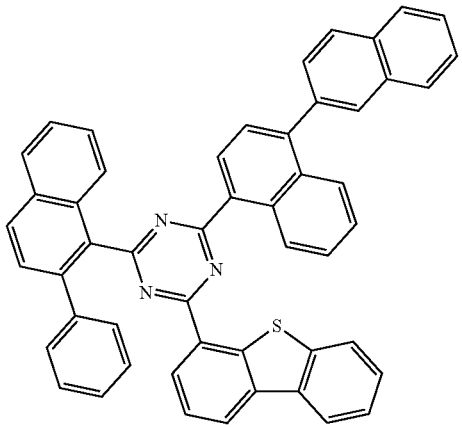

107
-continued
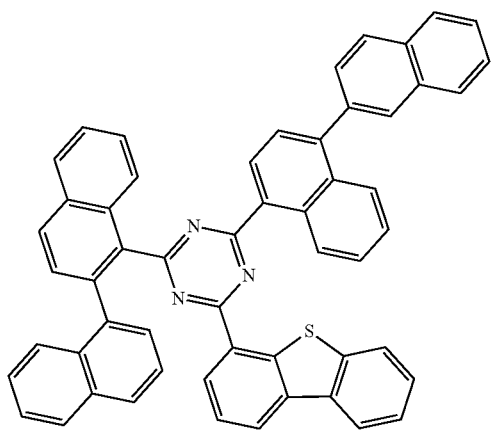
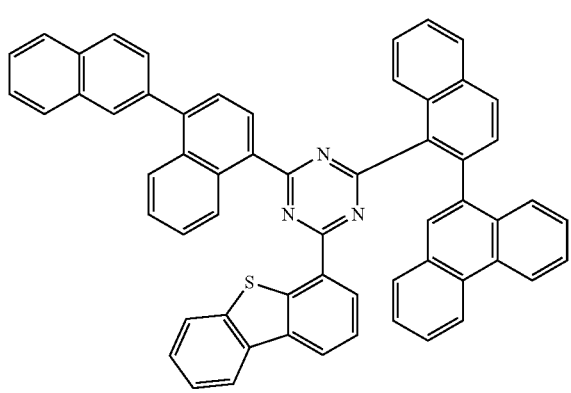
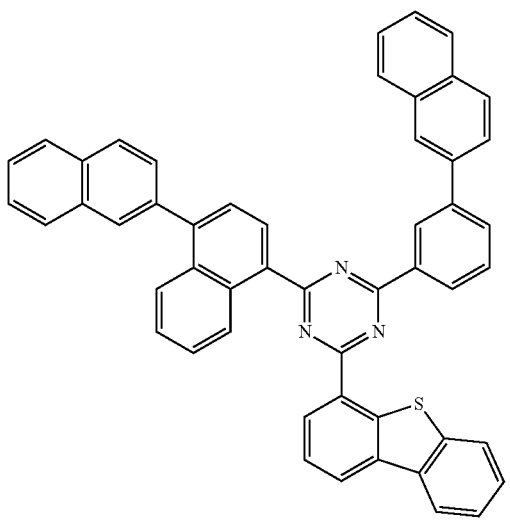
108
-continued
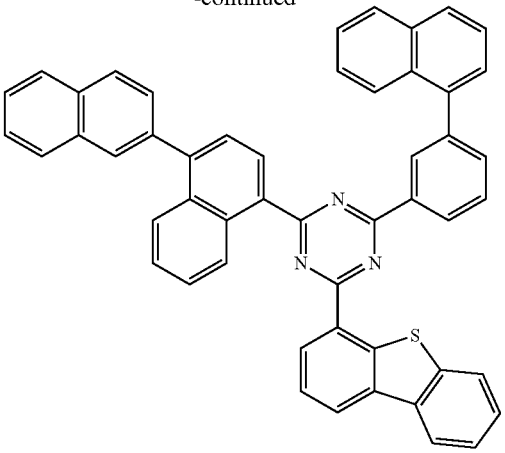
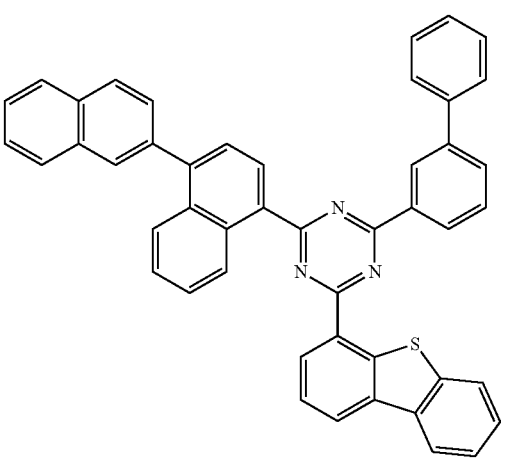
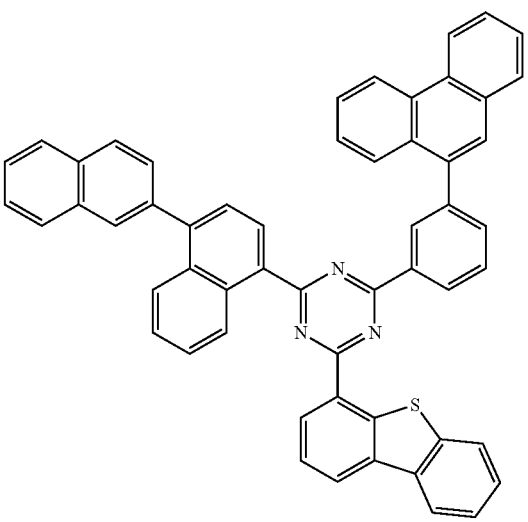

109
-continued
110
-continued
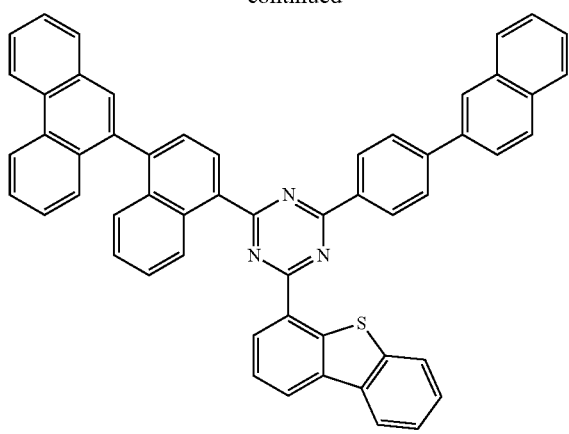
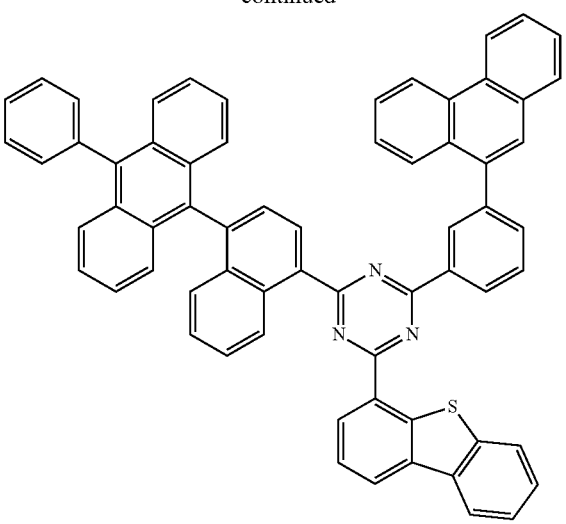
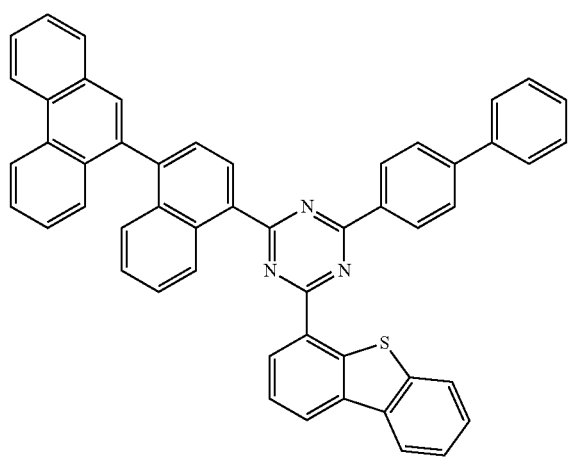

111
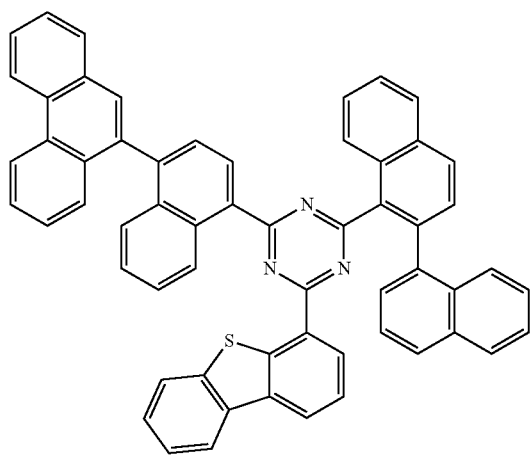
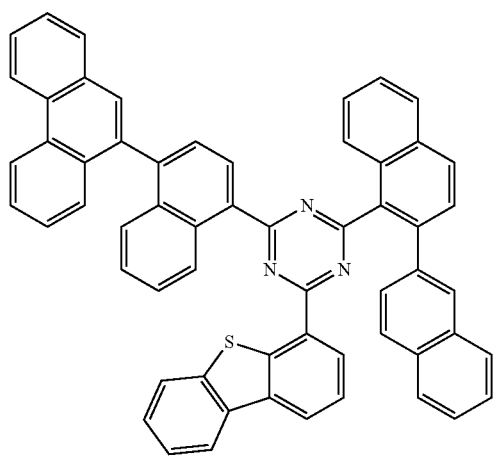
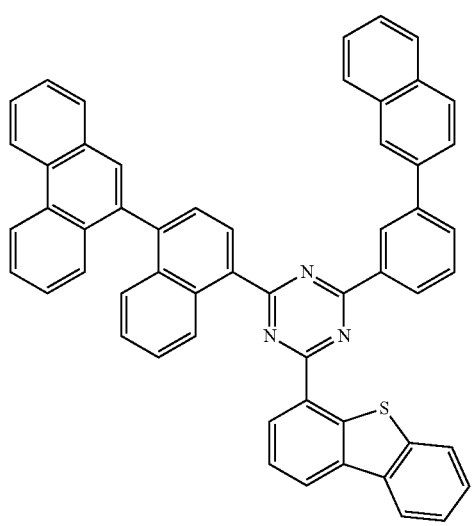
112
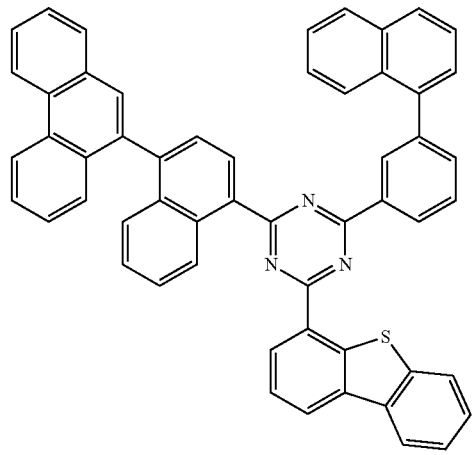
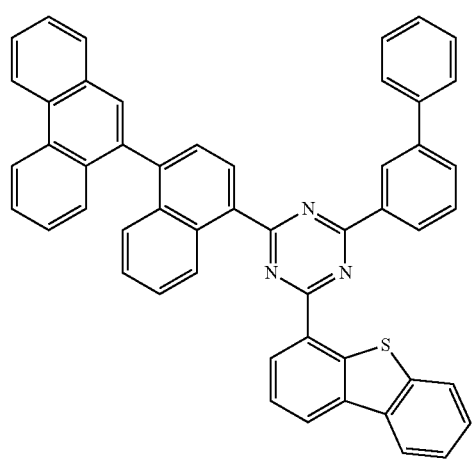
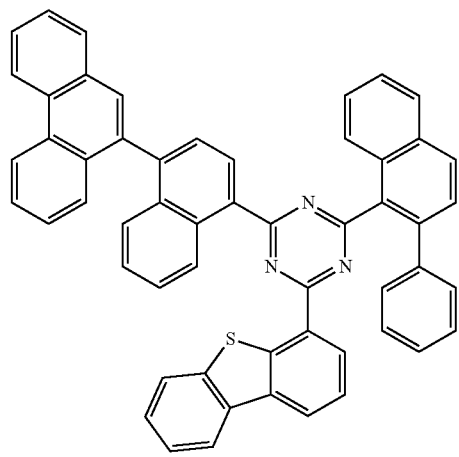

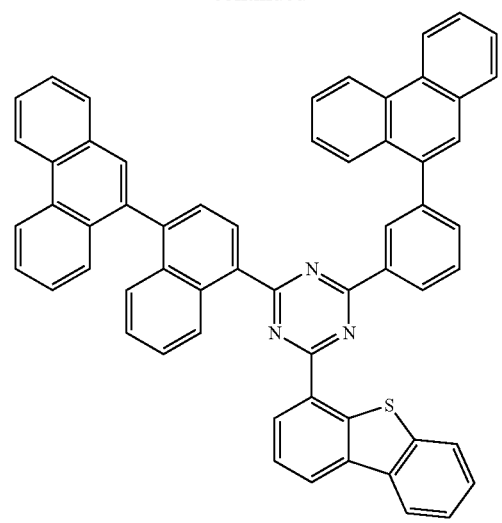
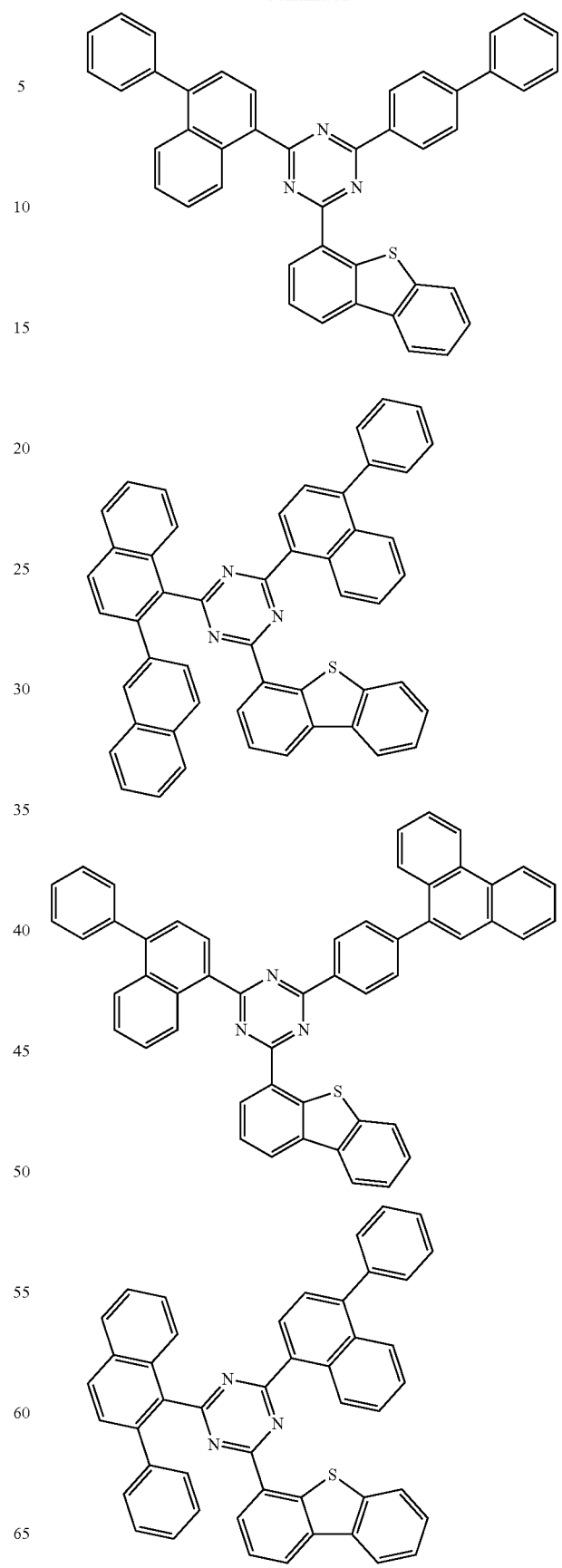

115
-continued
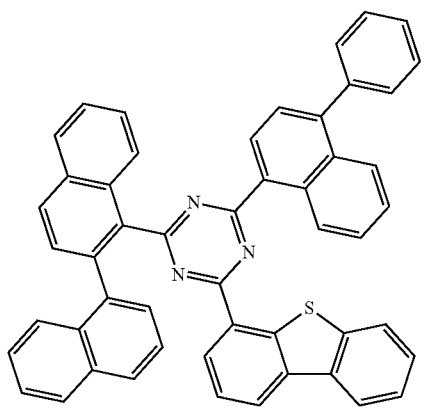
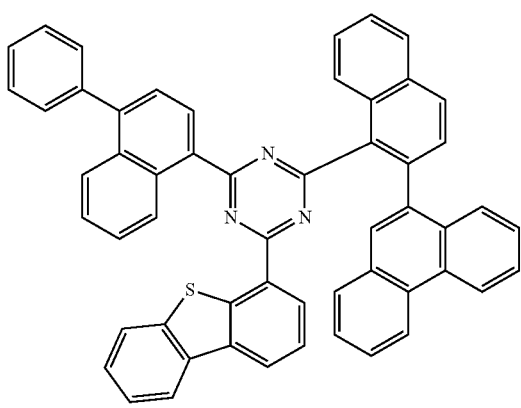
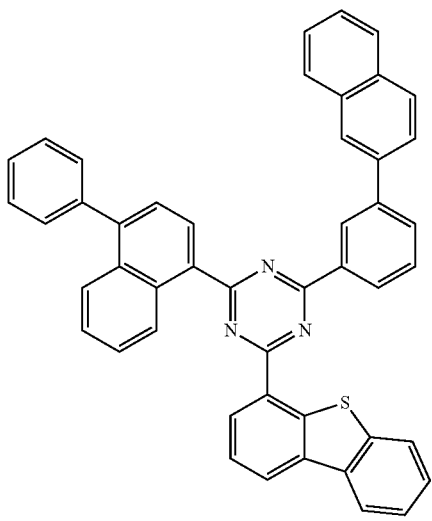
116
-continued
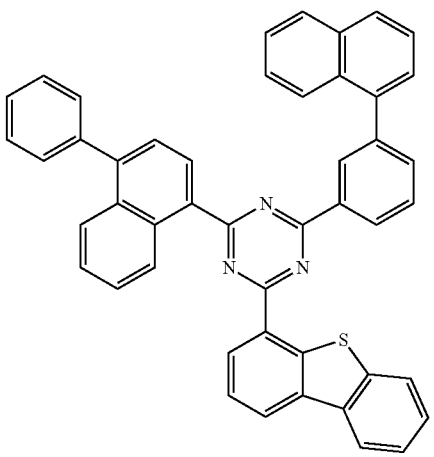
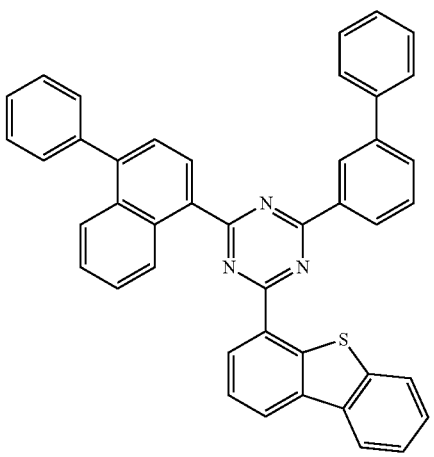
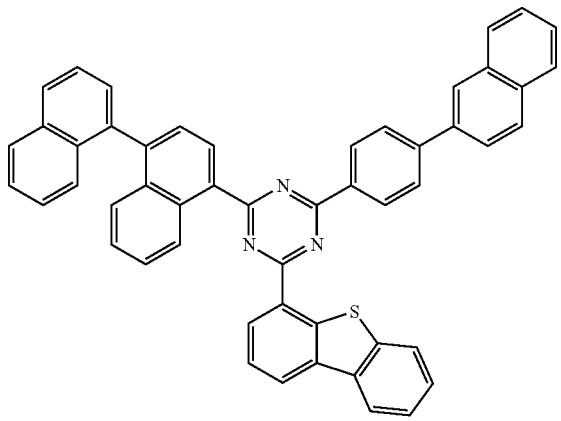

117
-continued
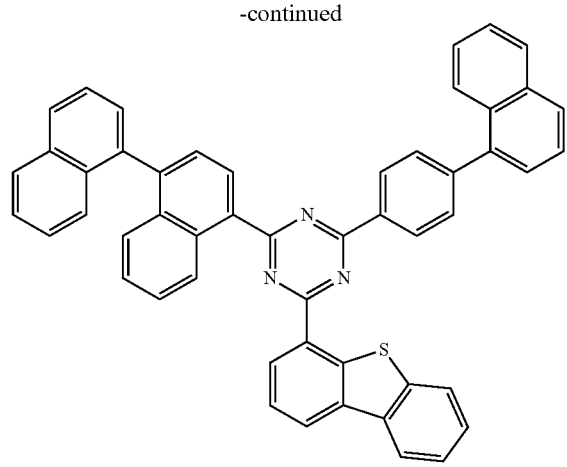
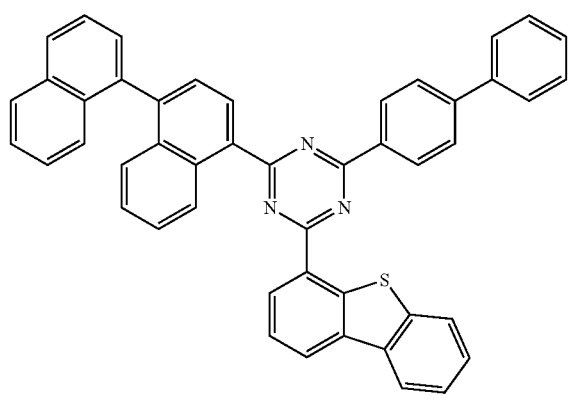
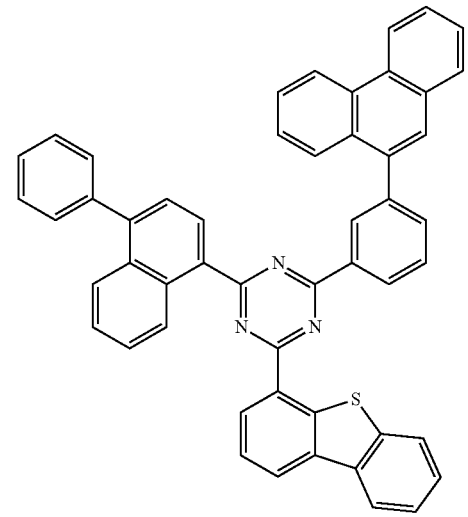
118
-continued
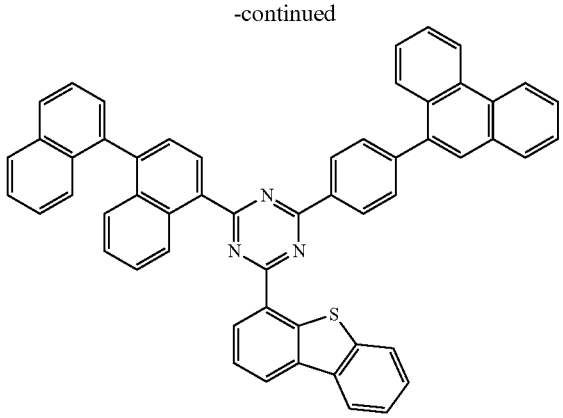
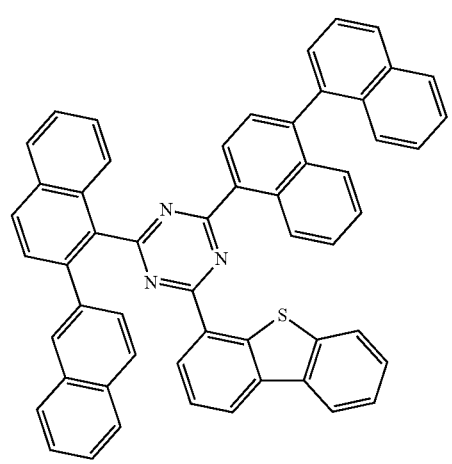
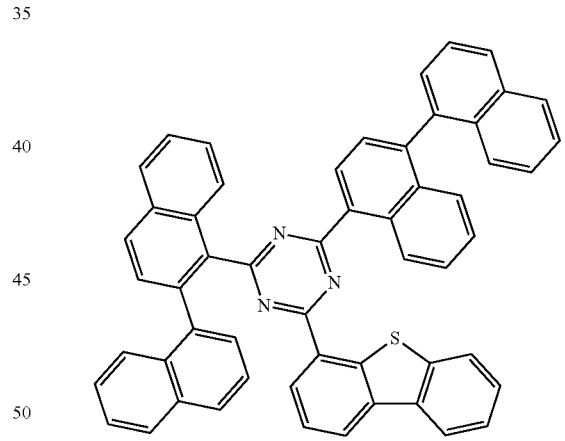
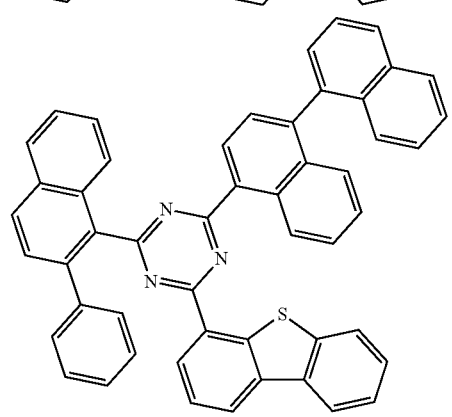

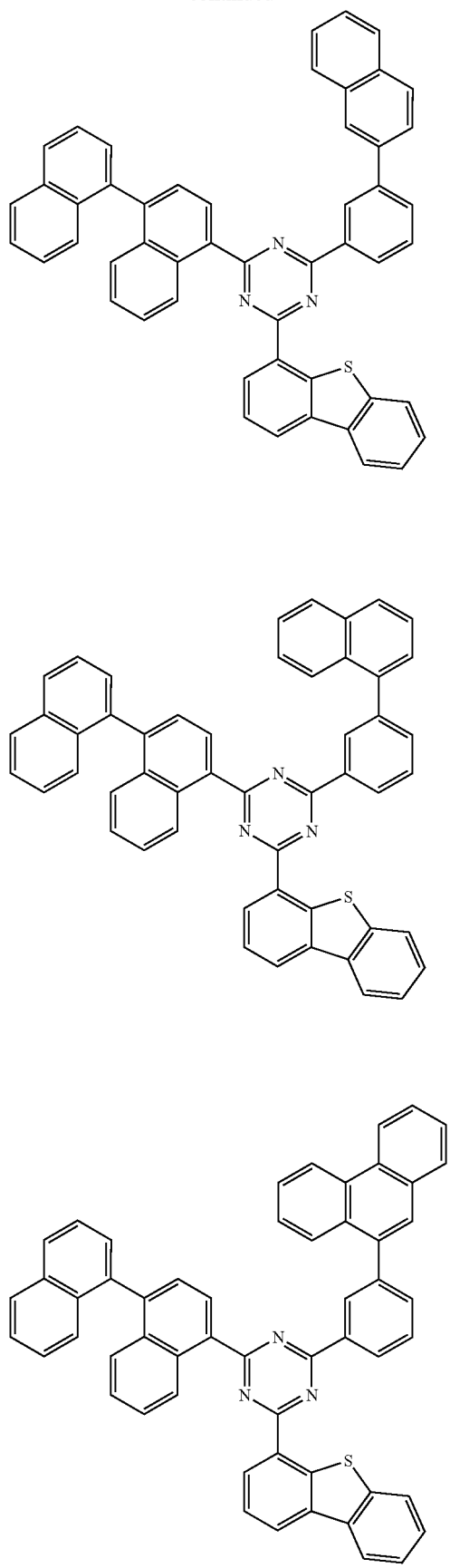
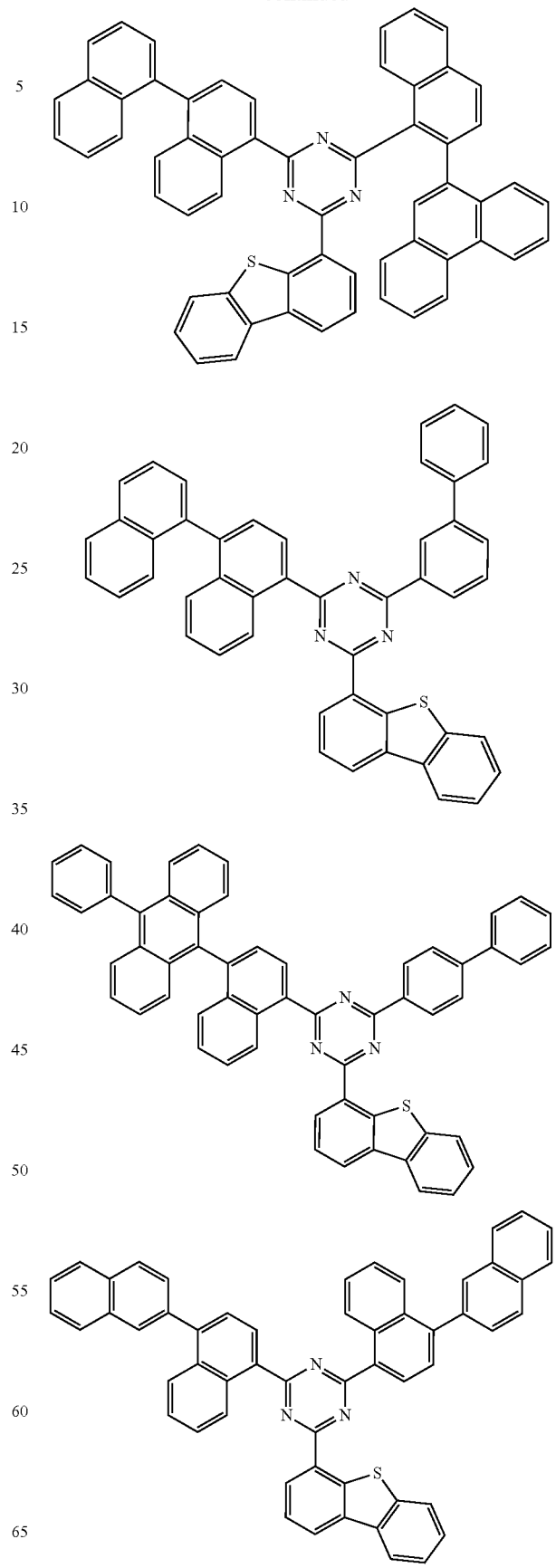

121
-continued
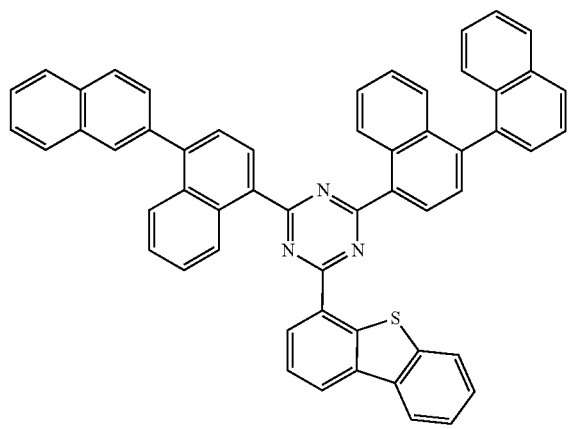
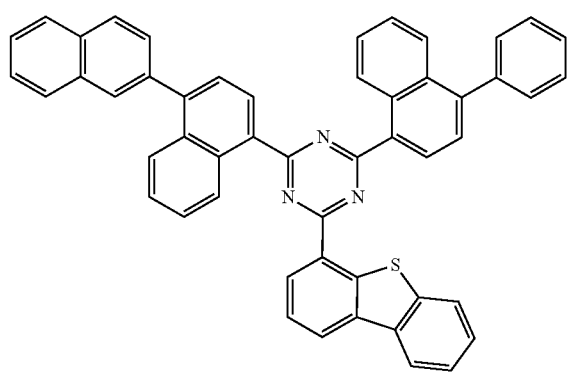
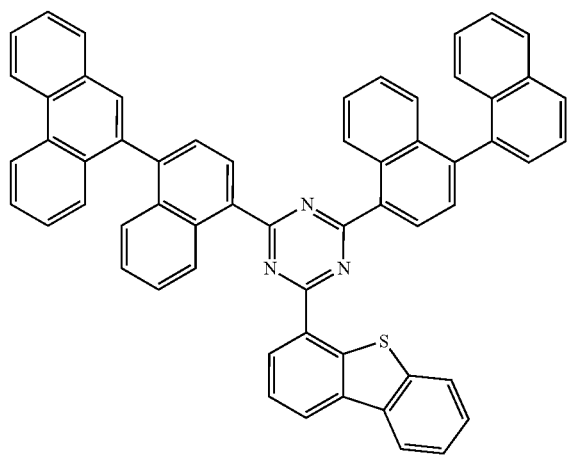
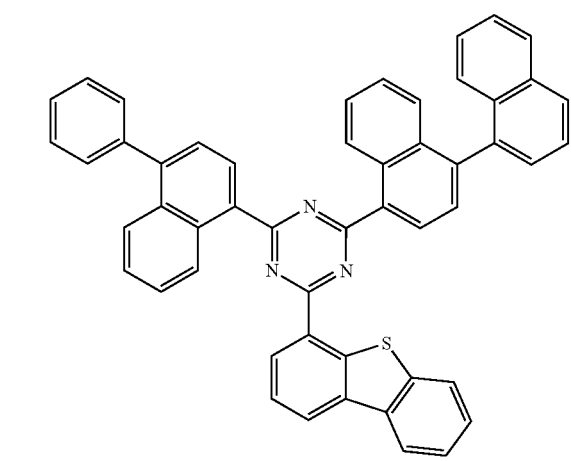
122
-continued
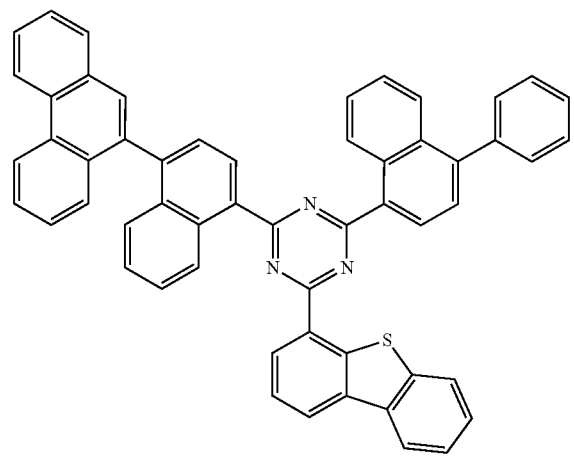
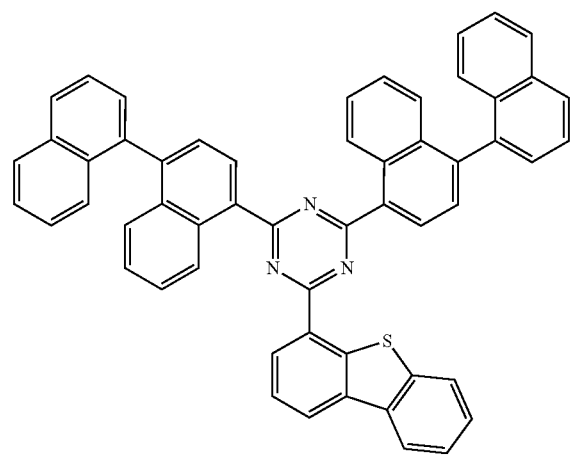
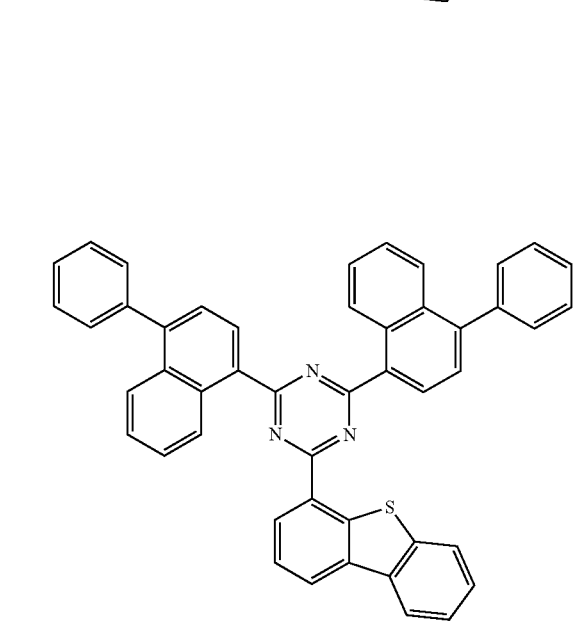

123
-continued
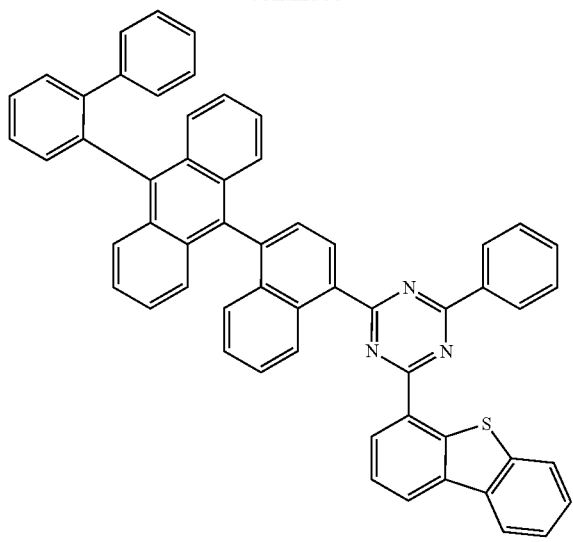
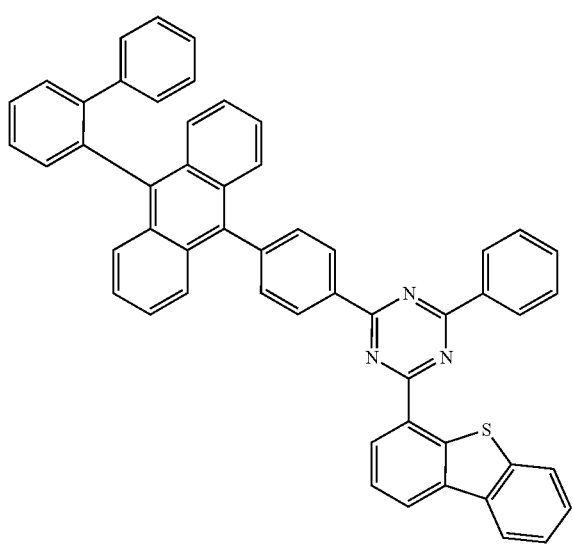
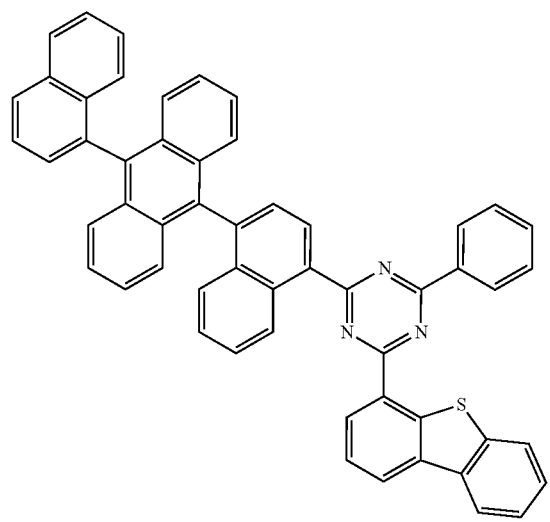
124
-continued
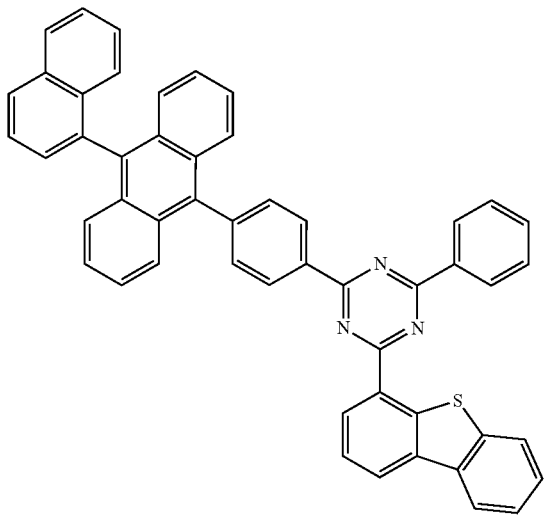
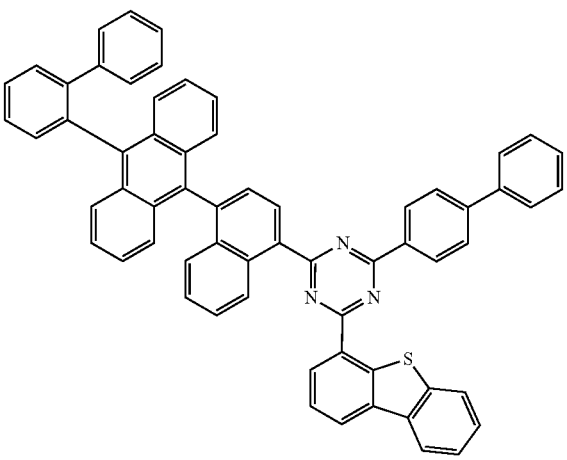
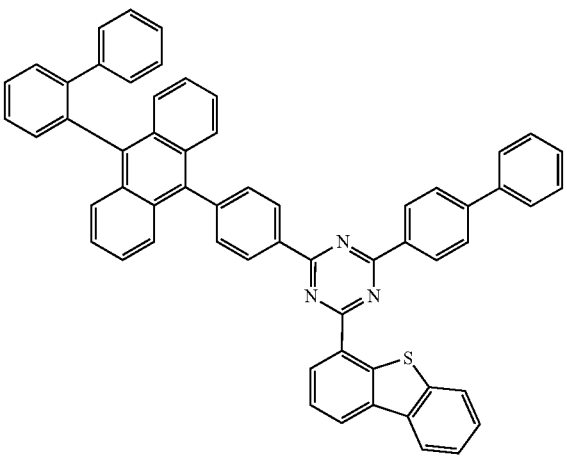

125
-continued
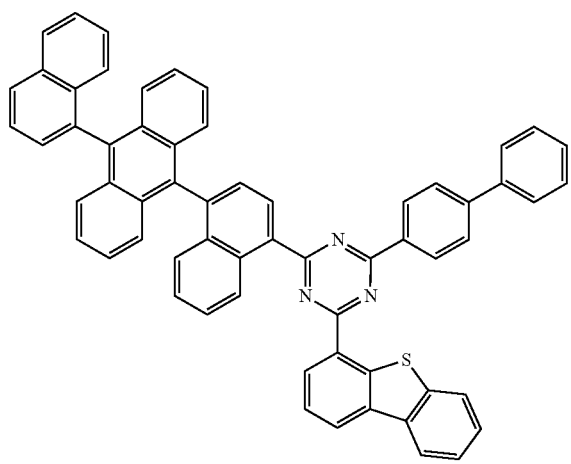
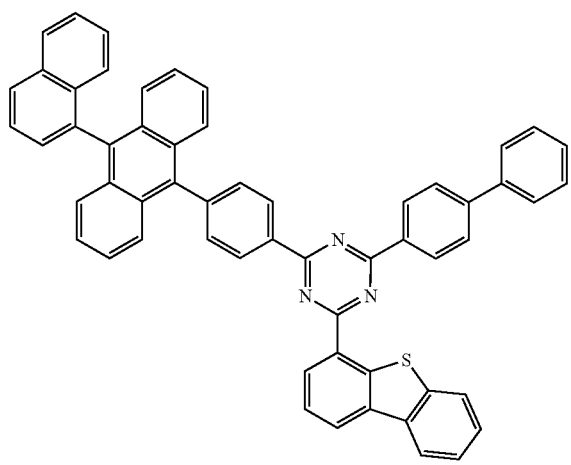
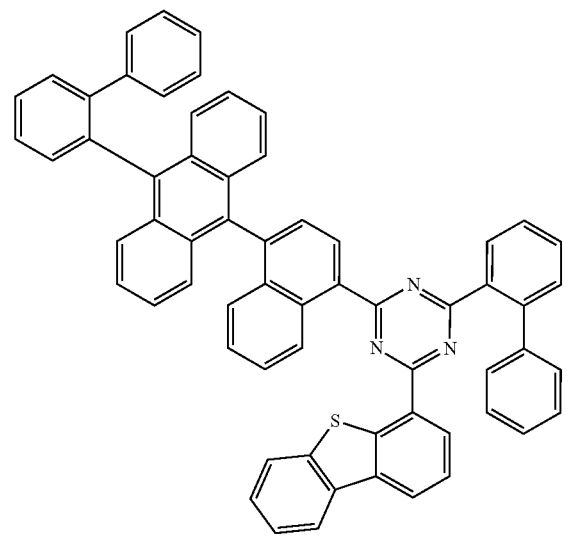
126
-continued
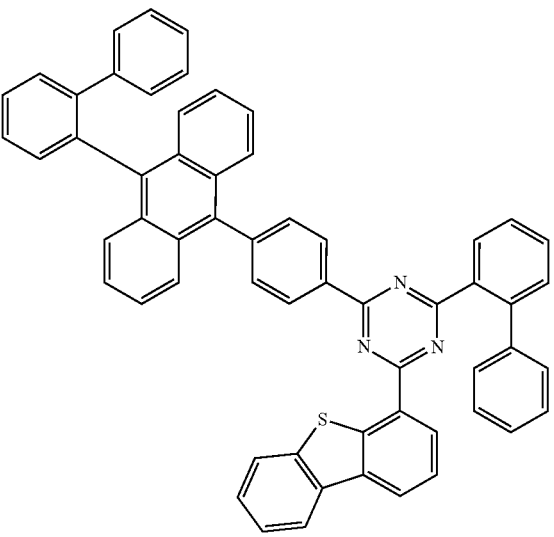
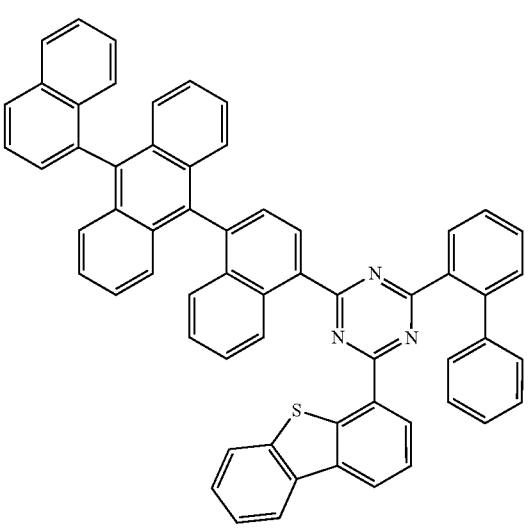
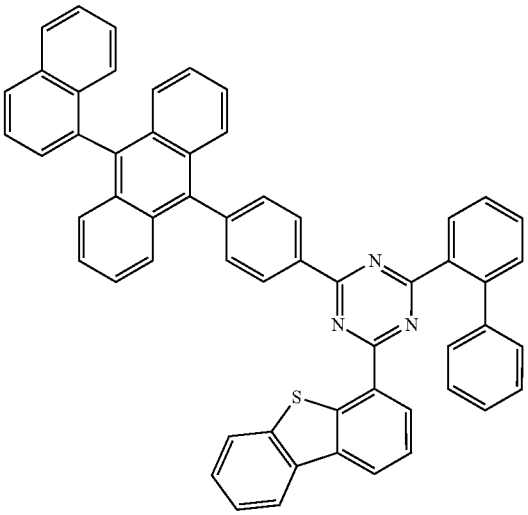

127
-continued
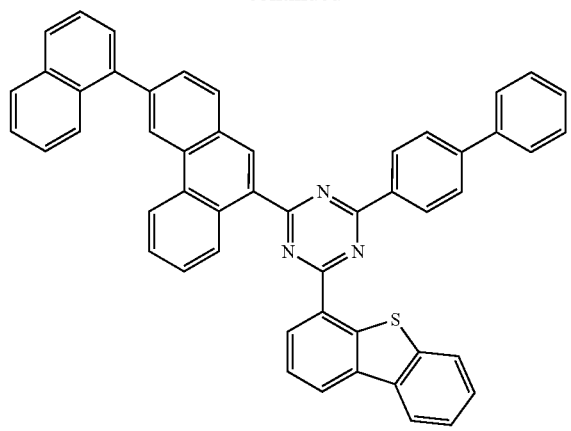
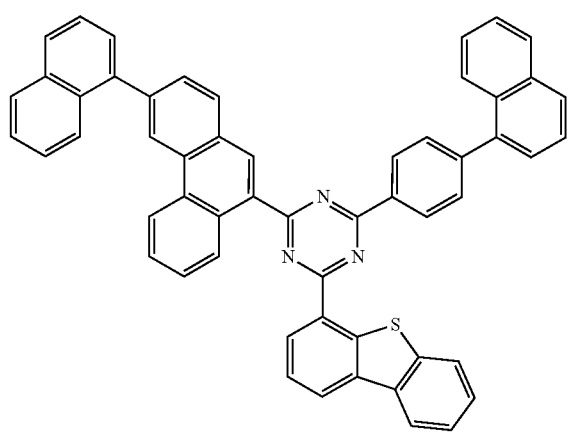
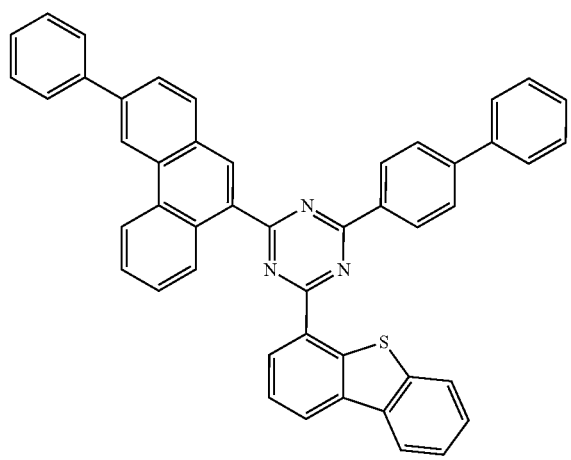
128
-continued
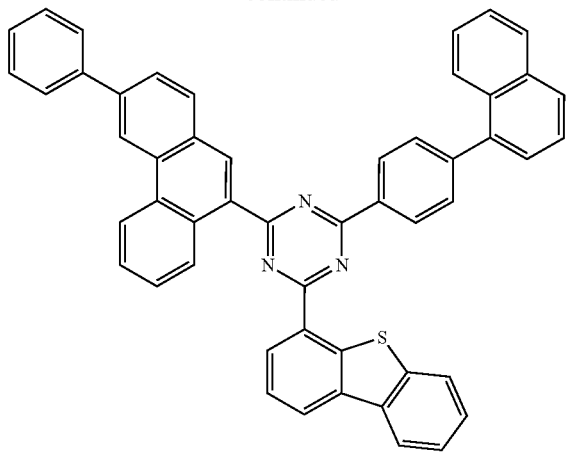
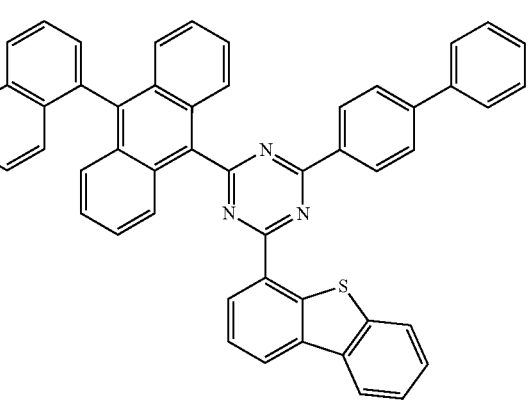
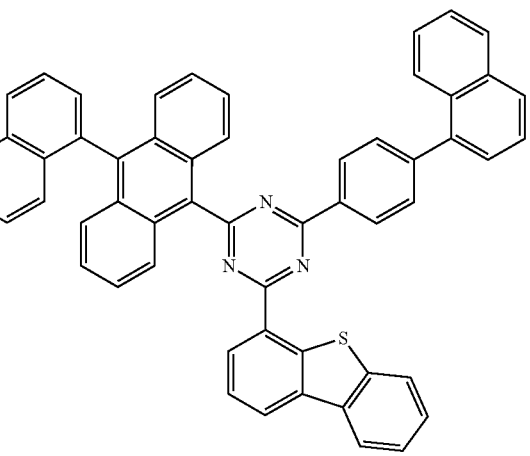
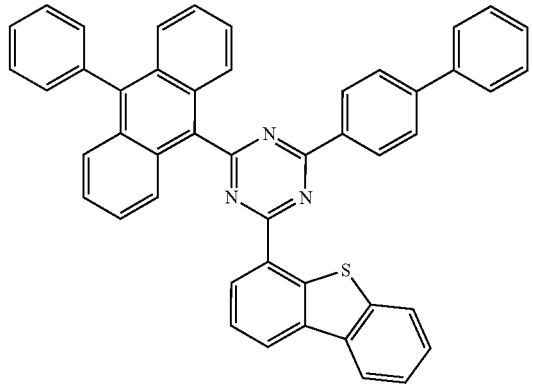

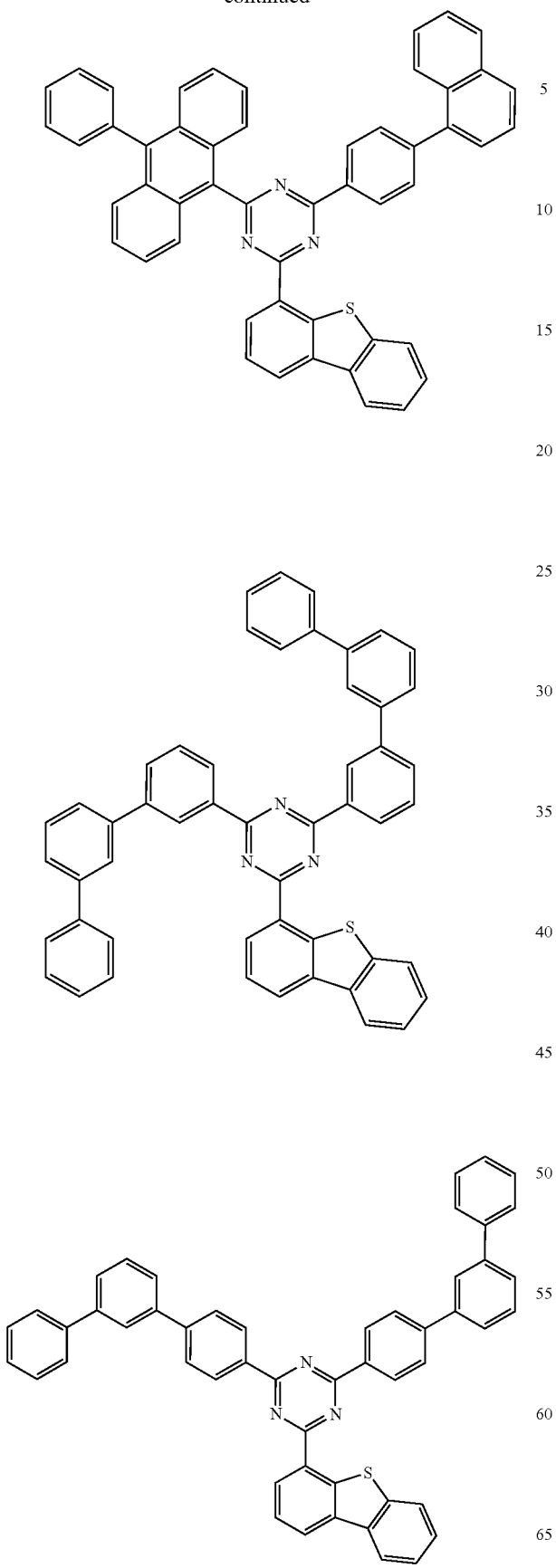
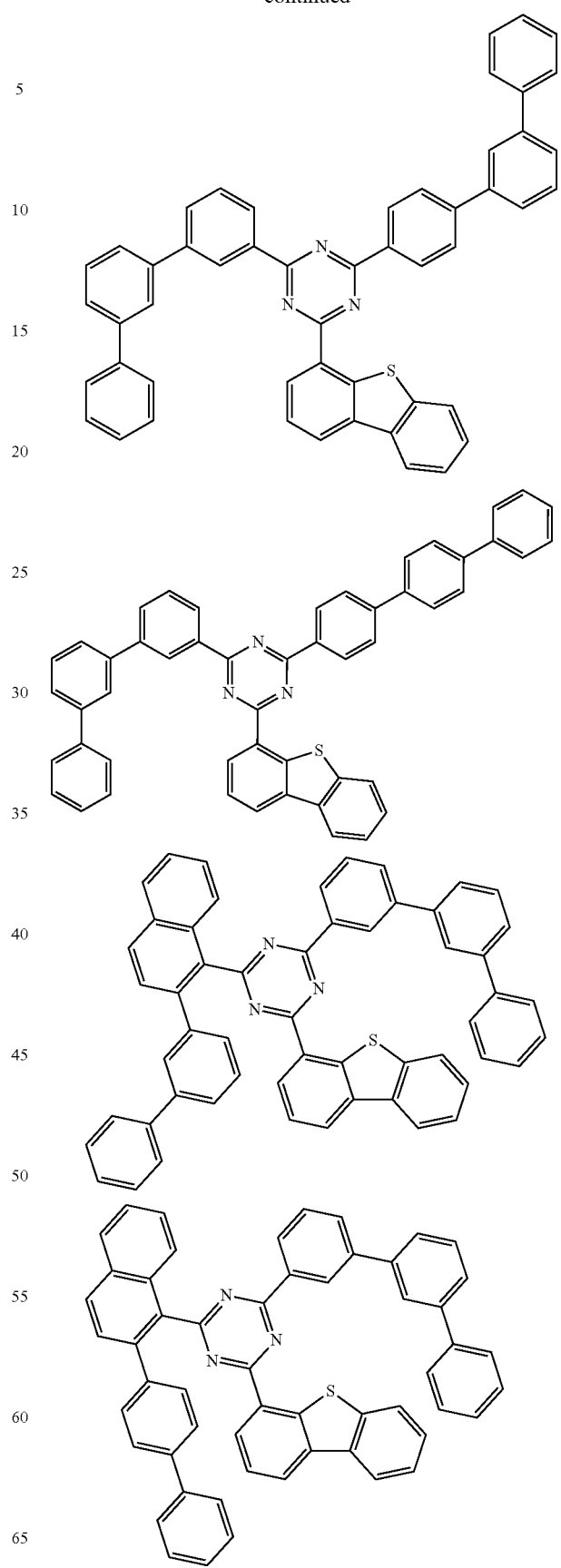

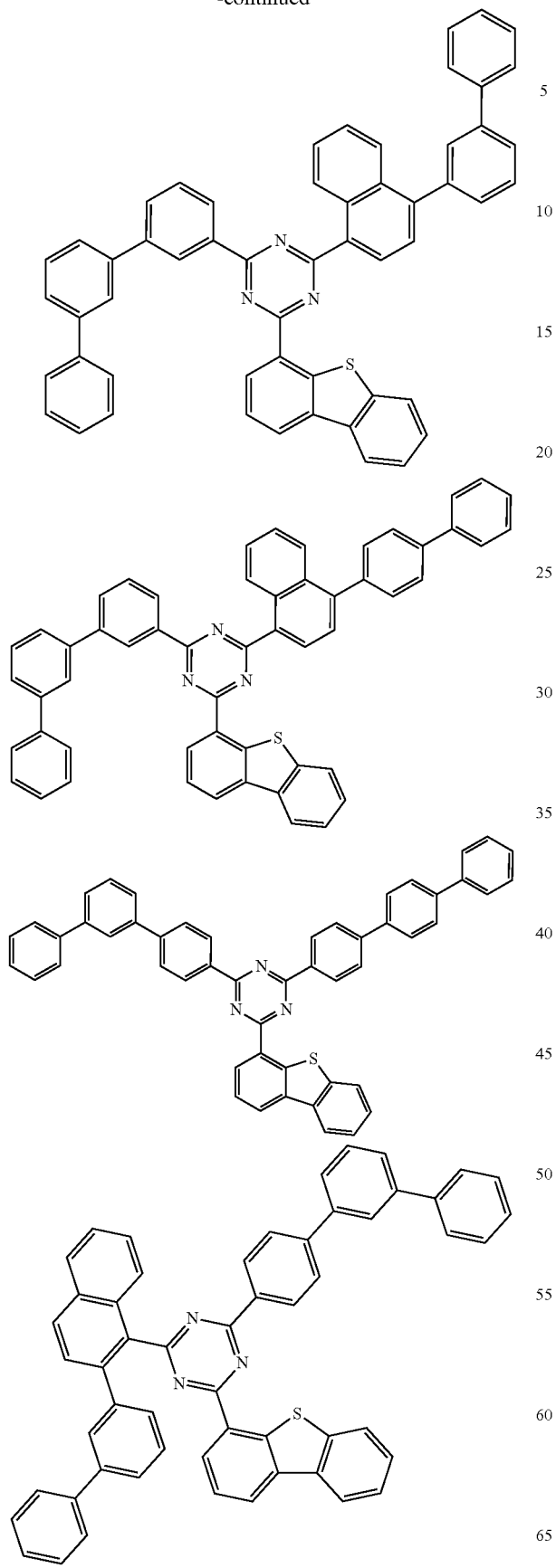
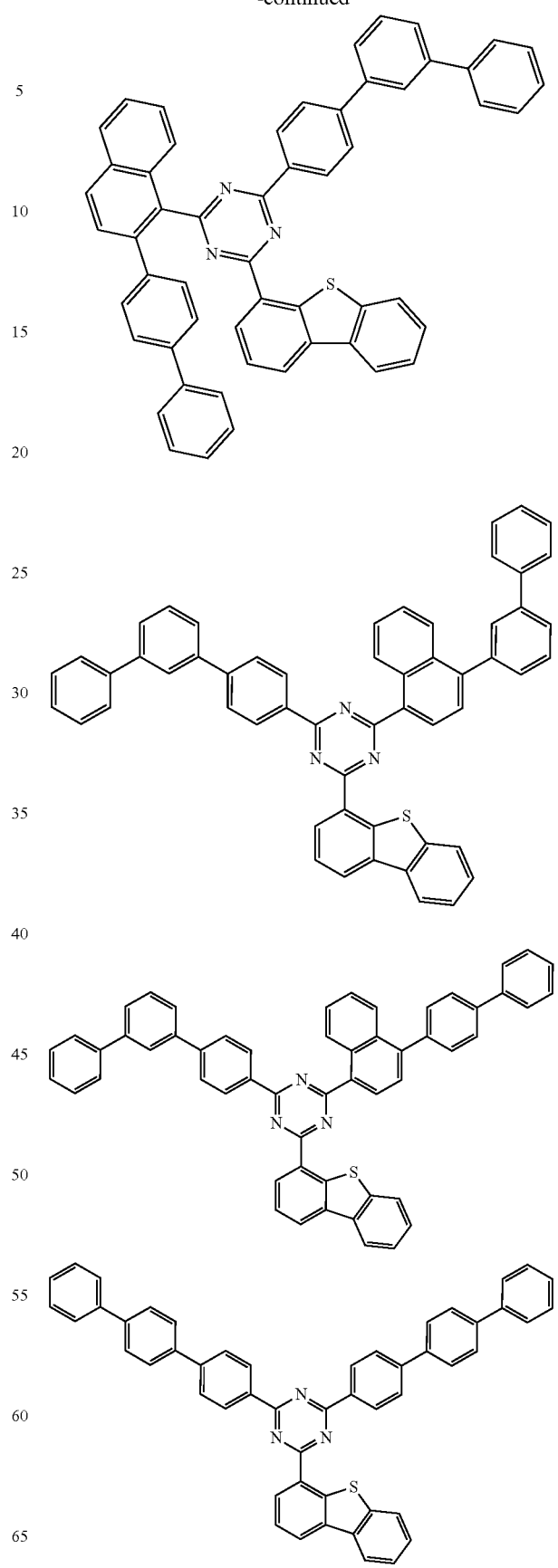

133
-continued
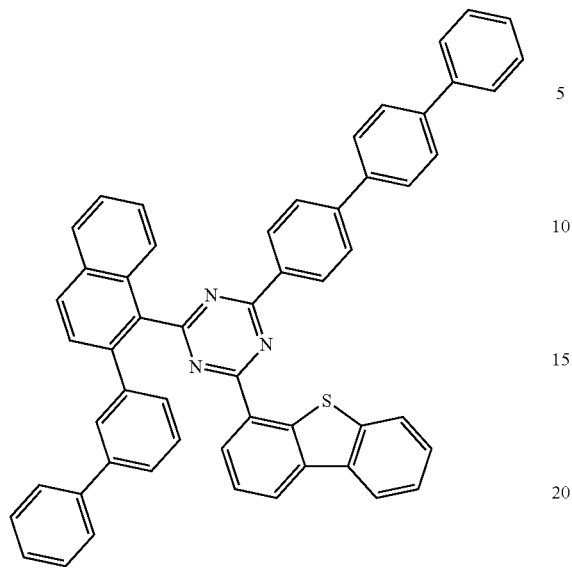
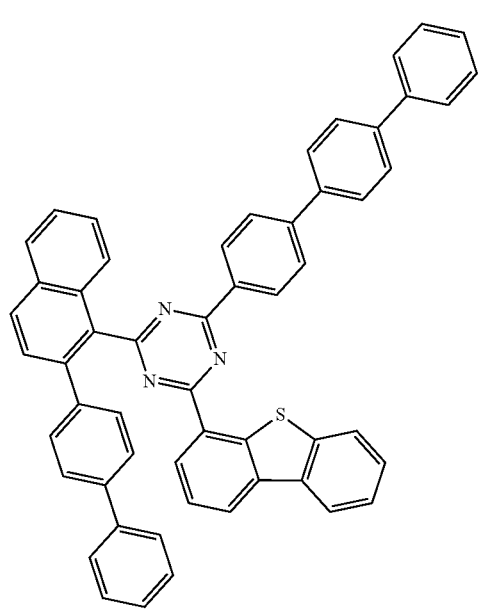
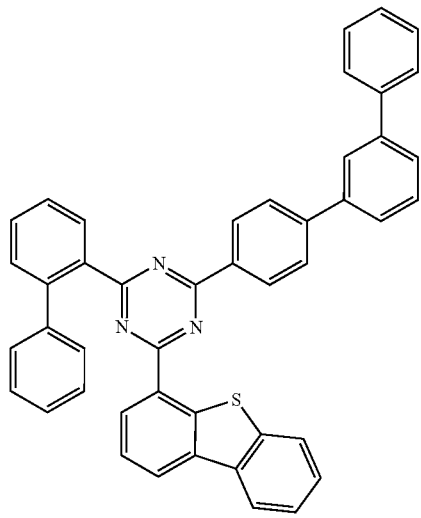
134
-continued
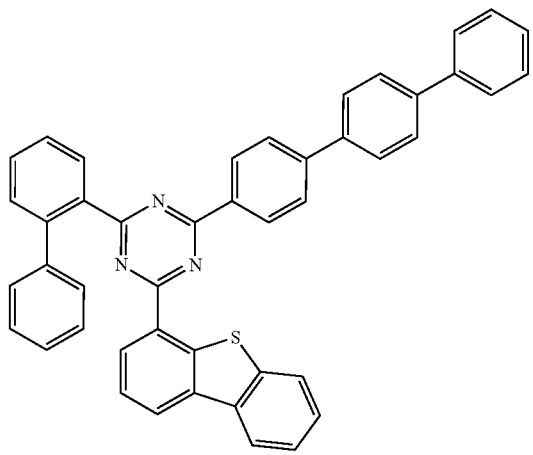
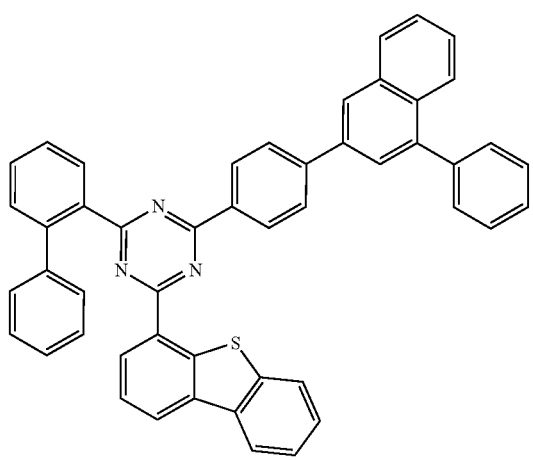
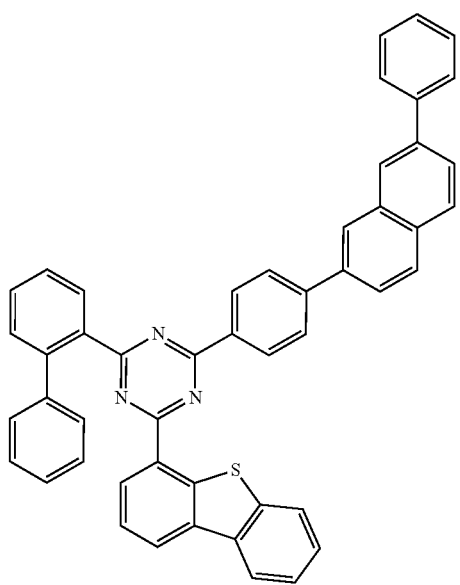

135
-continued
136
-continued
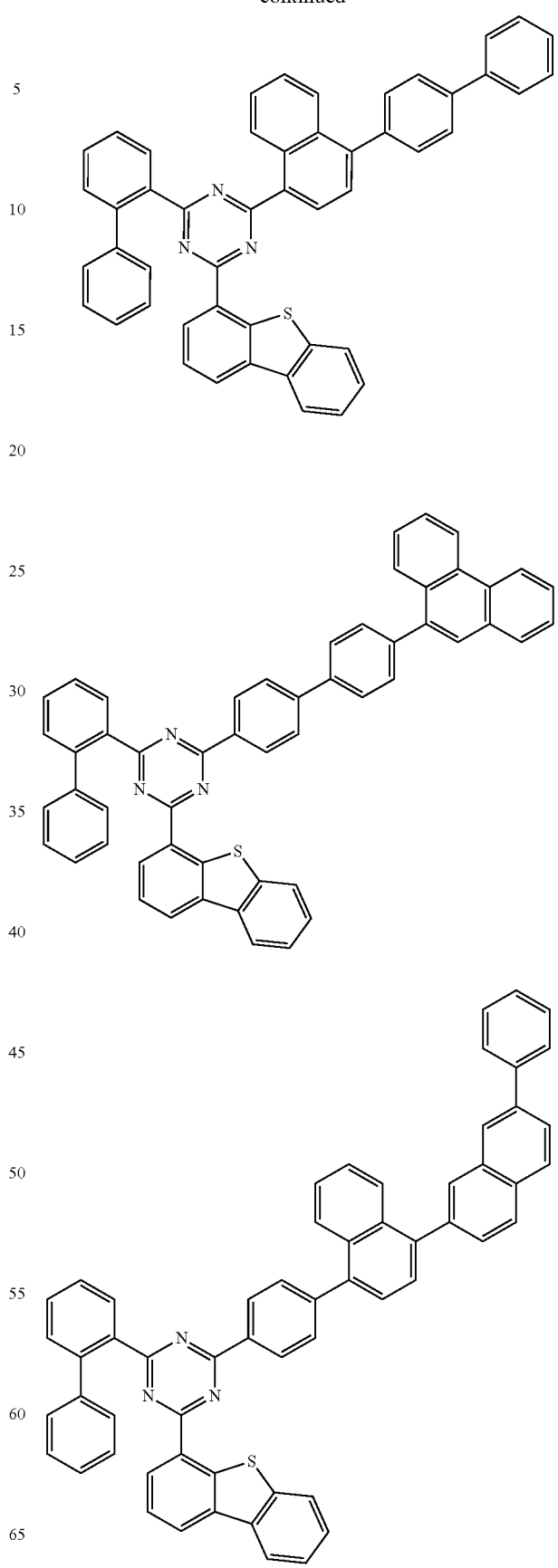

137
-continued
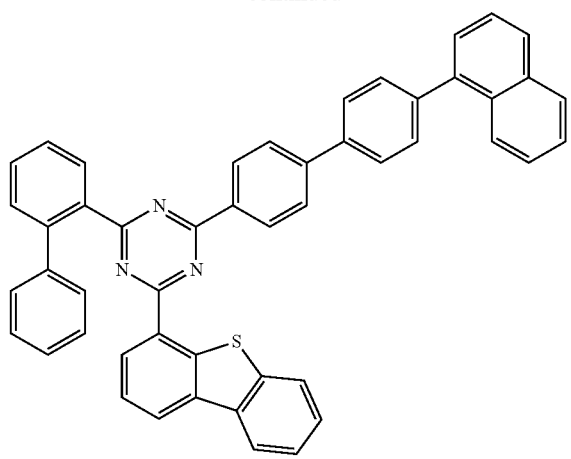
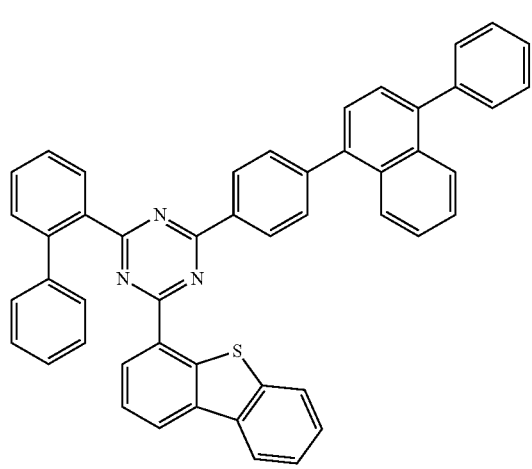
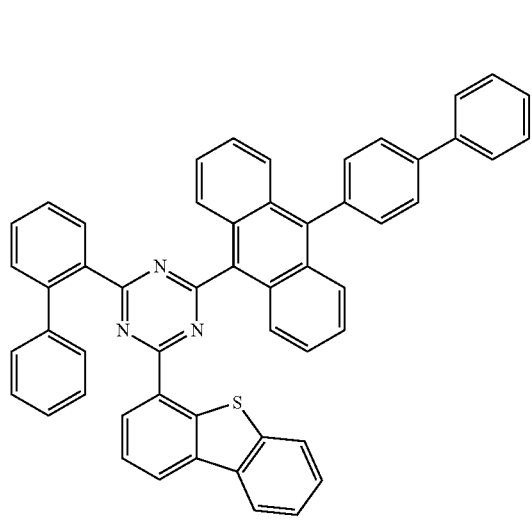
138
-continued
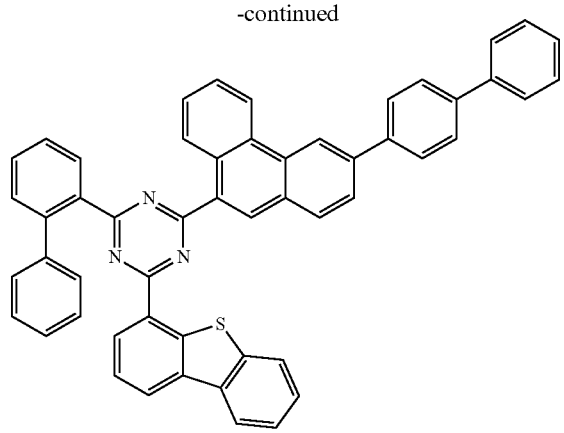
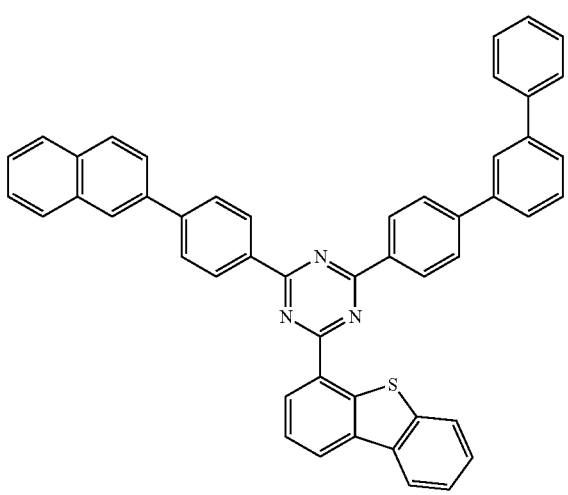
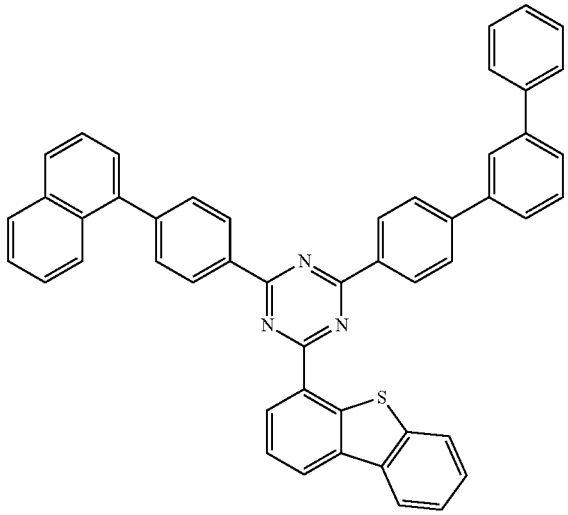

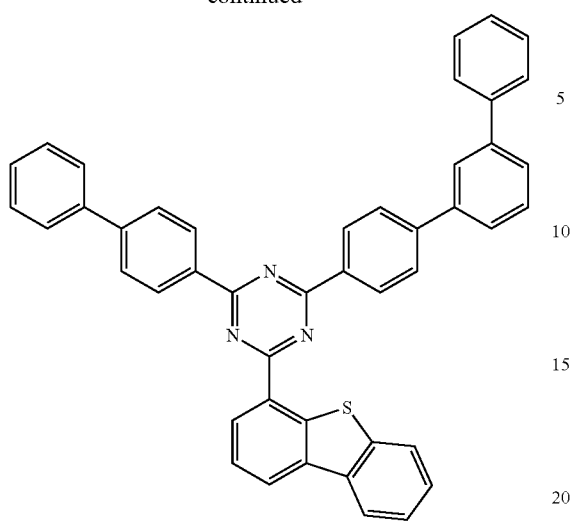
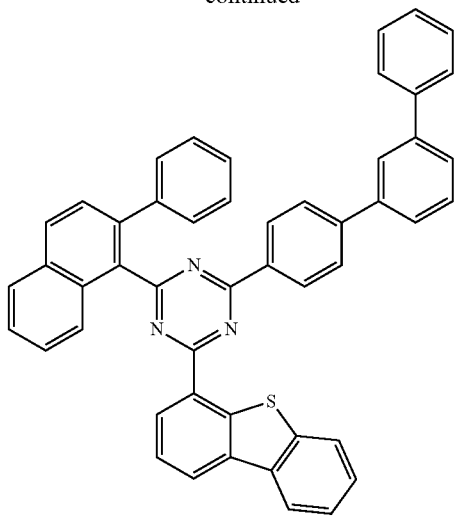
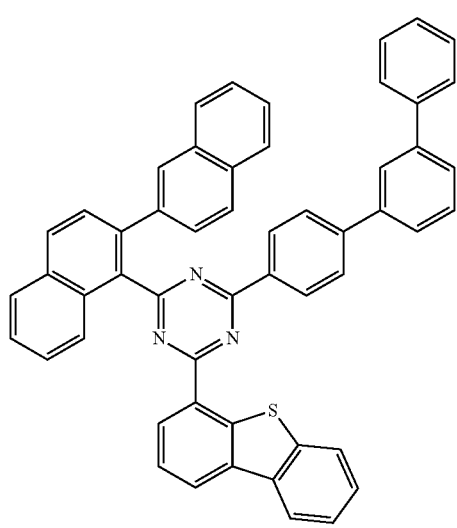
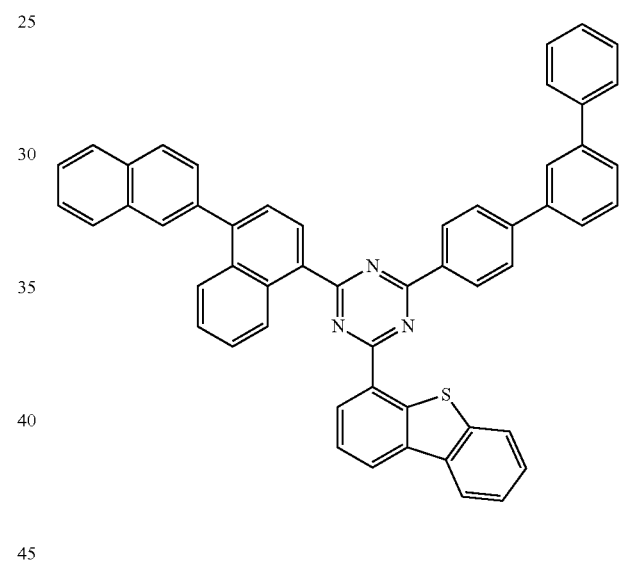
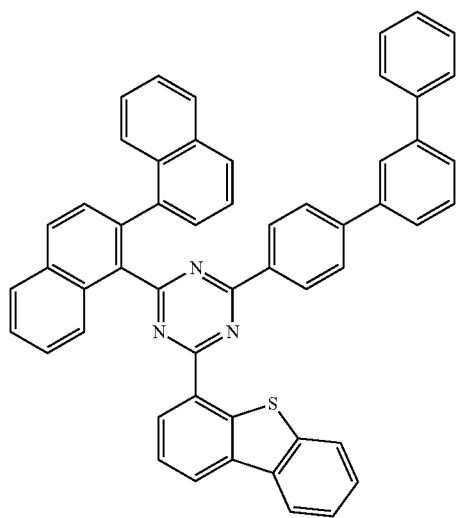
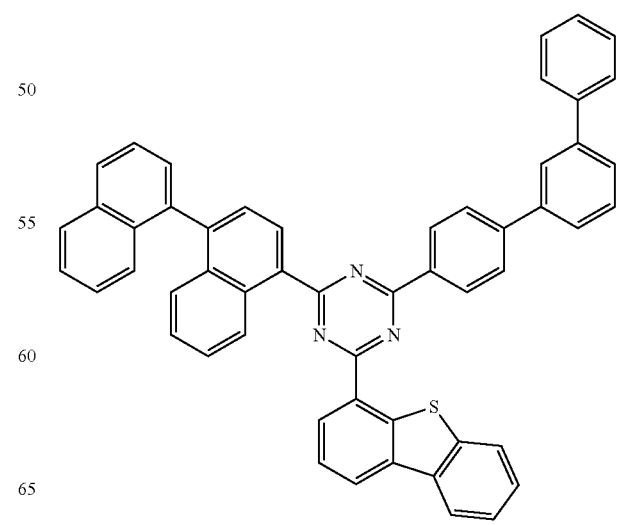

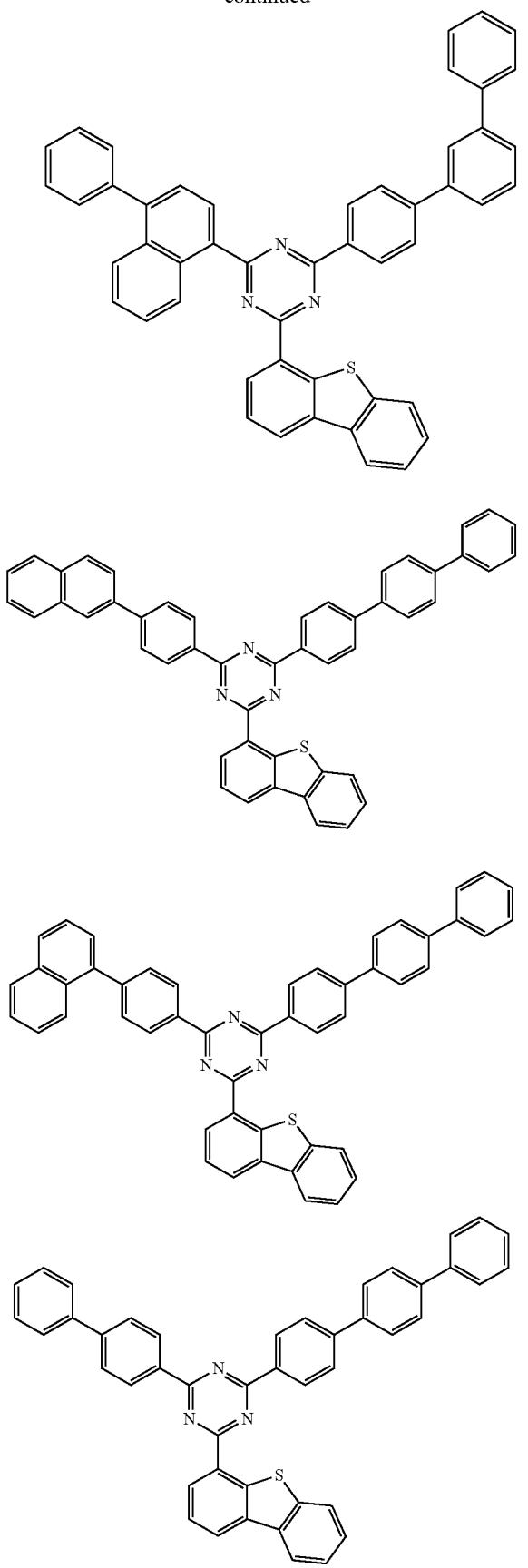
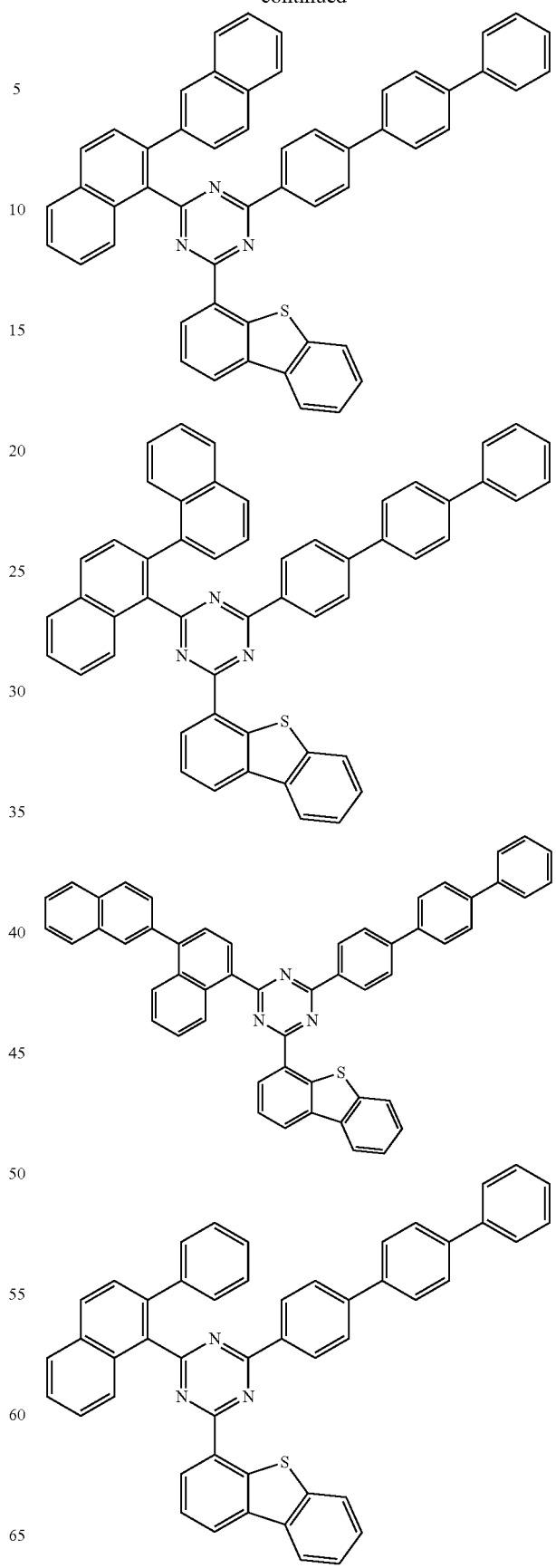

143
-continued
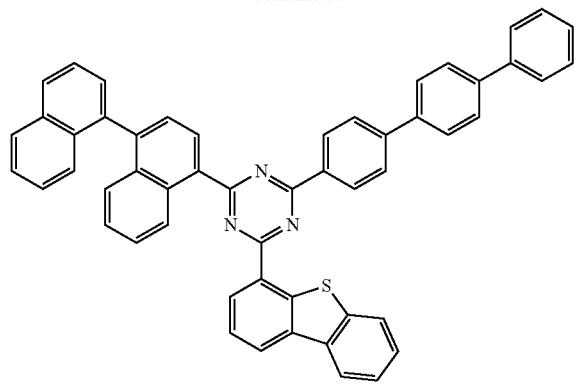
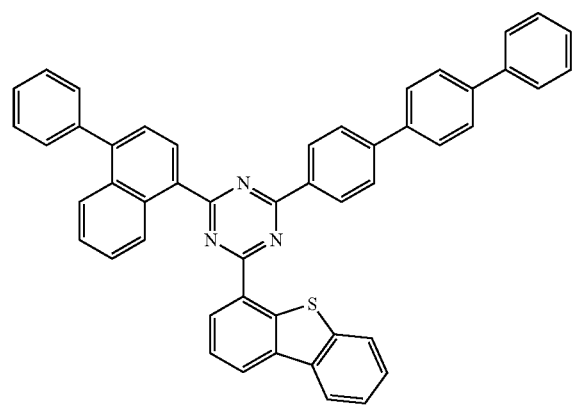
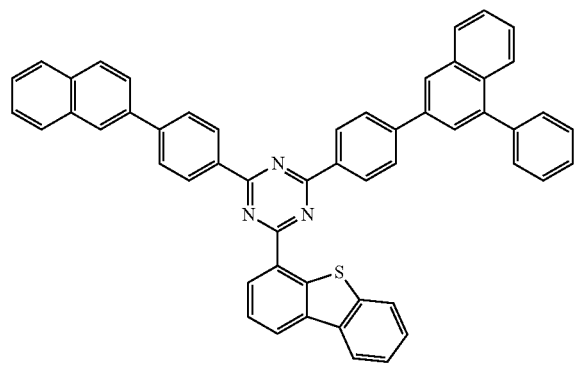
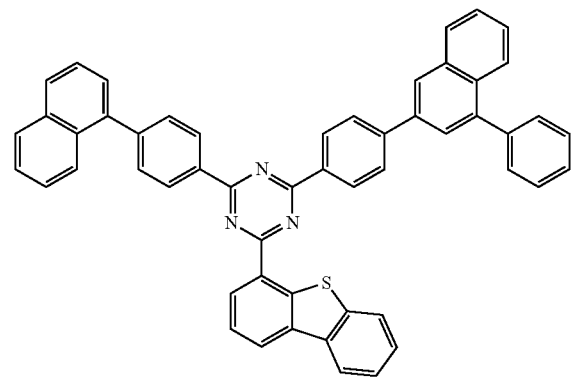
144
-continued
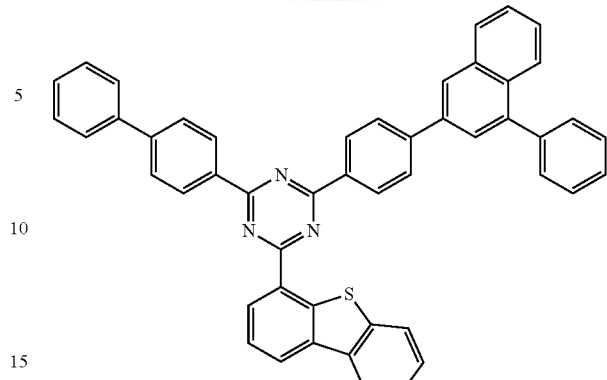
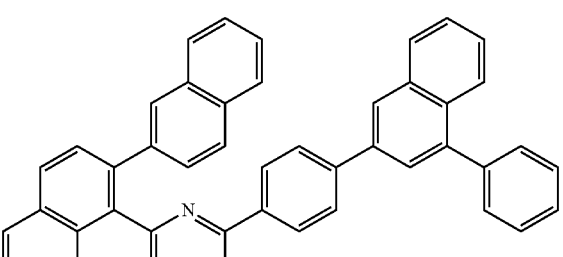
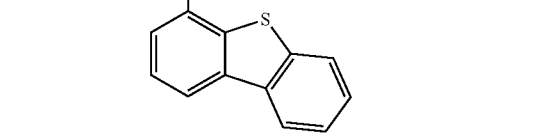
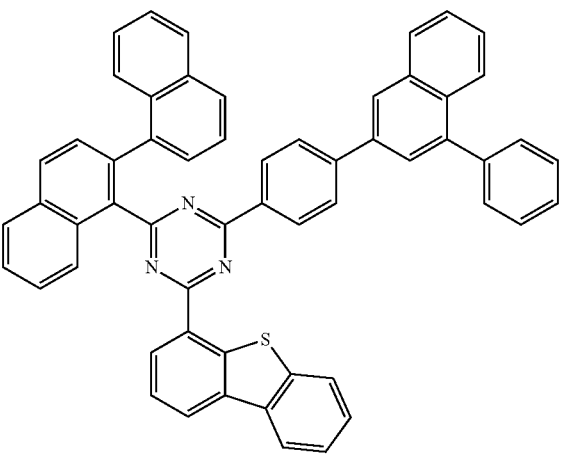

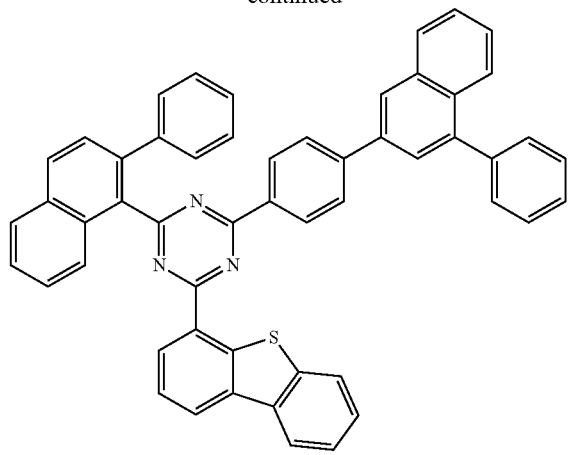
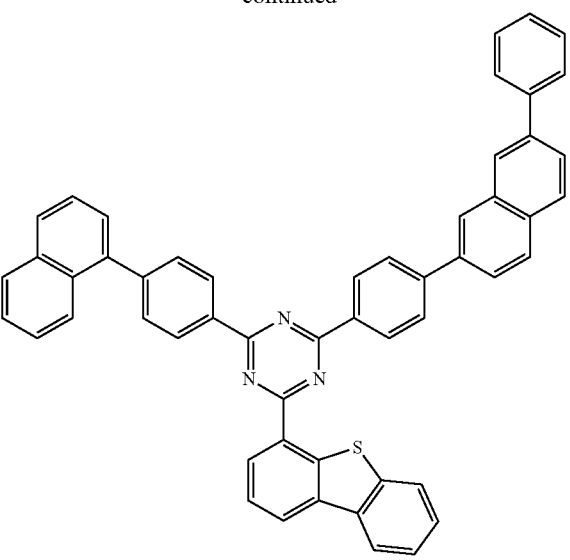
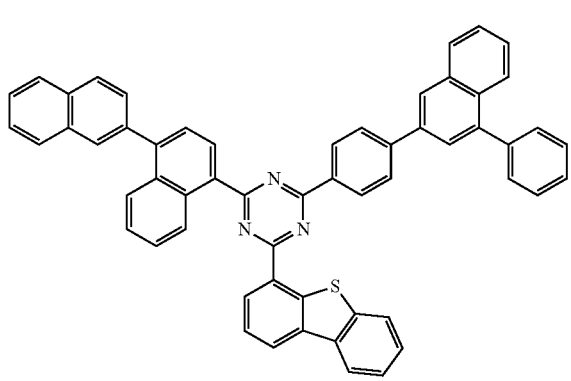
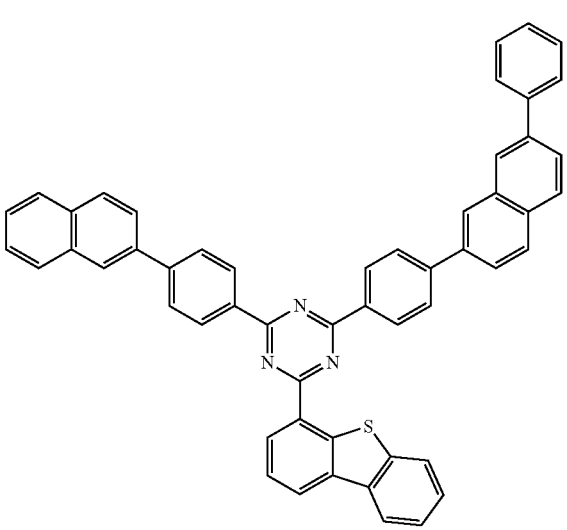
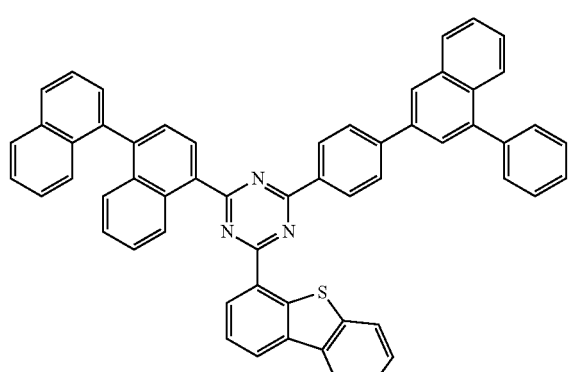
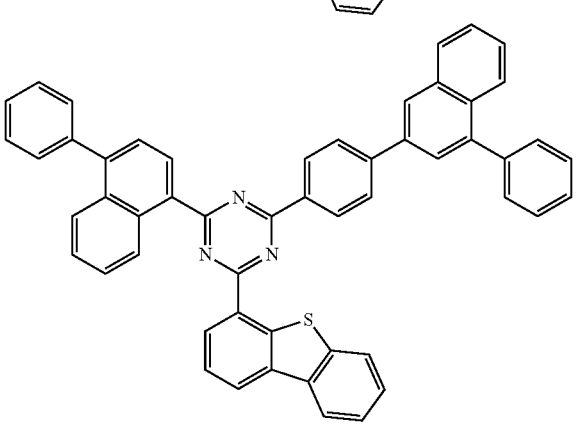
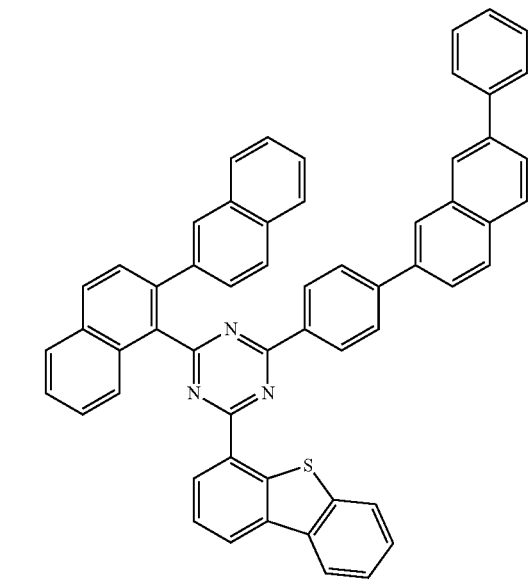

147
-continued
148
-continued
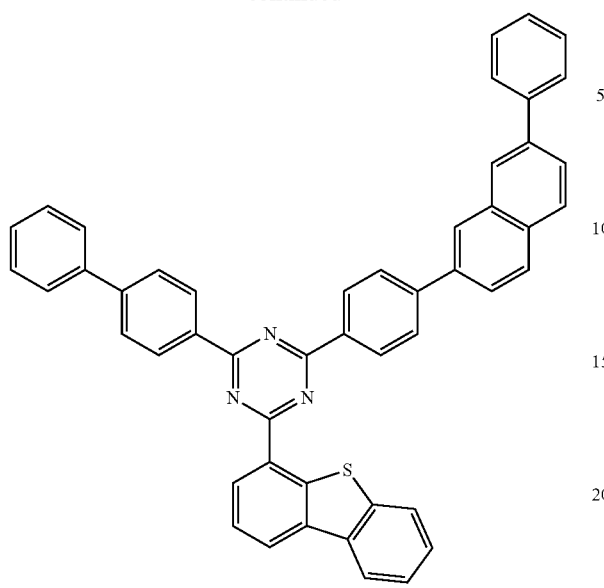
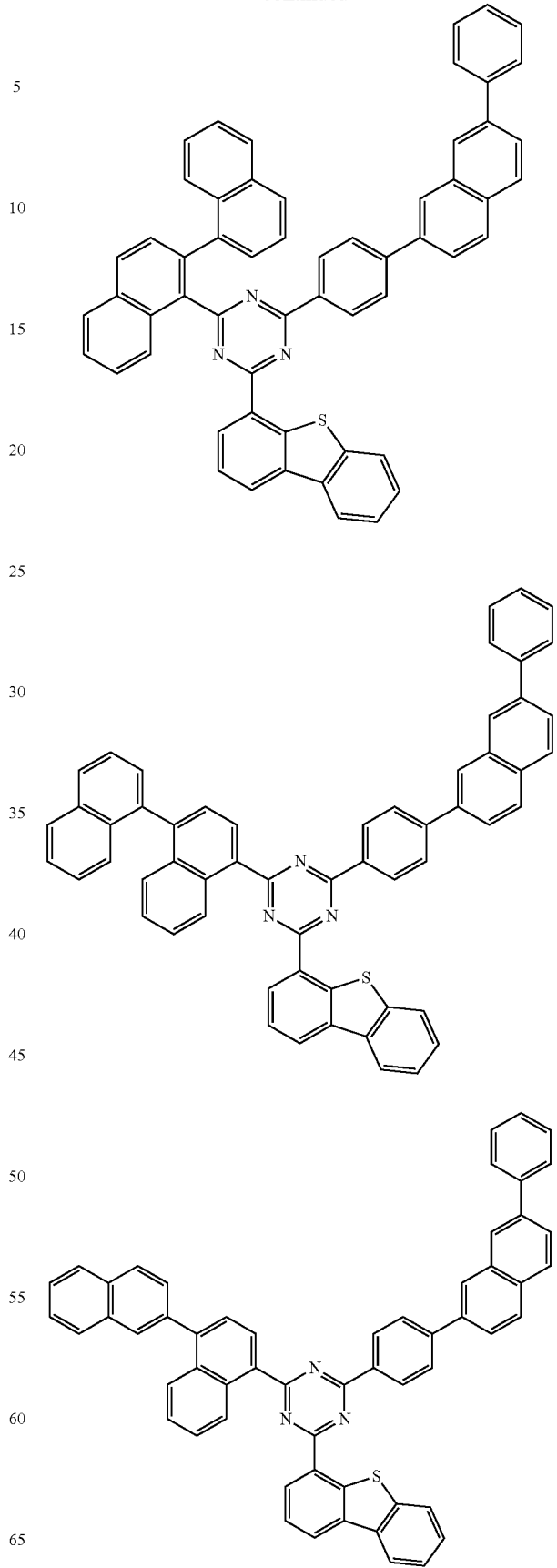

149
-continued
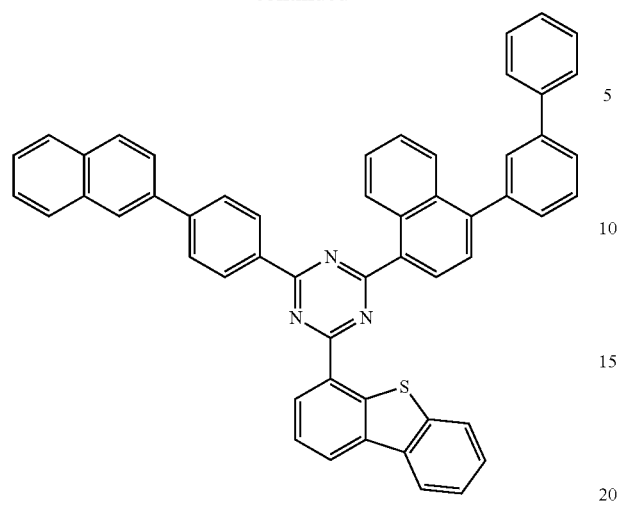
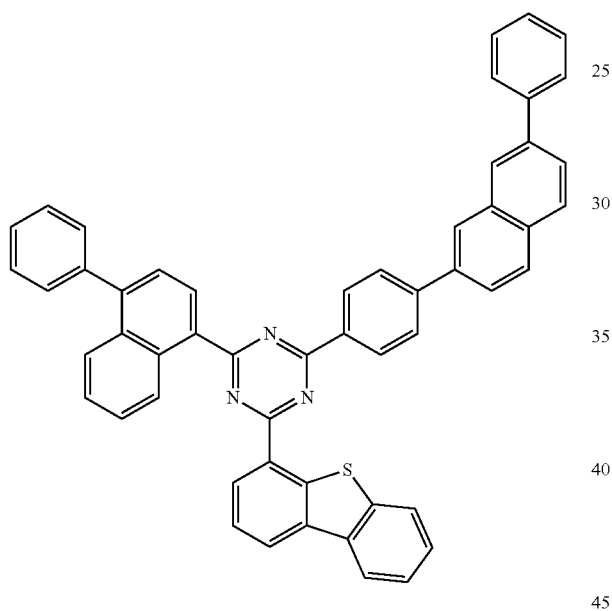
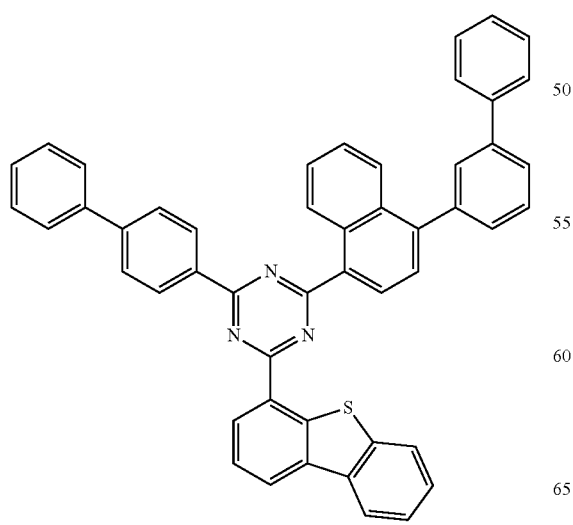
150
-continued
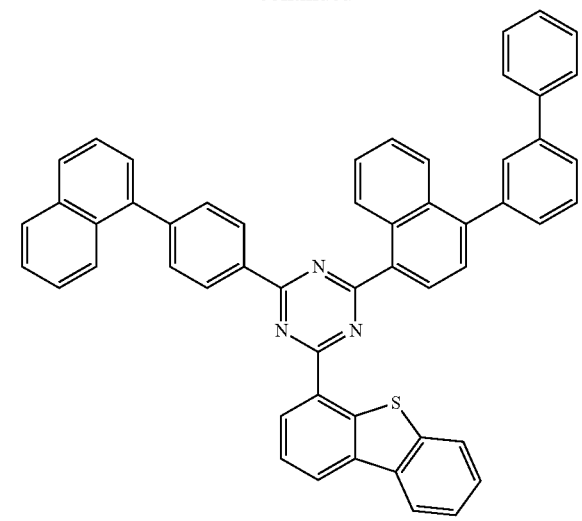
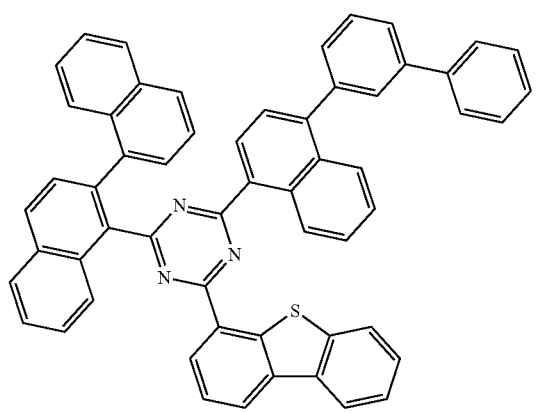
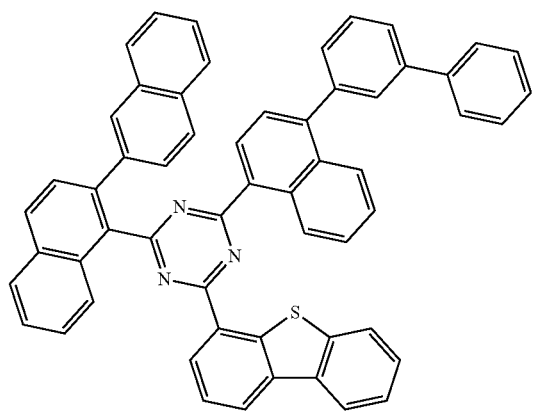

151
-continued
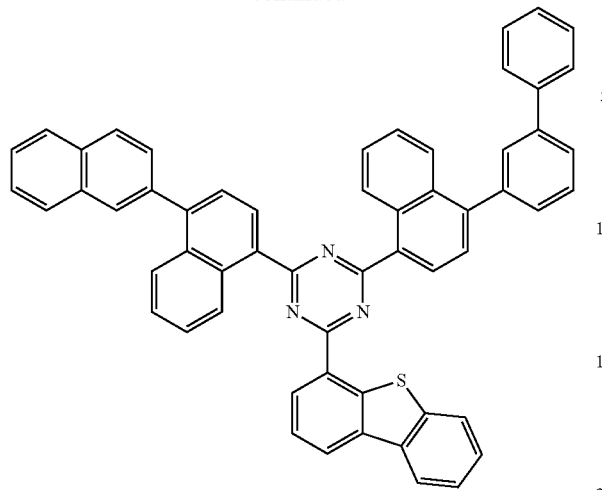
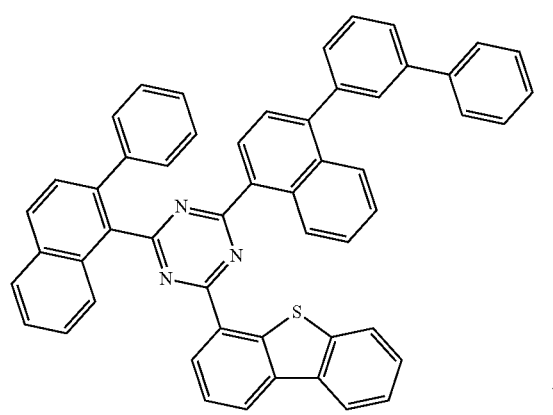
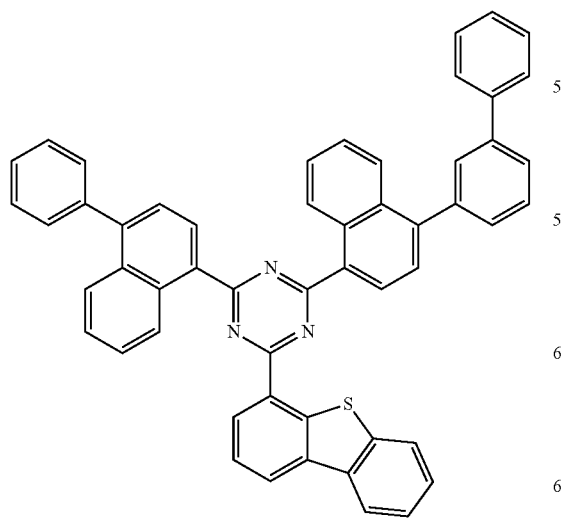
152
-continued
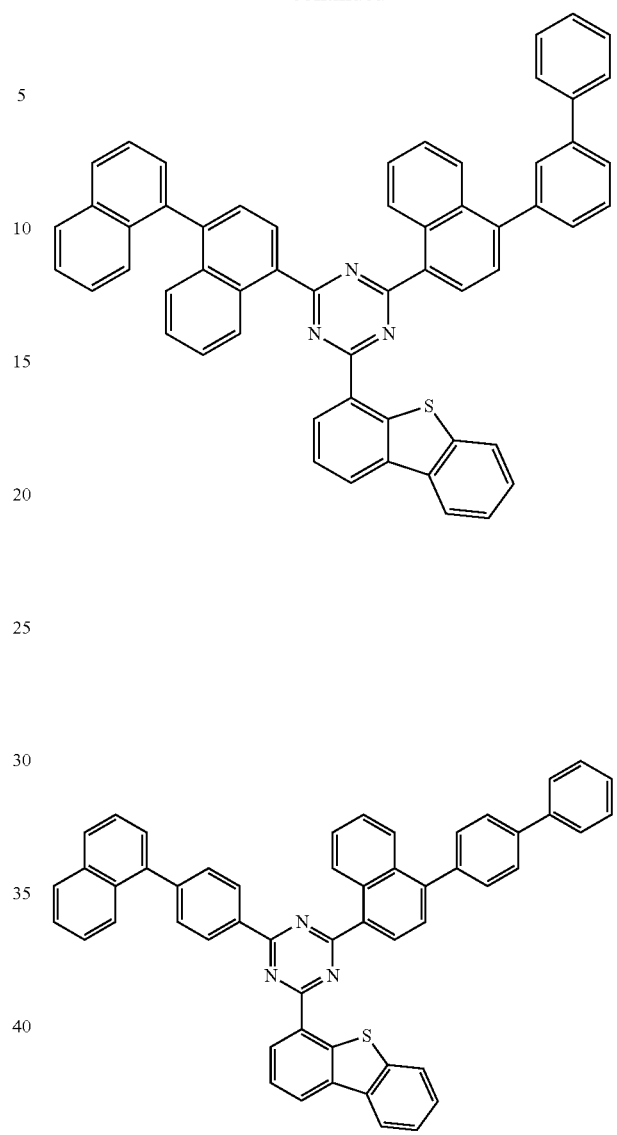

153
-continued
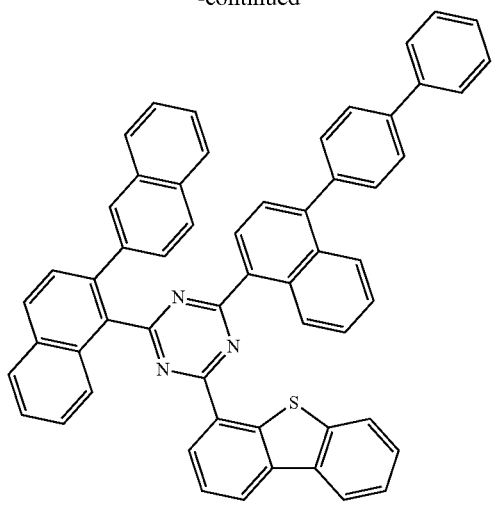
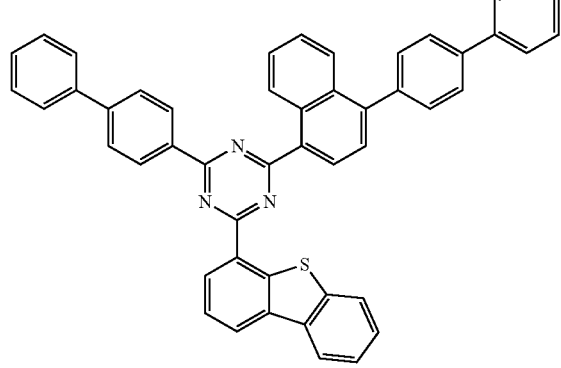
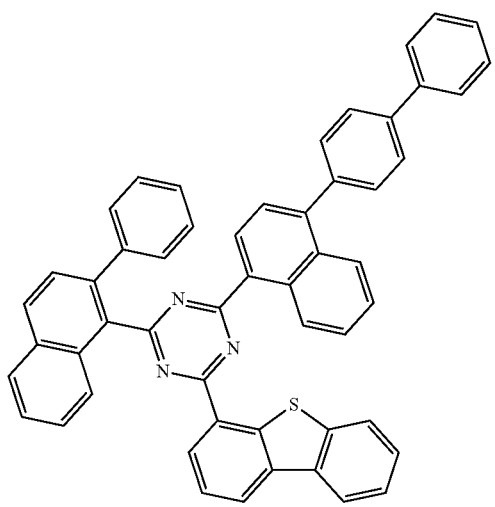
154
-continued
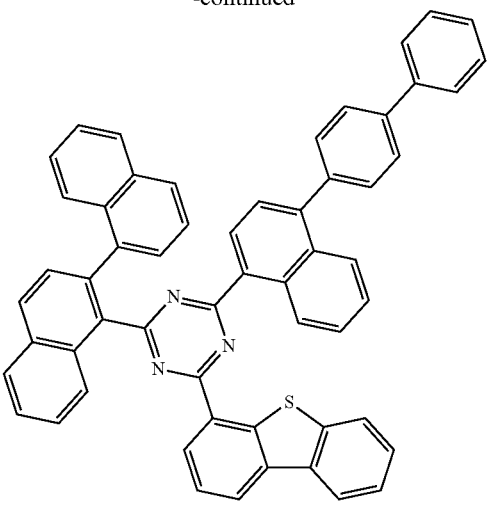
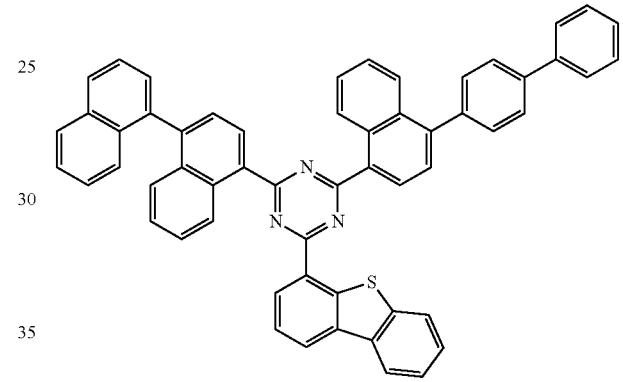
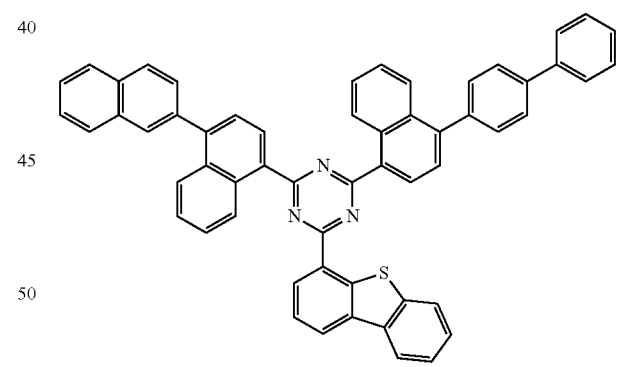
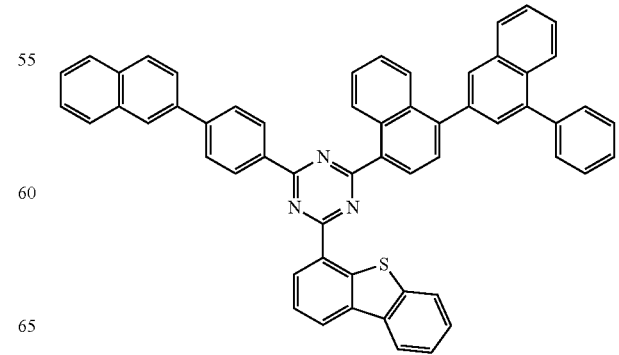

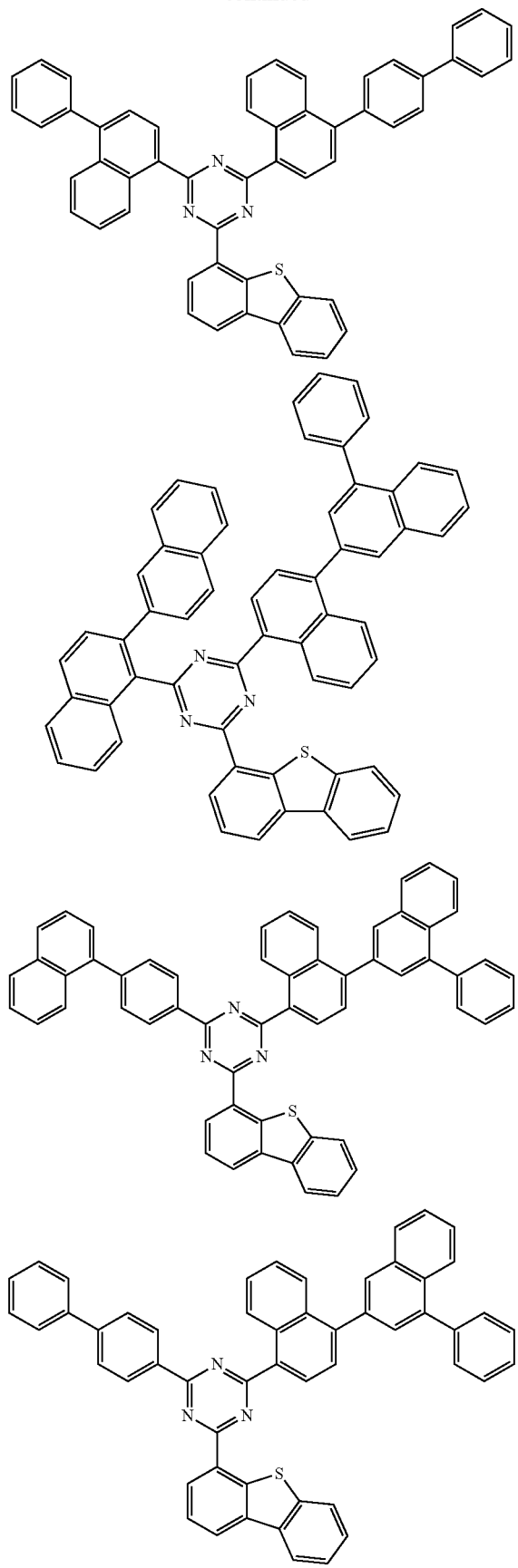

-continued
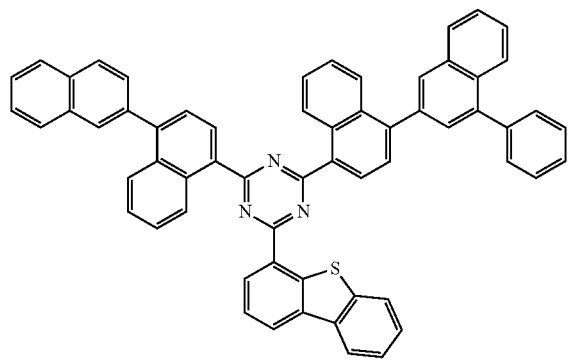
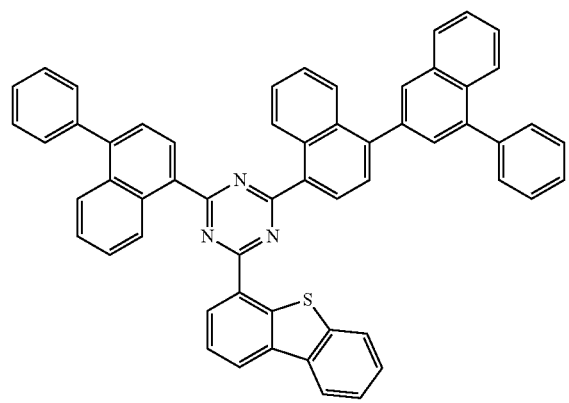
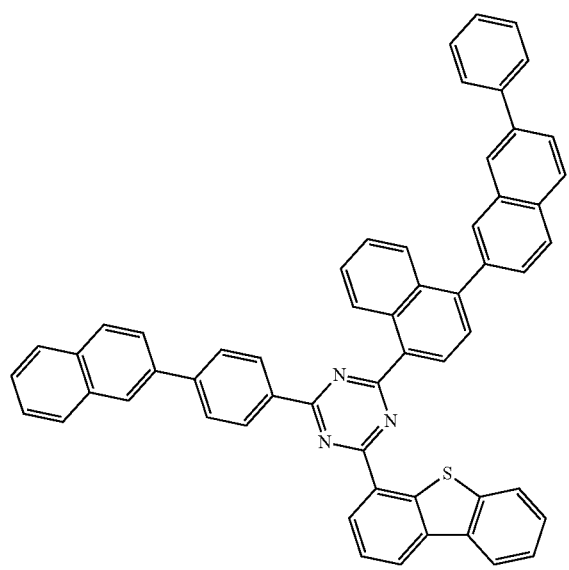
-continued
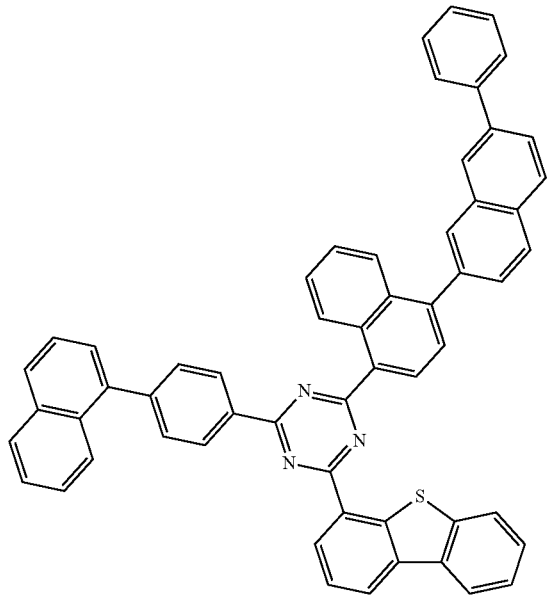
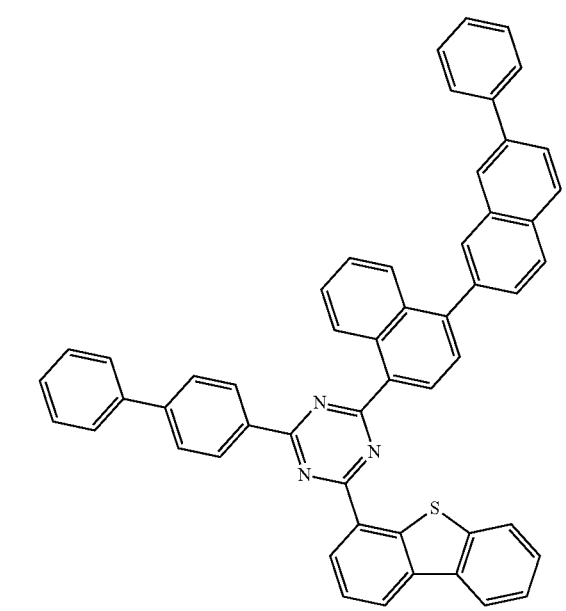
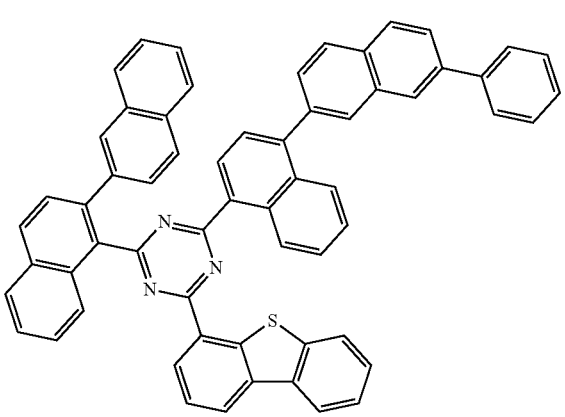

159
-continued
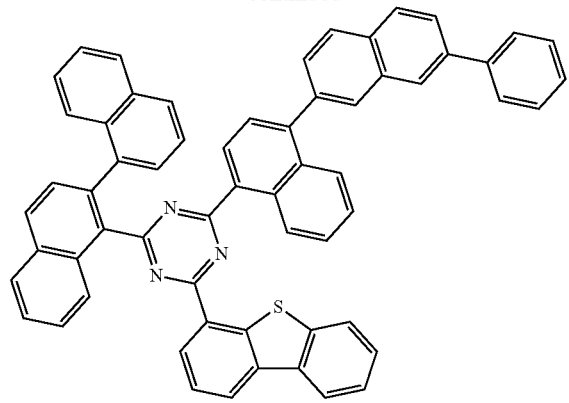
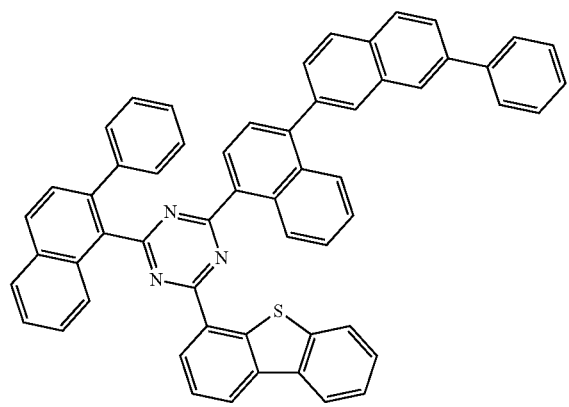
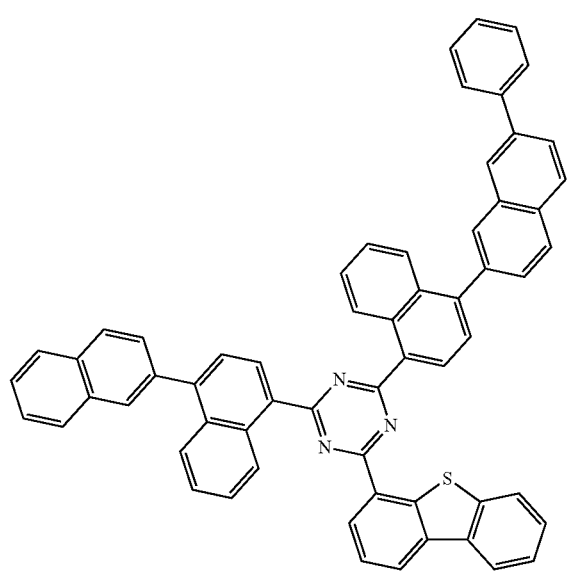
160
-continued
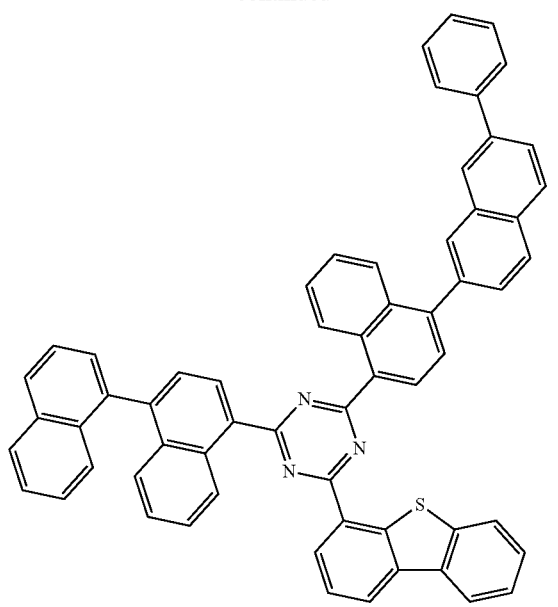
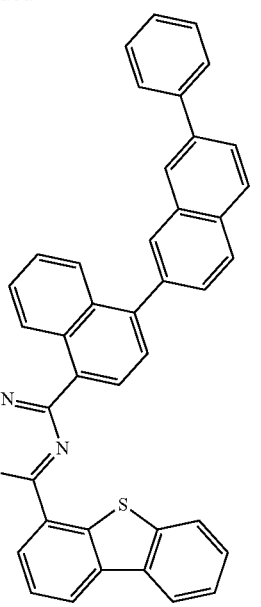
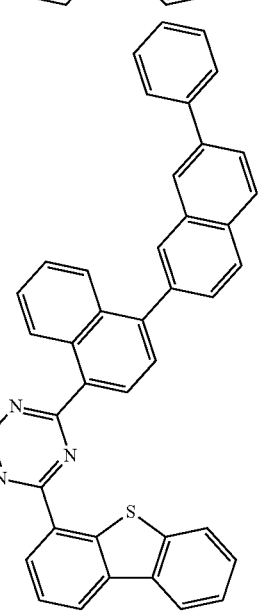

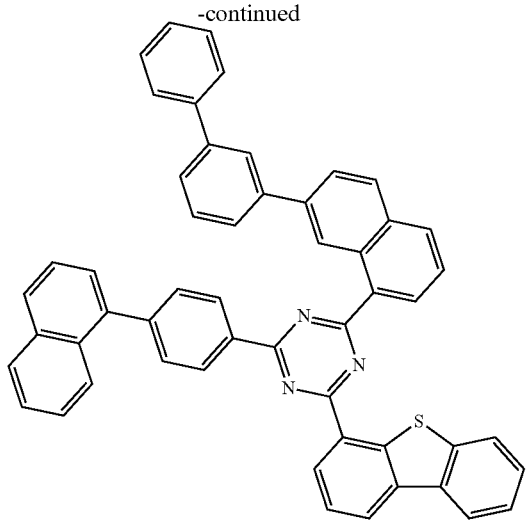
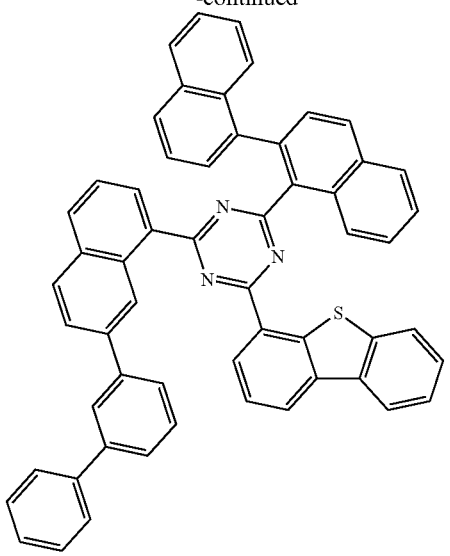
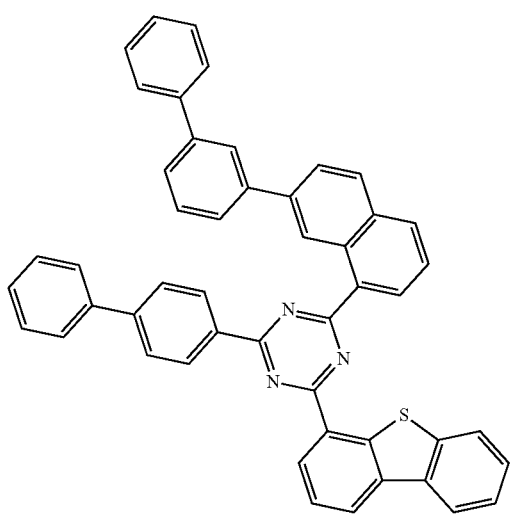
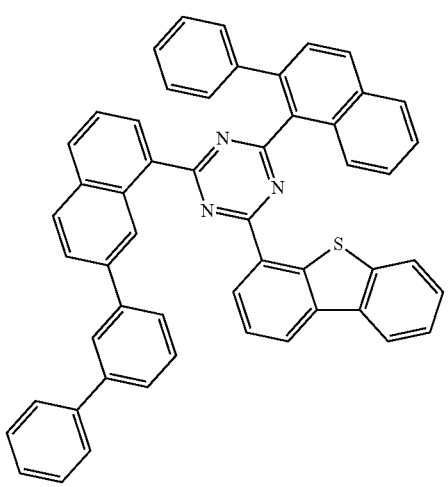
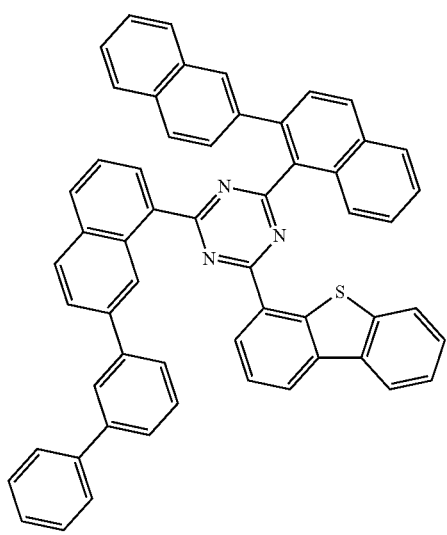
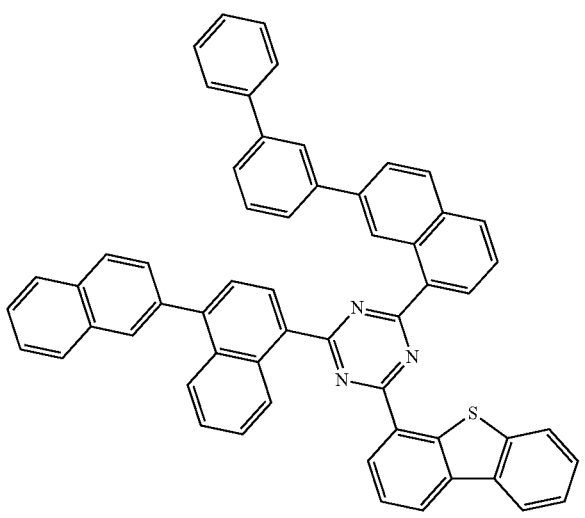

163
-continued
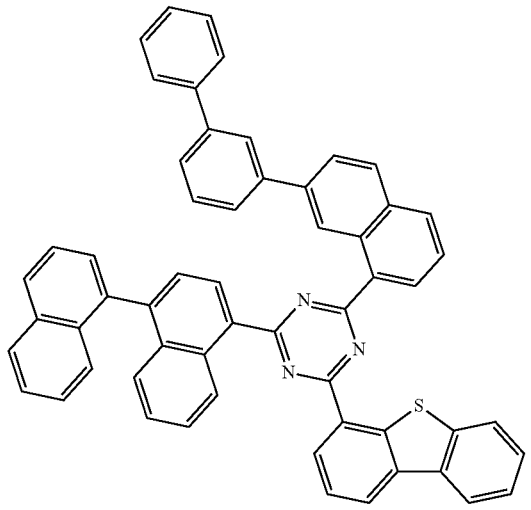
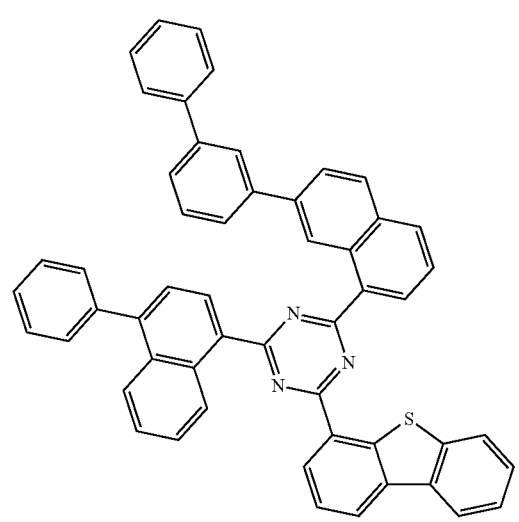
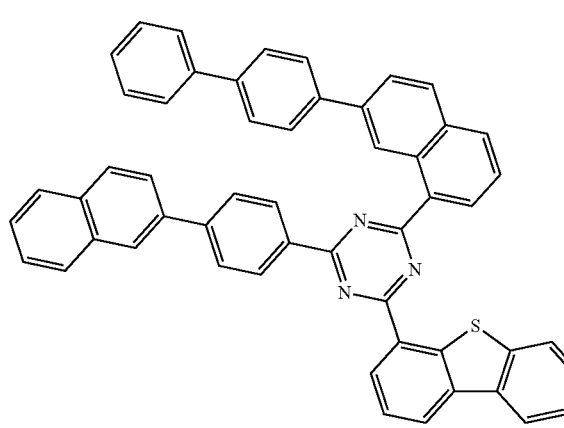
164
-continued
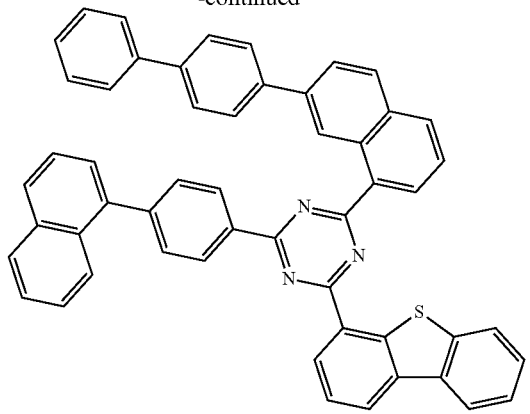
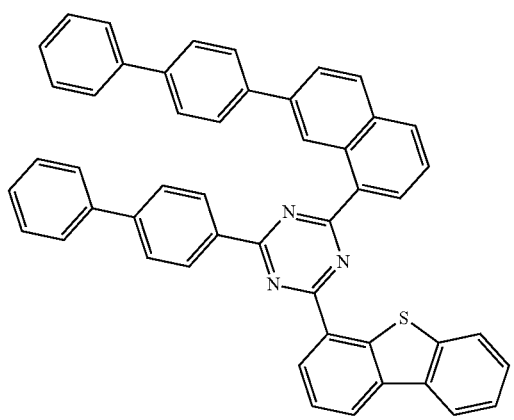
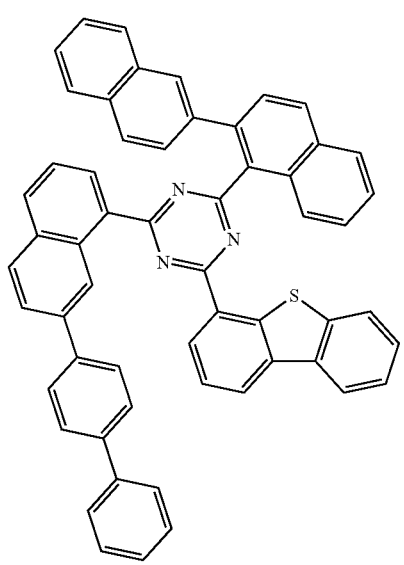

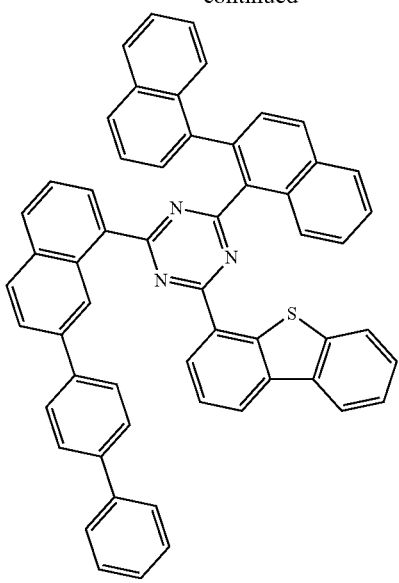
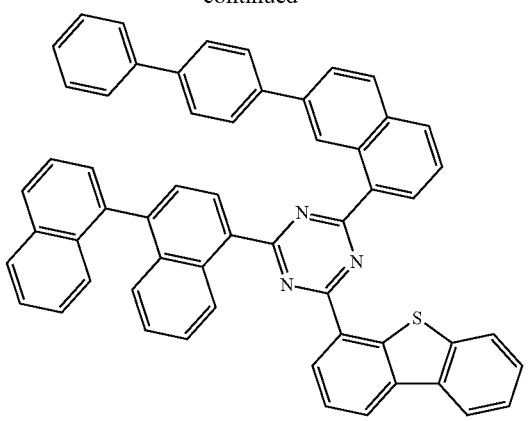
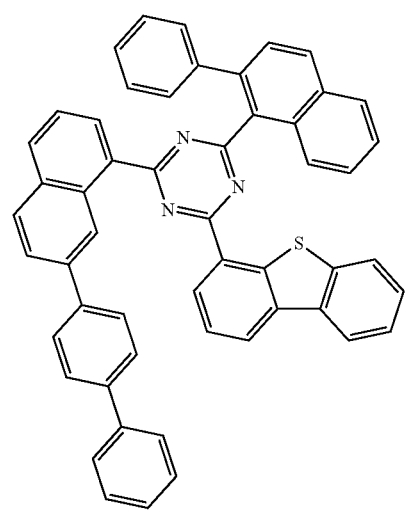
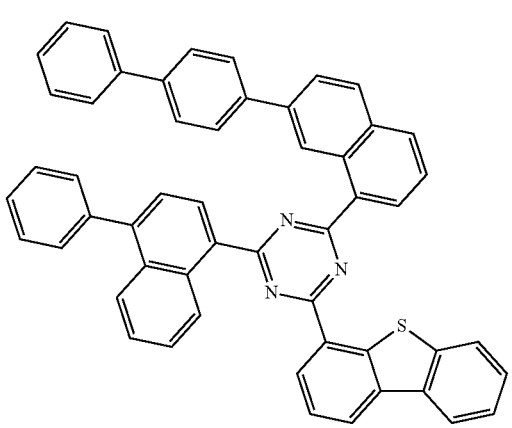
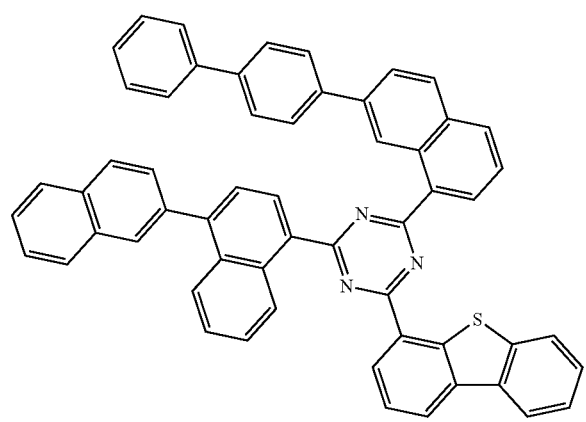
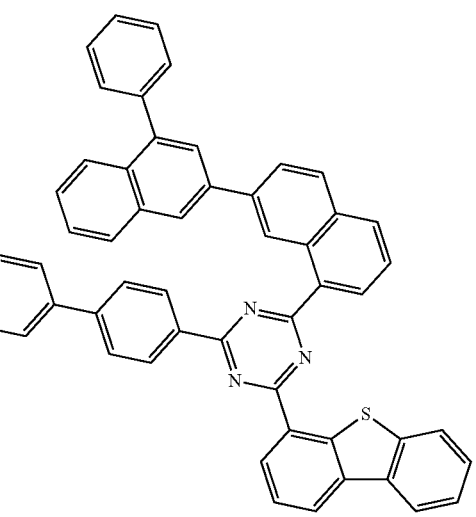

167
-continued
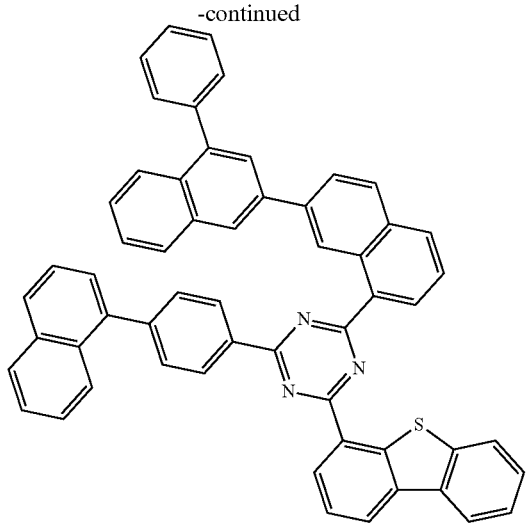
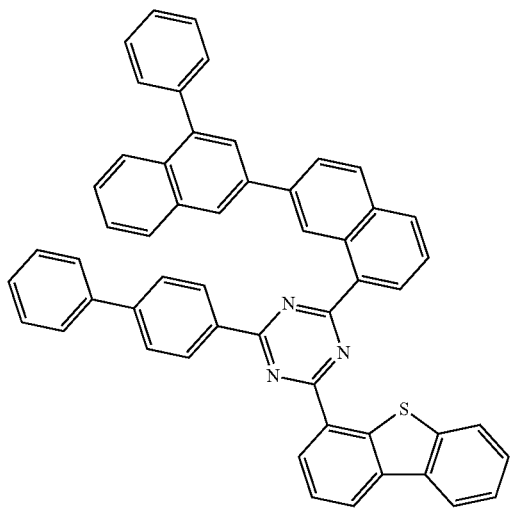
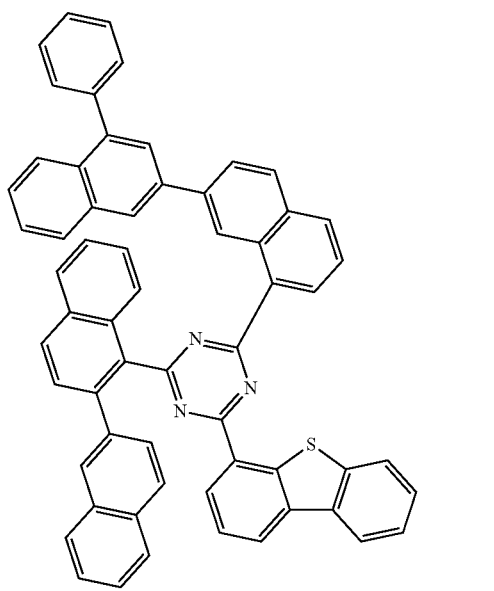
168
-continued
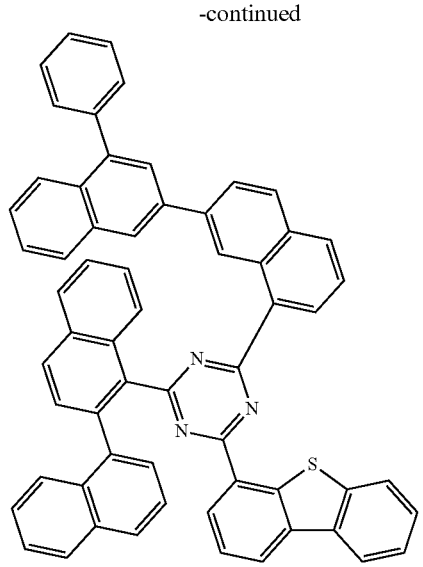
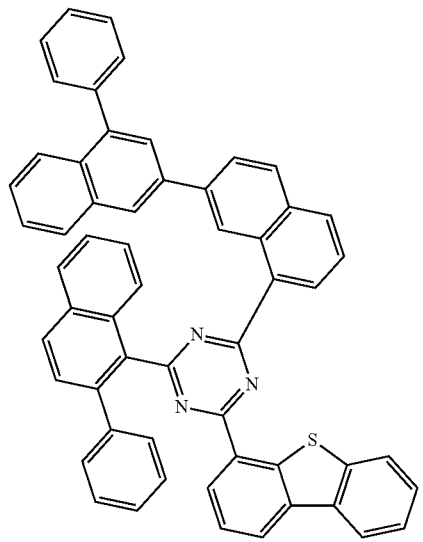
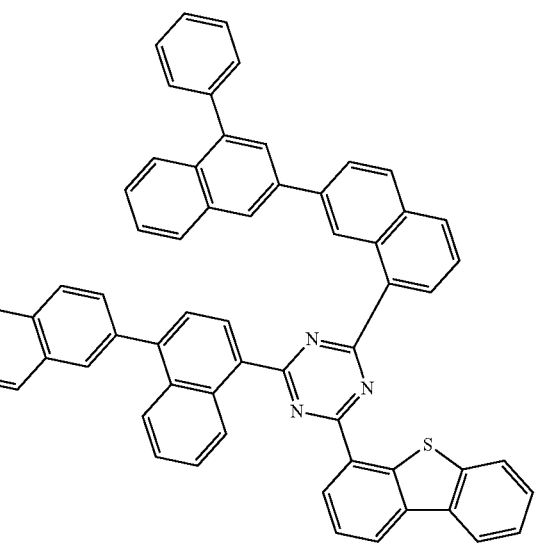

169
-continued
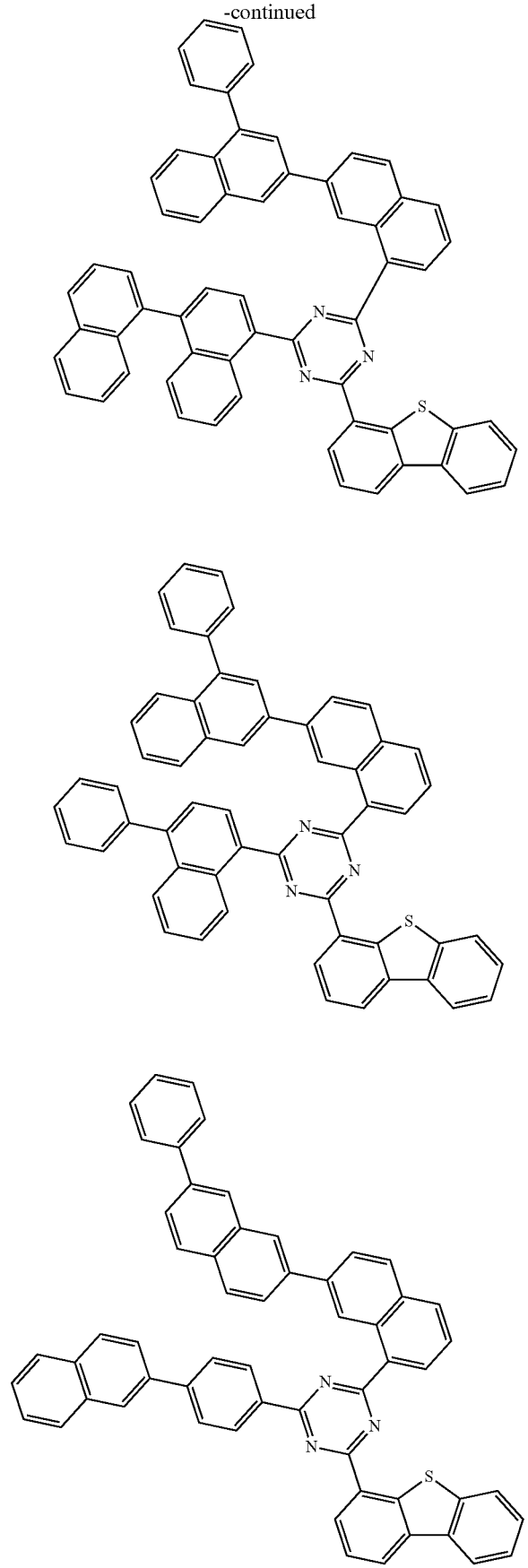
170
-continued

171
-continued
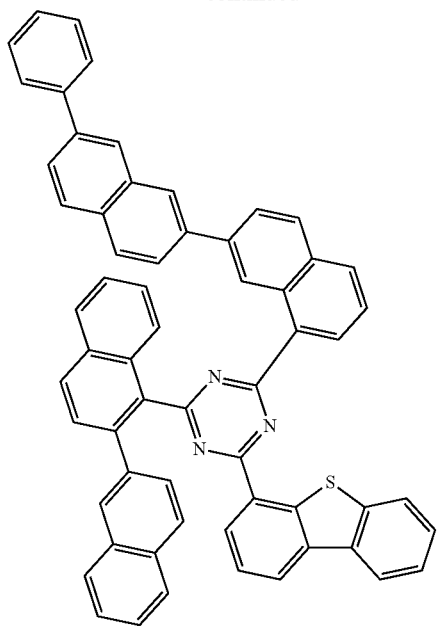
172
-continued
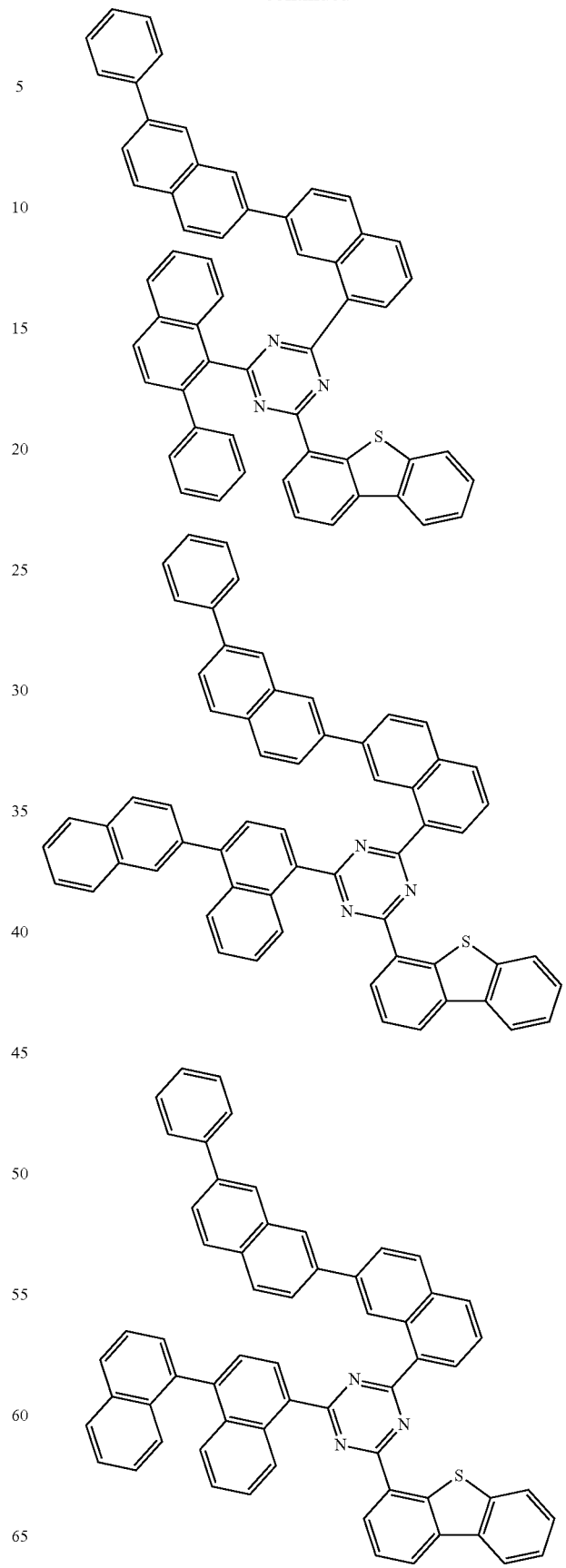
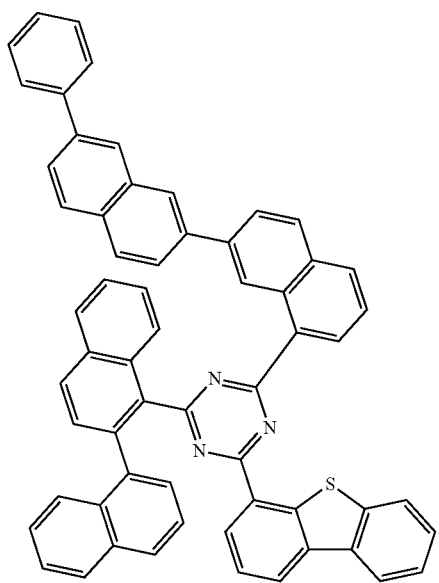

173
-continued
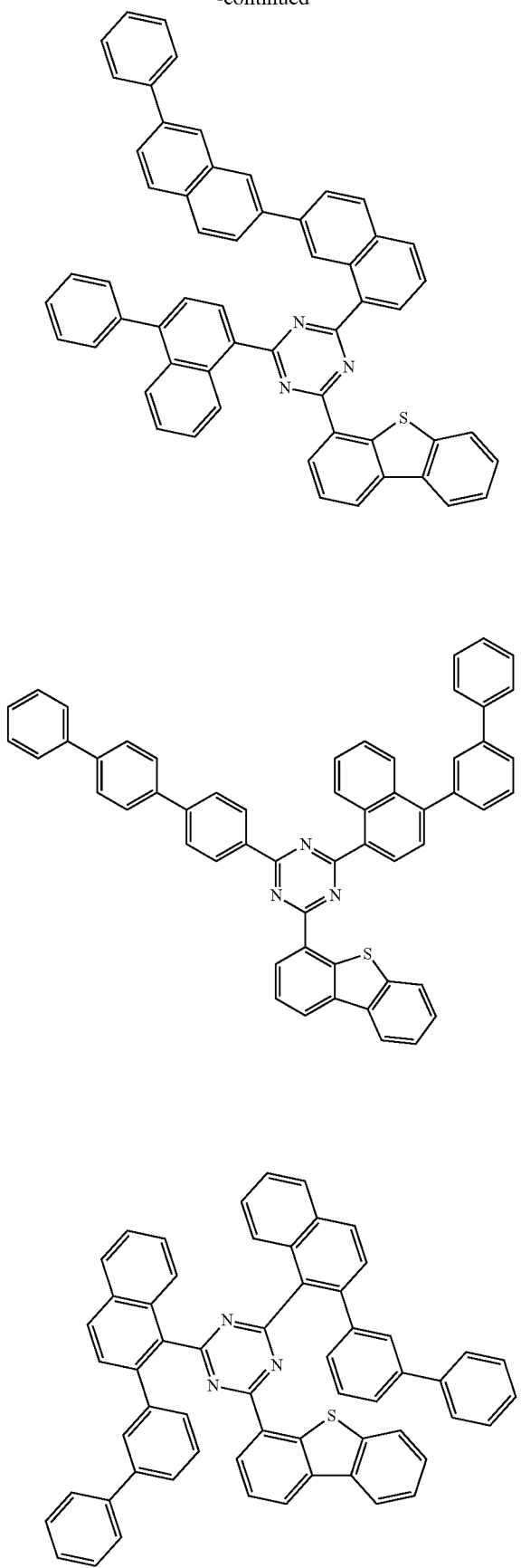
174
-continued
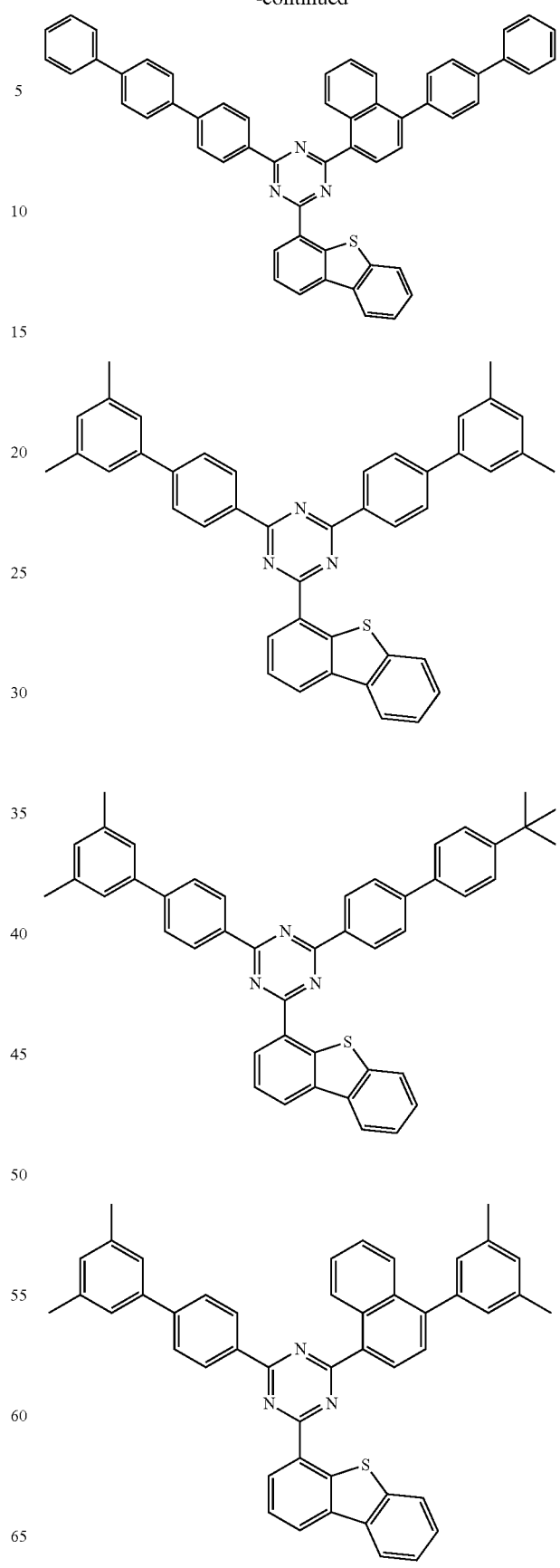

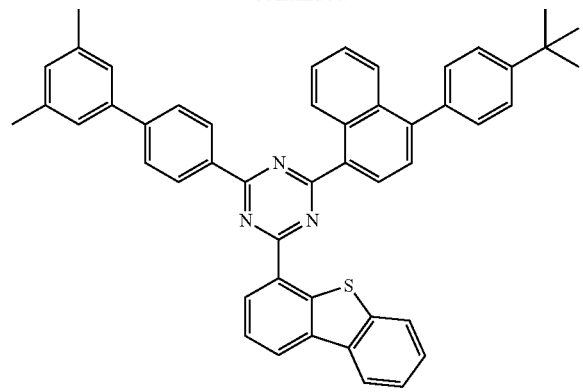
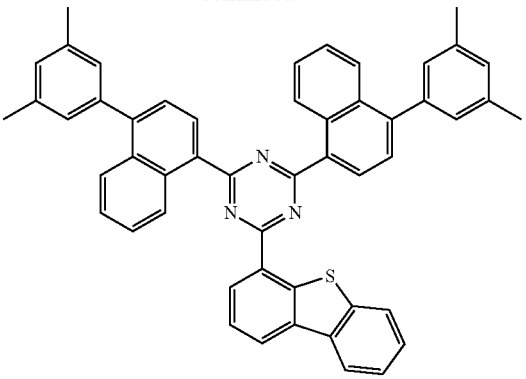

177
-continued
178
-continued
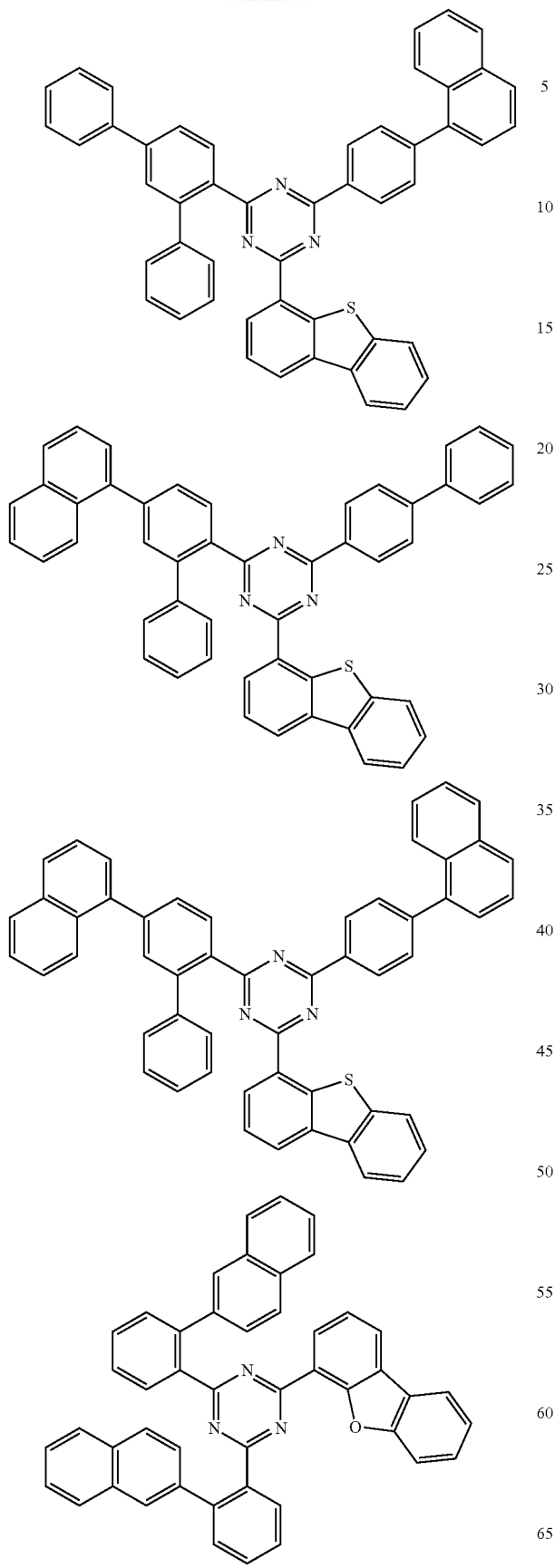
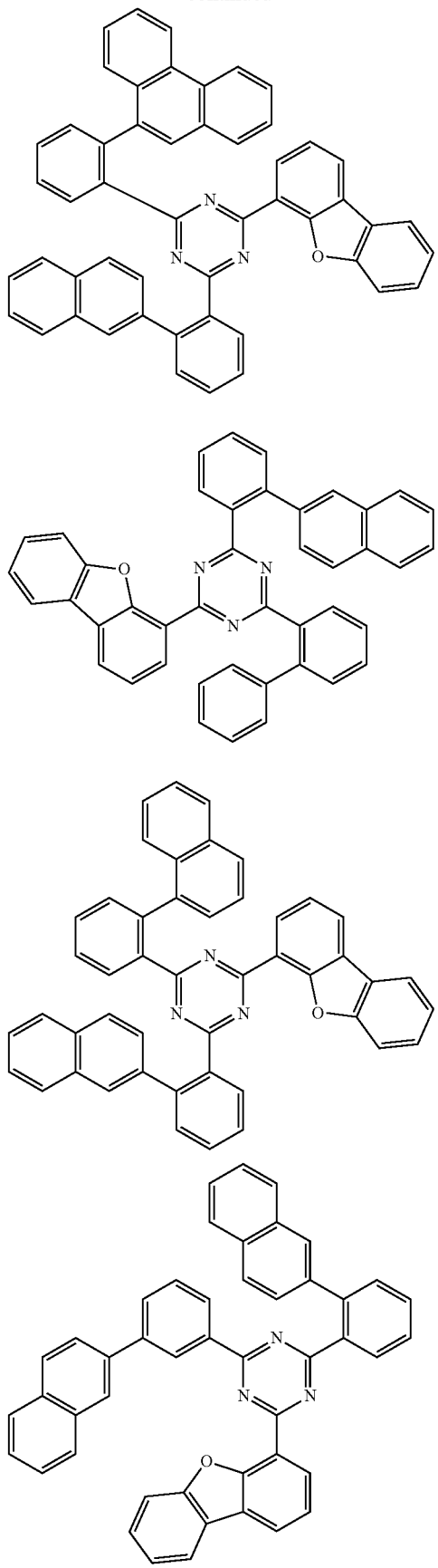

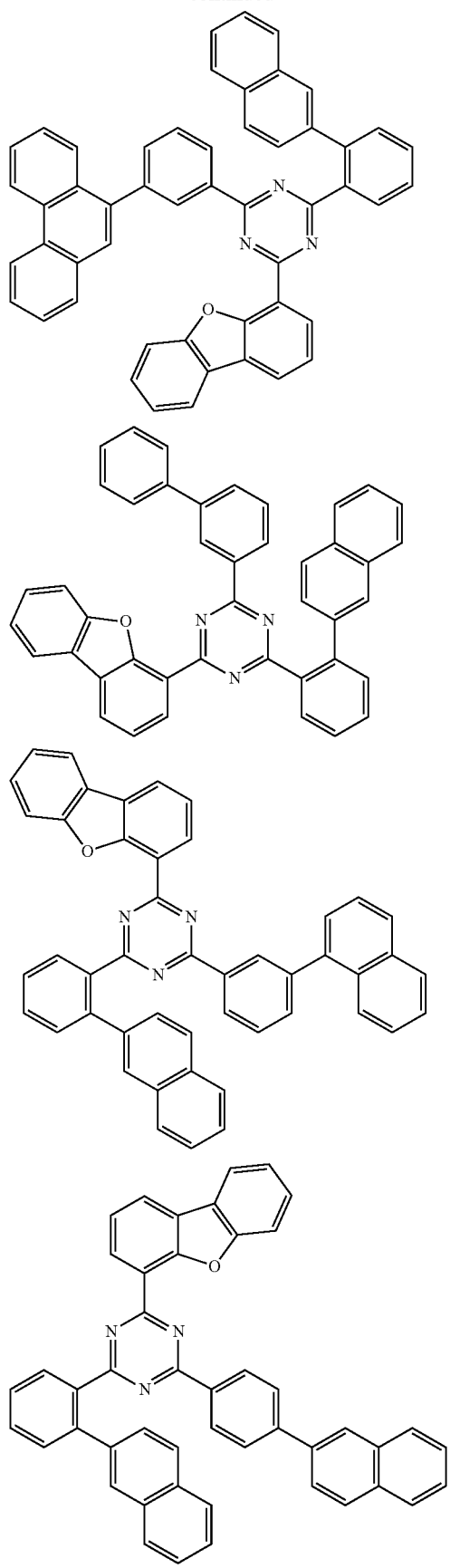
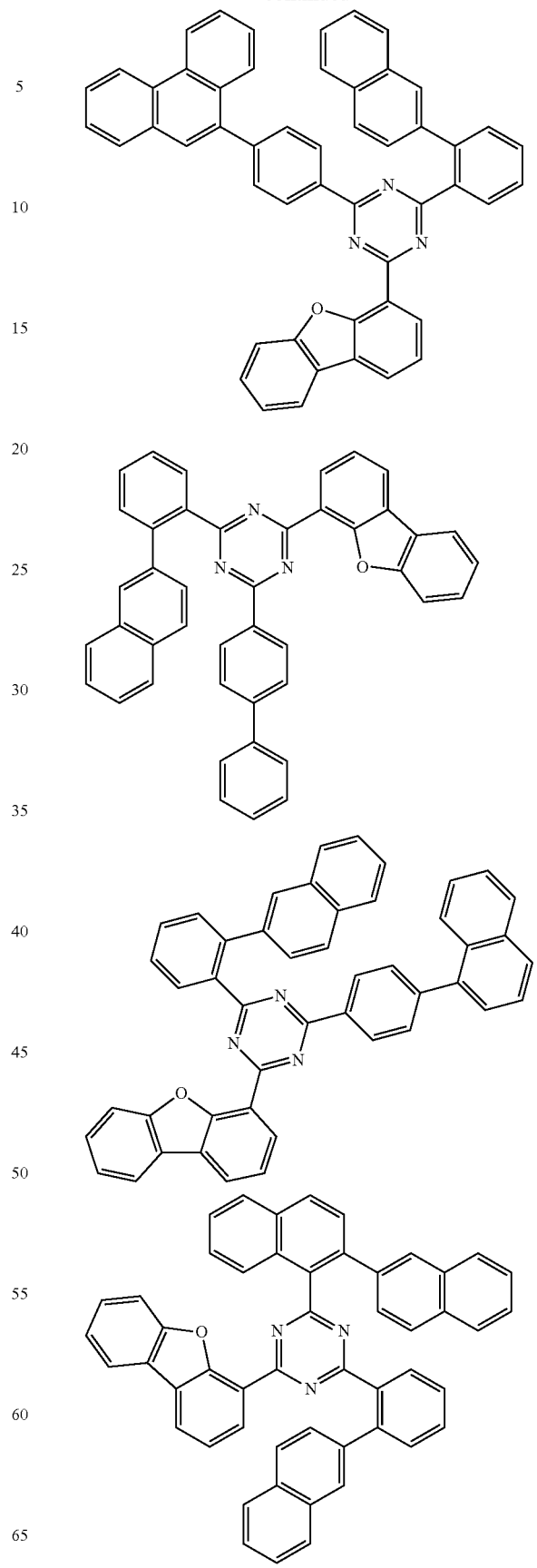

181
-continued
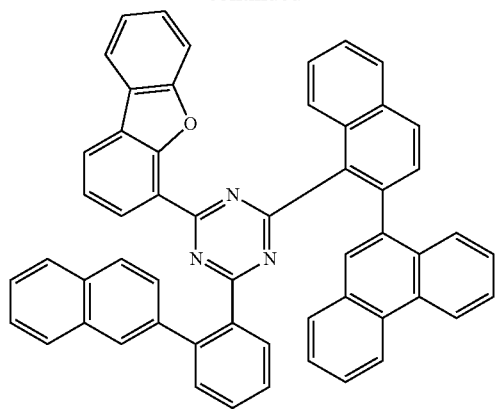
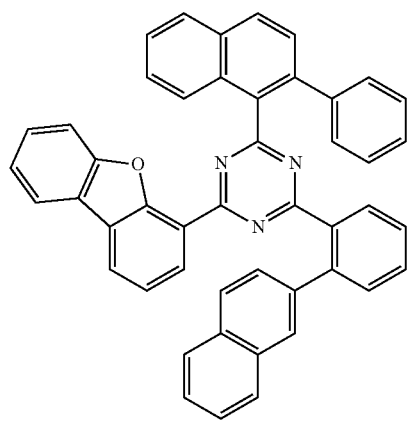
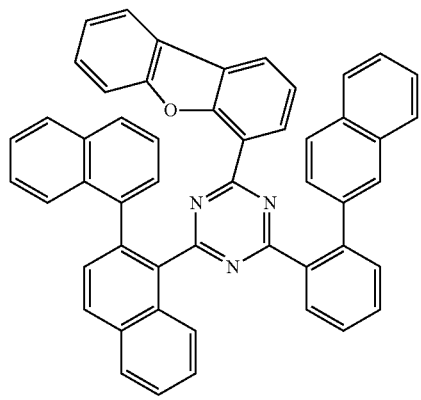
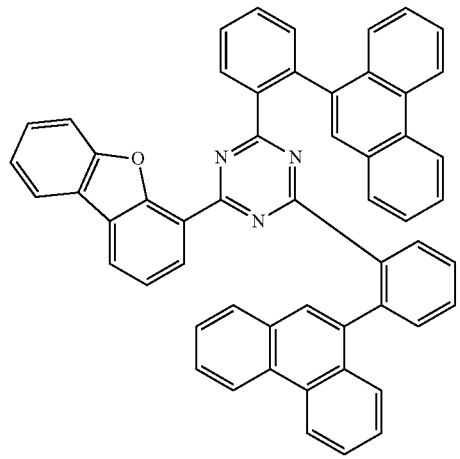
182
-continued
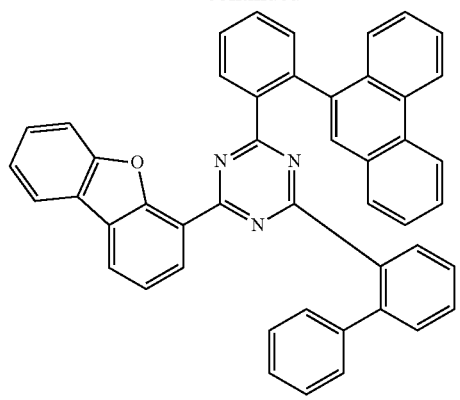
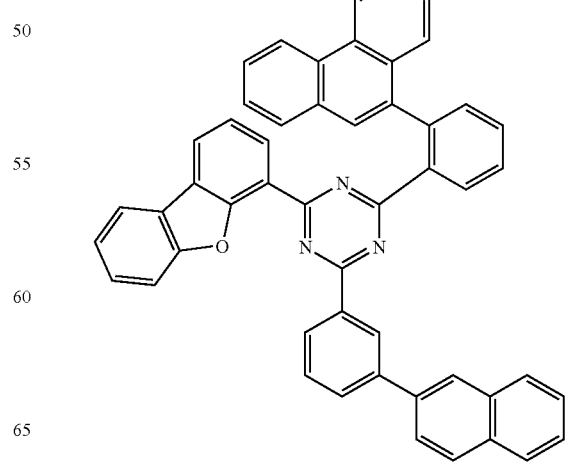

183
-continued
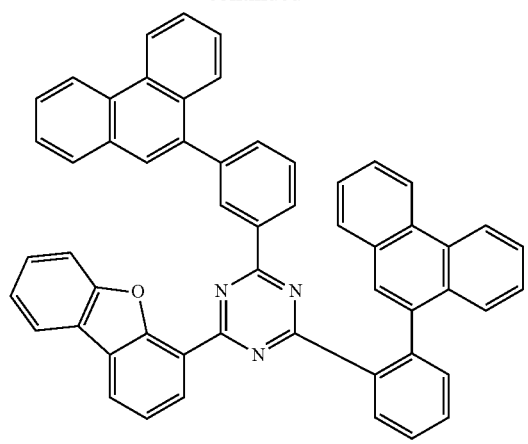
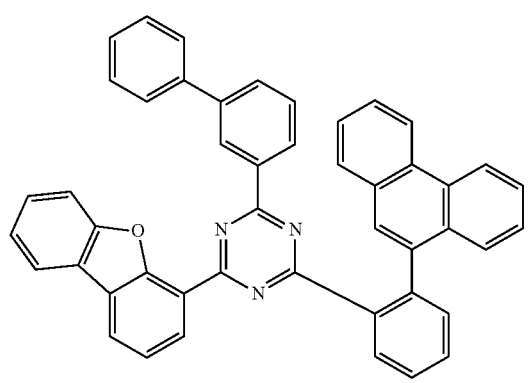
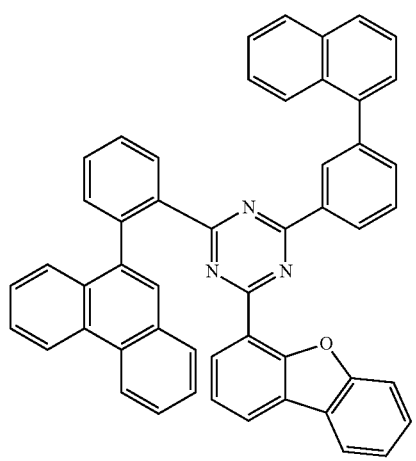
184
-continued
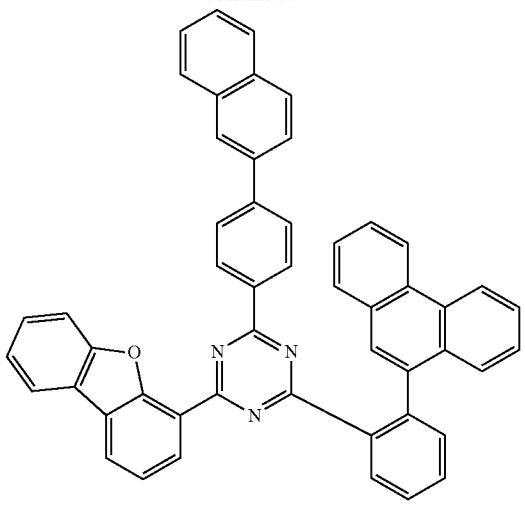
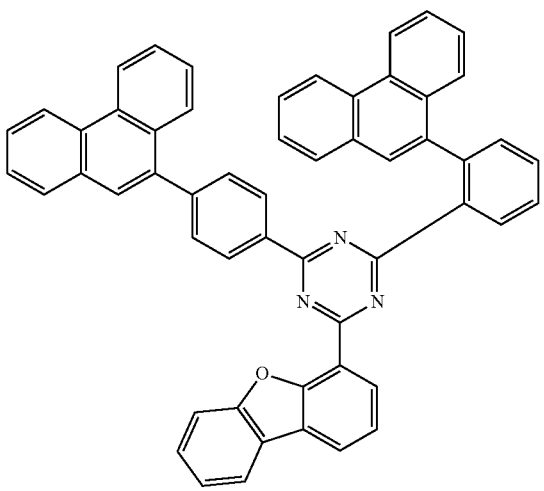
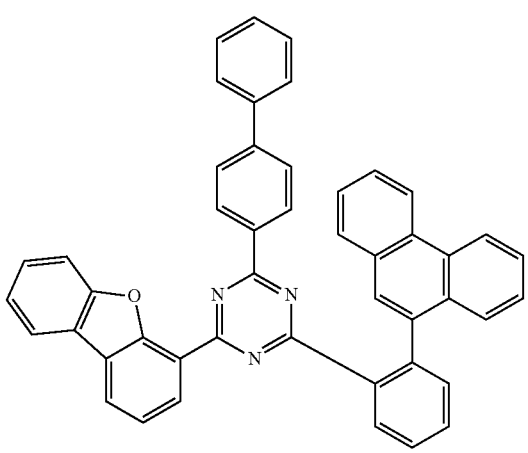

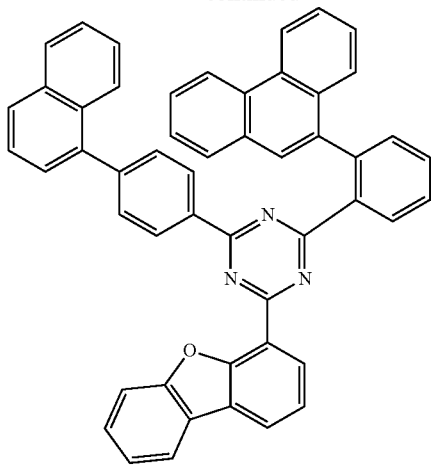
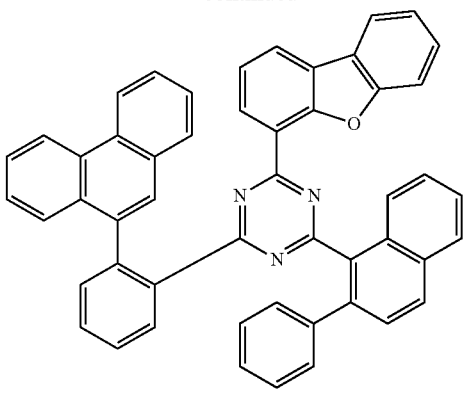
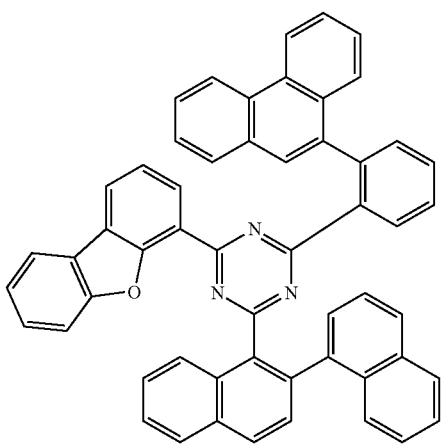
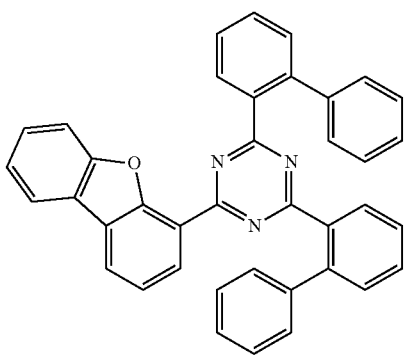
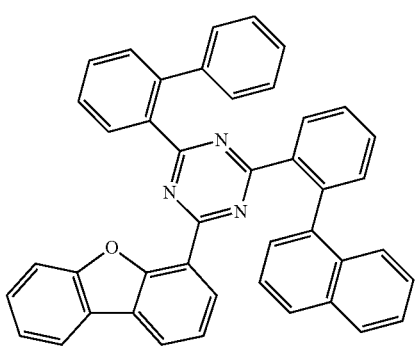

187
-continued
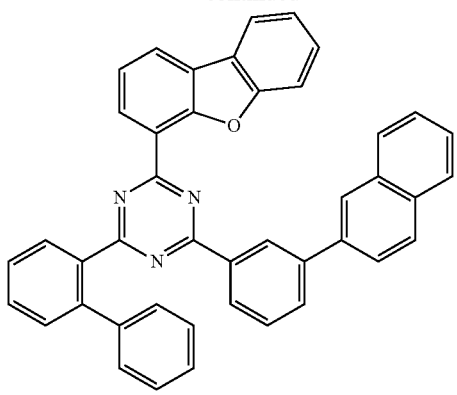
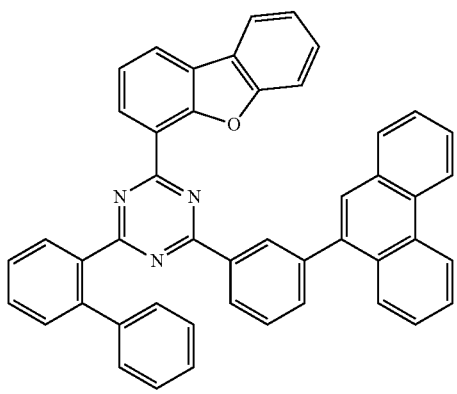
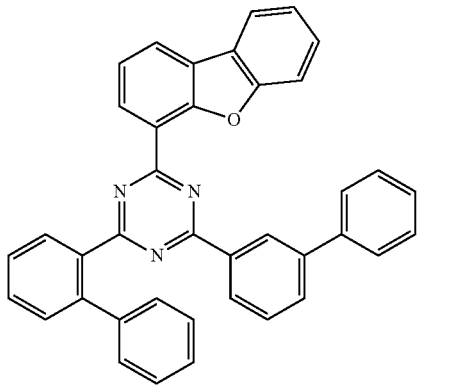
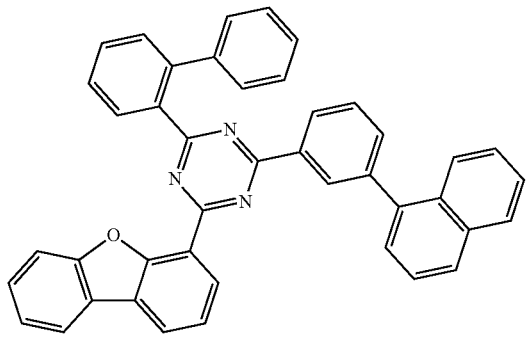
188
-continued
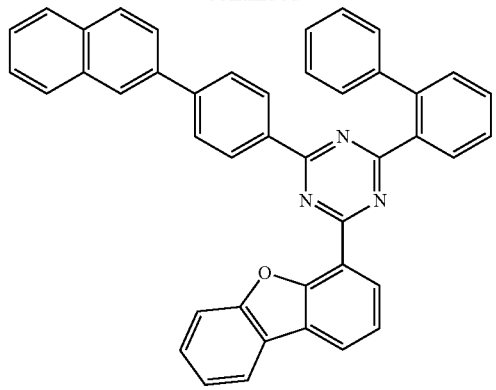
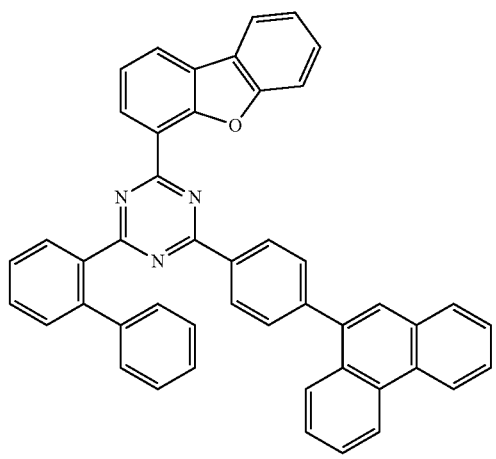
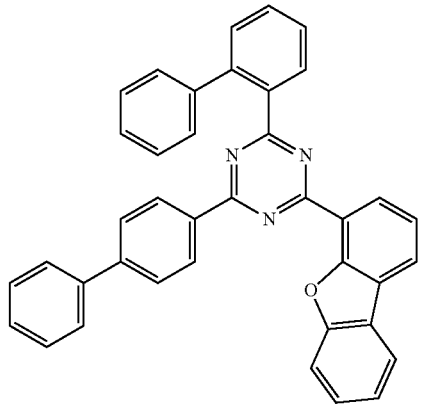
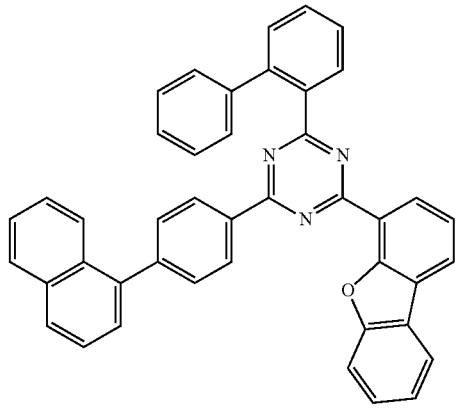

189
-continued
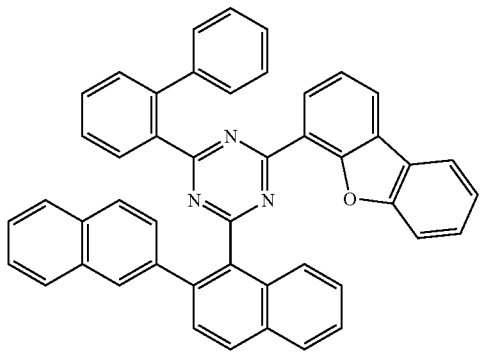
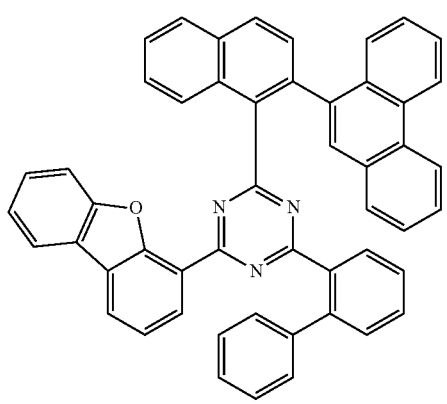
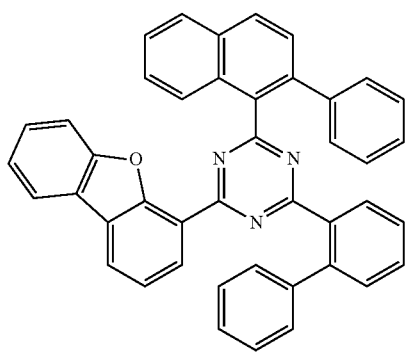
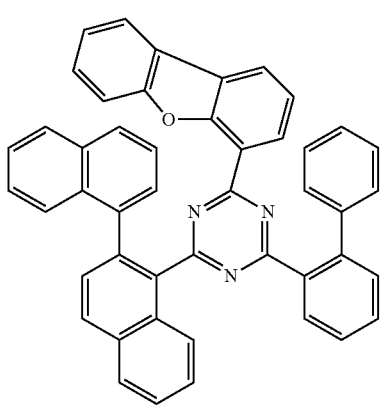
190
-continued
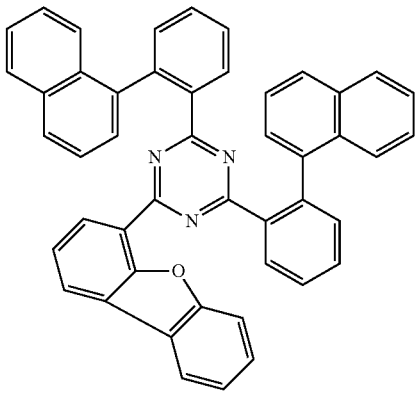
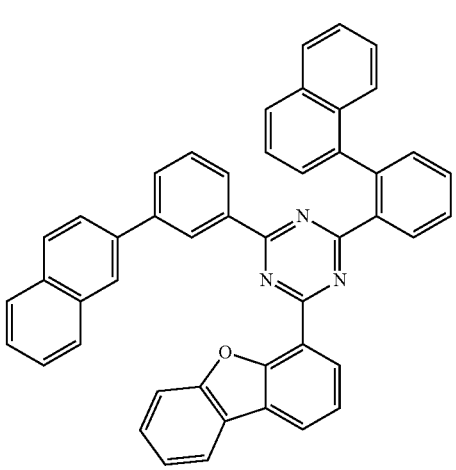
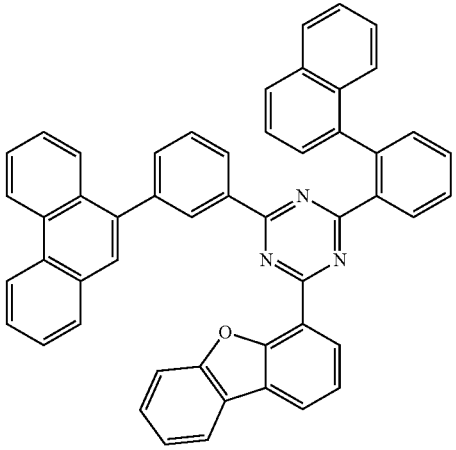
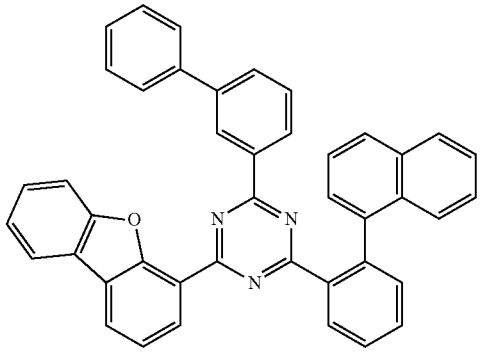

191
-continued
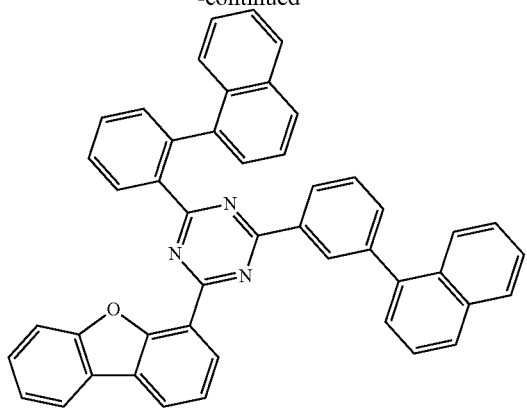
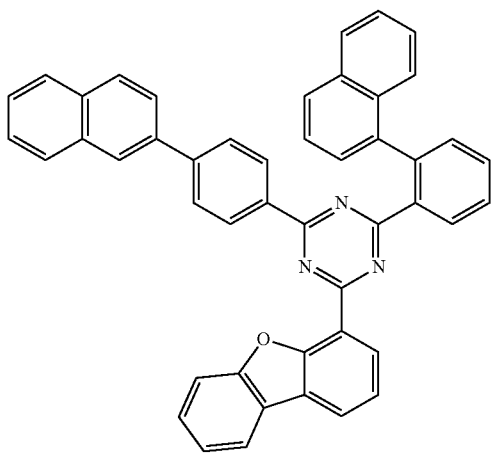
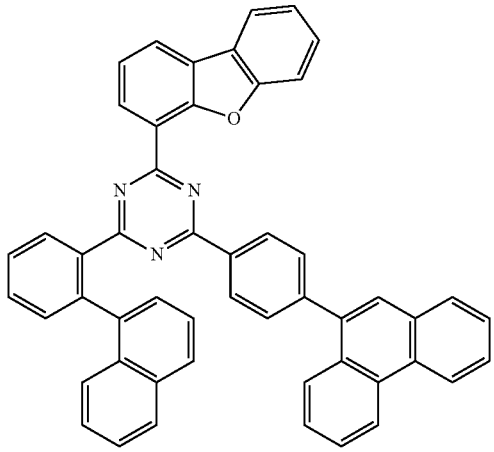
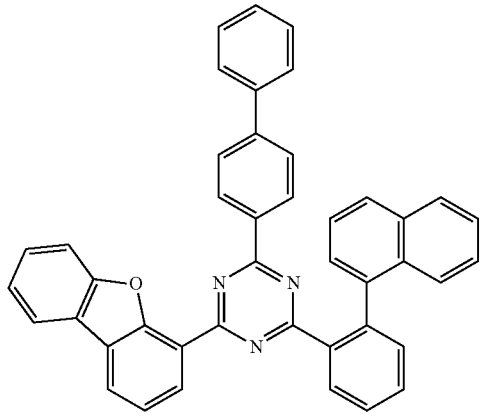
192
-continued
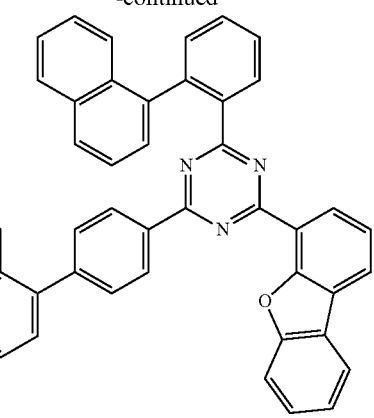
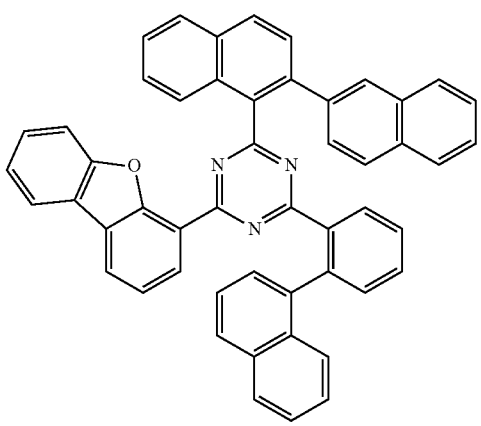
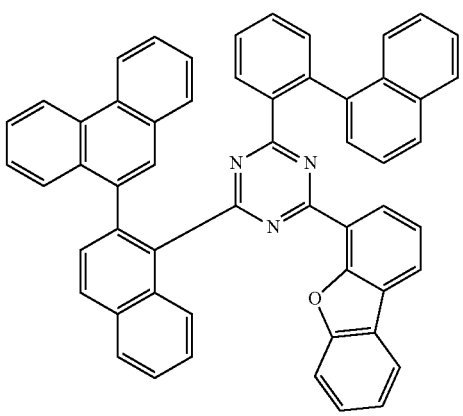
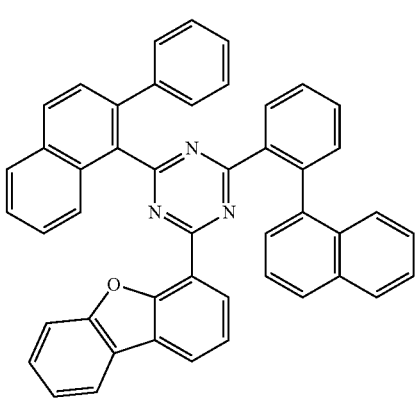

193
-continued
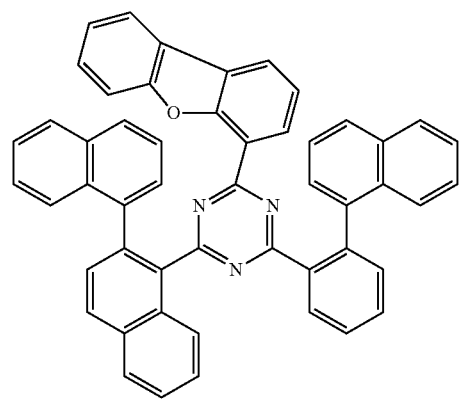
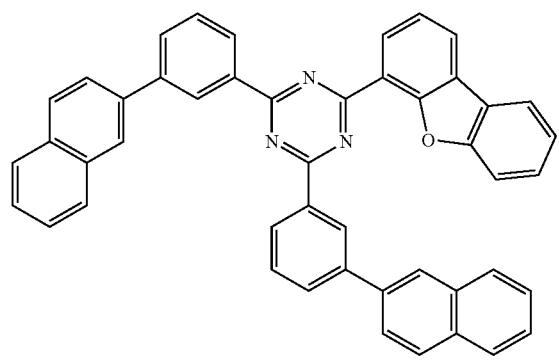
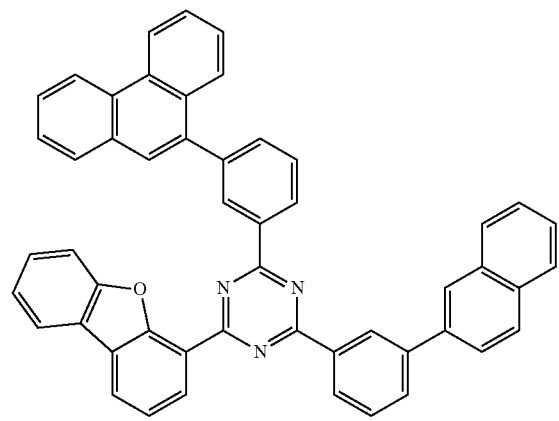
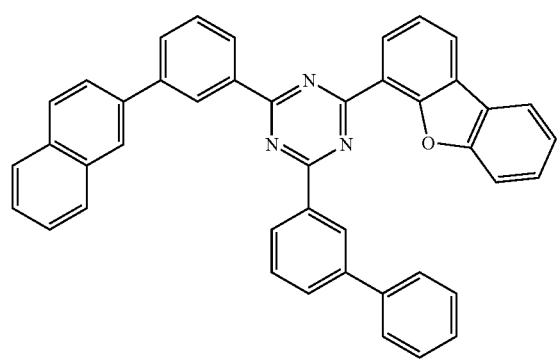
194
-continued
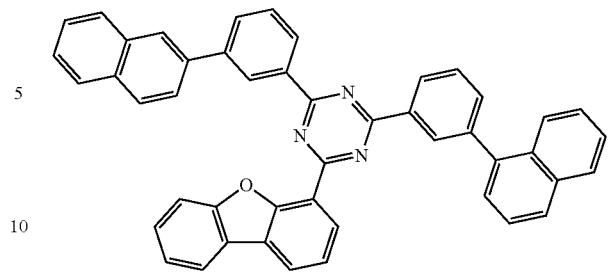
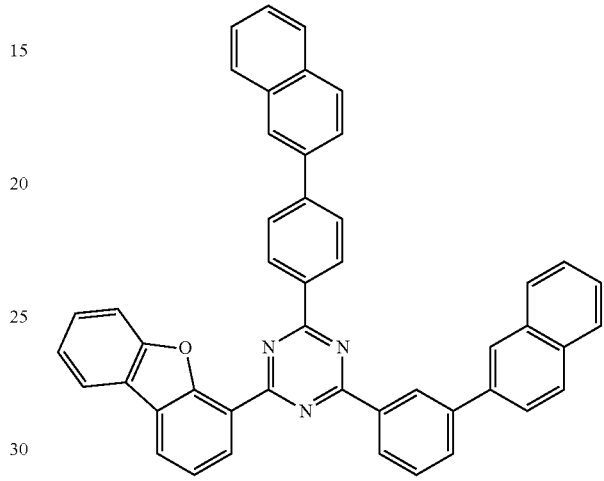
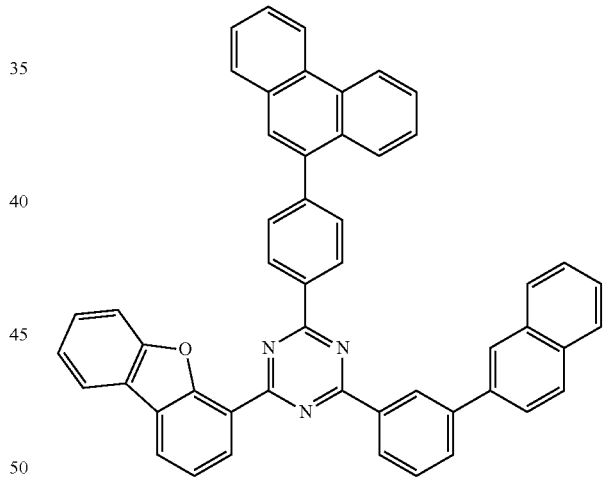
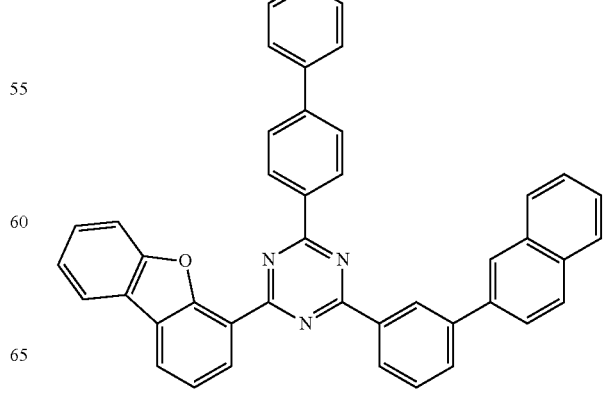

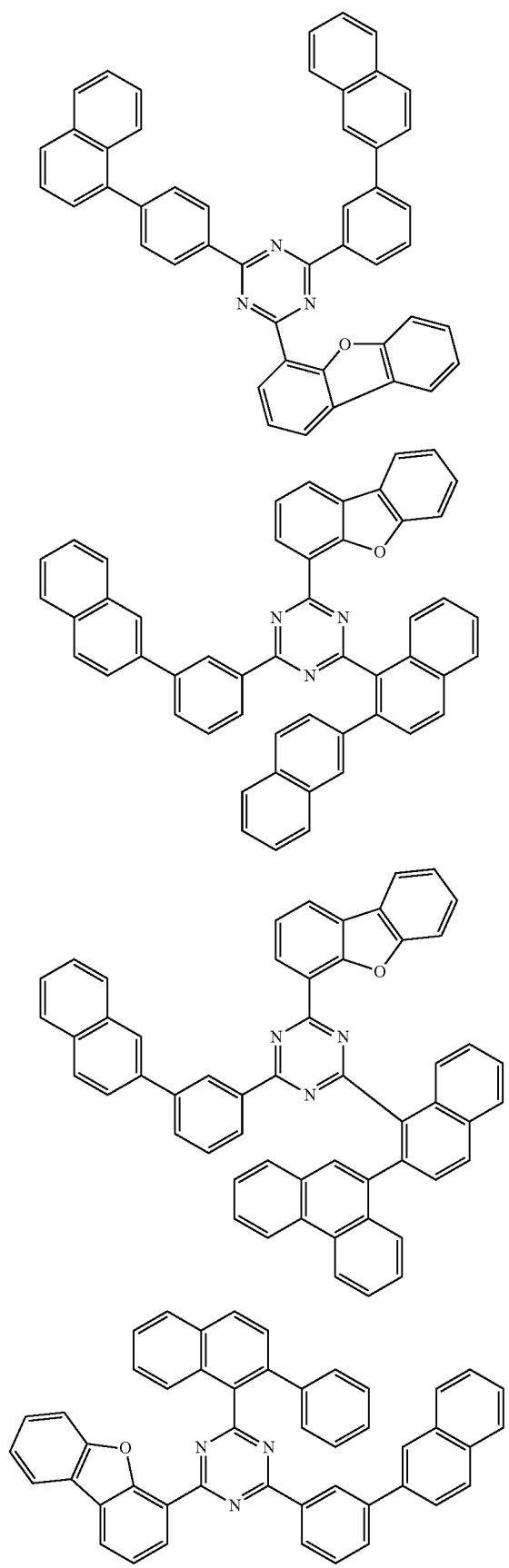
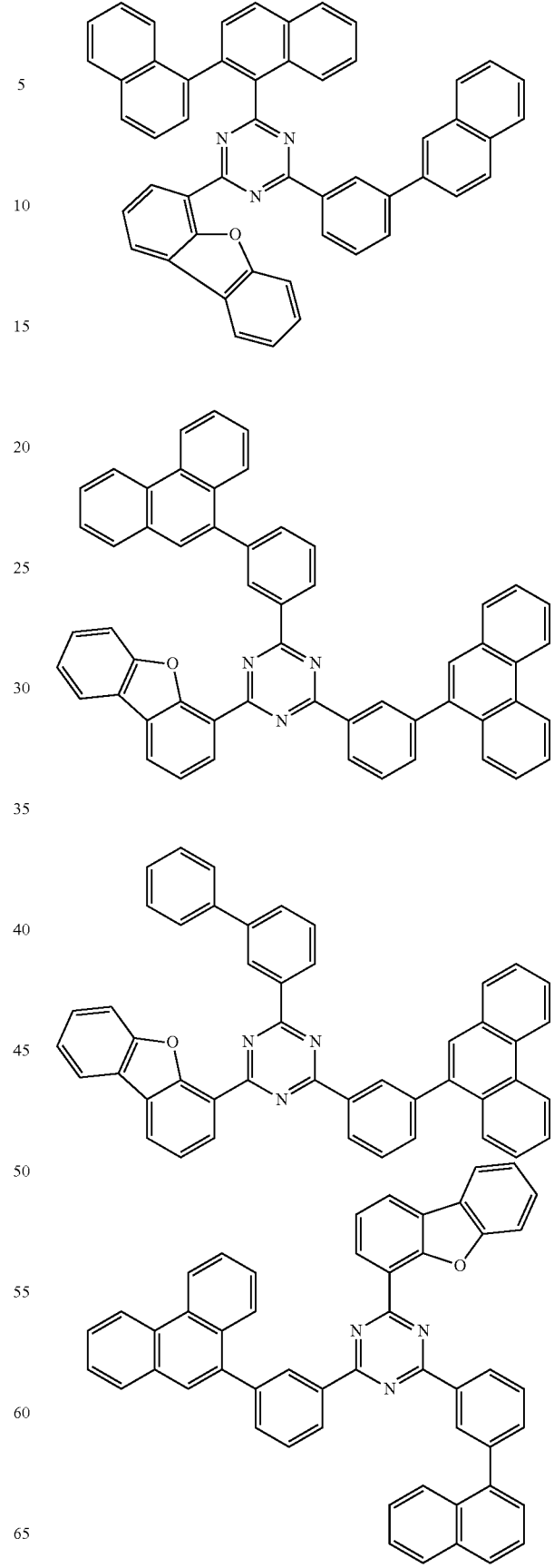

| 197 | 198 |
|---|---|
| -continued | -continued |
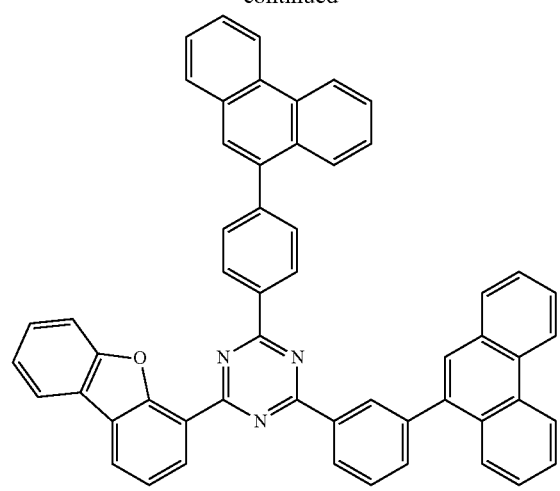
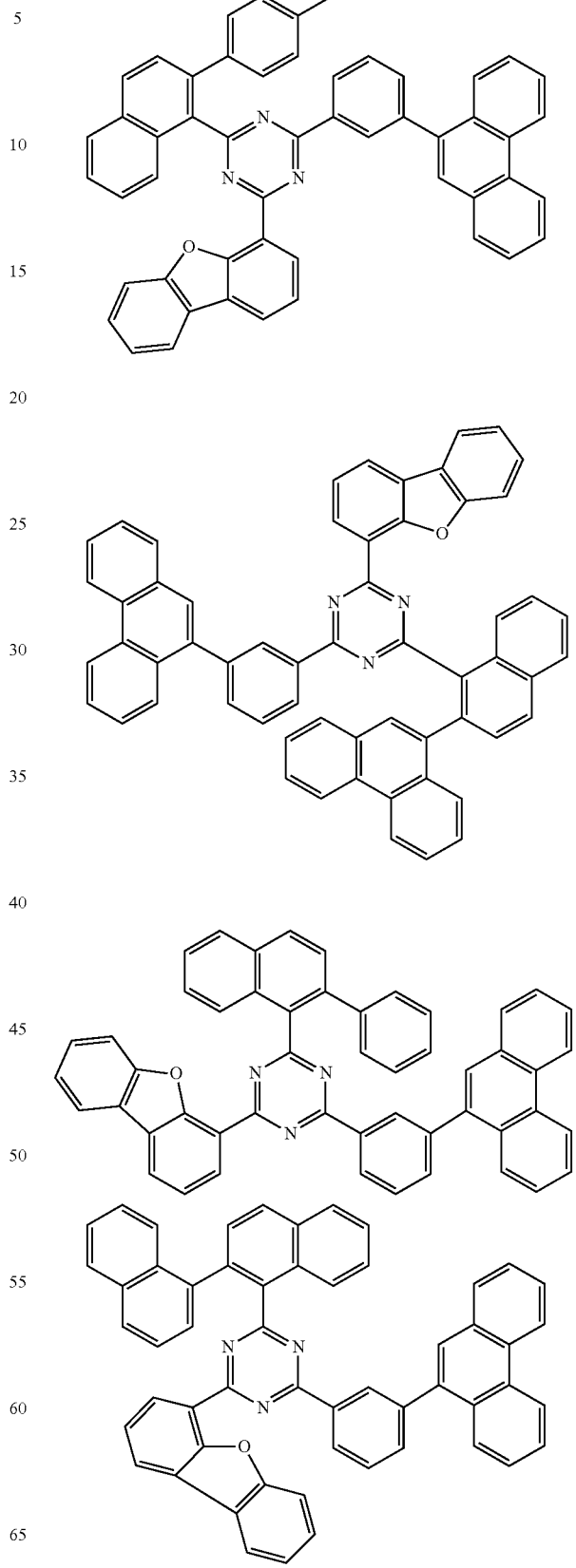

199
-continued
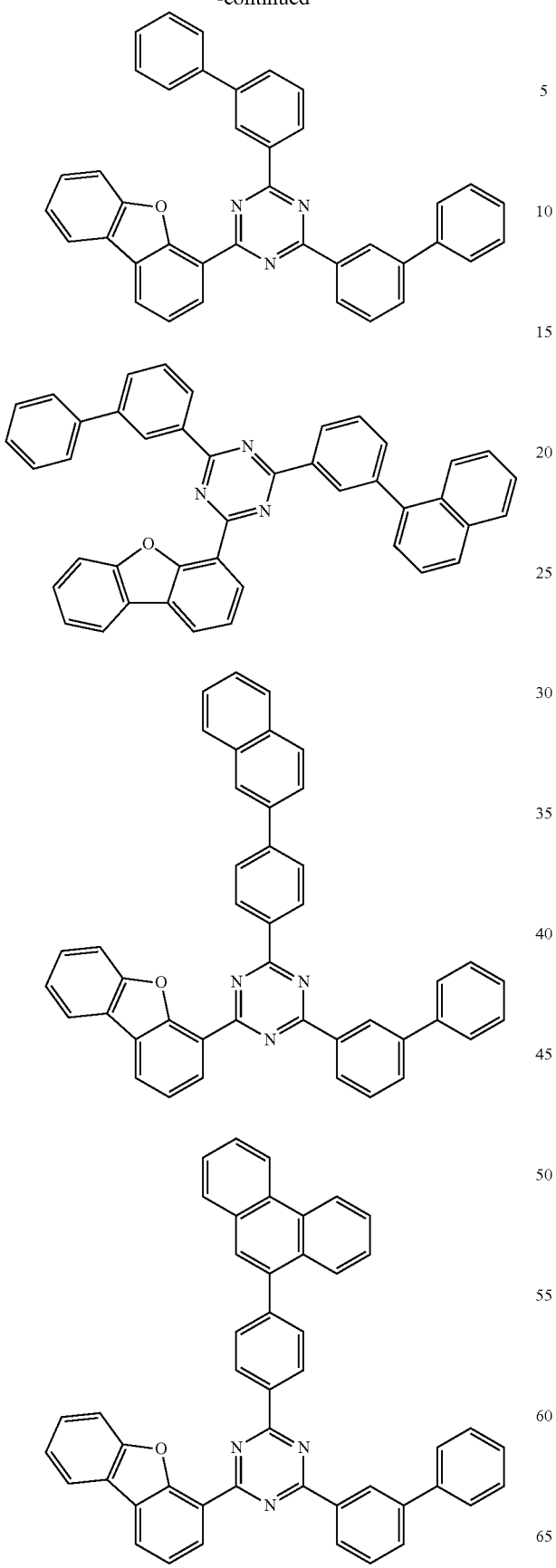
200
-continued
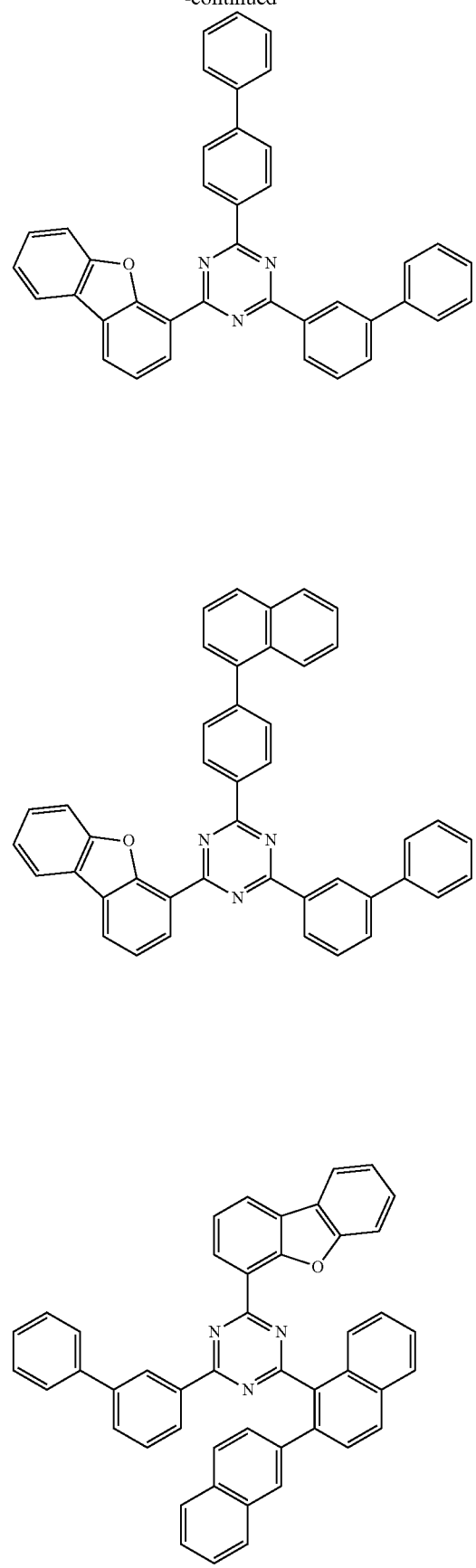

201
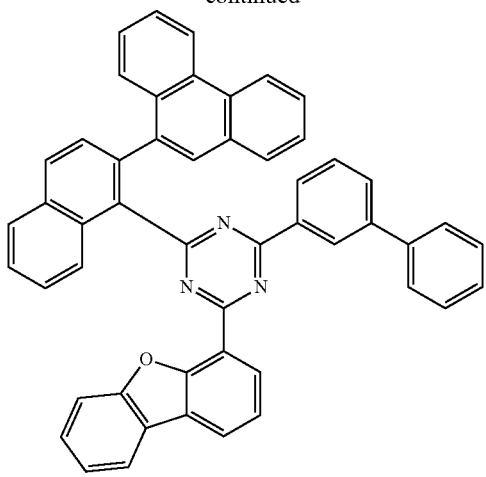
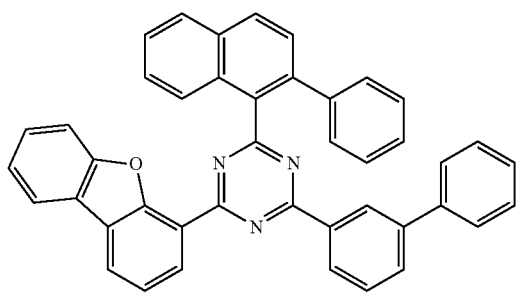
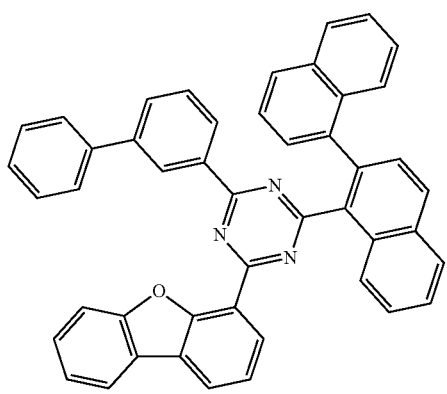
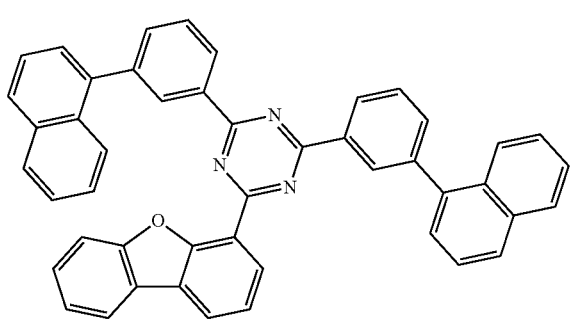
202
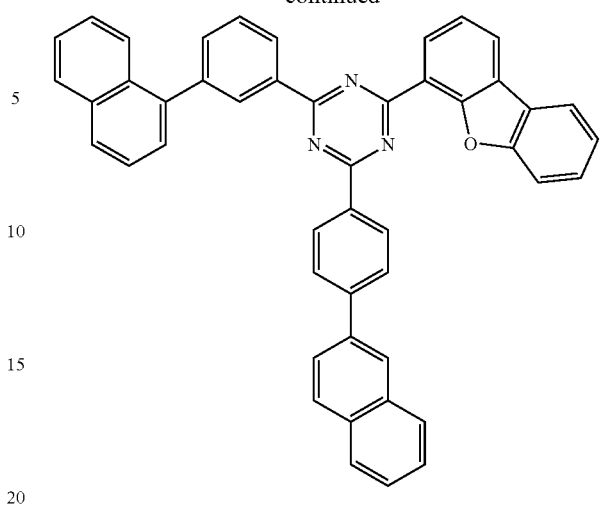
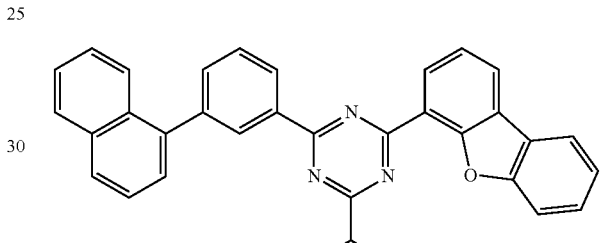
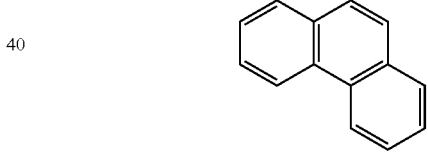
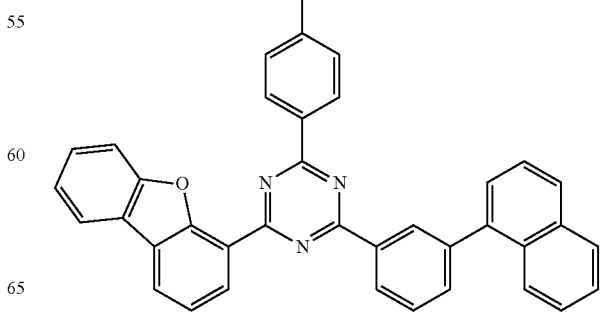

203
-continued
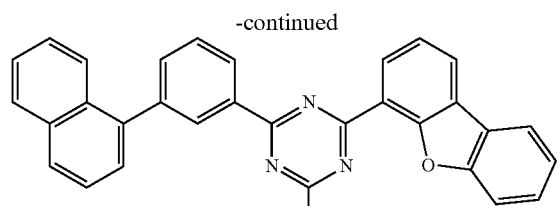
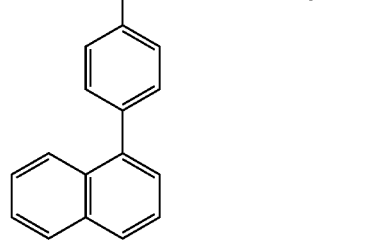
204
-continued
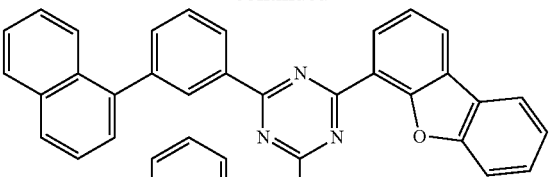
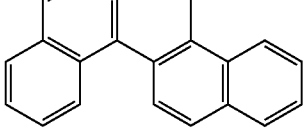
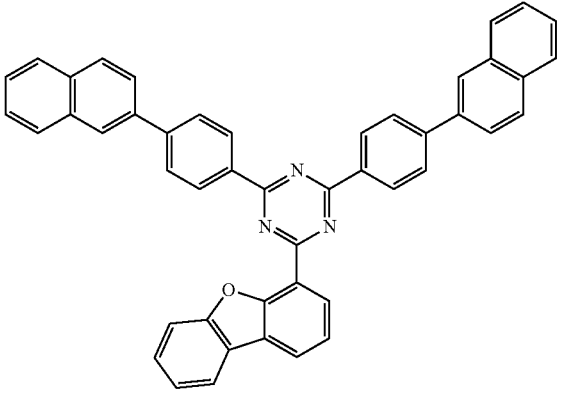
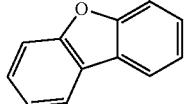
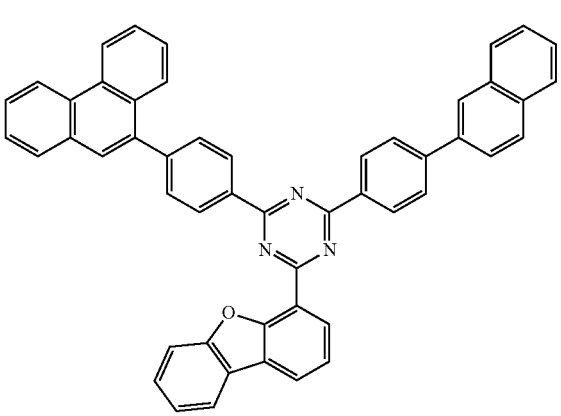
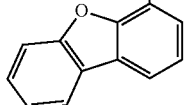
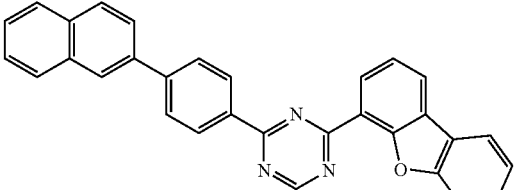
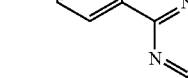
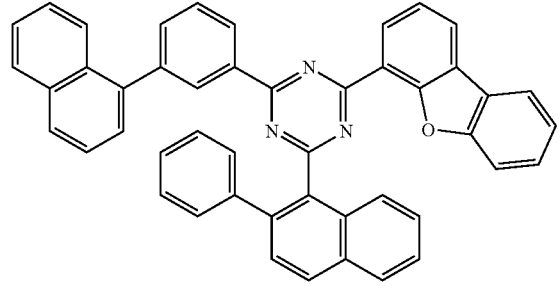

205
-continued
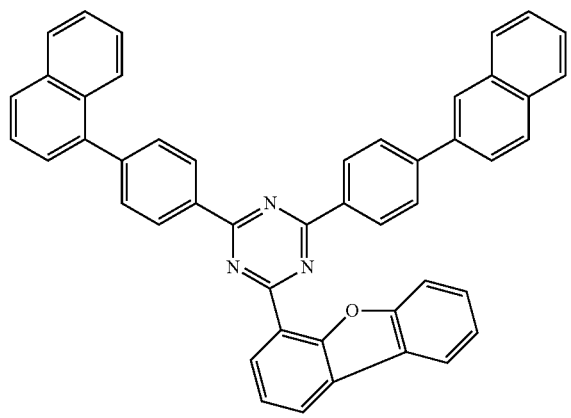
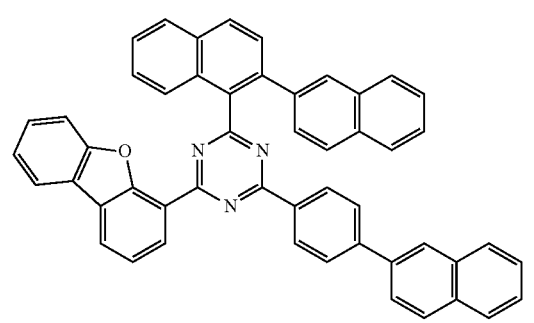
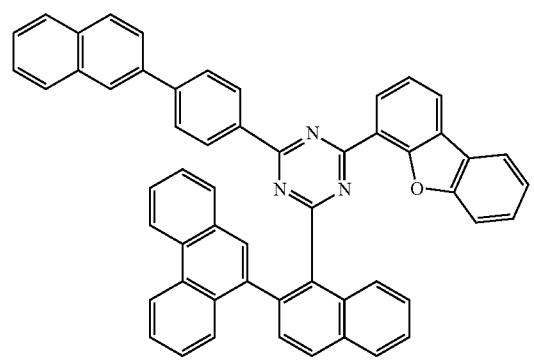
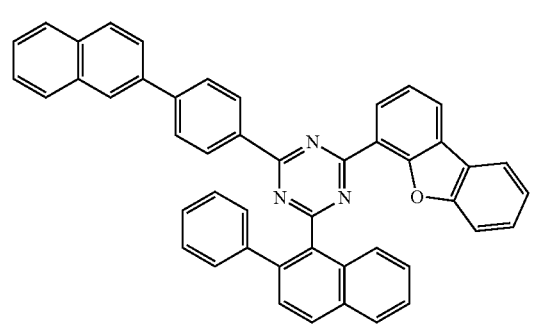
206
-continued
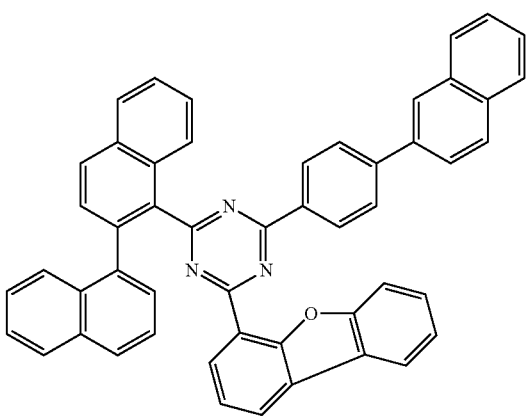
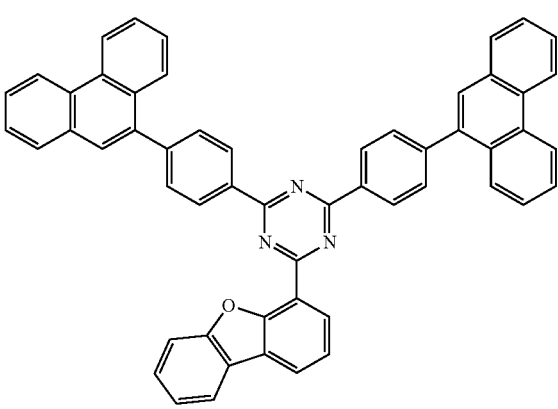
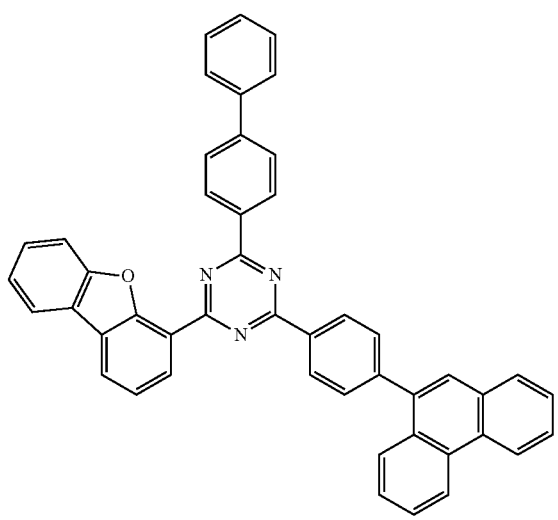

207
-continued
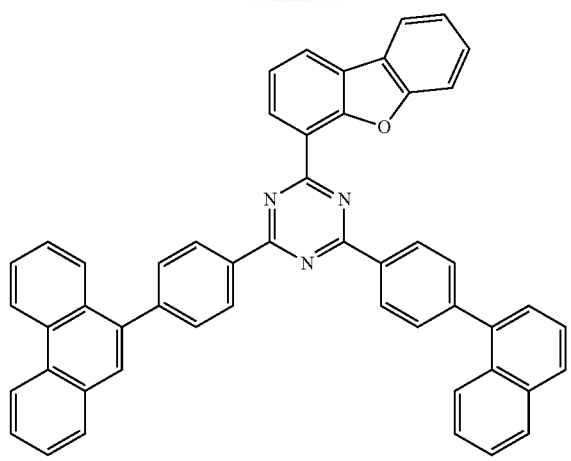
208
-continued
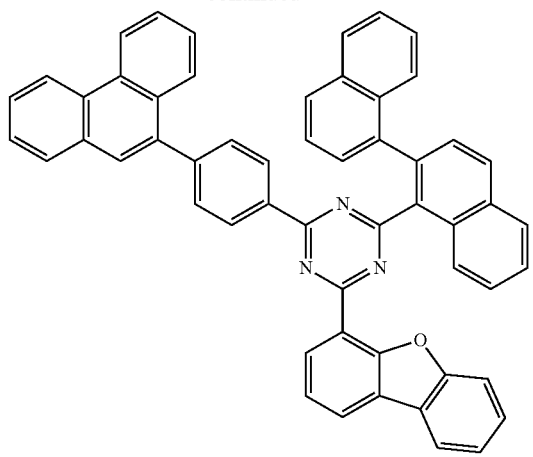
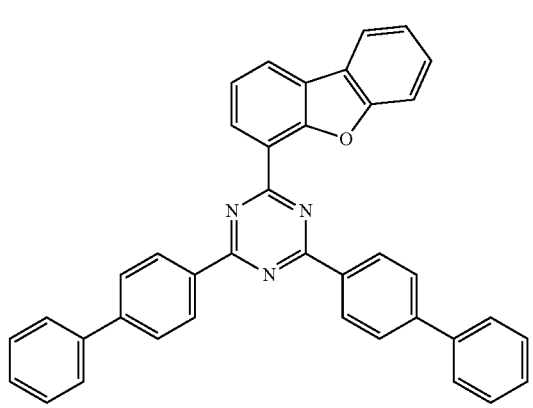
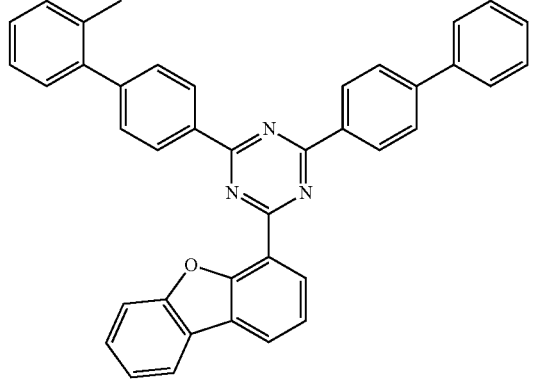
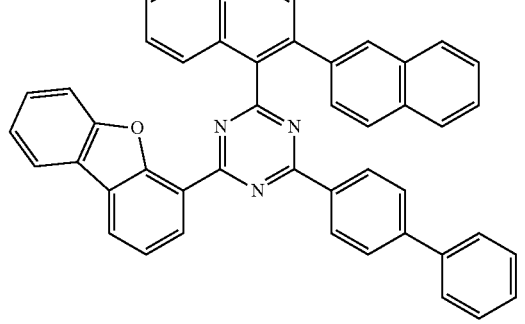

-continued
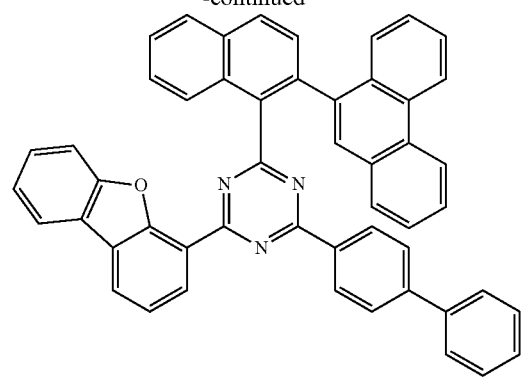
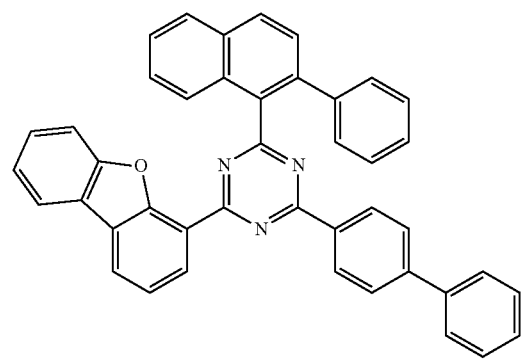
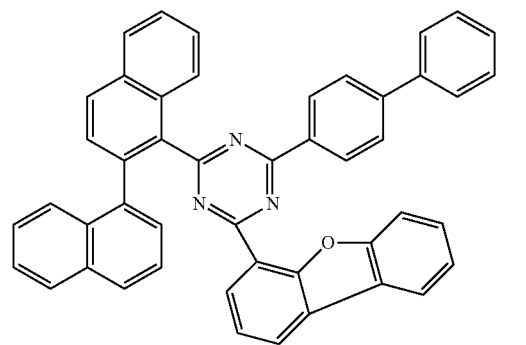
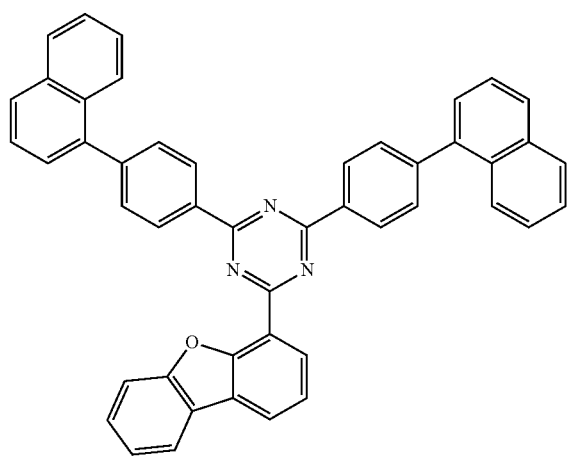
-continued
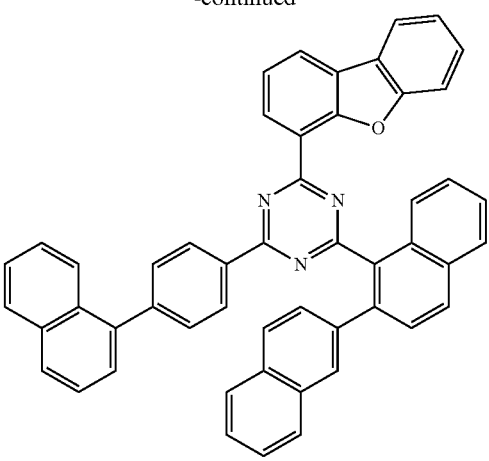
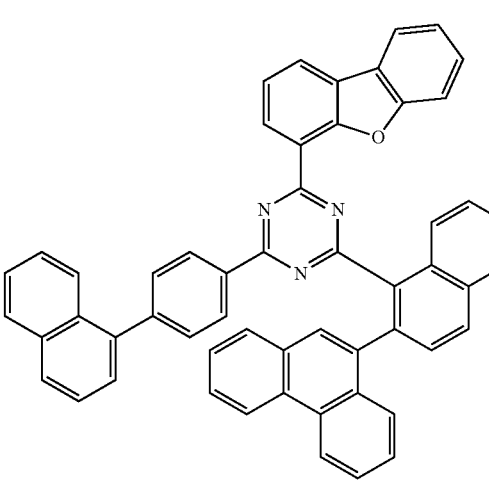
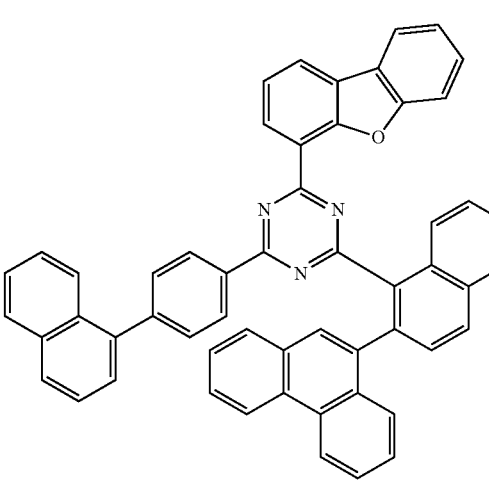
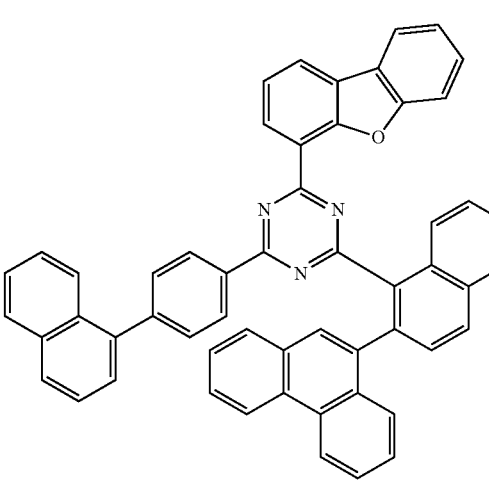

211
-continued
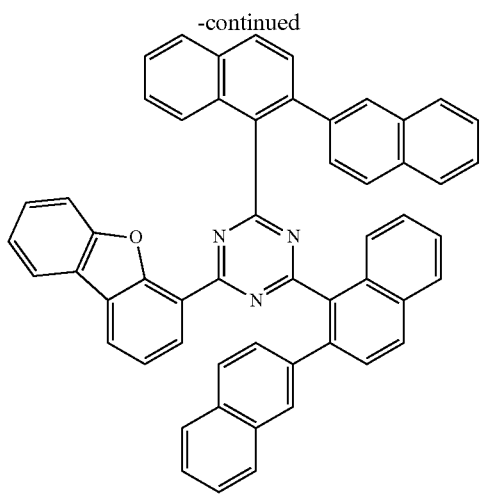
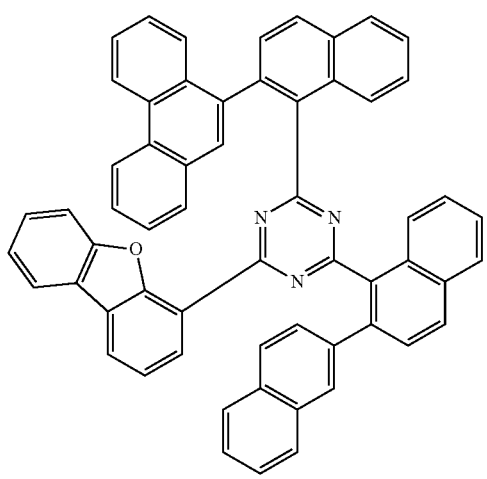
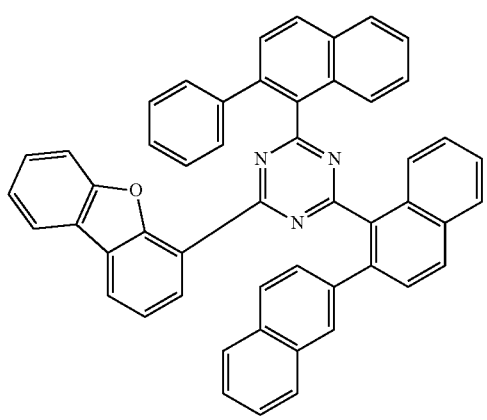
212
-continued
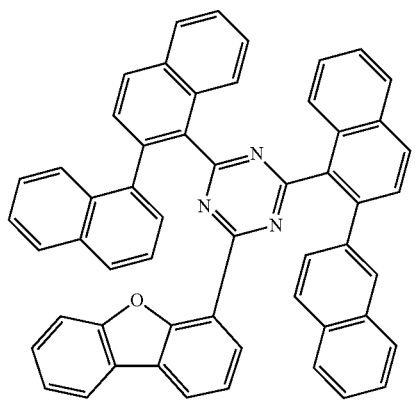
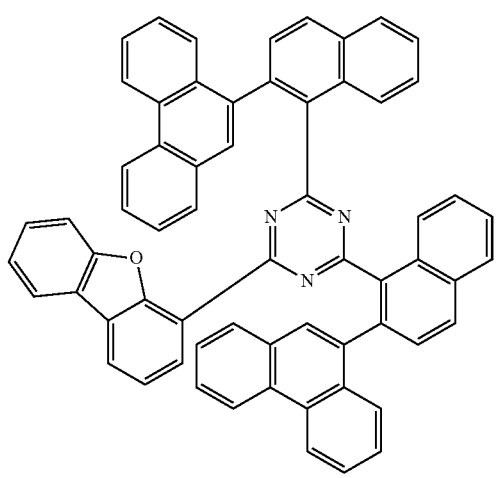
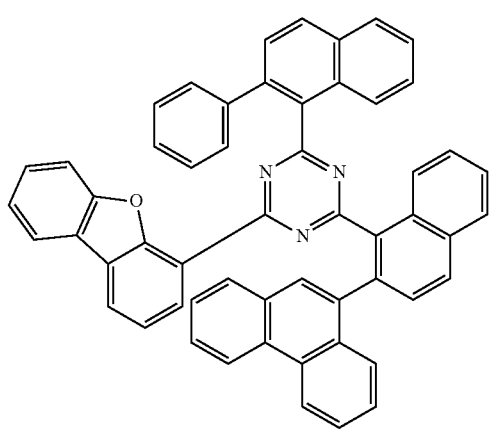

213
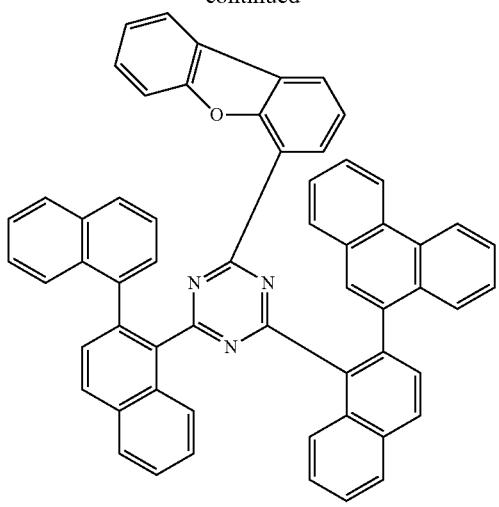
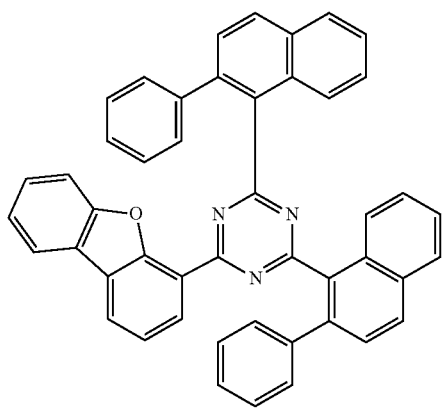
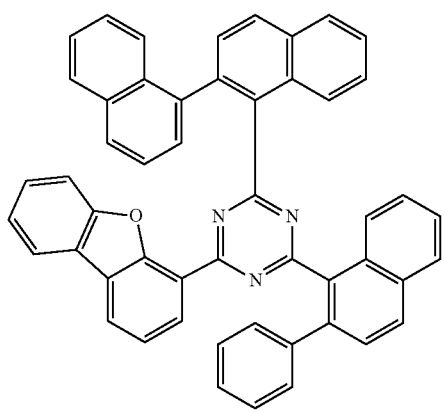
214
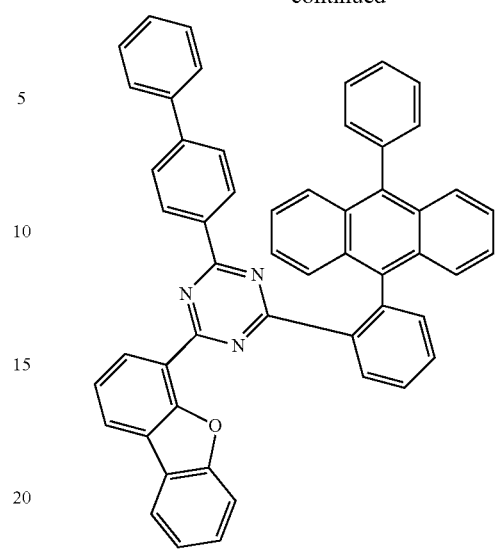
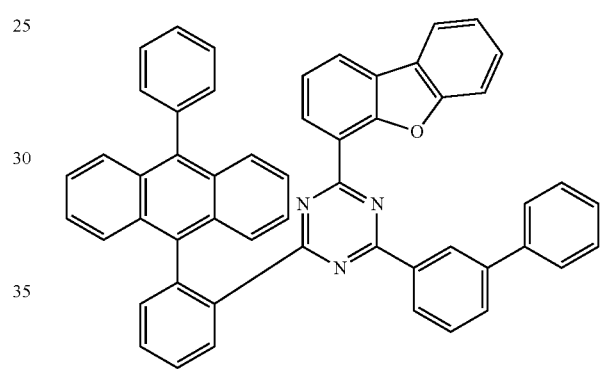
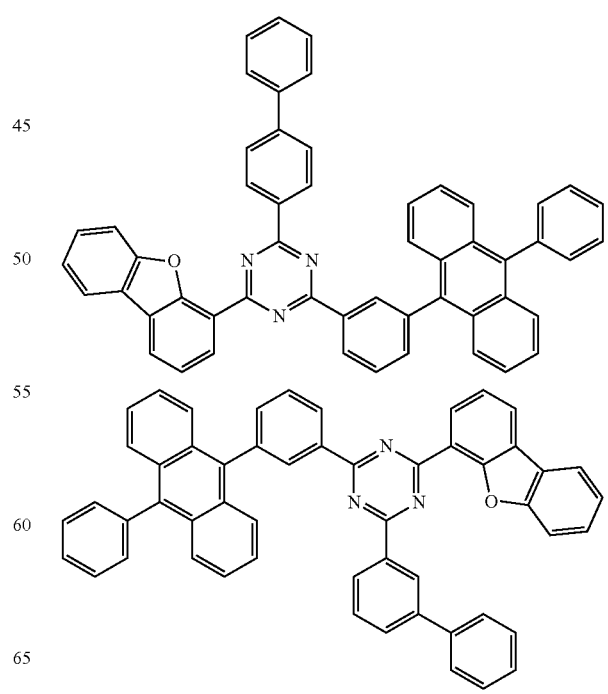

215
-continued
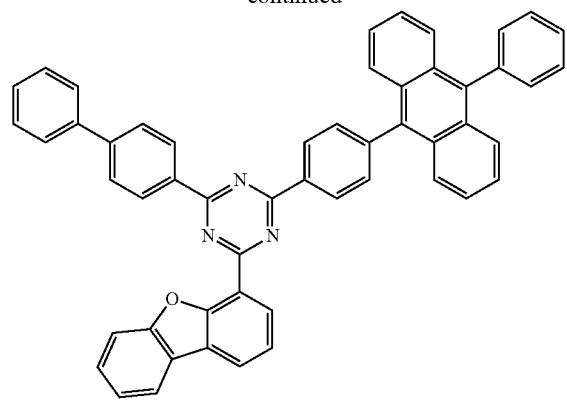
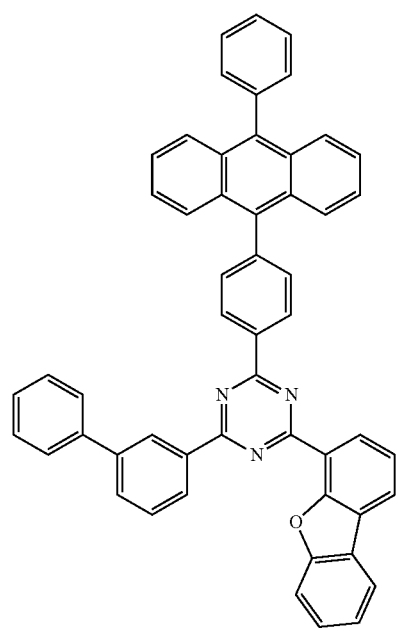
216
-continued
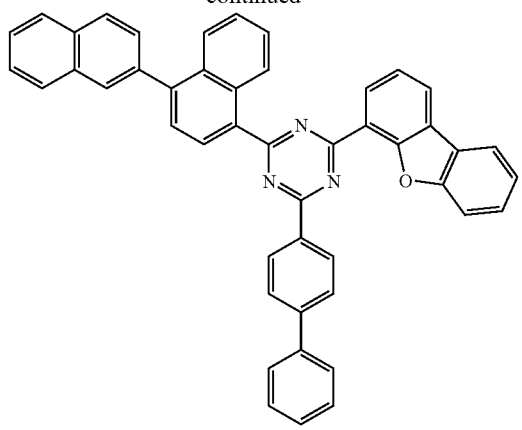
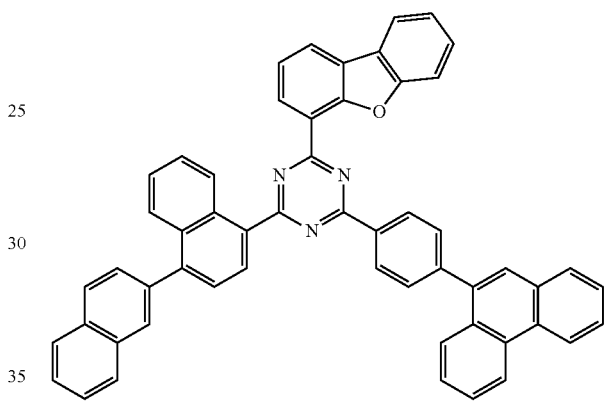
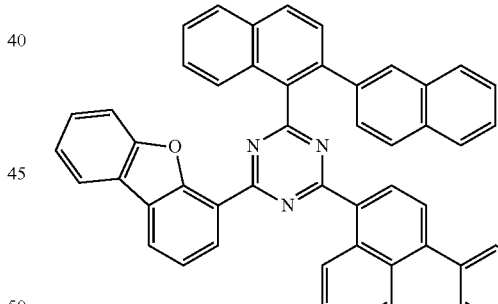
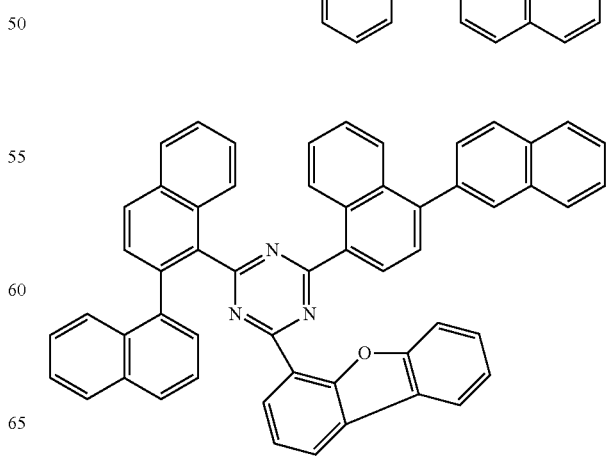

217
-continued
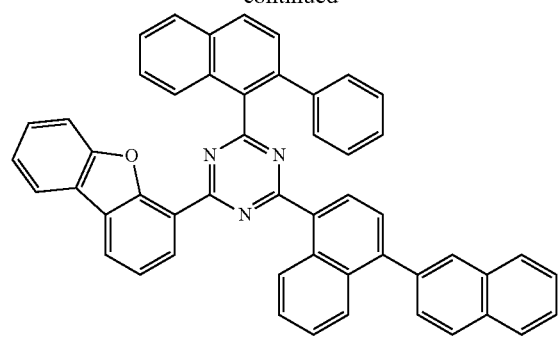
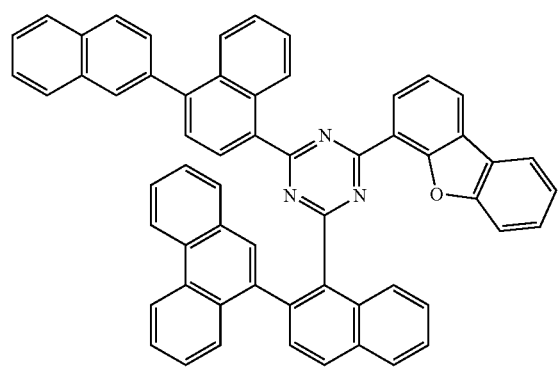
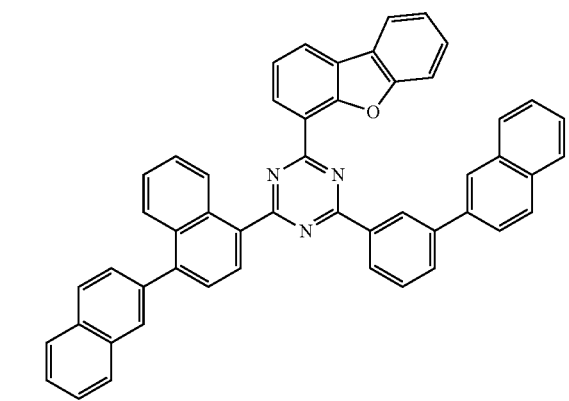
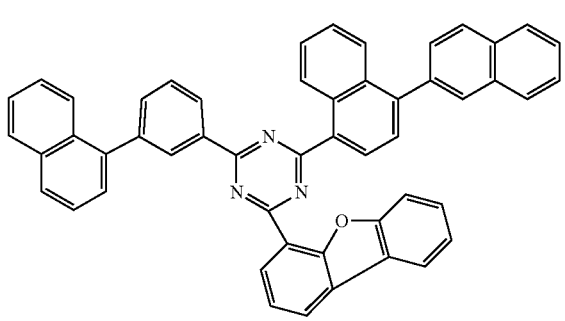
218
-continued
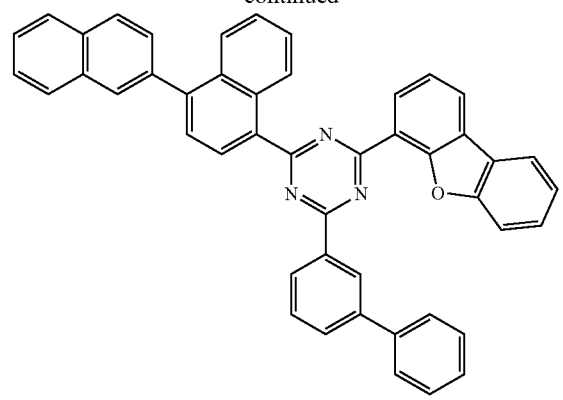
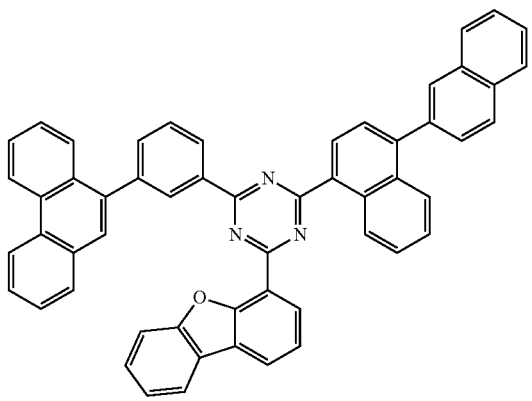
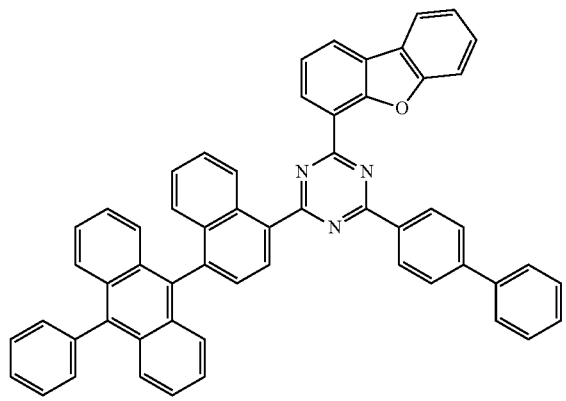
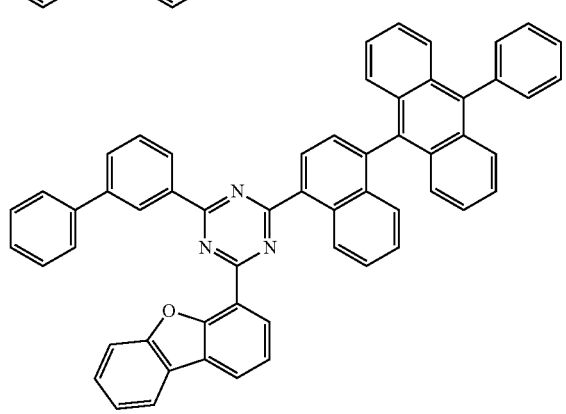

219
-continued
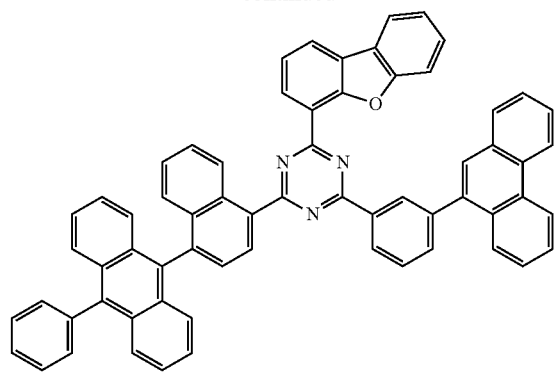
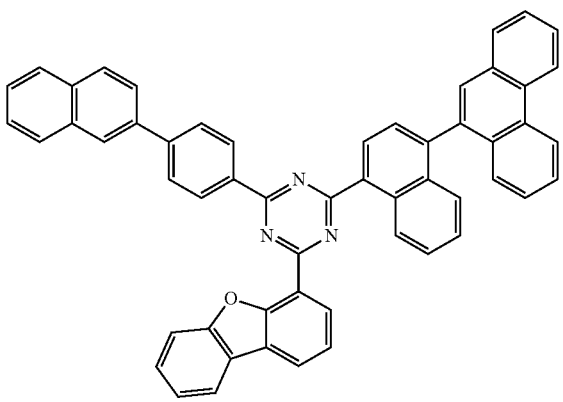
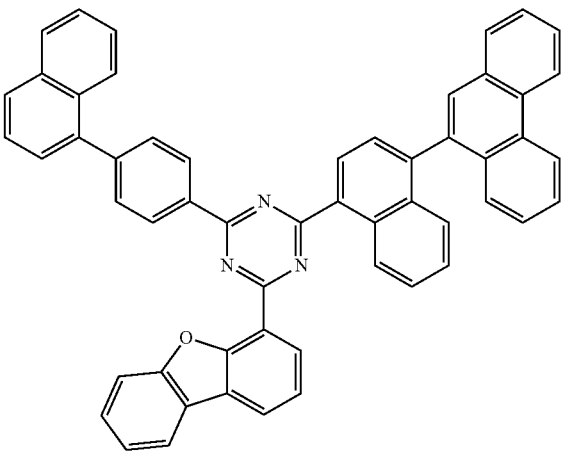
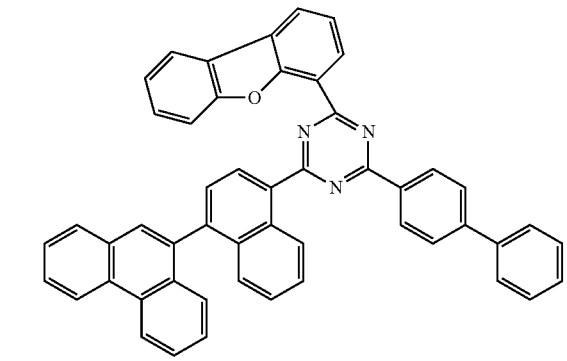
220
-continued
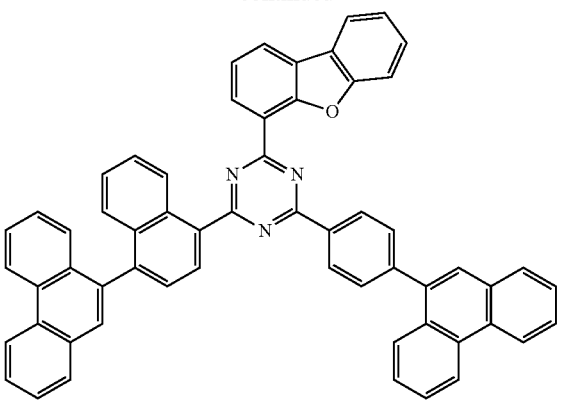
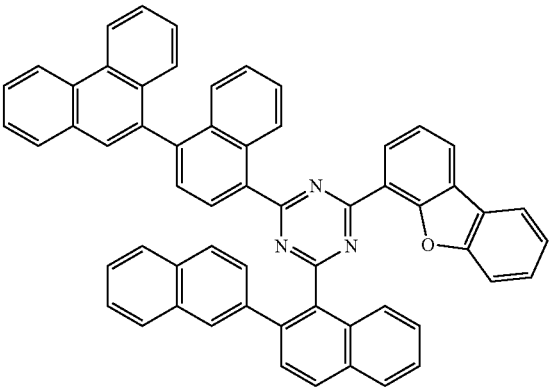
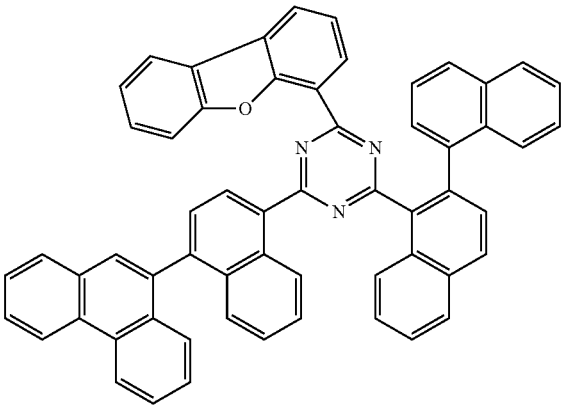

221
-continued
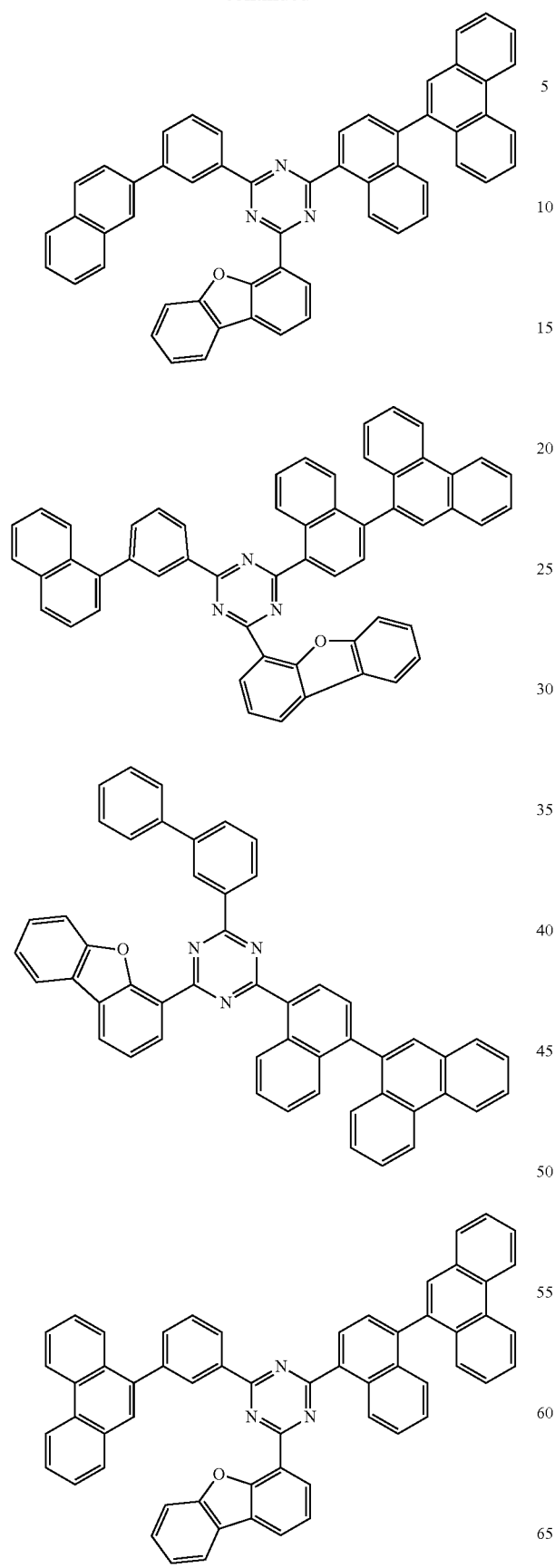
222
-continued
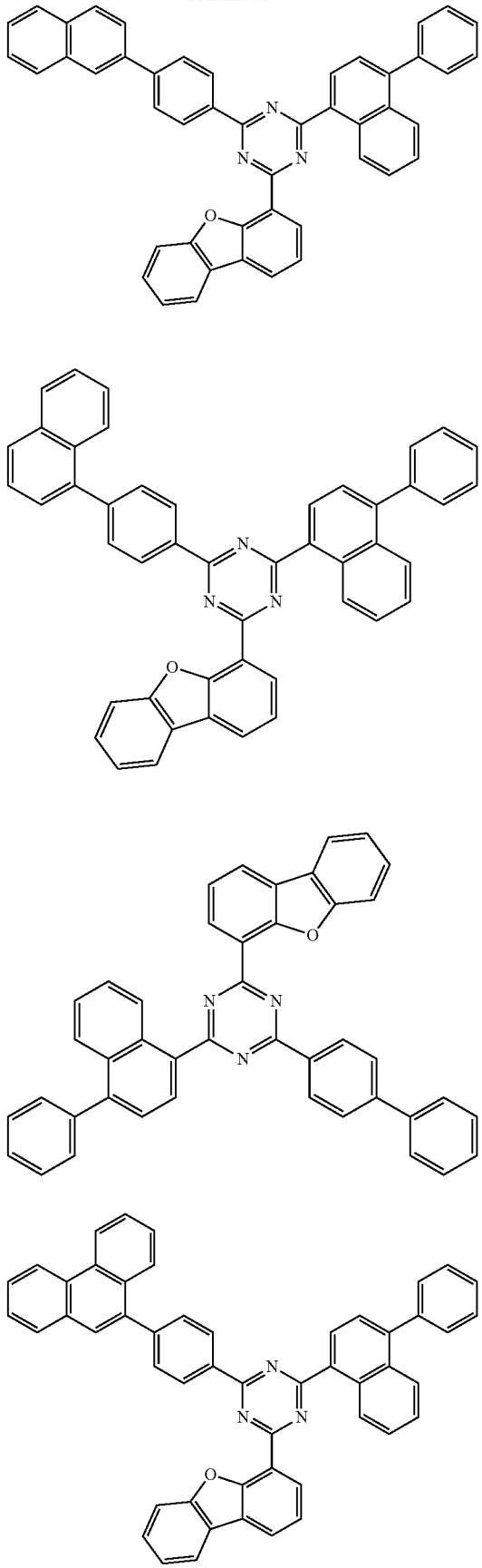

223
-continued
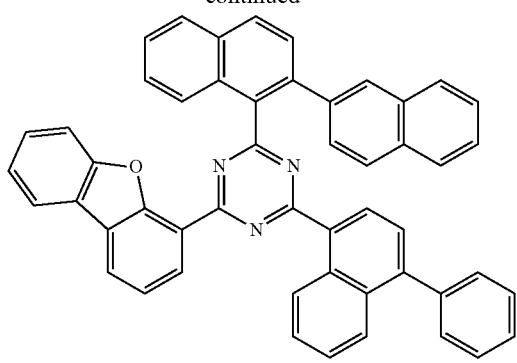
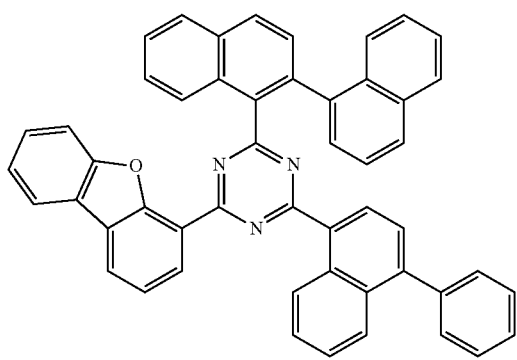
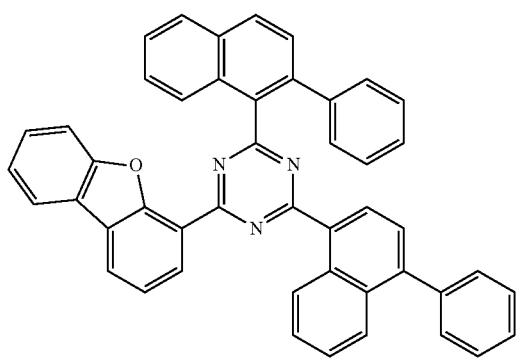
224
-continued
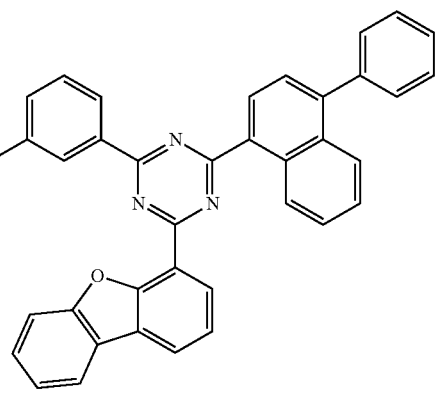
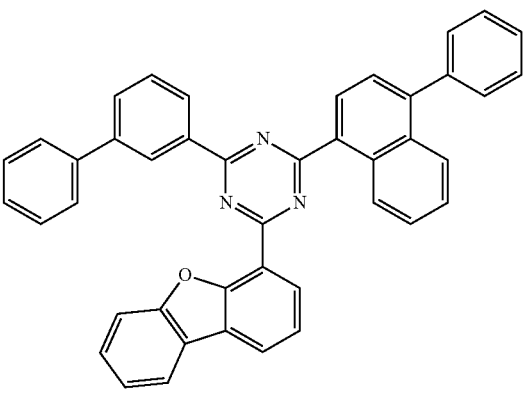

225
-continued
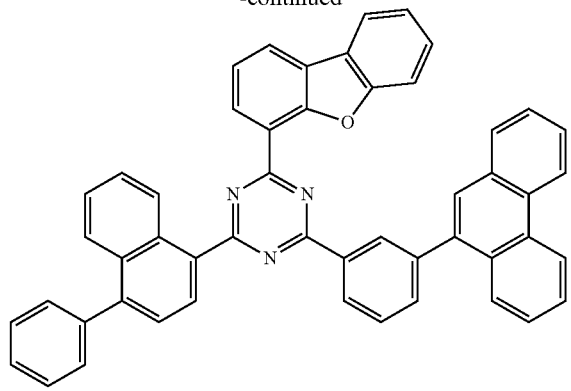
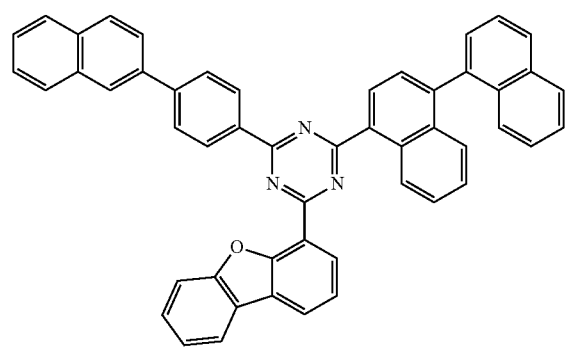
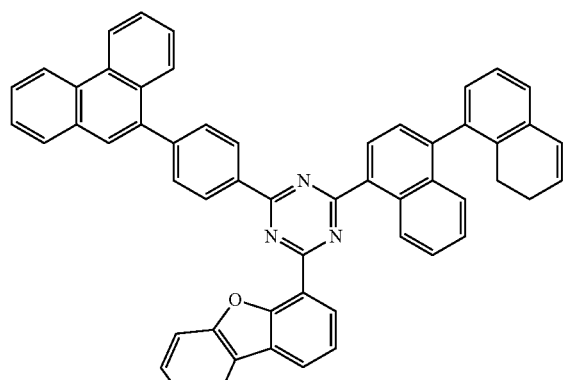
226
-continued
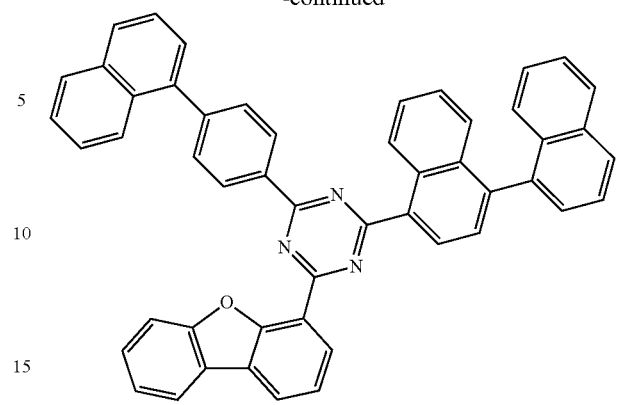
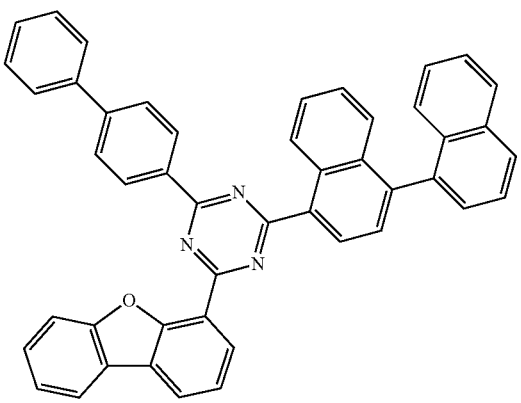
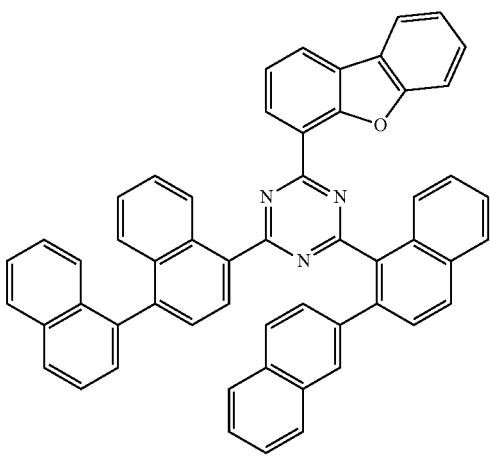

227 228
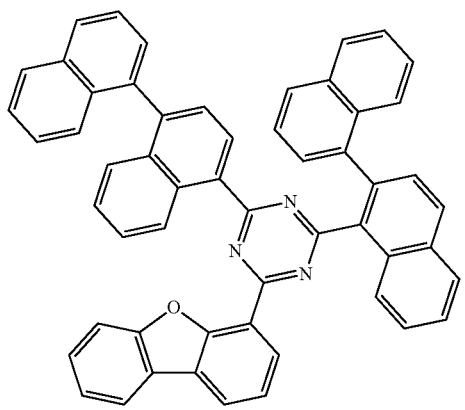
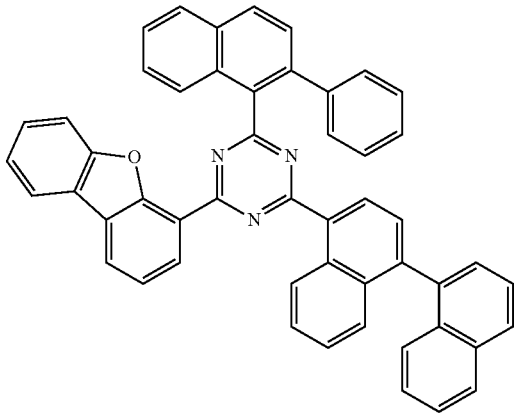
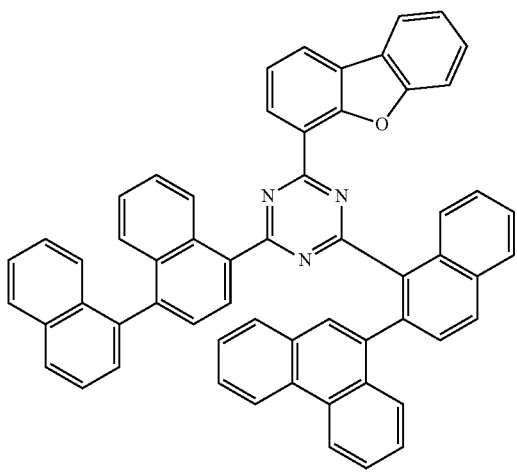
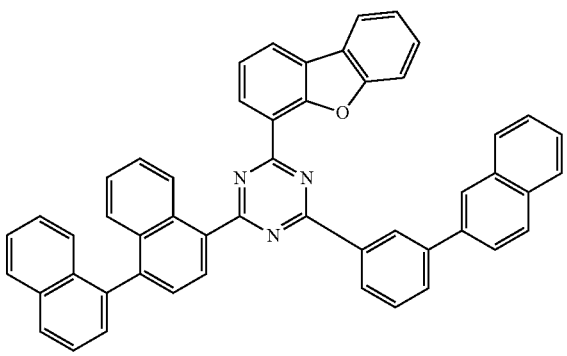
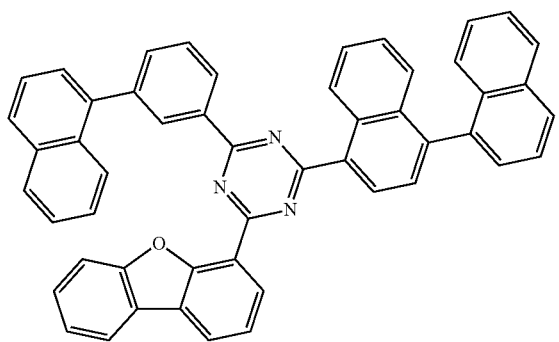
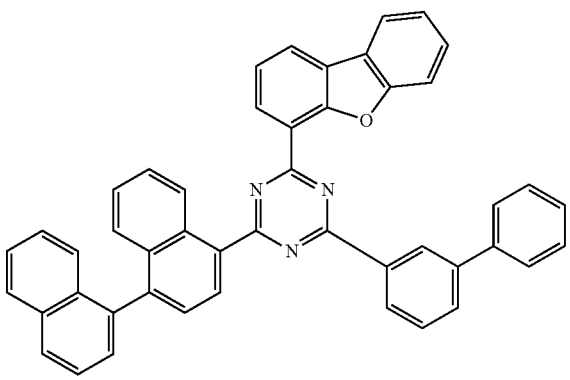
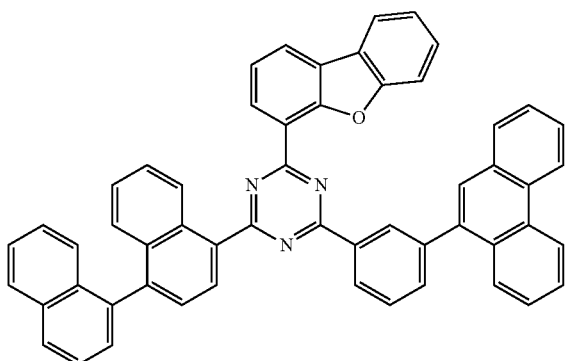
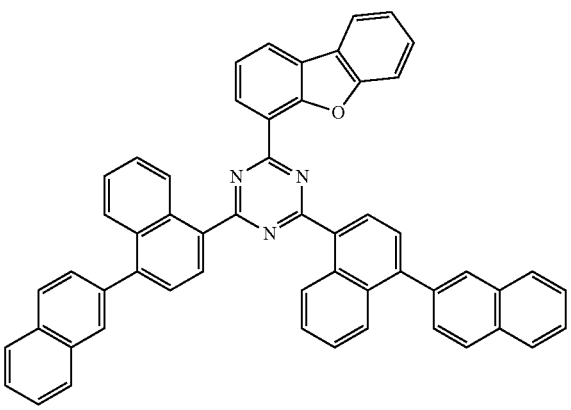

229 230
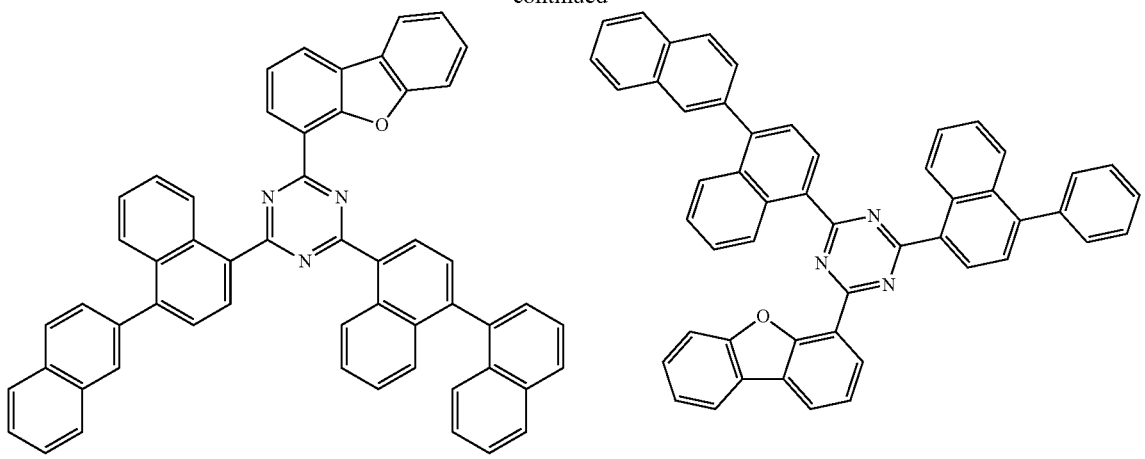
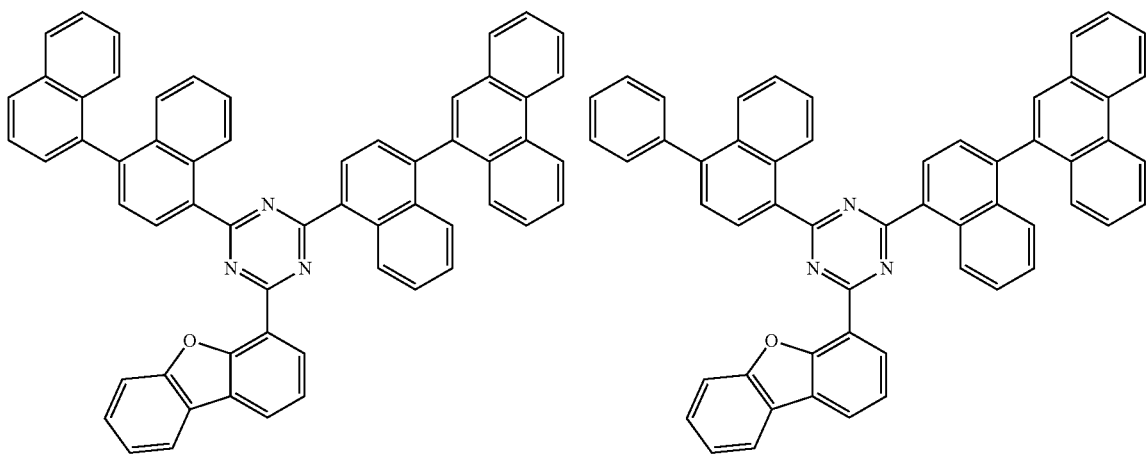
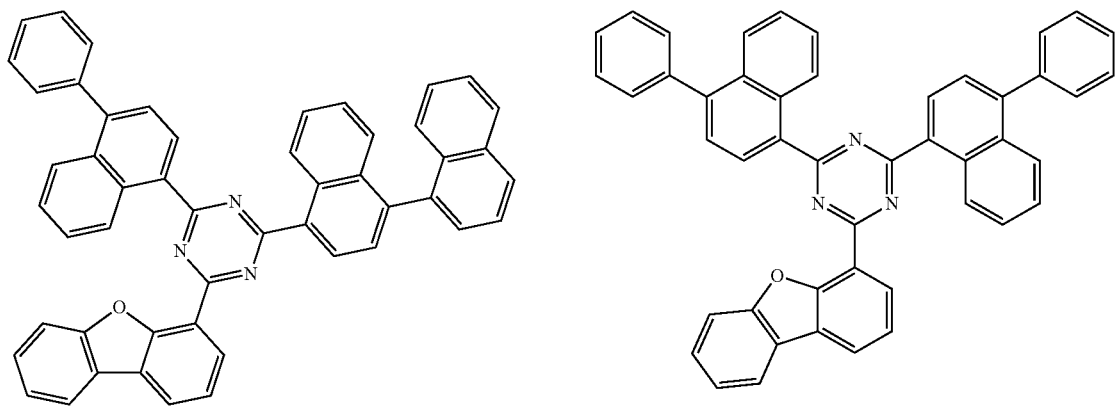

231 232
-continued
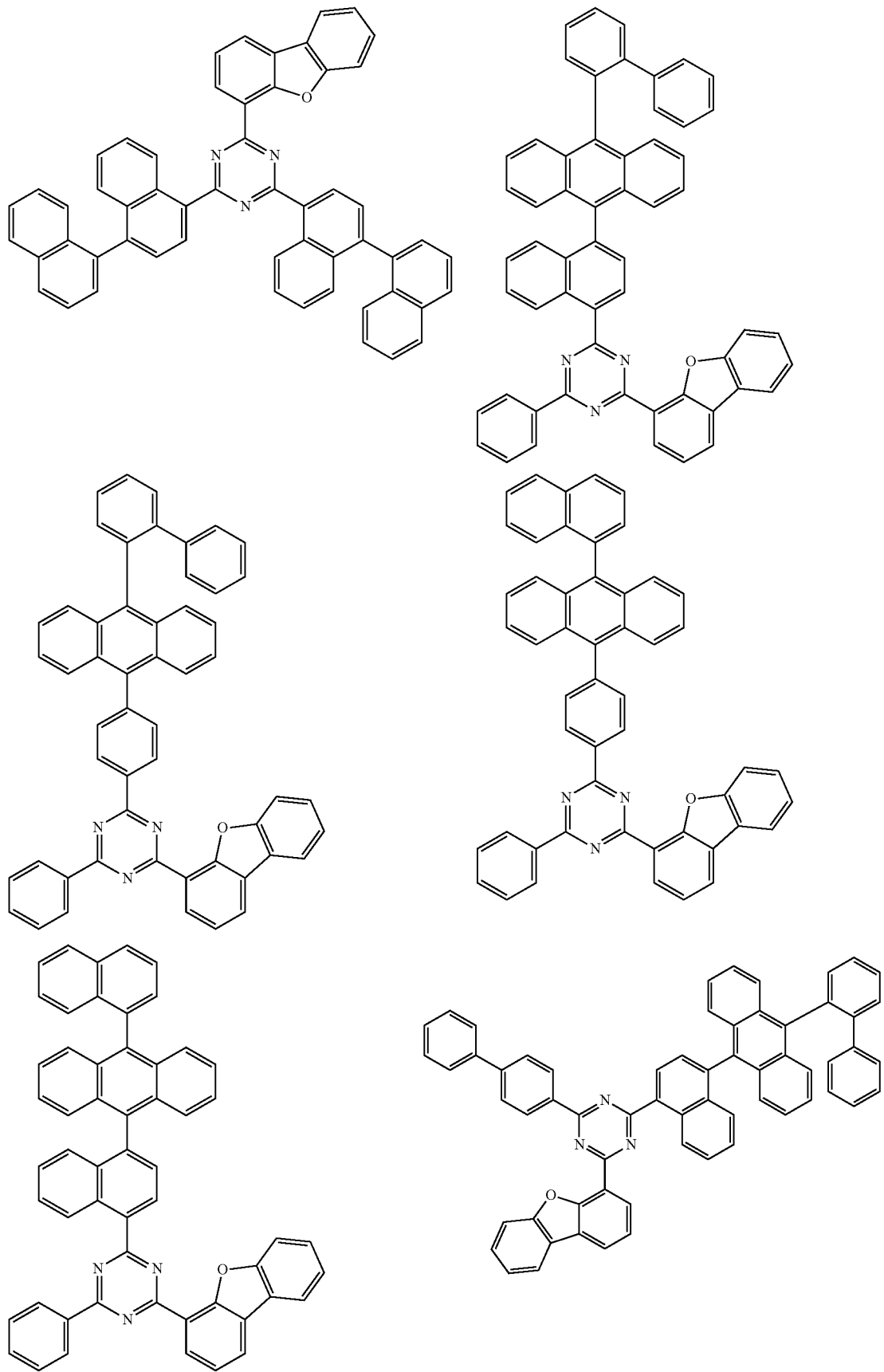

233
234
-continued
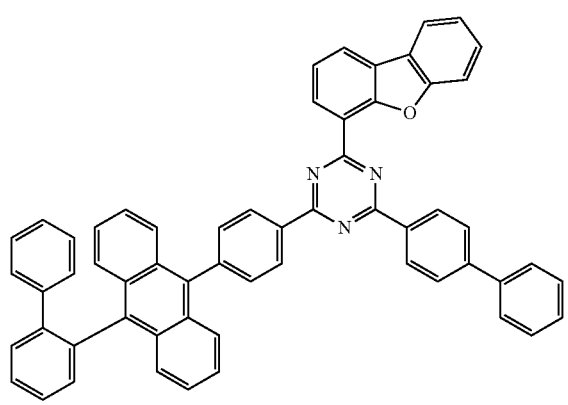
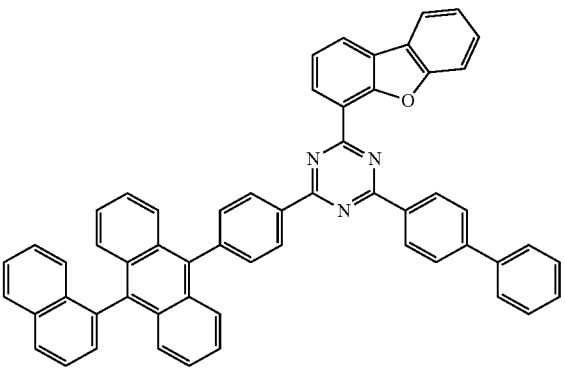
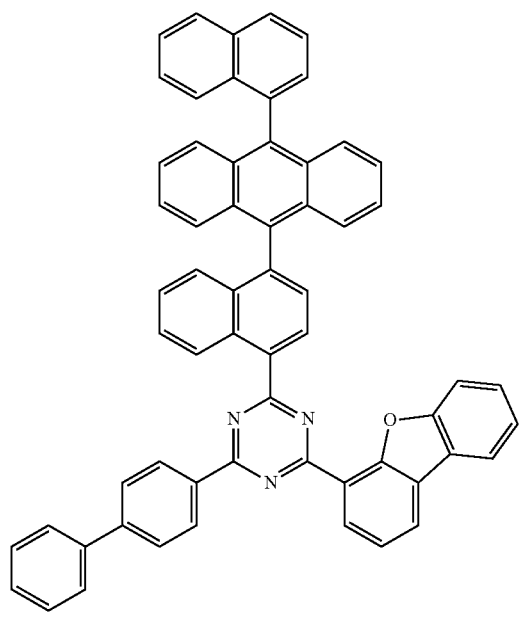
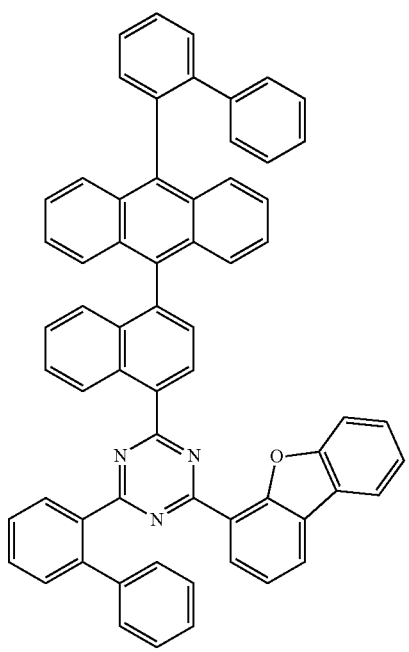
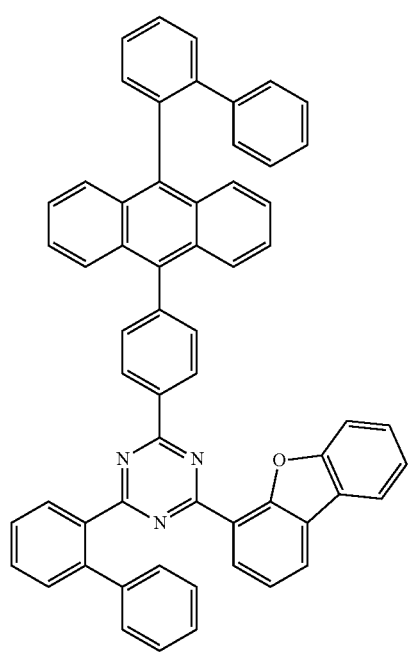
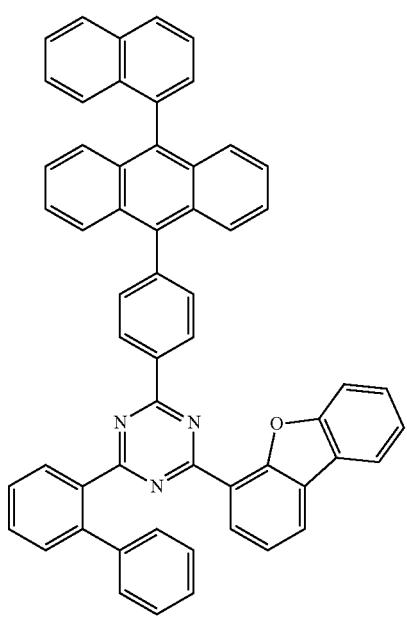

-continued
235
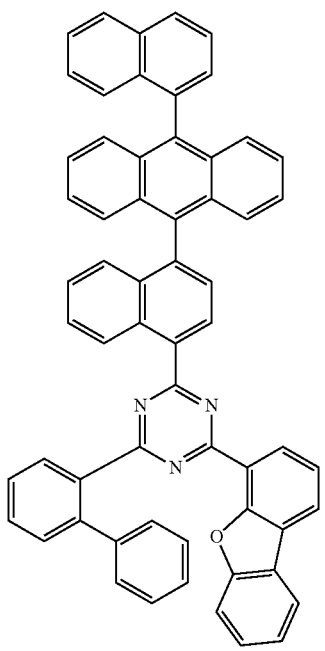
236
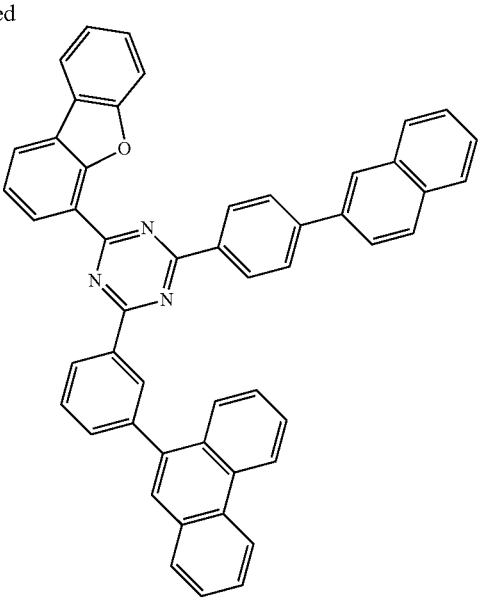
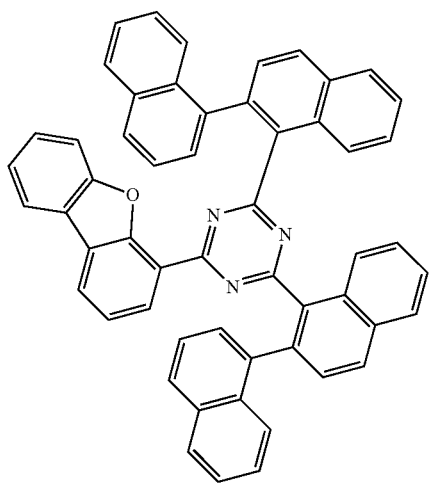

-continued
| 237 | 238 |
|---|---|
| 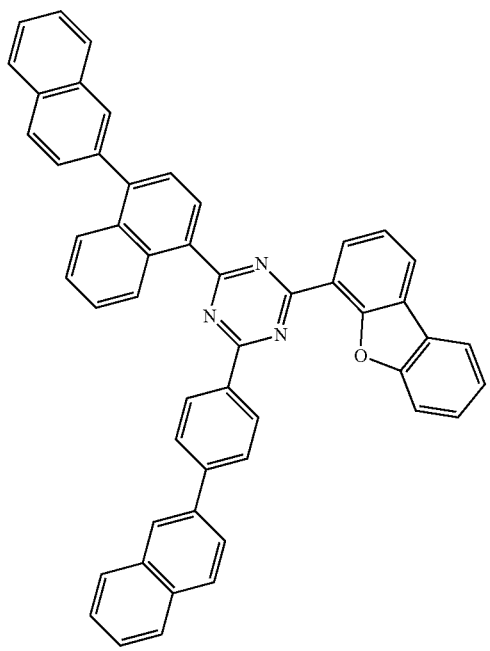 | 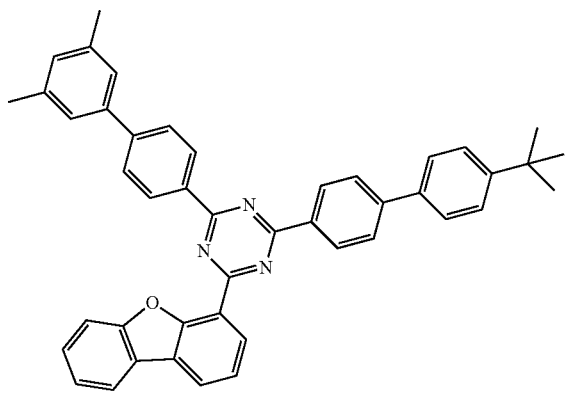 |
| 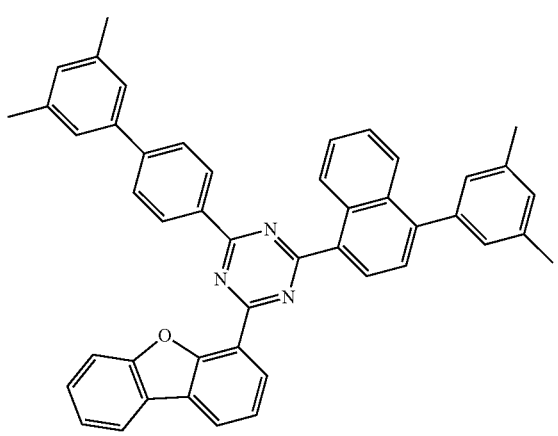 | 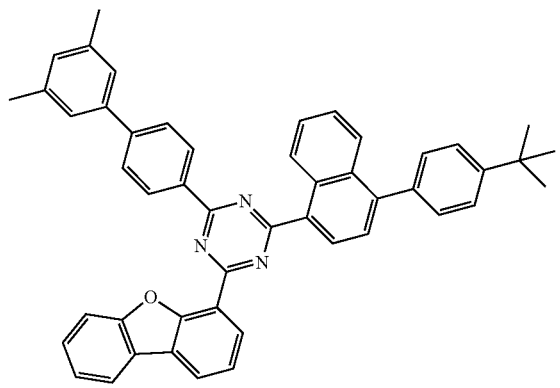 |
| 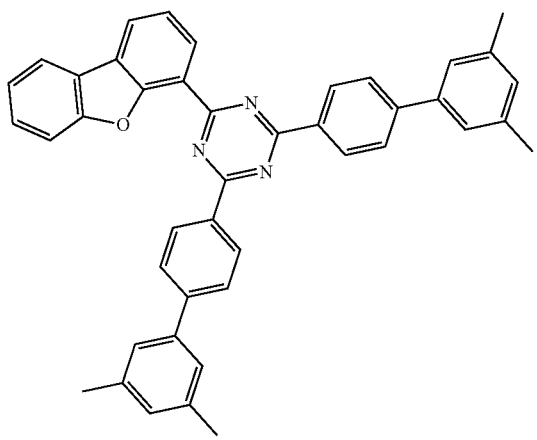 | 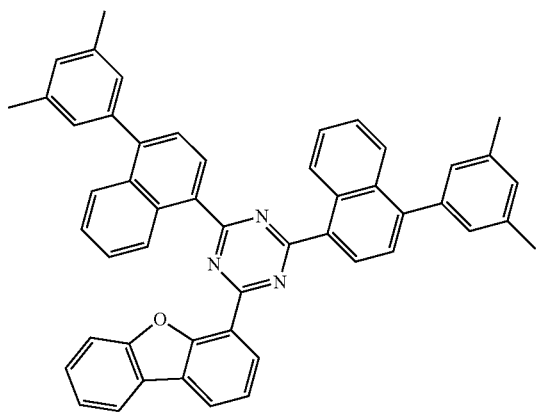 |

-continued
239
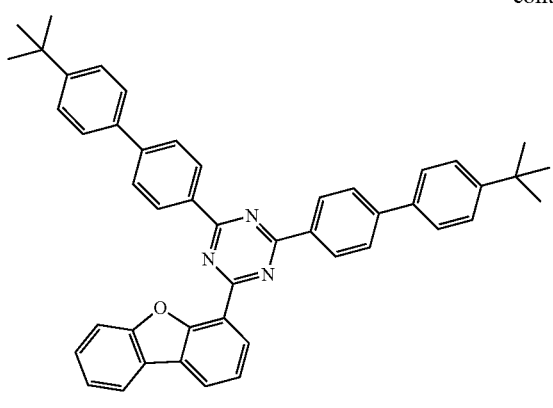
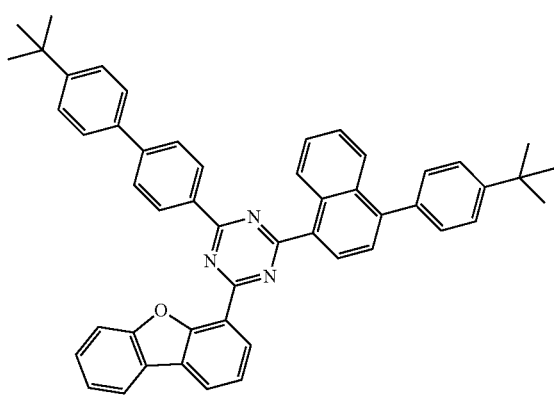
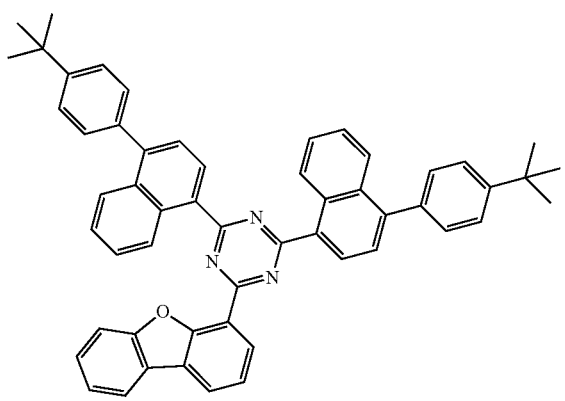
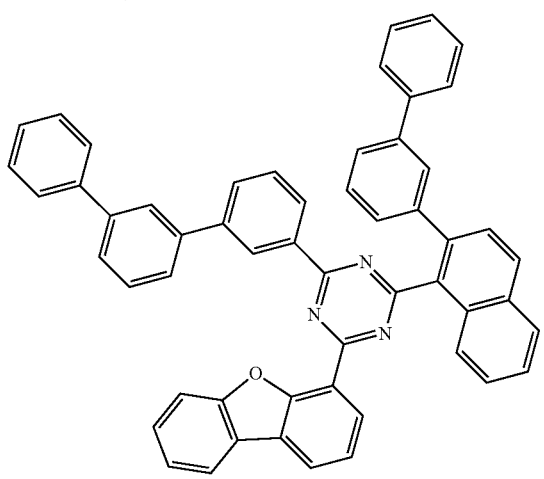
240
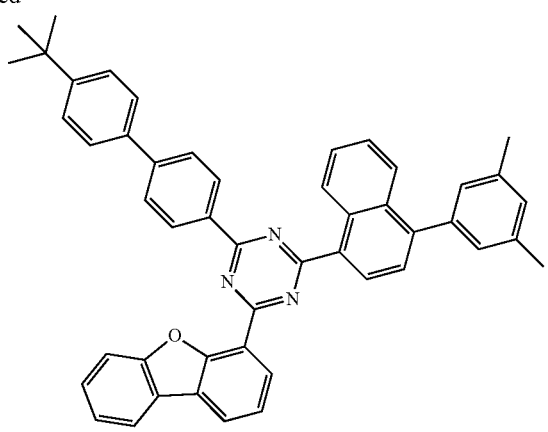
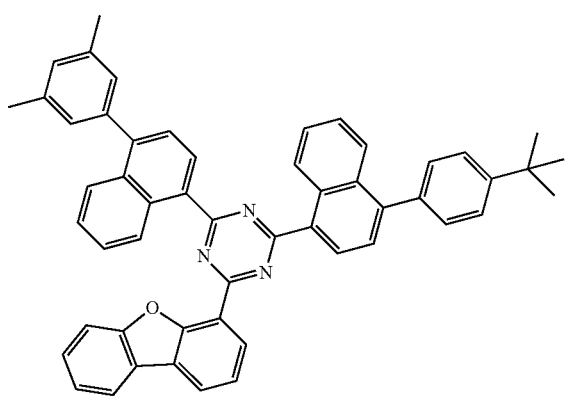
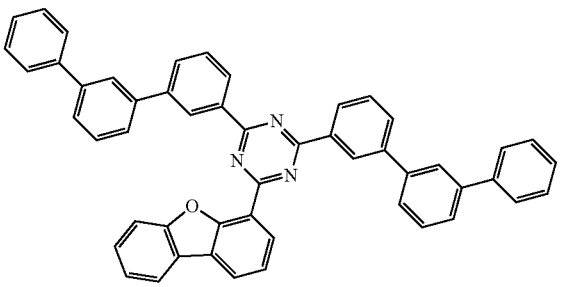
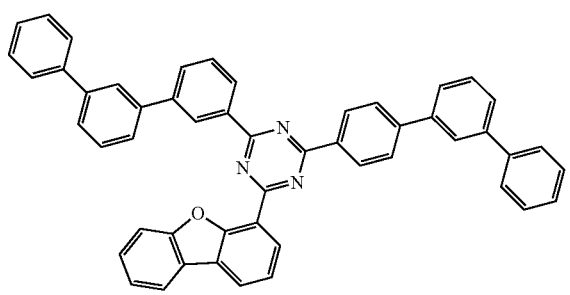

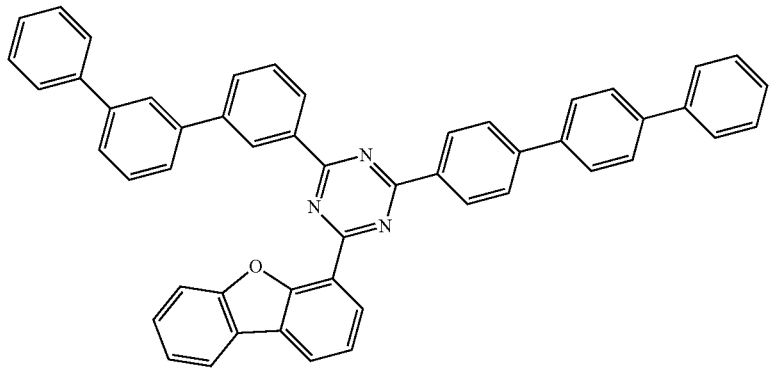
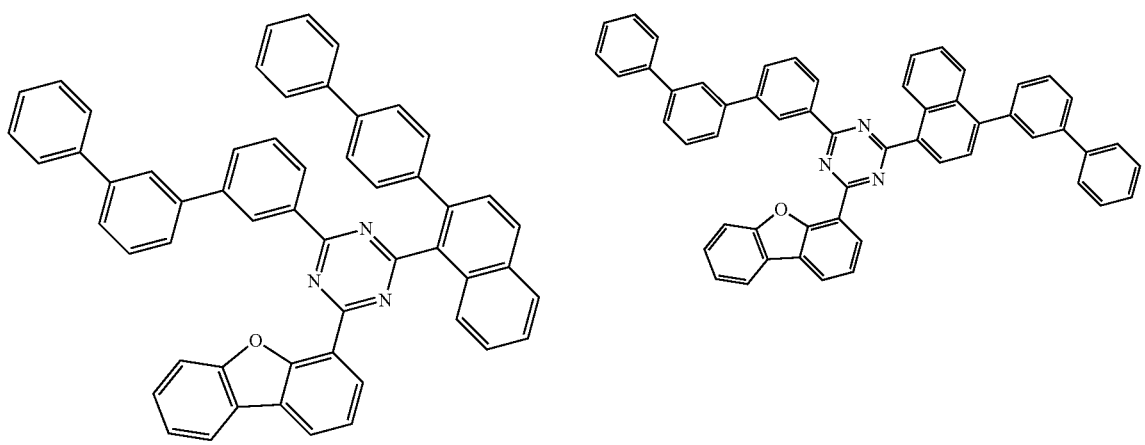
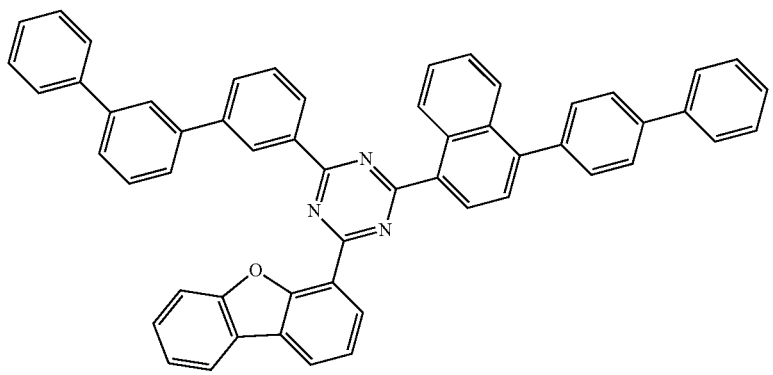
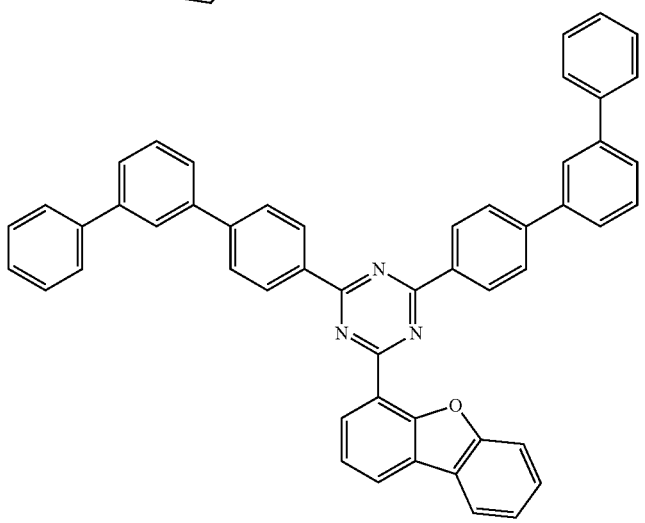

243
244
-continued
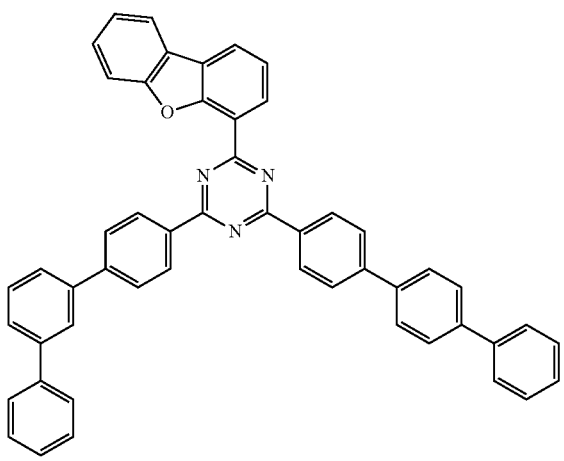
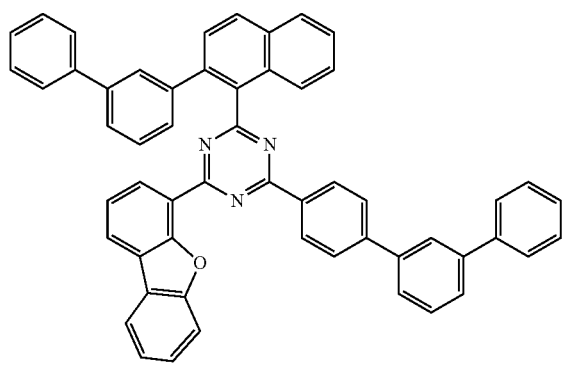
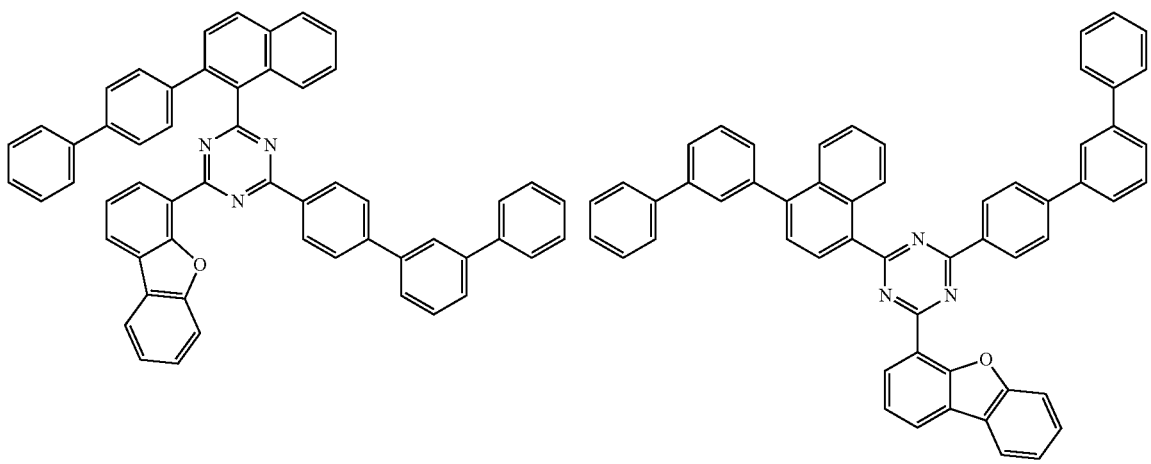
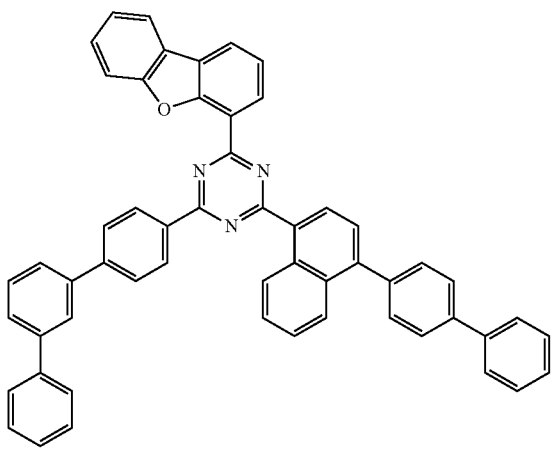
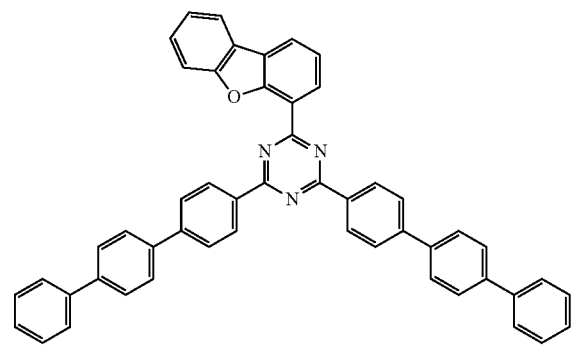

-continued
245
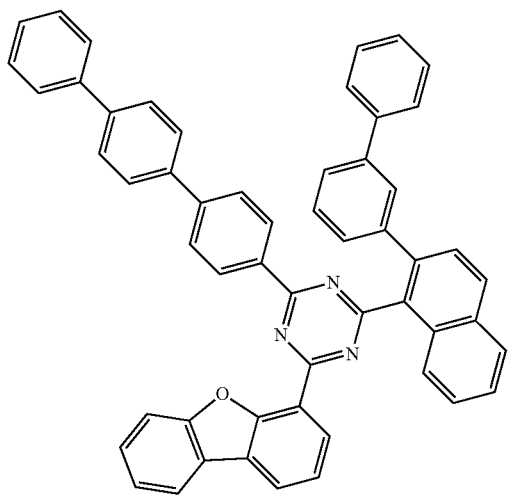
246
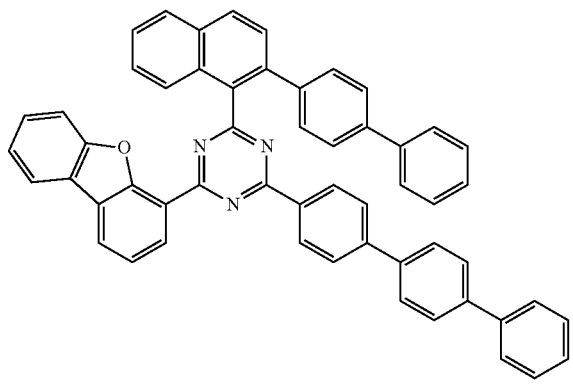
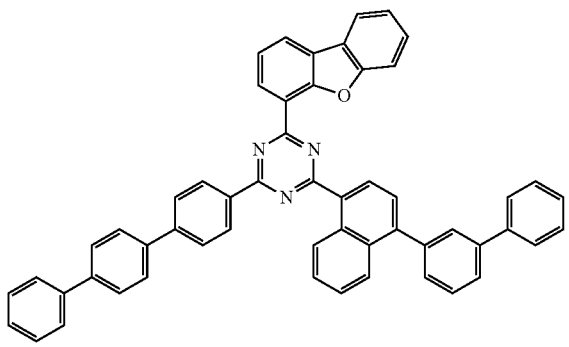
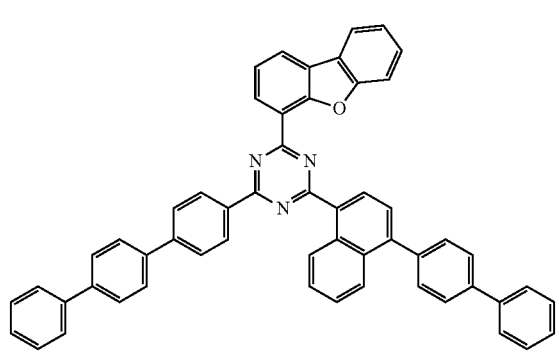
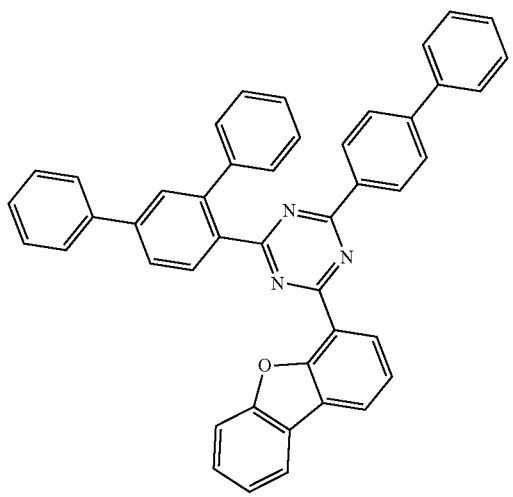
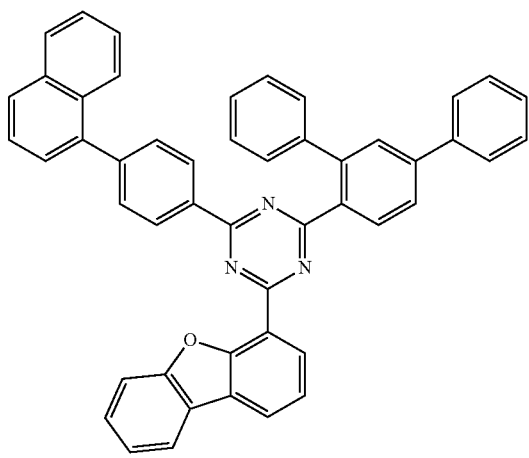

| 247 | 248 |
|---|---|
| 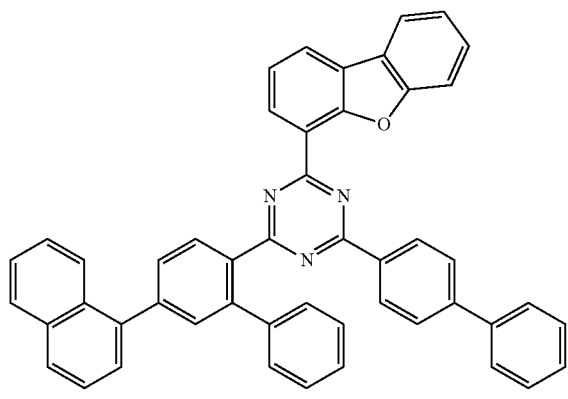 | 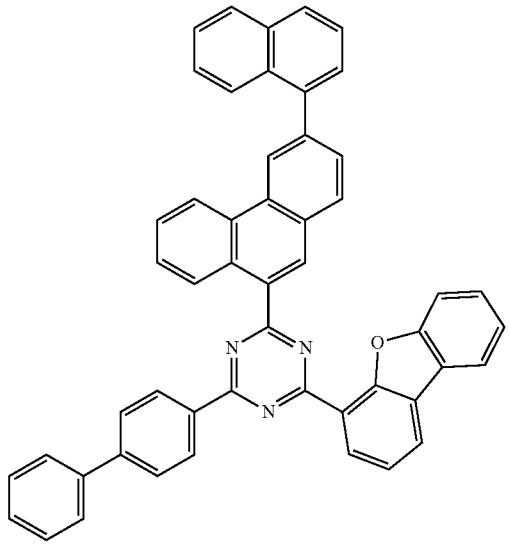 |
| 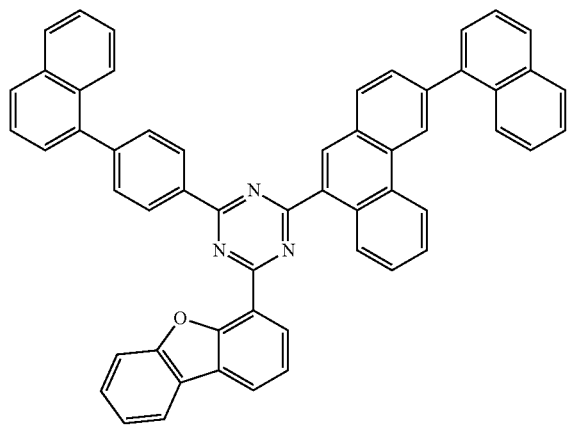 | 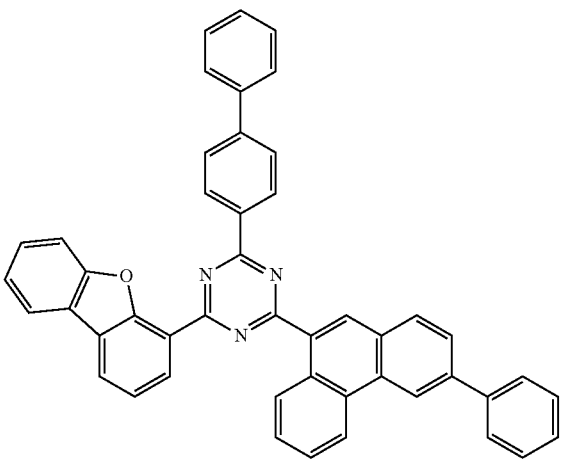 |
| 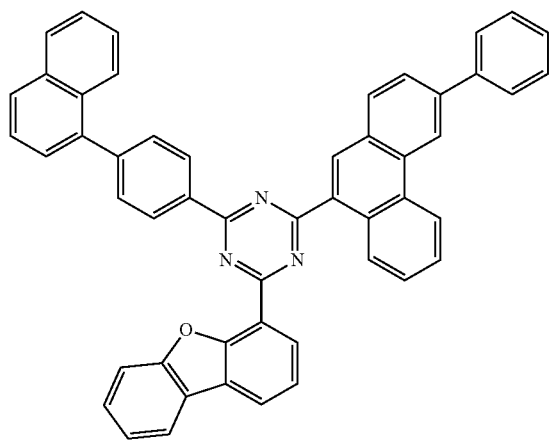 | 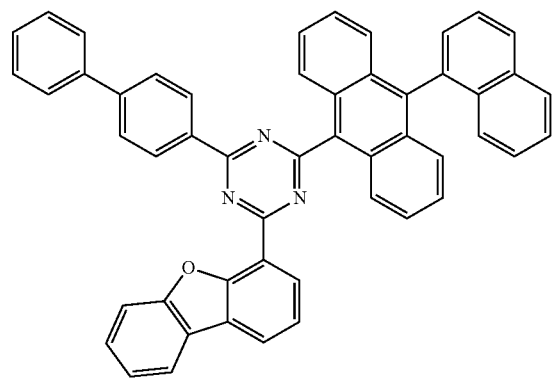 |

-continued
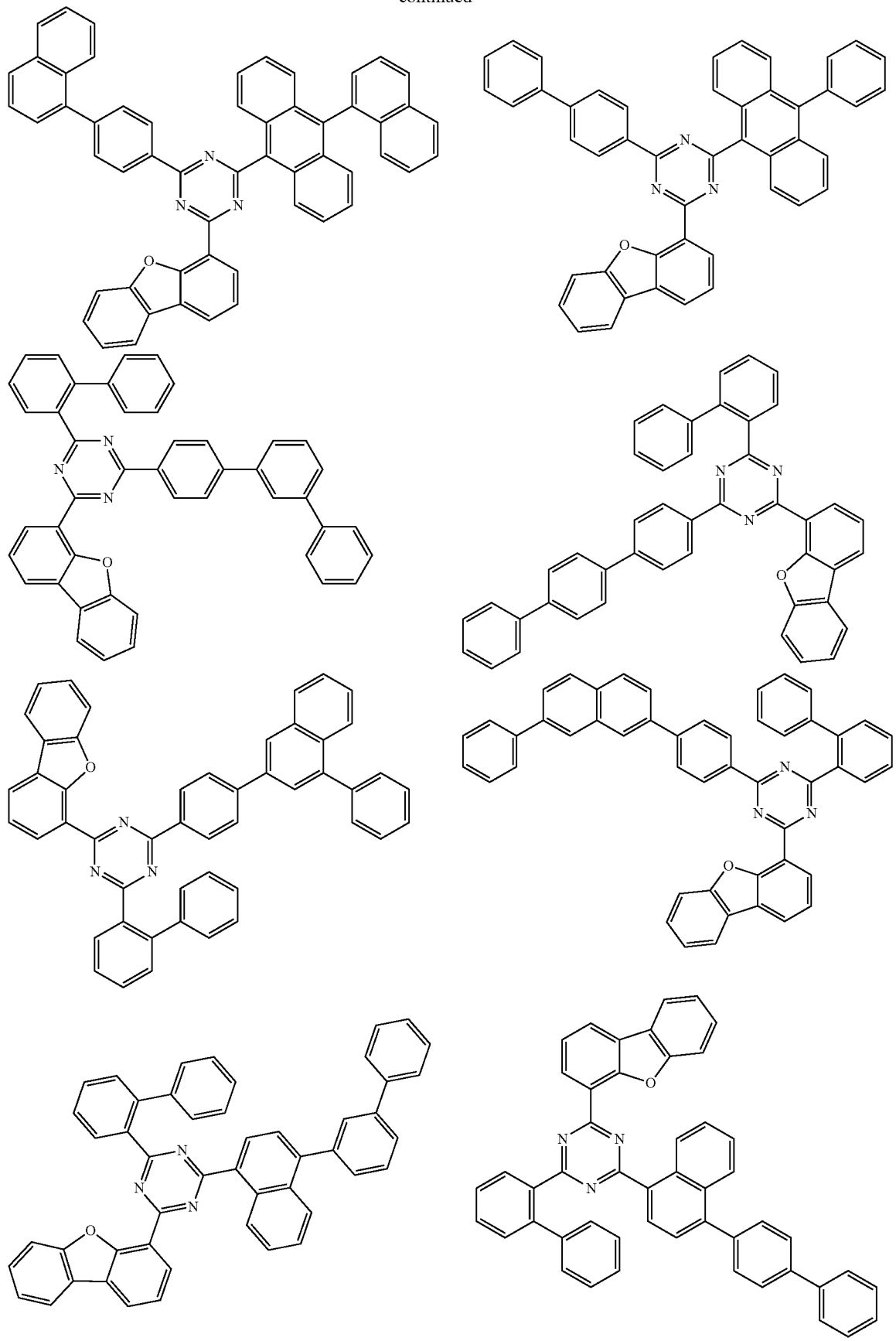

251 252
-continued
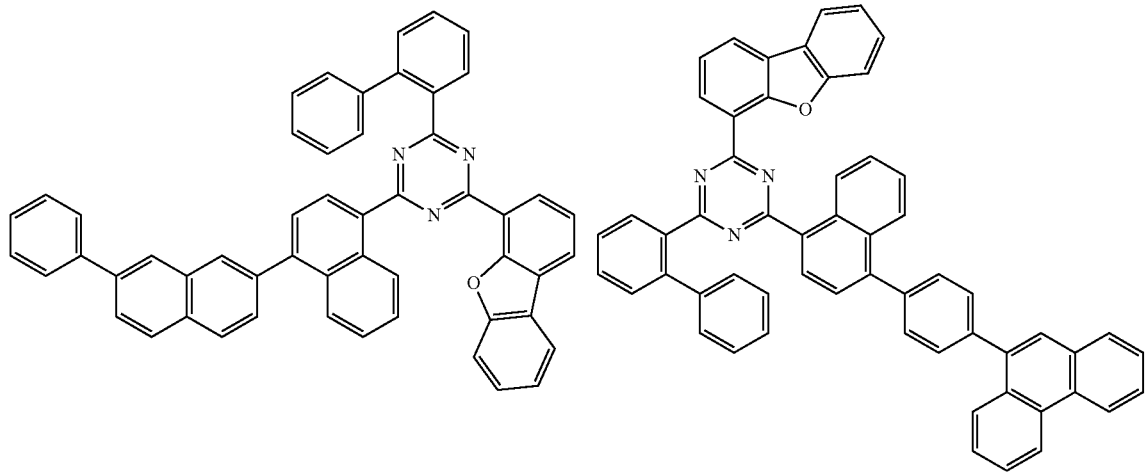
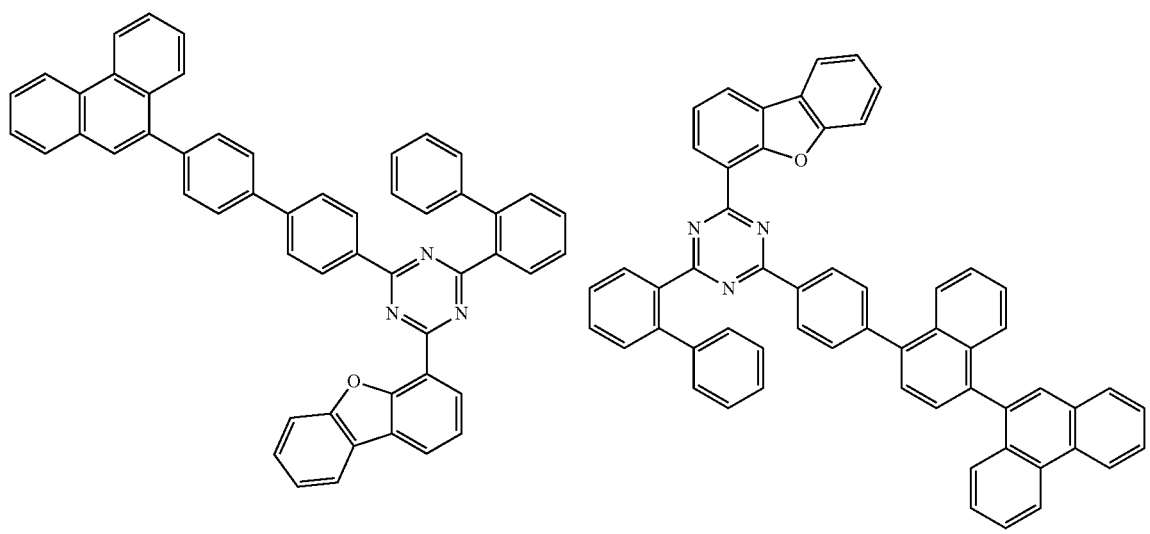
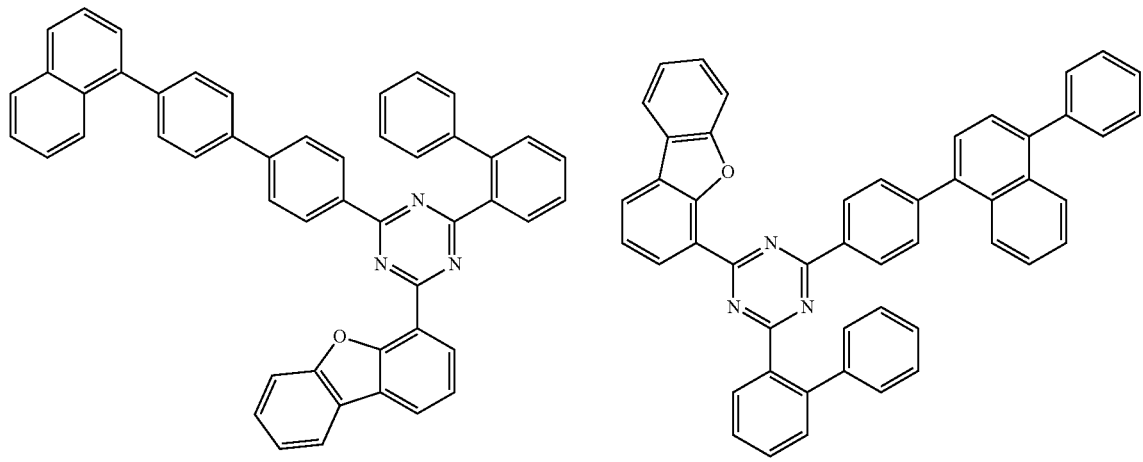

253 254
-continued
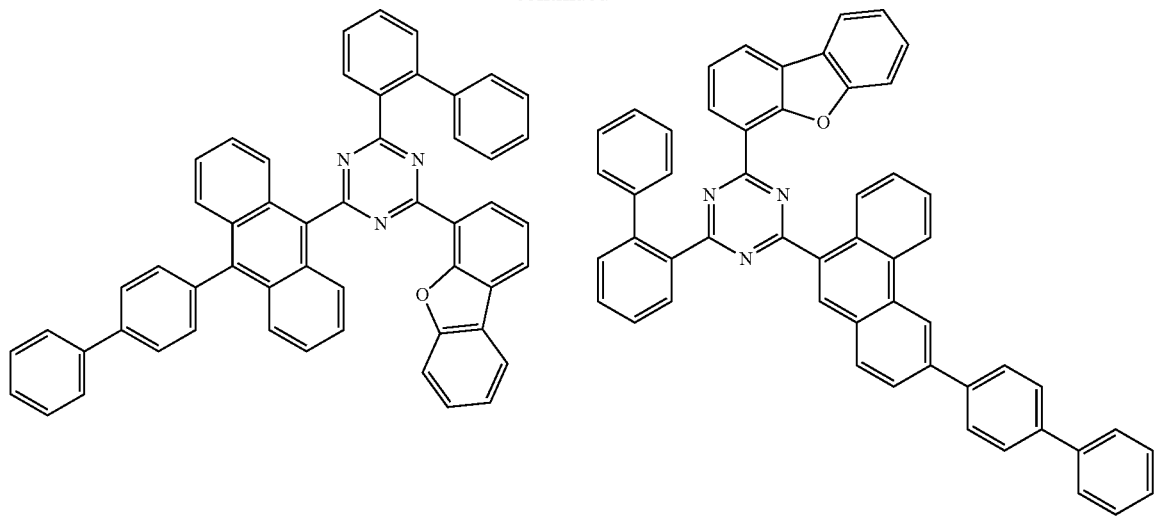
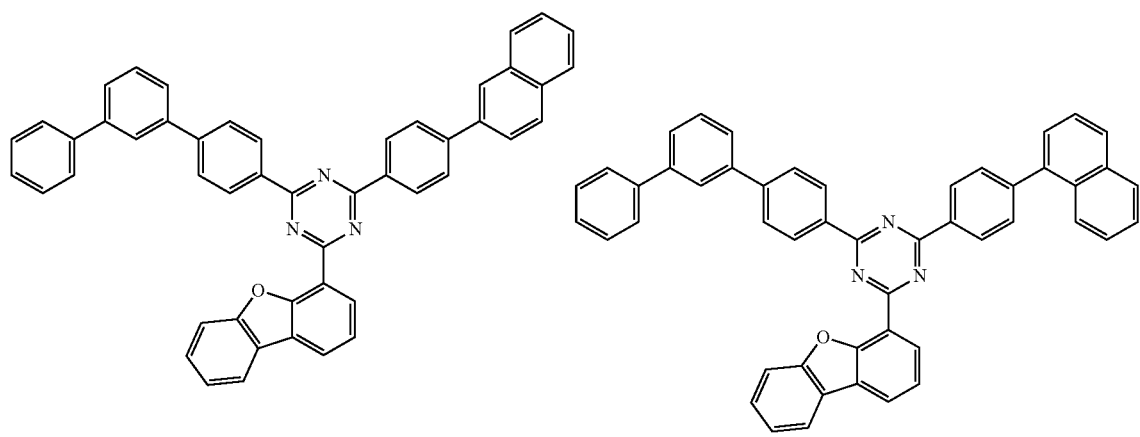
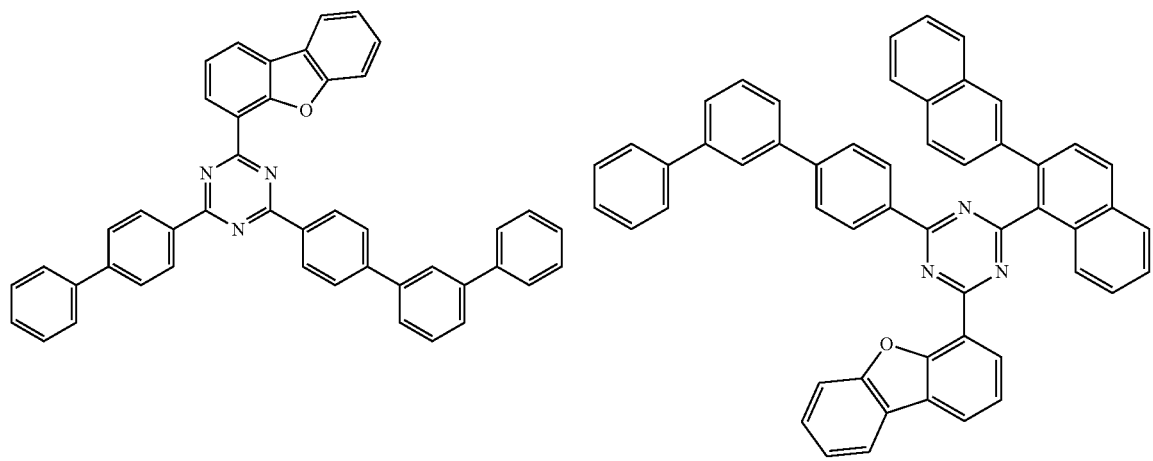

255 256
-continued
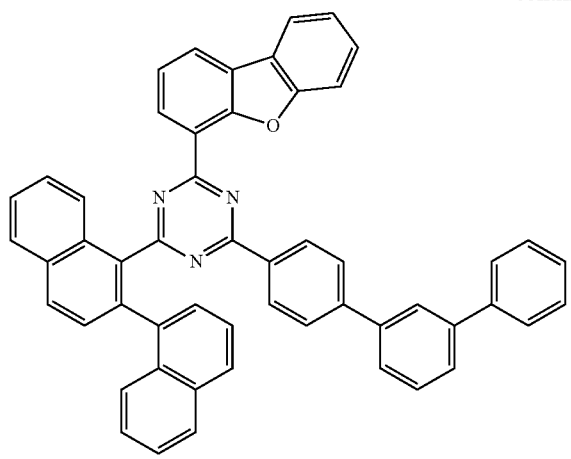
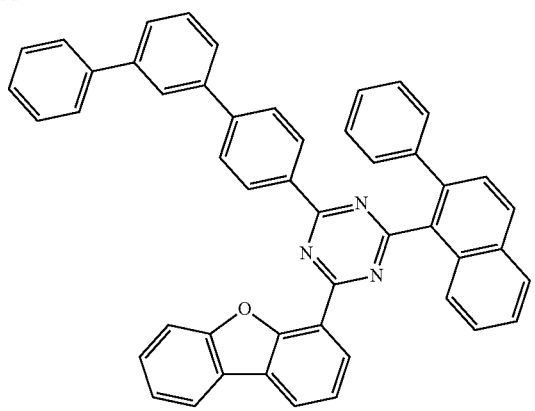
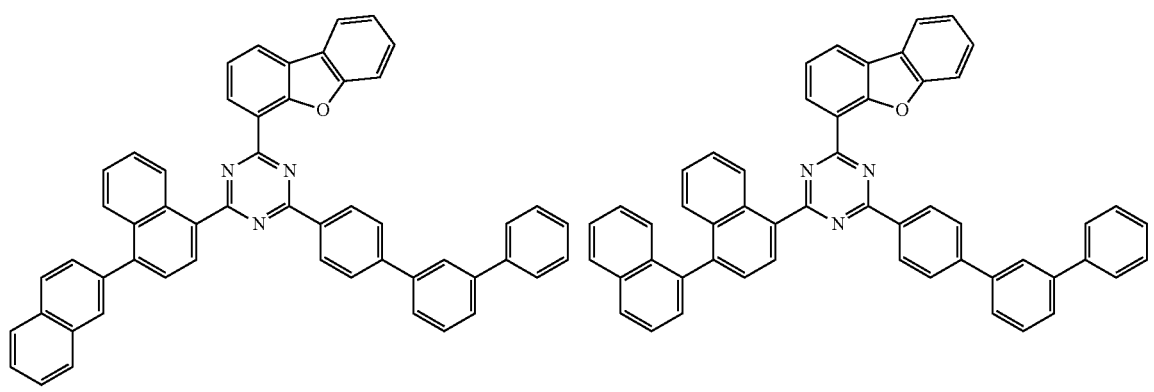
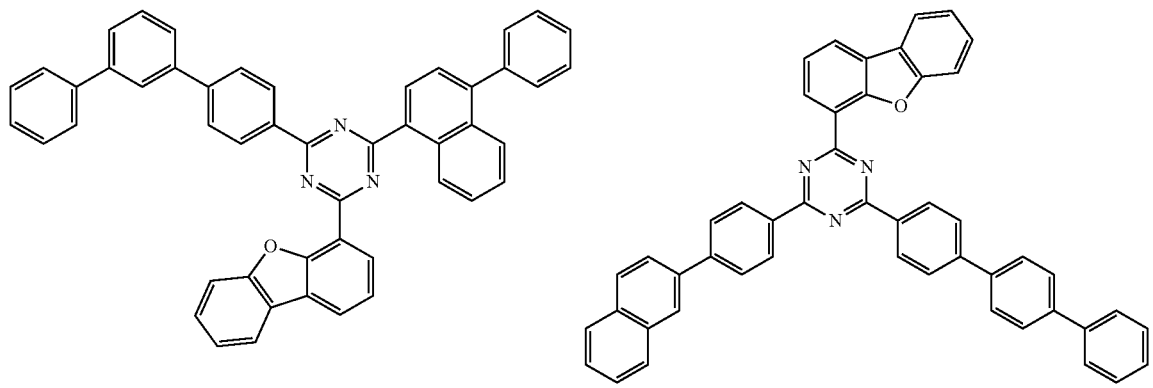
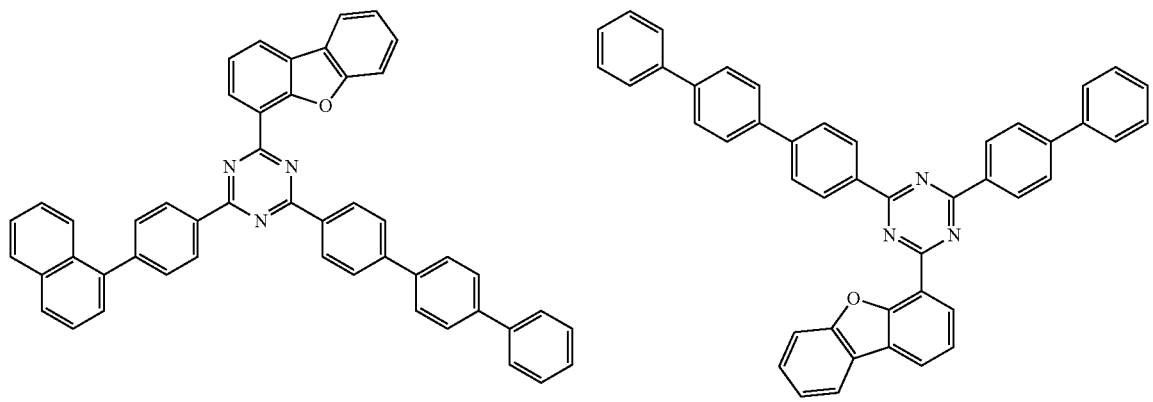

257 258
-continued
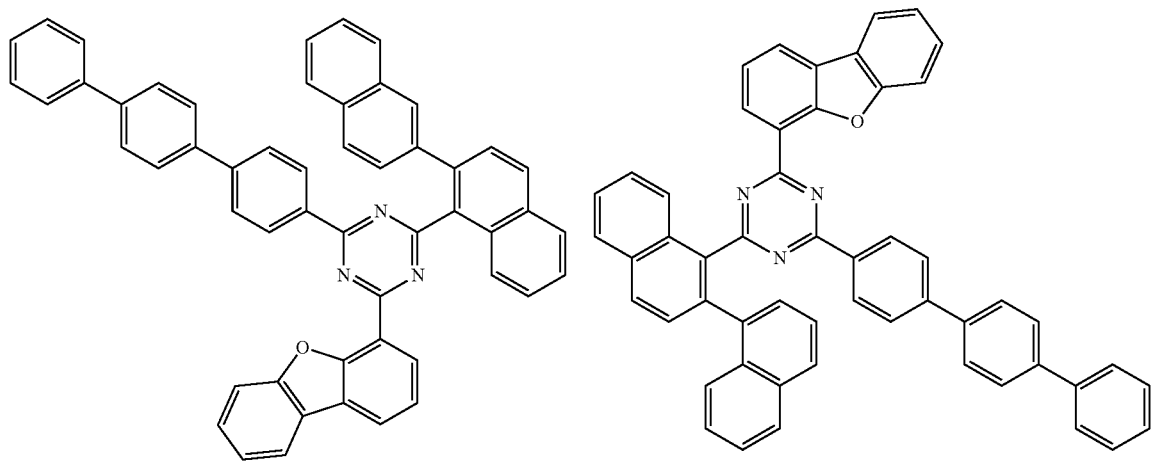
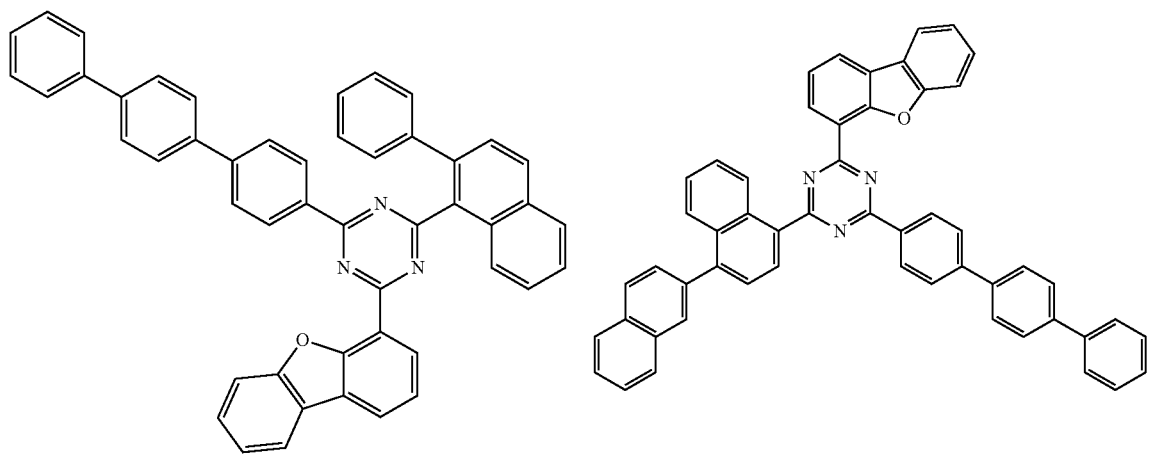
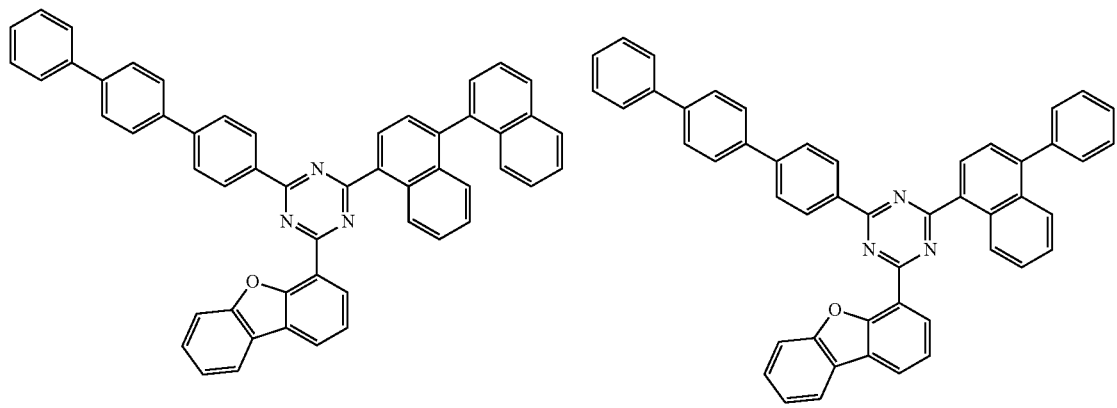

259 260
-continued
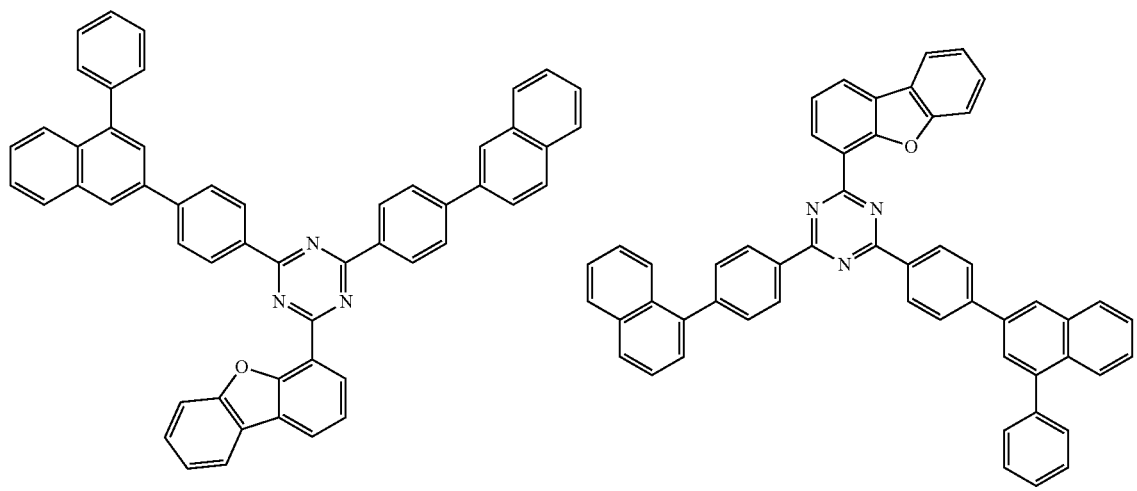
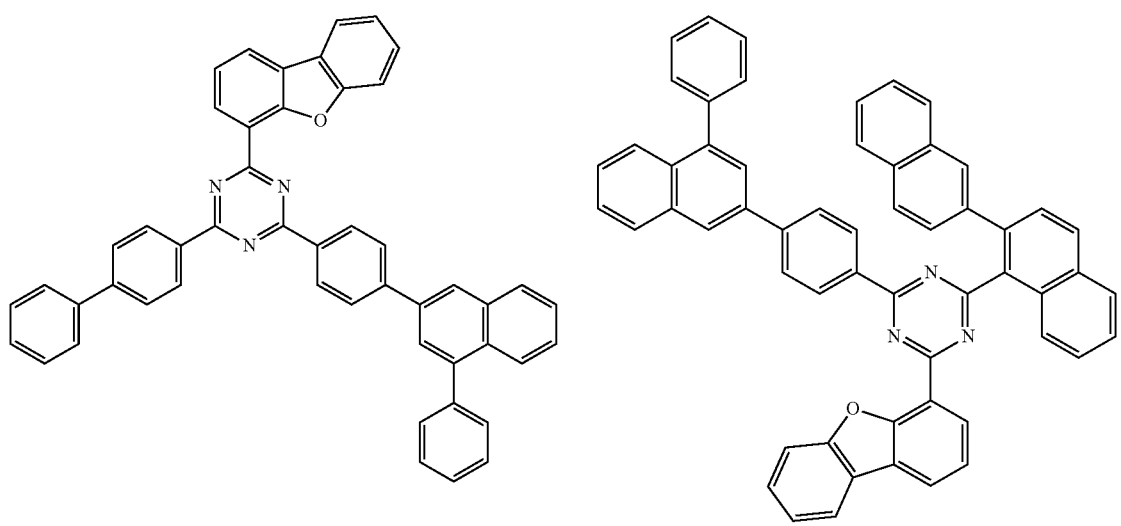
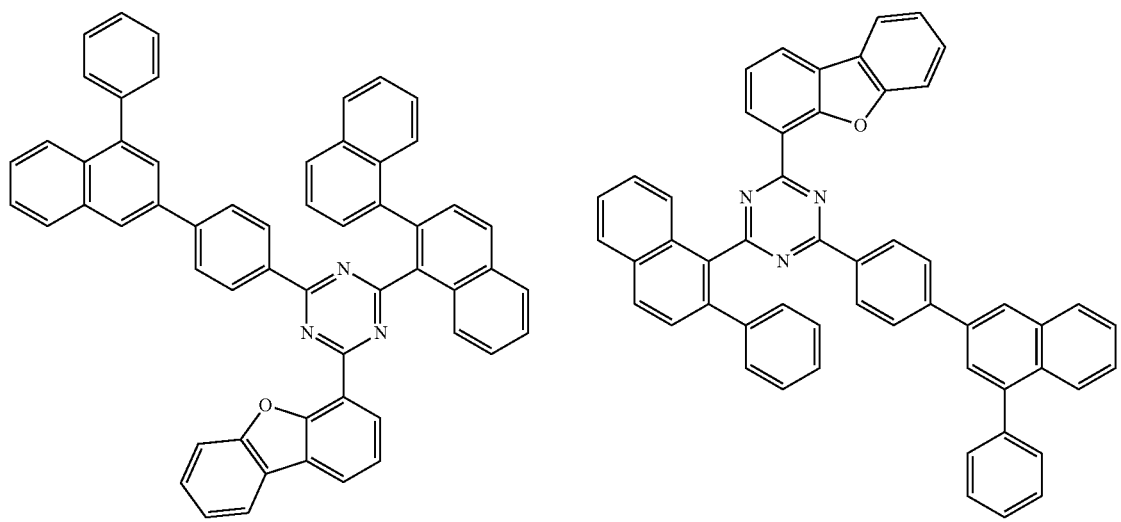

-continued
| 261 | 262 |
|---|---|
| 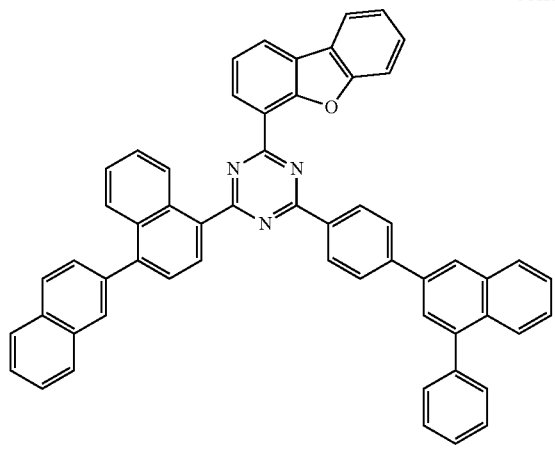 | 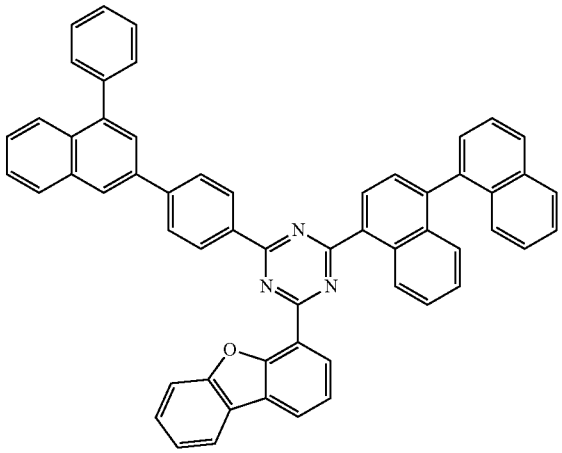 |
| 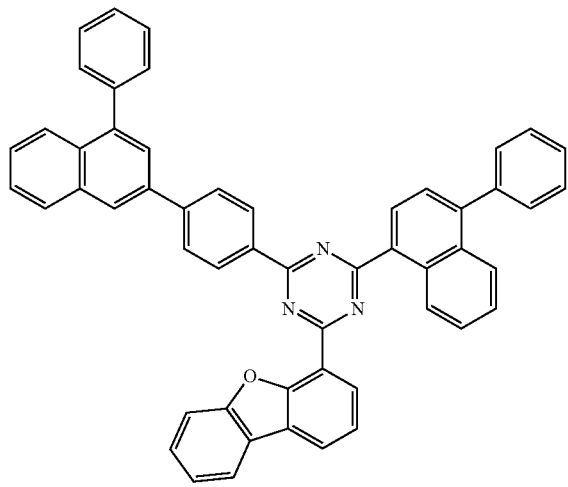 | 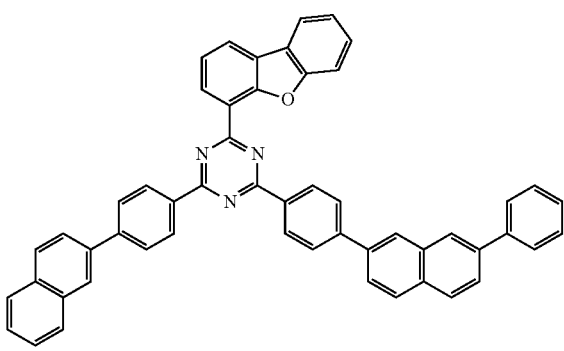 |
| 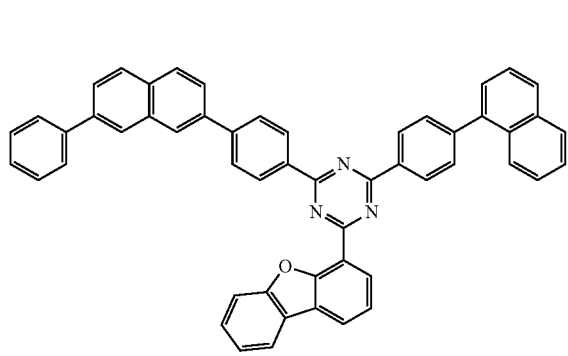 | 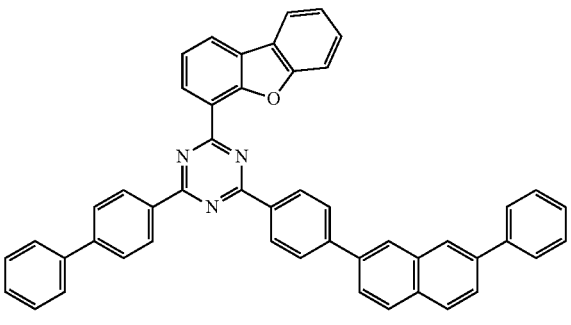 |
| 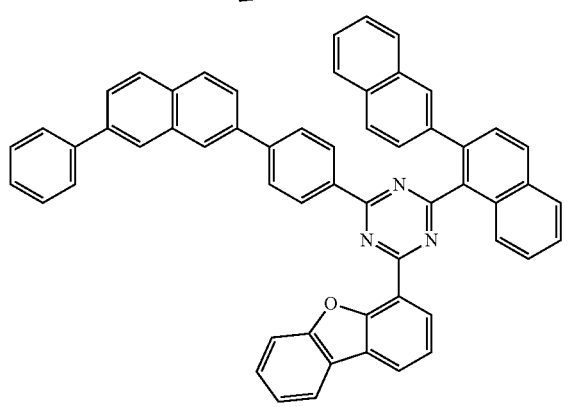 | 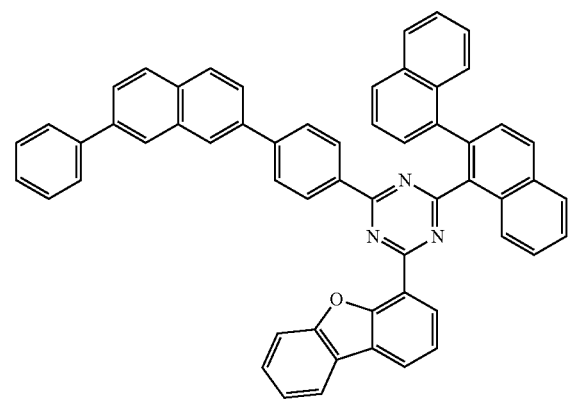 |

263 264
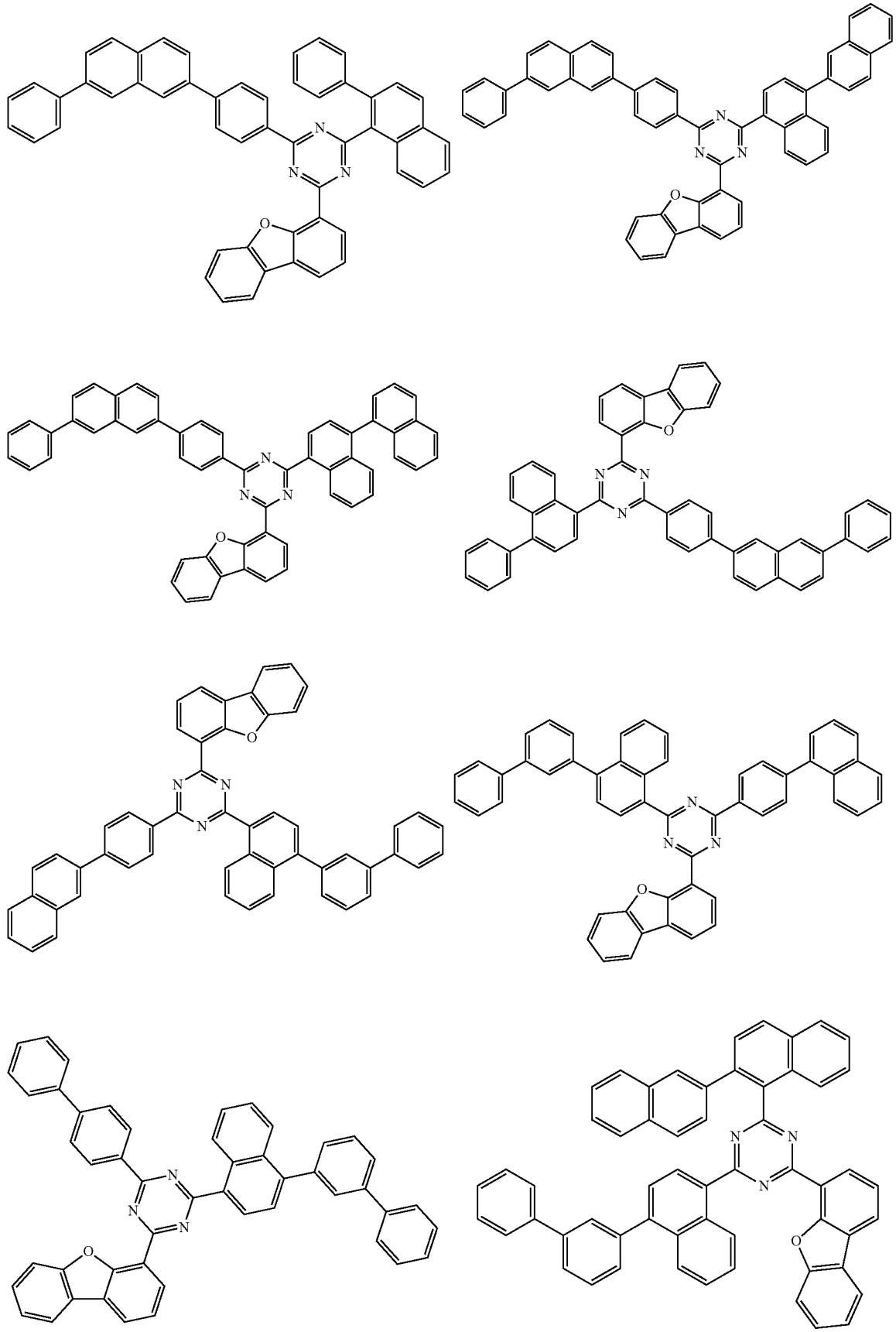

265
266
-continued
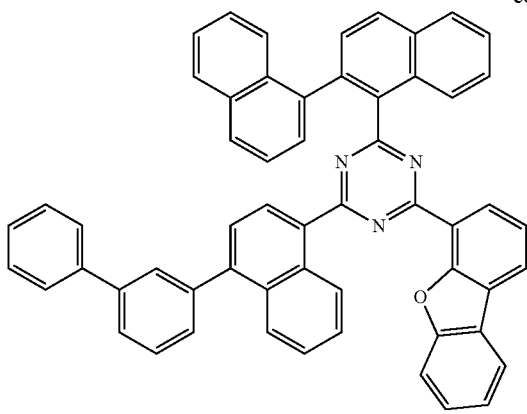
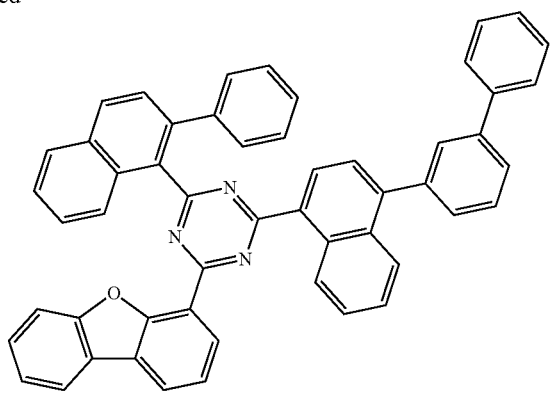
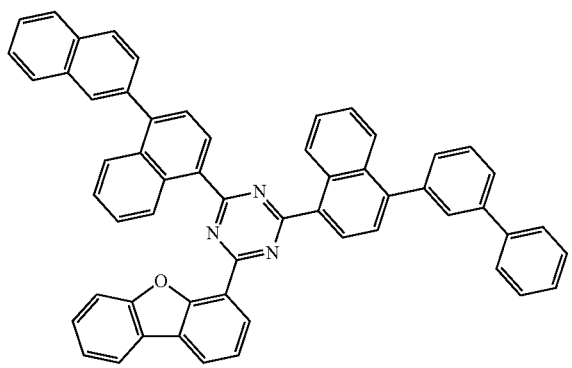
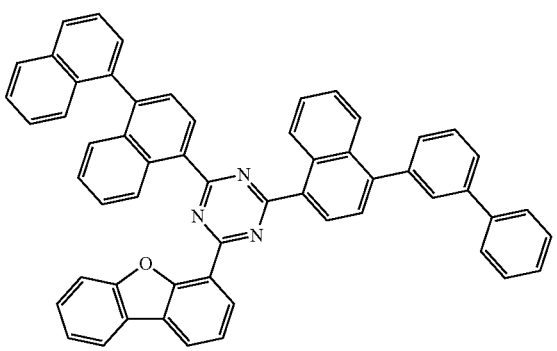
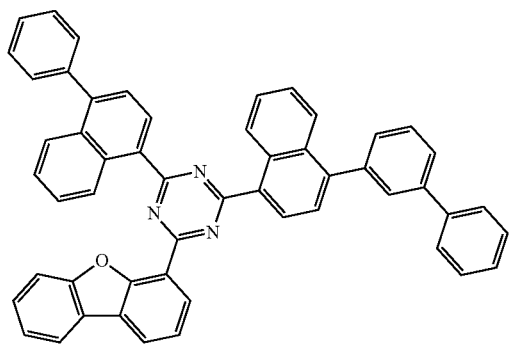
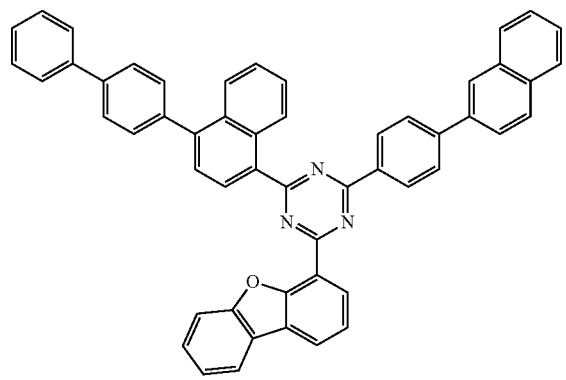
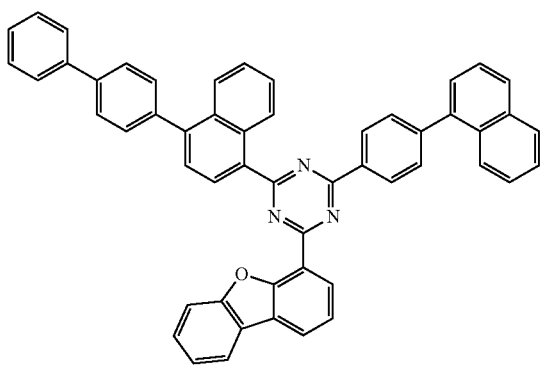
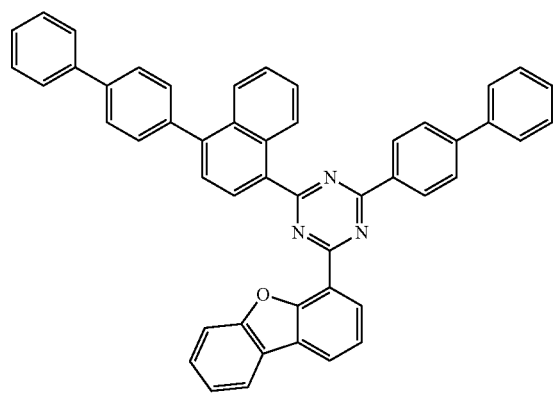

267
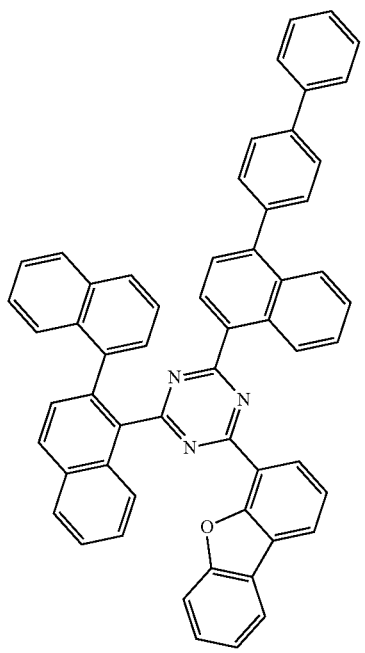
268
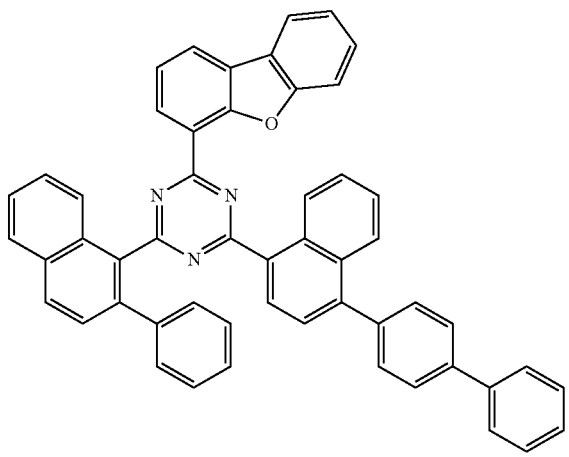
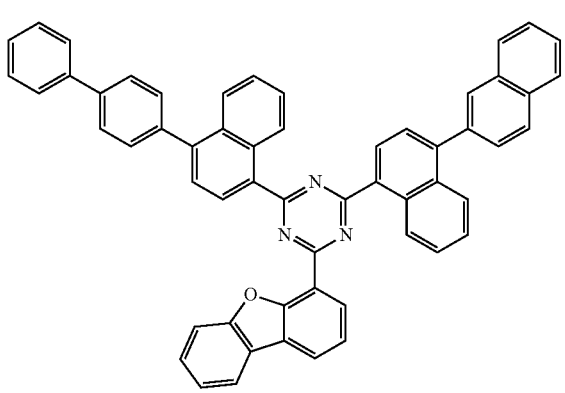
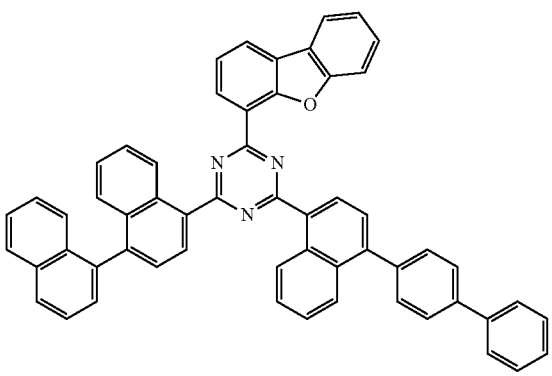
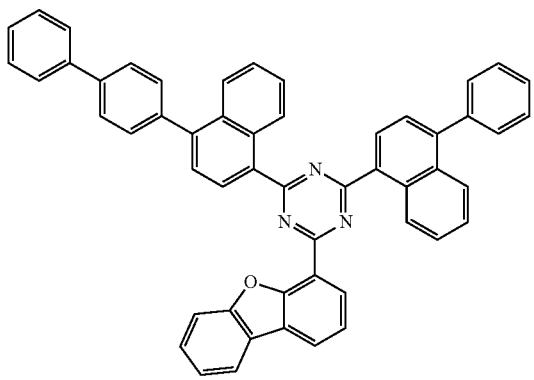
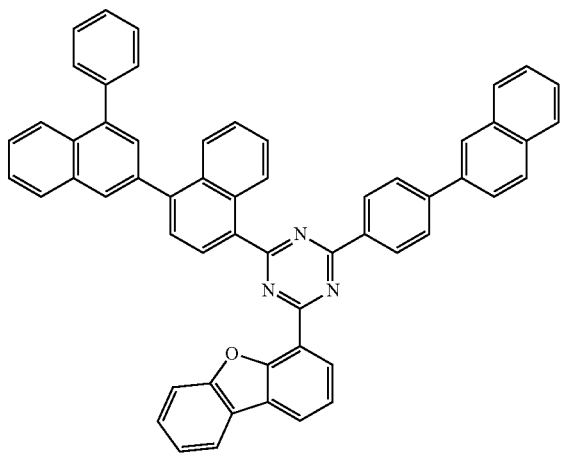

269
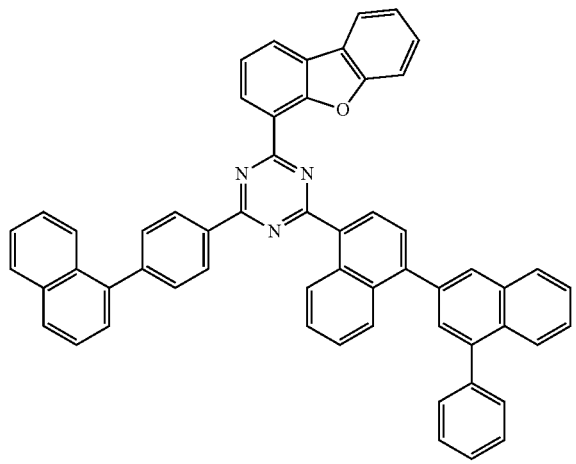
-continued
270
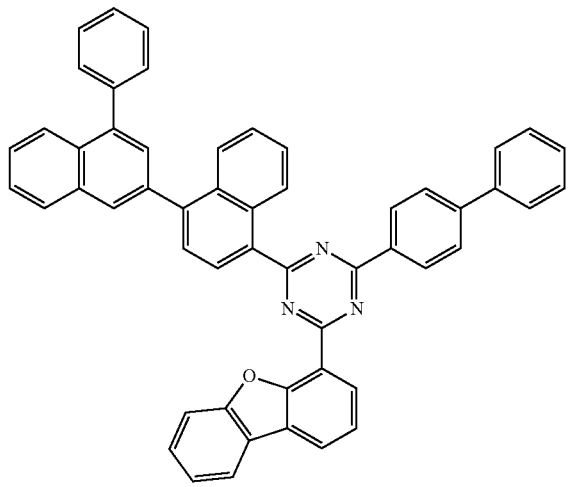
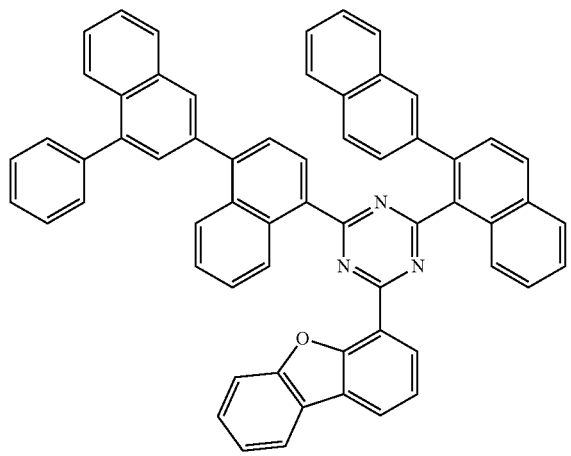
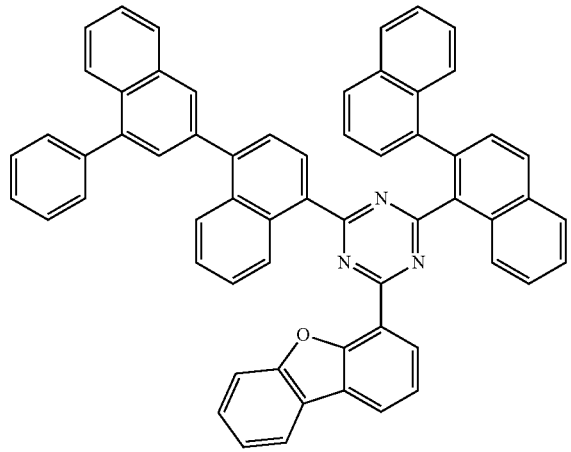
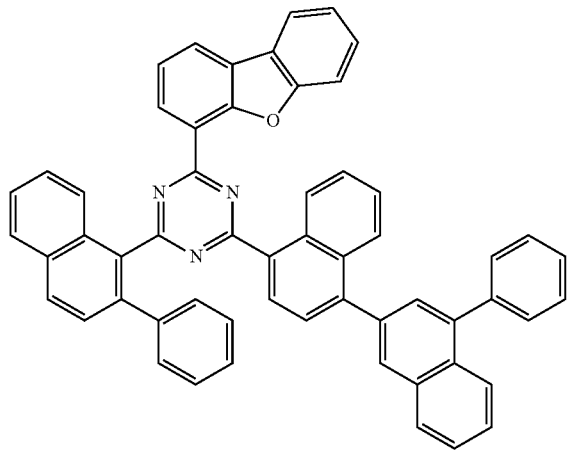
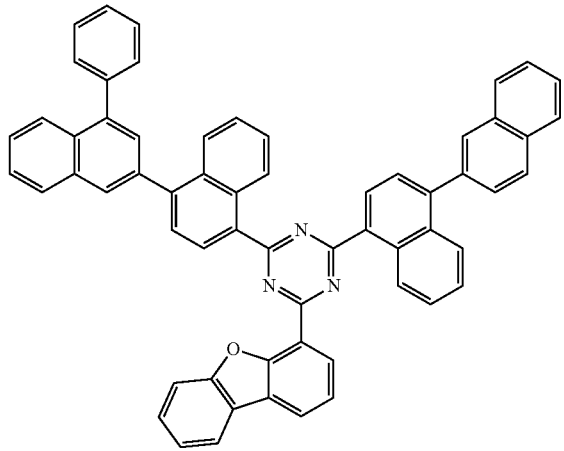

271
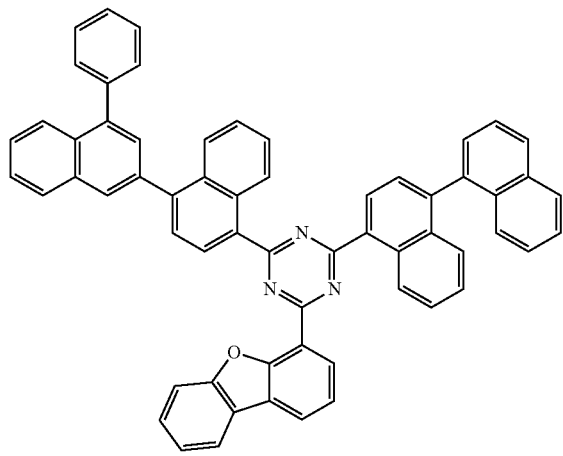
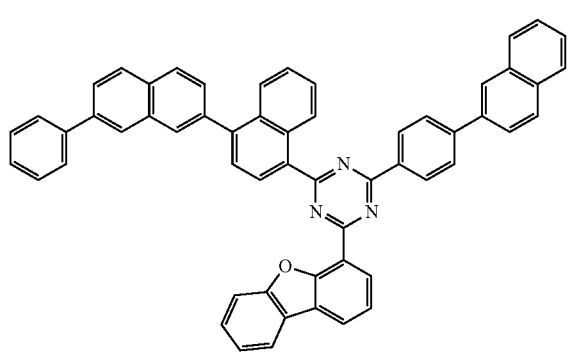
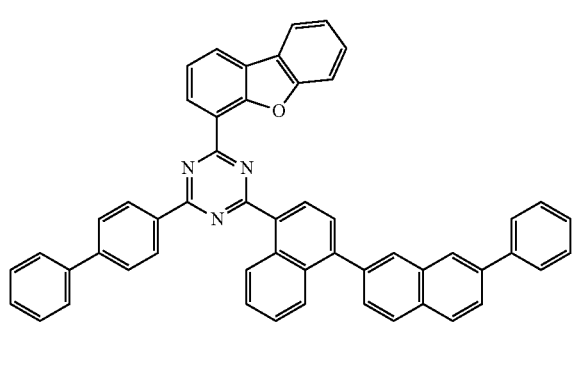
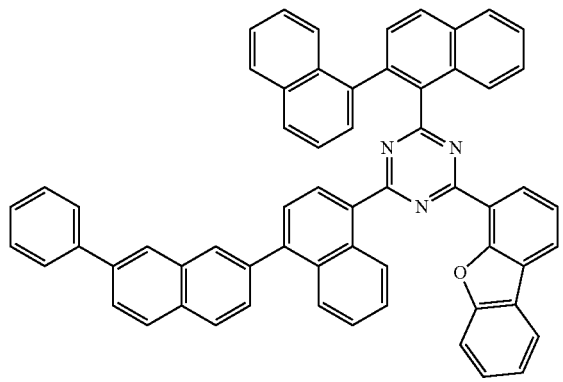
272
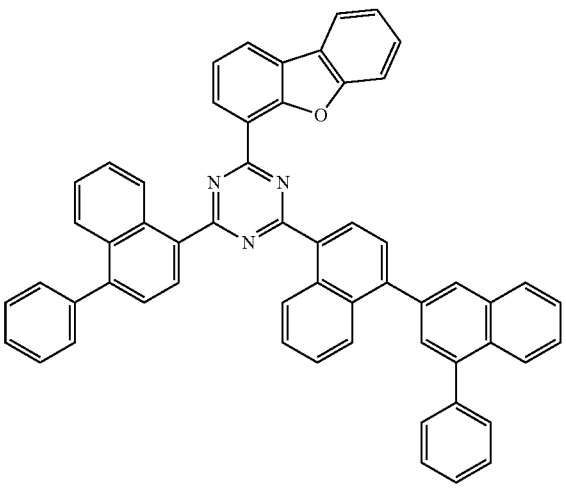
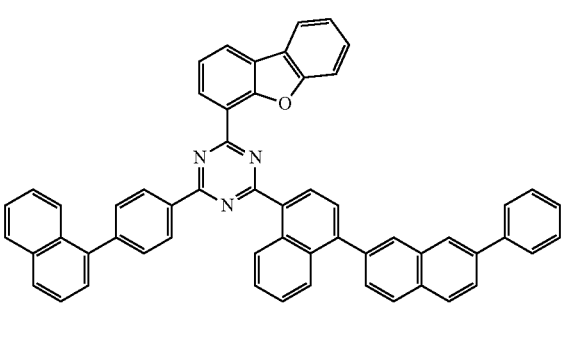
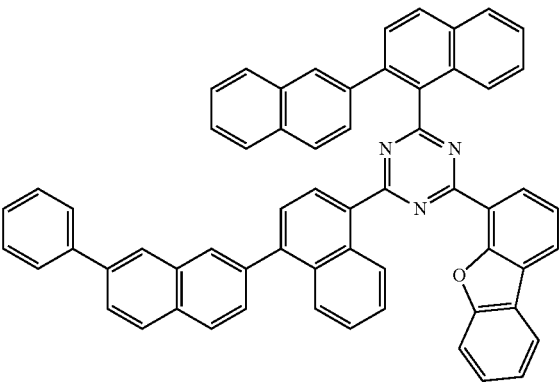
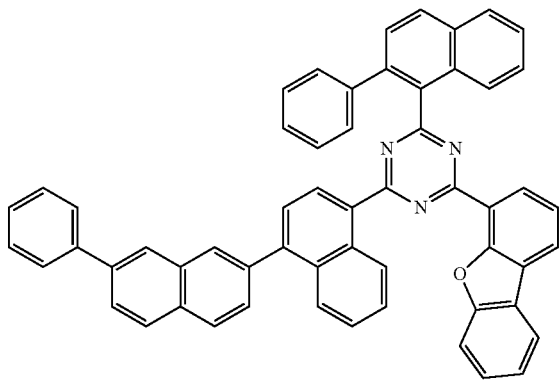

273
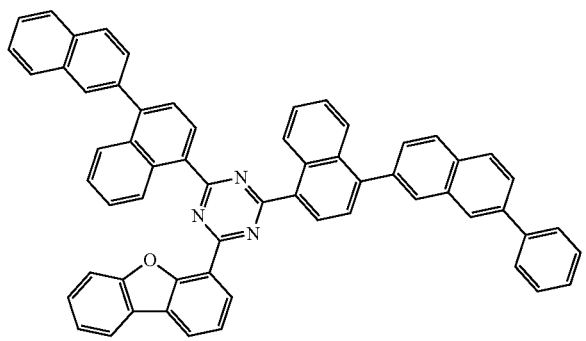
-continued
274
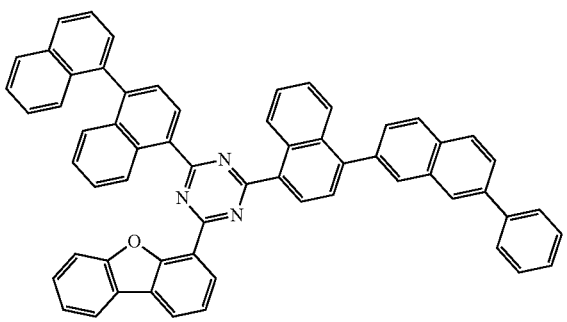
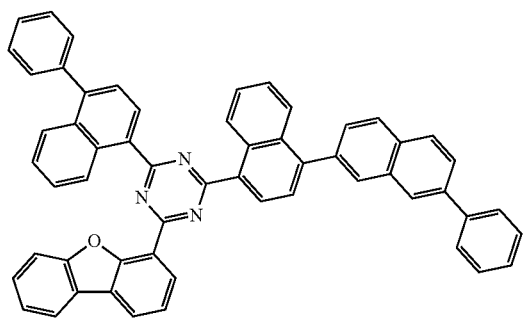
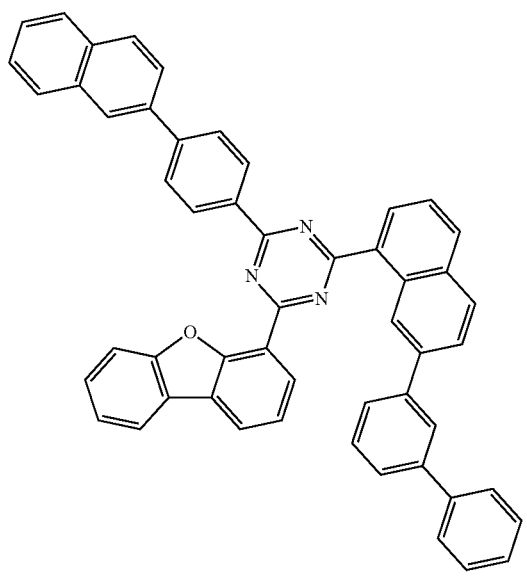
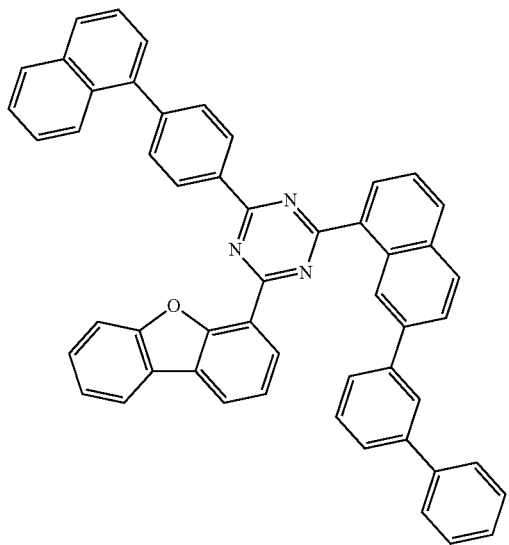
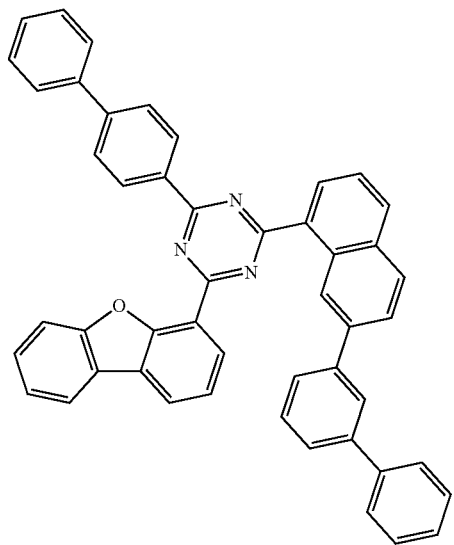

275
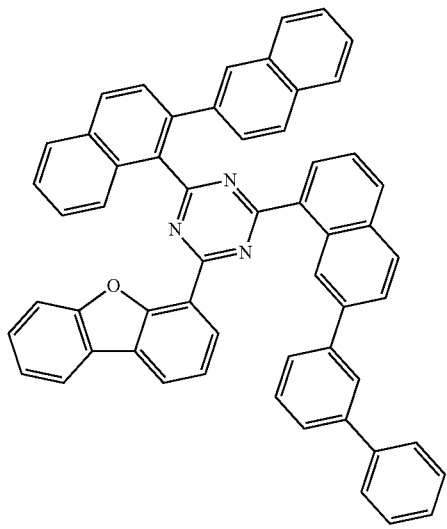
276
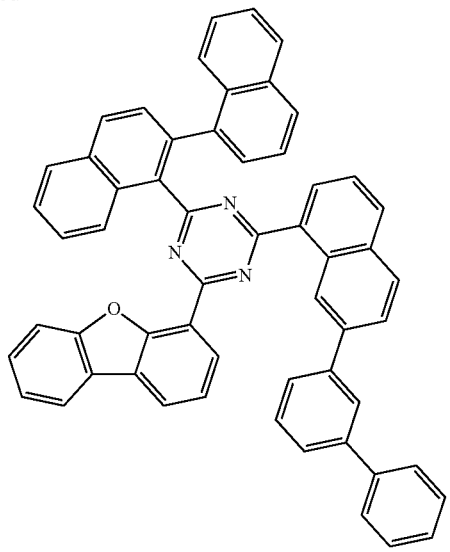
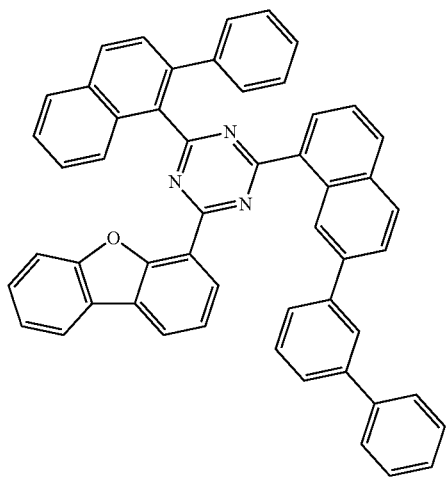
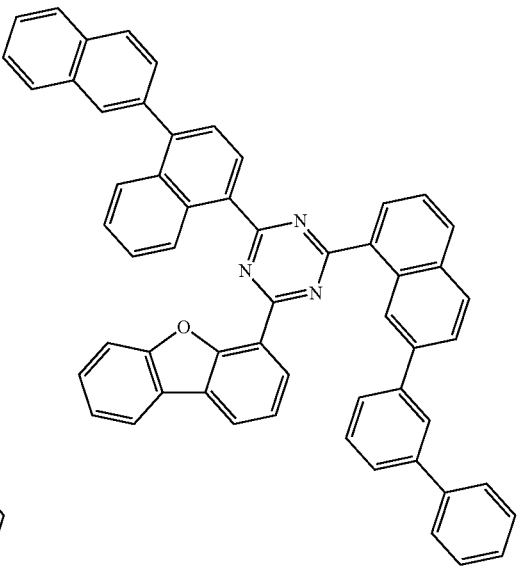
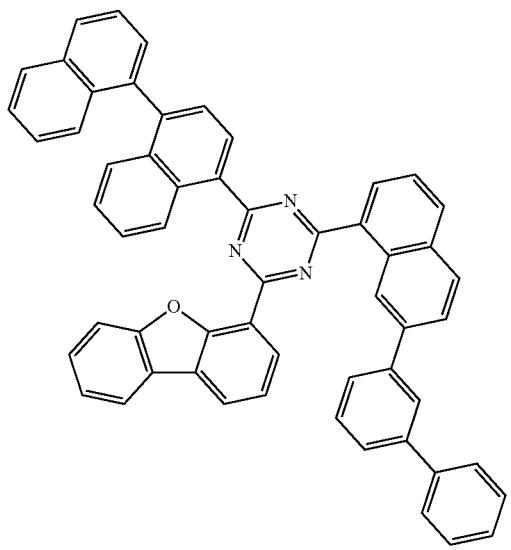
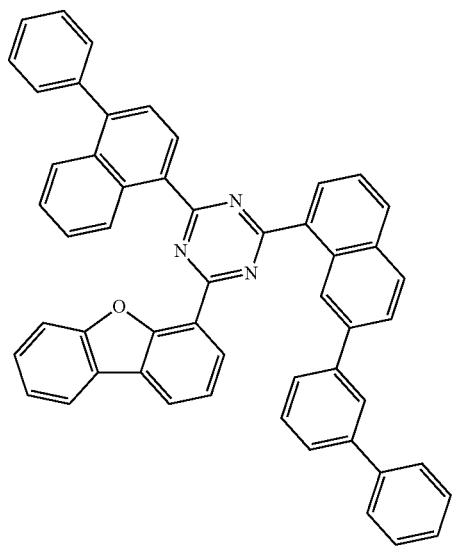

277
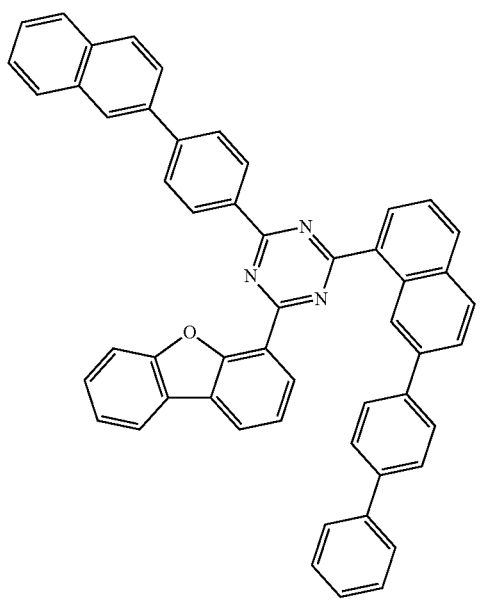
278
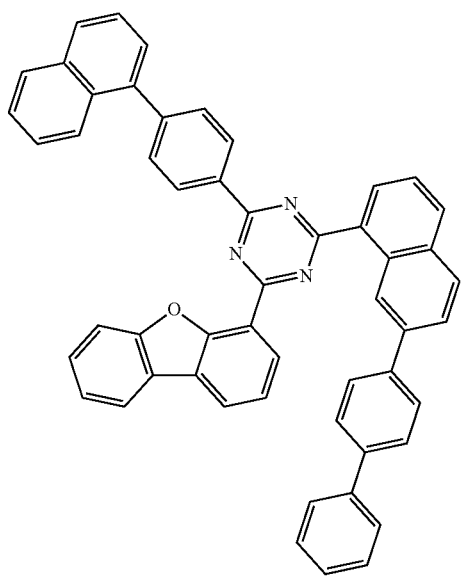
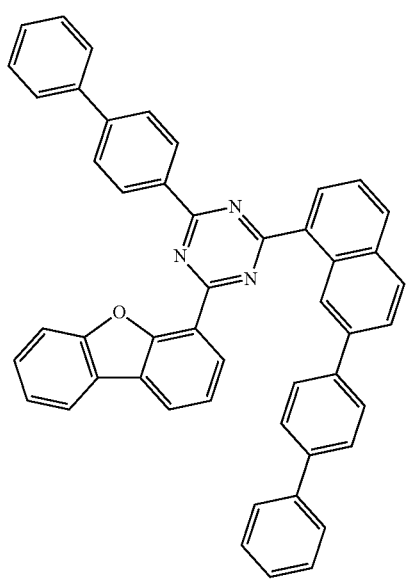
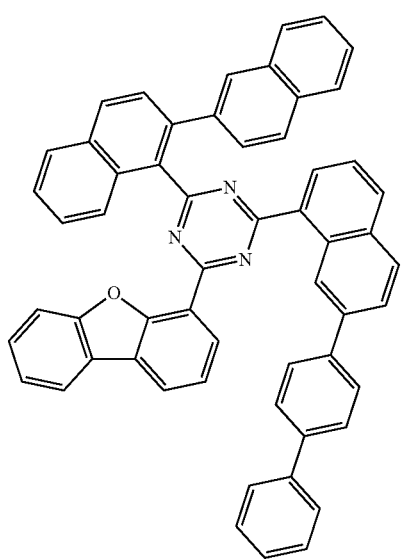

279
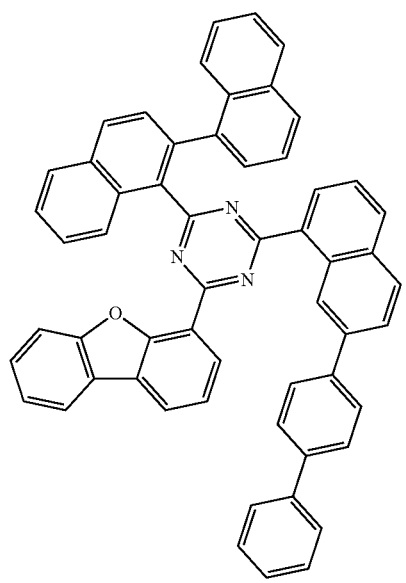
280
-continued
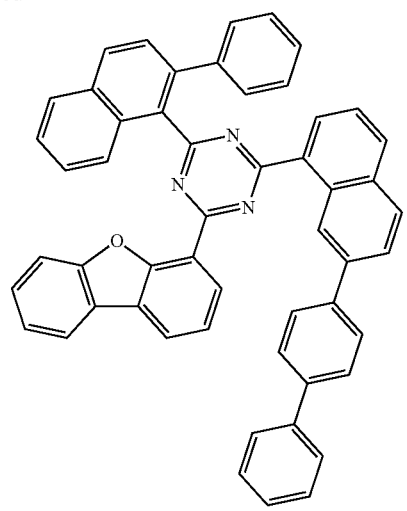
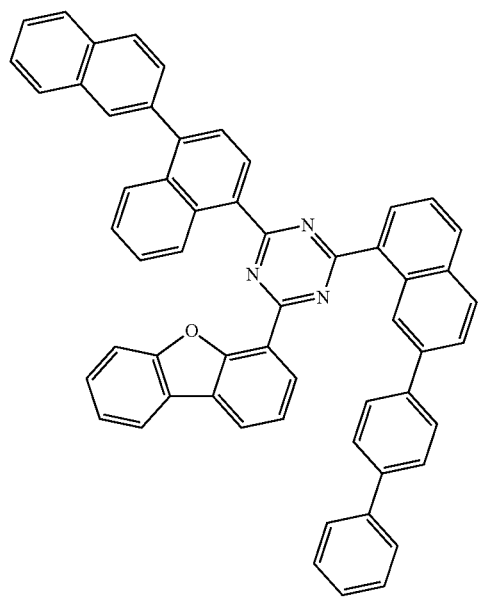
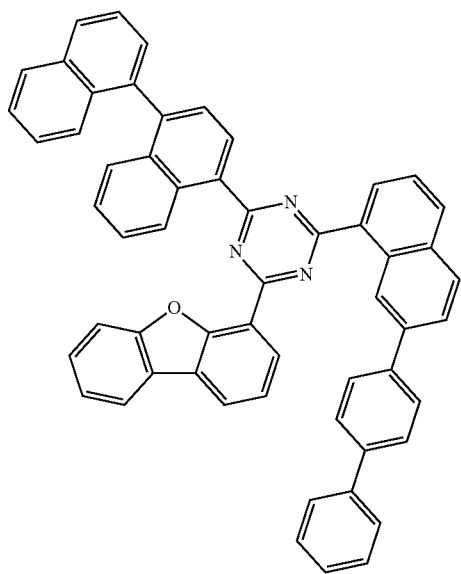

-continued
281
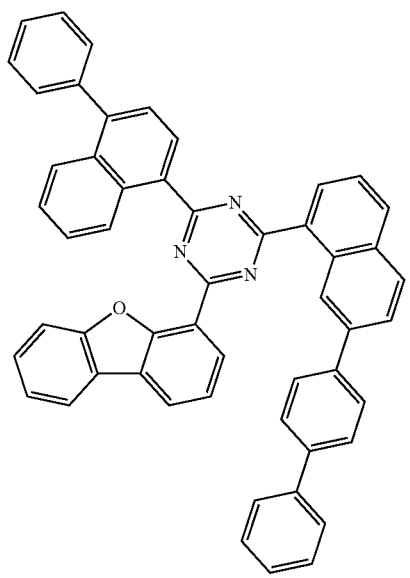
282
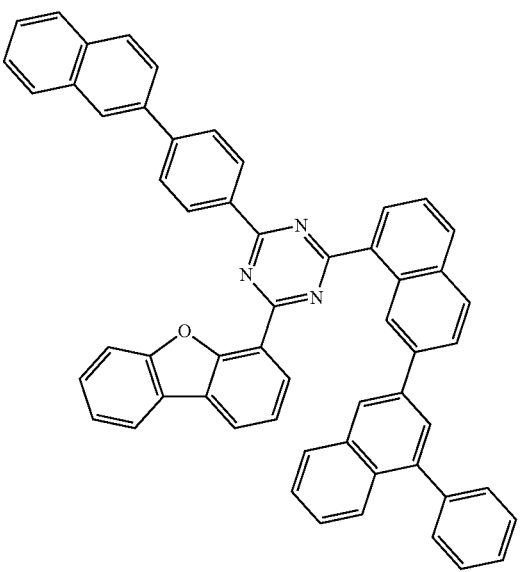
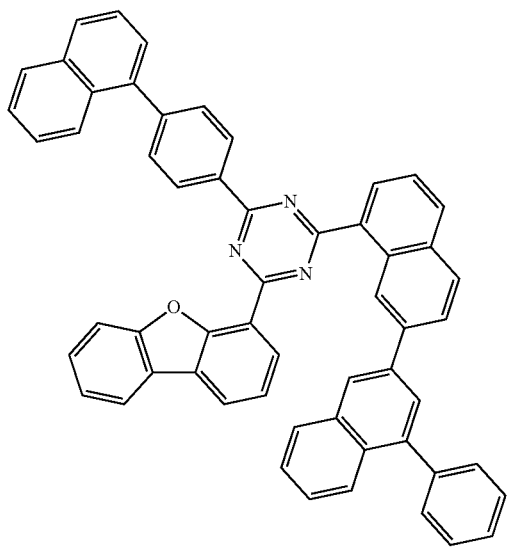
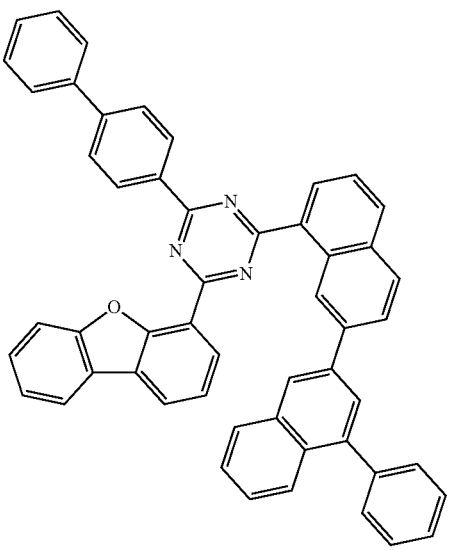

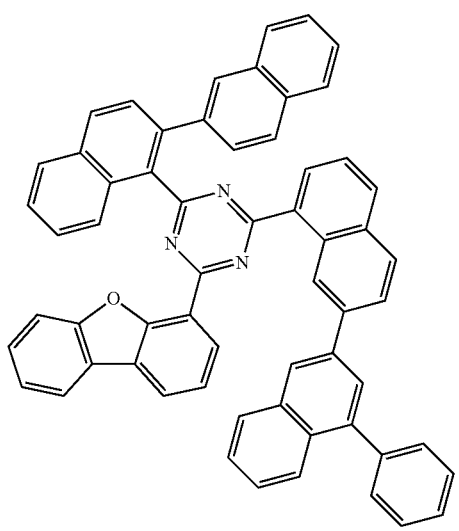
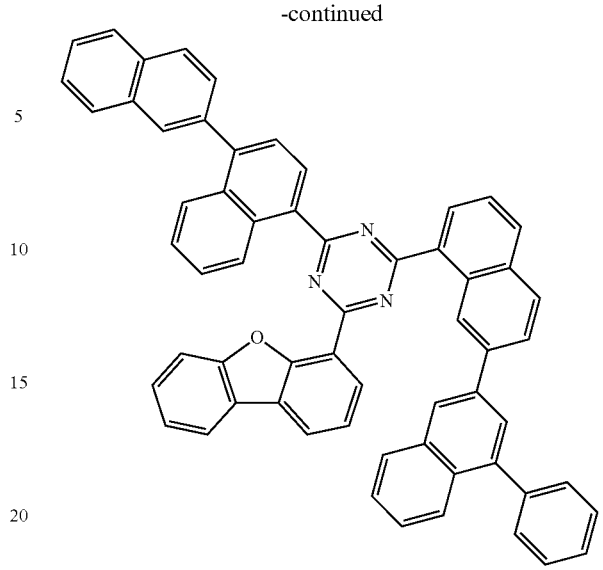
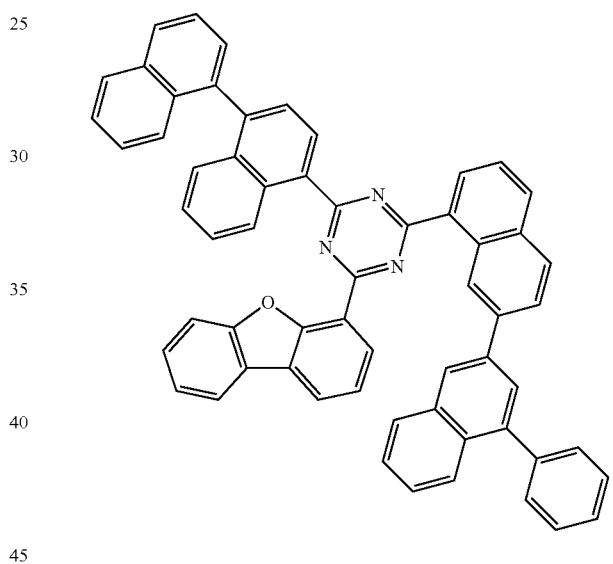
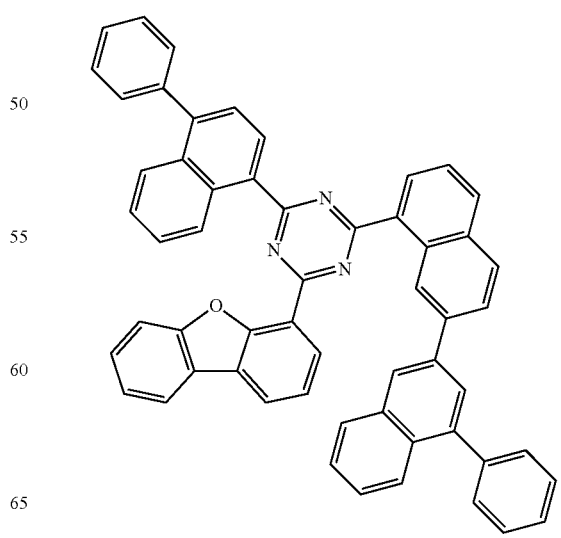

285
-continued
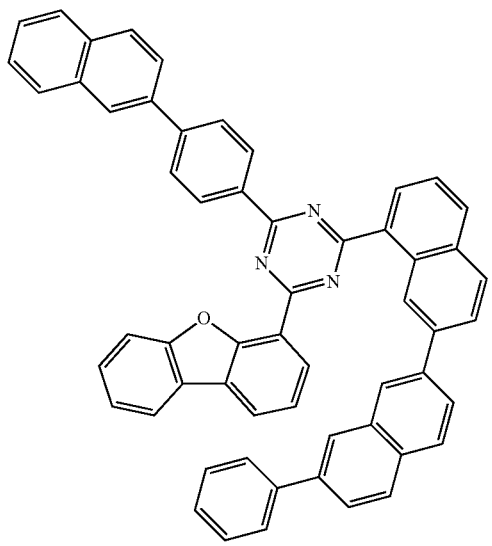
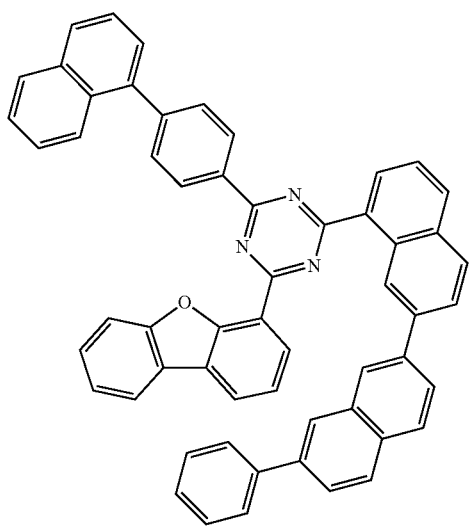
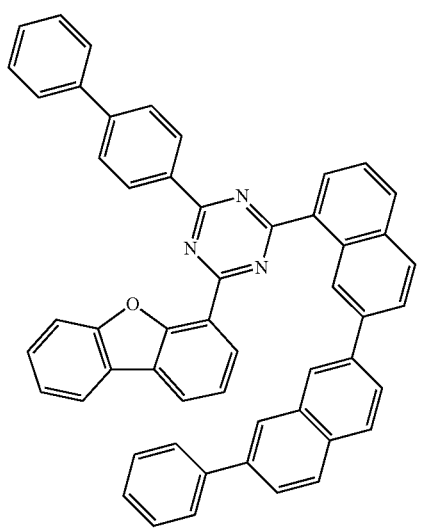
286
-continued
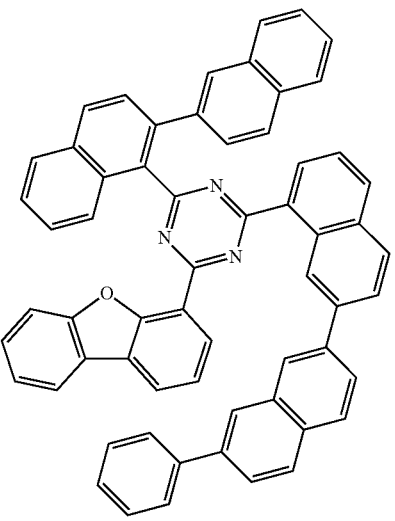
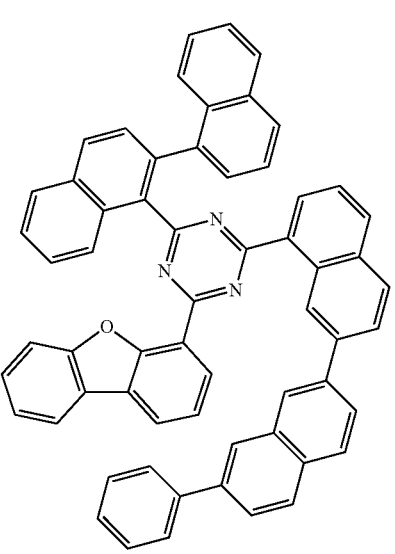
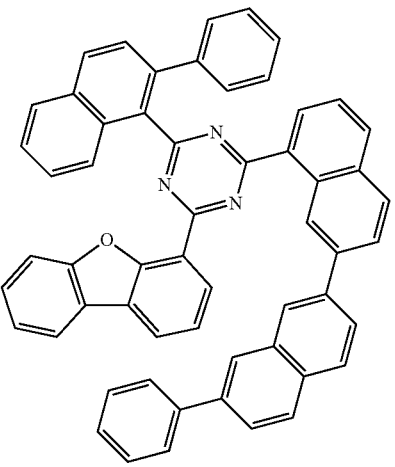

287
-continued
288
-continued
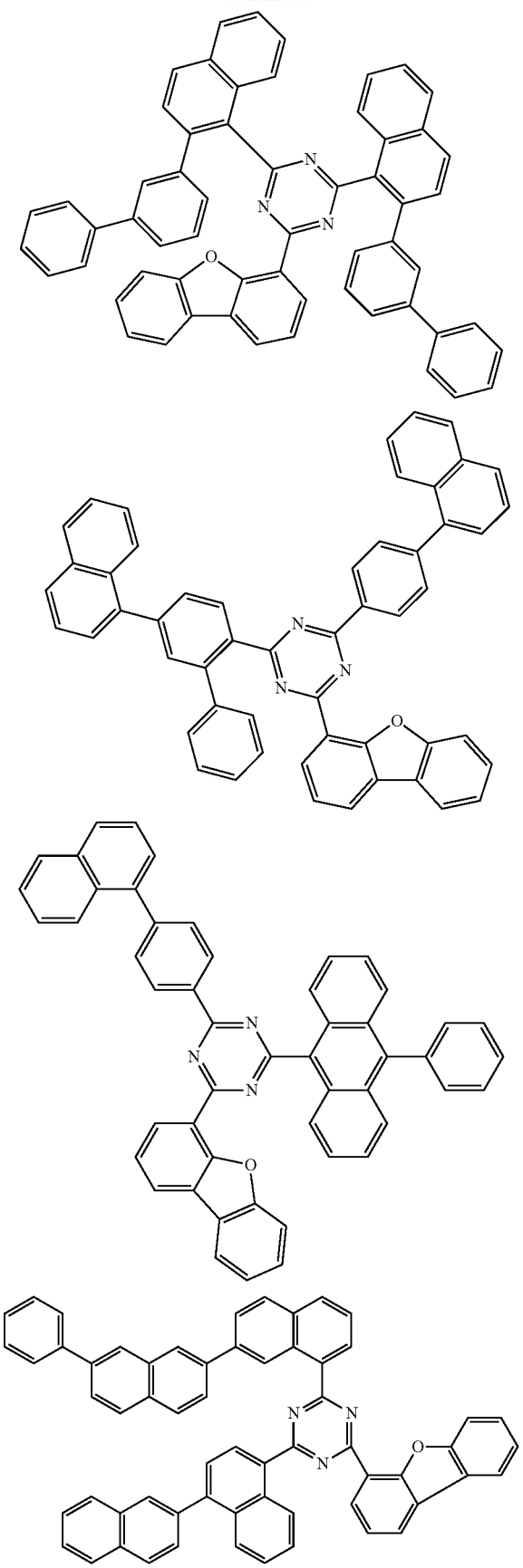
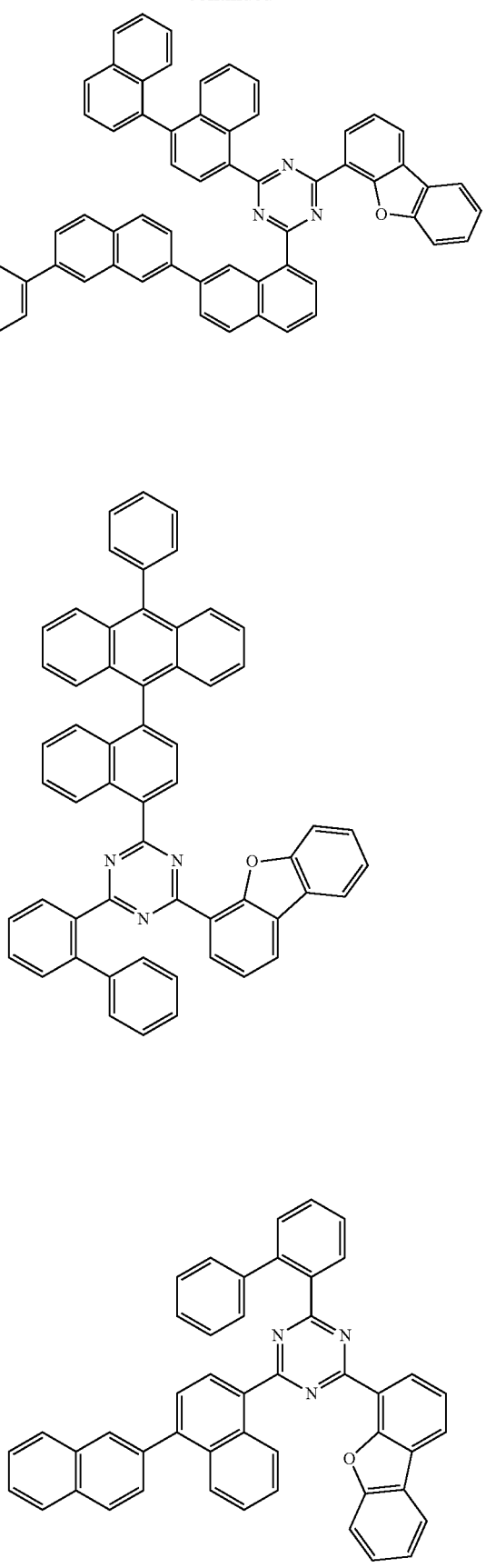

289
-continued
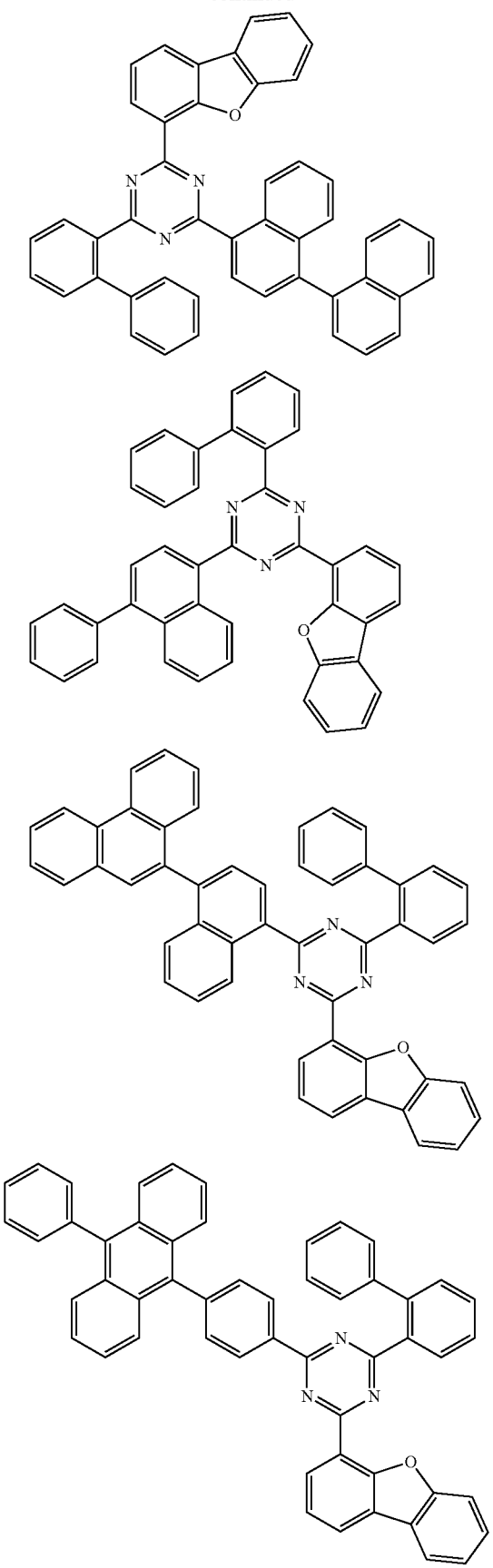
290
-continued
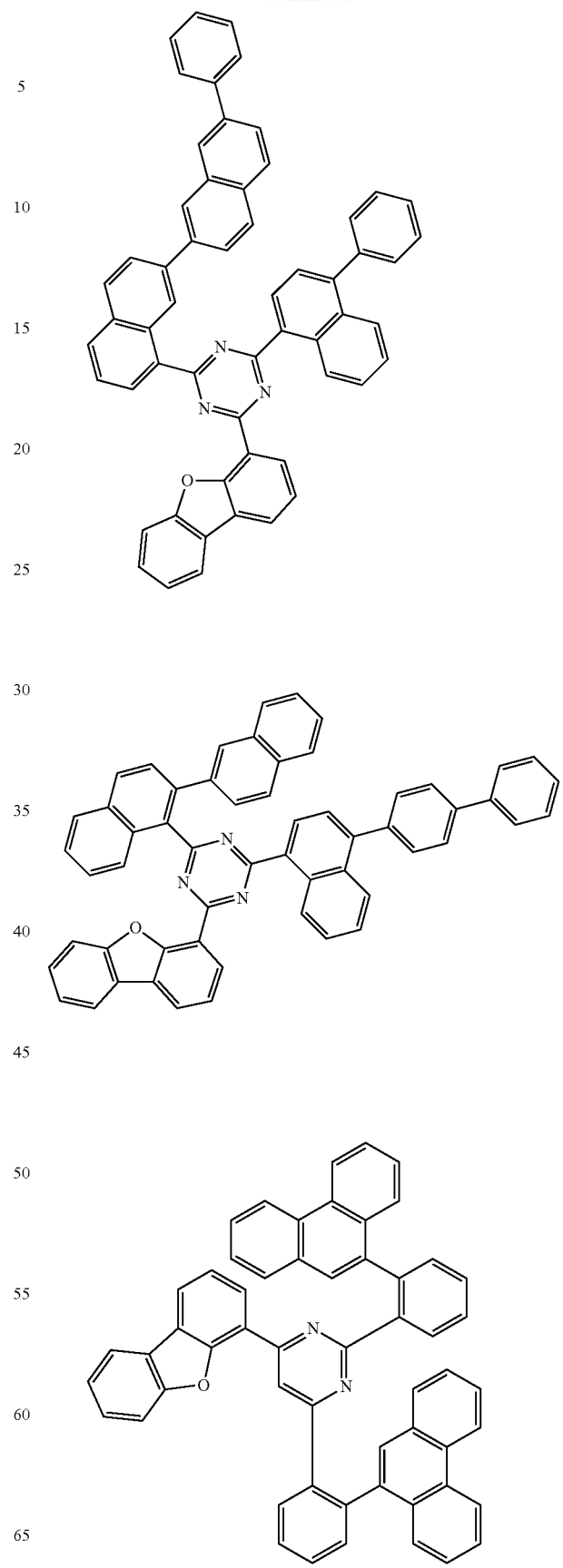

291
-continued
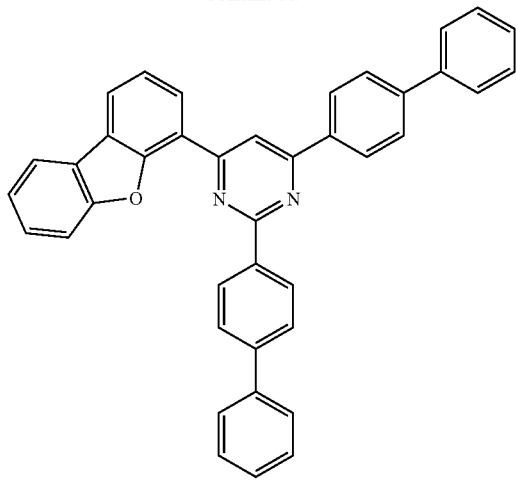
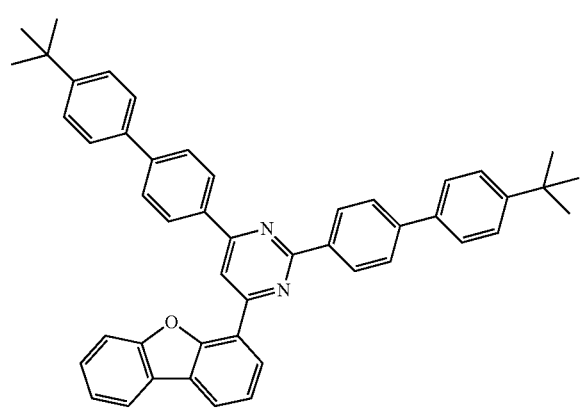
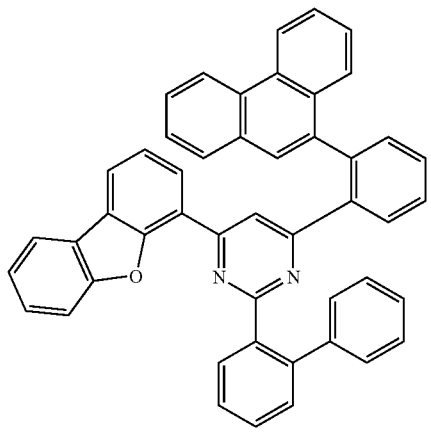
292
-continued
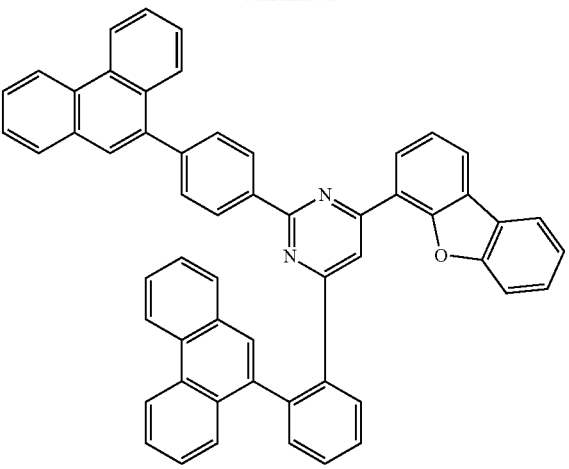
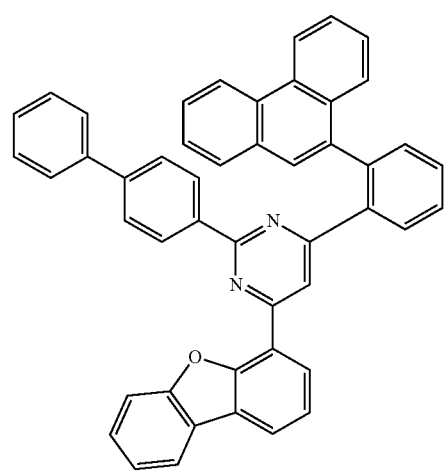
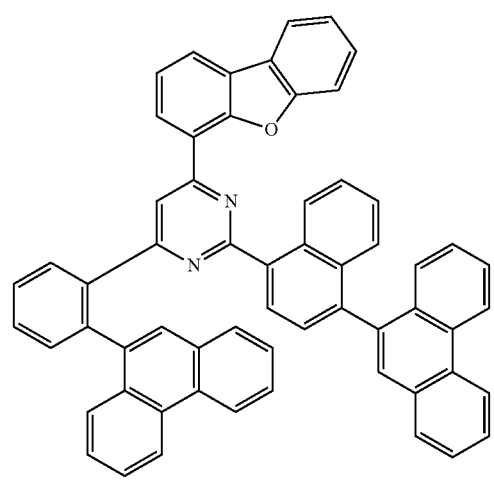

293
-continued
294
-continued
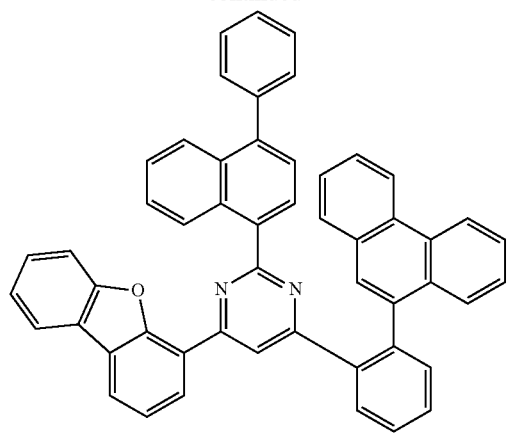
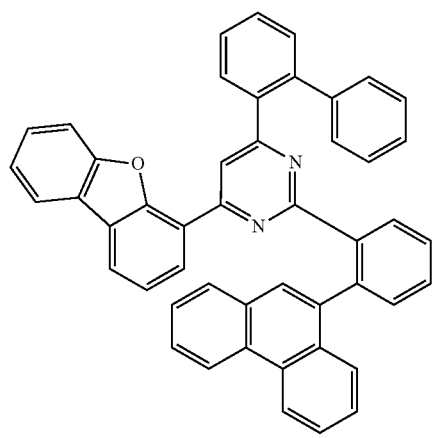
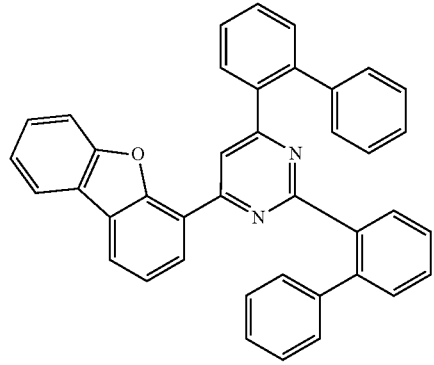
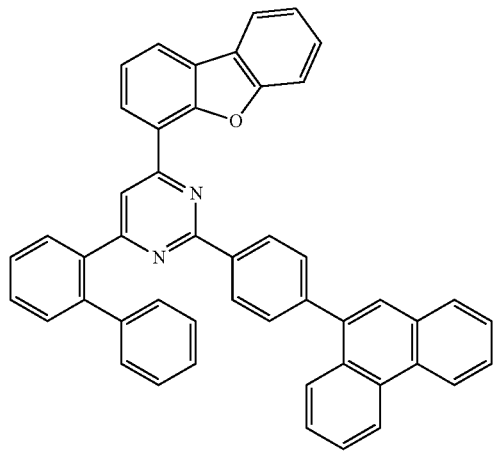
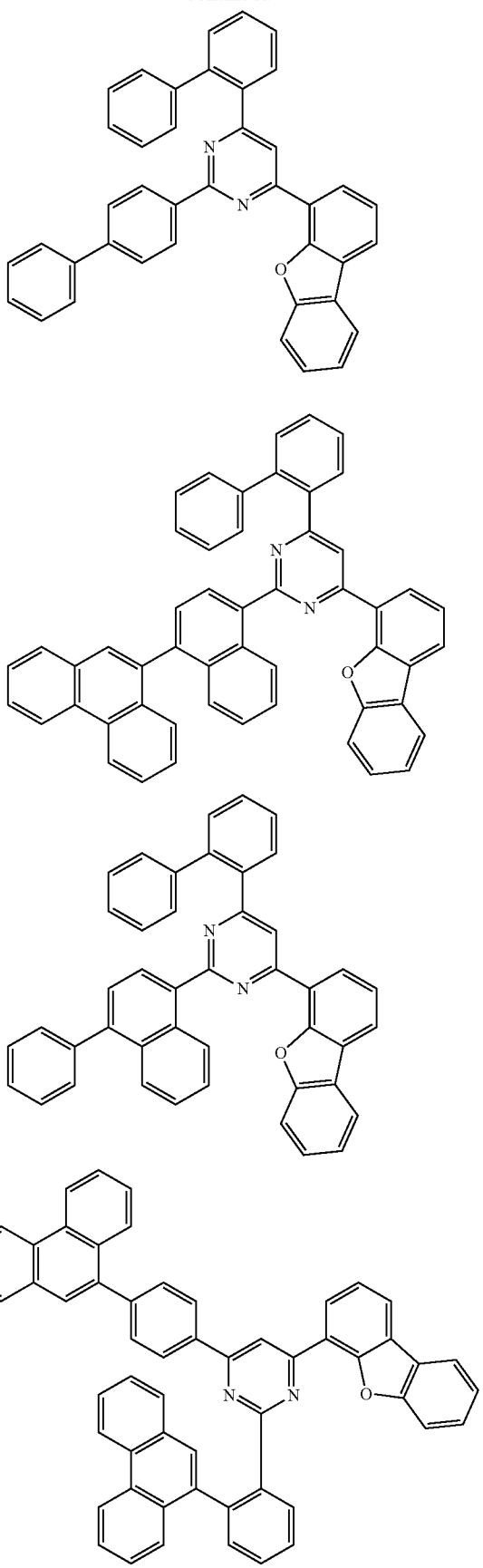

295
-continued
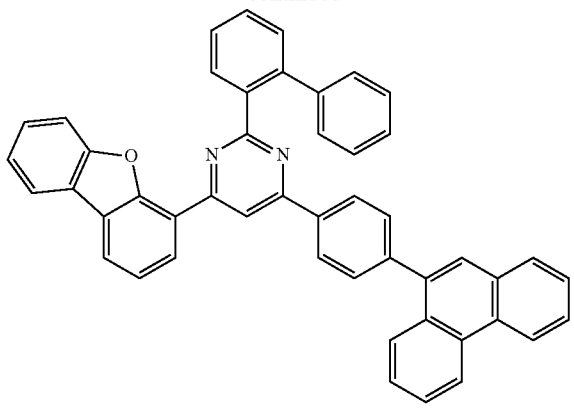
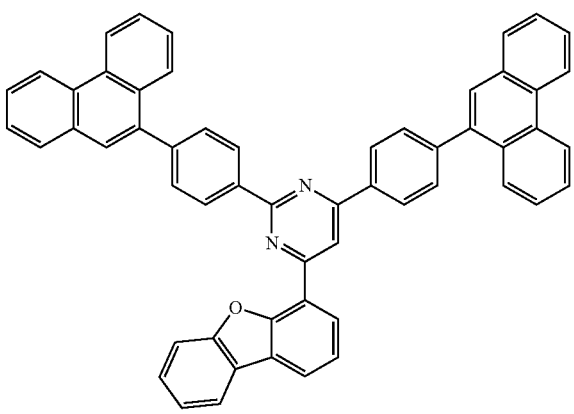
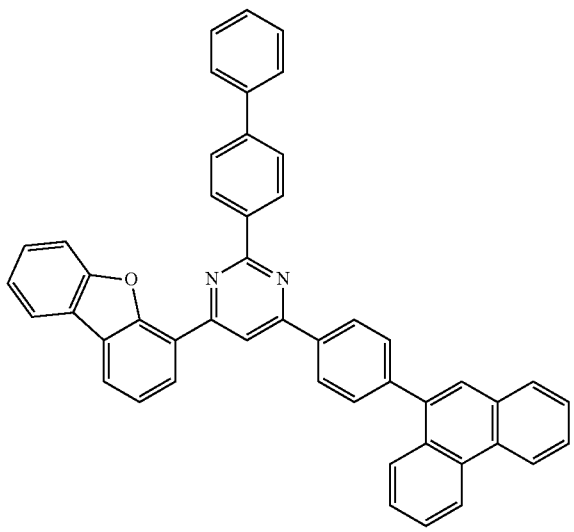
296
-continued
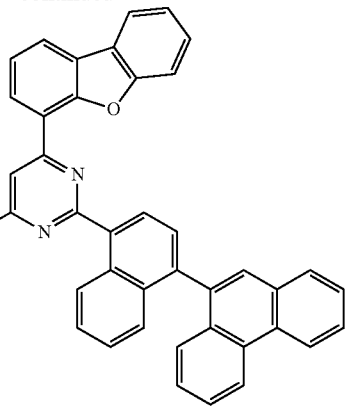
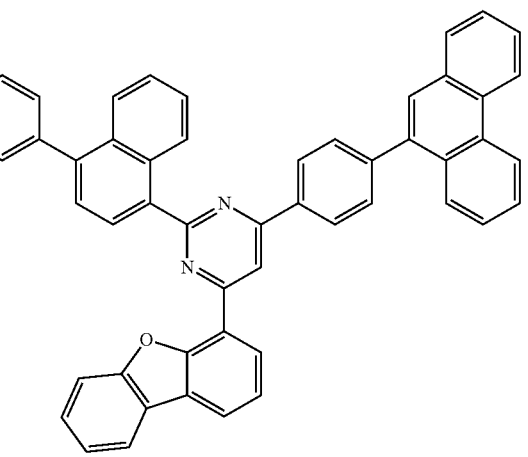
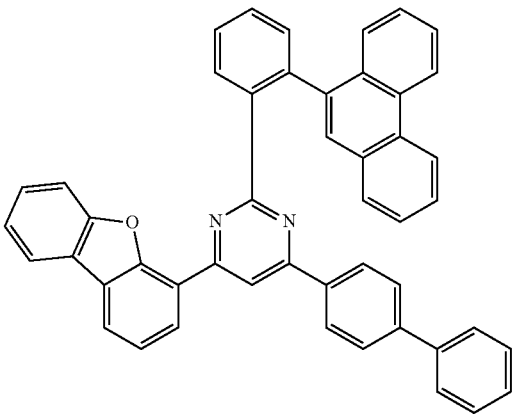
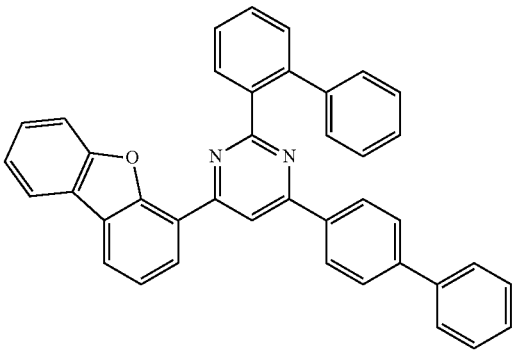

297
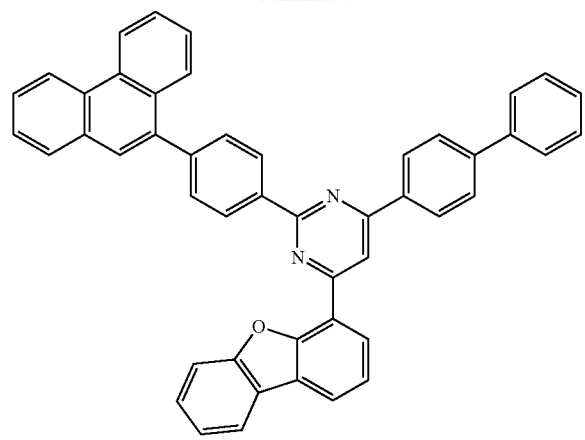
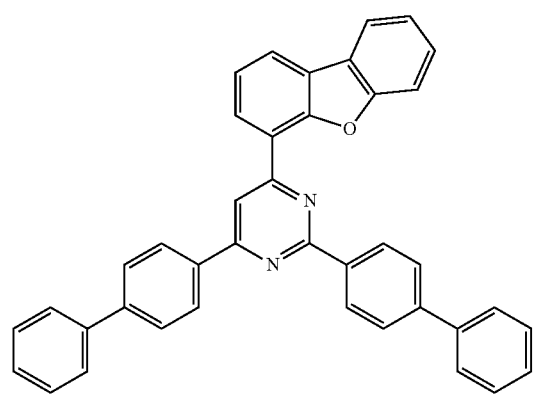
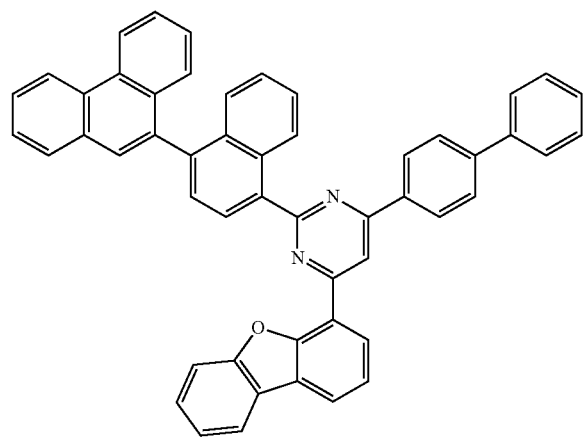
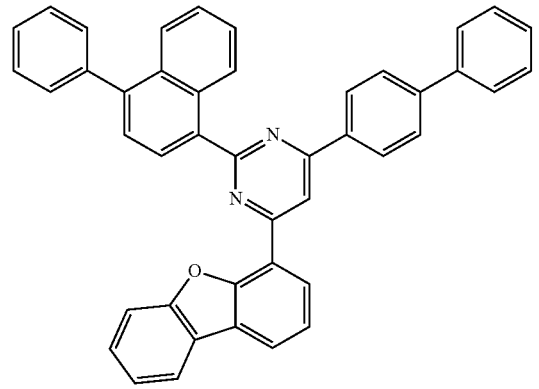
298
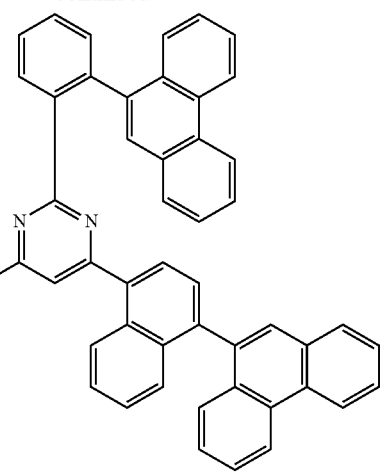
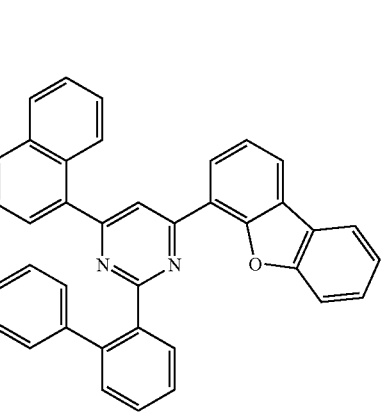
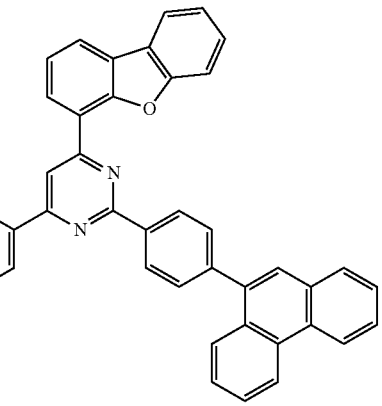
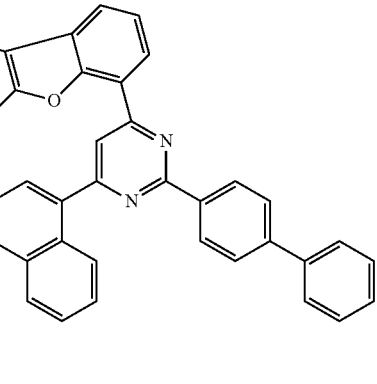

299
-continued
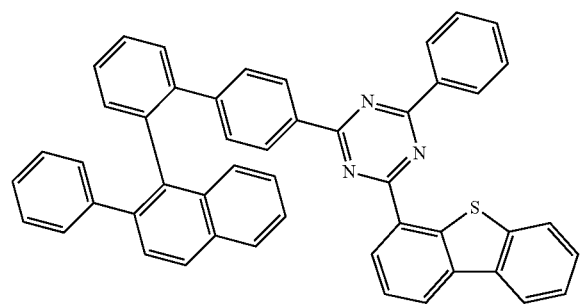
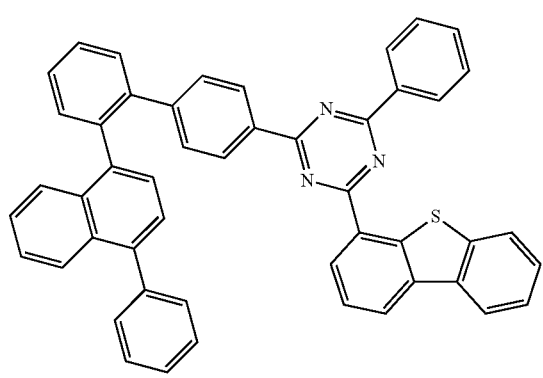
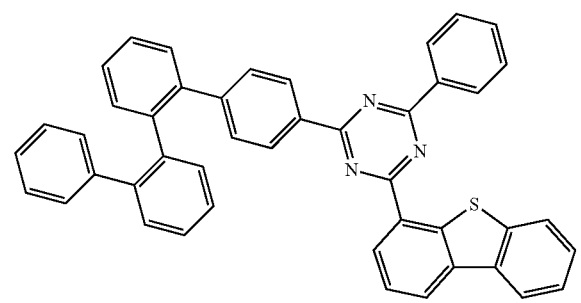
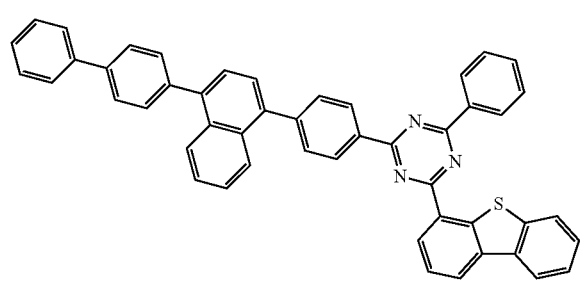
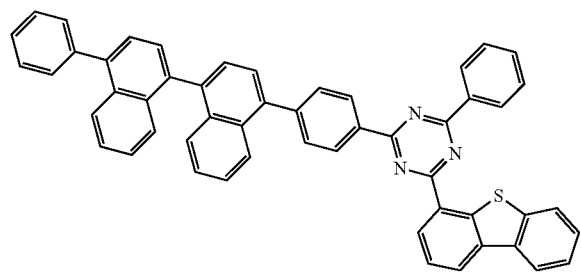
300
-continued
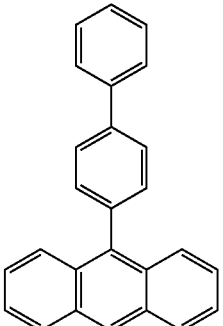
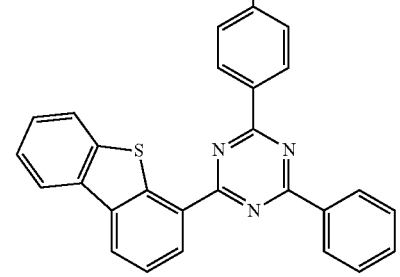
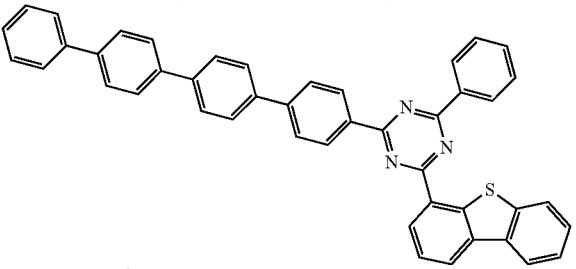
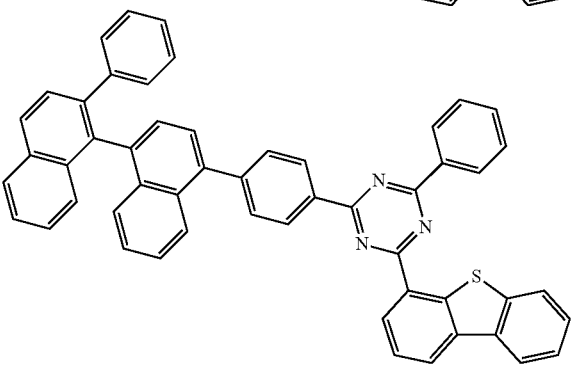
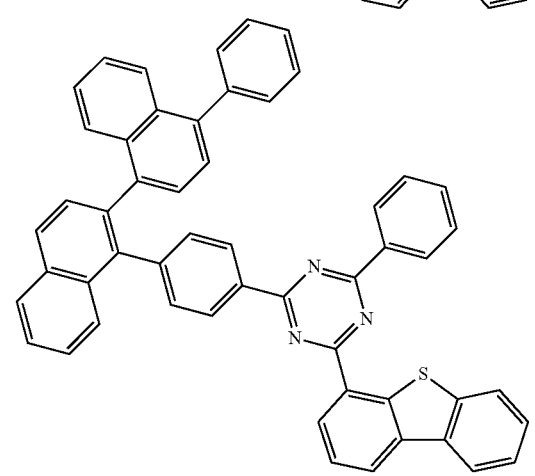

301
-continued
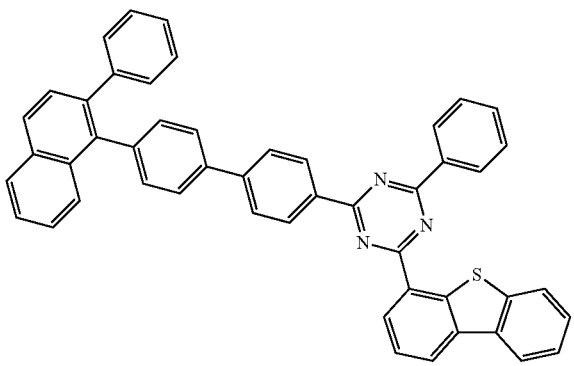
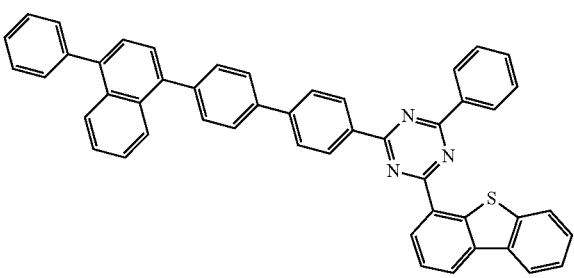
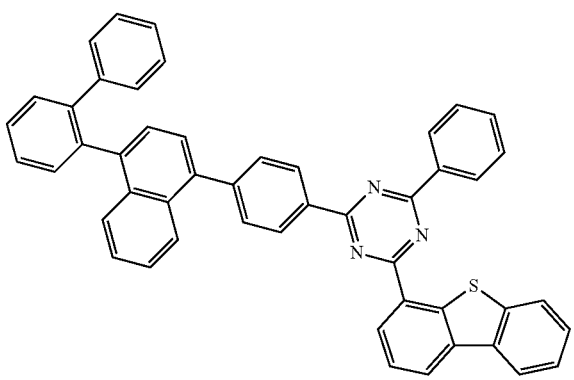
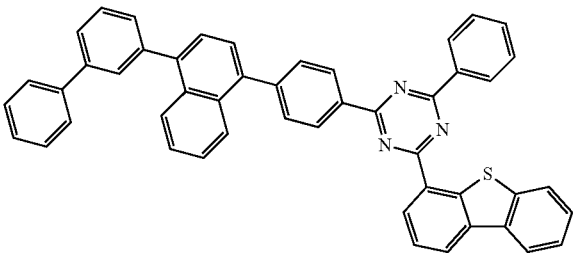
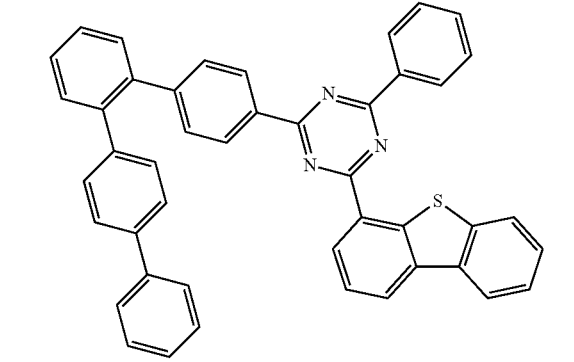
302
-continued
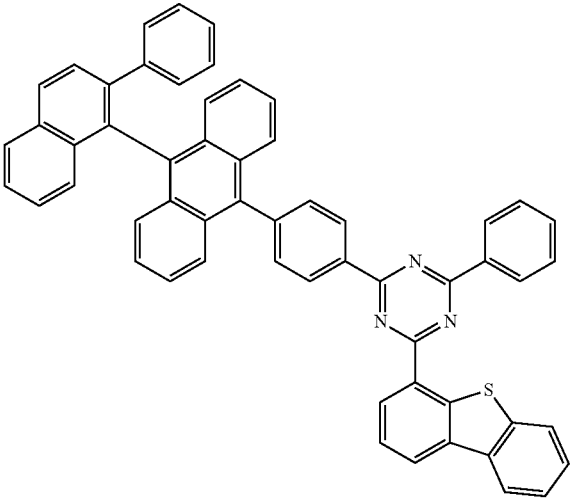
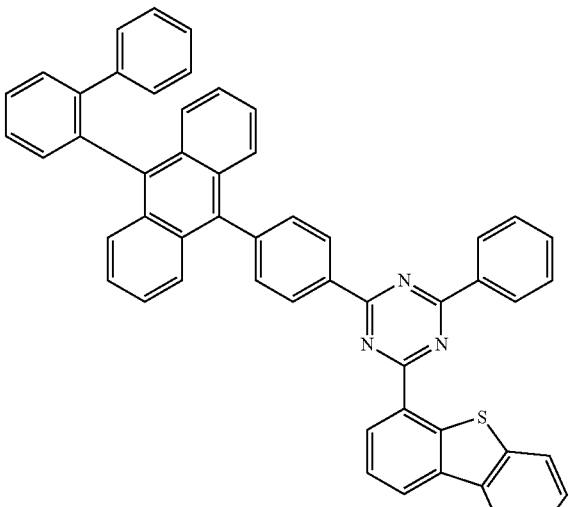
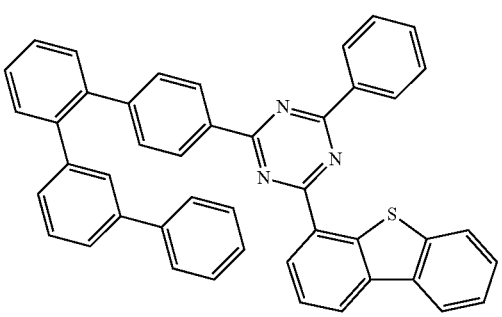

303 -continued
304 -continued
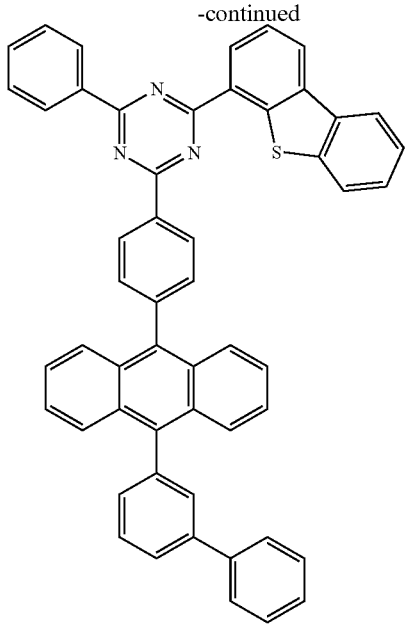
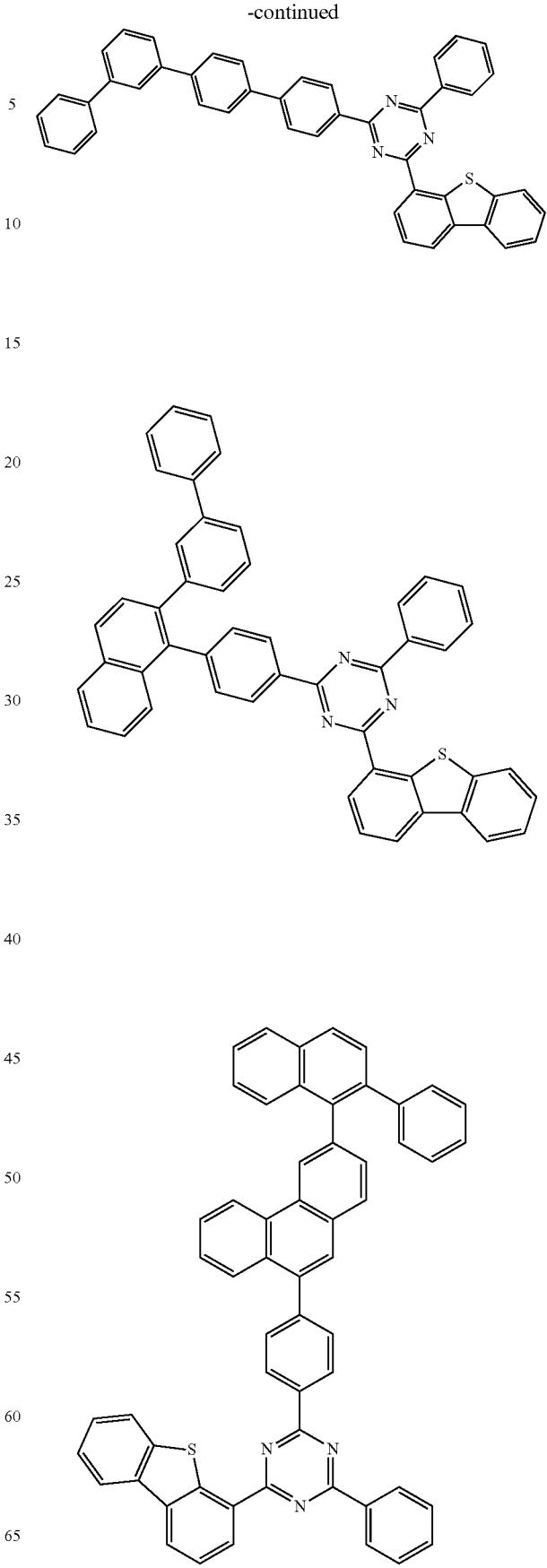

305
-continued
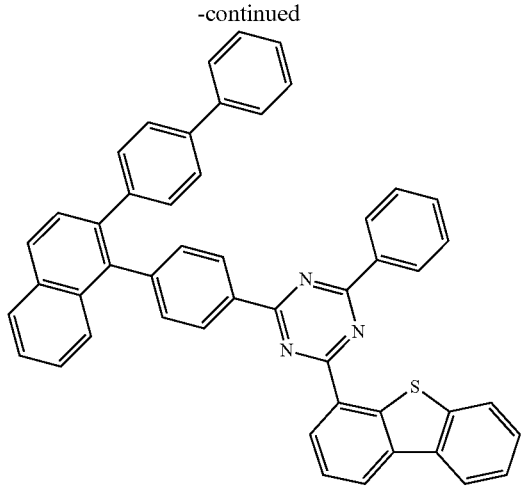
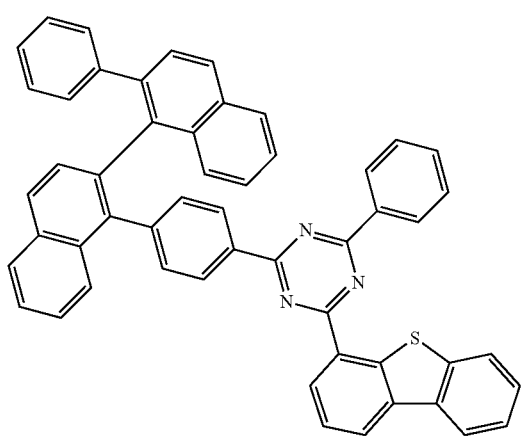
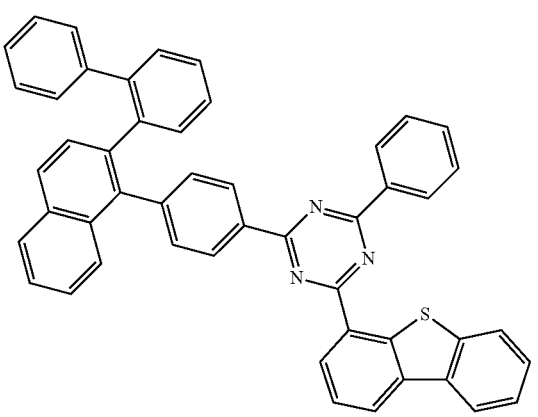
306
-continued
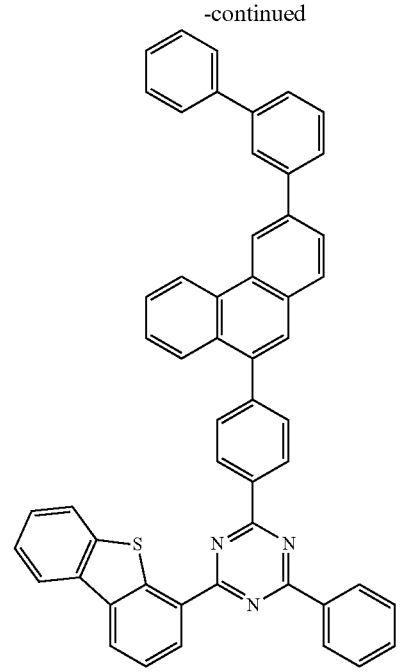
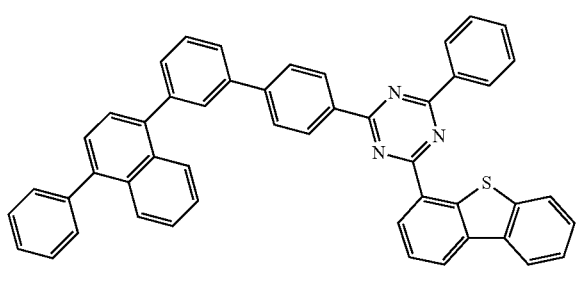
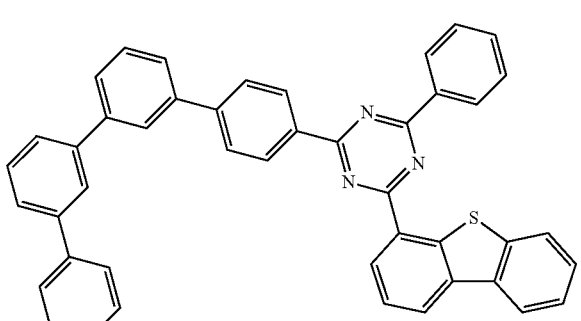
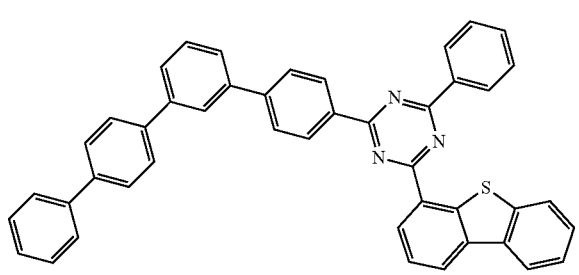

307
-continued
308
-continued
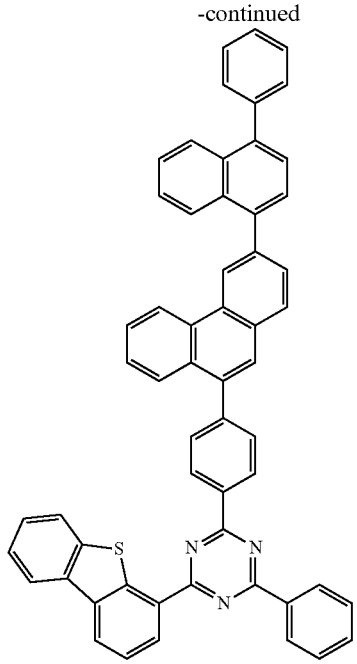
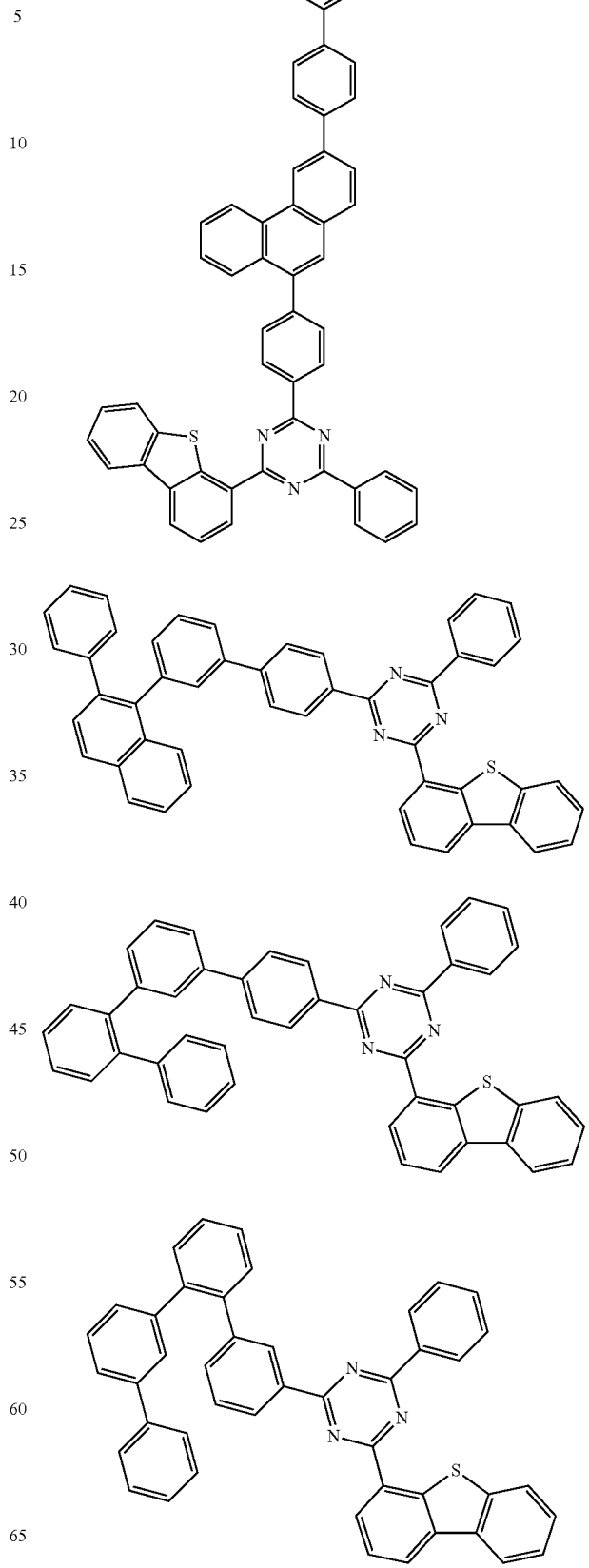

309
-continued
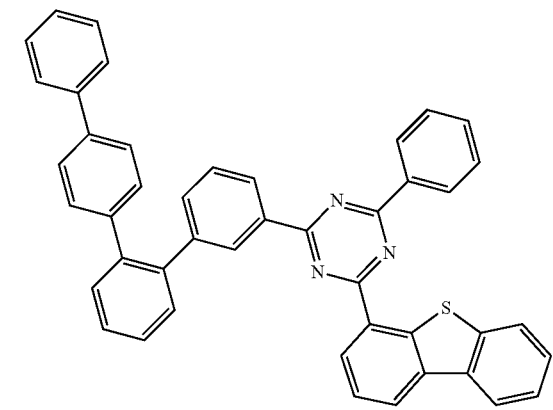
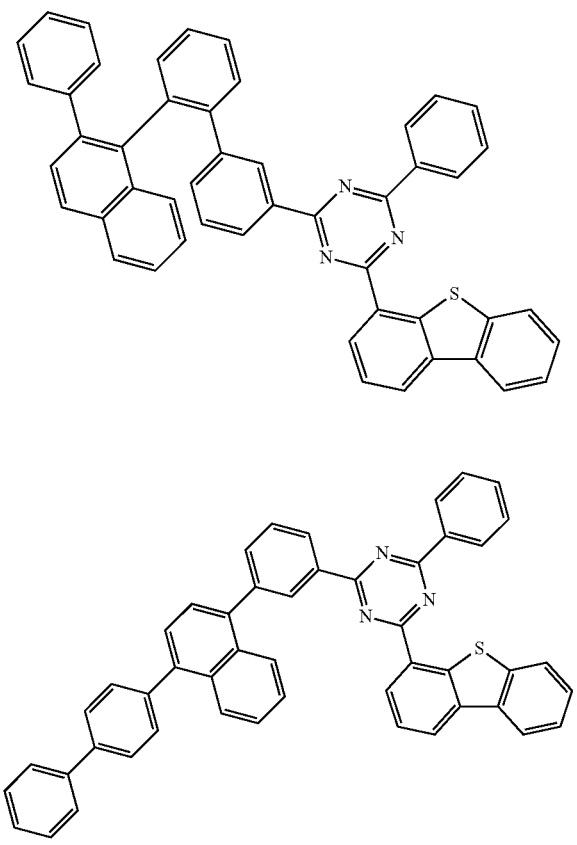
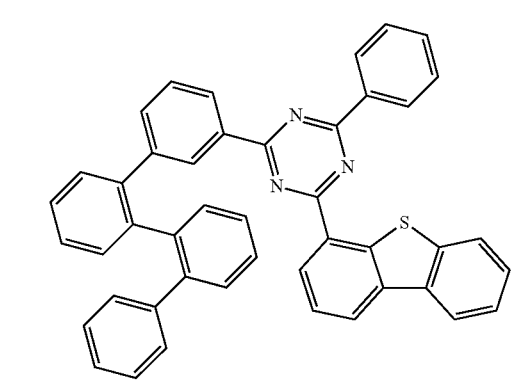
310
-continued
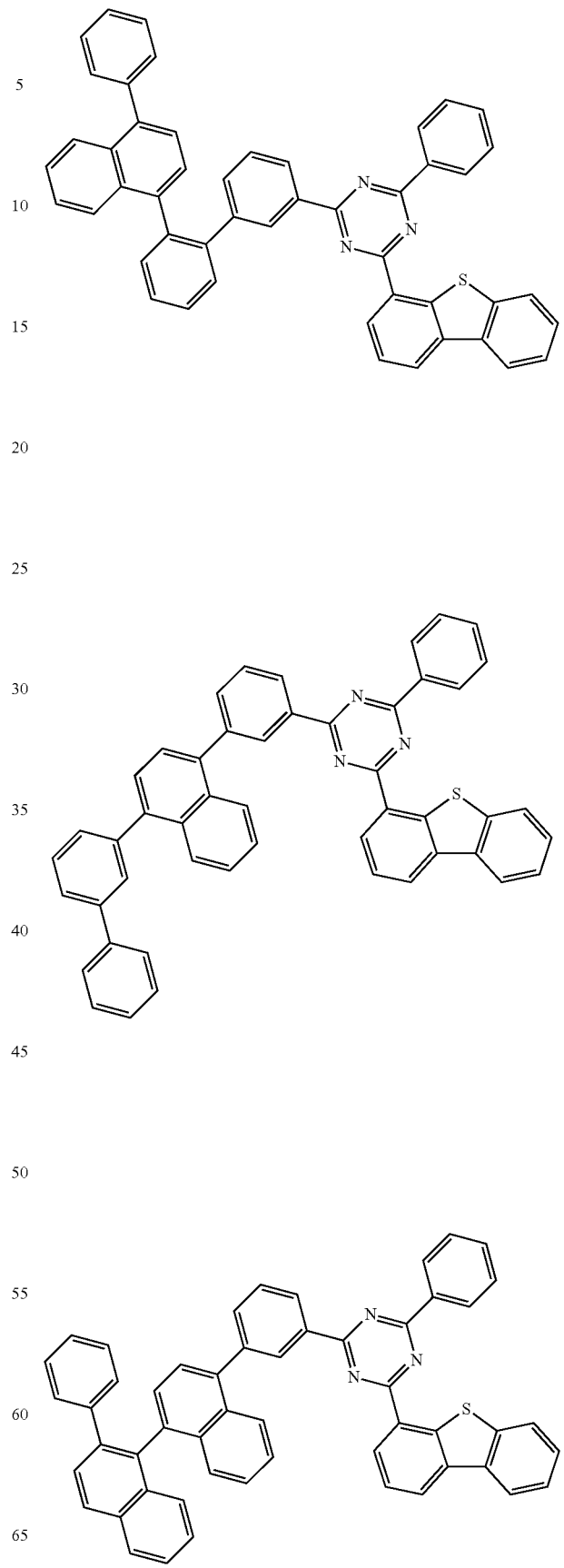

311
-continued
312
-continued
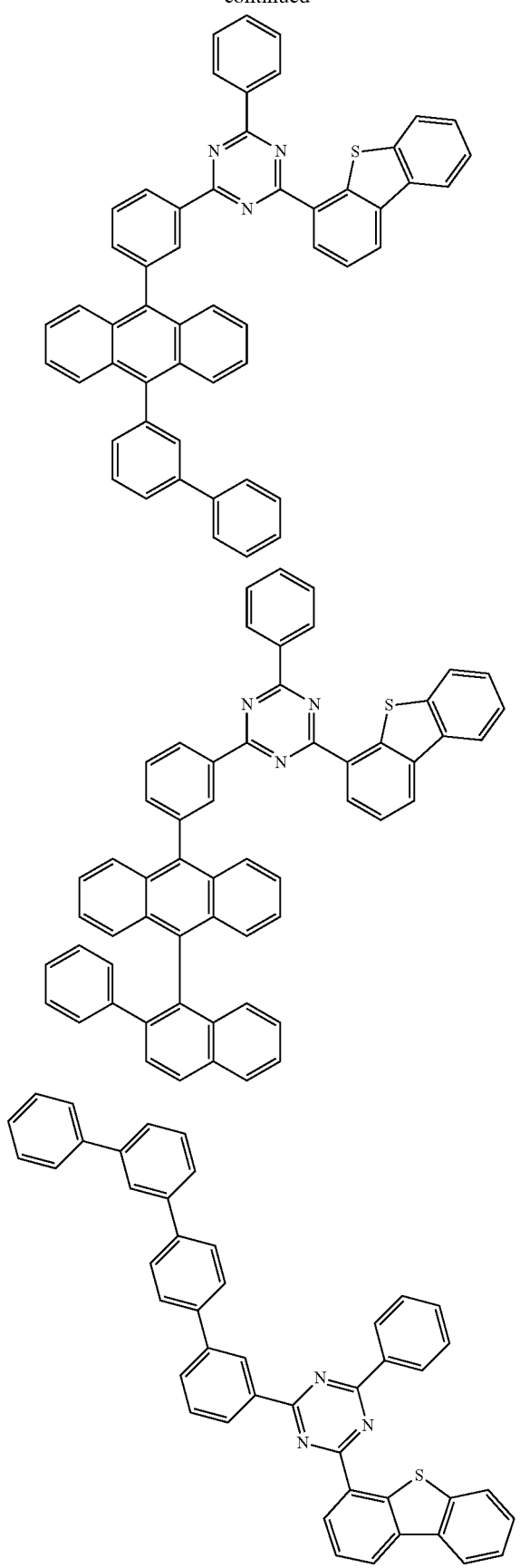
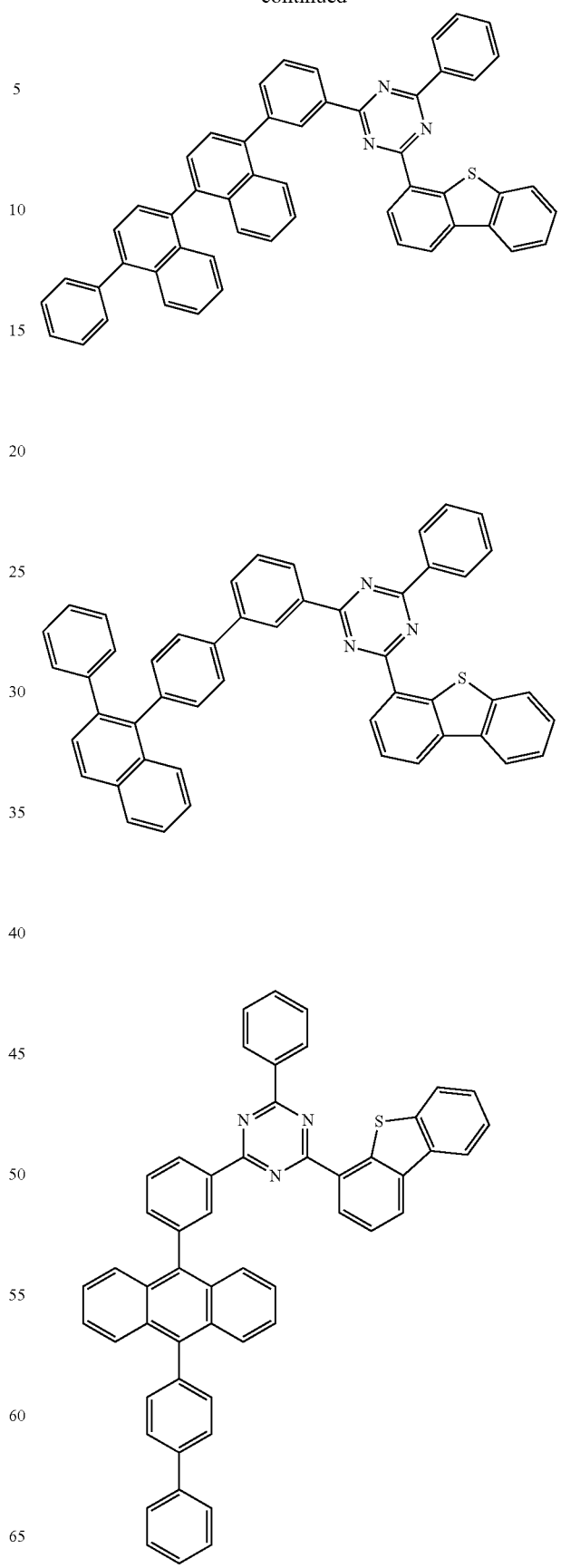

313
-continued
314
-continued
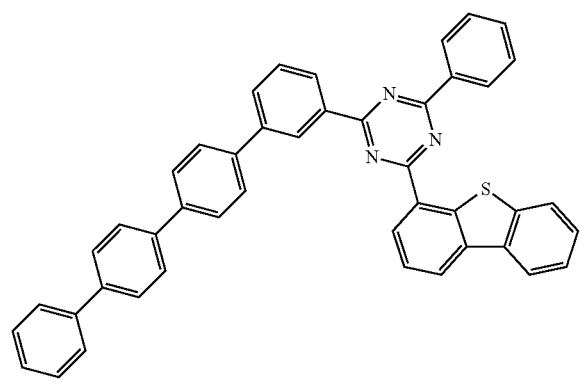
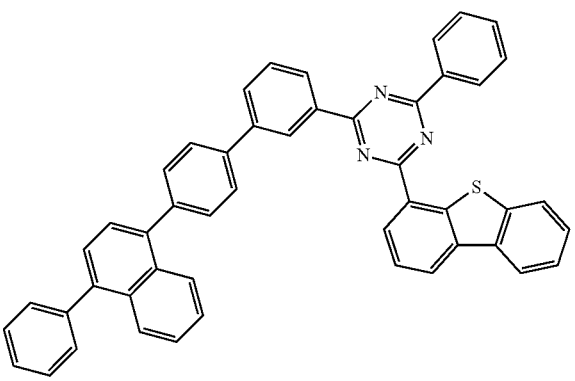
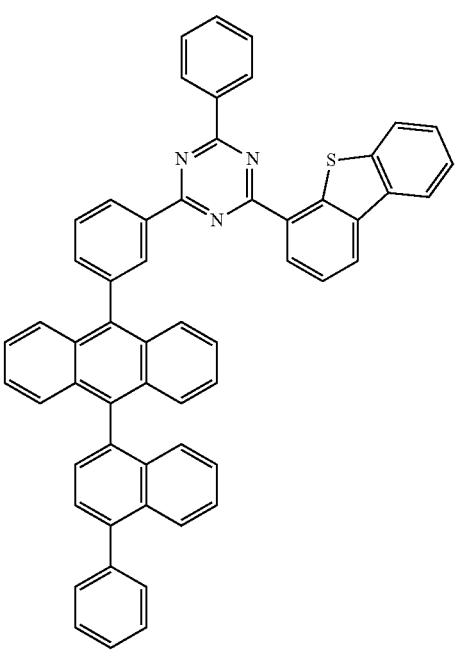
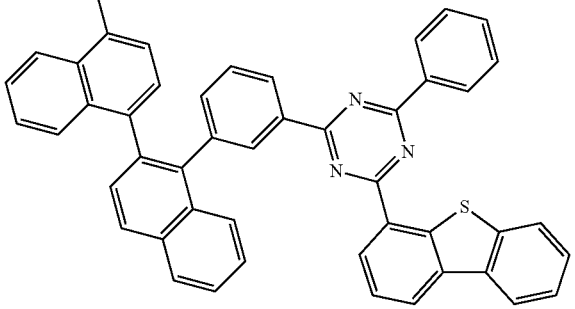

315
-continued
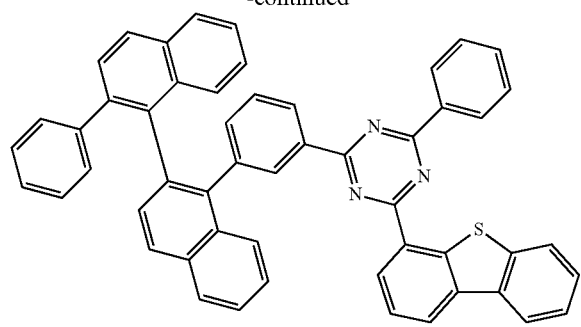
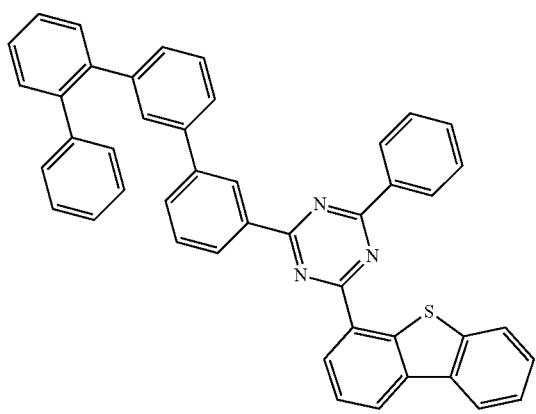
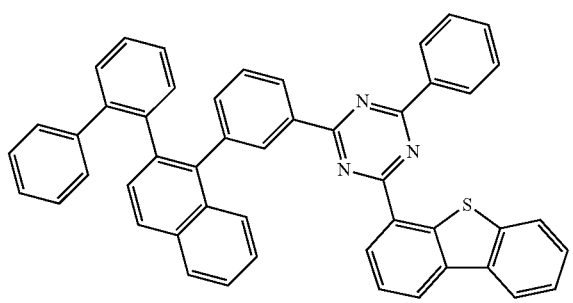
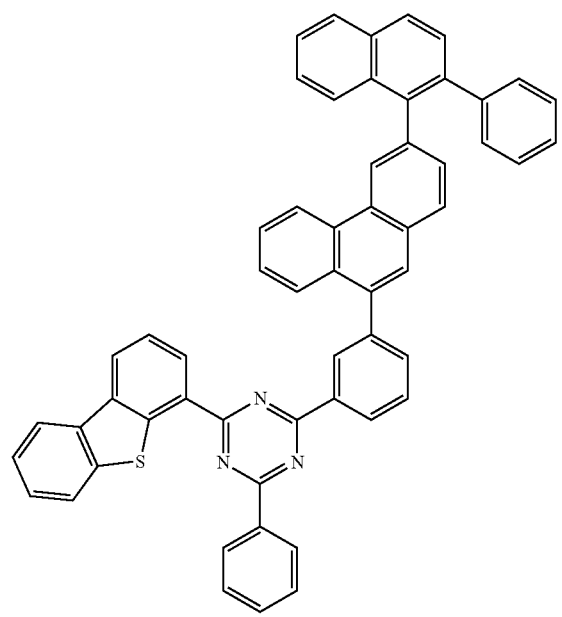
316
-continued
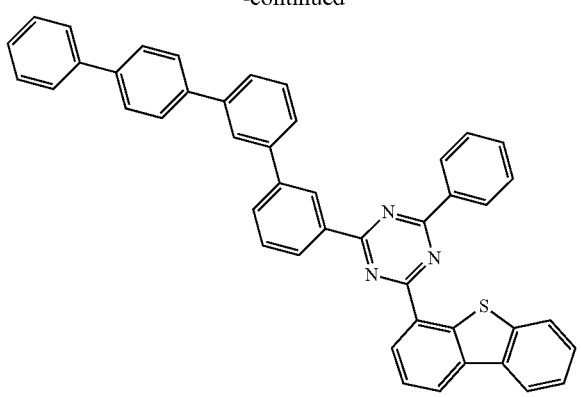
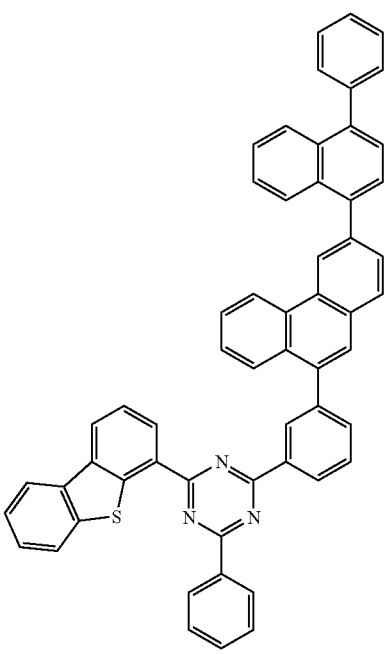
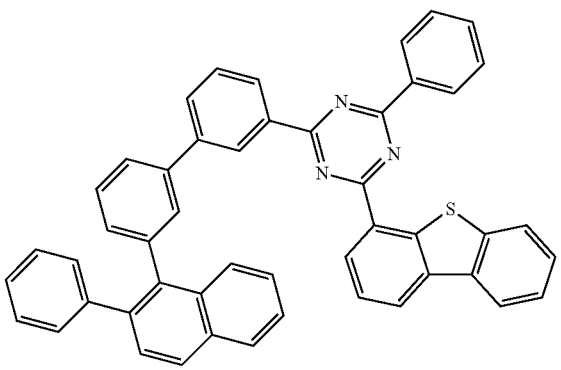

317
-continued
318
-continued
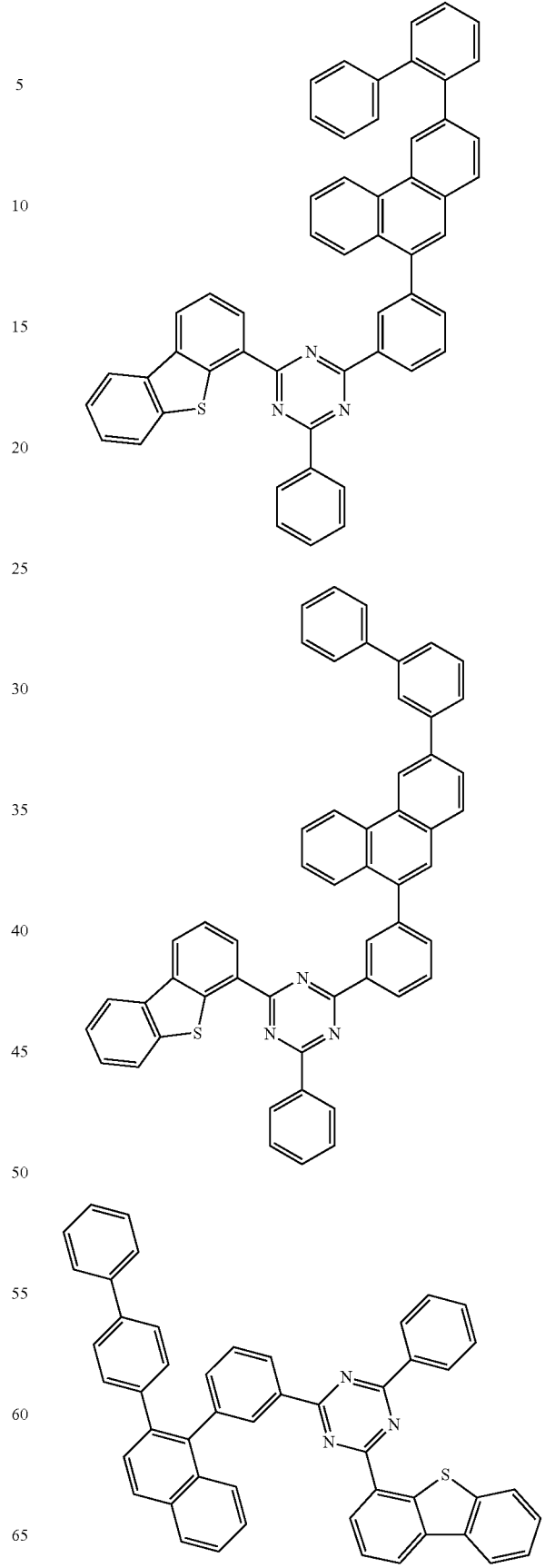

319
-continued
320
-continued
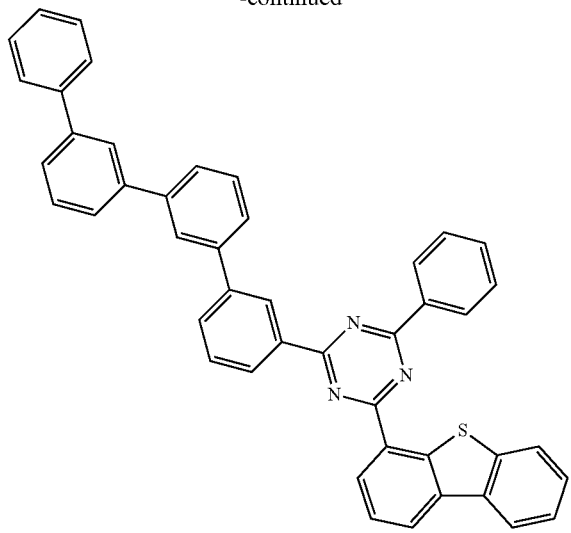
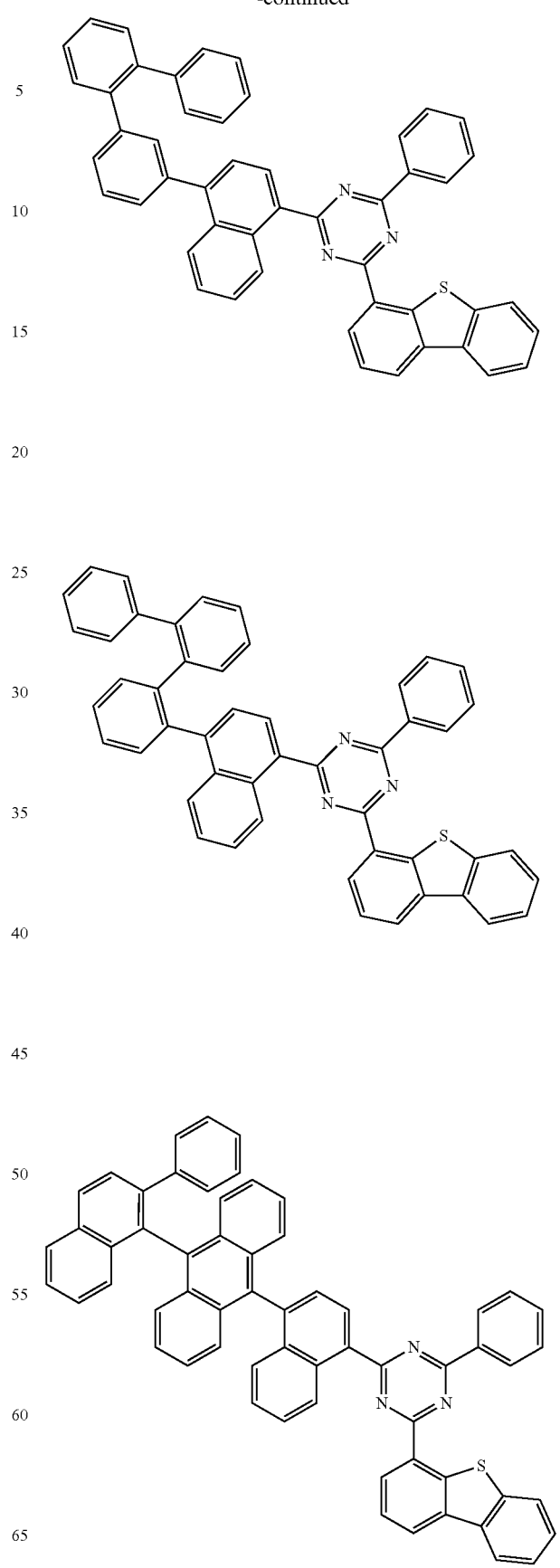

321
-continued
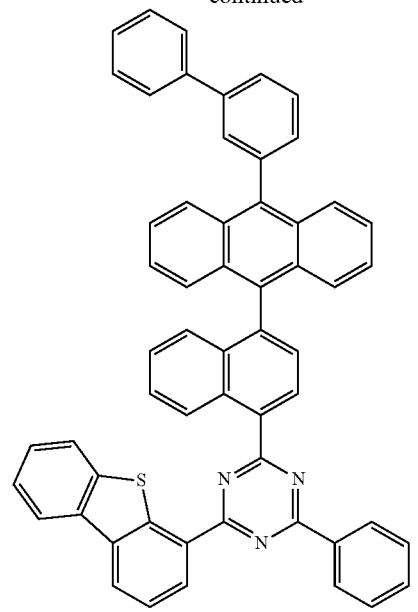
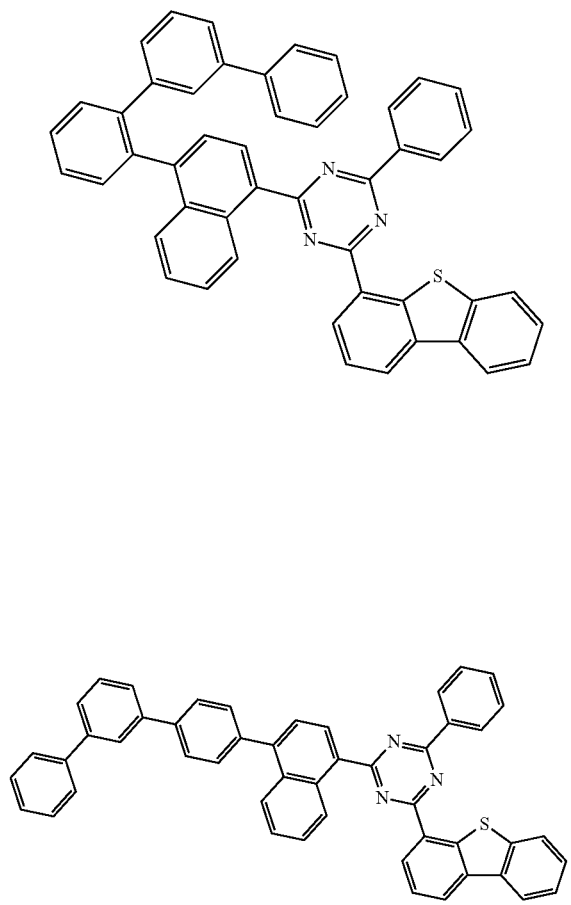
322
-continued
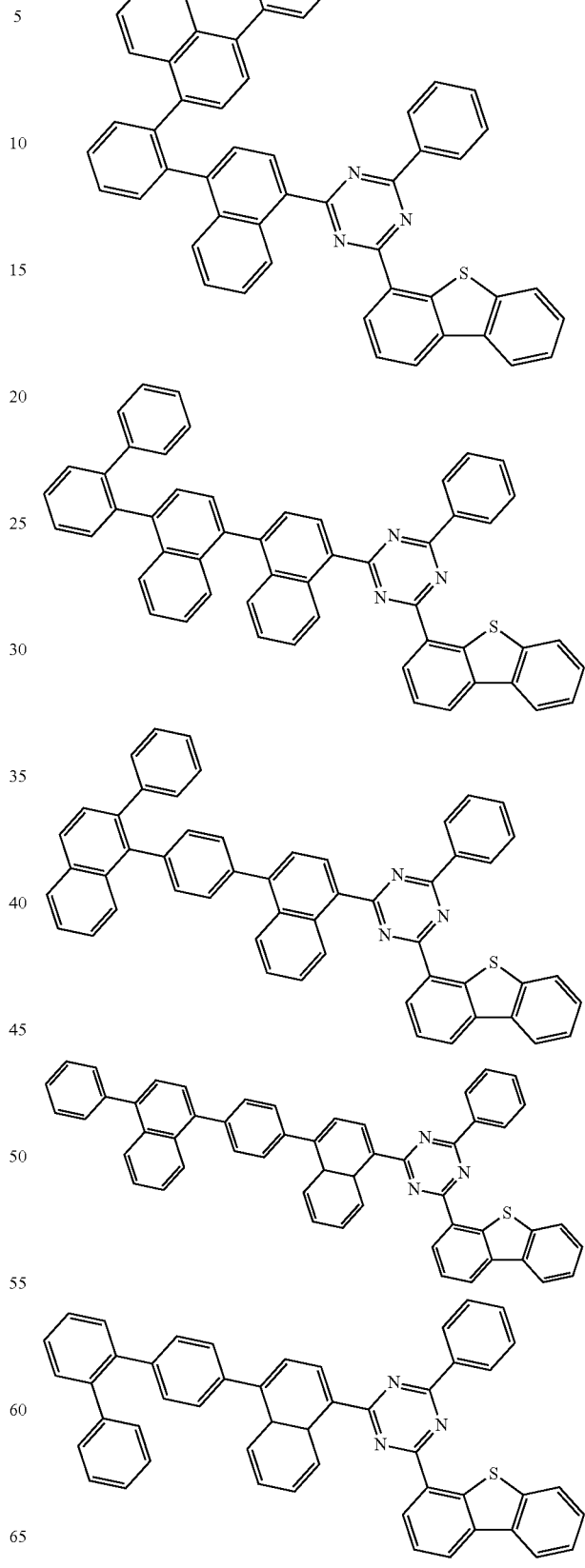

323
-continued
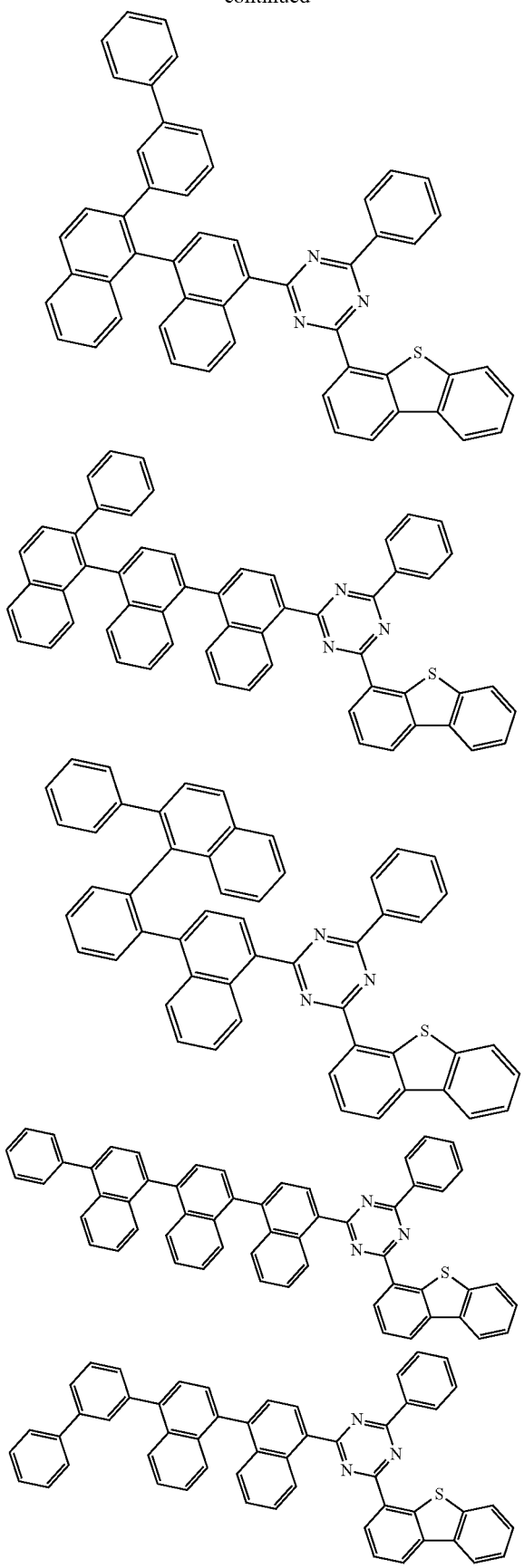
324
-continued
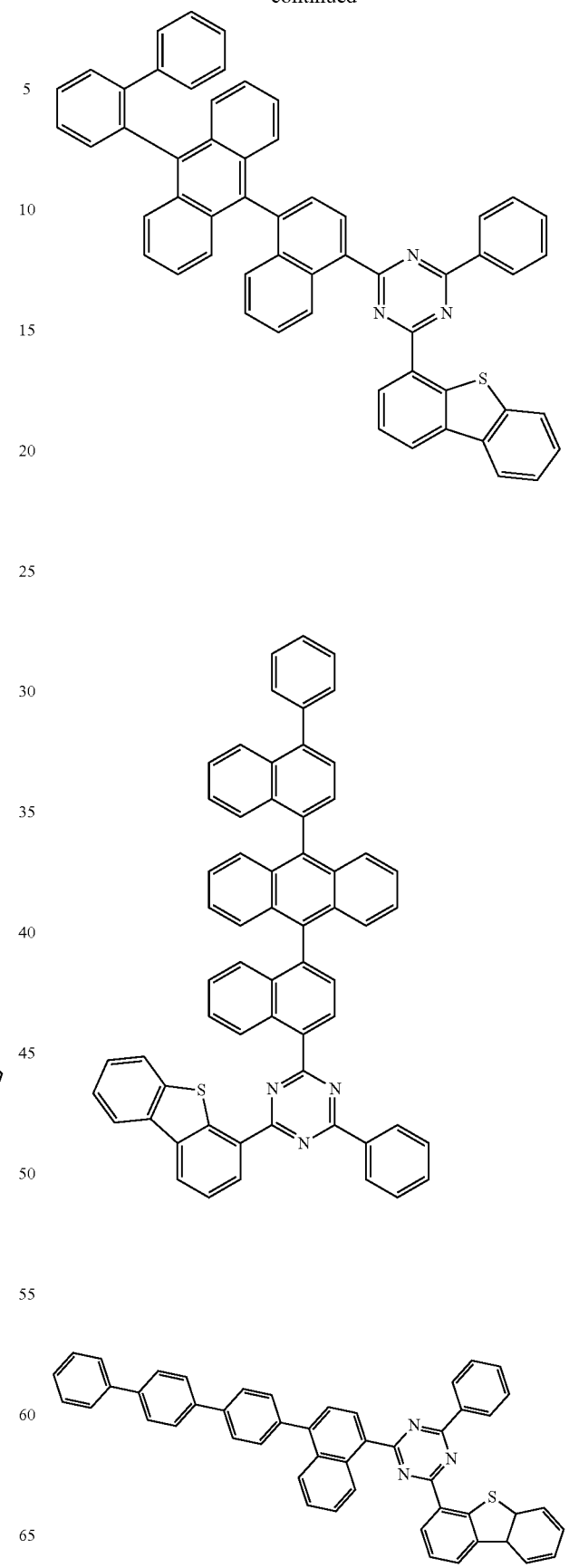

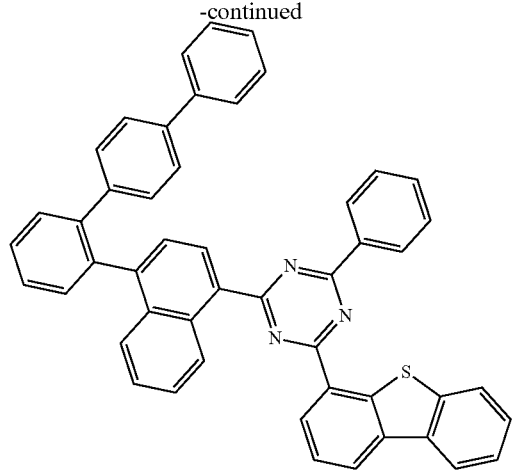
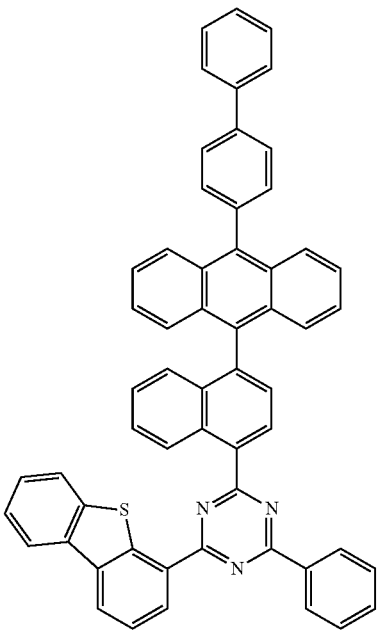
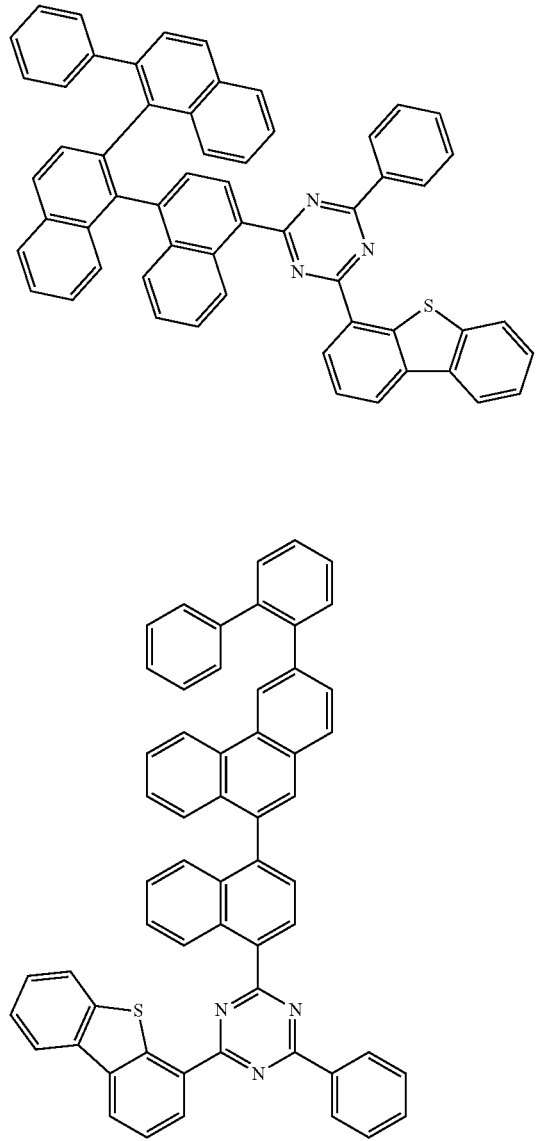
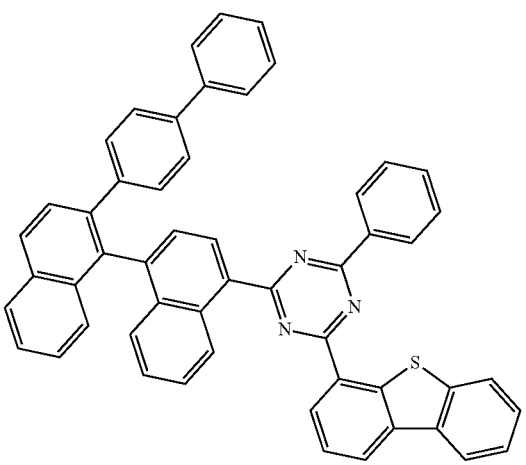
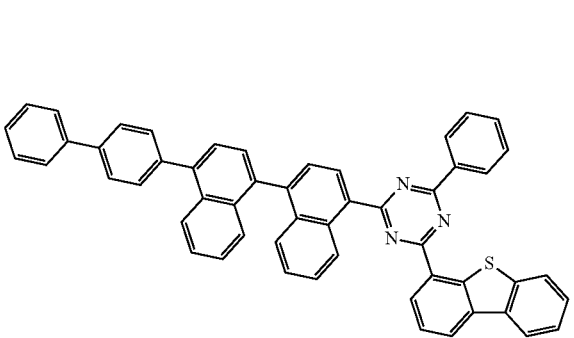

327
-continued
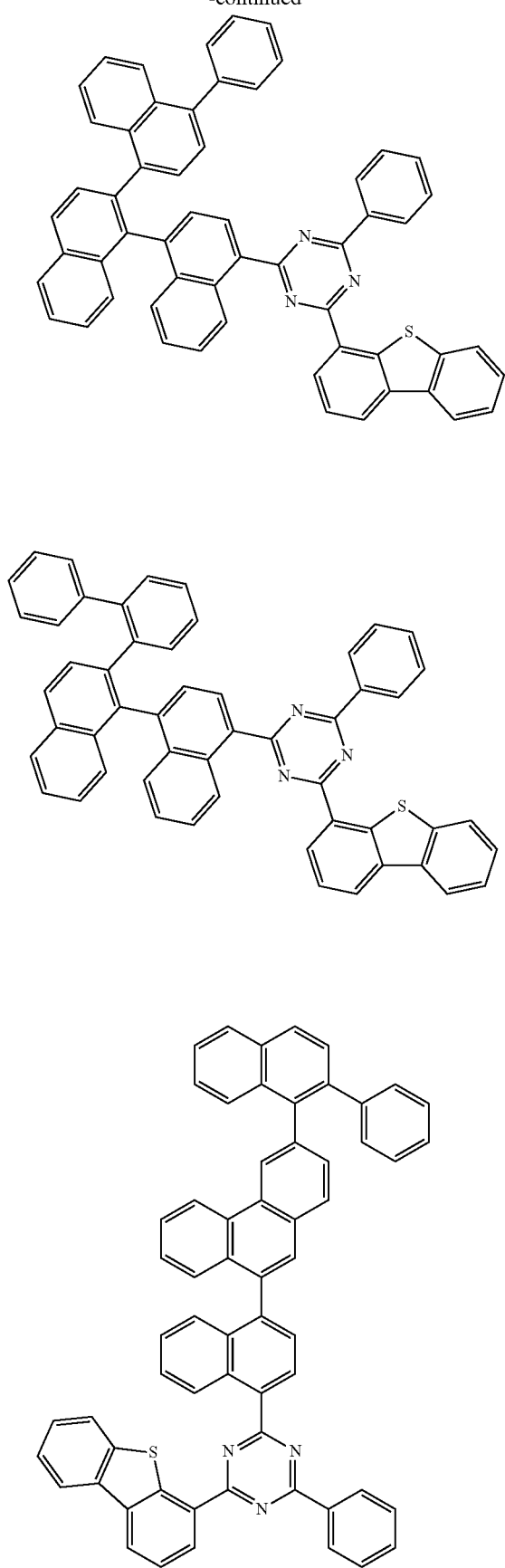
328
-continued
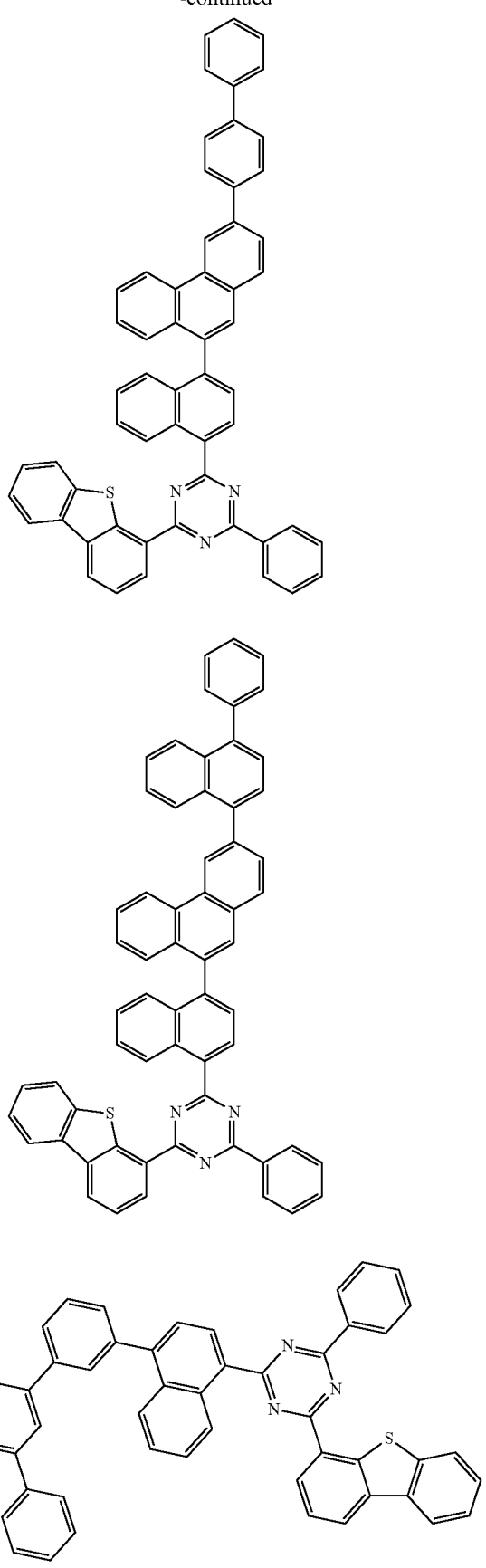

329
-continued
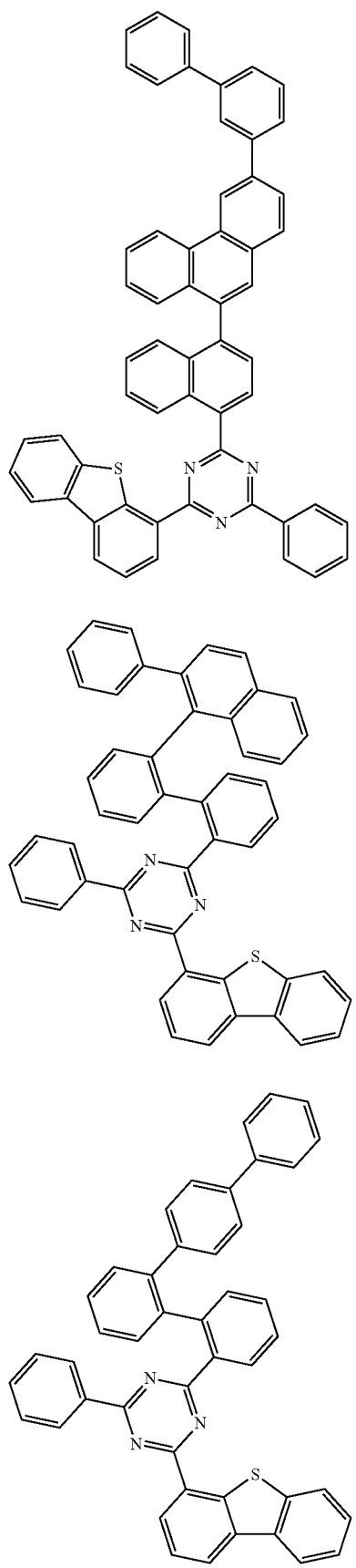
330
-continued
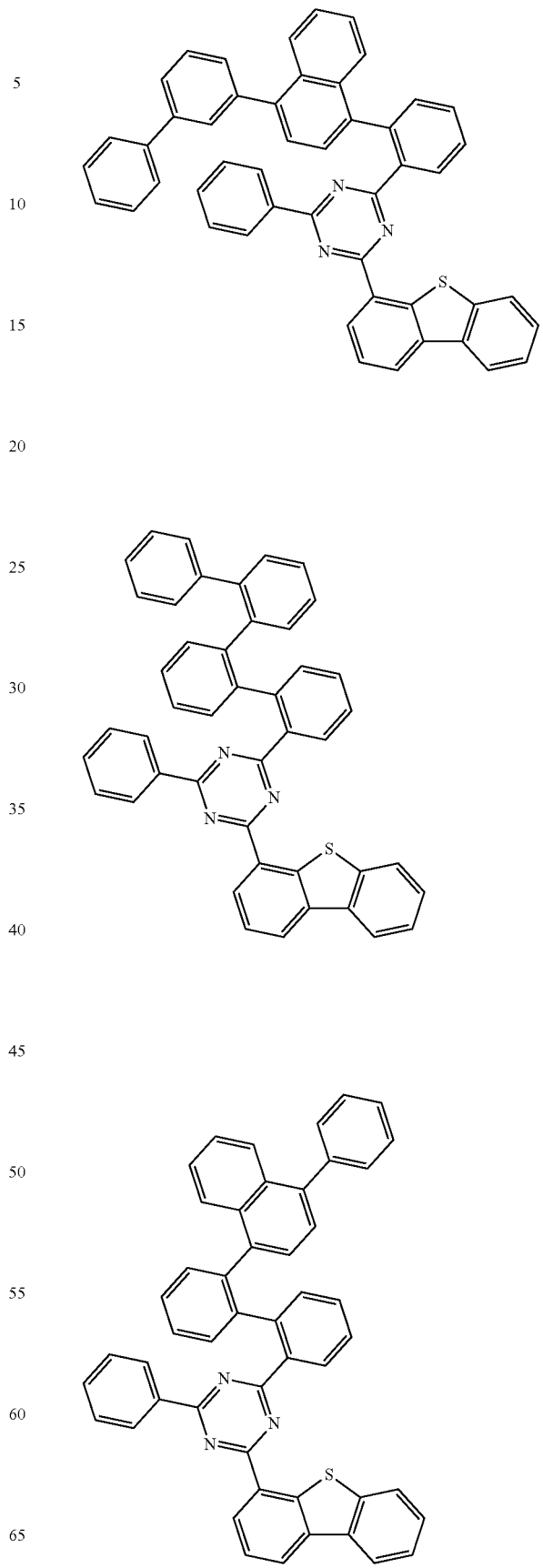

331
-continued
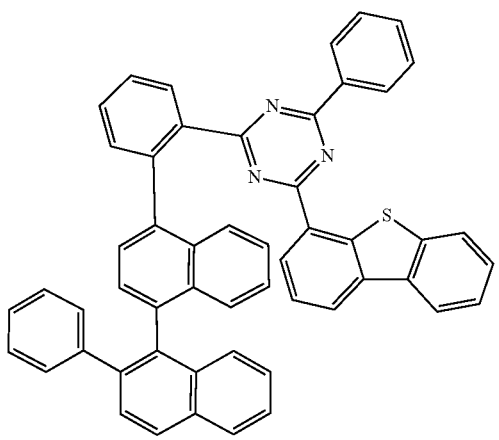
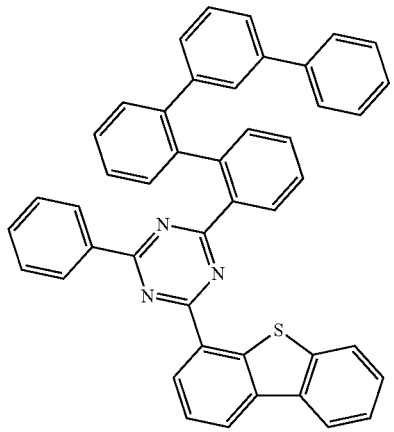
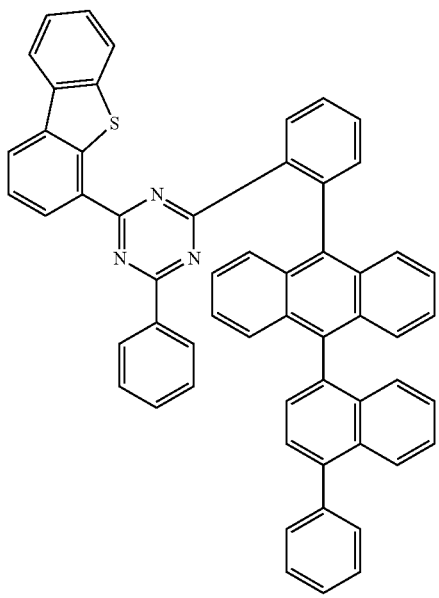
332
-continued
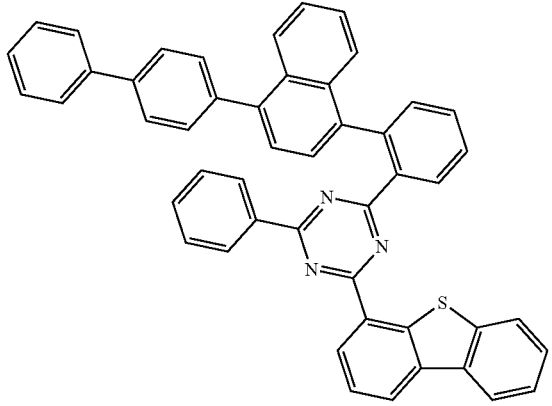
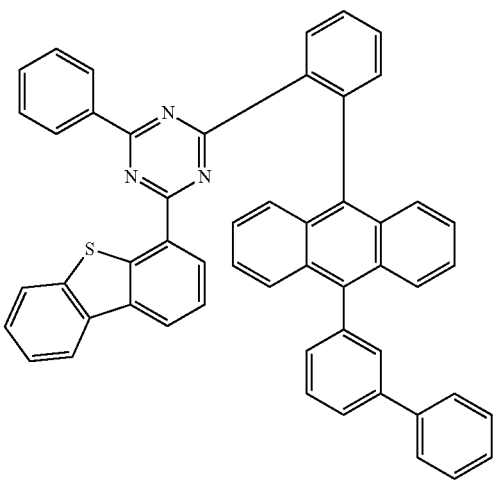
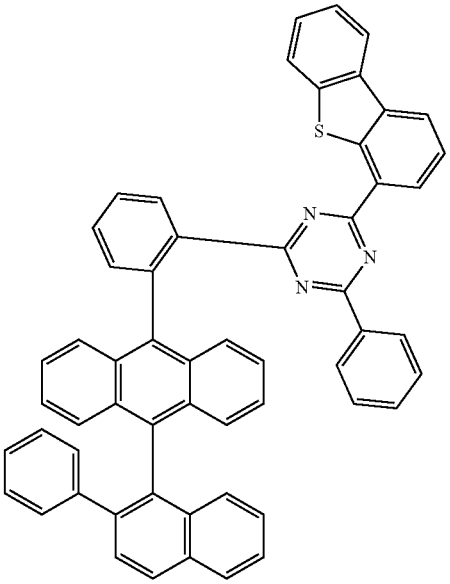

333
-continued
334
-continued
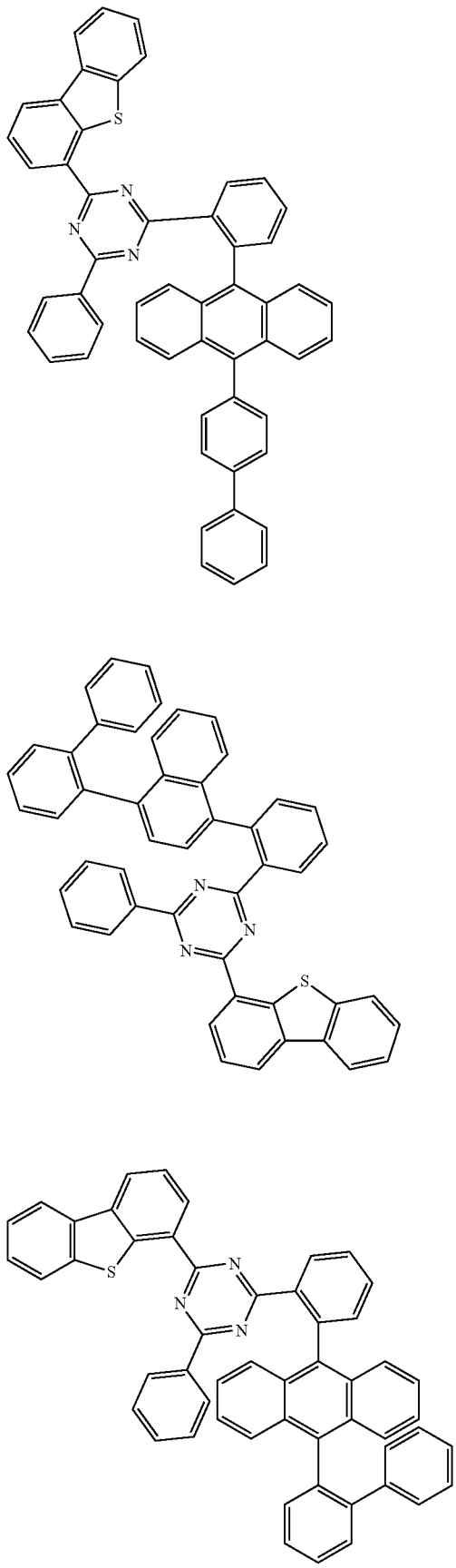
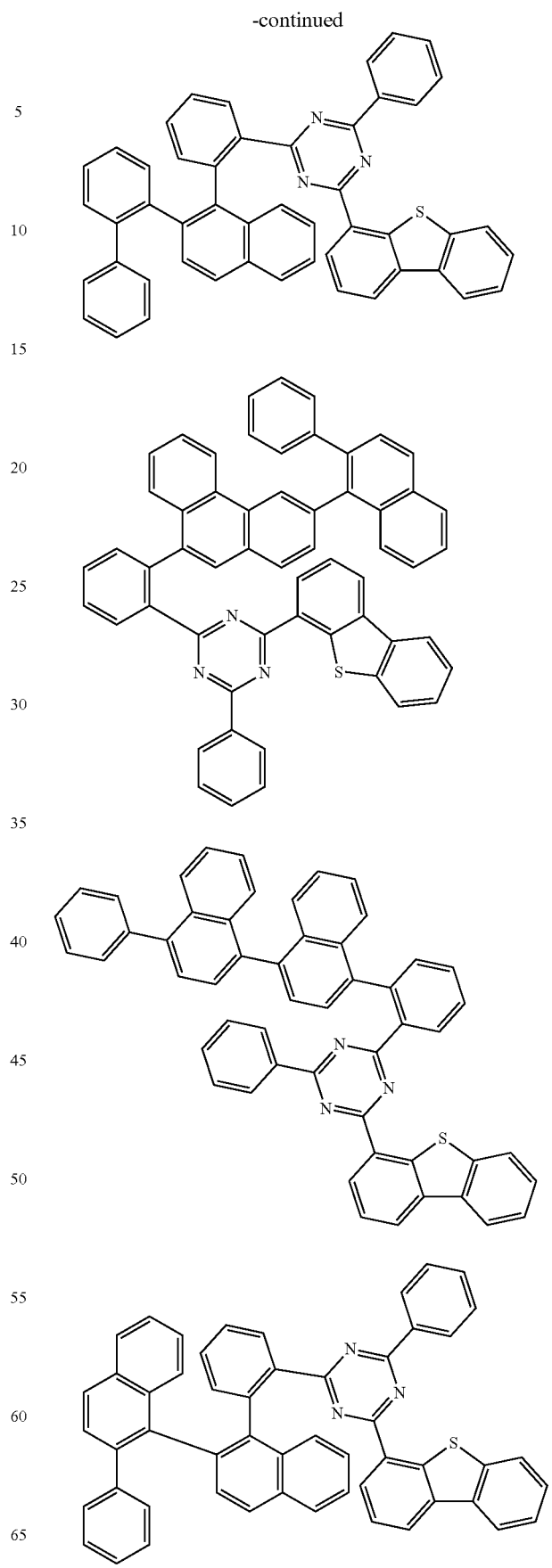

335
-continued
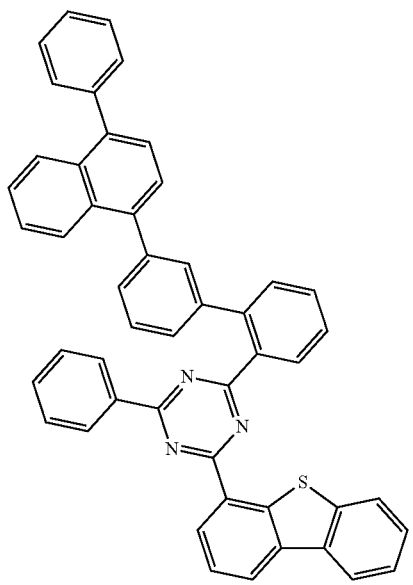
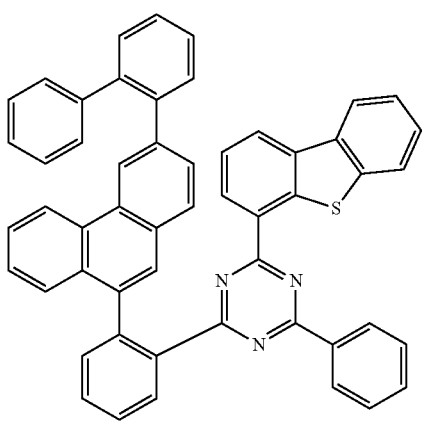
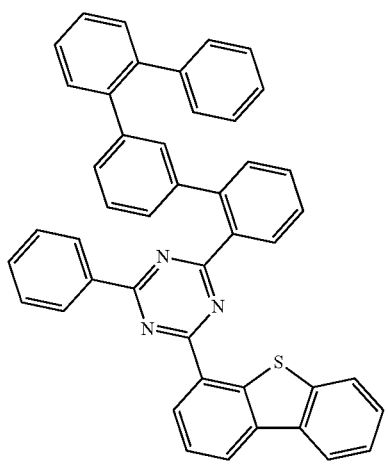
336
-continued
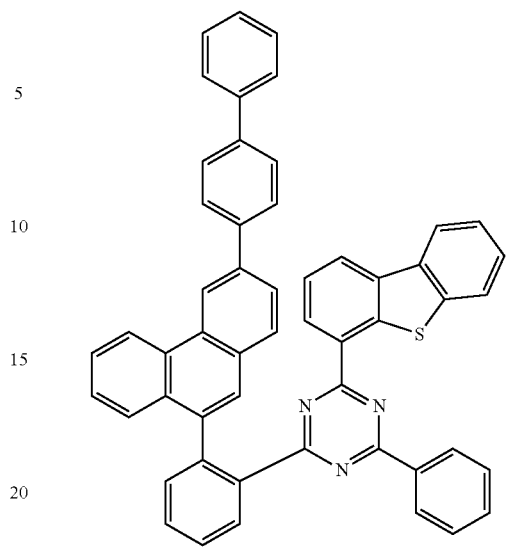
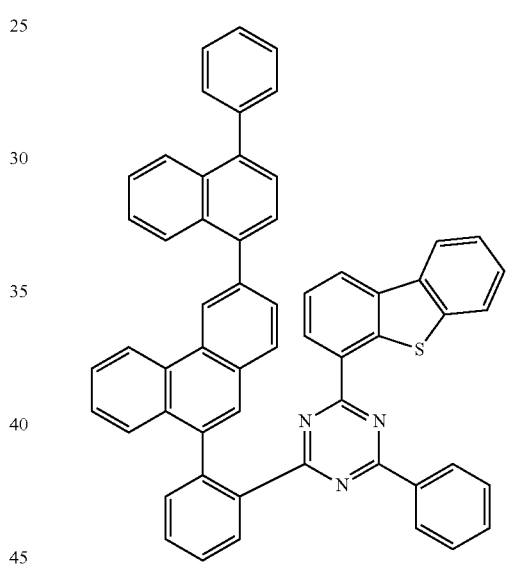
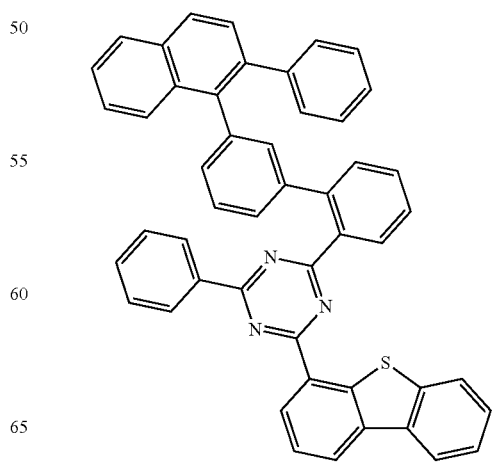

337
-continued
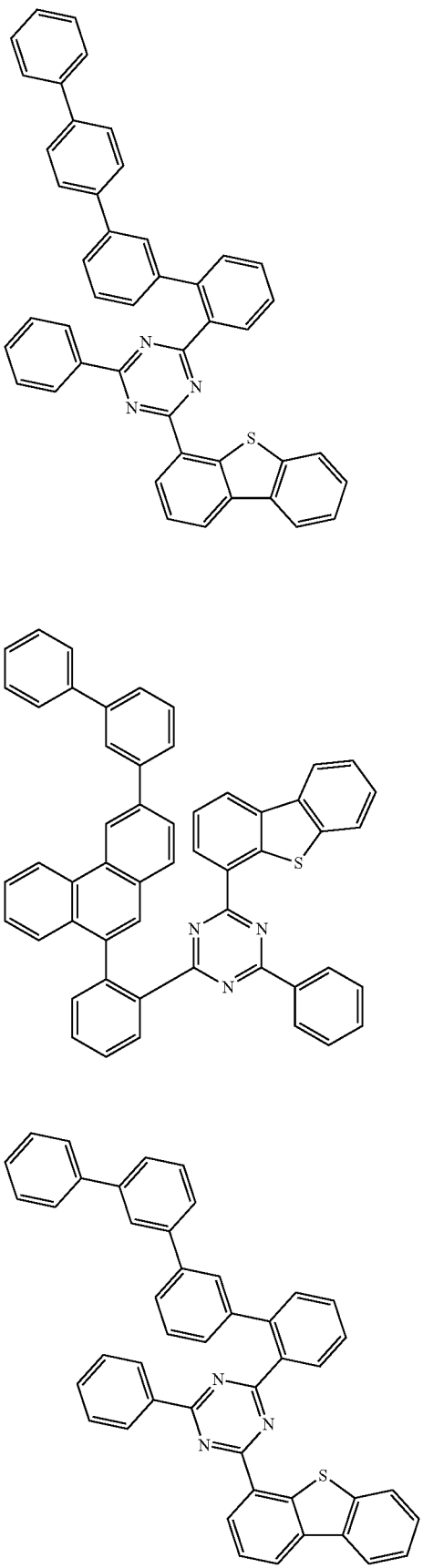
338
-continued
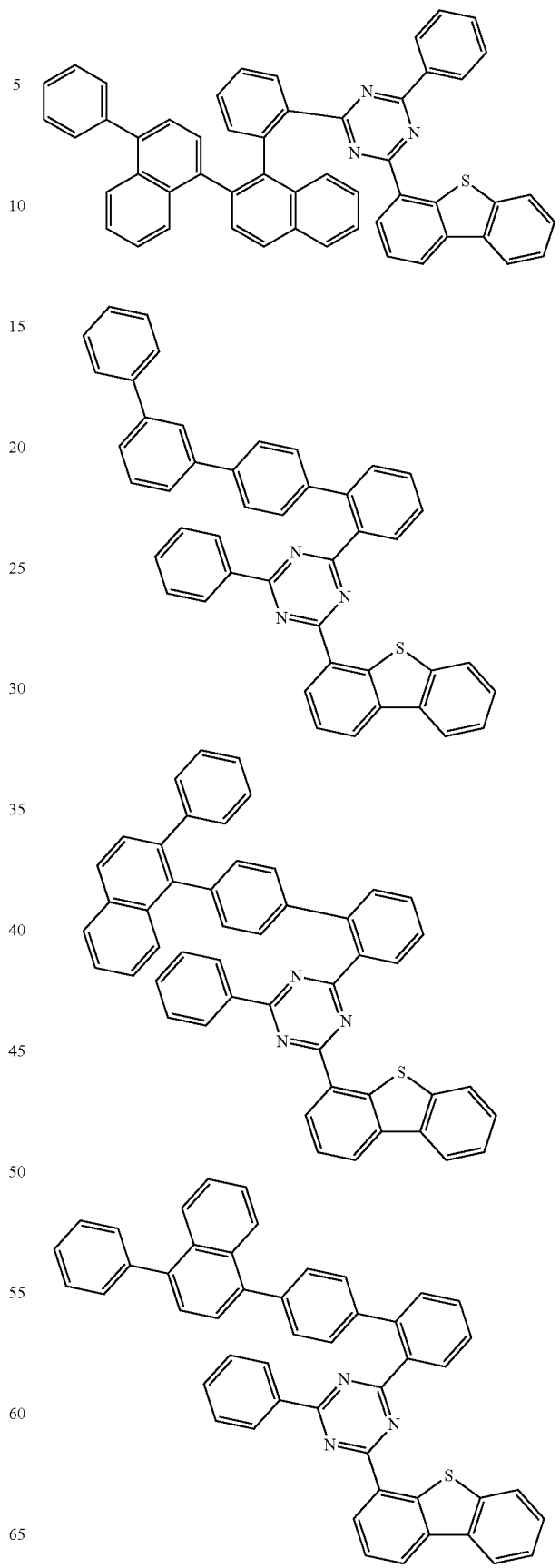

339
-continued
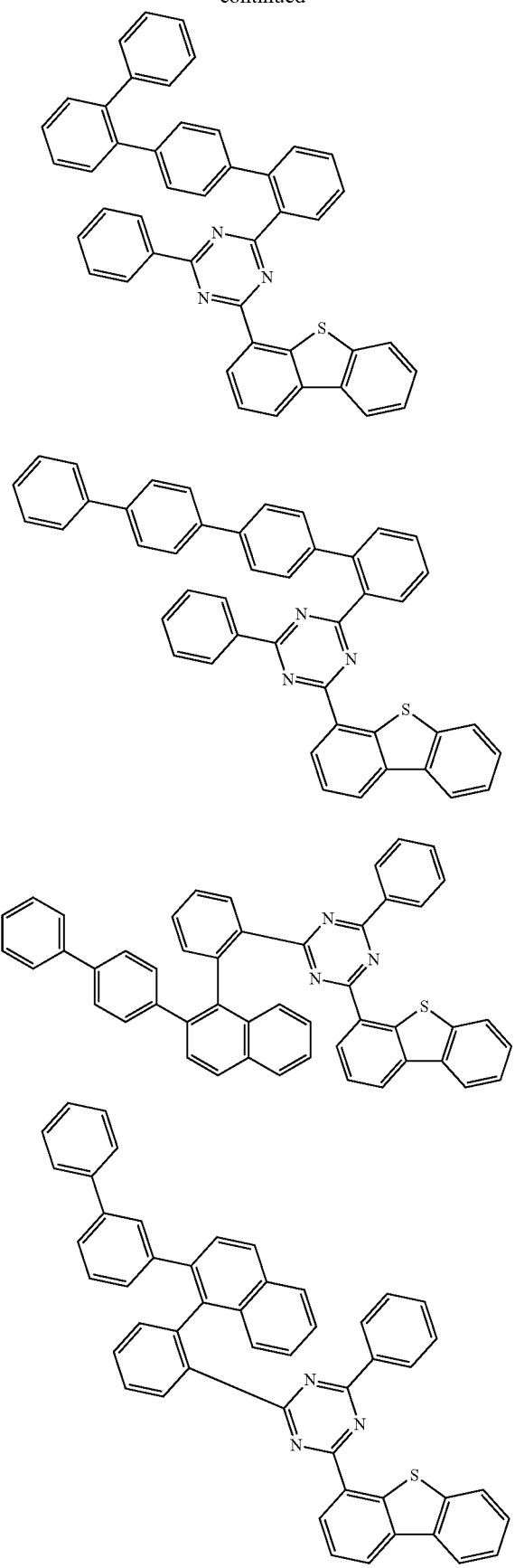
340
-continued
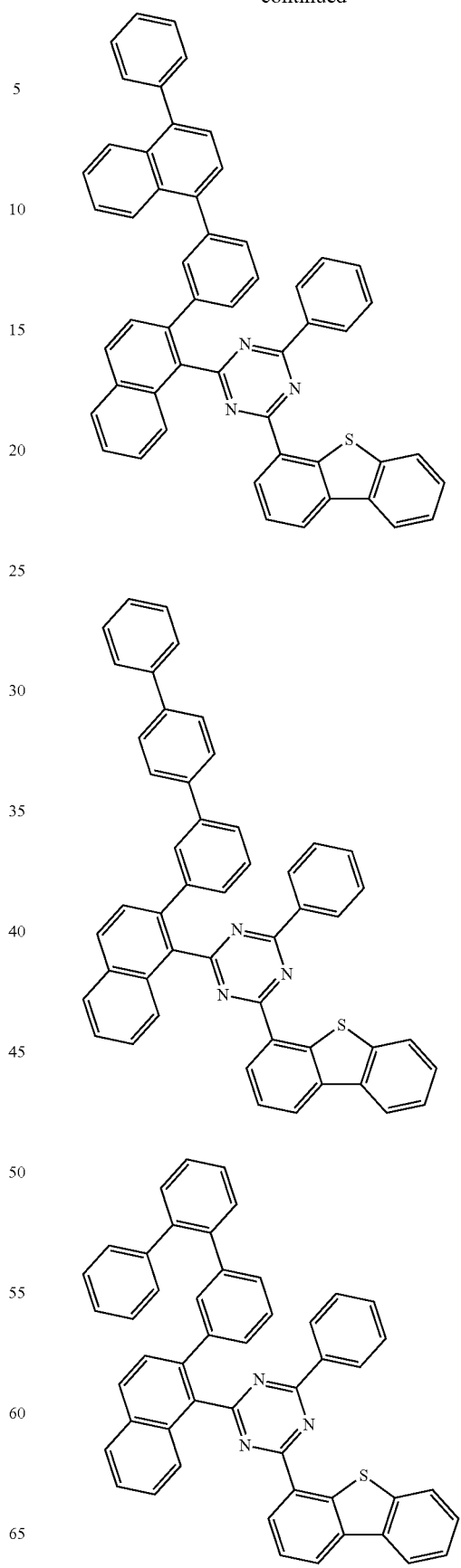

341
-continued
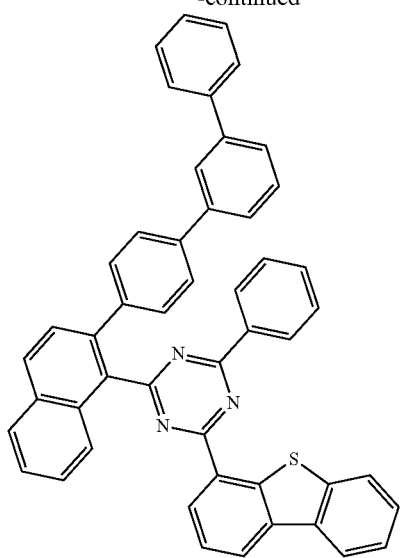
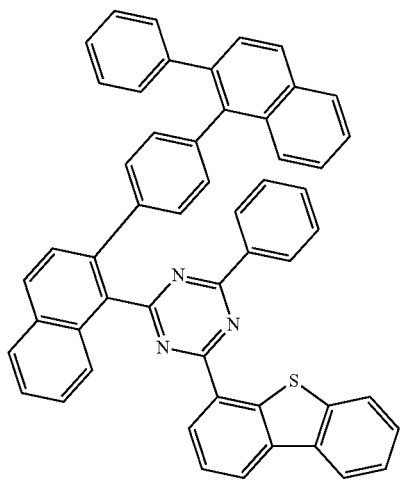
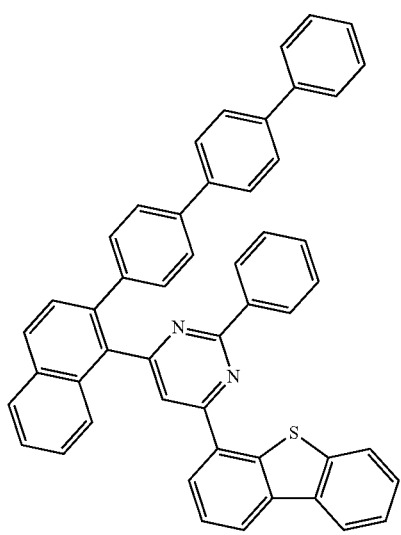
342
-continued
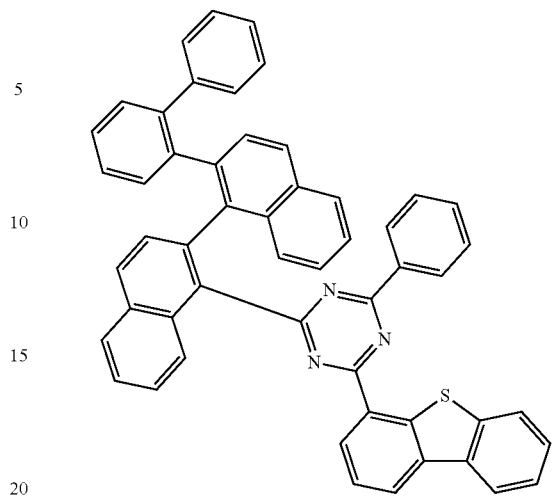
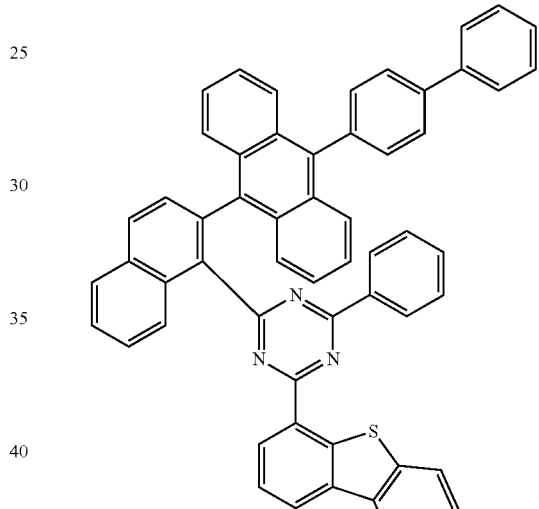
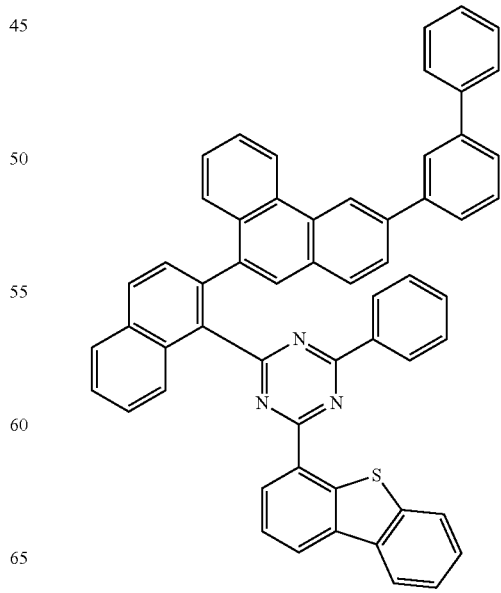

343
-continued
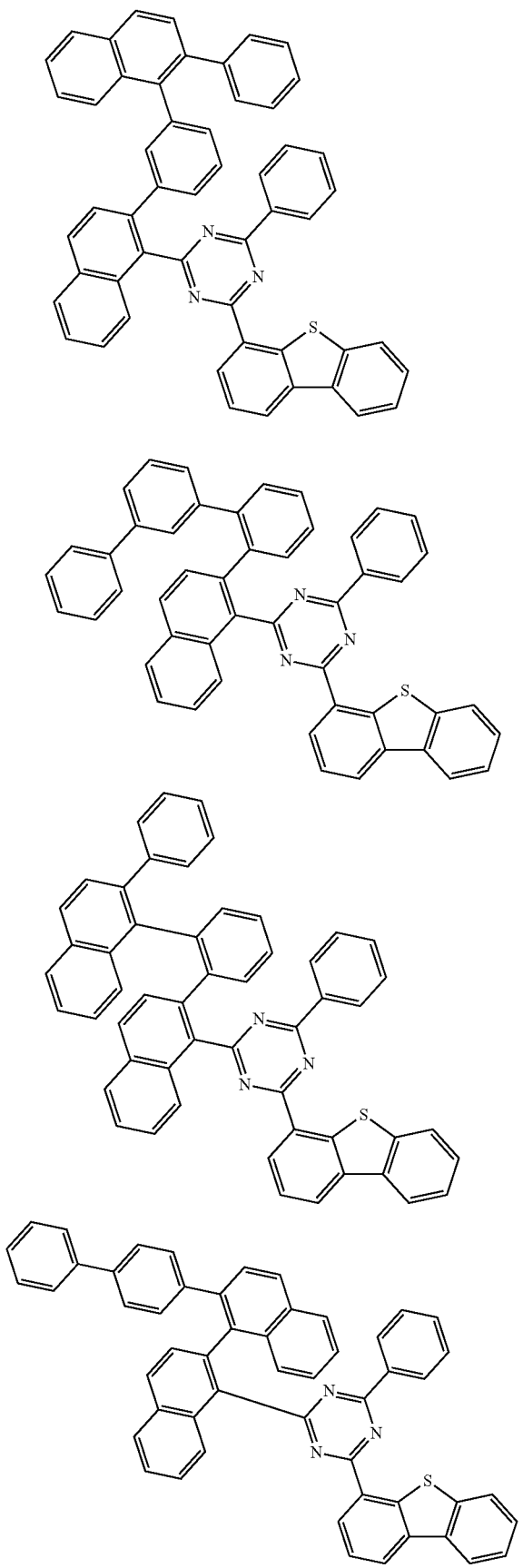
344
-continued
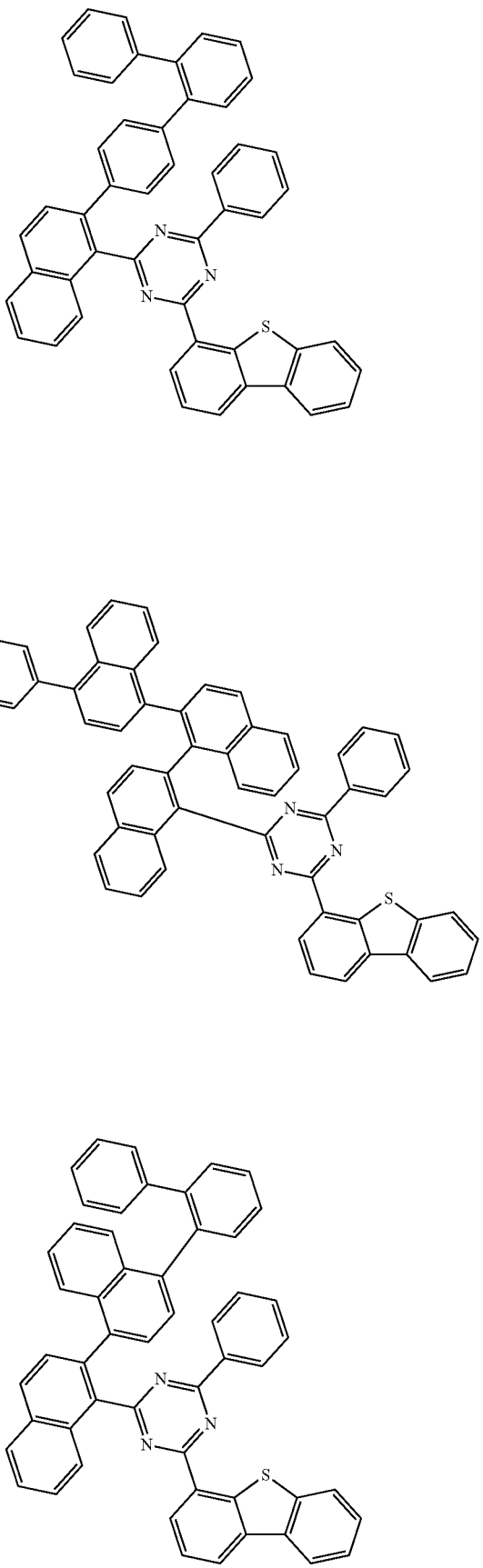

345
-continued
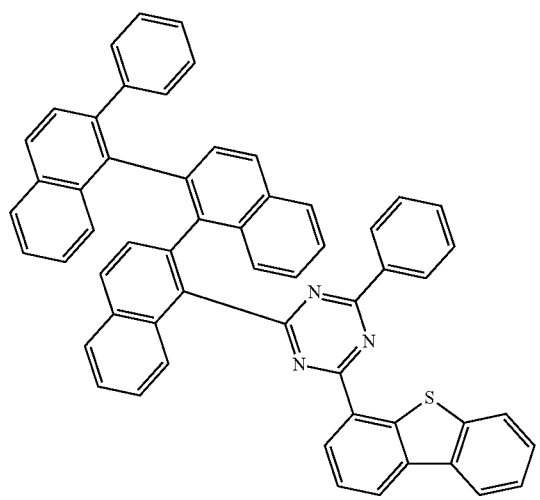
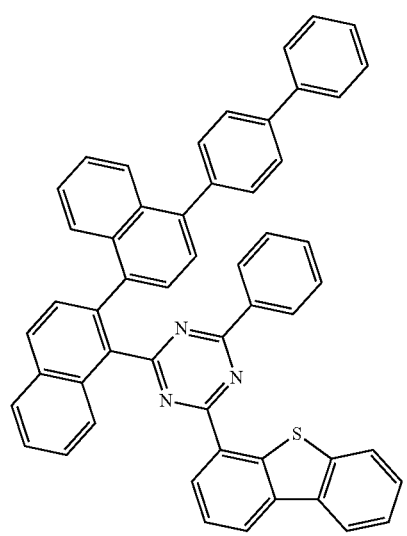
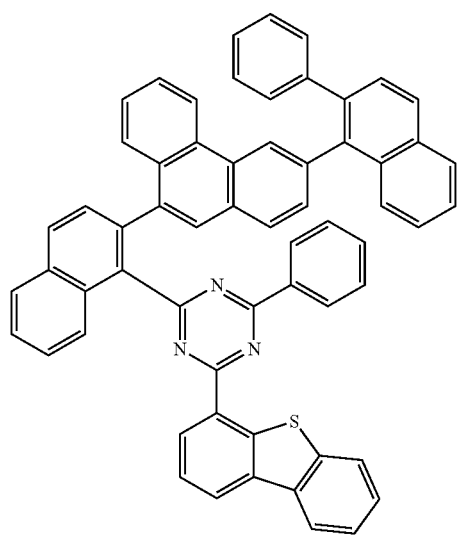
346
-continued
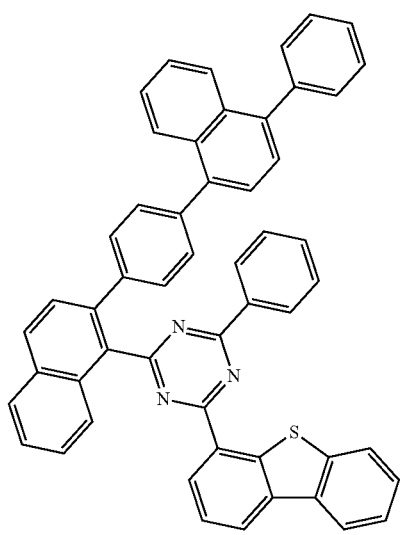
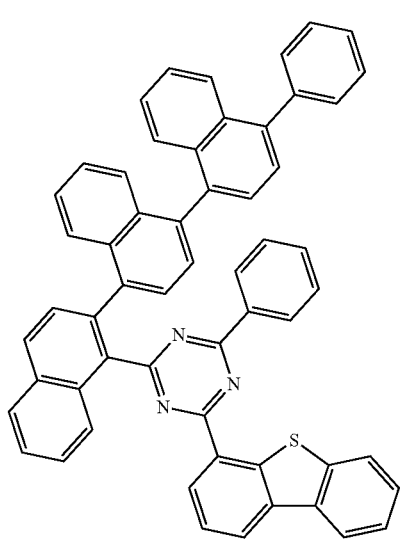
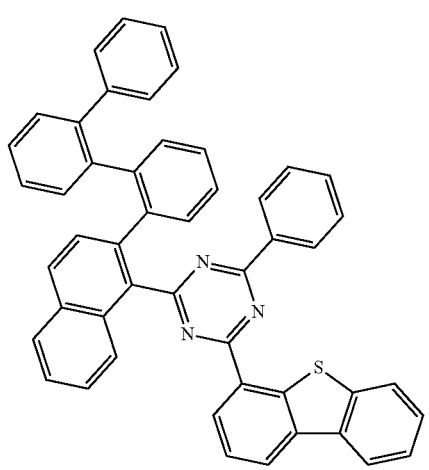

347
-continued
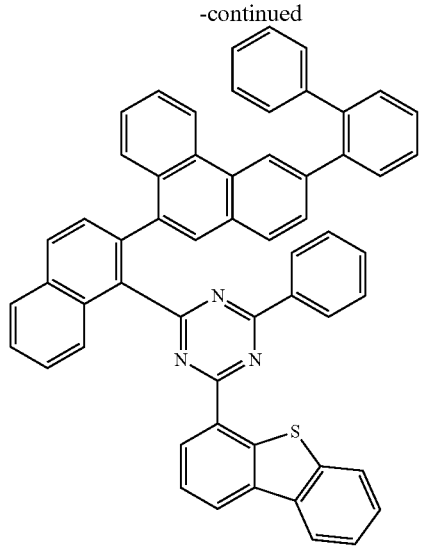
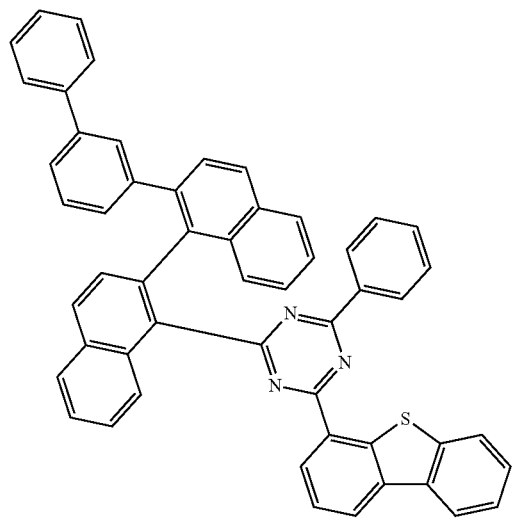
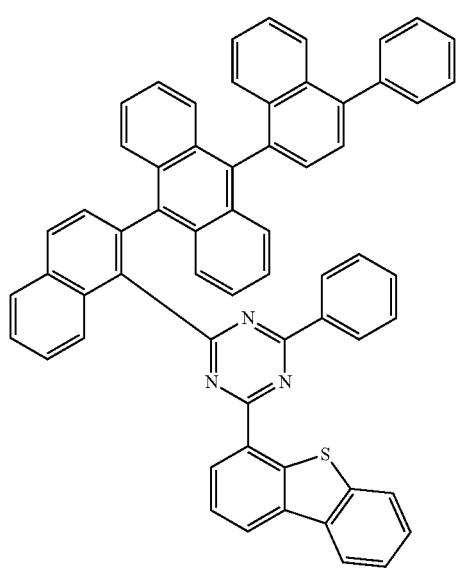
348
-continued
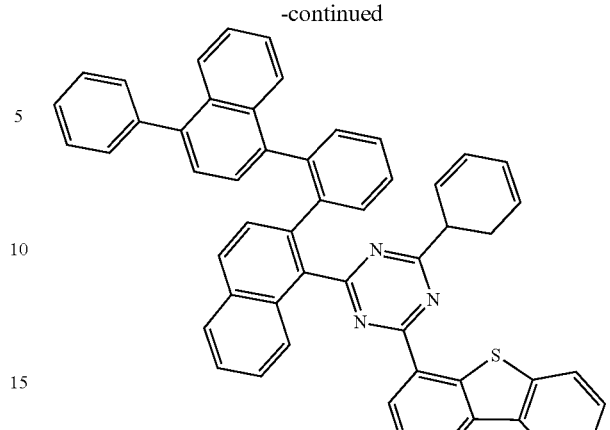
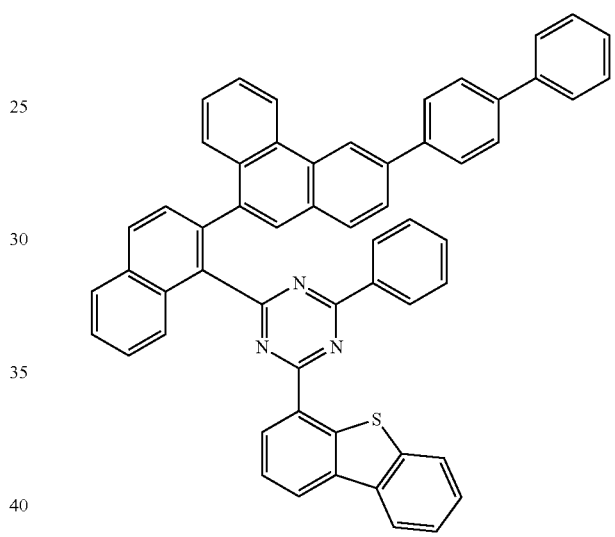
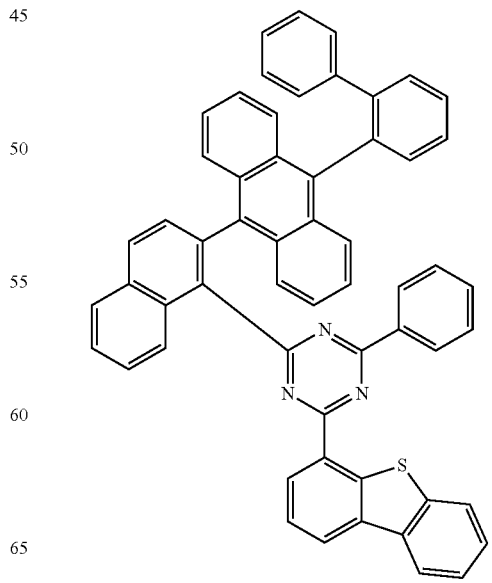

349
-continued
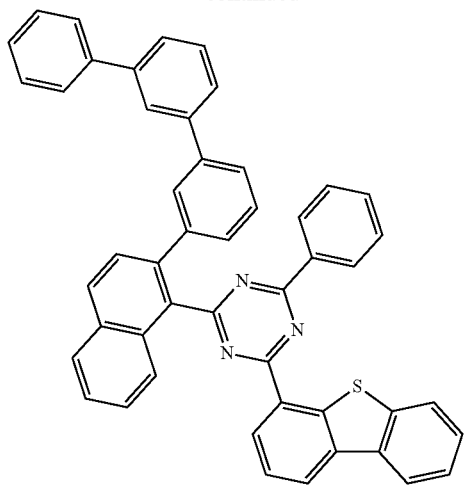
350
-continued
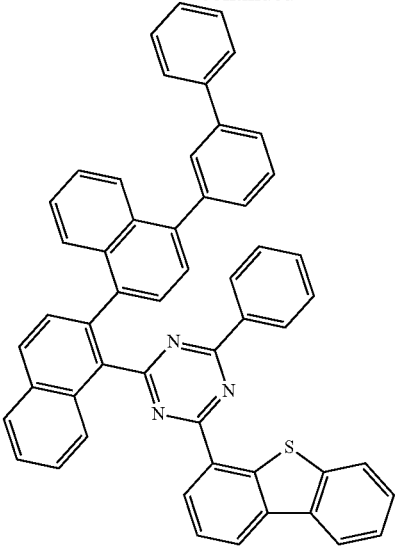
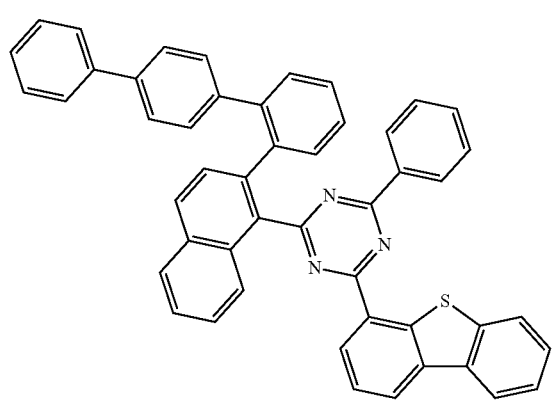
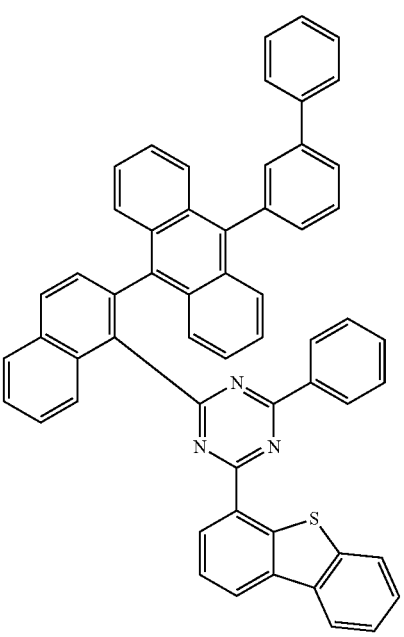
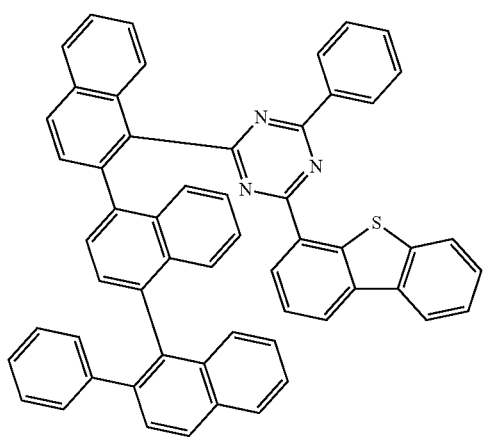
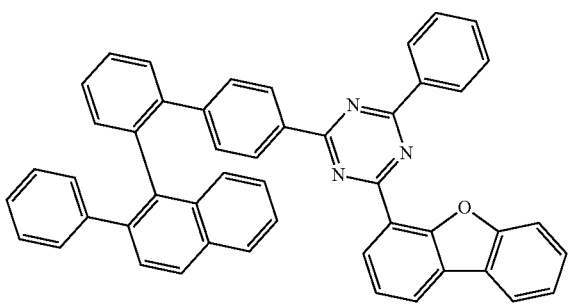

351
-continued
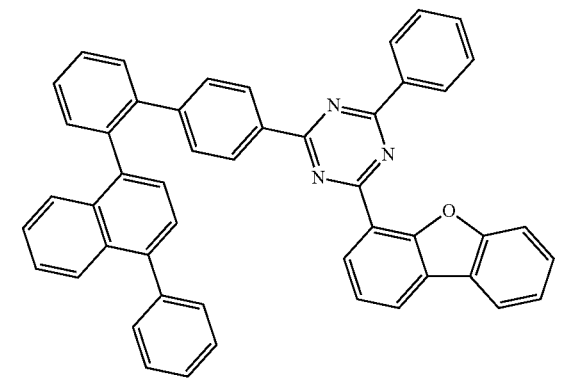
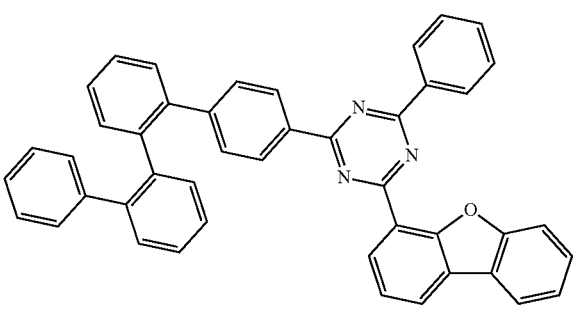
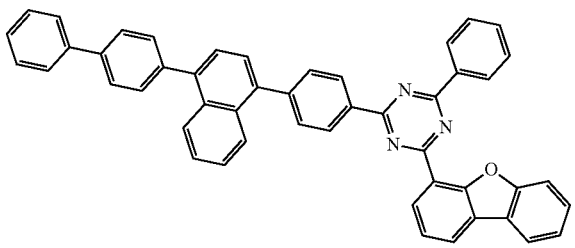
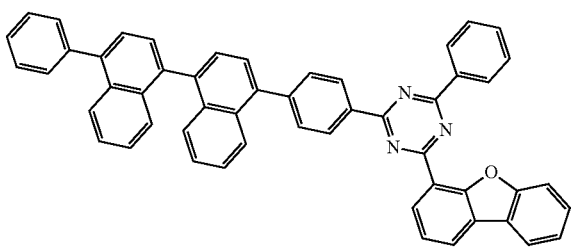
352
-continued
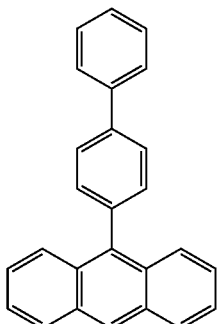
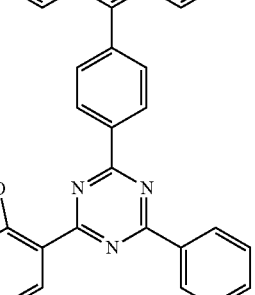
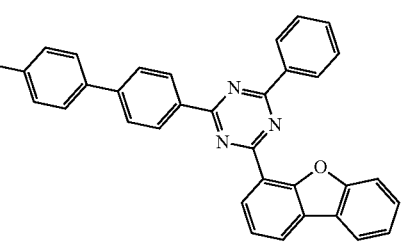
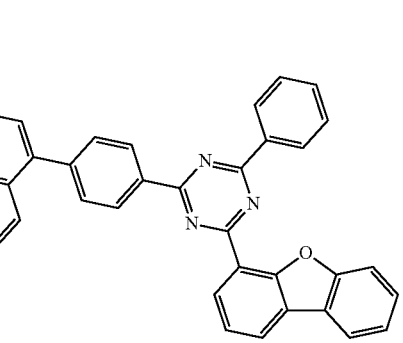
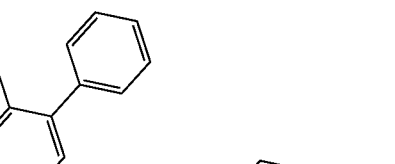
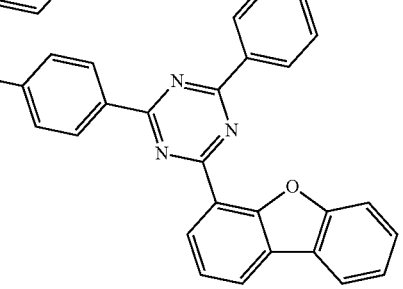

353
-continued
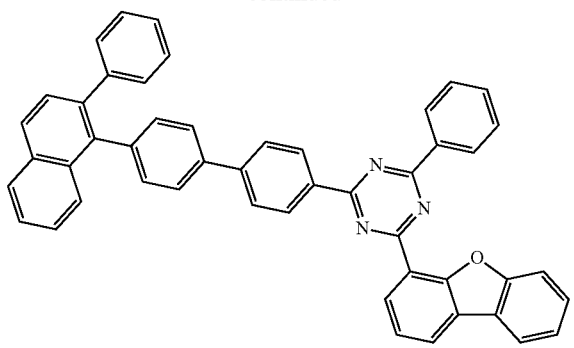
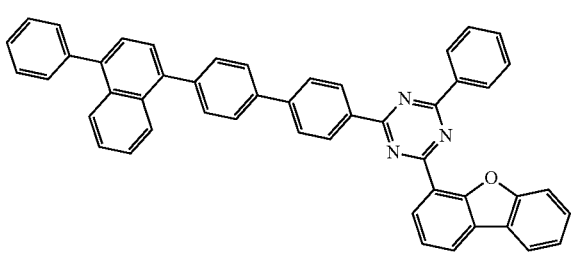
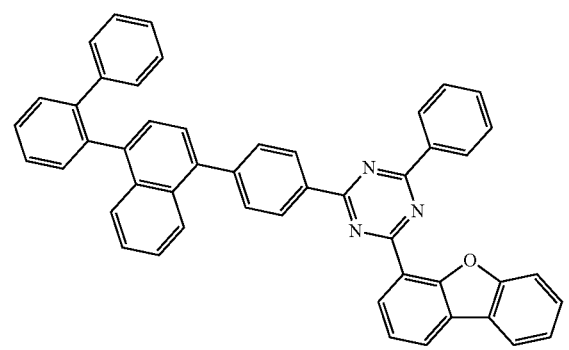
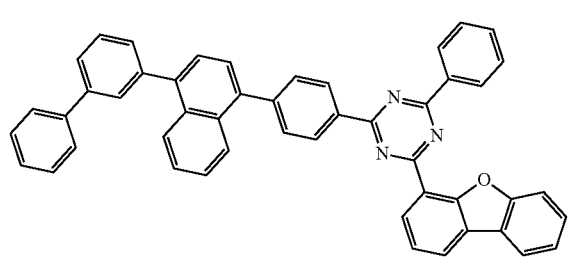
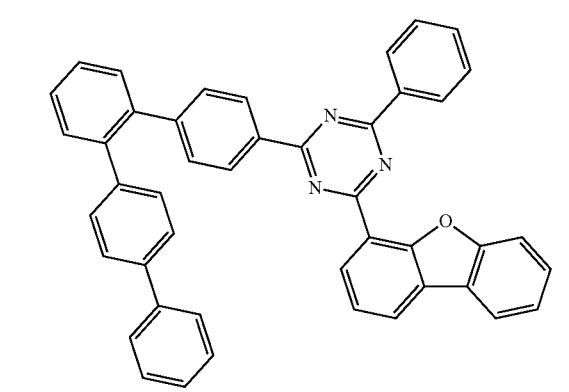
354
-continued
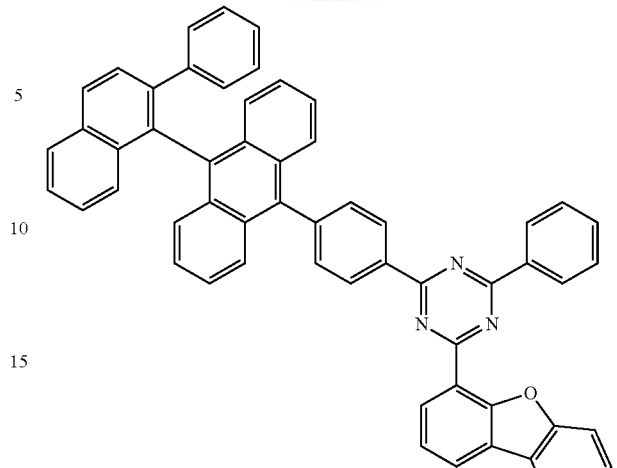
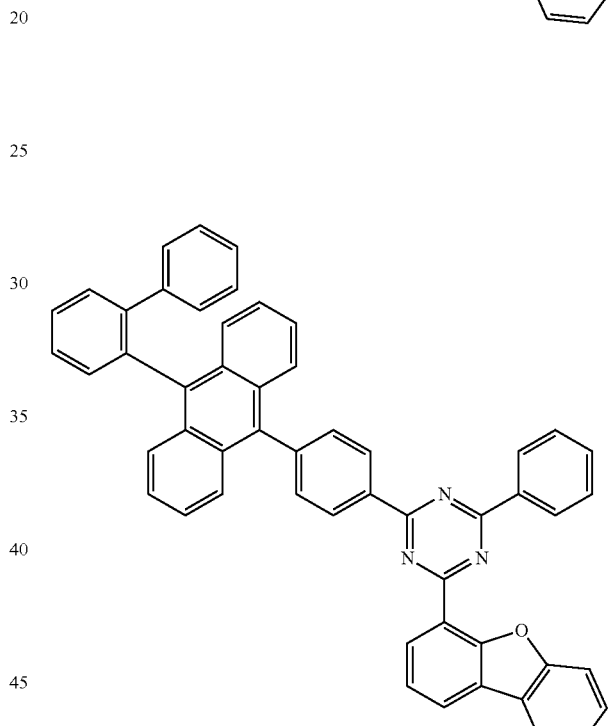
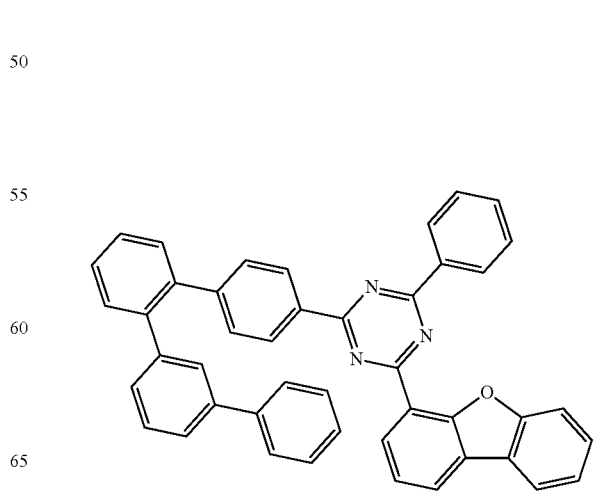

355
-continued
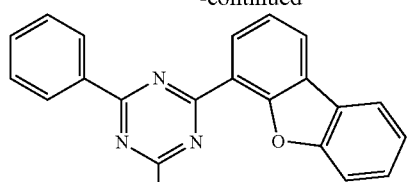
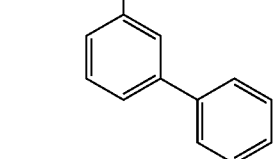
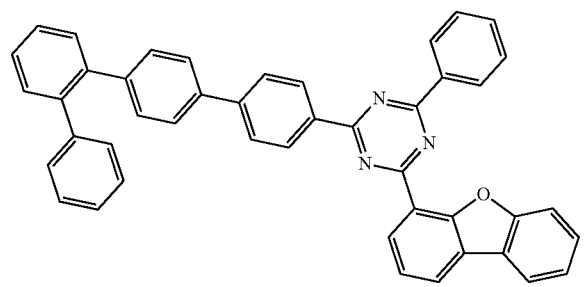
356
-continued
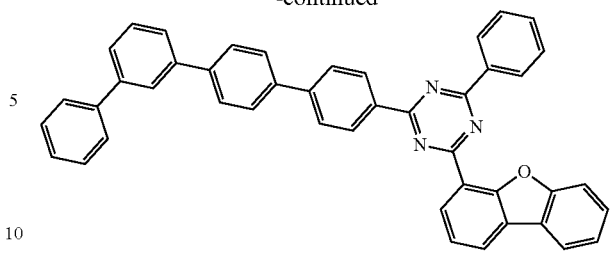
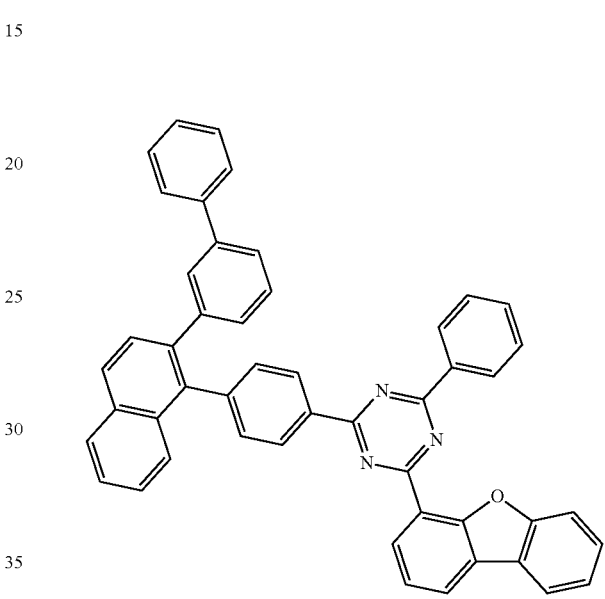
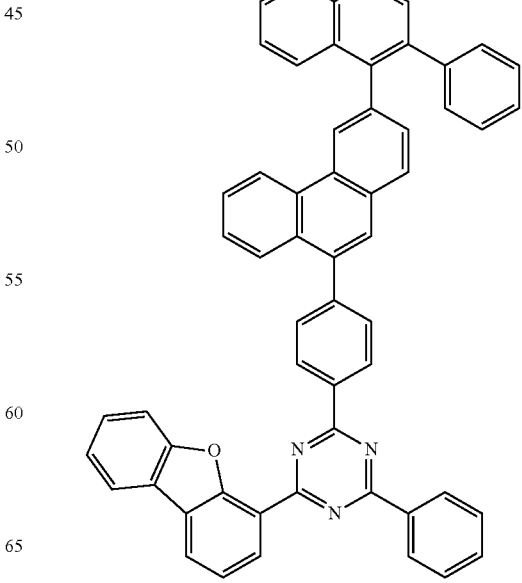

357
-continued
358
-continued
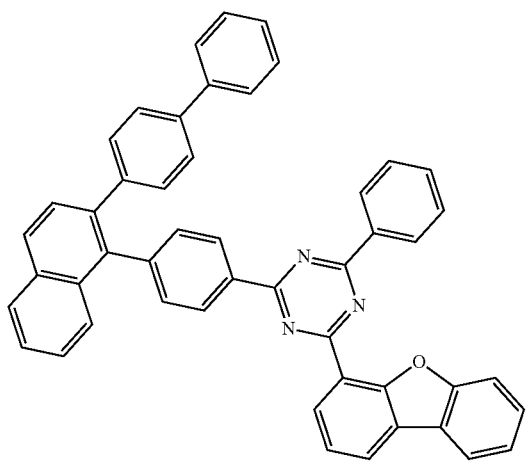
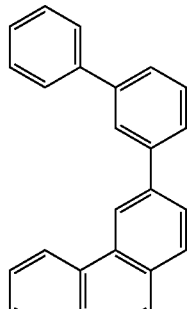
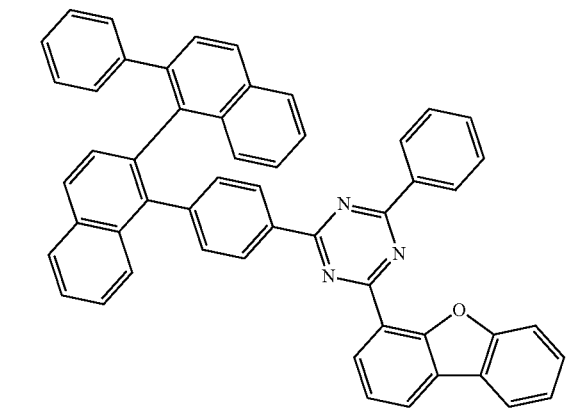
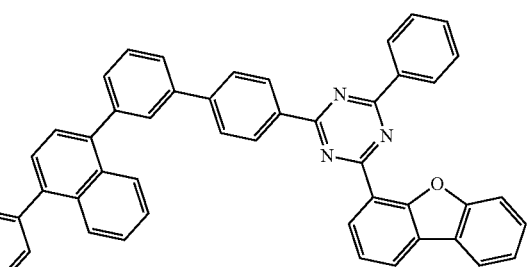
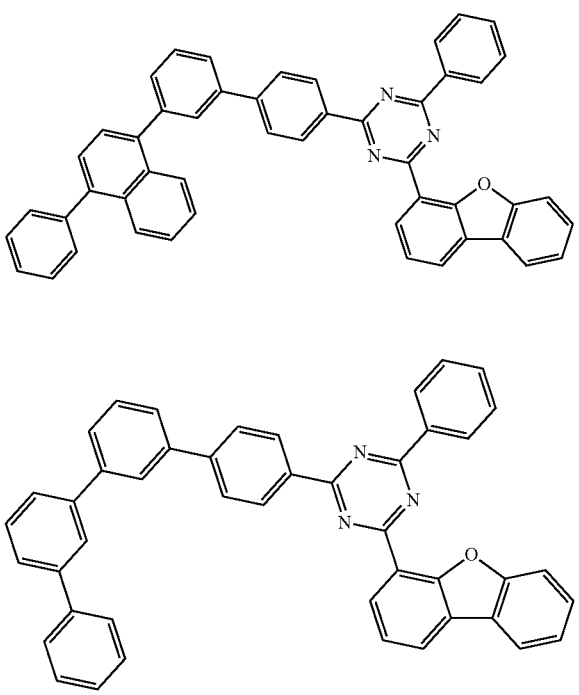
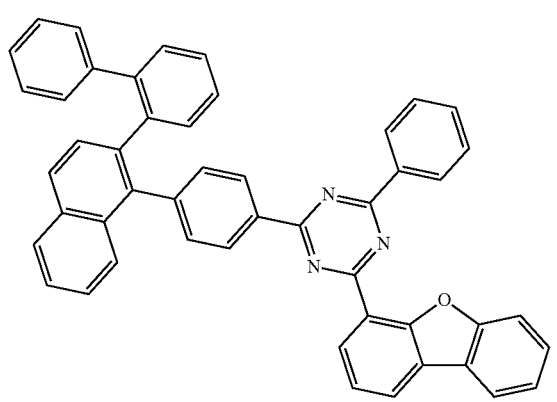
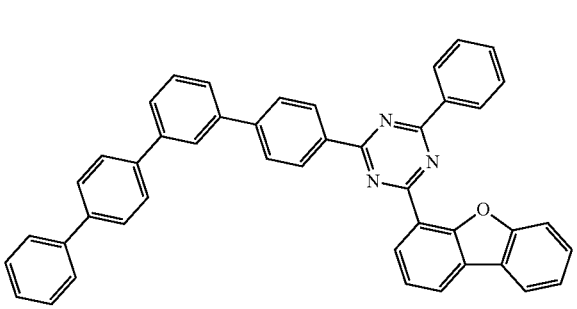

359
-continued
360
-continued
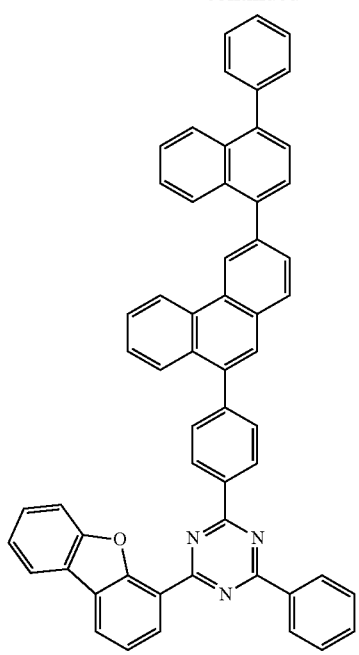
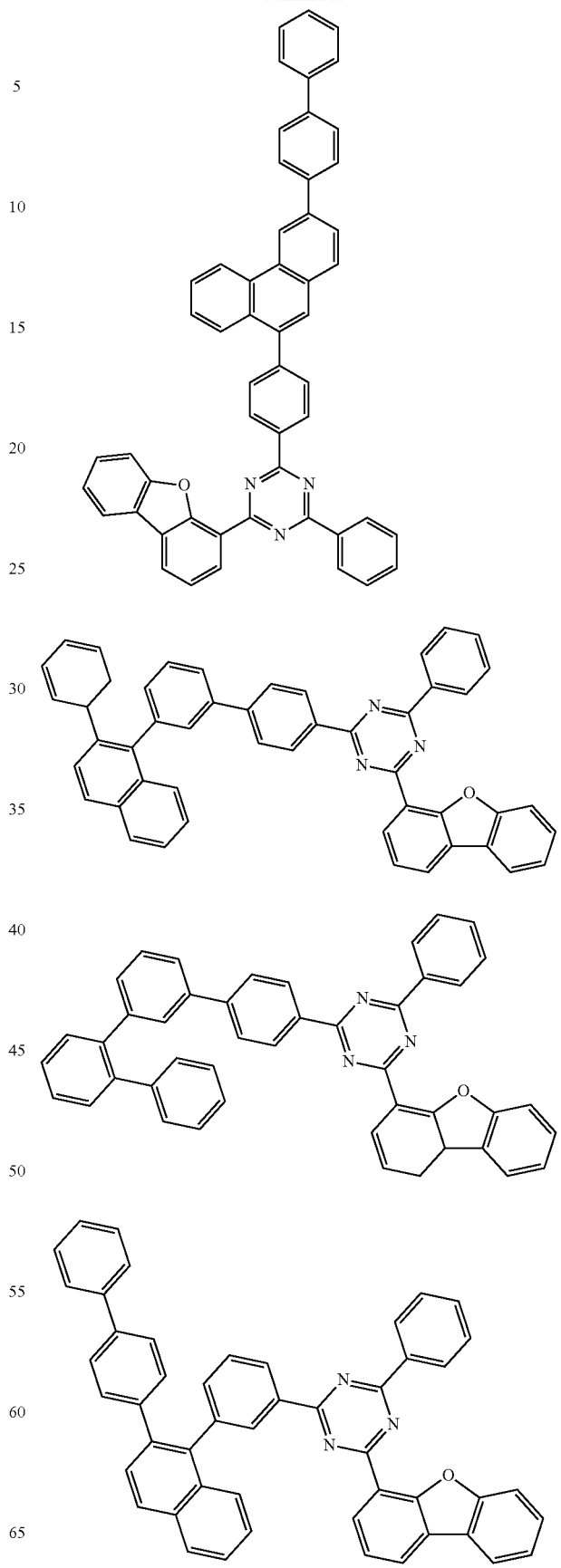

361
-continued
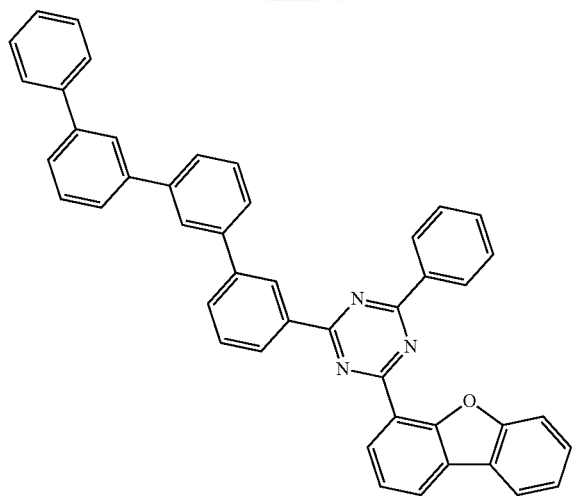
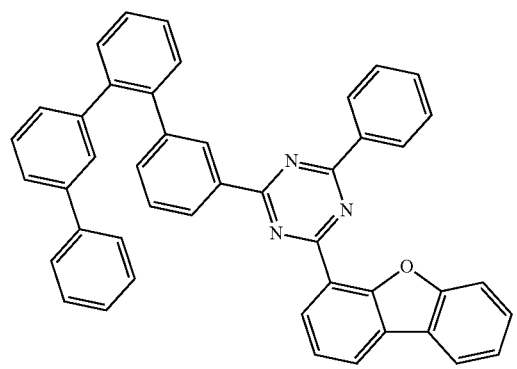
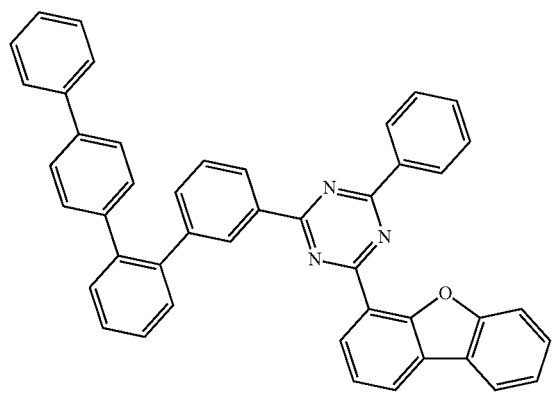
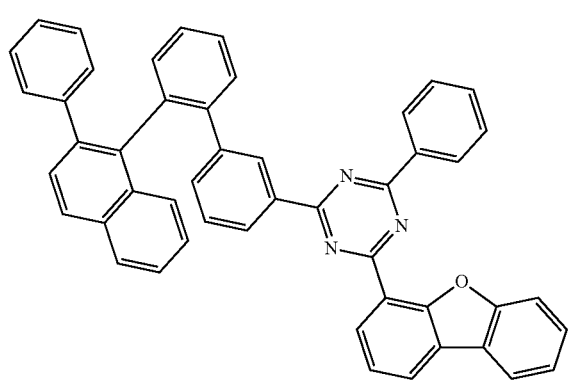
362
-continued
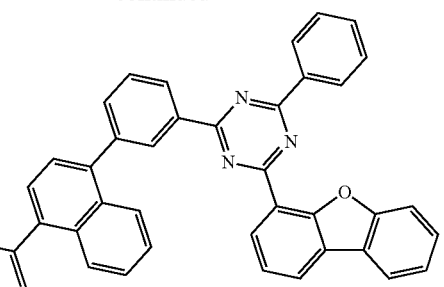
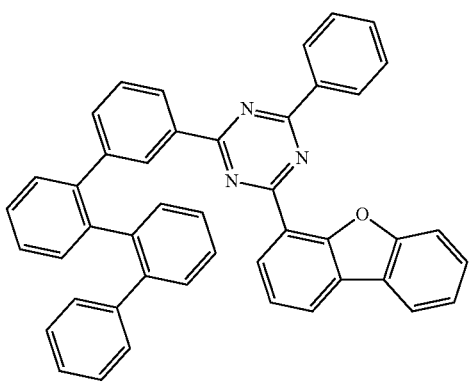
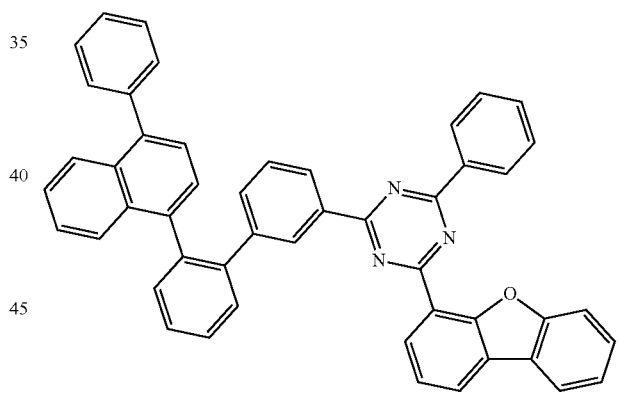
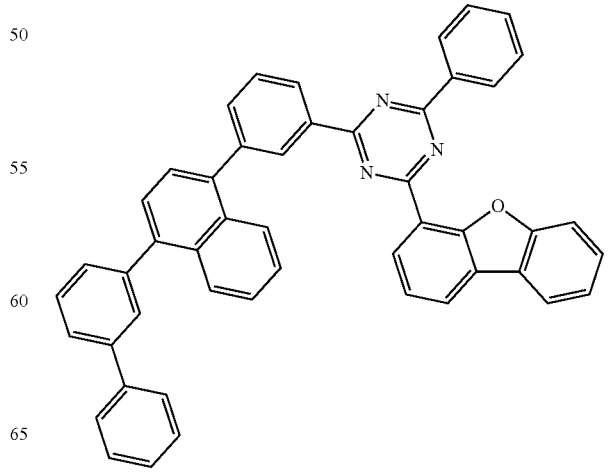

363
-continued
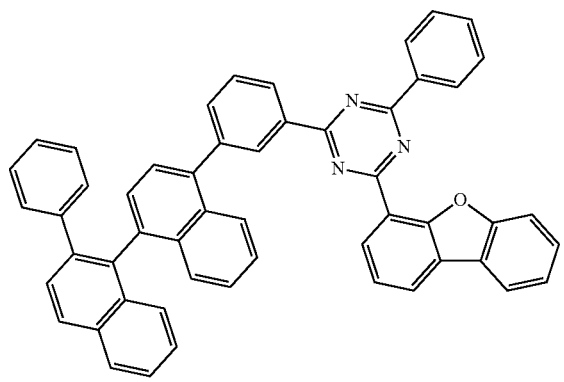
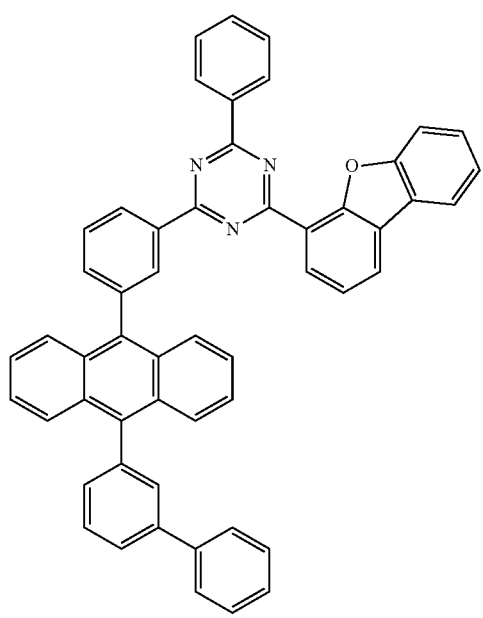
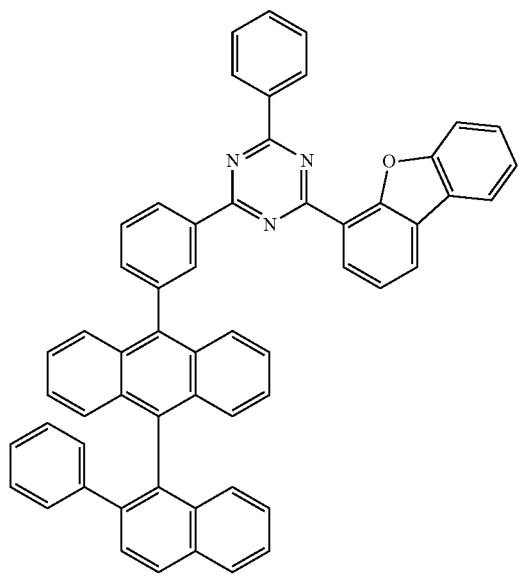
364
-continued
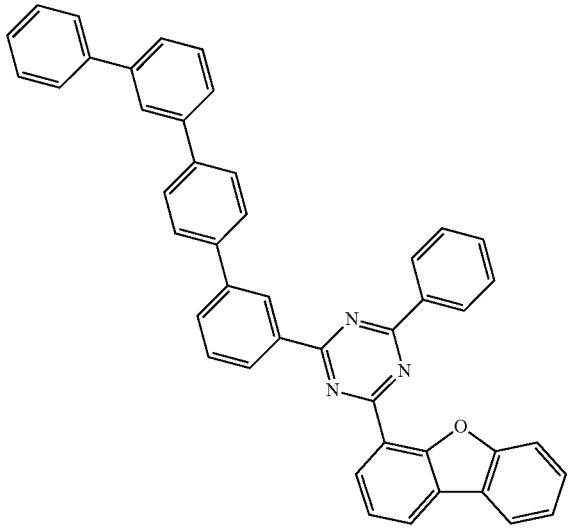
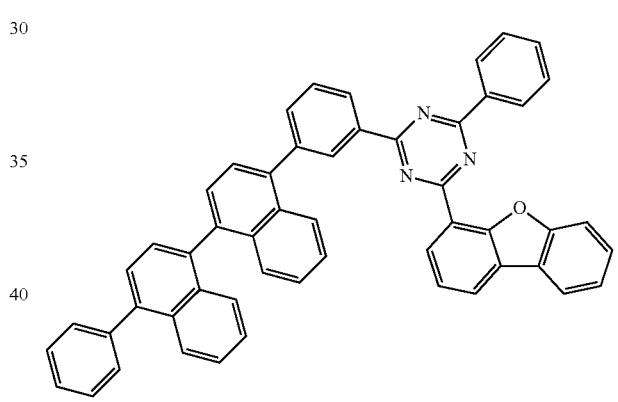
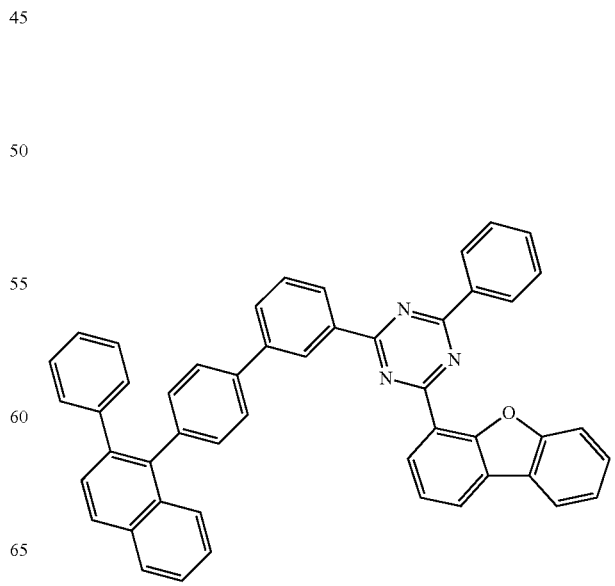

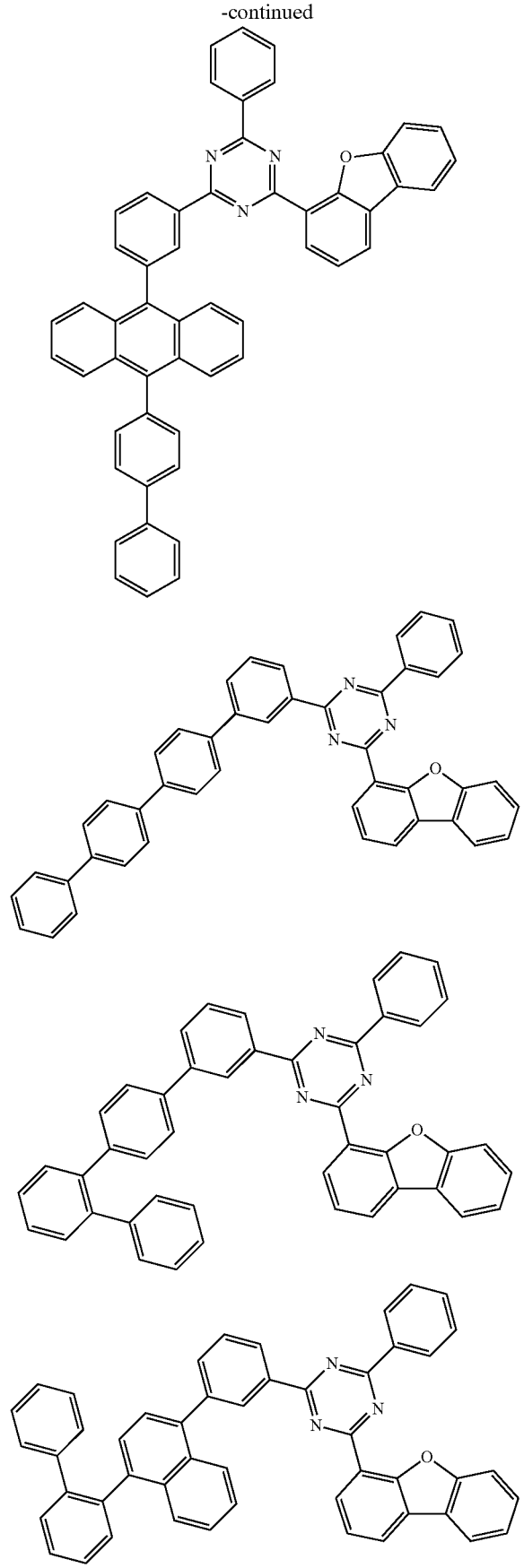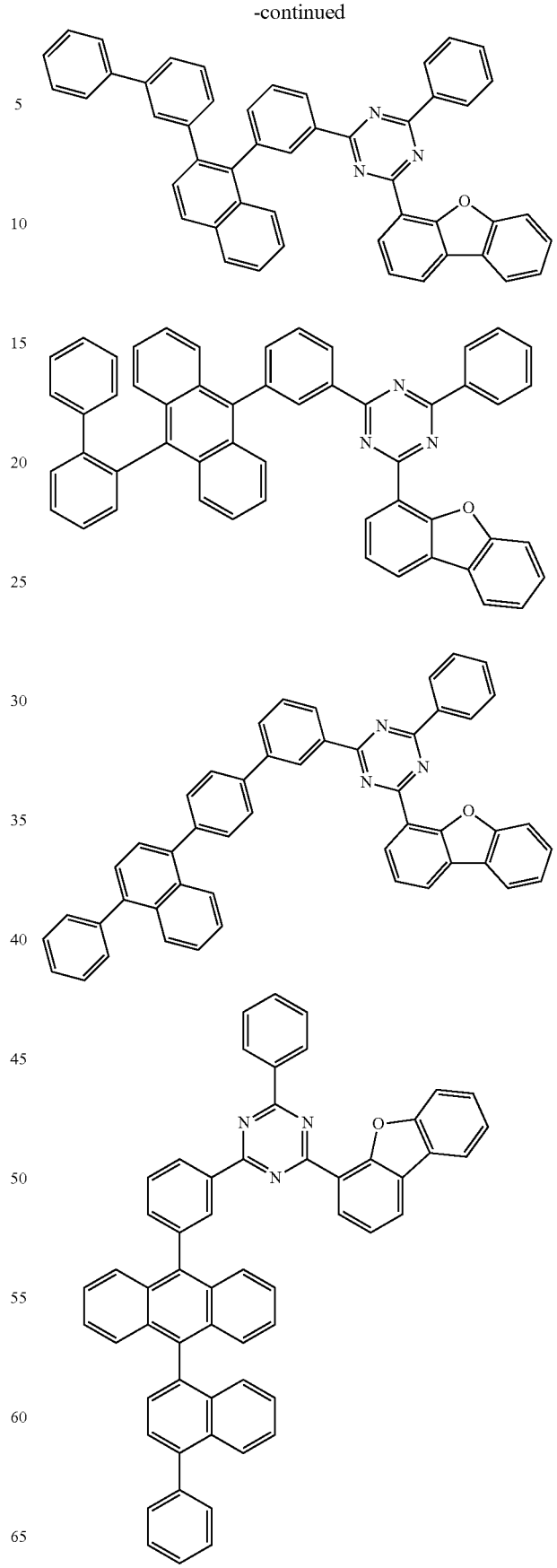

367
-continued
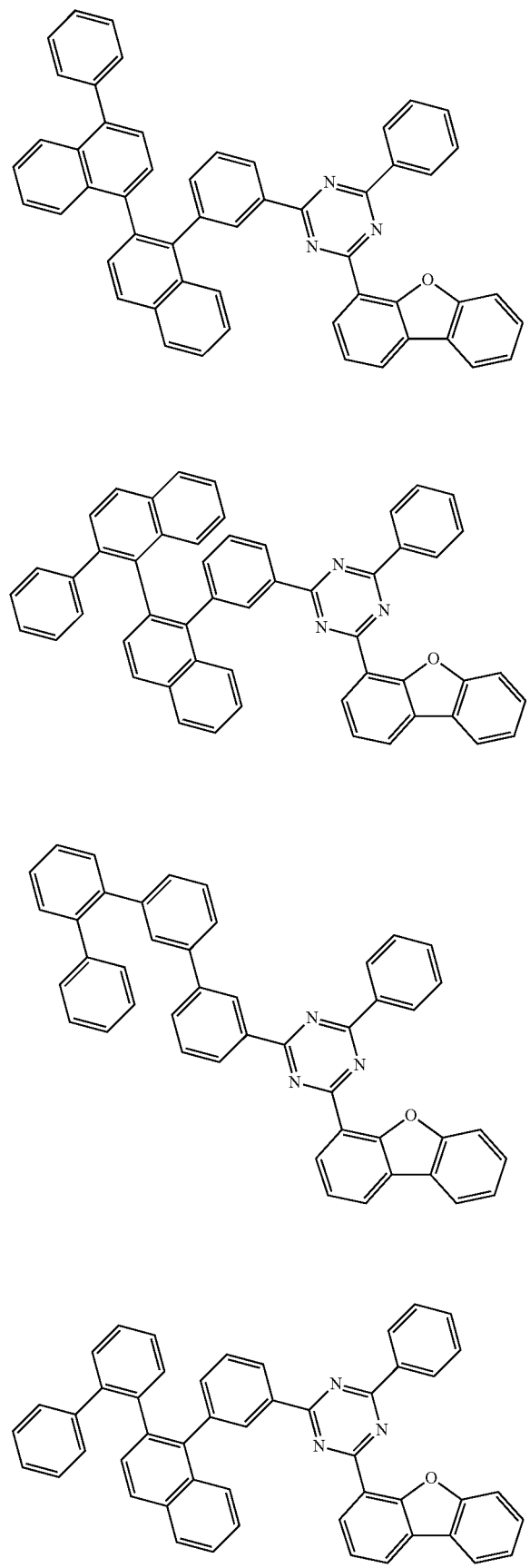
368
-continued
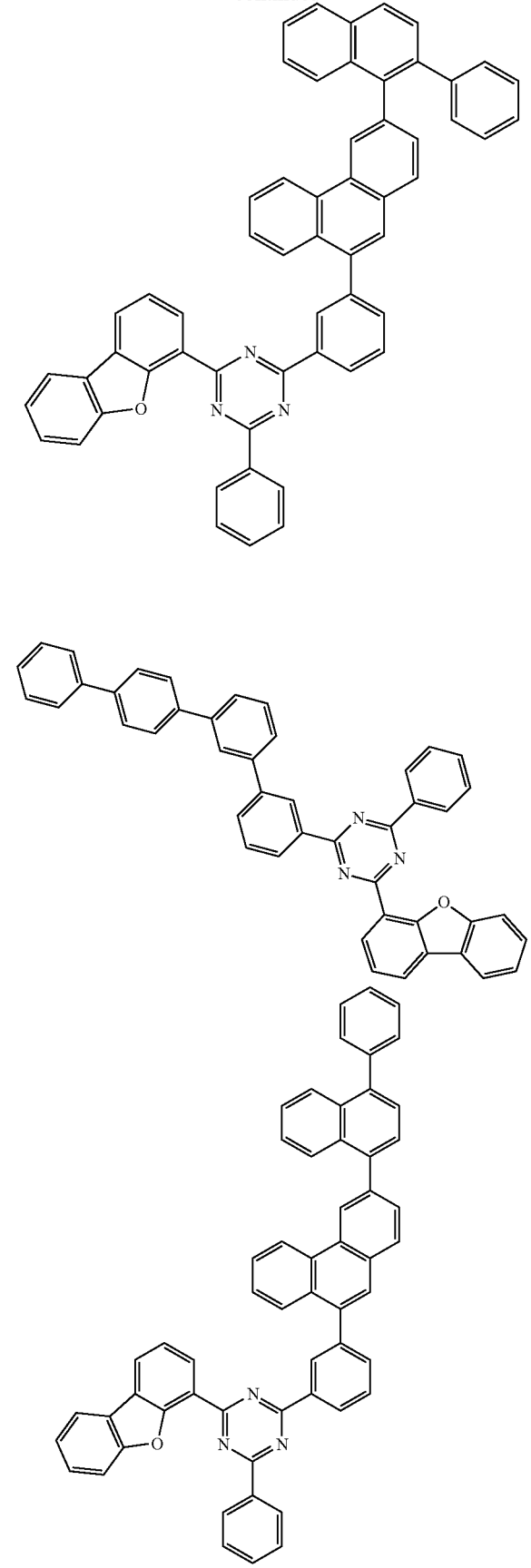

369
-continued
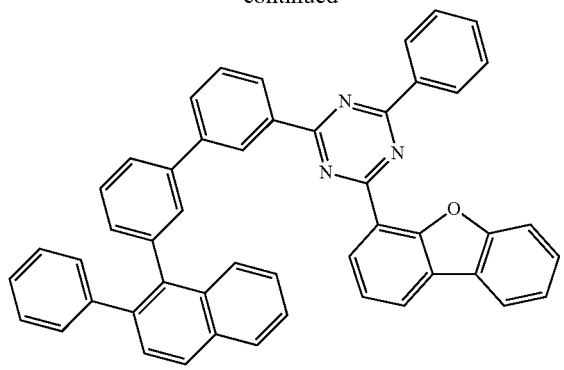
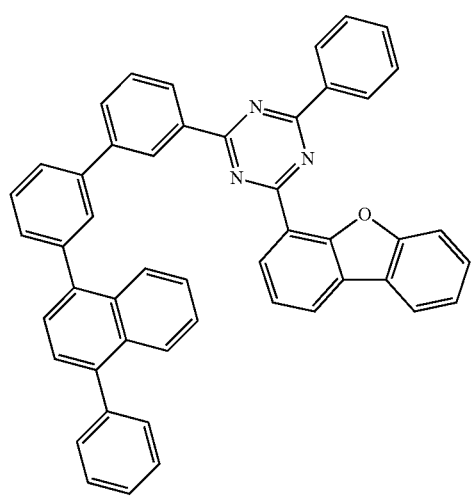
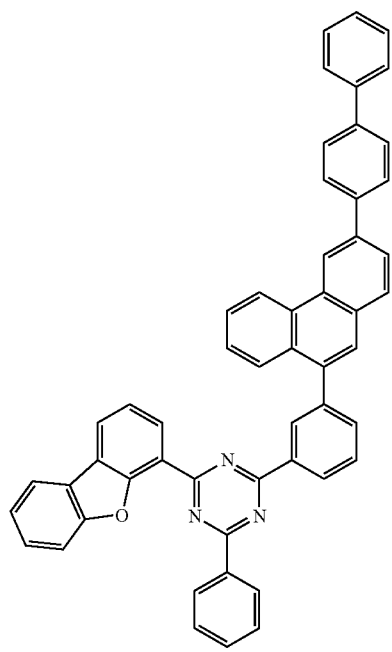
370
-continued
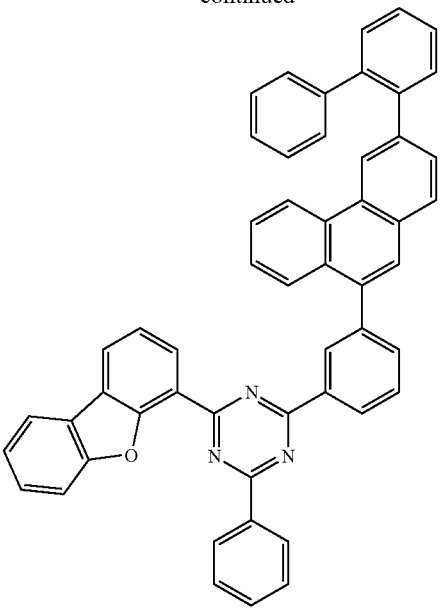
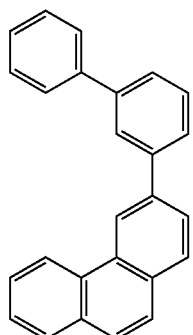
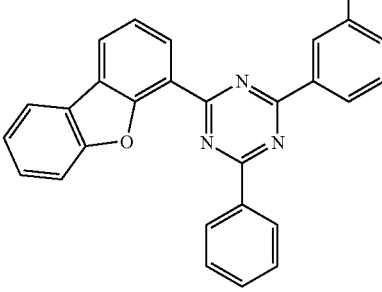
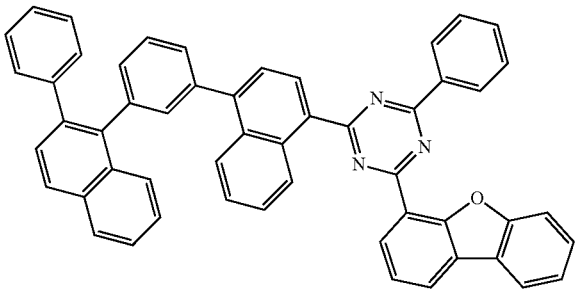

371
-continued
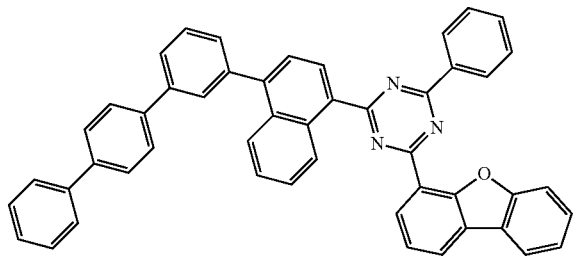
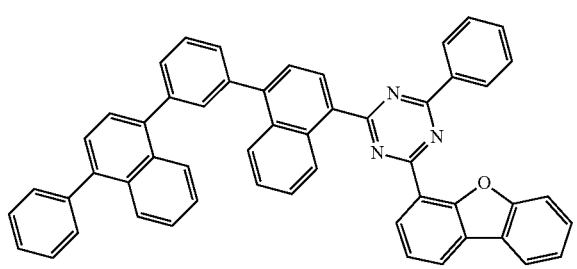
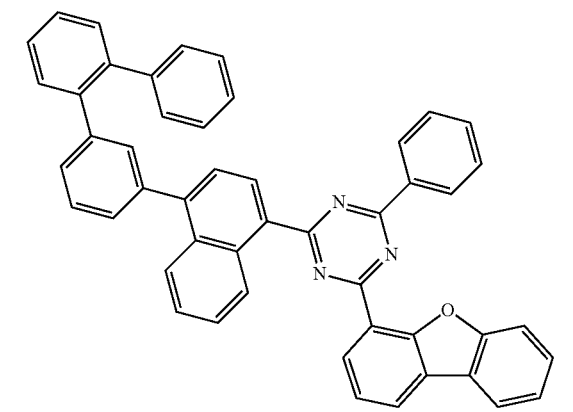
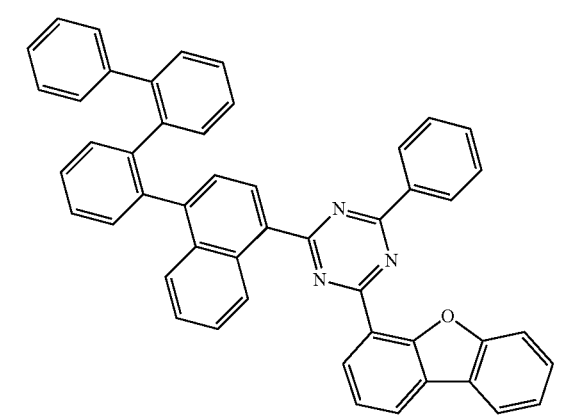
372
-continued
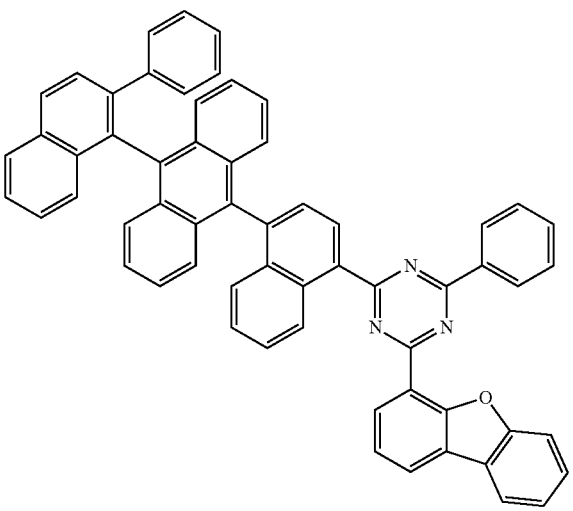
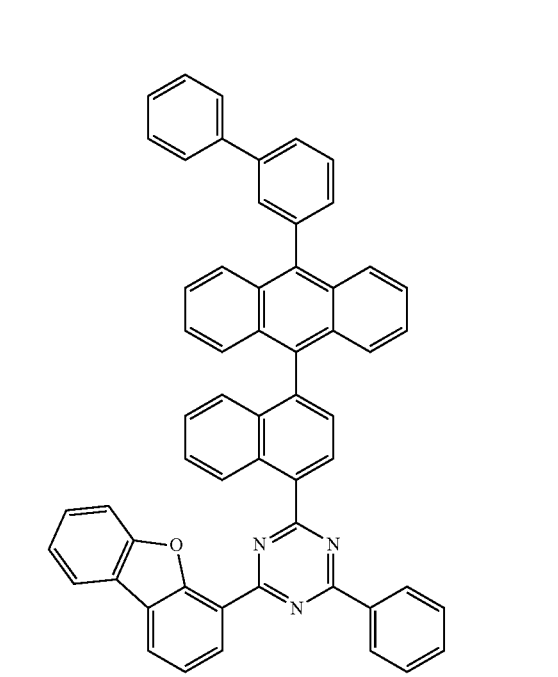

373
-continued
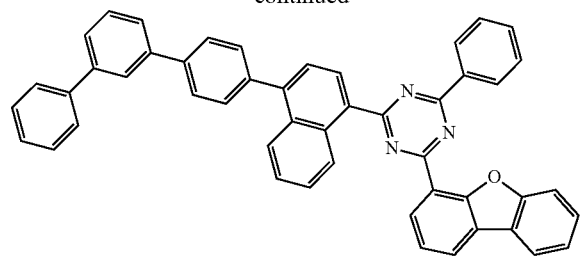
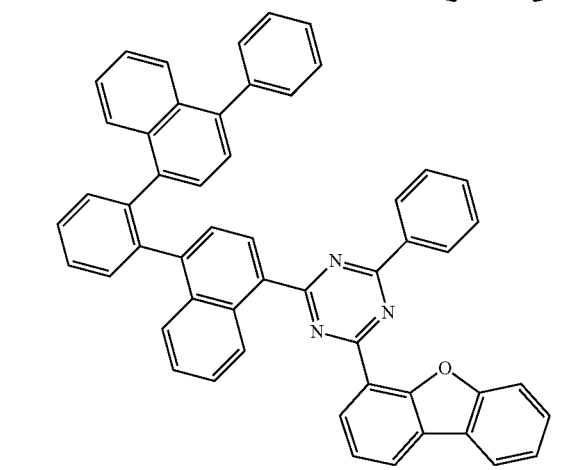
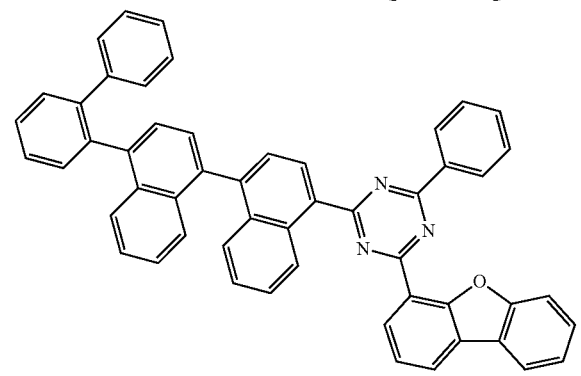
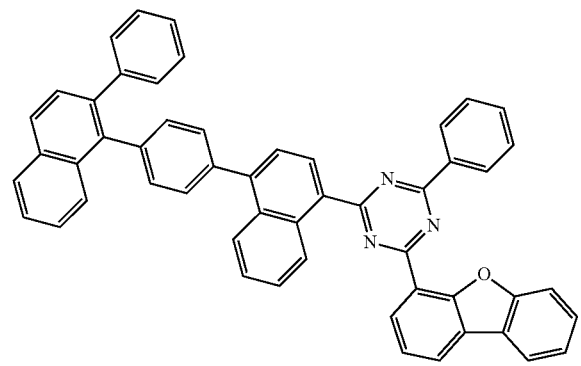
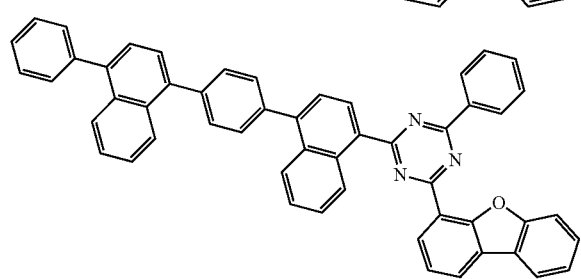
374
-continued
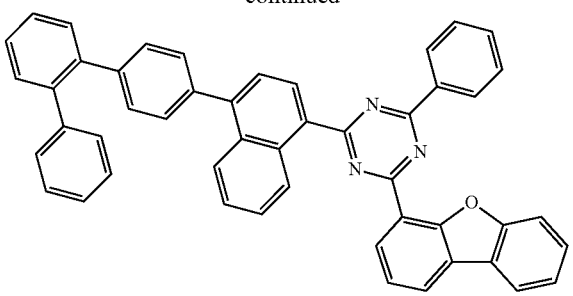
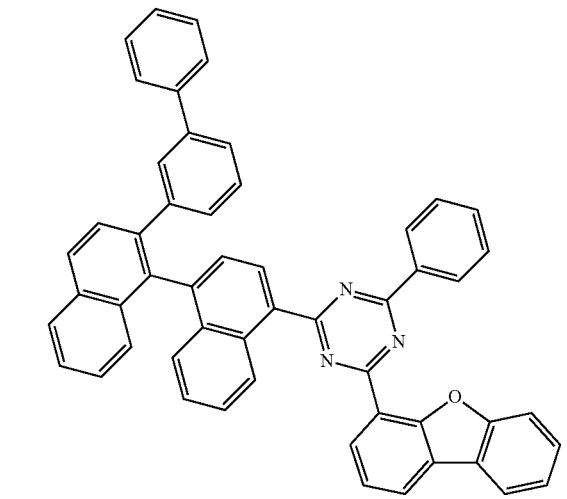
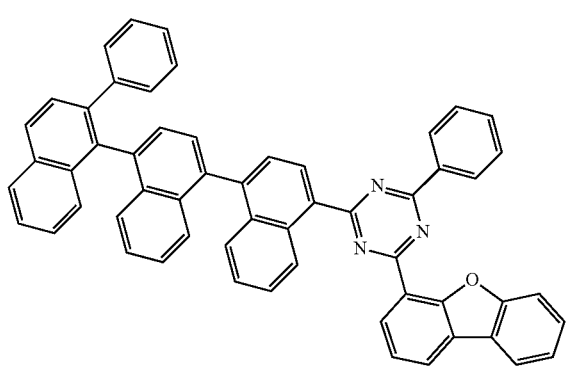
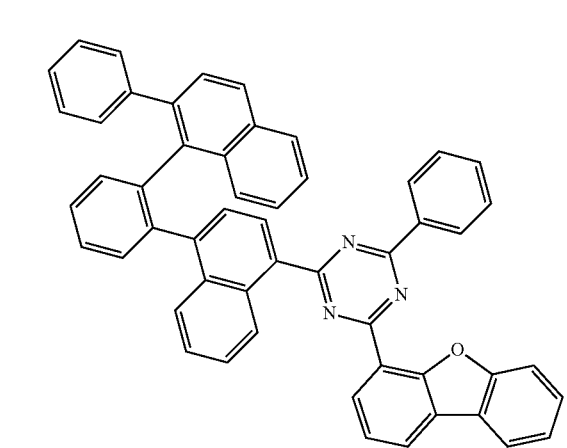

375
-continued
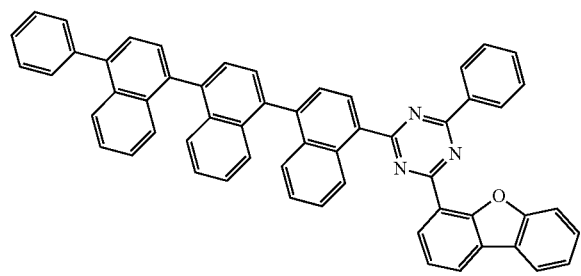
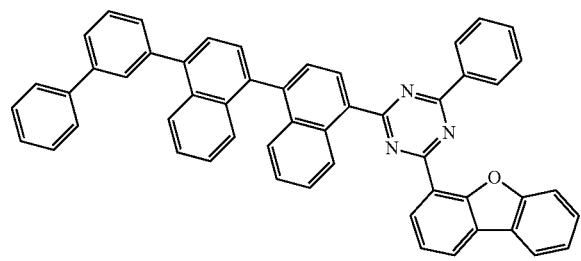
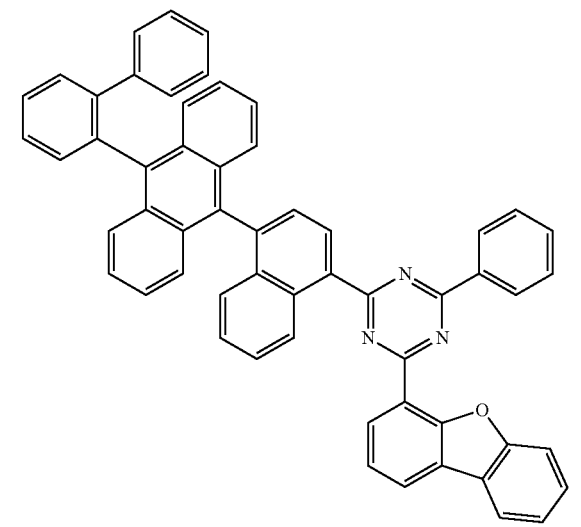
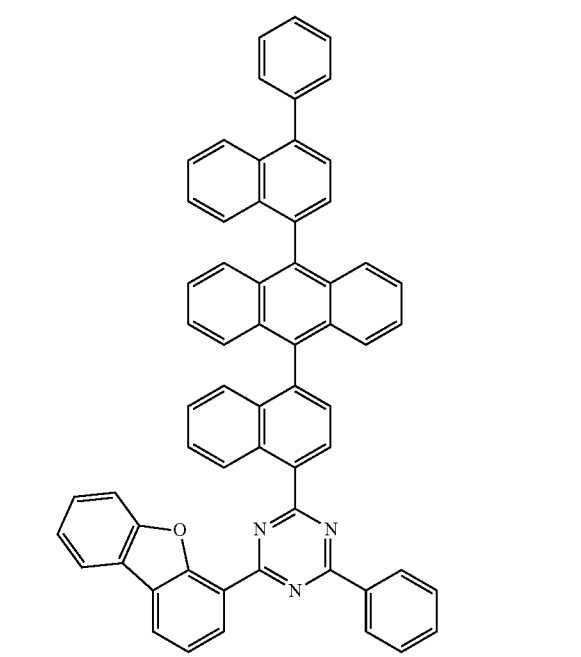
376
-continued
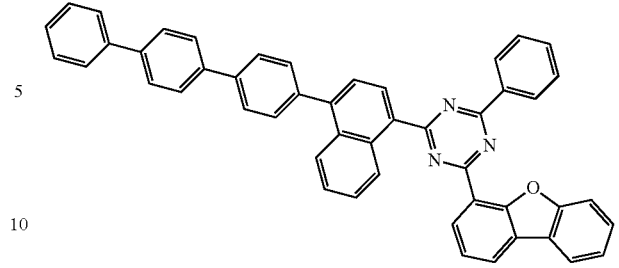
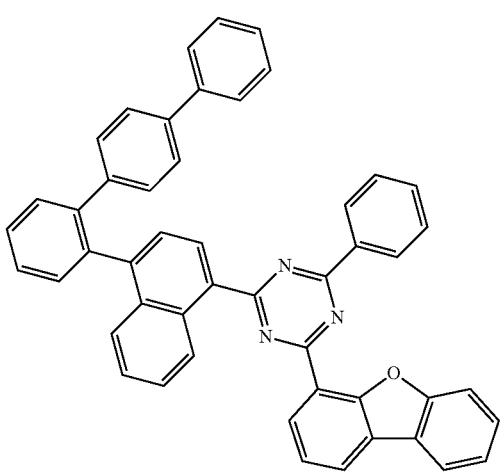
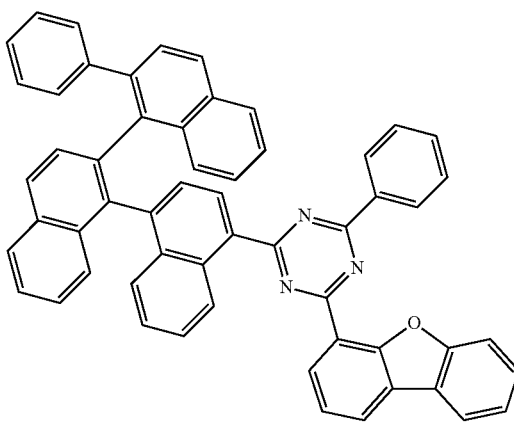

377
-continued
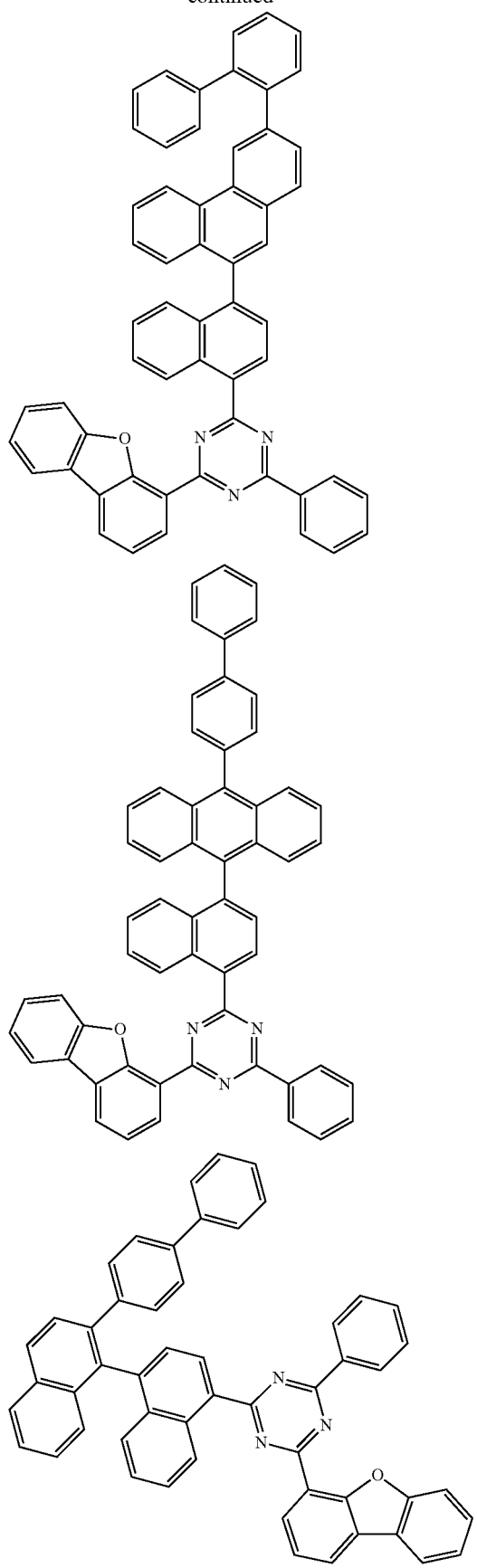
378
-continued
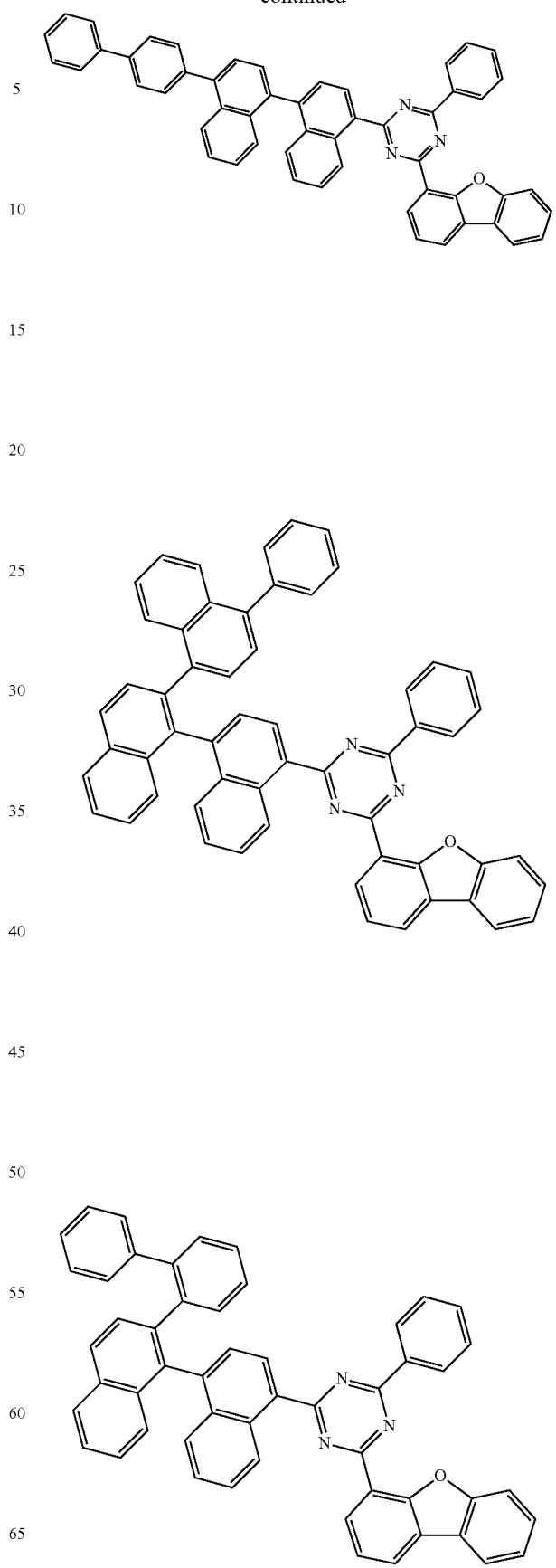

379
-continued
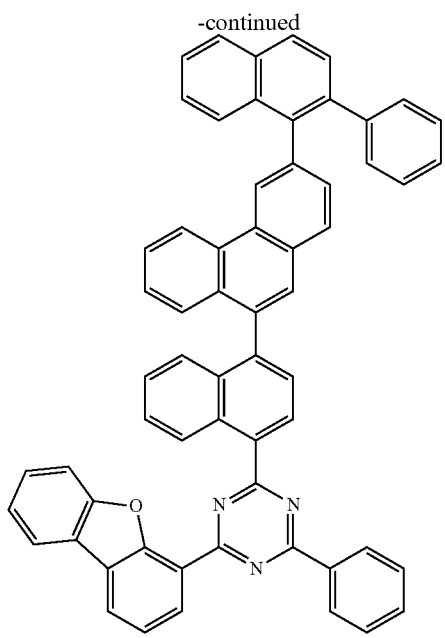
380
-continued
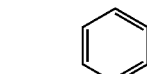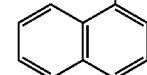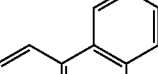
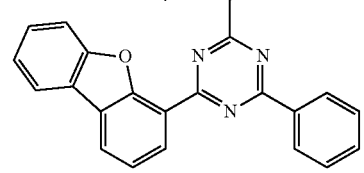
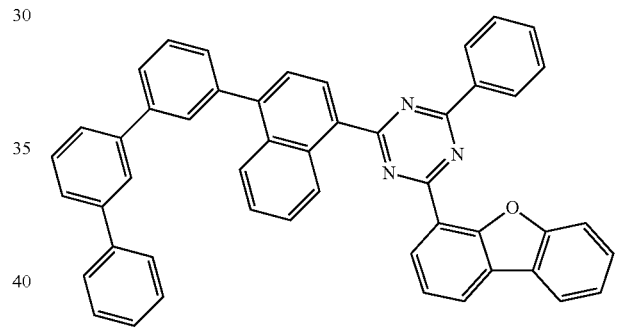
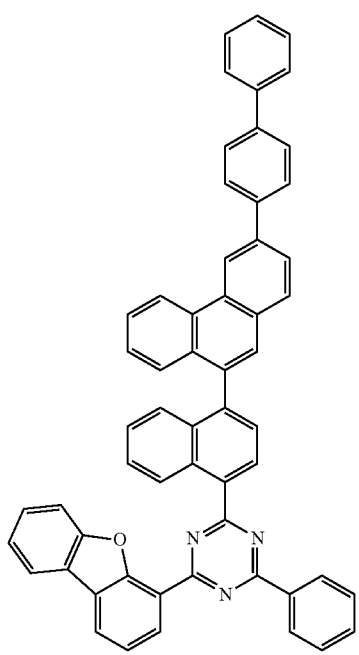
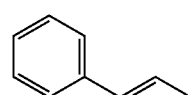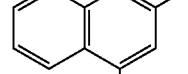
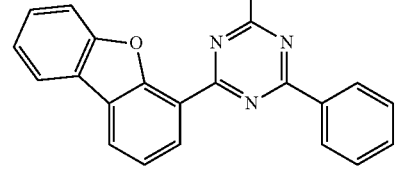

381
-continued
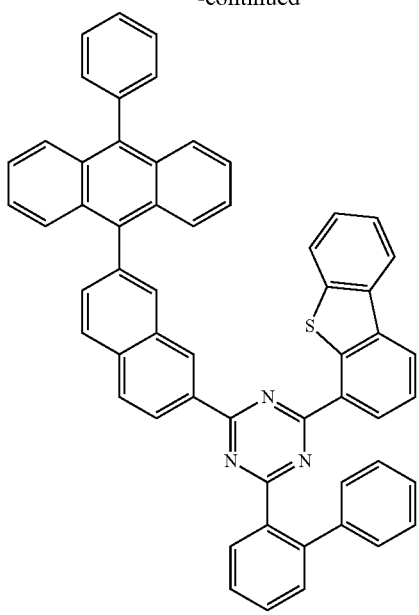
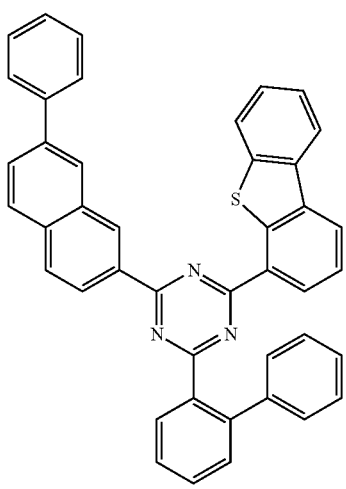
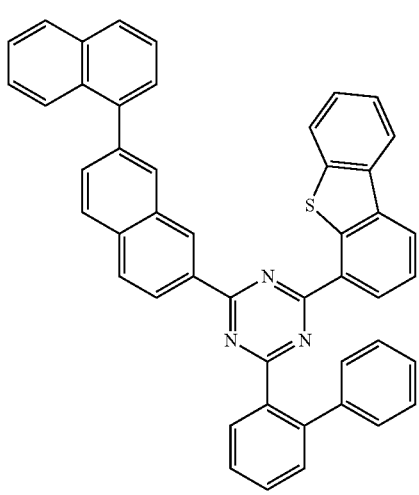
382
-continued
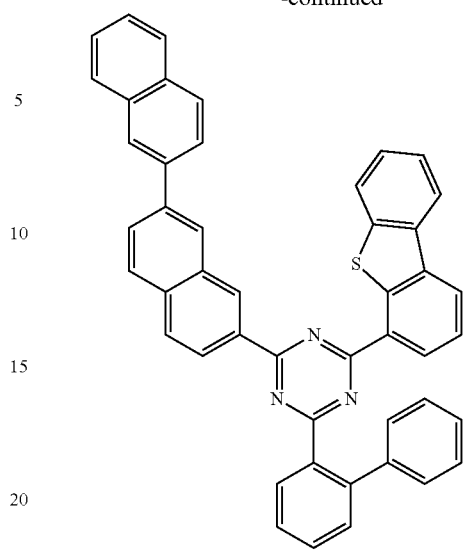
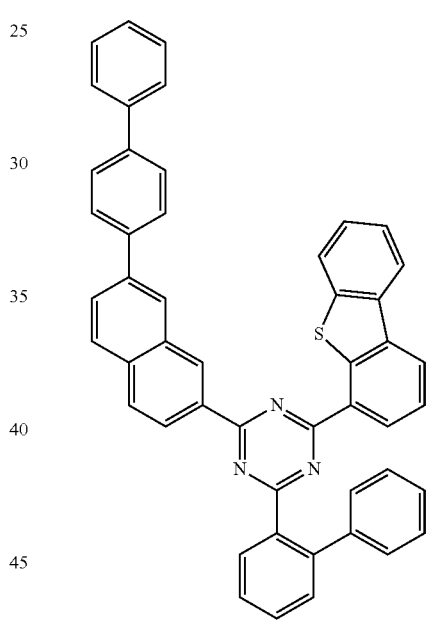

383
-continued
384
-continued
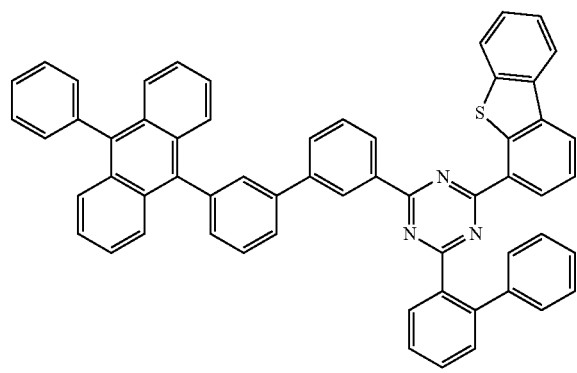
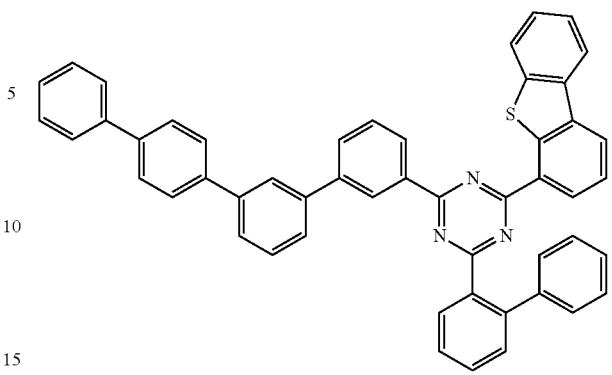
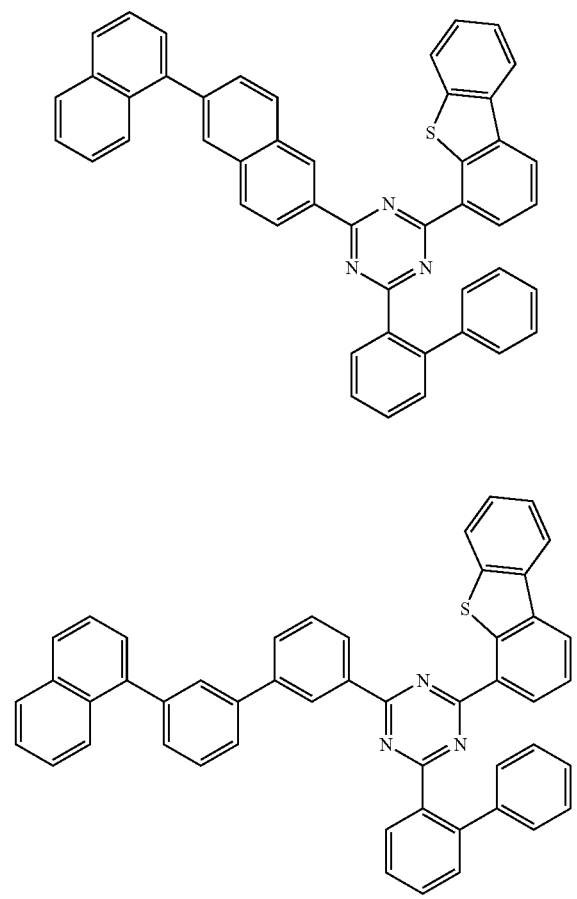
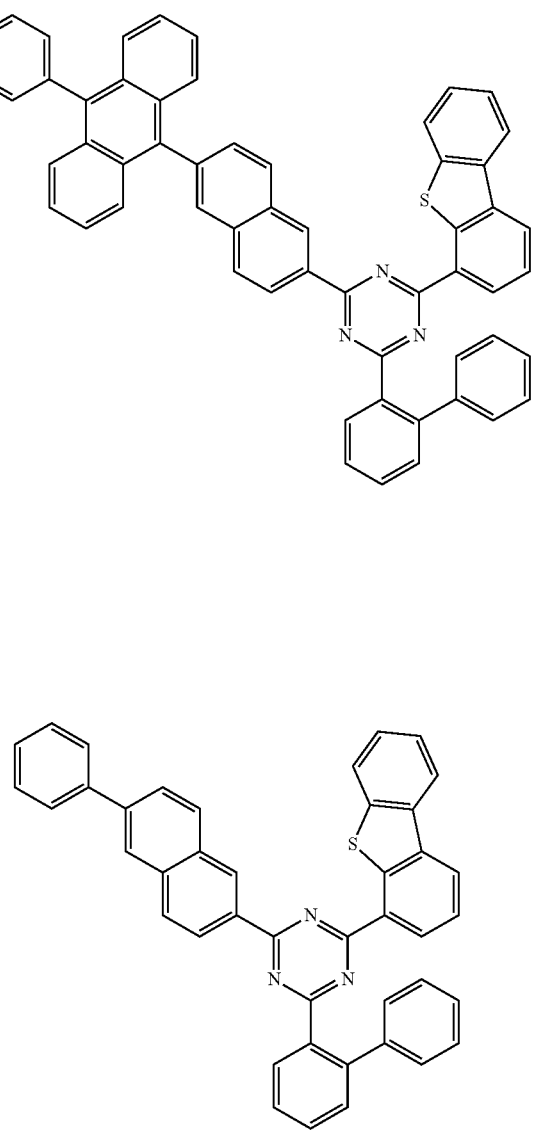
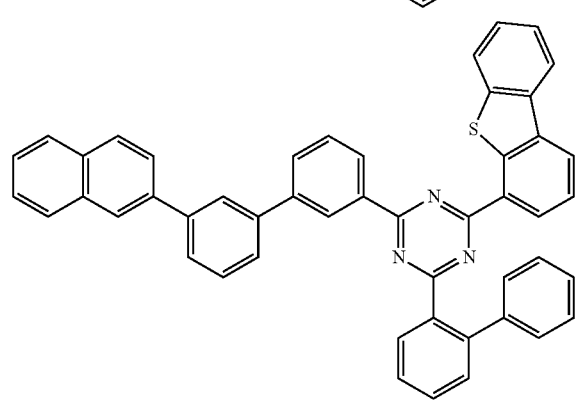

385
-continued
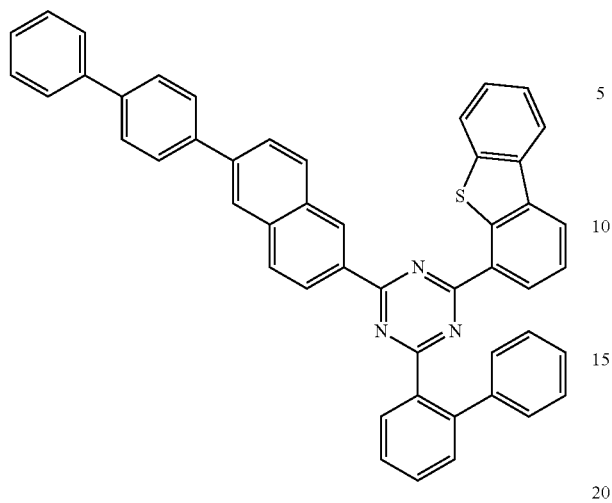
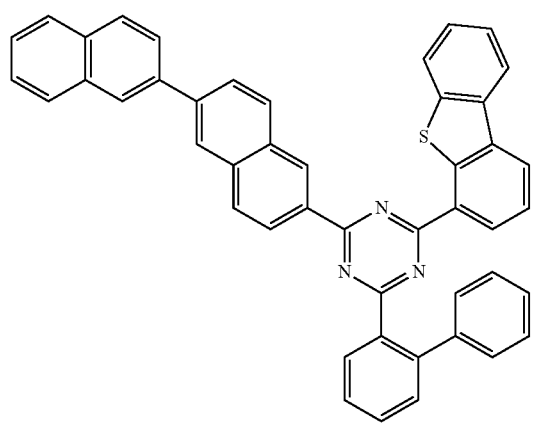
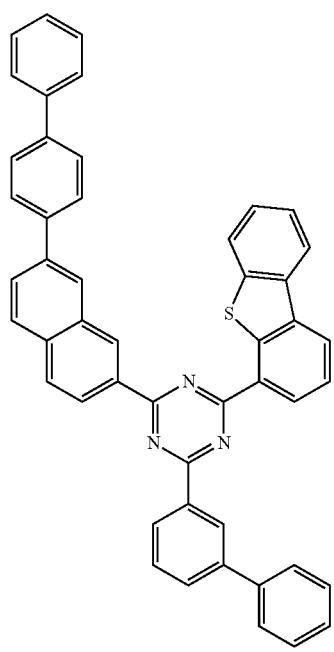
386
-continued
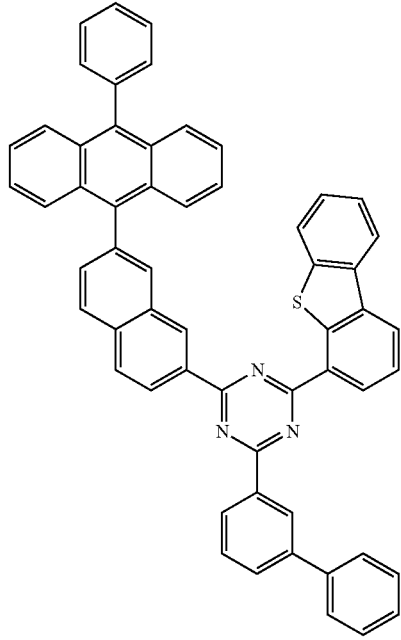
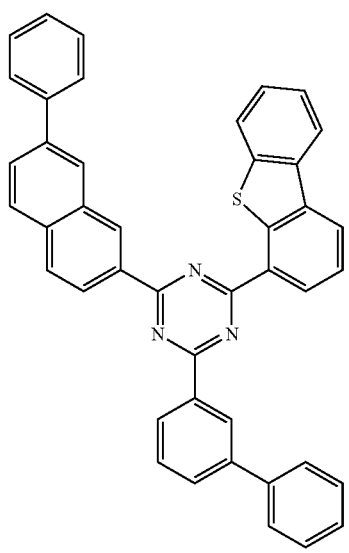
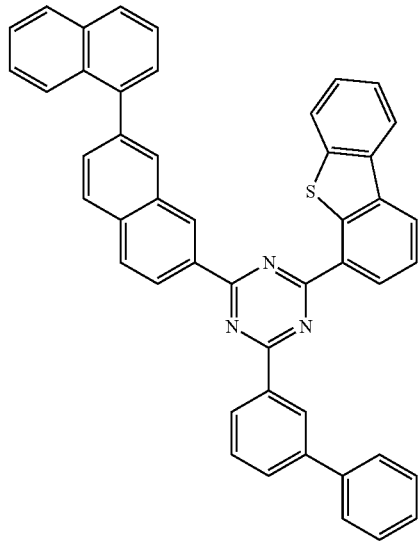

387
-continued
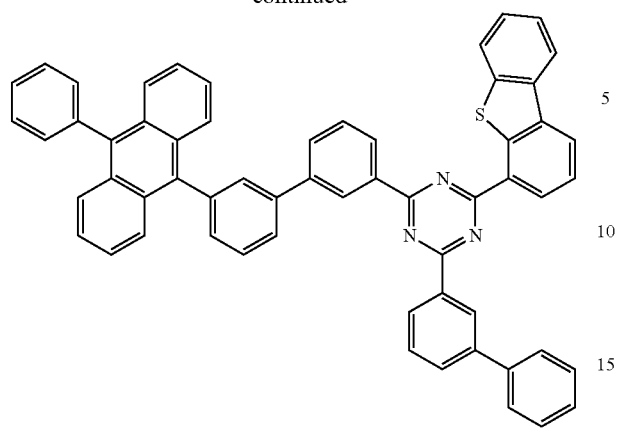
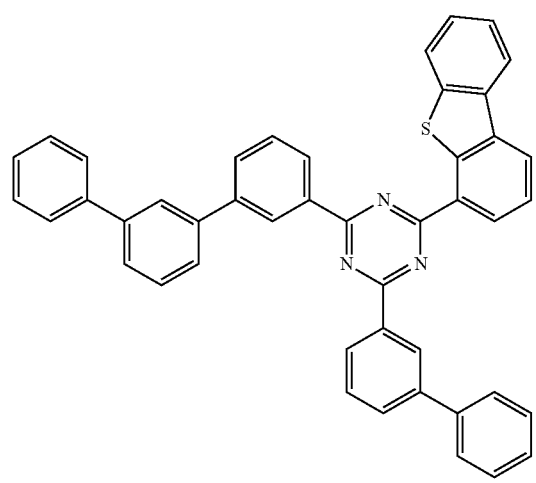
388
-continued
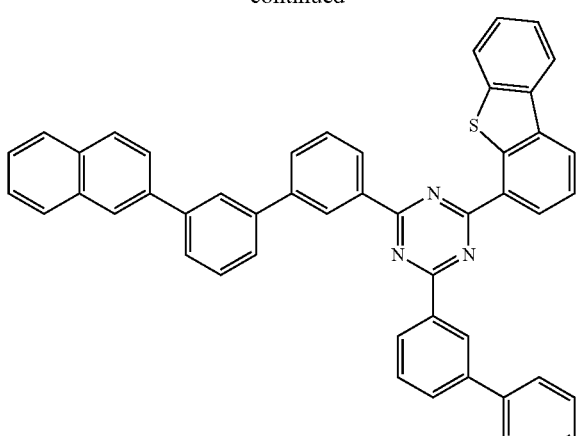
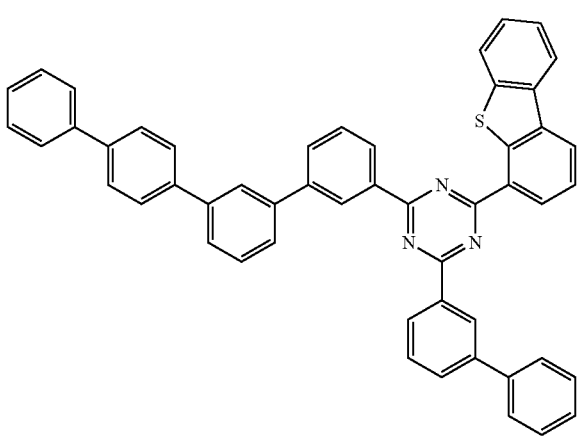
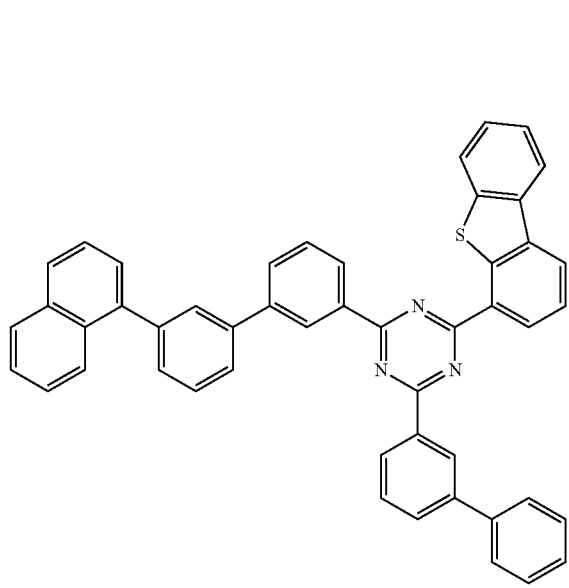
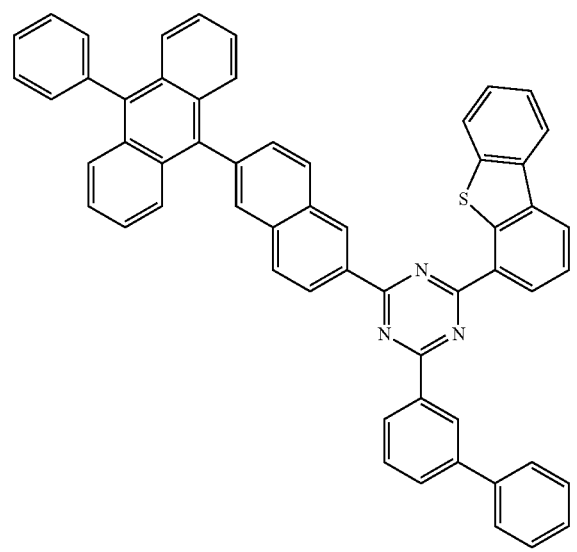

389
-continued
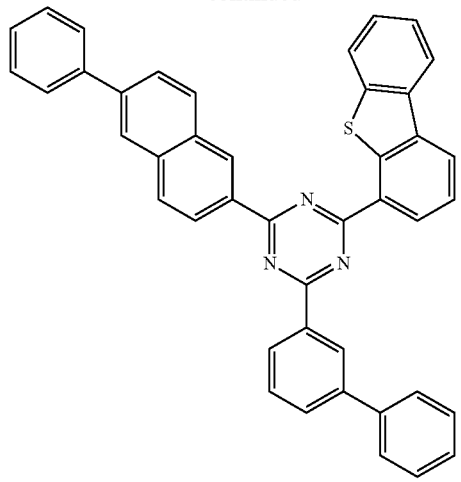
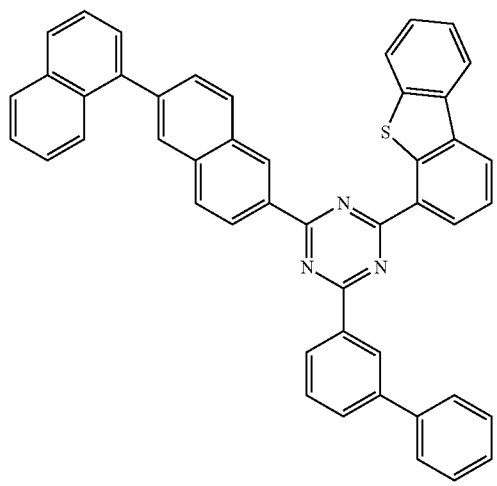
390
-continued
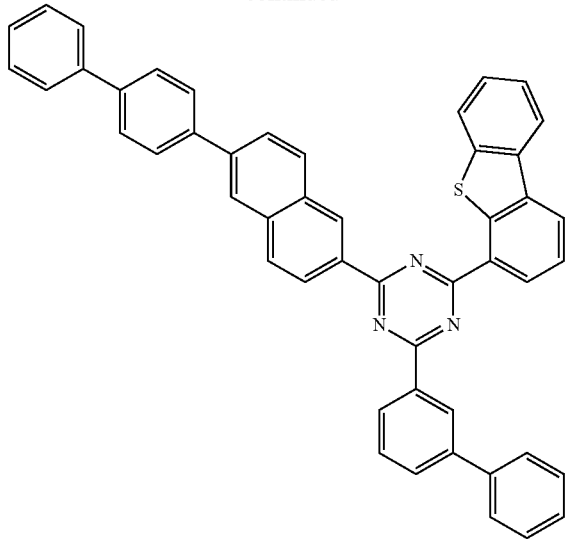
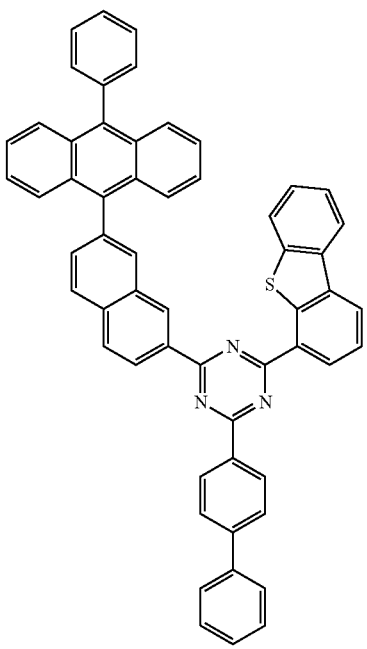

391
-continued
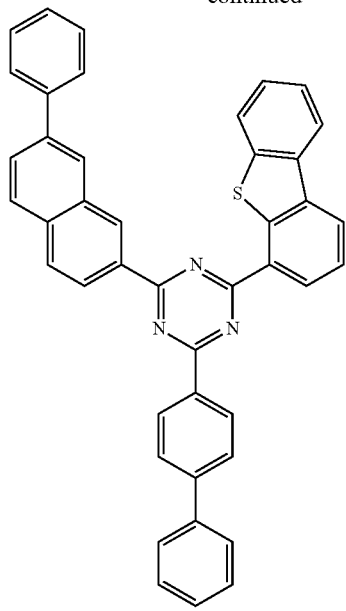
392
-continued
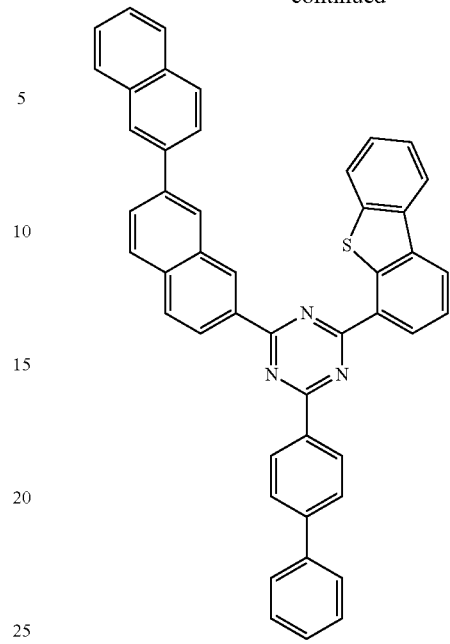
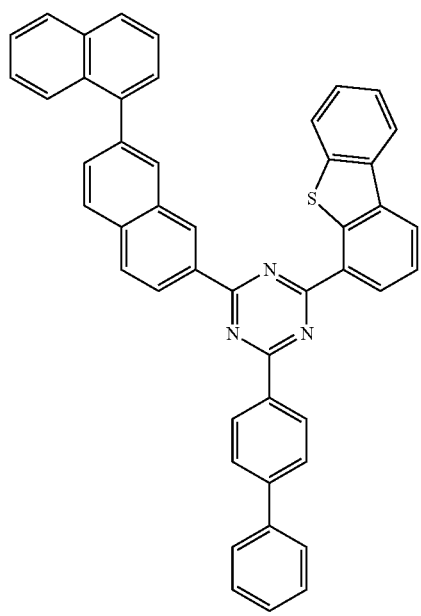
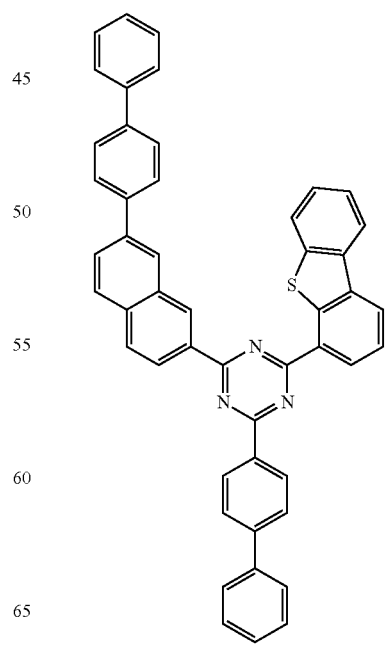

393
-continued
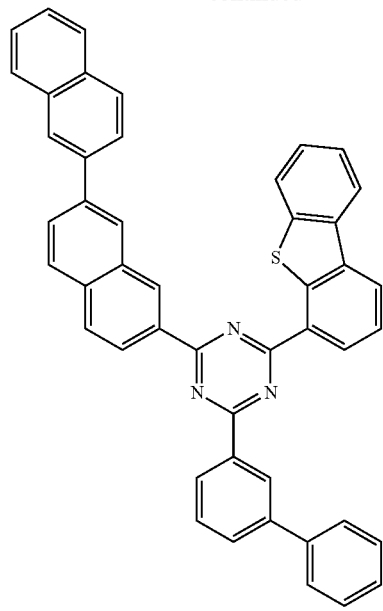
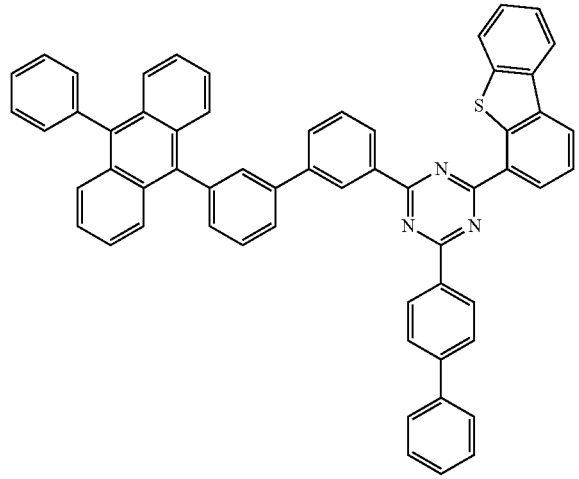
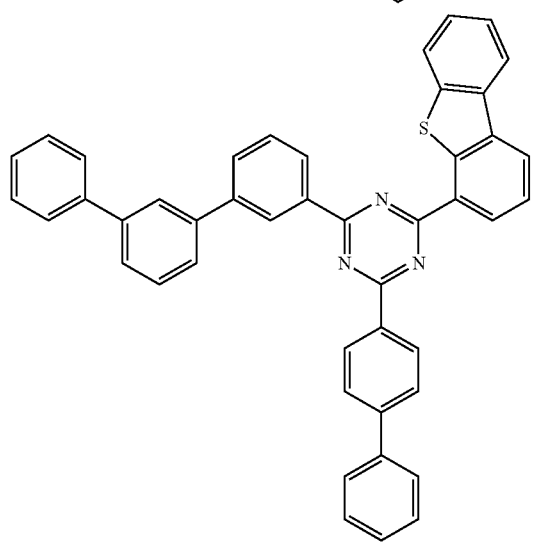
394
-continued
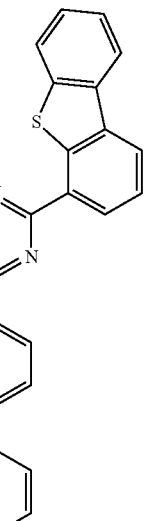
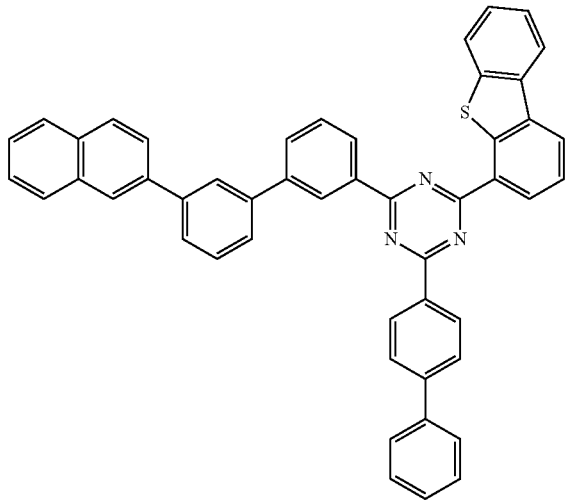
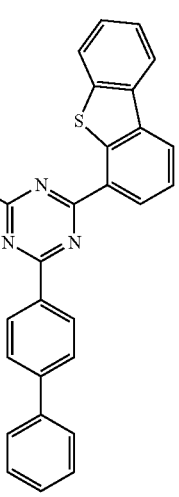

395
-continued
396
-continued
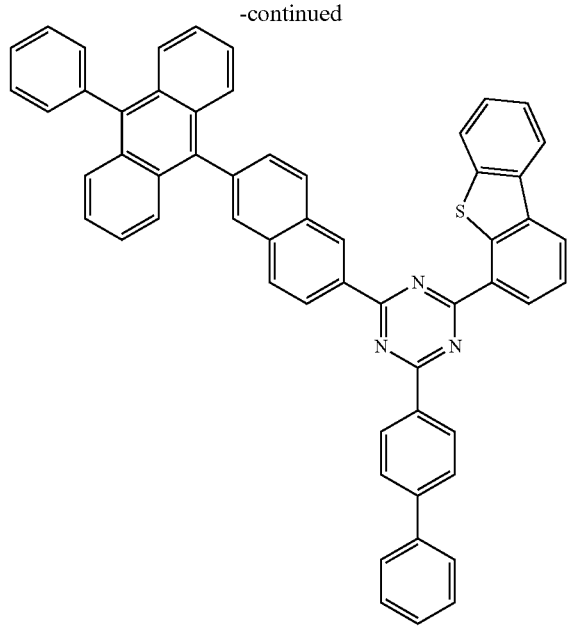
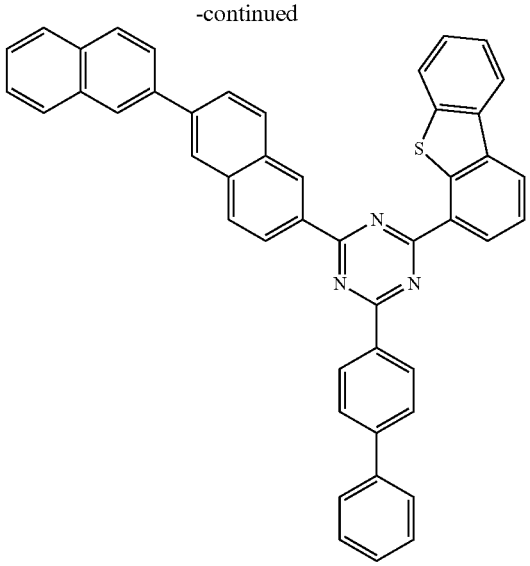
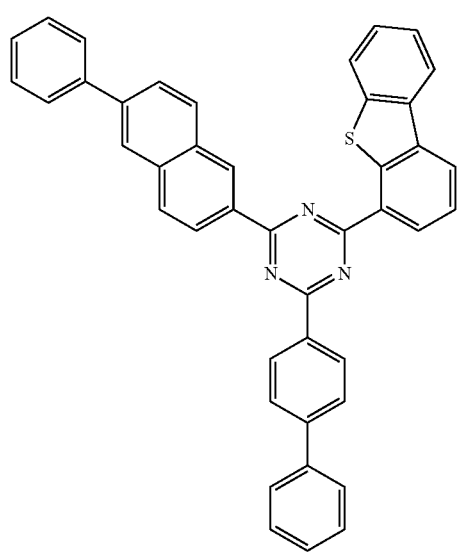
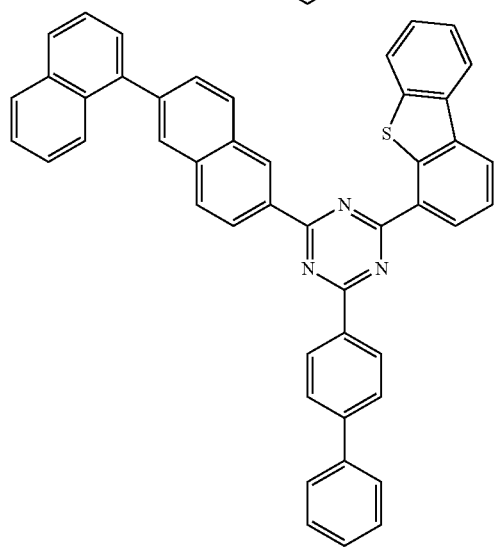

397
-continued
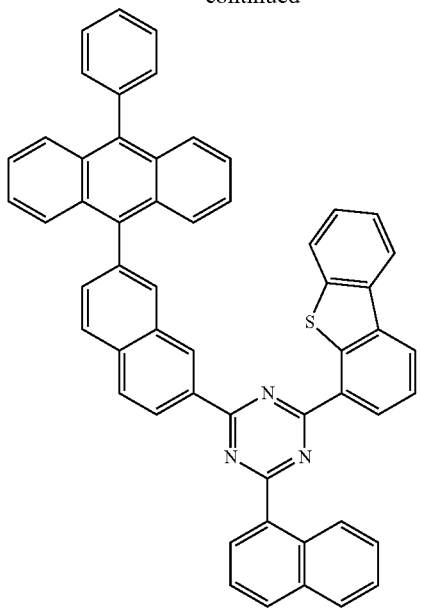
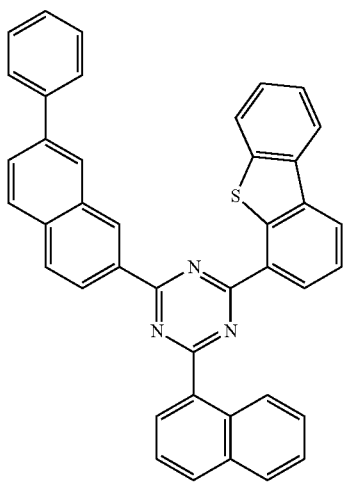
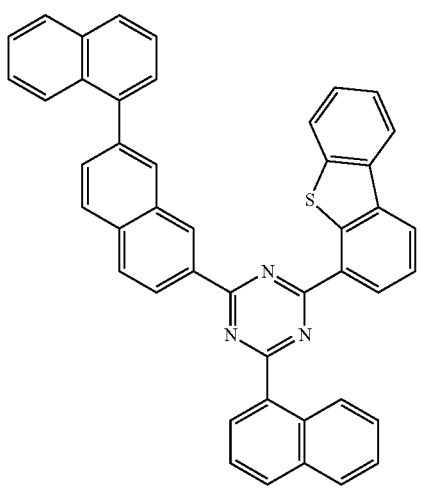
398
-continued
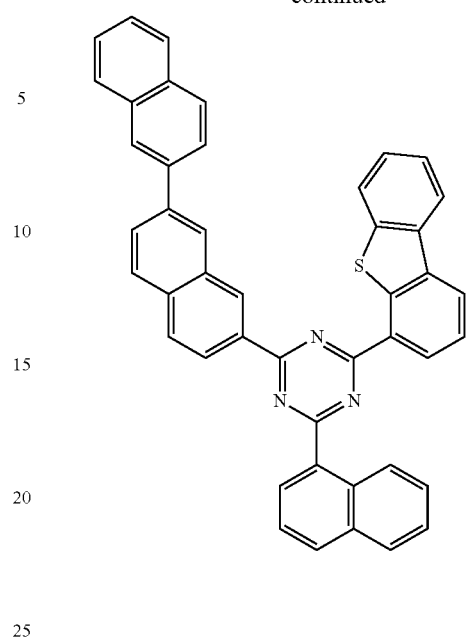
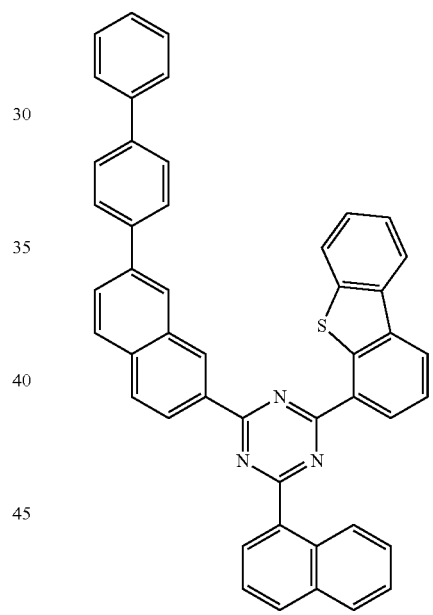
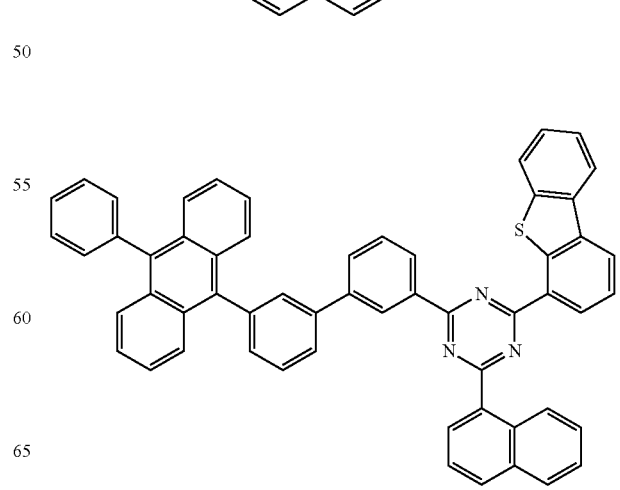

399
-continued
400
-continued
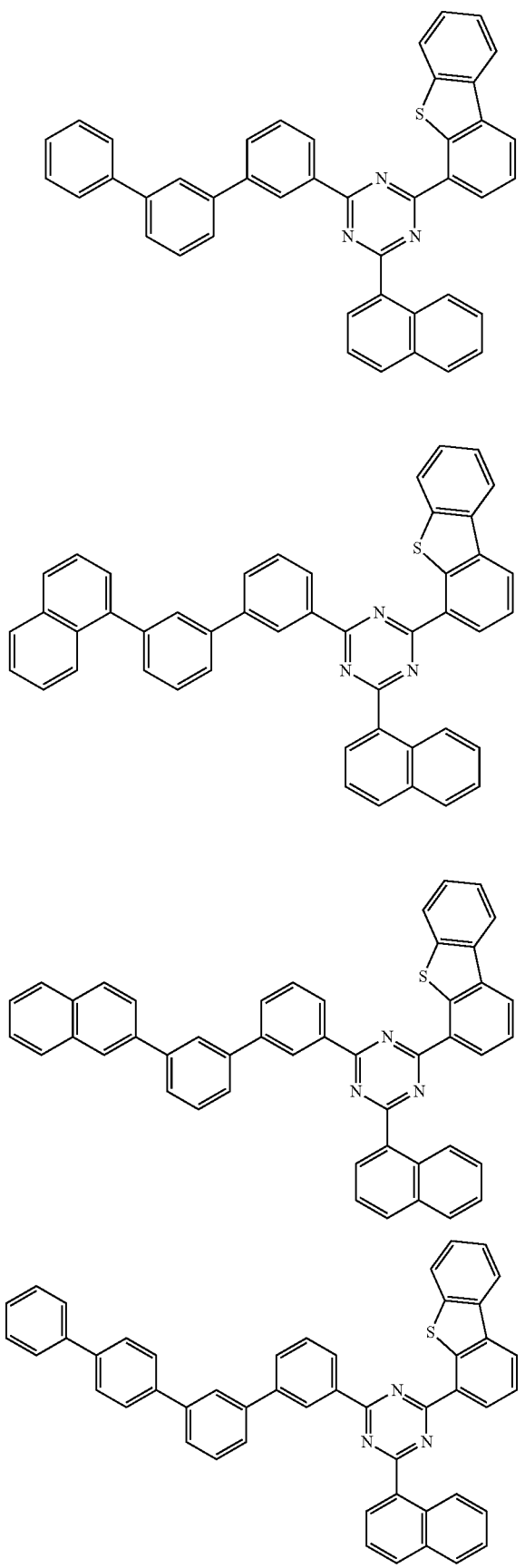
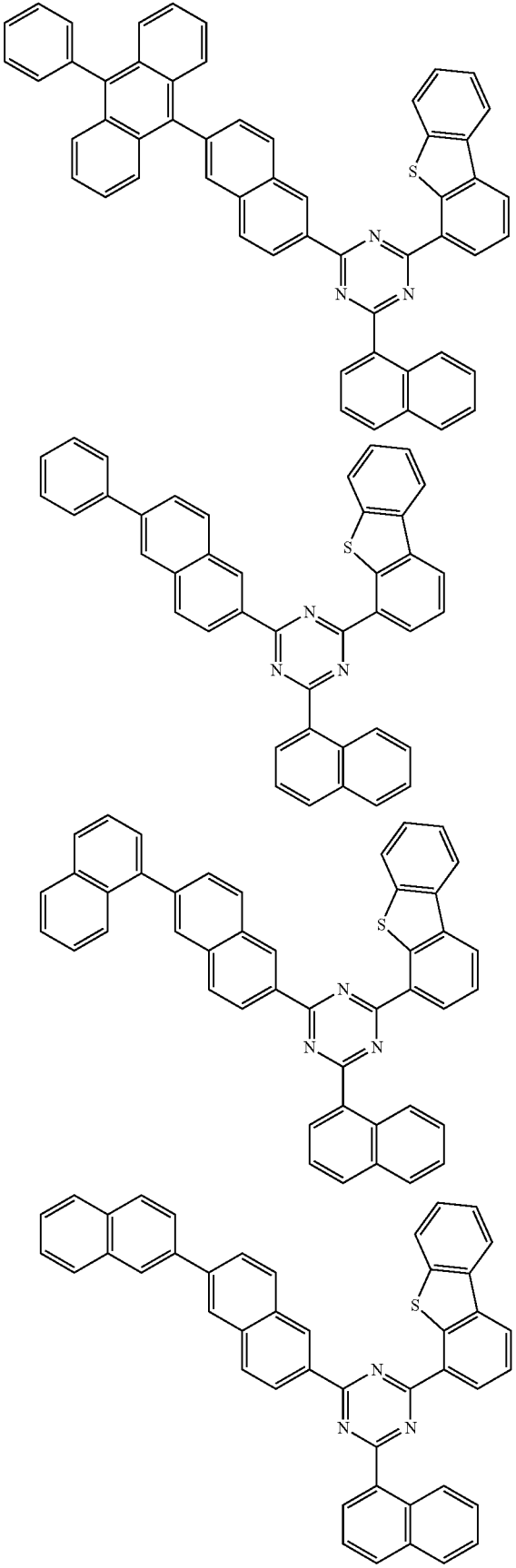

401
-continued
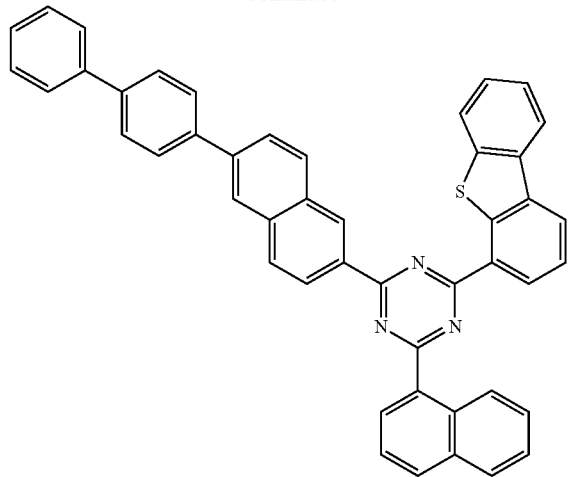 [SMILES: c1ccc(-c2ccc(-c3ccc4cc(-c5nc(-c6ccccc6)nc(-c6cccc7c6sc6ccccc67)n5)ccc4c3)cc2)cc1]
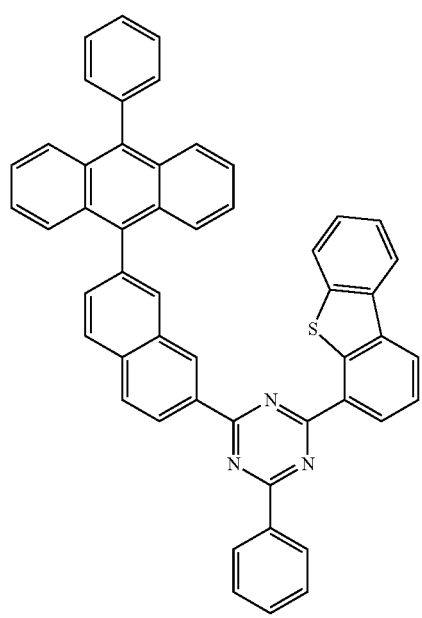
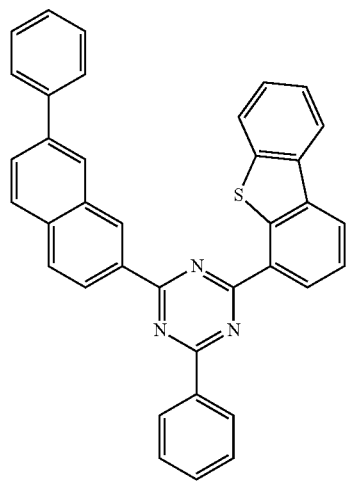
402
-continued
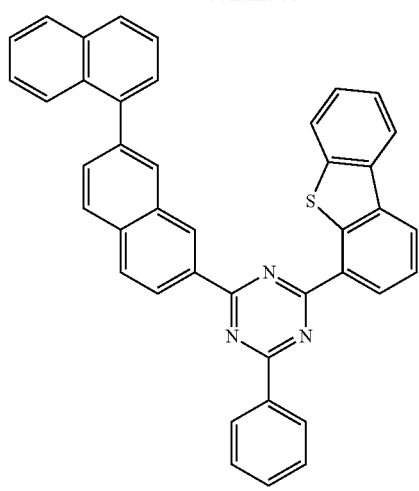
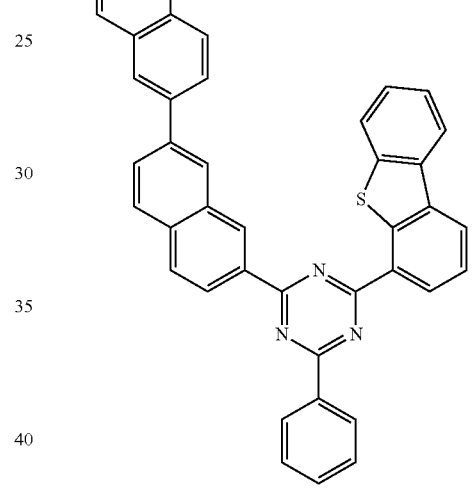
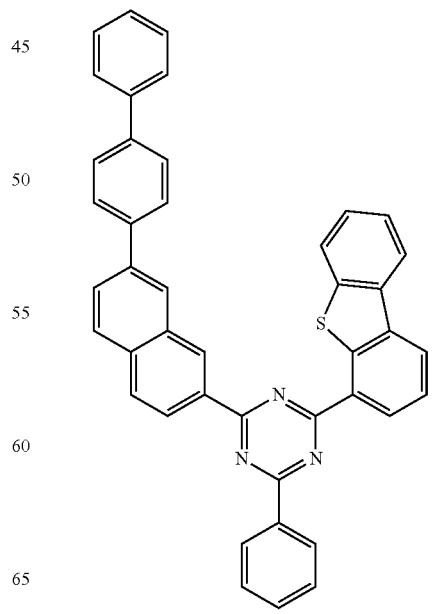

403
-continued
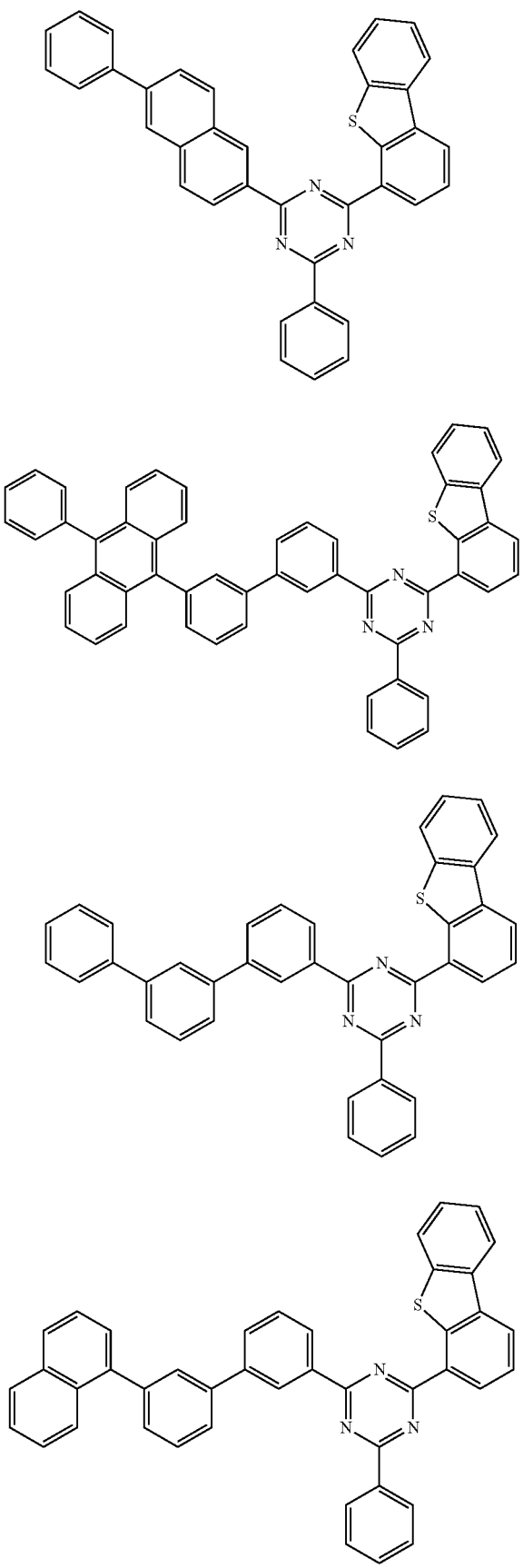
404
-continued
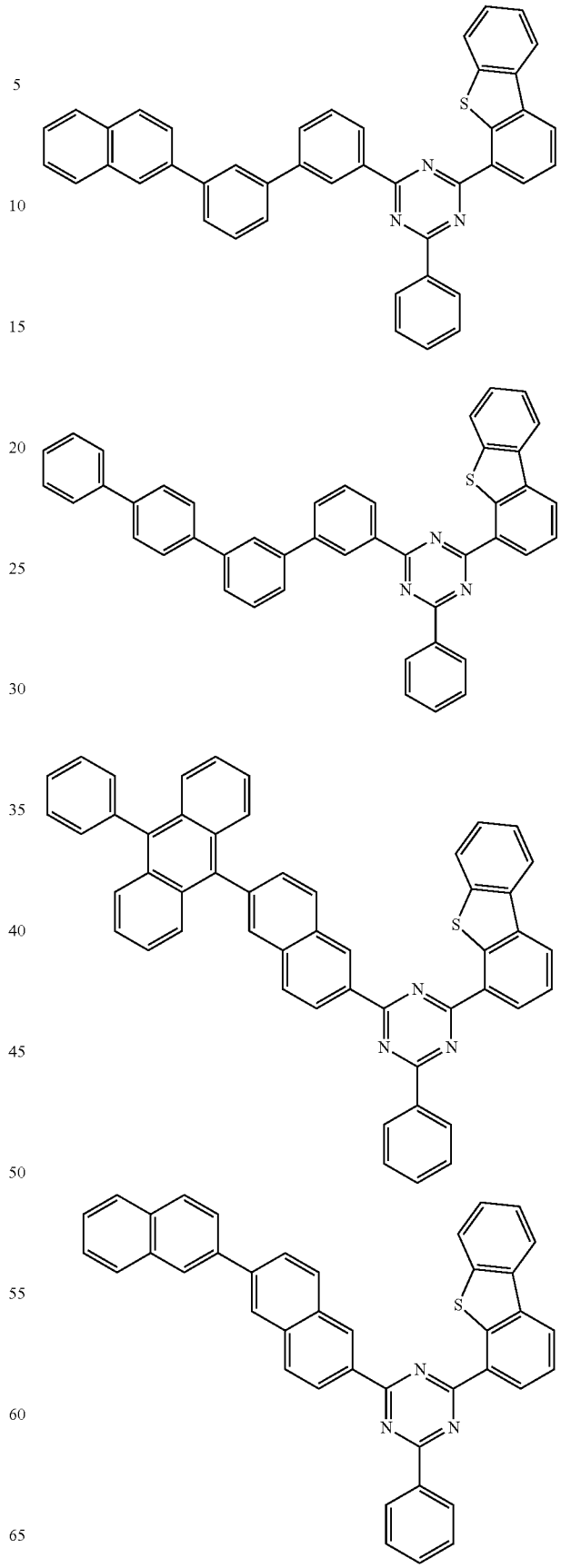

-continued

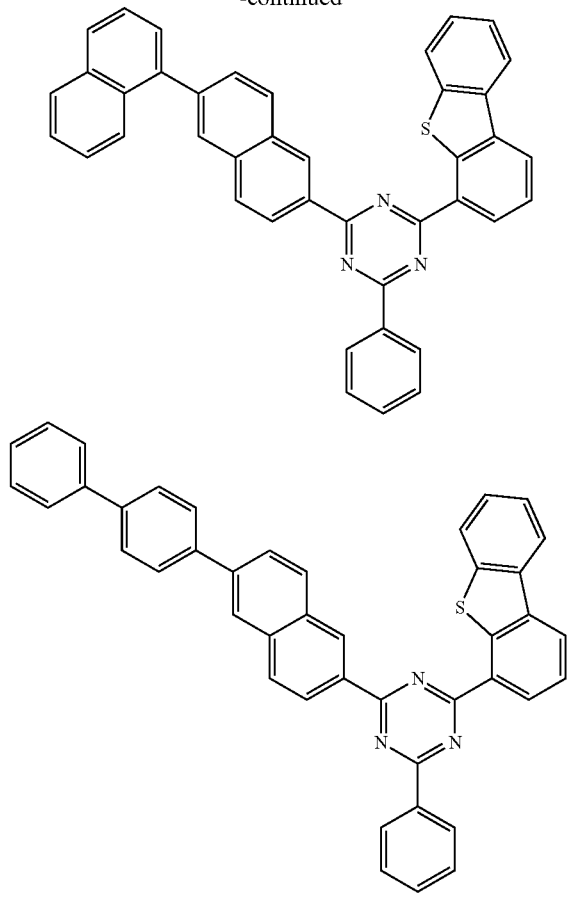

Known alternative reaction or raw materials according to an intended product are used in copying the synthesis in Examples described later, whereby the compound represented by the formula (1) can be synthesized.

[Electron-Transporting Material for Organic EL Device]

The compound represented by the formula (1) according to an aspect of the invention is useful as a material for an organic EL device, and particularly useful as an electron-transporting material or a phosphorescent host material.

The electron-transporting material for an organic EL device according to an aspect of the invention comprises the compound represented by the formula (1).

[Organic Electroluminescence Device]

The organic electroluminescence device according to an aspect of the invention comprises an anode, an organic layer, and a cathode in this order, wherein the organic layer comprises the compound represented by the formula (1).

When the organic EL device comprises a plurality of organic layers, the compound represented by the formula (1) may be contained any layer among the plurality of the organic layers. The types of organic layers will be described later.

Also, the organic electroluminescence device according to an aspect of the invention comprises an anode, an emitting layer, an electron-transporting region, and a cathode, in this order, wherein the electron transporting region comprises the compound represented by the formula (1).

In one embodiment, the electron-transporting region comprises a first electron-transporting layer, and a second electron-transporting layer, and the emitting layer, the first electron-transporting layer, the second electron-transporting layer and the cathode in this order, and at least one of the first electron-transporting layer and the second electron-transporting layer comprises the compound represented by the formula (1).

Inclusion of the compound represented by the formula (1) in one or both of the first electron-transporting layer and the second electron-transporting layer results in an organic EL device having a high luminous efficiency.

Schematic configuration of organic EL device according to one aspect of the invention will be explained referring to the FIGURE.

Organic EL device 1 according to one aspect of the invention comprises: substrate 2; anode 3; organic thin film layer 4; emitting layer 5; organic thin film layer 6; and cathode 10 in this order. The organic thin film layer 4, which is positioned between the anode 3 and the emitting layer 5, functions as a hole-transporting region, and the organic thin film layer 6, which is positioned between the emitting layer 5 and the cathode 10, functions as an electron-transporting region.

The organic thin film layer 6 includes a first electron-transporting layer 6a which is positioned to the emitting layer 5 side and a second electron-transporting layer 6b which is positioned to the cathode 10 side.

One or both of the first electron-transporting layer 6a and the second electron-transporting layer 6b include the compound represented by the formula (1). By including the compound represented by the formula (1) in the first electron-transporting layer 6a or the second electron-transporting layer 6b, an organic EL device with improved luminous efficiency can be obtained.

In one embodiment, the emitting layer comprises the compound represented by the following formula (11).

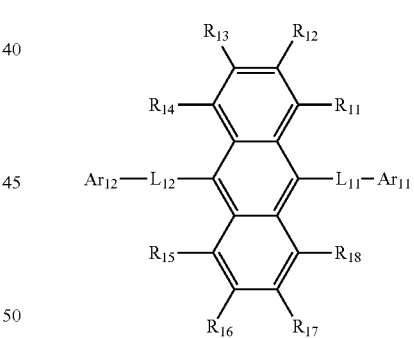

(11)

In the formula (11),
$R_{11}$ to $R_{18}$ are independently a hydrogen atom,
a substituted or unsubstituted alkyl group including 1 to 50 carbon atoms,
a substituted or unsubstituted alkenyl group including 2 to 50 carbon atoms,
a substituted or unsubstituted alkynyl group including 2 to 50 carbon atoms,
a substituted or unsubstituted cycloalkyl group including 3 to 50 ring carbon atoms,
—Si($R_{901}$)($R_{922}$)($R_{903}$),
—O—($R_{904}$),
—S—($R_{905}$),
—N($R_{906}$)($R_{907}$),
a halogen atom, a cyano group, a nitro group, a substituted or unsubstituted aryl group including 6 to 50 ring carbon atoms, or
a substituted or unsubstituted monovalent heterocyclic group including 5 to 50 ring atoms;
$R_{901}$ to $R_{907}$ are independently a hydrogen atom,
a substituted or unsubstituted alkyl group including 1 to 50 carbon atoms,
a substituted or unsubstituted cycloalkyl group including 3 to 50 ring carbon atoms,
a substituted or unsubstituted aryl group including 6 to 50 ring carbon atoms, or
a substituted or unsubstituted monovalent heterocyclic group including 5 to 50 ring atoms;
when two or more of each of $R_{901}$ to $R_{907}$ are present, two or more of each of $R_{901}$ to $R_{907}$ may be the same as or different to each other;
adjacent two or more of $R_{11}$ to $R_{14}$, and adjacent two or more $R_{15}$ to $R_{18}$ do not form a ring by bonding with each other;
$L_{11}$ and $L_{12}$ are independently a single bond,
a substituted or unsubstituted arylene group including 6 to 50 ring carbon atoms, or
a substituted or unsubstituted divalent heterocyclic group including 5 to 50 ring atoms; and
$Ar_{11}$ and $Ar_{12}$ are independently
a substituted or unsubstituted aryl group including 6 to 50 ring carbon atoms, or
a substituted or unsubstituted monovalent heterocyclic group including 5 to 50 ring atoms.

Inclusion of the compound represented by the formula (11) in the emitting layer results in an organic EL device having a more increased luminous efficiency.

In one embodiment, the compound represented by the formula (11) is the compound represented by the following formula (12).

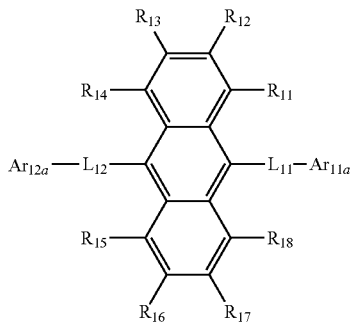

(12)

In the formula (12), $R_{11}$ to $R_{18}$, $L_{11}$ and $L_{12}$ are as defined in the formula (11);
at least one of $Ar_{11a}$ and $Ar_{12a}$ is the monovalent group represented by the following formula (20):

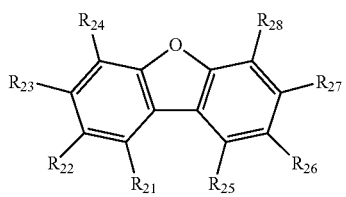

(20)

wherein in the formula (20),
at least one of $R_{21}$ to $R_{28}$ is bonded with $L_{11}$ or $L_{12}$;
$R_{21}$ to $R_{28}$ that are not bonded with $L_{11}$ or $L_{12}$ are independently
a hydrogen atom,
a substituted or unsubstituted alkyl group including 1 to 50 carbon atoms,
a substituted or unsubstituted alkenyl group including 2 to 50 carbon atoms,
a substituted or unsubstituted alkynyl group including 2 to 50 carbon atoms,
a substituted or unsubstituted cycloalkyl group including 3 to 50 ring carbon atoms,
—Si($R_{901}$)($R_{902}$)($R_{933}$),
—O—($R_{904}$),
—S—($R_{905}$),
—N($R_{906}$)($R_{907}$),
a halogen atom, a cyano group, a nitro group,
a substituted or unsubstituted aryl group including 6 to 50 ring carbon atoms, or
a substituted or unsubstituted monovalent heterocyclic group including 5 to 50 ring atoms;
$R_{901}$ to $R_{907}$ are as defined in the formula (11); and
adjacent two or more of $R_{21}$ to $R_{28}$ that are not bonded with $L_{11}$ or $L_{12}$ do not form a ring by bonding with each other;
$Ar_{11a}$ or $Ar_{12a}$ that is not a monovalent group represented by the formula (20) is
a substituted or unsubstituted aryl group including 6 to 50 ring carbon atoms, or
a substituted or unsubstituted monovalent heterocyclic group including 5 to 50 ring atoms, other than the monovalent group represented by the formula (20).

In one embodiment, the compound represented by the formula (12) is the compound represented by the following formula (12-1).

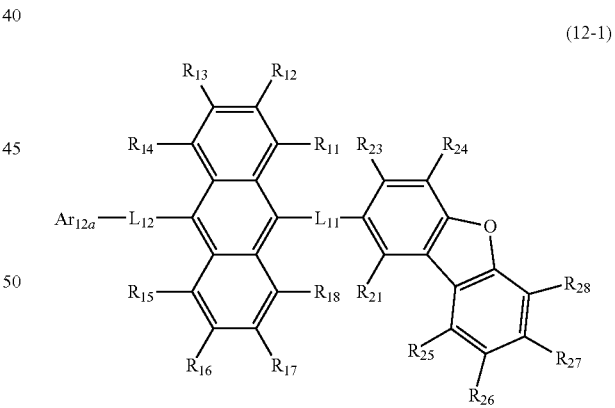

(12-1)

In the formula (12-1), $R_{11}$ to $R_{18}$, $L_{11}$ and $L_{12}$ are as defined in the formula (11);
$Ar_{12a}$ is a substituted or unsubstituted aryl group including 6 to 50 ring carbon atoms, or
a substituted or unsubstituted monovalent heterocyclic group including 5 to 50 ring atoms, other than the monovalent group represented by the formula (20);
$R_{21}$ and $R_{23}$ to $R_{28}$ are independently
a hydrogen atom,
a substituted or unsubstituted alkyl group including 1 to 50 carbon atoms, a substituted or unsubstituted alkenyl group including 2 to 50 carbon atoms
a substituted or unsubstituted alkynyl group including 2 to 50 carbon atoms,
a substituted or unsubstituted cycloalkyl group including 3 to 50 ring carbon atoms,
—Si($R_{901}$)($R_{902}$)($R_{903}$),
—O—($R_{904}$),
—S—($R_{905}$),
—N($R_{906}$)($R_{907}$),
a halogen atom, a cyano group, a nitro group,
a substituted or unsubstituted aryl group including 6 to 50 ring carbon atoms, or
a substituted or unsubstituted monovalent heterocyclic group including 5 to 50 ring atoms; and $R_{901}$ to $R_{907}$ are as defined in the formula (11).

In one embodiment, the compound represented by the formula (11) is the compound represented by the following formula (13).

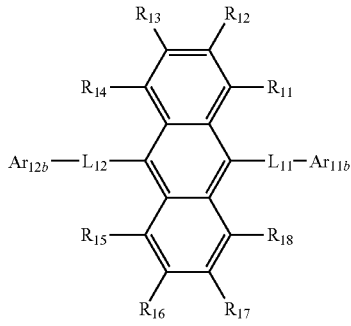

(13)

In the formula (13), $R_{11}$ to $R_{18}$, $L_{11}$ and $L_{12}$ are as defined in the formula (11);

$Ar_{11b}$ and $Ar_{12b}$ are independently a substituted or unsubstituted aryl group including 6 to 50 ring carbon atoms, that is constituted only with a benzene ring.

In one embodiment, the compound represented by the formula (13) is the compound represented by the following formula (13-1).

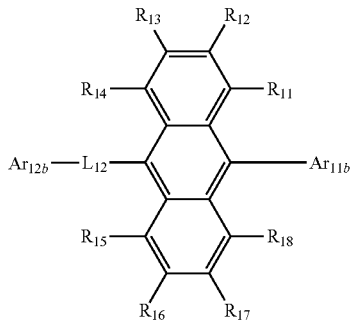

(13-1)

In the formula (13-1), $R_{11}$ to $R_{18}$ and $L_{12}$ are as defined in the formula (11); and $Ar_{11b}$ and $Ar_{12b}$ are independently a substituted or unsubstituted aryl group including 6 to 50 ring carbon atoms, that are constituted only with a benzene ring.

Here, the aryl group "constituted only with a benzene ring" means that aryl groups including a ring other than the benzene ring are excluded. Specifically, a group derived from a fluorene ring which includes a 5-membered ring in addition to benzene rings, and the like are excluded.

The aryl group "constituted only of a benzene ring" includes a group composed of a monocycle of a benzene ring (namely, a phenyl group), a group in which two or more benzene rings are sequentially linked via a single bond (for example, a biphenylyl group, or the like), and a group formed by fusing benzene rings (for example, a naphthyl group, or the like).

The aryl group constituted only of a benzene ring may be substituted by an optional substituent In one embodiment, $Ar_{11b}$ and $Ar_{12b}$ are independently a substituted or unsubstituted phenyl group,
a substituted or unsubstituted naphthyl group,
a substituted or unsubstituted biphenylyl group,
a substituted or unsubstituted terphenylyl group,
a substituted or unsubstituted anthryl group, or
a substituted or unsubstituted phenanthryl group.

In one embodiment, the compound represented by the formula (11) is a compound represented by the following formula (14).

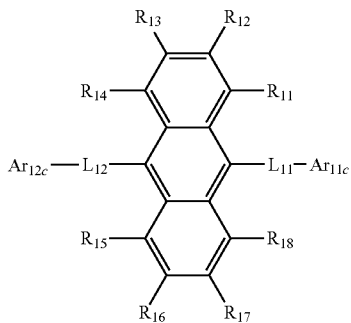

(14)

In the formula (14), $R_{11}$ to $R_{18}$, $L_{11}$ and $L_{12}$ are as defined in the formula (11);

at least one of $Ar_{11c}$ and $Ar_{12c}$ is a monovalent group represented by the following formula (30):

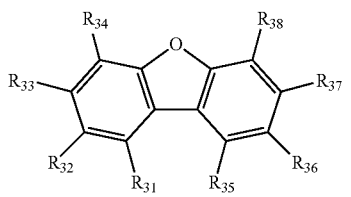

(30)

wherein in the formula (30), adjacent two of $R_{31}$ to $R_{34}$, or adjacent two of $R_{35}$ to $R_{38}$ form an unsaturated ring represented by the following formula (40) by bonding with each other:

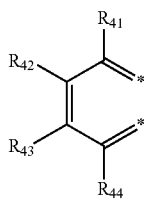

(40)

wherein in the formula (40), two *'s are bonding positions with the adjacent two of $R_{31}$ to $R_{34}$, or the adjacent two of $R_{35}$ to $R_{38}$;

adjacent two or more of $R_{31}$ to $R_{38}$, and $R_{41}$ to $R_{44}$, which do not form the unsaturated ring represented by the formula (40), do not form a ring by bonding with each other;

one of $R_{31}$ to $R_{38}$ and $R_{41}$ to $R_{44}$, which do not form the unsaturated ring represented by the formula (40), is bonded with $L_{11}$ or $L_{12}$;

$R_{31}$ to $R_{38}$ which do not form the unsaturated ring represented by the formula (40) and are not bonded with $L_{11}$ or $L_{12}$, and $R_{41}$ to $R_{44}$ which are not bonded with $L_{11}$ or $L_{12}$ are independently a hydrogen atom, a substituted or unsubstituted alkyl group including 1 to 50 carbon atoms, a substituted or unsubstituted alkenyl group including 2 to 50 carbon atoms, a substituted or unsubstituted alkynyl group including 2 to 50 carbon atoms, a substituted or unsubstituted cycloalkyl group including 3 to 50 ring carbon atoms, —Si($R_{901}$)($R_{902}$)($R_{903}$),

—O—($R_{904}$),

—S—($R_{905}$),

—N($R_{906}$)($R_{907}$), a halogen atom, a cyano group, a nitro group, a substituted or unsubstituted aryl group including 6 to 50 ring carbon atoms, or a substituted or unsubstituted monovalent heterocyclic group including 5 to 50 ring atoms.

$R_{901}$ to $R_{907}$ are as defined in the formula (11).

In one embodiment, the monovalent group represented by the formula (30) is selected from monovalent groups represented by any of the following formulas (30A) to (30F).

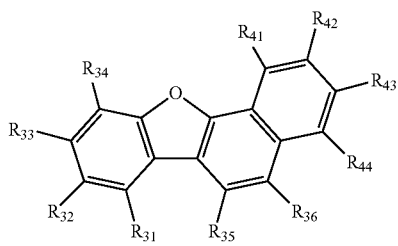

(30A)

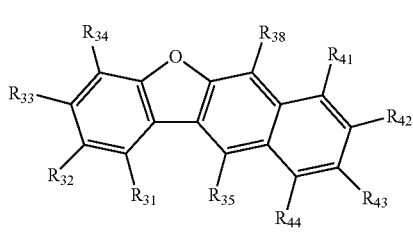

(30B)

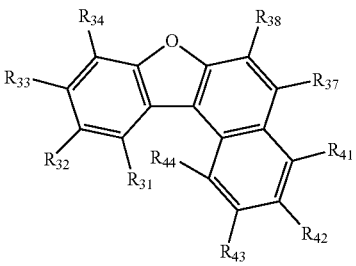

(30C)

In the formulas (30A) to (30C), $R_{31}$ to $R_{36}$ and $R_{41}$ to $R_{44}$ are as defined in the formula (14).

In one embodiment, the compound represented by the formula (11) is a compound represented by the following formula (15).

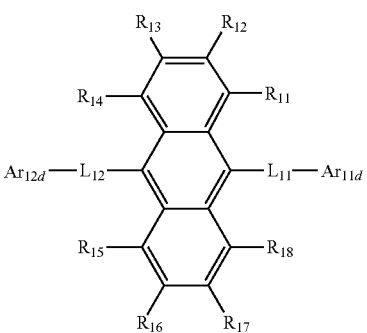

(15)

In the formula (15), $R_{11}$ to $R_{18}$, $L_{11}$ and $L_{12}$ are as defined in the formula (11);

at least one of $Ar_{11d}$ and $Ar_{12d}$ is a monovalent group represented by the following formula (50);

$Ar_{11d}$ and $Ar_{12d}$ which is not the monovalent group represented by the following formula (50) is a substituted or unsubstituted aryl group including 6 to 50 ring carbon atoms, or a substituted or unsubstituted monovalent heterocyclic group including 5 to 50 ring atoms; and when $Ar_{11d}$ and $Ar_{12d}$ are both the monovalent group represented by the following formula (50), $Ar_{11d}$ and $Ar_{12d}$ which are the monovalent groups represented by the following formula (50) may be the same as or different to each other,

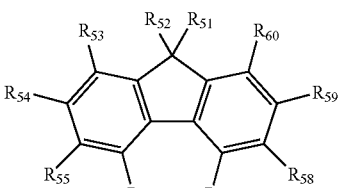

(50)

wherein in the formula (50), $R_{51}$ and $R_{52}$ are independently a hydrogen atom, a halogen atom, a cyano group, a nitro group, a substituted or unsubstituted alkyl group including 1 to 50 carbon atoms, a substituted or unsubstituted alkenyl group including 2 to 50 carbon atoms,
a substituted or unsubstituted alkynyl group including 2 to 50 carbon atoms, or
a substituted or unsubstituted cycloalkyl group including 3 to 50 ring carbon atoms;

$R_{51}$ and $R_{52}$ do not form a ring by bonding with each other;

one or more sets of adjacent two or more of $R_{53}$ to $R_{60}$ form by bonding with each other an unsaturated ring represented by the following formula (60), or do not form the unsubstituted ring represented by the following formula (60);

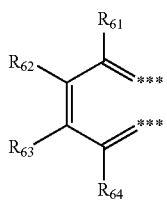

(60)

wherein in the formula (60), "***" indicates a position bonding to adjacent two of $R_{53}$ to $R_{60}$;

when one or more sets of adjacent two of $R_{53}$ to $R_{60}$ form the unsaturated ring represented by the formula (60) by bonding with each other, one of $R_{53}$ to $R_{60}$ that do not form the unsaturated ring represented by the formula (60), and $R_{61}$ to $R_{64}$ is a single bond bonding with $L_{11}$ or $L_{12}$;

when two or more of the unsaturated rings represented by the formula (60) are formed, a plurality of each of $R_{61}$ to $R_{64}$ may be the same as or different to each other;

when one or more sets of adjacent two of $R_{53}$ to $R_{60}$ do not form the unsaturated ring represented by the formula (60), one of $R_{53}$ to $R_{60}$ is a single bond bonding with $L_{11}$ or $L_{12}$;

In the case where the unsaturated ring represented by the formula (60) is formed, and the case where the unsaturated ring represented by the formula (60) is not formed, one or more sets of adjacent two of $R_{53}$ to $R_{60}$, that do not form the unsaturated ring represented by the formula (60) and that are not a single bond bonding with $L_{11}$ or $L_{12}$, form a substituted or unsubstituted, saturated or unsaturated ring other than the unsaturated ring represented by the formula (60), or do not form a substituted or unsubstituted, saturated or unsaturated ring.

$R_{53}$ to $R_{60}$ that do not form the unsaturated ring represented by the formula (60), do not form a substituted or unsubstituted, saturated or unsaturated ring other than the unsaturated ring represented by the formula (60), and are not a single bond bonding with $L_{11}$ or $L_{12}$, and $R_{61}$ to $R_{64}$ that are not a single bond bonding with $L_{11}$ or $L_{12}$ are independently, a hydrogen atom, a halogen atom, a cyano group, a nitro group,
a substituted or unsubstituted alkyl group including 1 to 50 carbon atoms,
a substituted or unsubstituted alkenyl group including 2 to 50 carbon atoms,
a substituted or unsubstituted alkynyl group including 2 to 50 carbon atoms,
a substituted or unsubstituted cycloalkyl group including 3 to 50 ring carbon atoms,
—Si($R_{90}$)($R_{902}$)($R_{903}$),
—O—($R_{905}$),
—S—($R_{905}$),
—N($R_{906}$)($R_{907}$),
a substituted or unsubstituted aryl group including 6 to 50 ring carbon atoms, or
a substituted or unsubstituted monovalent heterocyclic group including 5 to 50 ring atoms; and $R_{901}$ to $R_{907}$ are as defined in the formula (11).

In one embodiment, the compound represented by the formula (15) is a compound represented by the following formula (15-1).

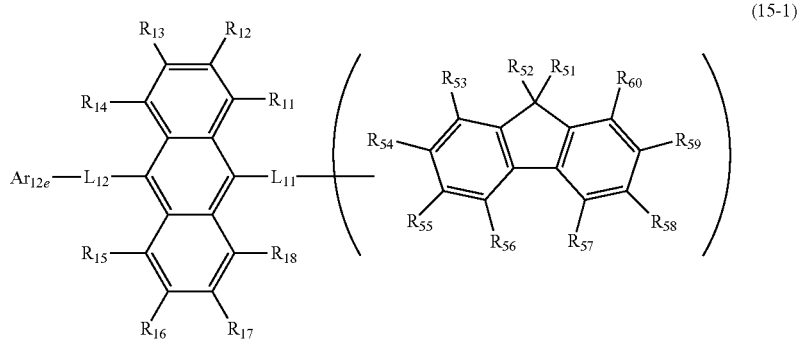

(15-1)

In the formula (15-1), $R_{11}$ to $R_{18}$, $L_{11}$, $L_{12}$ and $R_{51}$ to $R_{60}$ are as defined in the formula (15); and $Ar_{12e}$ is a substituted or unsubstituted aryl group including 6 to 50 ring carbon atoms, other than the monovalent group represented by the formula (50), or a substituted or unsubstituted monovalent heterocyclic group including 5 to 50 ring atoms.

In one embodiment, $R_{11}$ to $R_{18}$ in the formulas (11) to (15) are a hydrogen atom.

In one embodiment, $L_{11}$ and $L_{12}$ in the formulas (11) to (15) are independently
a single bond,
an unsubstituted phenylene group,
an unsubstituted naphthylene group,
an unsubstituted biphenyldiyl group, or
an unsubstituted terphenyldiyl group.

In one embodiment, one or both of the first electron-transporting layer and the second electron-transporting layer further includes one or two or more kinds selected from the group consisting of an alkali metal, an alkaline earth metal, a rare earth metal, an alkali metal oxide, an alkali metal halide, an alkaline earth metal oxide, an alkaline earth metal halide, a rare earth metal oxide, a rare earth metal halide, an organic complex containing an alkali metal, an organic complex containing an alkaline earth metal, and an organic complex containing a rare earth metal.

In one embodiment, a hole-transporting layer is disposed between the anode and the emitting layer.

Hereinafter, a layer configuration of the organic EL device according to one aspect of the invention will be described.

The organic EL device according to one aspect of the invention has an organic layer between a pair of electrodes of a cathode and an anode. The organic layer contains at least one layer containing an organic compound. Alternatively, the organic layer is formed by stacking a plurality of layers containing an organic compound. The organic layer may have a layer consisting only of one or more organic compounds. The organic layer may have a layer containing an organic compound and an inorganic compound together. The organic layer may have a layer consisting only of one or more inorganic compounds.

At least one of the layers contained by the organic layer is an emitting layer. The organic layer may be formed, for example, as one layer of the emitting layer, or may contain other layers which can be adopted in the layer configuration of an organic EL device. Layers that can be employed in the layer configuration of an organic EL device include, but are not limited to, a hole-transporting region (a hole-transporting layer, a hole-injecting layer, an electron-blocking layer, an exciton-blocking layer, etc.) provided between an anode and an emitting layer; an emitting layer, a spacing layer, an electron-transporting region (an electron-transporting layer, an electron-injecting layer, a hole-blocking layer, etc.) provided between a cathode and an emitting layer, and the like.

The organic EL device according to one aspect of the invention may be, for example, a monochromatic emitting device of a fluorescent or phosphorescent type, or a white emitting device of a fluorescent/phosphorescent hybrid type. In addition, it may be a simple type containing a single light emitting unit or a tandem type containing a plurality of light emitting units.

The "emitting unit" refers to the smallest unit which contains organic layers, in which at least one of the organic layers is an emitting layer, and which emits light by recombination of injected holes and electrons.

The "emitting layer" described in this specification is an organic layer having an emitting function. The emitting layer is, for example, a phosphorescent emitting layer, a fluorescent emitting layer, or the like, and may be a single layer or a plurality of layers.

The light-emitting unit may be of a stacked type containing a plurality of a phosphorescent emitting layer and a fluorescent emitting layer, and in this case, for example, may contain a spacing layer between the emitting layers for preventing excitons generated by the phosphorescent emitting layer from diffusing into the fluorescent emitting layer.

The simple type organic EL device includes, for example, a device configuration such as anode/emitting unit/cathode.

Typical layer configurations of the emitting unit are shown below. The layers in parentheses are optional layers.
(a) (hole-injecting layer/) hole-transporting layer/fluorescent emitting layer (/electron-transporting layer/electron-injecting layer)
(b) (hole-injecting layer/) hole-transporting layer/phosphorescent emitting layer (/electron-transporting layer/electron-injecting layer)
(c) (hole-injecting layer/) hole-transporting layer/first fluorescent emitting layer/second fluorescent emitting layer (/electron-transporting layer/electron-injecting layer)
(d) (hole-injecting layer/) hole-transporting layer/first phosphorescent emitting layer/second phosphorescent emitting layer (/electron-transporting layer/electron-injecting layer)
(e) (hole-injecting layer/) hole-transporting layer/phosphorescent emitting layer/spacing layer/fluorescent emitting layer (/electron-transporting layer/electron-injecting layer)
(f) (hole-injecting layer/) hole-transporting layer/first phosphorescent emitting layer/second phosphorescent emitting layer/spacing layer/fluorescent emitting layer (/electron-transporting layer/electron-injecting layer)
(g) (hole-injecting layer/) hole-transporting layer/first phosphorescent layer/spacing layer/second phosphorescent emitting layer/spacing layer/fluorescent emitting layer (/electron-transporting layer/electron-injecting layer)
(h) (hole-injecting layer/) hole-transporting layer/phosphorescent emitting layer/spacing layer/first fluorescent emitting layer/second fluorescent emitting layer (/electron-transporting layer/electron-injecting layer)
(i) (hole-injecting layer/) hole-transporting layer/electron-blocking layer/fluorescent emitting layer (/electron-transporting layer/electron-injecting layer)
(j) (hole-injecting layer/) hole-transporting layer/electron-blocking layer/phosphorescent emitting layer (/electron-transporting layer/electron-injecting layer)
(k) (hole-injecting layer/) hole-transporting layer/exciton-blocking layer/fluorescent emitting layer (/electron-transporting layer/electron-injecting layer)
(l) (hole-injecting layer/) hole-transporting layer/exciton-blocking layer/phosphorescent emitting layer (/electron-transporting layer/electron-injecting layer)
(m) (hole-injecting layer/) first hole-transporting layer/second hole-transporting layer/fluorescent emitting layer (/electron-transporting layer/electron-injecting layer)
(n) (hole-injecting layer/) first hole-transporting layer/second hole-transporting layer/fluorescent emitting layer (/first electron-transporting layer/second electron-transporting layer/electron-injecting layer)
(o) (hole-injecting layer/) first hole-transporting layer/second hole-transporting layer/phosphorescent emitting layer (/electron-transporting layer/electron-injecting layer)
(p) (hole-injecting layer/) first hole-transporting layer/second hole-transporting layer/phosphorescent emitting layer (/first electron-transporting layer/second electron-transporting layer/electron-injecting layer)
(q) (hole-injecting layer/) hole-transporting layer/fluorescent emitting layer/hole-blocking layer (/electron-transporting layer/electron-injecting layer)
(r) (hole-injecting layer/) hole-transporting layer/phosphorescent emitting layer/hole-blocking layer (/electron-transporting layer/electron-injecting layer)
(s) (hole-injecting layer/) hole-transporting layer/fluorescent emitting layer/exciton-blocking layer (/electron-transporting layer/electron-injecting layer)
(t) (hole-injecting layer/) hole-transporting layer/phosphorescent emitting layer/exciton-blocking layer (/electron-transporting layer/electron-injecting layer)

However, the layer configuration of the organic EL device according to one aspect of the invention is not limited thereto. For example, when the organic EL device has a hole-injecting layer and a hole-transporting layer, it is preferred that a hole-injecting layer be provided between the hole-transporting layer and the anode. Further, when the organic EL device has an electron-injecting layer and an electron-transporting layer, it is preferred that an electron-injecting layer be provided between the electron-transporting layer and the cathode. Further, each of the hole-injecting layer, the hole-transporting layer, the electron-transporting layer and the electron-injecting layer may be constituted of a single layer or of a plurality of layers.

The plurality of phosphorescent emitting layers, and the plurality of the phosphorescent emitting layer and the fluorescent emitting layer may be emitting layers that emit mutually different colors. For example, the emitting unit (f) may contain a hole-transporting layer/first phosphorescent layer (red light emission)/second phosphorescent emitting layer (green light emission)/spacing layer/fluorescent emitting layer (blue light emission)/electron-transporting layer.

An electron-blocking layer may be provided between each light emitting layer and the hole-transporting layer or the spacing layer. Further, a hole-blocking layer may be provided between each emitting layer and the electron-transporting layer. By providing the electron-blocking layer or the hole-blocking layer, it is possible to confine electrons or holes in the emitting layer, thereby to improve the recombination probability of carriers in the emitting layer, and to improve luminous efficiency.

As a representative device configuration of a tandem type organic EL device, for example, a device configuration such as anode/first emitting unit/intermediate layer/second emitting unit/cathode can be given.

The first emitting unit and the second emitting unit are independently selected from the above-mentioned emitting units, for example.

The intermediate layer is also generally referred to as an intermediate electrode, an intermediate conductive layer, a charge generating layer, an electron withdrawing layer, a connecting layer, a connector layer, or an intermediate insulating layer. The intermediate layer is a layer that supplies electrons to the first emitting unit and holes to the second emitting unit, and can be formed of known materials.

Hereinbelow, an explanation will be made on function, materials, etc. of each layer constituting the organic EL device described in this specification.
(Substrate)

The substrate is used as a support of the organic EL device. The substrate preferably has a light transmittance of 50% or more in the visible light region within a wavelength of 400 to 700 nm, and a smooth substrate is preferable. Examples of the material of the substrate include soda-lime glass, aluminosilicate glass, quartz glass, plastic and the like. As the substrate, a flexible substrate can be used. The flexible substrate means a substrate that can be bent (flexible), and examples thereof include a plastic substrate and the like. Specific examples of the material for forming the plastic substrate include polycarbonate, polyallylate, polyether sulfone, polypropylene, polyester, polyvinyl fluoride, polyvinyl chloride, polyimide, polyethylene naphthalate and the like. Also, an inorganic vapor deposited film can be used.
(Anode)

As the anode, for example, it is preferable to use a metal, an alloy, a conductive compound, a mixture thereof or the like, which has a high work function (specifically, 4.0 eV or more). Specific examples of the material of the anode include indium oxide-tin oxide (ITO: Indium Tin Oxide), indium oxide-tin oxide containing silicon or silicon oxide, indium oxide-zinc oxide, indium oxide containing tungsten oxide or zinc oxide, graphene and the like. In addition, it is possible to use gold, silver, platinum, nickel, tungsten, chromium, molybdenum, iron, cobalt, copper, palladium, titanium, nitrides of these metals (e.g. titanium nitride) and the like.

The anode is normally formed by depositing these materials on the substrate by a sputtering method. For example, indium oxide-zinc oxide can be formed by a sputtering method by using a target in which 1 to 10 mass % zinc oxide is added to indium oxide. Further, indium oxide containing tungsten oxide or zinc oxide can be formed by a sputtering method by using a target in which 0.5 to 5 mass % of tungsten oxide or 0.1 to 1 mass % of zinc oxide is added to indium oxide.

As the other methods for forming the anode, a vacuum deposition method, a coating method, an inkjet method, a spin coating method or the like can be given. When silver paste or the like is used, it is possible to use a coating method, an inkjet method or the like.

The hole-injecting layer formed in contact with the anode is formed by using a material that allows easy hole injection regardless of the work function of the anode. For this reason, in the anode, it is possible to use a common electrode material, for example, a metal, an alloy, a conductive compound and a mixture thereof. Specifically, materials having a small work function such as alkaline metals such as lithium and cesium; magnesium; alkaline earth metals such as calcium and strontium; alloys containing these metals (for example, magnesium-silver and aluminum-lithium); rare earth metals such as europium and ytterbium; and an alloy containing rare earth metals can also be used for the anode.
(Hole-Injecting Layer)

A hole-injecting layer is a layer that contains a substance having a high hole-injecting property and has a function of injecting holes from the anode to the organic layer. As the substance having a high hole-injecting property, molybdenum oxide, titanium oxide, vanadium oxide, rhenium oxide, ruthenium oxide, chromium oxide, zirconium oxide, hafnium oxide, tantalum oxide, silver oxide, tungsten oxide, manganese oxide, an aromatic amine compound, an electron-attracting (acceptor) compound, a polymeric compound (oligomer, dendrimer, polymer, etc.) and the like can be given. Among these, an aromatic amine compound and an acceptor compound are preferable, with an acceptor compound being more preferable.

Specific examples of the aromatic amine compound include 4,4',4"-tris(N,N-diphenylamino)triphenylamine (abbreviation: TDATA), 4,4',4"-tris[N-(3-methylphenyl)-N-phenylamino]triphenylamine (abbreviation: MTDATA), 4,4'-bis[N-(4-diphenylaminophenyl)-N-phenylamino]biphenyl (abbreviation: DPAB), 4,4'-bis(N-(4-{N'-(3-methylphenyl)-N'-phenylamino)phenyl}-N-phenylamino)biphenyl (abbreviation: DNTPD), 1,3,5-tris[N-(4-diphenylaminophenyl)-N-phenylamino]benzene (abbreviation: DPA3B), 3-[N-(9-phenylcarbazol-3-yl)-N-phenylamino]-9-phenylcarbazole (abbreviation: PCzPCA1), 3,6-bis[N-(9-phenylcarbazol-3-yl)-N-phenylamino]-9-phenylcarbazole (abbreviation: PCzPCA2), 3-[N-(1-naphthyl)-N-(9-phenylcarbazol-3-yl)amino]-9-phenylcarbazole (abbreviation: PCzPCN1), and the like.

The acceptor compound is preferably, for example, a heterocyclic ring derivative having an electron-attracting group, a quinone derivative having an electron-attracting group, an arylborane derivative, a heteroarylborane derivative, and the like, and specific examples include hexacyanohexaazatriphenylene, 2,3,5,6-tetrafluoro-7,7,8,8-tetracyanoquinodimethane (abbreviation: F4TCNQ), 1,2,3-tris[(cyano)(4-cyano-2,3,5,6-tetrafluorophenyl)methylene]cyclopropane, and the like.

When the acceptor compound is used, it is preferred that the hole-injecting layer further comprise a matrix material. As the matrix material, a material known as the material for an organic EL device can be used. For example, an electron-donating (donor) compound is preferable.

(Hole-Transporting Layer)

The hole-transporting layer is a layer that comprises a high hole-transporting property, and has a function of transporting holes from the anode to the organic layer.

As the substance having a high hole-transporting property, a substance having a hole mobility of $10^{-6}$ cm$^2$/(V·s) or more is preferable. For example, an aromatic amine compound, a carbazole derivative, an anthracene derivative, a polymeric compound, and the like can be given.

Specific examples of the aromatic amine compound include 4,4'-bis[N-(1-naphthyl)-N-phenylamino]biphenyl (abbreviation: NPB), N,N'-bis(3-methylphenyl)-N,N'-diphenyl-[1,1'-biphenyl]-4,4'-diamine (abbreviation: TPD), 4-phenyl-4'-(9-phenylfluoren-9-yl)triphenylamine (abbreviation: BAFLP), 4,4'-bis[N-(9,9-dimethylfluoren-2-yl)-N-phenylamino]biphenyl (abbreviation: DFLDPBi), 4,4',4''-tris(N,N-diphenylamino)triphenylamine (abbreviation: TDATA), 4,4',4''-tris[N-(3-methylphenyl)-N-phenylamino] triphenylamine (abbreviation: MTDATA), 4,4'-bis[N-(spiro-9,9'-bifluoren-2-yl)-N-phenylamino]biphenyl (abbreviation: BSPB), and the like.

Specific examples of the carbazole derivative include 4,4'-di(9-carbazolyl)biphenyl (abbreviation: CBP), 9-[4-(9-carbazolyl)phenyl]-10-phenylanthracene (abbreviation: CzPA), 9-phenyl-3-[4-(10-phenyl-9-anthryl)phenyl]-9H-carbazole (abbreviation: PCzPA) and the like.

Specific examples of the anthracene derivative include 2-t-butyl-9,10-di(2-naphthyl)anthracene (t-BuDNA), 9,10-di(2-naphthyl)anthracene (DNA), 9,10-diphenylanthracene (DPAnth), and the like.

Specific examples of the polymeric compound include poly(N-vinylcarbazole) (abbreviation: PVK), poly(4-vinyltriphenylamine) (abbreviation: PVTPA) and the like.

As long as a compound other than those mentioned above, that has a higher hole-transporting property as compared with electron-transporting property, such a compound can be used for the hole-transporting layer.

The hole-transporting layer may be a single layer or may be a stacked layer of two or more layers. In this case, it is preferred to arrange a layer that contains a substance having a larger energy gap among substances having a higher hole-transporting property, on a side nearer to the emitting layer.

(Emitting Layer)

The emitting layer is a layer containing a substance having a high emitting property (dopant material). As the dopant material, various types of material can be used. For example, a fluorescent emitting compound (fluorescent dopant), a phosphorescent emitting compound (phosphorescent dopant) or the like can be used. A fluorescent emitting compound is a compound capable of emitting light from the singlet excited state, and an emitting layer containing a fluorescent emitting compound is called as a fluorescent emitting layer. Further, a phosphorescent emitting compound is a compound capable of emitting light from the triplet excited state, and an emitting layer containing a phosphorescent emitting compound is called as a phosphorescent emitting layer.

The emitting layer normally contains a dopant material and a host material that allows the dopant material to emit light efficiently. In some literatures, a dopant material is called as a guest material, an emitter or an emitting material. In some literatures, a host material is called as a matrix material.

A single emitting layer may comprise plural dopant materials and plural host materials. Further, plural emitting layers may be present.

In this specification, a host material combined with the fluorescent dopant is referred to as a "fluorescent host" and a host material combined with the phosphorescent dopant is referred to as the "phosphorescent host". Note that the fluorescent host and the phosphorescent host are not classified only by the molecular structure. The phosphorescent host is a material for forming a phosphorescent emitting layer containing a phosphorescent dopant, but it does not mean that it cannot be used as a material for forming a fluorescent emitting layer. The same can be applied to the fluorescent host The content of the dopant material in the emitting layer is not particularly limited, but from the viewpoint of adequate luminescence and concentration quenching, it is preferable, for example, to be 0.1 to 70 mass %, more preferably 0.1 to 30 mass %, more preferably 1 to 30 mass %, still more preferably 1 to 20 mass %, and particularly preferably 1 to 10 mass %.

<Fluorescent Dopant>

As the fluorescent dopant, a fused polycyclic aromatic derivative, a styrylamine derivative, a fused ring amine derivative, a boron-containing compound, a pyrrole derivative, an indole derivative, a carbazole derivative can be given, for example. Among these, a fused ring amine derivative, a boron-containing compound, and a carbazole derivative are preferable.

As the fused ring amine derivative, a diaminopyrene derivative, a diaminochrysene derivative, a diaminoanthracene derivative, a diaminofluorene derivative, a diaminofluorene derivative with which one or more benzofuro skeletons are fused, and the like can be given.

As the boron-containing compound, a pyrromethene derivative, a triphenylborane derivative and the like can be given.

Examples of the blue fluorescent dopant include a pyrene derivative, a styrylamine derivative, a chrysene derivative, a fluoranthene derivative, a fluorene derivative, a diamine derivative, a triarylamine derivative, and the like. Specifically, N,N'-bis[4-(9H-carbazol-9-yl)phenyl]-N,N'-diphenyl-stilbene-4,4'-diamine (abbreviation: YGA2S), 4-(9H-carbazol-9-yl)-4'-(10-phenyl-9-anthryl)triphenylamine (abbreviation: YGAPA), 4-(10-phenyl-9-anthryl)-4'-(9-phenyl-9H-carbazol-3-yl)triphenylamine (abbreviation: PCBAPA) and the like can be given.

As the green fluorescent dopant, an aromatic amine derivative and the like can be given, for example. Specifically, N-(9,10-diphenyl-2-anthryl)-N,9-diphenyl-9H-carbazol-3-amine (abbreviation: 2PCAPA), N-[9,10-bis(1,1'-biphenyl-2-yl)-2-anthryl]-N,9-diphenyl-9H-carbazol-3-amine (abbreviation: 2PCABPhA), N-(9,10-diphenyl-2-anthryl)-N,N',N'-triphenyl-1,4-phenylenediamine (abbreviation: 2DPAPA), N-[9,10-bis(1,1'-biphenyl-2-yl)-2-anthryl]-N,N', N'-triphenyl-1,4-phenylenediamine (abbreviation: 2DPABPhA), N-[9,10-bis(1,1'-biphenyl-2-yl)]-N-[4-(9H-carbazol-9-yl) phenyl]-N-phenylanthracene-2-amine (abbreviation: 2YGABPhA), N,N,9-triphenylanthracene-9-amine (abbreviation: DPhAPhA), and the like can be given.

As the red fluorescent dopant, a tetracene derivative, a diamine derivative or the like can be given. Specifically, N,N,N',N'-tetrakis(4-methylphenyl)tetracen-5,11-diamine (abbreviation: p-mPhTD), 7,14-diphenyl-N,N,N',N'-tetrakis (4-methylphenyl)acenaphtho[1,2-a]fluoranthen-3,10-diamine (abbreviation: p-mPhAFD) and the like can be given.

<Phosphorescent Dopant>

As the phosphorescent dopant, a phosphorescent light-emitting heavy metal complex and a phosphorescent light-emitting rare earth metal complex can be given.

As the heavy metal complex, an iridium complex, an osmium complex, a platinum complex and the like can be given. As the heavy metal complex, an ortho-metalated complex of a metal selected from iridium, osmium and platinum.

As the rare earth metal complexes include a terbium complex, a europium complex and the like. Specifically, tris(acetylacetonate)(monophenanthroline)terbium (III) (abbreviation: Tb(acac)$_3$(Phen)), tris(1,3-diphenyl-1,3-propandionate)(monophenanthroline)europium (III) (abbreviation: Eu(DBM)$_3$(Phen)), tris[1-(2-thenoyl)-3,3,3-trifluoroacetonate](monophenanthroline)europium (III) (abbreviation: Eu(TTA)$_3$(Phen)) and the like can be given. These rare earth metal complexes are preferable as phosphorescent dopants since rare earth metal ions emit light due to electronic transition between different multiplicity.

As the blue phosphorescent dopant, an iridium complex, an osmium complex, a platinum complex, or the like can be given, for example. Specific examples include bis[2-(4',6'-difluorophenyl)pyridinato-N,C2]iridium (III) tetrakis(1-pyrazolyl)borate (abbreviation: Flr6), bis[2-(4',6'-difluorophenyl)pyridinato-N,C2]iridium (III) picolinate (abbreviation: Flrpic), bis[2-(3',5'-bistrofluoromethylphenyl)pyridinato-N,C2]iridium (III) picolinate (abbreviation: Ir(CF$_3$ppy)$_2$(pic)), bis[2-(4',6'-difluorophenyl)pyridinato-N,C2]iridium (III) acetylacetonate (abbreviation: Flracac), and the like.

As the green phosphorescent dopant, an iridium complex or the like can be given, for example. Specific examples include tris(2-phenylpyridinato-N,C2')iridium (III) (abbreviation: Ir(ppy)$_3$), bis(2-phenylpyridinato-N,C2')iridium (III) acetylacetonate (abbreviation: Ir(ppy)$_2$(acac)), bis(1,2-diphenyl-1H benzimidazolate)iridium (III) acetylacetonate (abbreviation: Ir(pbi)$_2$(acac)), bis(benzo[h]quinolinato) iridium (III) acetylacetonate (abbreviation: Ir(bzq)$_2$(acac)), and the like.

As the red phosphorescent dopant, an iridium complex, a platinum complex, a terbium complex, a europium complex and the like can be given. Specifically, bis[2-(2'-benzo[4,5-α] thienyl)pyridinato-N,C3]iridium (III) acetylacetonate (abbreviation: Ir(btp)$_2$(acac)), bis(1-phenylisoquinolinato-N,C2')iridium (III) acetylacetonate (abbreviation: Ir(piq)$_2$(acac)), (acetylacetonate)bis[2,3-bis(4-fluorophenyl)quinoxalinato]iridium (III) (abbreviation: Ir(Fdpq)$_2$(acac)), 2,3,7,8,12,13,17,18-octaethyl-21H,23H-porphyrin platinum (II) (abbreviation: PtOEP), and the like.

<Host Material>

Examples of the host material include metal complexes such as an aluminum complex, a beryllium complex, and a zinc complex; heterocyclic compounds such as an indole derivative, a pyridine derivative, a pyrimidine derivative, a triazine derivative, a quinoline derivative, an isoquinoline derivative, a quinazoline derivative, a dibenzofuran derivative, a dibenzothiophene derivative, an oxadiazole derivative, a benzimidazole derivative, a phenanthroline derivative; fused aromatic compounds such as a naphthalene derivative, a triphenylene derivative, a carbazole derivative, an anthracene derivative, a phenanthrene derivative, a pyrene derivative, a chrysene derivative, a naphthacene derivative, and a fluoranthene derivative; and aromatic amine compounds such as a triarylamine derivative, and a fused polycyclic aromatic amine derivative, and the like. Plural types of host materials can be used in combination.

Specific examples of the metal complex include tris(8-quinolinolato)aluminum(III) (abbreviation: Alq), tris(4-methyl-8-quinolinolato)aluminum(III) (abbreviation: Almq3), bis(10-hydroxybenzo[h]quinolinato)beryllium(II) (abbreviation: BeBq2), bis(2-methyl-8-quinolinolato)(4-phenylphenolato)aluminum(III) (abbreviation: BAlq), bis (8-quinolinolato)zinc(II) (abbreviation: Znq), bis[2-(2-benzoxazolyl)phenolato]zinc(II) (abbreviation: ZnPBO), bis[2-(2-benzothiazolyl) phenolato]zinc(II) (abbreviation: ZnBTZ), and the like.

Specific examples of the heterocyclic compound include 2-(4-biphenylyl)-5-(4-tert-butylphenyl)-1,3,4-oxadiazole (abbreviation: PBD), 1,3-bis[5-(p-tert-butylphenyl)-1,3,4-oxadiazol-2-yl]benzene (abbreviation: OXD-7), 3-(4-biphenylyl)-4-phenyl-5-(4-tert-butylphenyl)-1,2,4-triazole (abbreviation: TAZ), 2,2',2''-(1,3,5-benzenetriyl)tris(1-phenyl-1H-benzimidazole) (abbreviation: TPBI), bathophenanthroline (abbreviation: BPhen), bathocuproine (abbreviation: BCP), and the like.

Specific examples of the fused aromatic compound include 9-[4-(10-phenyl-9-anthryl)phenyl]-9H-carbazole (abbreviation: CzPA), 3,6-diphenyl-9-[4-(10-phenyl-9-anthryl)phenyl]-9H-carbazole (abbreviation: DPCzPA), 9,10-bis(3,5-diphenylphenyl)anthracene (abbreviation: DPPA), 9,10-di(2-naphthyl)anthracene (abbreviation: DNA), 2-tert-butyl-9,10-di(2-naphthyl)anthracene (abbreviation: t-BuDNA), 9,9'-bianthryl (abbreviation: BANT), 9,9'-(stilbene-3,3'-diyl)diphenanthrene (abbreviation: DPNS), 9,9'-(stilbene-4,4'-diyl)diphenanthrene (abbreviation: DPNS2), 3,3',3''-(benzene-1,3,5-triyl)tripyrene (abbreviation: TPB3), 9,10-diphenylanthracene (abbreviation: DPAnth), 6,12-dimethoxy-5,11-diphenylchrysene, and the like.

Specific examples of the aromatic amine compound include N,N-diphenyl-9-[4-(10-phenyl-9-anthryl)phenyl]-9H-carbazol-3-amine (abbreviation: CzA1PA), 4-(10-phenyl-9-anthryl)triphenylamine (abbreviation: DPhPA), N,9-diphenyl-N-[4-(10-phenyl-9-anthryl)phenyl]-9H-carbazol-3-amine (abbreviation: PCAPA), N,9-diphenyl-N-{4-[4-(10-phenyl-9-anthryl)phenyl]phenyl}-9H-carbazol-3-amine (abbreviation: PCAPBA), N-(9,10-diphenyl-2-anthryl)-N,9-diphenyl-9H-carbazol-3-amine (abbreviation: 2PCAPA), 4,4'-bis[N-(1-naphthyl)-N-phenylamino]biphenyl (abbreviation: NPB or α-NPD), N,N'-bis(3-methylphenyl)-N,N'-diphenyl-[1,1'-biphenyl]-4,4'-diamine (abbreviation: TPD), 4,4'-bis[N-(9,9-dimethylfluoren-2-yl)-N-phenylamino]biphenyl (abbreviation: DFLDPBi), 4,4'-bis[N-(spiro-9,9'-bifluoren-2-yl)-N-phenylamino]biphenyl (abbreviation: BSPB), and the like.

As the fluorescent host, a compound having a higher singlet energy level as compared with a fluorescent dopant is preferable. For example, a heterocyclic compound, a fused aromatic compound and the like can be given. As the fused aromatic compound, an anthracene derivative, a pyrene derivative, a chrysene derivative, a naphthacene derivative and the like are preferable.

As the phosphorescent host, a compound having a higher triplet energy level as compared with a phosphorescent dopant is preferable. For example, a metal complex, a heterocyclic compound, a fused aromatic compound and the like can be given. The compound represented by the formula (1) is also given. Among these, an indole derivative, a carbazole derivative, a pyridine derivative, a pyrimidine derivative, a triazine derivative, a quinoline derivative, an isoquinoline derivative, a quinazoline derivative, a dibenzofuran derivative, a dibenzothiophene derivative, a naphthalene derivative, a triphenylene derivative, a phenanthrene derivative, a fluoranthene derivative and the like are preferable.

(Electron-Transporting Layer)

An electron-transporting layer is a layer that comprises a substance having a high electron-transporting property. As the substance having a high electron-transporting property, a substance having an electron mobility of $10^{-6}$ cm$^2$/Vs or more is preferable. For example, a metal complex, an aromatic heterocyclic compound, an aromatic hydrocarbon compound, a polymeric compound and the like can be given.

As the metal complex, an aluminum complex, a beryllium complex, a zinc complex and the like can be given. Specific examples of the metal complex include tris(8-quinolinolato) aluminum (III) (abbreviation: Alq), tris(4-methyl-8-quinolinolato)aluminum (abbreviation: Almq3), bis(10-hydroxybenzo[h]quinolinato)beryllium (abbreviation: BeBq2), bis(2-methyl-8-quinolinolato)(4-phenylphenolato)aluminum (III) (abbreviation: BAlq), bis(8-quinolinolato)zinc (II) (abbreviation: Znq), bis[2-(2-benzoxazolyl)phenolato]zinc (II) (abbreviation: ZnPBO), bis[2-(2-benzothiazolyl) phenolato] zinc(II) (abbreviation: ZnBTZ), and the like.

As the aromatic heterocyclic compound, imidazole derivatives such as a benzimidazole derivative, an imidazopyridine derivative and a benzimidazophenanthridine derivative; azine derivatives such as a pyrimidine derivative and a triazine derivative; compounds having a nitrogen-containing 6-membered ring structure such as a quinoline derivative, an isoquinoline derivative, and a phenanthroline derivative (also including one having a phosphine oxide-based substituent on the heterocyclic ring) and the like can be given. Specifically, 2-(4-biphenylyl)-5-(4-tert-butylphenyl)-1,3,4-oxadiazole (abbreviation: PBD), 1,3-bis[5-(p-tert-butylphenyl)-1,3,4-oxadiazol-2-yl]benzene (abbreviation: OXD-7), 3-(4-tert-butylphenyl)-4-phenyl-5-(4-biphenylyl)-1,2,4-triazole (abbreviation: TAZ), 3-(4-tert-butylphenyl)-4-(4-ethylphenyl)-5-(4-biphenylyl)-1,2,4-triazole (abbreviation: p-EtTAZ), bathophenanthroline (abbreviation: BPhen), bathocuproine (abbreviation: BCP), 4,4'-bis(5-methylbenzoxazol-2-yl)stilbene (abbreviation: BzOs), and the like can be given.

As the aromatic hydrocarbon compound, an anthracene derivative, a fluoranthene derivative and the like can be given, for example.

As specific examples of the polymeric compound, poly [(9,9-dihexylfluoren-2,7-diyl)-co-(pyridine-3,5-diyl)] (abbreviation: PF-Py), poly[(9,9-dioctylfluoren-2,7-diyl)-co-(2, 2'-bipyridin-6,6'-diyl)] (abbreviation: PF-BPy) and the like can be given.

As long as a compound other than those mentioned above, that has a higher electron-transporting property as compared with hole-transporting property, such a compound may be used in the electron-transporting layer.

The electron-transporting layer may be a single layer, or a stacked layer of two or more layers. In this case, it is preferable to arrange a layer that contains a substance having a larger energy gap, among substances having a high electron-transporting property, on the side nearer to the emitting layer.

The electron-transporting layer may contain a metal such as an alkali metal, magnesium, an alkaline earth metal, or an alloy containing two or more of these metals; a metal compound such as an alkali metal compound such as 8-quinolinolato lithium (Liq), or an alkaline earth metal compound. When a metal such as an alkali metal, magnesium, an alkaline earth metal, or an alloy containing two or more of these metals is contained in the electron-transporting layer, the content of the metal is not particularly limited, but is preferably from 0.1 to 50 mass %, more preferably from 0.1 to 20 mass %, further preferably from 1 to 10 mass %.

When a metal compound such as an alkali metal compound or an alkaline earth metal compound is contained in the electron-transporting layer, the content of the metal compound is preferably from 1 to 99 mass %, more preferably from 10 to 90 mass %. When plural electron-transporting layers are provided, the layer on the emitting layer side can be formed only from the metal compound as mentioned above.

(Electron-Injecting Layer)

The electron-injecting layer is a layer that contains a substance having a high electron-injecting property, and has the function of efficiently injecting electrons from a cathode to an emitting layer. Examples of the substance that has a high electron-injecting property include an alkali metal, magnesium, an alkaline earth metal, a compound thereof, and the like. Specific examples thereof include lithium, cesium, calcium, lithium fluoride, cesium fluoride, calcium fluoride, lithium oxide, and the like. In addition, a material in which an alkali metal, magnesium, an alkaline earth metal, or a compound thereof is incorporated to an electron-transporting substance having an electron-transporting property, for example, Alq incorporated with magnesium, may also be used.

Alternatively, a composite material that includes an organic compound and a donor compound may also be used in the electron-injecting layer. Such a composite material is excellent in the electron-injecting property and the electron-transporting property since the organic compound receives electrons from the donor compound.

The organic compound is preferably a substance excellent in transporting property of the received electrons, and specifically, for example, the metal complex, the aromatic heterocyclic compound, and the like, which are a substance that has a high electron-transporting property as mentioned above, can be used.

Any material capable of donating electrons to an organic compound can be used as the donor compound. Examples thereof include an alkali metal, magnesium, an alkaline earth metal, a rare earth metal and the like. Specific examples thereof include lithium, cesium, magnesium, calcium, erbium, ytterbium, and the like. Further, an alkali metal oxide and an alkaline earth metal oxide are preferred, and examples thereof include lithium oxide, calcium oxide, barium oxide, and the like. Lewis bases such as magnesium oxide can also be used. Alternatively, an organic compound such as tetrathiafulvalene (abbreviation: TTF) can be used.

(Cathode)

For the cathode, a metal, an alloy, an electrically conductive compound, and a mixture thereof, each having a small work function (specifically, a work function of 3.8 eV or less) are preferably used. Specific examples of the material for the cathode include alkali metals such as lithium and cesium; magnesium; alkaline earth metals such as calcium, and strontium; alloys containing these metals (for example, magnesium-silver, and aluminum-lithium); rare earth metals such as europium and ytterbium; alloys containing a rare earth metal, and the like.

The cathode is usually formed by a vacuum vapor deposition or a sputtering method. Further, in the case of using a silver paste or the like, a coating method, an inkjet method, or the like can be employed.

In the case where the electron-injecting layer is provided, a cathode can be formed from a substance selected from various electrically conductive materials such as aluminum, silver, ITO, graphene, indium oxide-tin oxide containing silicon or silicon oxide, regardless of the work function value. These electrically conductive materials are made into films by using a sputtering method, an inkjet method, a spin coating method, or the like.

(Insulating Layer)

In the organic EL device, pixel defects based on leakage or a short circuit are easily generated since an electric field is applied to a thin film. In order to prevent this, an insulating thin layer may be inserted between a pair of electrodes.

Examples of substances used for the insulating layer include aluminum oxide, lithium fluoride, lithium oxide, cesium fluoride, cesium oxide, magnesium oxide, magnesium fluoride, calcium oxide, calcium fluoride, aluminum nitride, titanium oxide, silicon oxide, germanium oxide, silicon nitride, boron nitride, molybdenum oxide, ruthenium oxide, vanadium oxide, and the like. A mixture thereof may be used in the insulating layer, and a stacked body of a plurality of layers that include these substances can be also used for the insulating layer.

(Spacing Layer)

The spacing layer is a layer provided between a fluorescent emitting layer and a phosphorescent emitting layer when the fluorescent emitting layer and the phosphorescent emitting layer are stacked, in order to prevent diffusion of excitons generated in the phosphorescent emitting layer to the fluorescent emitting layer or in order to adjust the carrier balance. Further, the spacing layer can be provided between plural phosphorescent emitting layers.

Since the spacing layer is provided between the emitting layers, the material used for the spacing layer is preferably a substance that has both electron-transporting property and hole-transporting property. In order to prevent diffusion of the triplet energy in adjacent phosphorescent emitting layers, it is preferred that the material used for the spacing layer have a triplet energy of 2.6 eV or more.

As the material used for the spacing layer, the same materials as those used in the above-mentioned hole-transporting layer can be given.

(Electron-Blocking Layer, Hole-Blocking Layer, Exciton-Blocking Layer)

An electron-blocking layer, a hole-blocking layer, an exciton (triplet)-blocking layer, and the like may be provided in adjacent to the emitting layer.

The electron-blocking layer has a function of preventing leakage of electrons from the emitting layer to the hole-transporting layer. The hole-blocking layer has a function of preventing leakage of holes from the emitting layer to the electron-transporting layer. The exciton-blocking layer has a function of preventing diffusion of excitons generated in the emitting layer to the adjacent layers to confine the excitons within the emitting layer.

(Capping Layer)

The organic EL device can be provided with a capping layer above the cathode in order to adjust the intensity of the outcoupled light with the optical interference effect.

For the capping layer, for example, a polymer compound, a metal oxide, a metal fluoride, a metal boride, silicon nitride, a silicon compound (silicon oxide, etc.) and the like can be used.

Further, an aromatic amine derivative, an anthracene derivative, a pyrene derivative, a fluorene derivative, and a dibenzofuran derivative can also be used for the capping layer.

A stacked body in which layers containing these substances are stacked can also be used as a capping layer.

(Intermediate Layer)

In tandem-type organic EL device, an intermediate layer is provided.

(Method for Forming a Layer)

The method for forming each layer of the organic EL device is not particularly limited unless otherwise specified. As the film forming method, a known film-forming method such as a dry film-forming method, a wet film-forming method or the like can be used. Specific examples of the dry film-forming method include a vacuum deposition method, a sputtering method, a plasma method, an ion plating method, and the like. Specific examples of the wet film-forming method include various coating methods such as a spin coating method, a dipping method, a flow coating method, and an inkjet method.

(Film Thickness)

The film thickness of each layer of the organic EL device is not particularly limited unless otherwise specified. If the film thickness is too small, defects such as pinholes are likely to occur to make it difficult to obtain an enough luminance. On the other hand, if the film thickness is too large, a high driving voltage is required to be applied, leading to a lowering in efficiency. In this respect, the film thickness is preferably 1 nm to 10 μm, and more preferably 1 nm to 0.2 μm.

[Electronic Apparatus]

The electronic apparatus according to one aspect of the invention includes the above-described organic EL device according to one aspect of the invention. Examples of the electronic apparatus include display parts such as an organic EL panel module; display devices of television sets, mobile phones, smart phones, personal computers, and the like; and emitting devices of a lighting device and a vehicle lighting device.

EXAMPLES

Next, the invention will be explained in more detail with reference to Examples and Comparative Examples. However, it should be noted that the invention be not limited due to the description of these Examples at all.

Synthesis Example 1 (Synthesis of Compound ET-1)

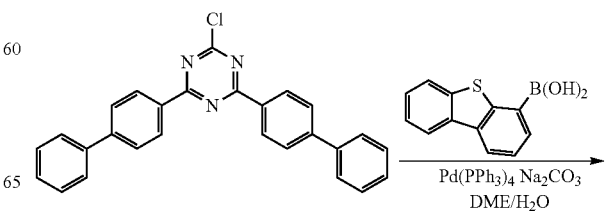

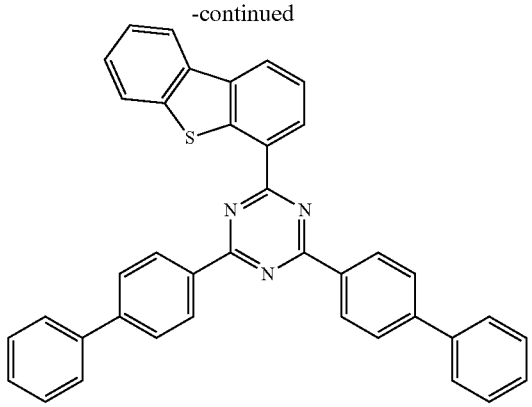

ET-1

2,4-bis(4-biphenyl-yl)-6-chloro-1,3,5-triazine (5.0 g) and dibenzothiophene-4-boronic acid (3.0 g) were added to dimethoxyethane (200 mL), and argon gas was passed through the solution for 5 minutes. Tetrakis(triphenylphosphine)palladium (0.55 g) and an aqueous solution of sodium carbonate (2M, 18 mL) were added thereto, and under an argon atmosphere, the mixture was stirred under the condition of refluxing with heat for 5 hours. Solids precipitated by brought the mixture back to room temperature were collected by filtration, and washed with methanol and water. The solids was dissolved in 200 mL of chlorobenzene by heating, and insoluble matter was filtered off with celite. The solids precipitated by concentration under reduced pressure were recrystallized from toluene to obtain Compound ET-1 (5.8 g, 86% in yield). The molecular weight of Compound ET-1 was 567.71, and the mass spectrum of the resulting compound was analyzed as m/z (ratio of mass to charge) =567, thereby identified as Compound ET-1.

Synthesis Example 2 (Synthesis of Compound ET-2)

(1) Synthesis of Intermediate A

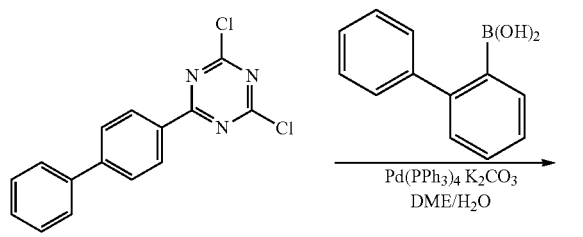

Intermediate A 2-(4-biphenylyl)-4,6-dichloro-1,3,5-triazine (2.0 g) and 2-biphenylboronic acid (1.18 g) were dissolved in dimethoxyethane (90 mL), and argon gas was passed through the solution for 5 minutes. Tetrakis(triphenylphosphine)palladium (15 mg) and an aqueous solution of potassium carbonate (2M, 10 mL) was added thereto, and the mixture was heated at 65° C. for 5 hours with stirring under an argon atmosphere. The reaction solution was subjected to column chromatography to obtain Intermediate A (0.8 g, 29% in yield).

(2) Synthesis of Compound ET-2

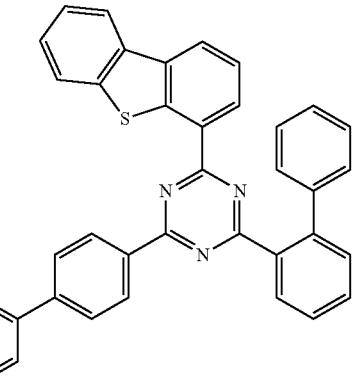

ET-2

Intermediate A (0.8 g) and dibenzothiophene-4-boronic acid (0.65 g) were added to dimethoxyethane (30 mL), and argon gas was passed through the solution for 5 minutes. Tetrakis(triphenylphosphine)palladium (4.0 mg) and an aqueous solution of potassium carbonate (2M, 3.0 mL) was added thereto, and the mixture was heated at 65° C. for 3 hours with stirring under an argon atmosphere. The reaction solution was subjected to column chromatography to obtain Compound ET-2 (0.70 g, 65% in yield). The molecular weight of Compound ET-2 was 567.71, and the mass spectrum of the resulting compound was analyzed as m/z (ratio of mass to charge)=567, thereby identified as Compound ET-2.

Synthesis Example 3 (Synthesis of Compound ET-3)

(1) Synthesis of Intermediate B

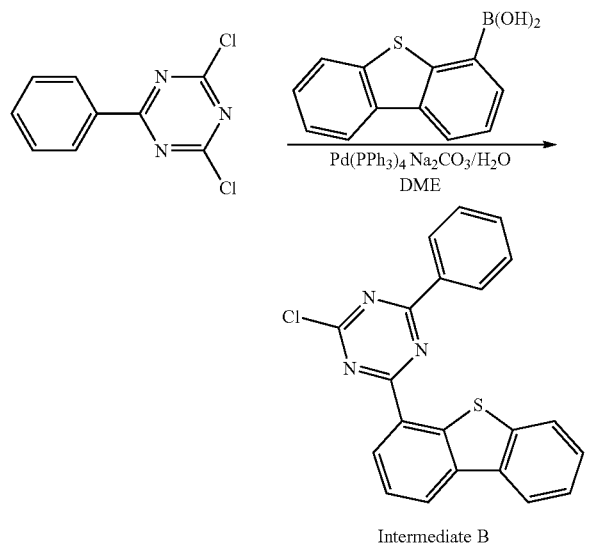

2,4-dichloro-6-phenyl-1,3,5-triazine (5.0 g) and dibenzothiophene-4-boronic acid (4.5 g), tetrakis(triphenylphosphine)palladium (0.5 g) were dissolved in dimethoxyethane (221 mL), and the inside of the vessel was replaced with nitrogen. Thereafter, a 2M aqueous solution of sodium carbonate (33 mL) was added thereto, and the mixture was heated at 80° C. under a nitrogen atmosphere and stirred for 6 hours. Water was added to the reaction solution, and precipitated solids were collected by filtration. The solids were washed with acetone to obtain Intermediate B (5.0 g, 60% in yield).

(2) Synthesis of Intermediate C

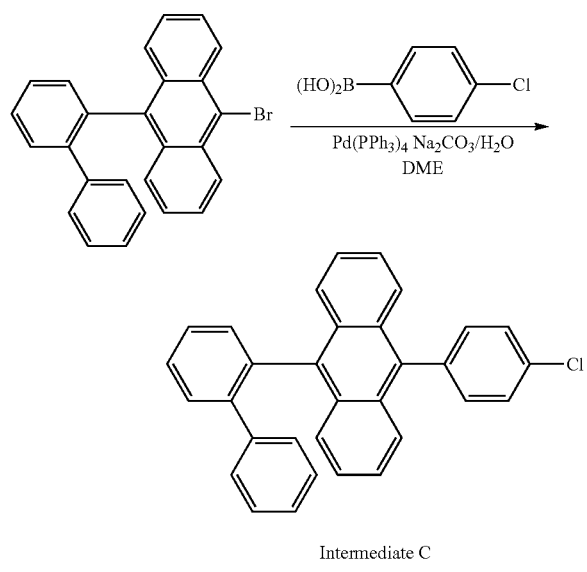

9-([1,1'-biphenyl]-2-yl)-10-bromoanthracene (10.0 g) and 4-chlorophenylboronic acid (3.8 g) were dissolved in dimethoxyethane (244 mL), and tetrakis(triphenylphosphine)palladium (0.35 g) was added to thereto, and the inside of the vessel was replaced with nitrogen. Thereafter, a 2M aqueous solution of sodium carbonate (37 mL) was added, and the mixture was heated at 75° C. under a nitrogen atmosphere and stirred overnight. The reaction solution was purified by column chromatography to obtain Intermediate C (10.1 g, 94% in yield).

(3) Synthesis of Intermediate D

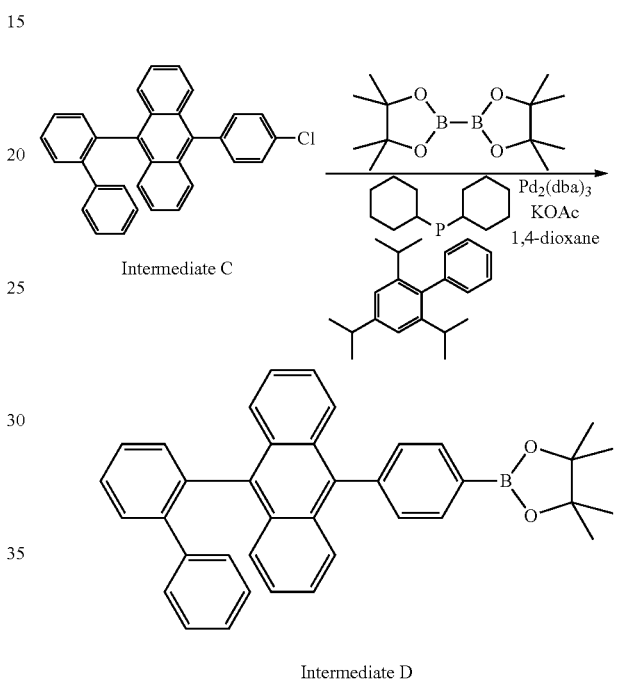

Intermediate C (12.6 g), bis(pinacolato)diboron (7.3 g), potassium acetate (8.4 g), 2-dicyclohexylphosphino-2',4',6'-triisopropylbiphenyl (1.1 g), tris(dibenzylideneacetone)diparazium (1.0 g) were added to 1,4-dioxane (286 mL), and the inside of the vessel was replaced with nitrogen. Thereafter, the mixture was heated at 100° C. and stirred for 6 hours under a nitrogen atmosphere. The reaction solution was purified by column chromatography to obtain Intermediate D (14.0 g, 91% in yield).

(4) Synthesis of Compound ET-3

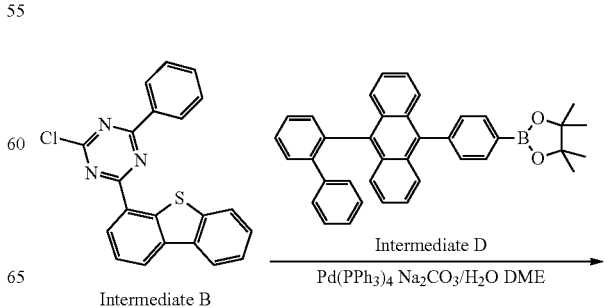

(2) Synthesis of Compound ET-4

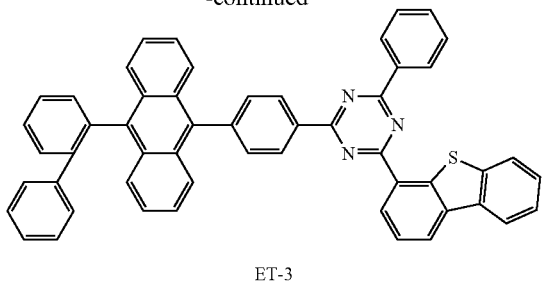

ET-3

Intermediate B (4.6 g), Intermediate D (5.2 g), and tetrakis(triphenylphosphine)palladium (0.4 g) were added to dimethoxyethane (123 mL), and the inside of the vessel was replaced with nitrogen. Thereafter, a 2M aqueous solution of sodium carbonate (18 mL) was added thereto, and the mixture was refluxed with heat under nitrogen atmosphere, and stirred overnight. Methanol was added to the reaction solution, and precipitated solids were collected by filtration. The solids were recrystallized from toluene to obtain Compound ET-3 (7.7 g, 84% in yield). The molecular weight of Compound ET-3 was 743.93, and the mass spectrum of the resulting compound was analyzed as m/z (ratio of mass to charge)=743, thereby identified as Compound ET-3.

Synthesis Example 4 (Synthesis of Compound ET-4)

(1) Synthesis of Intermediate E

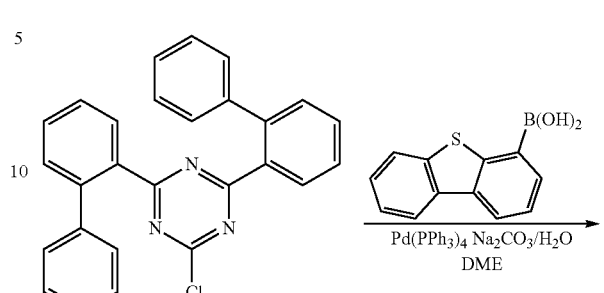

Intermediate E

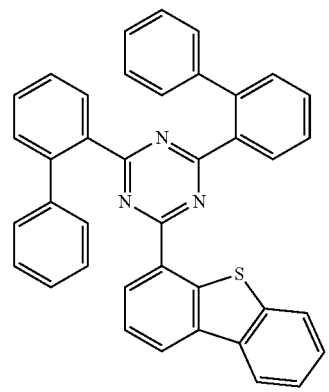

ET-4

Cyanuric acid chloride (5.0 g) and 2-biphenylboronic acid (21 g) were dissolved in toluene (271 mL), and dichlorobis(triphenylphosphine)palladium (0.04 g) was added thereto, and the inside of the vessel was replaced with argon. Thereafter, a 2M aqueous solution of potassium carbonate (81 mL) was added thereto, and the mixture was heated at 50° C. under an argon atmosphere, and stirred for 12 hours. The reaction solution was purified by column chromatography to obtain Intermediate E (5.0 g, 22% in yield).

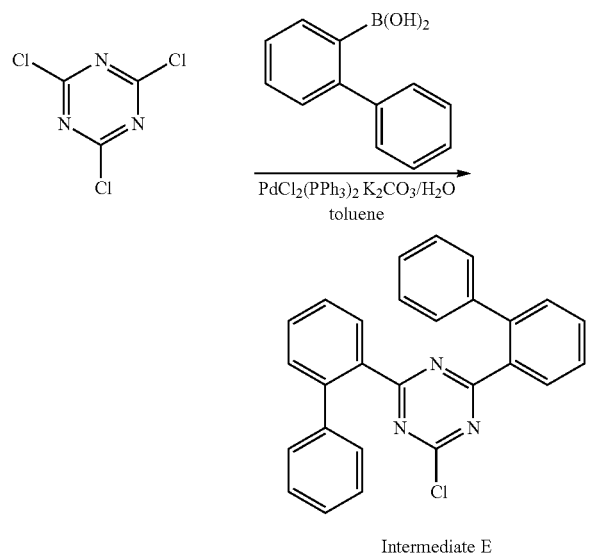

Intermediate E

Intermediate E (5.0 g) and dibenzothiophene-4-boronic acid (3.3 g) were dissolved in dimethoxyethane (120 mL), and tetrakis(triphenylphosphine)palladium (0.55 g) was added thereto, and the inside of the vessel was replaced with argon. Thereafter, a 2M aqueous solution of sodium carbonate (18 mL) was added thereto, and the mixture was refluxed with heat under an argon atmosphere, and stirred for 5 hours. The reaction solution was concentrated, and the resulting solids were recrystallized from toluene to obtain Compound ET-4 (4.8 g, 71% in yield). The molecular weight of Compound ET-4 was 567.71, and the mass spectrum of the resulting compound was analyzed as m/z (ratio of mass to charge)=567, thereby identified as Compound ET-4.

Synthesis Example 5 (Synthesis of Compound ET-5)

(1) Synthesis of Intermediate F

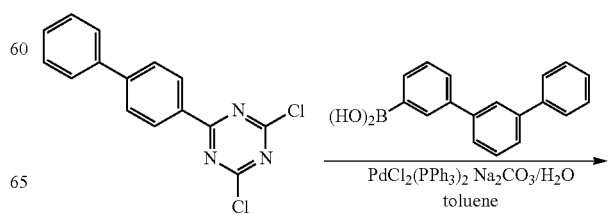

Synthesis Example 6 (Synthesis of Compound ET-6)

(1) Synthesis of Intermediate G

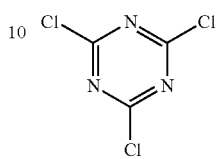
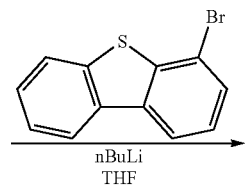

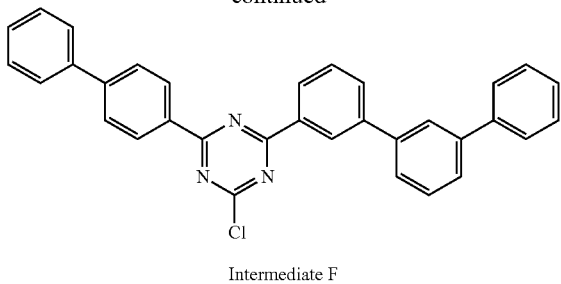

Intermediate F 2-(4-biphenylyl)-4,6-dichloro-1,3,5-triazine (0.5 g) and [1,1': 3',1"-terphenyl]-3-yl-boronic acid (synthesized according to the description of JP5357150B2) (0.5 g), dichlorobis(triphenylphosphine)palladium (1.1 mg) was dissolved in toluene (8 mL), and the inside of the vessel was replaced with argon. Thereafter, a 2M aqueous solution of sodium carbonate (33 mL) was added thereto, and the mixture was heated at 60° C. under an argon atmosphere and stirred for 4 hours. Water was added to the reaction solution, and precipitated solids were collected by filtration. The solids were recrystallized from toluene to obtain Intermediate F (0.46 g, 57% in yield).

(2) Synthesis of Compound ET-5

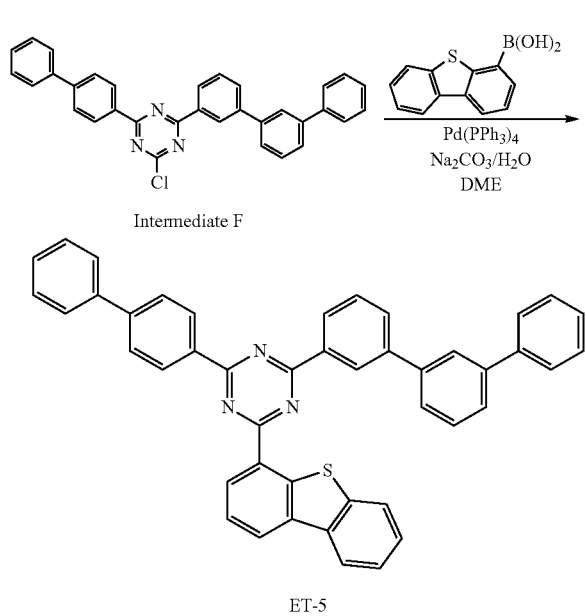

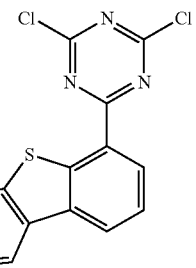

Intermediate G 4-bromodibenzothiophene (5.0 g) was dissolved in tetrahydrofuran (50 mL). The reaction vessel was cooled to −78° C. under an argon atmosphere and a 1.6M n-butyllithium solution (14 mL) was dropwise added to this solution. After stirring for 30 minutes, the solution was dropwise added to a tetrahydro tetrahydrofuran solution of cyanuric acid chloride (3.5 g) (50 mL) cooled to −78° C. over 30 minutes. After stirring at room temperature overnight, the solvent was distilled off under reduced pressure, and precipitated solids were washed with acetone to obtain Intermediate G (2.6 g, 41% in yield).

Intermediate F (0.47 g) and dibenzothiophene-4-boronic acid (0.32 g) were dissolved in dimethoxyethane (9.4 mL), and tetrakis(triphenylphosphine)palladium (43 mg) was added thereto, and the inside of the vessel was replaced with argon. Thereafter, a 2M aqueous solution of sodium carbonate (1.2 mL) was added thereto, and the mixture was refluxed with heat under an argon atmosphere for 3 hours. The reaction solution was concentrated and the resulting solids were recrystallized from toluene to obtain Compound ET-5 (0.4 g, 66% in yield). The molecular weight of Compound ET-5 was 643.81, and the mass spectrum of the resulting compound was analyzed as m/z (ratio of mass to charge)=643, thereby identified as Compound ET-5.

(2) Synthesis of Compound ET-6

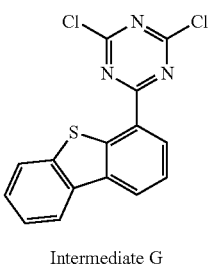
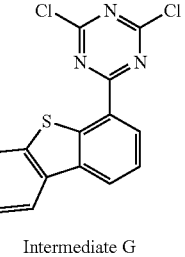

-continued

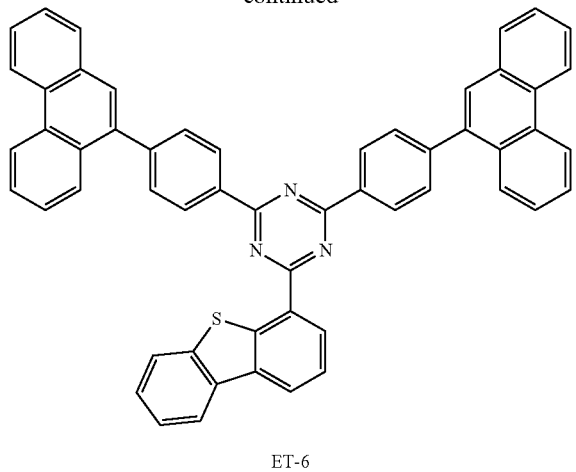

ET-6

Intermediate G (2.5 g) and 4-(9-phenanthrenyl)phenylboronic acid (synthesized according to the description of U.S. Pat. No. 8,940,412B2) (1.4 g) were dissolved in dimethoxyethane (40 mL), and tetrakis(triphenylphosphine)palladium (0.1 g) was added thereto. After the inside of the vessel was replaced with argon, a 2M aqueous solution of potassium carbonate (13 mL) was added thereto and refluxed with heat under stirring for 4 hours. Water was added to the reaction solution, and precipitated solids were collected by filtration. The solids were washed with dichloromethane and recrystallized from toluene to obtain Compound ET-6 (0.9 g, 28%). The molecular weight of Compound ET-6 was 767.95, and the mass spectrum of the resulting compound was analyzed as m/z (ratio of mass to charge)=767, thereby identified as Compound ET-6.

Synthesis Example 7 (Synthesis of Compound ET-7)

Intermediate D

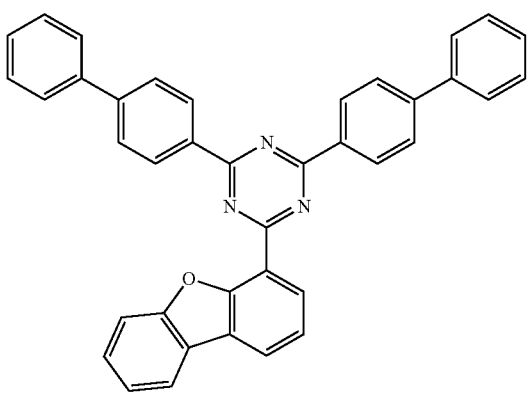

ET-7

Except for the use of 2-chloro-4-(4-dibenzothienyl)-6-phenyltriazine (synthesized by the method as described in US20180006237A1) in place of Intermediate B, ET-7 was synthesized in the same manner as in Synthetic Example 3.

The molecular weight of Compound ET-7 was 727.87, and the mass spectrum of the resulting compound was analyzed as m/z (ratio of mass to charge)=727, thereby identified as Compound ET-7.

Synthesis Example 8 (Synthesis of Compound ET-8)

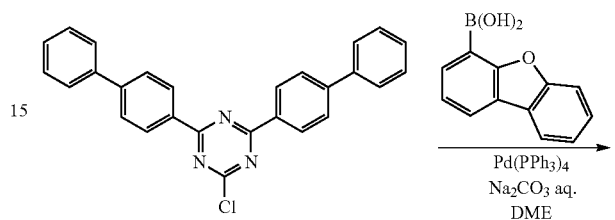

ET-8

2,4-bis(4-biphenyl-yl)-6-chloro-1,3,5-triazine (5.0 g) and dibenzofuran-4-boronic acid (3.8 g) were added to dimethoxyethane (200 mL), and argon gas was passed through the solution for 5 minutes. Tetrakis(triphenylphosphine) palladium (0.55 g) and an aqueous solution of sodium carbonate (2M, 18 mL) were added thereto, and under an argon atmosphere, the mixture was stirred under the condition of refluxing with heat for 5 hours. Solids precipitated by brought the mixture back to room temperature were collected by filtration, and washed with methanol and water. The solids were dissolved with 200 mL of chlorobenzene by heating, and insoluble matter was filtered off with celite. Solids precipitated by concentration under reduced pressure were recrystallized from toluene to obtain Compound ET-8 (5.3 g, 80% in yield). The molecular weight of Compound ET-8 was 551.65, and the mass spectrum of the resulting compound was analyzed as m/z (ratio of mass to charge)= 551, thereby identified as Compound ET-8.

Synthesis Example 9 (Synthesis of Compound ET-9)

(1) Synthesis of Intermediate H

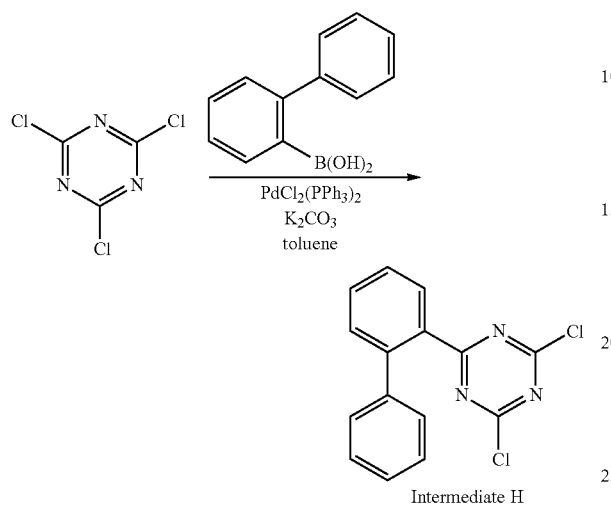

Cyanuric acid chloride (9.3 g) and 2-biphenylboronic acid (9.9 g) were dissolved in toluene (250 mL), and argon gas was passed through the solution for 5 minutes. Dichlorobis(triphenylphosphine)palladium (176 mg) and potassium carbonate (28 g) were added thereto and heated at 60° C. for 4 hours with stirring under an argon atmosphere. The reaction solution was subjected to column chromatography to obtain Intermediate H (3.4 g, 23% in yield).

(2) Synthesis of Intermediate I

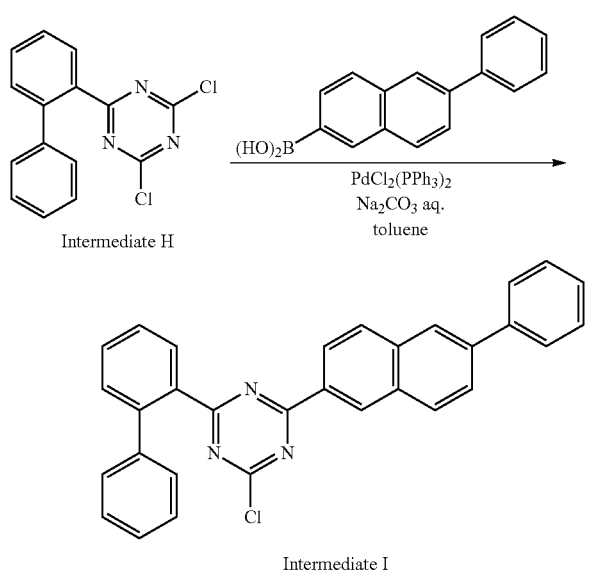

Intermediate H (4.4 g) and 6-phenyl-2-naphthalenylboronic acid (synthesized according to JP2010-241688A) (4.0 g) were added to toluene (73 mL), and argon gas was passed through the solution for 5 minutes. Dichlorobis(triphenylphosphine)palladium (10 mg) and an aqueous solution of sodium carbonate (2M, 22 mL) was added thereto and heated at 65° C. overnight with stirring under an argon atmosphere. The reaction solution was subjected to column chromatography to obtain Intermediate I (2.9 g, 42% in yield).

(3) Synthesis of Compound ET-9

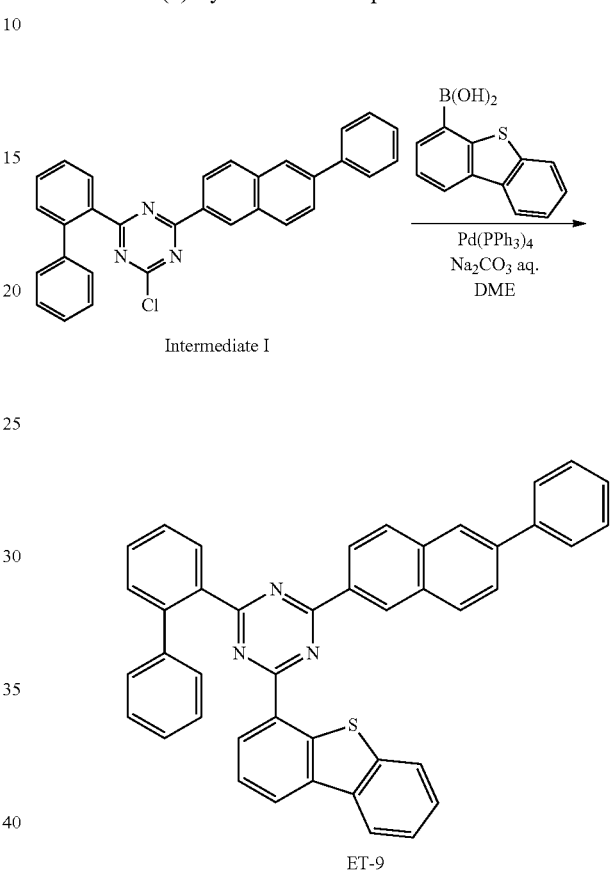

Intermediate I (2.9 g) and dibenzothiophene-4-boronic acid (2.1 g) were dissolved in dimethoxyethane (62 mL), and tetrakis(triphenylphosphine)palladium (290 mg) was added thereto, and the inside of the vessel was replaced with argon. Thereafter, a 2M aqueous solution of sodium carbonate (9.3 mL) was added thereto, and under an argon atmosphere, the mixture was refluxed with heat for 3 hours. The reaction solution was allowed to cool, and then solids were collected by filtration. To the solids, 500 mL of toluene was added, and the mixture was heated to dissolve the solids, and insoluble matter was filtered off by silica gel. Solids precipitated by concentration under reduced pressure were recrystallized from toluene to obtain Compound ET-9 (2.9 g, 76% in yield). The molecular weight of Compound ET-9 was 617.77, and the mass spectrum of the resulting compound was analyzed as m/z (ratio of mass to charge)=617, thereby identified as Compound ET-9.

Synthesis Example 10 (Synthesis of Compound ET-10)

(1) Synthesis of Intermediate J

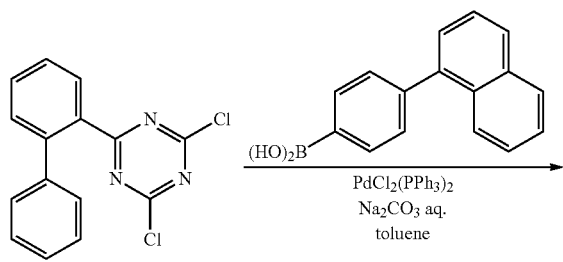

Intermediate H

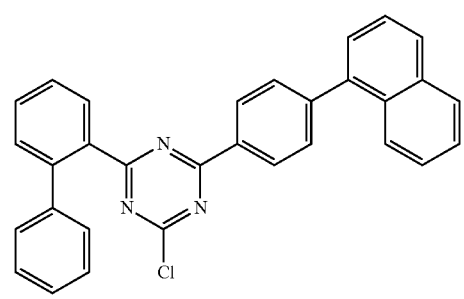

Intermediate J

Intermediate H (5.2 g) and 4-1-(naphthalenyl)phenylboronic acid (synthesized according to JP2013-546171A) (4.7 g) were added to toluene (86 mL), and argon gas was passed through the solution for 5 minutes. Dichlorobis(triphenylphosphine)palladium (12 mg) and an aqueous solution of sodium carbonate (2M, 21 mL) were added thereto and heated at 60° C. overnight with stirring under an argon atmosphere. The reaction solution was subjected to column chromatography to obtain Intermediate J (7.1 g, 81% in yield).

(2) Synthesis of Compound ET-10

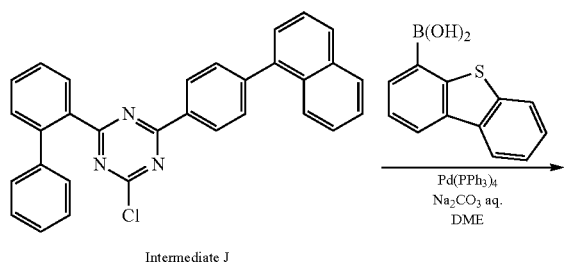

Intermediate J

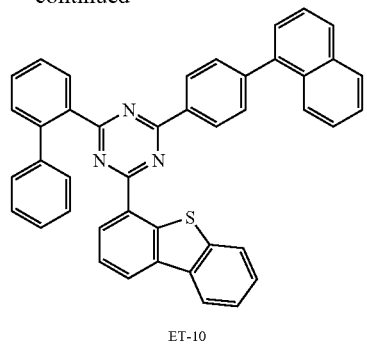

ET-10

Intermediate J (7.0 g) and dibenzothiophene-4-boronic acid (5.1 g) were dissolved in dimethoxyethane (150 mL), and tetrakis(triphenylphosphine)palladium (690 mg) was added thereto, and the inside of the vessel was replaced with argon. Thereafter, a 2M aqueous solution of sodium carbonate (19 mL) was added thereto, and the mixture was refluxed with heat under an argon atmosphere for 3 hours. The reaction solution was allowed to cool, and then solids were collected by filtration. To the solids, 580 mL of toluene was added, and the mixture was heated to dissolve the solids, and insoluble matter was filtered off by silica gel. Solids precipitated by concentration under reduced pressure were recrystallized from toluene to obtain Compound ET-10 (9.2 g, 68% in yield). The molecular weight of Compound ET-10 was 617.77, and the mass spectrum of the resulting compound was analyzed as m/z (ratio of mass to charge)=617, thereby identified as Compound ET-10.

Synthesis Example 11 (Synthesis of Compound ET-11)

(1) Synthesis of Intermediate K

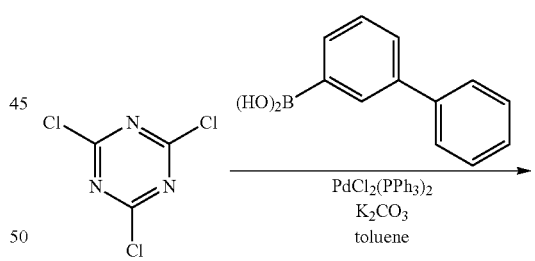

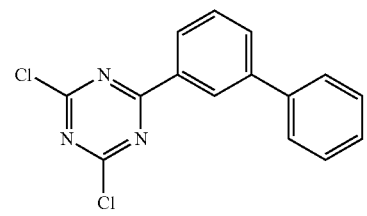

Intermediate K

Cyanuric acid chloride (9.3 g) and 3-biphenylboronic acid (9.9 g) were dissolved in toluene (250 mL), and argon gas was passed through the solution for 5 minutes. Dichlorobis(triphenylphosphine)palladium (180 mg) and potassium carbonate (28 g) was added thereto and heated at 60° C. for 4 hours with stirring under an argon atmosphere. The reaction solution was filtered, followed by concentration of the filtrate. The residue was subjected to column chromatography to obtain Intermediate K (5.9 g, 40% in yield).

(2) Synthesis of Intermediate L

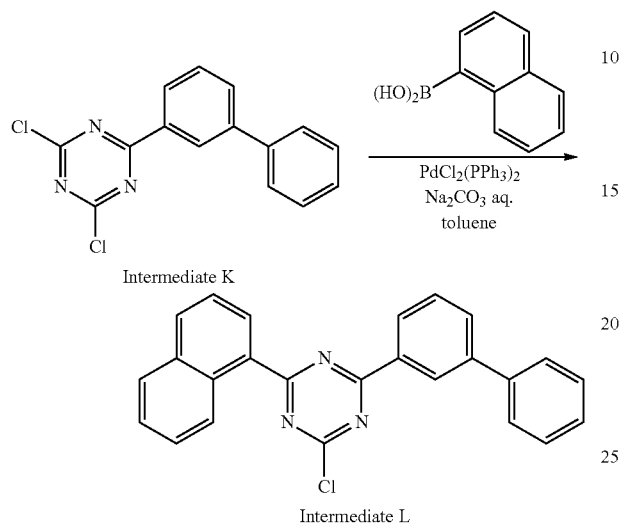

Intermediate K (4.5 g) and naphthalene-1-boronic acid (2.8 g) were added to toluene (80 mL), and argon gas was passed through the solution for 5 minutes. Dichlorobis(triphenylphosphine)palladium (10 mg) and an aqueous solution of sodium carbonate (2M, 25 mL) were added thereto and heated at 60° C. overnight with stirring under an argon atmosphere. The reaction solution was subjected to column chromatography to obtain Intermediate L (3.5 g, 60% in yield).

(3) Synthesis of Compound ET-11

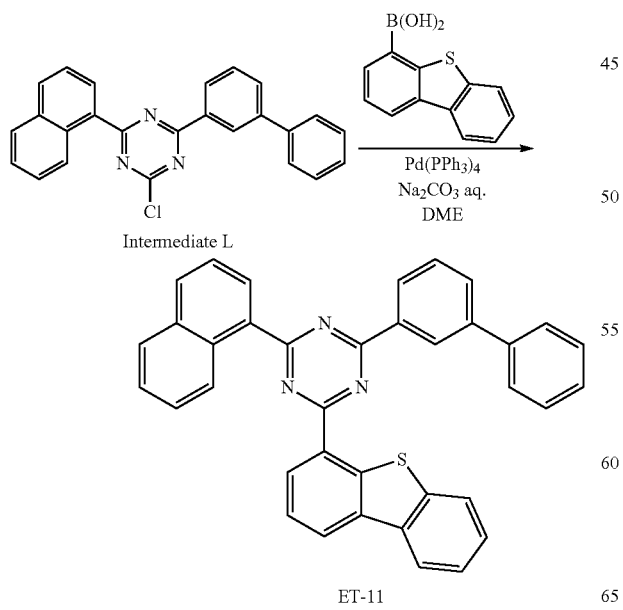

Intermediate L (3.5 g) and dibenzothiophene-4-boronic acid (3.0 g) were dissolved in dimethoxyethane (80 mL), and tetrakis(triphenylphosphine)palladium (310 mg) was added thereto, and the inside of the vessel was replaced with argon. Thereafter, a 2M aqueous solution of sodium carbonate (11 mL) was added thereto, and the mixture was refluxed with heat under an argon atmosphere for 3 hours. The reaction solution was allowed to cool, and then solids were collected by filtration. To the solids, toluene (700 mL) was added, and the mixture was heated to dissolve the solids, and insoluble matter was filtered off by silica gel. Solids precipitated by concentration under reduced pressure were recrystallized from toluene to obtain Compound ET-11 (3.4 g, 71% in yield). The molecular weight of Compound ET-11 was 541.67, and the mass spectrum of the resulting compound was analyzed as m/z (ratio of mass to charge)=541, thereby identified as Compound ET-11.

Synthesis Example 12 (Synthesis of Compound ET-12)

(1) Synthesis of Intermediate M

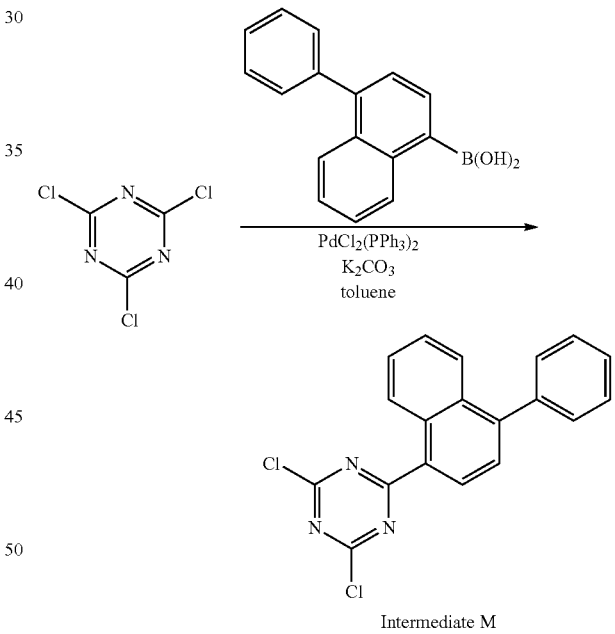

Cyanuric acid chloride (9.5 g) and 4-phenylnaphthalene-1-boronic acid (12 g) were dissolved in toluene (200 mL), and argon gas was passed through the solution for 5 minutes. Dichlorobis(triphenylphosphine)palladium (190 mg) and potassium carbonate (31 g) were added thereto and heated at 60° C. for 4 hours with stirring under an argon atmosphere. The reaction solution was filtered, followed by concentration of the filtrate. The residue was subjected to column chromatography to obtain Intermediate M (10 g, 55% in yield).

(2) Synthesis of Intermediate N

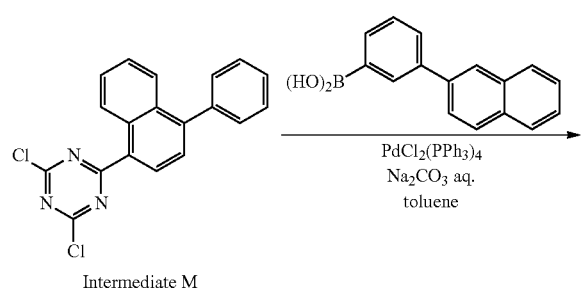

Intermediate M

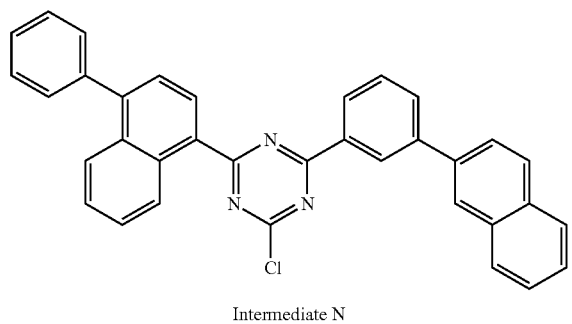

Intermediate N

Intermediate M (8.2 g) and 3-(2-naphthyl)phenylboronic acid (6.4 g) were added to toluene (110 mL), and argon gas was passed through the solution for 5 minutes. Dichlorobis(triphenylphosphine)palladium (21 mg) and an aqueous solution of sodium carbonate (2M, 20 mL) were added thereto and heated at 60° C. overnight with stirring under an argon atmosphere. The reaction solution was subjected to column chromatography to obtain Intermediate N (8.9 g, 73% in yield).

(3) Synthesis of Compound ET-12

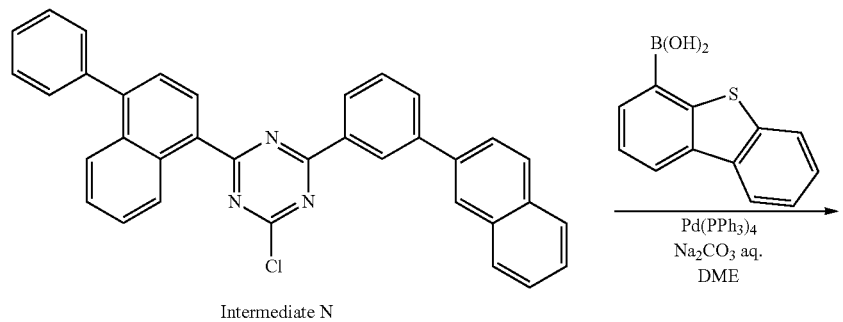

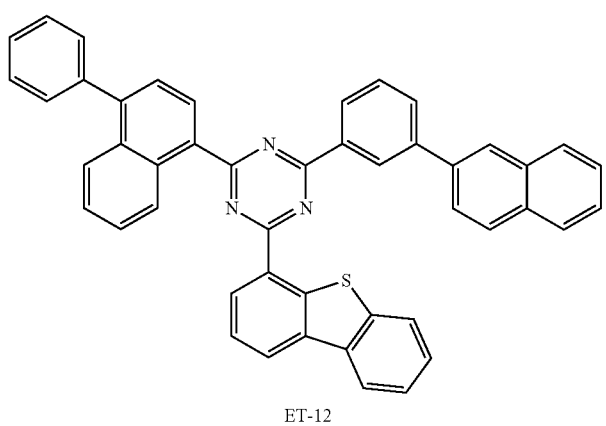

ET-12

Intermediate N (7.5 g) and dibenzothiophene-4-boronic acid (4.9 g) were dissolved in dimethoxyethane (130 mL), and tetrakis(triphenylphosphine)palladium (420 mg) was added thereto, and the inside of the vessel was replaced with argon. Thereafter, a 2M aqueous solution of sodium carbonate (20 mL) was added thereto, and the mixture was refluxed with heat under an argon atmosphere for 5 hours. The reaction solution was allowed to cool, and then solids were collected by filtration. To the solids, toluene (300 mL) was added, and the mixture was heated to dissolve the solids, and insoluble matter was filtered off by silica gel. Solids precipitated by concentration under reduced pressure were recrystallized from toluene to obtain Compound ET-12 (4.1 g, 43% in yield). The molecular weight of Compound ET-12 was 667.83, and the mass spectrum of the resulting compound was analyzed as m/z (ratio of mass to charge)=667, thereby identified as Compound ET-12.

Synthesis Example 13 (Synthesis of Compound ET-13)

(1) Synthesis of Intermediate O

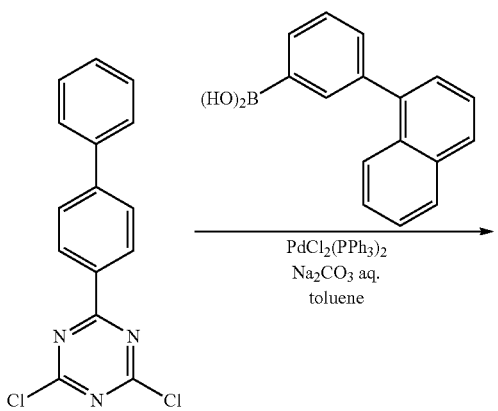

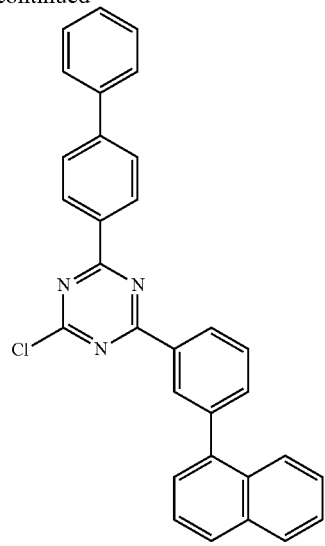

Intermediate O 2-(4-biphenylyl)-4,6-dichloro-1,3,5-triazine (5.6 g), 3-(1-naphthyl) phenylboronic acid (4.5 g) and dichlorobis(triphenylphosphine)palladium (24 mg) were dissolved in toluene (90 mL), and the inside of the vessel was replaced with argon. Thereafter, a 2M aqueous solution of sodium carbonate (15 mL) was added thereto, and the mixture was heated at 60° C. under an argon atmosphere and stirred overnight. Water was added to the reaction solution, and precipitated solids were collected by filtration. The solids were dissolved in toluene and filtered, followed by concentration of the filtrate. The resulting solids were recrystallized from toluene to obtain Intermediate O (6.0 g, 69% in yield).

(2) Synthesis of Compound ET-13

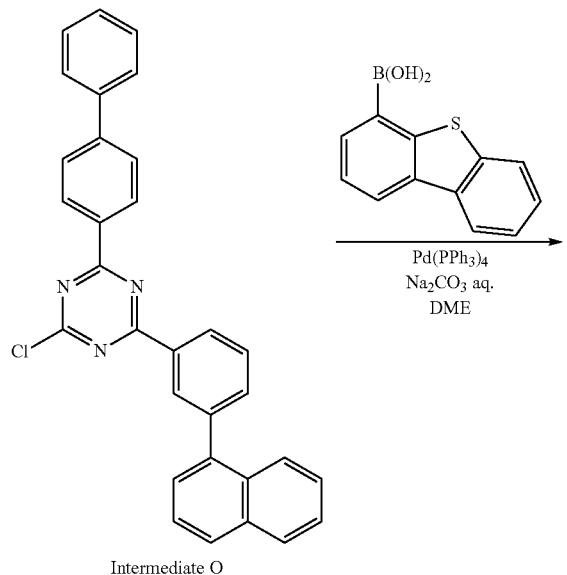

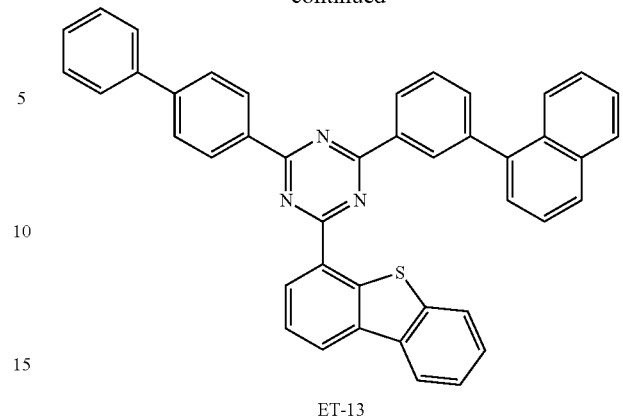

ET-13

Intermediate O (5.3 g) and dibenzothiophene-4-boronic acid (3.9 g) were dissolved in dimethoxyethane (200 mL) and tetrakis(triphenylphosphine)palladium (450 mg) was added thereto and the inside of the vessel was replaced with argon. Thereafter, a 2M aqueous solution of sodium carbonate (17 mL) was added thereto, and the mixture was heated and refluxed under an argon atmosphere, and stirred for 6 hours. The reaction solution was allowed to cool, and then solids were collected by filtration. To the solid, toluene (620 mL) was added, and the solids were dissolved with heat, and insoluble matter was filtered off by silica gel. Solids precipitated by concentration under reduced pressure were recrystallized from toluene to obtain Compound ET-13 (5.7 g, 82% in yield). The molecular weight of Compound ET-13 was 617.77, and the mass spectrum of the resulting compound was analyzed as m/z (ratio of mass to charge)=617, thereby identified as Compound ET-13.

Synthesis Example 14 (Synthesis of Compound ET-14)

(1) Synthesis of Intermediate P

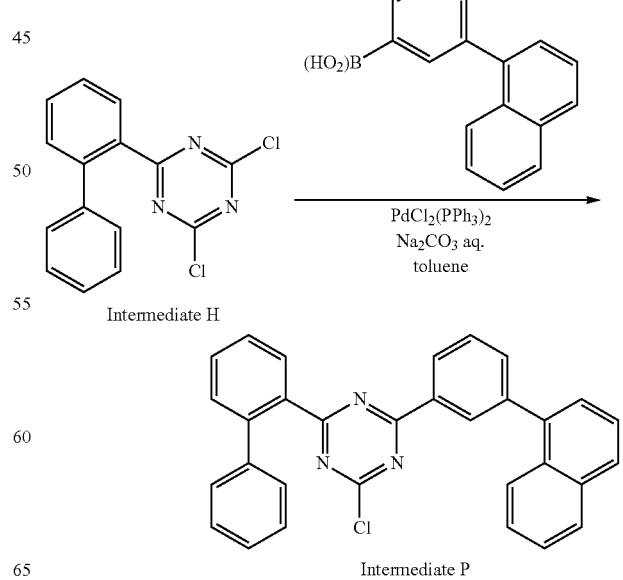

Intermediate P

Intermediate H (6.3 g), 3-(1-naphthyl)phenylboronic acid (4.9 g), dichlorobis(triphenylphosphine)palladium (15 mg) were dissolved in toluene (84 mL) and the inside of the vessel was replaced with argon. Thereafter, a 2M aqueous solution of sodium carbonate (14 mL) was added thereto, and the mixture was heated at 60° C. under an argon atmosphere and stirred for 4 hours. Water was added to the reaction solution, and precipitated solids were collected by filtration. The solids were dissolved in toluene and filtered, followed by concentration of the filtrate. The resulting solids were recrystallized from toluene to obtain Intermediate P (6.3 g, 65% in yield).

(2) Synthesis of Compound ET-14

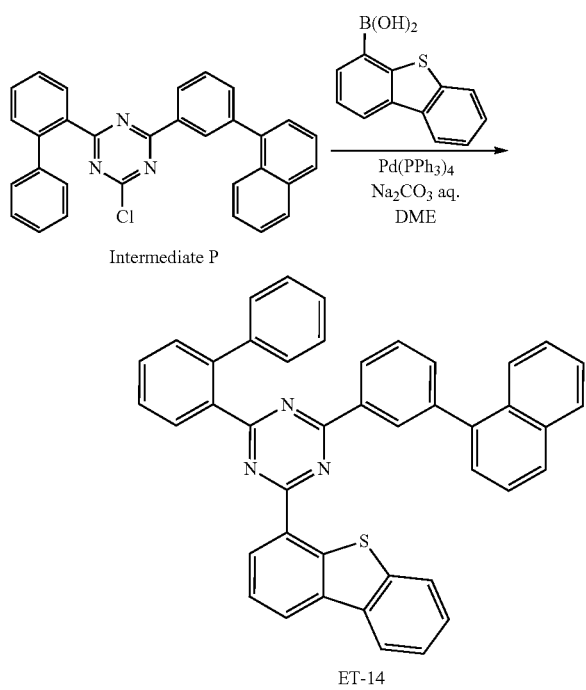

Intermediate P (5.6 g), dibenzothiophene-4-boronic acid (4.1 g) were dissolved in dimethoxyethane (130 mL), and tetrakis(triphenylphosphine)palladium (554 mg) was added thereto, and the inside of the vessel was replaced with argon. Thereafter, a 2M aqueous solution of sodium carbonate (15 mL) was added thereto, and the mixture was refluxed with heat under an argon atmosphere for 4 hours. The reaction solution was allowed to cool, and then solids were collected by filtration. To the solids, toluene (350 mL) was added, and the mixture was heated to dissolve the solids, and insoluble matter was filtered off by silica gel. Solids precipitated by concentration under reduced pressure were recrystallized from toluene to obtain Compound ET-14 (6.5 g, 88% in yield). The molecular weight of Compound ET-14 was 617.77, and the mass spectrum of the resulting compound was analyzed as m/z (ratio of mass to charge)=617, thereby identified as Compound ET-14.

Example 1

(Fabrication of Organic EL Device)

A 25 mm×75 mm×1.1 mm-thick glass substrate with an ITO transparent electrode (anode) (manufactured by GEO-MATEC Co., Ltd.) was subjected to ultrasonic cleaning in isopropyl alcohol for 5 minutes, and then subjected to UV-ozone cleaning for 30 minutes. The thickness of the ITO film was 130 nm.

The glass substrate with the transparent electrode after being cleaned was mounted onto a substrate holder in a vacuum vapor deposition apparatus. First, Compound HI was deposited on the surface of the glass substrate on which the transparent electrode was formed so as to cover the transparent electrode to form a HI film having a thickness of 5 nm. This HI film functions as a hole-injecting layer.

Following the formation of the HI film, Compound HT-1 was deposited to form a HT-1 film having a thickness of 80 nm on the HI film. The HT-1 film functions as a hole-transporting layer (first hole-transporting layer).

After formation of the HT-1 film, Compound HT-2 was deposited to form a HT-2 film having a thickness of 10 nm on the HT-1 film. The HT-2 film functions as an electron-blocking layer (second hole-transporting layer).

Compound BH-1 (host material) and Compound BD-1 (dopant material) were co-deposited on the HT-2 film so as to be 4 mass % in a proportion (mass ratio) of Compound BD-1, thereby forming a BH-1:BD-1 film having a thickness of 25 nm. This BH-1:BD-1 film functions as an emitting layer.

Compound ET-1 and Liq were co-deposited on this emitting layer so as to be 50 mass % in a proportion of Liq, thereby forming a ET-1:Liq film having a thickness of 25 nm. The ET-1:Liq film functions as a first electron-transporting layer (hole barrier layer).

Liq was deposited on this first electron-transporting layer to form a Liq film having a thickness of 1 nm. The Liq film functions as a second electron-transporting layer.

Metal Al was deposited on the second electron-transporting layer to form a metal cathode having a thickness of 80 nm to obtain an organic EL device.

The layer configuration of the obtained organic EL device is as follows. ITO(130)/HI(5)/HT-1(80)/HT-2(10)/BH-1: BD-1(25; 4 mass %)/ET-1: Lig(25; 50 mass %)/Liq(1)/Al (80)

Numerical values in parentheses indicate film thickness (unit: nm).

(Evaluation of Organic EL Device)

Initial characteristics of the obtained organic EL devices were measured by driving at a constant current of 10 mA/cm² of DC (direct current) at room temperature. The measurement results of the driving voltage are shown in Table 1.

Furthermore, voltage was applied to the organic EL device so as to be 10 mA/cm² in current density, thereby obtaining an EL emission spectrum by using Spectroradiometer CS-1000 (manufactured by Konica Minolta, Inc.). External quantum efficiency (EQE) (%) was calculated from the obtained spectral radiance spectrum. The results are shown in Table 1.

Examples 2 to 8 and Comparative Example 1

The organic EL devices were fabricated and evaluated in the same manner as in Example 1 except that the compounds shown in Table 1 were used as materials of the first electron-transporting layer. The results are shown in Table 1.

Compounds used in Examples 1 to 8 and Comparative Example 1 are as follows.

-continued
HI
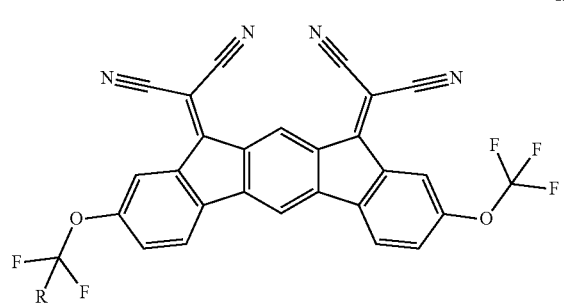
HT-1
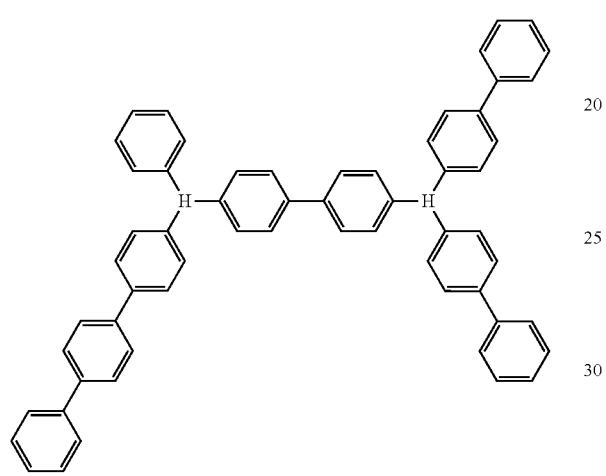
HT-2
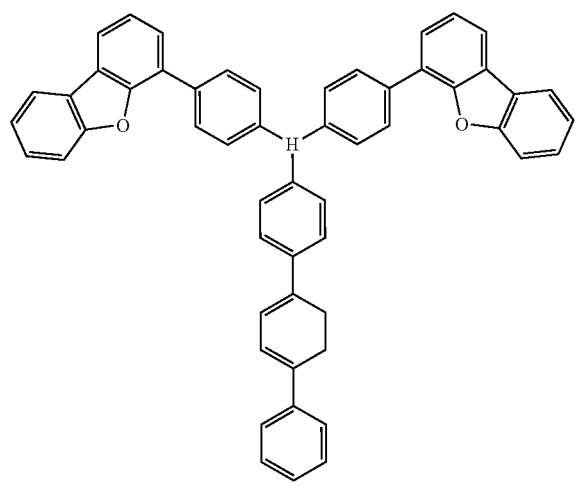
BH-1
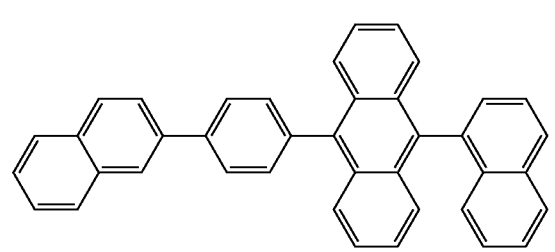
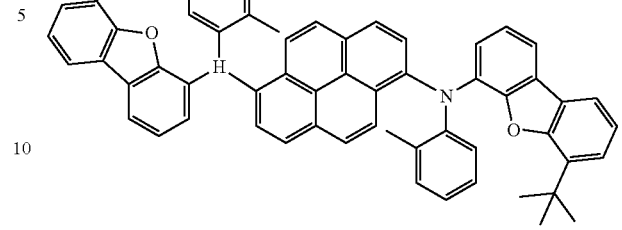
Liq
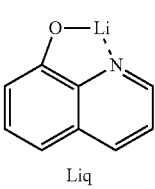
Comp. ET-1
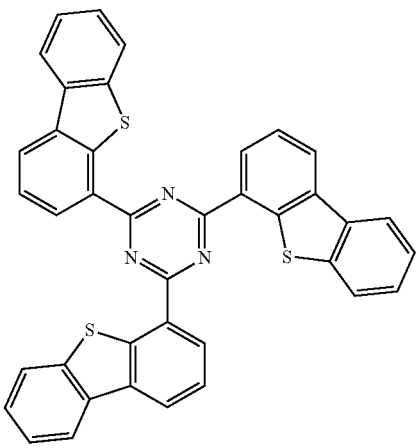
ET-1
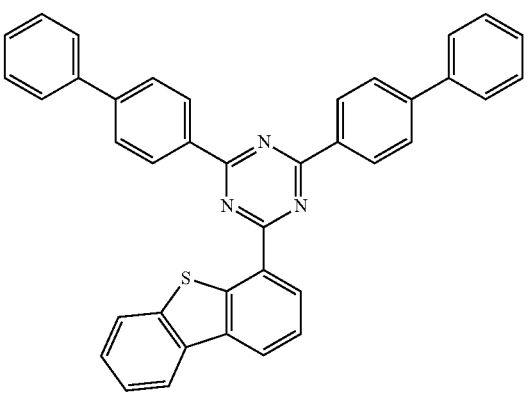

-continued

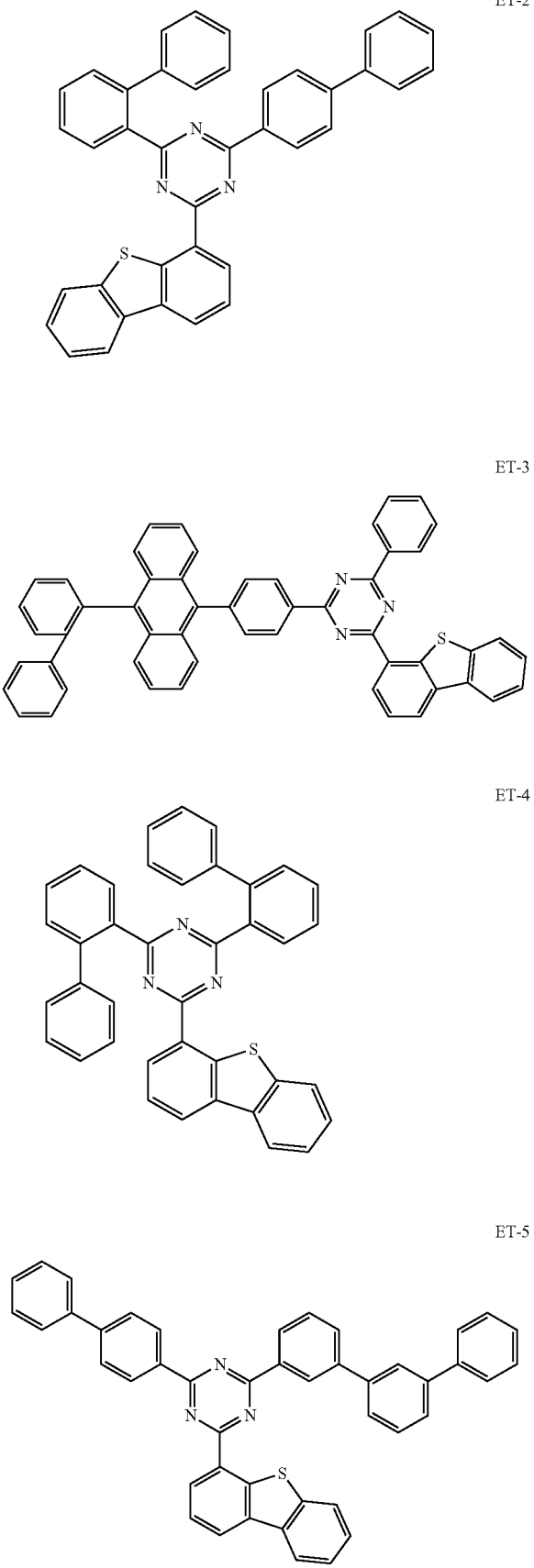

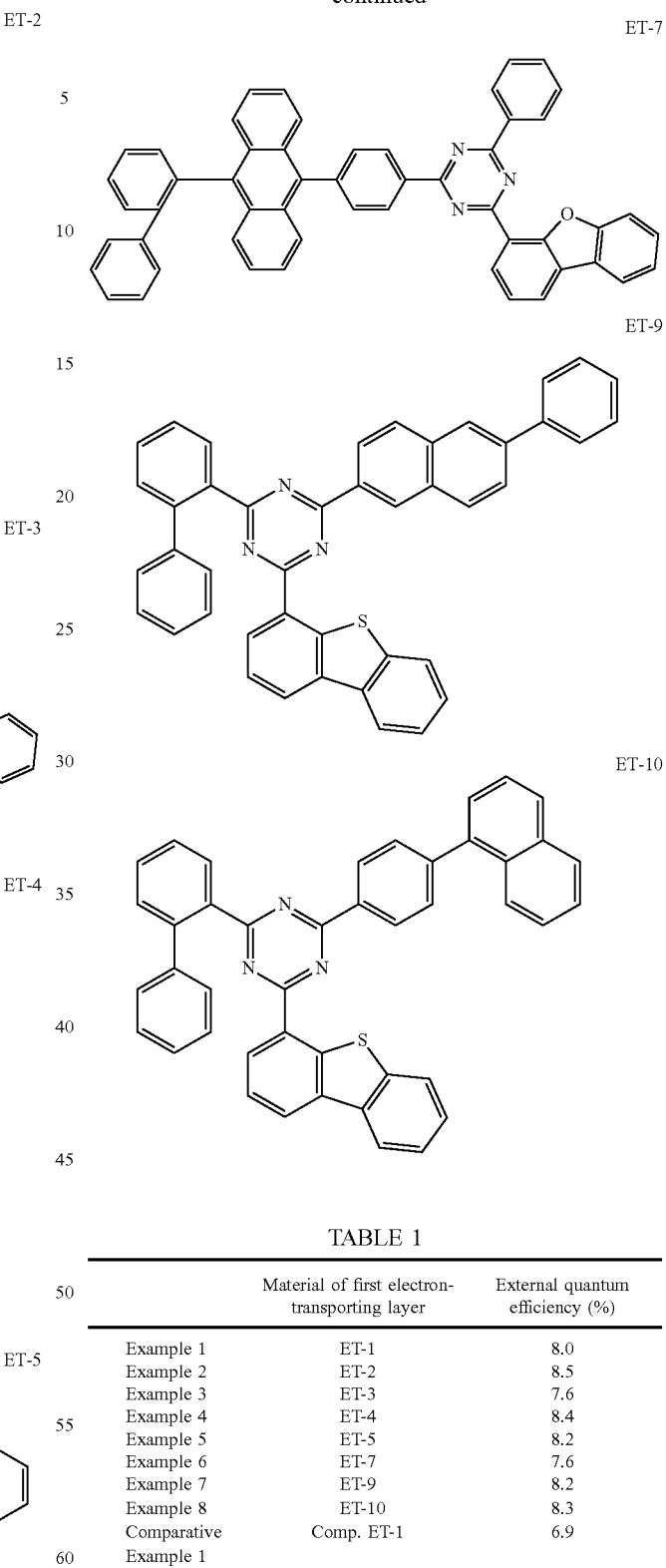

TABLE 1

| | Material of first electron-transporting layer | External quantum efficiency (%) |
|---|---|---|
| Example 1 | ET-1 | 8.0 |
| Example 2 | ET-2 | 8.5 |
| Example 3 | ET-3 | 7.6 |
| Example 4 | ET-4 | 8.4 |
| Example 5 | ET-5 | 8.2 |
| Example 6 | ET-7 | 7.6 |
| Example 7 | ET-9 | 8.2 |
| Example 8 | ET-10 | 8.3 |
| Comparative Example 1 | Comp. ET-1 | 6.9 |

From the results in Table 1, it is found that organic EL devices of Examples 1 to 8, in which a specific compound was used for the first electron-transporting layer, exhibited higher external quantum efficiencies compared to the organic EL device of Comparative Example 1.

Example 9

(Fabrication of Organic EL Device)

A 25 mm×75 mm×1.1 mm-thick glass substrate with an ITO transparent electrode (anode) (manufactured by GEO-MATEC Co., Ltd.) was subjected to ultrasonic cleaning in isopropyl alcohol for 5 minutes, and then subjected to UV-ozone cleaning for 30 minutes. The thickness of the ITO film was 130 nm.

The glass substrate with the transparent electrode after being cleaned was mounted onto a substrate holder in a vacuum vapor deposition apparatus. First, Compound HT-3 and Compound HI-2 were deposited on the surface of the glass substrate on which the transparent electrode was formed so as to cover the transparent electrode so as to be 3% in a proportion (mass ratio) of Compound HI-2, thereby forming a HT-3:HI-2 film having a thickness of 5 nm. This HT-3:HI-2 film functions as a hole-injecting layer.

Following the deposition of the HT-3:HI-2 film, Compound HT-3 was deposited to form a HT-3 film having a thickness of 90 nm on the HT-3:HI-2 film. The HT-3 film functions as a first hole-transporting layer.

Following the deposition of the HT-3 film, Compound EB was deposited to form a EB film having a thickness of 5 nm on the HT-3 film. The EB film functions as a second hole-transporting layer.

Compound BH-2 (host material) and Compound BD-2 (dopant material) were co-deposited on the EB film so as to be 4% in a proportion (mass ratio) of Compound BD-2 to form a BH-2:BD-2 film having a thickness of 20 nm. This BH-2:BD-2 film functions as an emitting layer.

Compound HB was deposited on the emitting layer to form a HB film having a thickness of 5 nm. The HB film functions as a first electron-transporting layer. Following the deposition of the HB film, Compound ET-1 and Liq were co-deposited so as to be 50% in a proportion (mass ratio) of Liq to form a ET-1:Liq film having a thickness of 20 nm. This ET-1:Liq film functions as a second electron-transporting layer. Liq was deposited on this ET-1:Liq film to form a Liq film having a thickness of 1 nm. Metal Al was deposited on this Liq film to form a metal cathode having a thickness of 80 nm, to obtain an organic EL device.

The layered configuration of the obtained organic EL device is as follows.

ITO(130) HT-3:HI-2 (5; 3 mass %)/HT-3 (90)/EB (5)/BH-2:BD-2 (20; 4 mass %)/HB (5)/ET-1: Liq (20; 50 mass %)/Liq (1)Al (80)

Numerical values in parentheses indicate film thickness (unit: nm).

(Evaluation of Organic EL Device)

Voltage was applied to the obtained organic EL device so as to be 10 mA/cm$^2$ in current density, thereby obtaining an EL emission spectrum by using Spectroradiometer CS-2000 (manufactured by Konica Minolta, Inc.). External quantum efficiency (EQE) (%) was calculated from the obtained spectral radiance spectrum. The results are shown in Table 2.

Examples 10 to 12

The organic EL devices were fabricated and evaluated in the same manner as in Example 9 except that the compounds shown in Table 2 were used as the host materials of the emitting layer. The results are shown in Table 2.

Compounds used in Examples 9 to 12 are as follows.

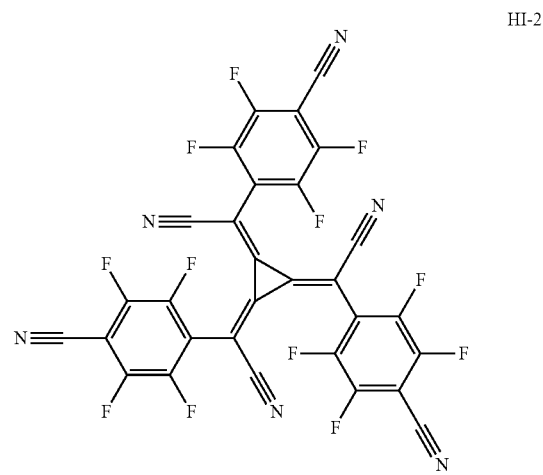

HI-2

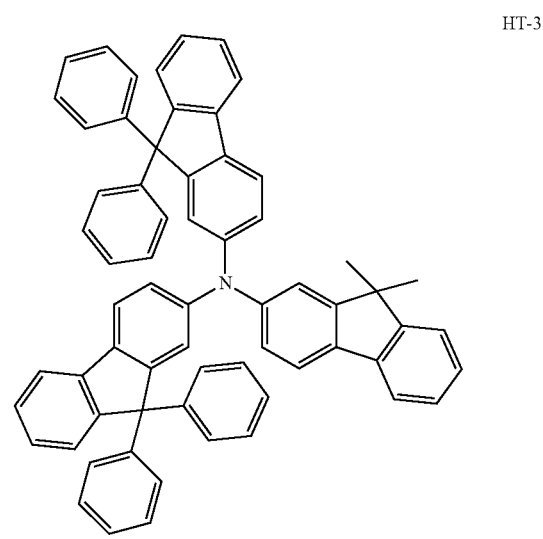

HT-3

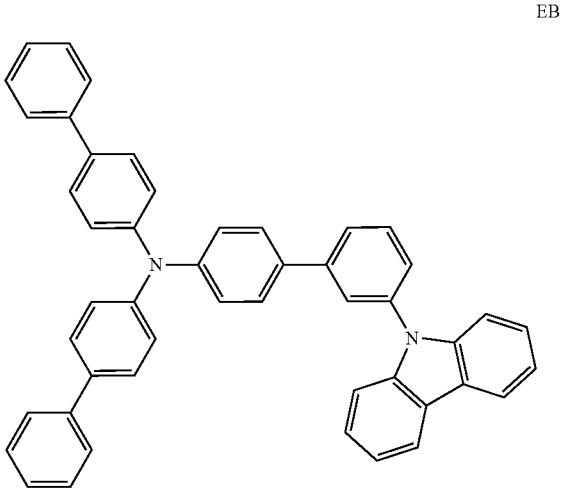

EB

-continued

BH-2
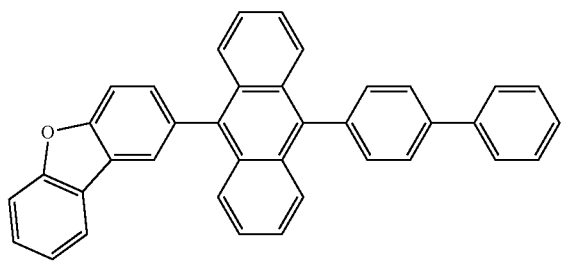

BH-3
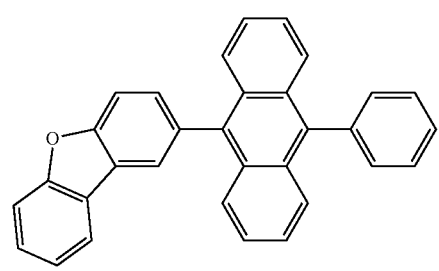

BH-4
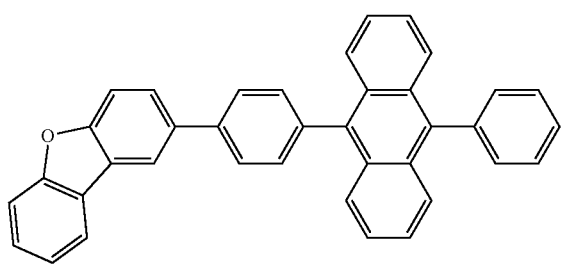

BH-5
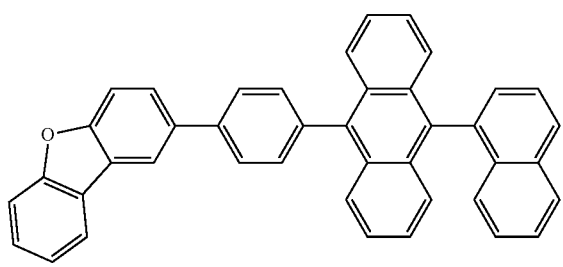

BD-2
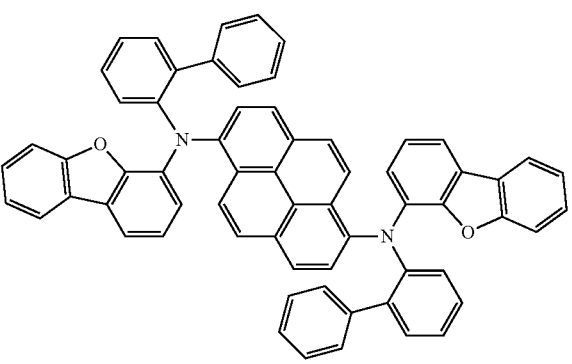

-continued

HB
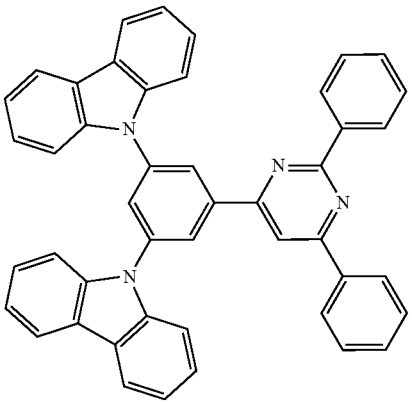

ET-1
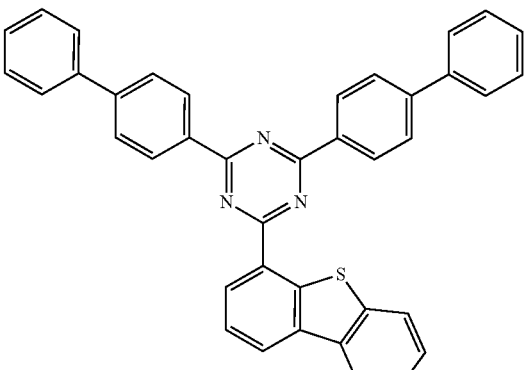

Liq
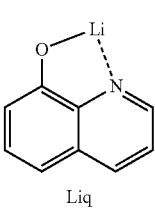

TABLE 2

| | Host material | External quantum efficiency (%) |
|---|---|---|
| Example 9 | BH-2 | 10.3 |
| Example 10 | BH-3 | 9.9 |
| Example 11 | BH-4 | 9.9 |
| Example 12 | BH-5 | 10.2 |

From the results shown in Table 1 and Table 2, it is found that by using a compound in which one dibenzothiophene ring is bonded with the 4th position of an azine ring in an electron-transporting region (the first electron-transporting layer in Examples 1 to 8 and the second electron-transporting layer in Examples 9 to 12), luminous efficiency is improved.

From the results shown in Table 2, it is found that higher external quantum efficiencies can be obtained even when a host material having a dibenzofuran ring as a side chain (Compounds BH-2 to BH-5) (Examples 9 to 12), which differs from the host material used in the devices of Examples 1 to 8 (Compound BH-1), is used.

Although only some exemplary embodiments and/or examples of this invention have been described in detail above, those skilled in the art will readily appreciate that many modifications are possible in the exemplary embodiments and/or examples without materially departing from the novel teachings and advantages of this invention. Accordingly, all such modifications are intended to be included within the scope of this invention.

The documents described in this specification and the entire contents of the application which is the basis of the priority under the Paris Convention of this application are incorporated in this specification by reference in its entirety.

The invention claimed is:

1. A compound represented by the following formula (1),

[Chemical structure of formula (1)]

wherein in the formula (1),
$X_1$ is O or S;
$Y_1$, $Y_2$ and $Y_3$ are each N;
$Ar_1$ is
a substituted or unsubstituted phenylene group,
a substituted or unsubstituted naphthylene group,
a substituted or unsubstituted phenanthrylene group, or
a substituted or unsubstituted anthrylene group;
$Ar_3$ is
a single bond,
a substituted or unsubstituted phenylene group,
a substituted or unsubstituted naphthylene group,
a substituted or unsubstituted phenanthrylene group, or
a substituted or unsubstituted anthrylene group;
$Ar_2$ and $Ar_1$ are independently
a substituted or unsubstituted phenyl group,
a substituted or unsubstituted naphthyl group,
a substituted or unsubstituted phenanthryl group, or
a substituted or unsubstituted anthryl group;
$Ar_1$ and $Ar_2$, and $Ar_3$ and $Ar_4$ do not form a ring by bonding with each $Ar_1$ and $Ar_2$, and $Ar_3$ and $Ar_4$ do not form a ring with each other;
a substituent in the case of the "substituted" is selected from the group consisting of:
an unsubstituted alkyl group having 1 to 50 carbon atoms,
an unsubstituted alkenyl group having 2 to 50 carbon atoms,
an unsubstituted alkynyl group having 2 to 50 carbon atoms,
an unsubstituted cycloalkyl group having 3 to 50 ring carbon atoms,
a cyano group, a nitro group, and
an unsubstituted aryl group having 6 to 50 ring carbon atoms;
and
provided that the case where either one or both of —$Ar_1$-$Ar_2$ and —$Ar_1$-$Ar_2$ is the following group is excluded group is excluded

[Chemical structure]

2. The compound according to claim 1, wherein $Ar_2$ and $Ar_4$ are independently
an unsubstituted phenyl group,
a substituted or unsubstituted naphthyl group,
a substituted or unsubstituted phenanthryl group, or
a substituted or unsubstituted anthryl group,
wherein a substituent in the case of the "substituted" is selected from the group consisting of:
an unsubstituted alkyl group having 1 to 50 carbon atoms,
an unsubstituted alkenyl group having 2 to 50 carbon atoms,
an unsubstituted alkynyl group having 2 to 50 carbon atoms,
an unsubstituted cycloalkyl group having 3 to 50 ring carbon atoms,
a cyano group, a nitro group, and
an unsubstituted aryl group having 6 to 50 ring carbon atoms.

3. The compound according to claim 1, wherein
when $Ar_1$ and $Ar_3$ are an unsubstituted phenylene group, $Ar_2$ and $Ar_4$ are independently
an unsubstituted phenyl group,
a substituted or unsubstituted naphthyl group,
a substituted or unsubstituted phenanthryl group, or
a substituted or unsubstituted anthryl group, wherein a substituent in the case of the "substituted" is selected from the group consisting of
an unsubstituted alkyl group having 1 to 50 carbon atoms,
an unsubstituted alkenyl group having 2 to 50 carbon atoms,
an unsubstituted alkynyl group having 2 to 50 carbon atoms,
an unsubstituted cycloalkyl group having 3 to 50 ring carbon atoms,
a cyano group, a nitro group, and
an unsubstituted aryl group having 6 to 50 ring carbon atoms.

4. The compound according to claim 1, wherein
when $Ar_1$ to $Ar_4$ are substituted by a substituent, the substituent is
an unsubstituted phenyl group,
an unsubstituted naphthyl group,
an unsubstituted phenanthryl group,
an unsubstituted anthryl group,
an unsubstituted biphenyl group,
an unsubstituted alkyl group including 1 to 50 carbon atoms, or
an unsubstituted cycloalkyl group including 3 to 50 ring carbon atoms.

5. The compound according to claim 1, wherein
—$Ar_1$-$Ar_2$ is selected from the group consisting of the groups represented by any of the following formulas (a2) to (a11), and $Ar_3$-$Ar_4$ is selected from the group consisting of the groups represented by any of the following formulas (a1) to (a11):

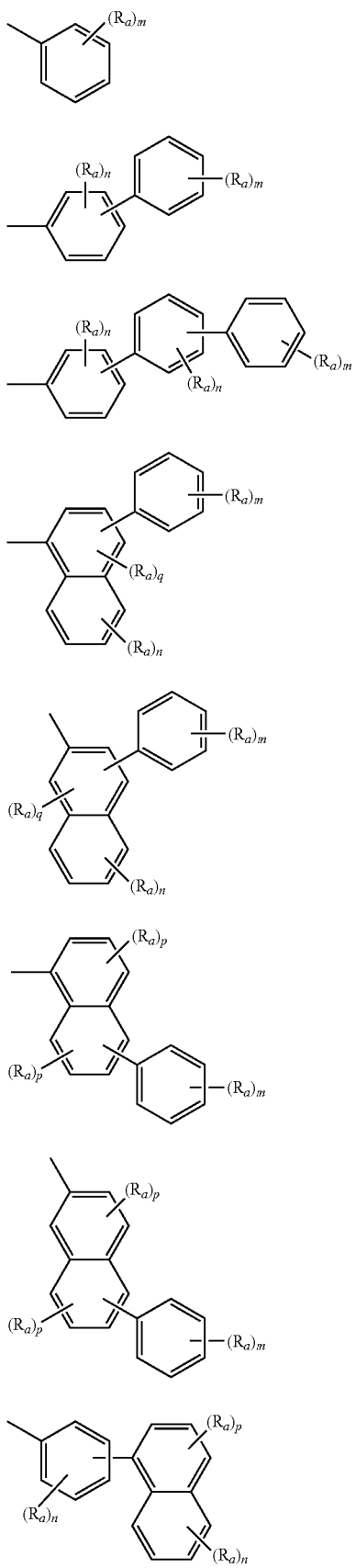

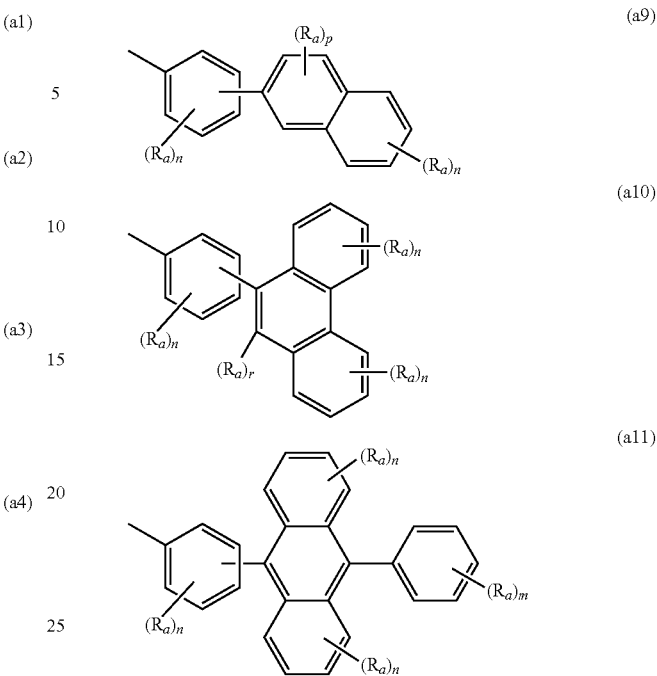

wherein in the formulas (a1) to (a11),
$R_a$ is
a substituted or unsubstituted phenyl group,
a substituted or unsubstituted naphthyl group,
a substituted or unsubstituted phenanthryl group,
a substituted or unsubstituted anthryl group,
a substituted or unsubstituted alkyl group including 1 to 50 carbon atoms, or
a substituted or unsubstituted cycloalkyl group including 3 to 50 ring carbon atoms;
each m is an integer of 0 to 5;
each n is an integer of 0 to 4;
each p is an integer of 0 to 3;
each q is an integer of 0 to 2;
r is an integer of 0 or 1;
when two or more $R_a$'s are present, two or more $R_a$'s may be the same as or different to each other and do not form a ring with each other.

6. The compound according to claim 1, wherein —$Ar_1$-$Ar_2$ is selected from the group consisting of the groups represented by any of the following formulas (aa2) to (aa8), $Ar_3$-$Ar_4$ is selected from the group consisting of the groups represented by any of the following formulas (aa1) to (aa8):

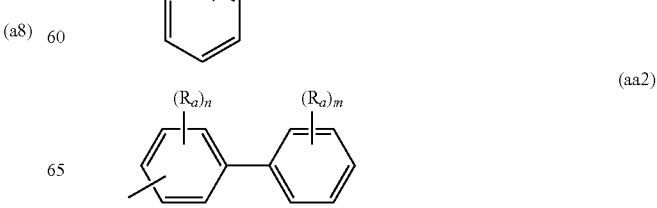

-continued

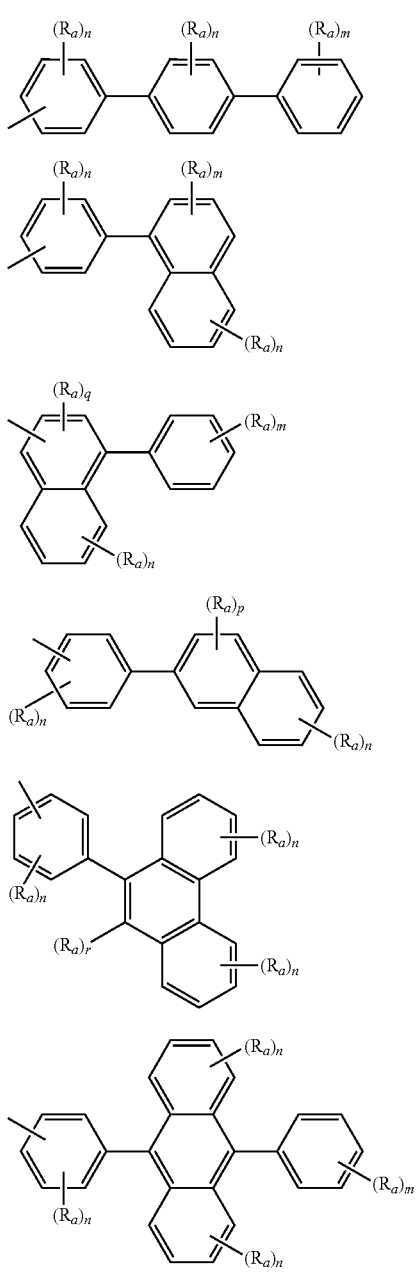

wherein in the formulas (aa1) to (aa8),
$R_a$ is
a substituted or unsubstituted phenyl group,
a substituted or unsubstituted naphthyl group,
a substituted or unsubstituted phenanthryl group,
a substituted or unsubstituted anthryl group,
a substituted or unsubstituted alkyl group including 1 to 50 carbon atoms, or
a substituted or unsubstituted cycloalkyl group including 3 to 50 ring carbon atoms;
each m is an integer of 0 to 5;
each n is an integer of 0 to 4;
each p is an integer of 0 to 3;
q is an integer of 0 to 2;
r is an integer of 0 or 1;
when two or more $R_a$'s are present, two or more $R_a$'s may be the same as or different to each other and do not form a ring with each other.

7. The compound according to claim 1, wherein —$Ar_1$-$Ar_2$ and —$Ar_3$-$Ar_4$ are independently selected from the group consisting of the groups represented by any of the following formulas (ab1) to (ab7):

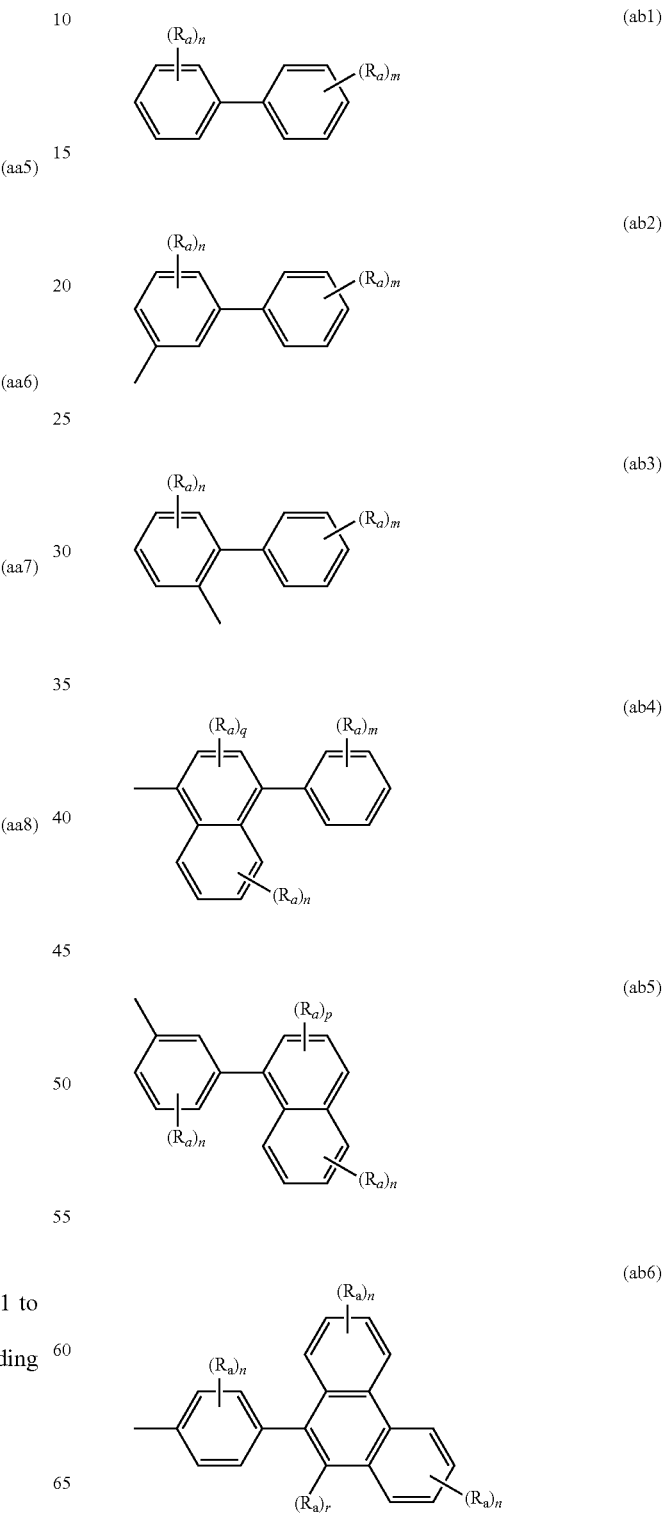

(ab7)

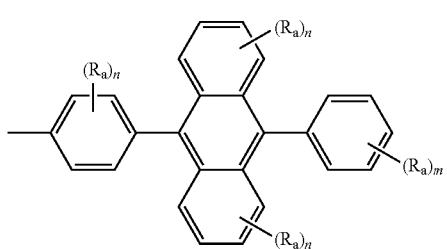

wherein in the formulas (ab1) to (ab7), $R_a$ is a substituted or unsubstituted phenyl group, a substituted or unsubstituted naphthyl group, a substituted or unsubstituted phenanthryl group, a substituted or unsubstituted anthryl group, a substituted or unsubstituted alkyl group including 1 to 50 carbon atoms, or a substituted or unsubstituted cycloalkyl group including 3 to 50 ring carbon atoms;

each m is an integer of 0 to 5;

each n is an integer of 0 to 4;

p is an integer of 0 to 3;

q is an integer of 0 to 2;

r is an integer of 0 or 1;

when two or more $R_a$'s are present, two or more $R_a$'s may be the same as or different to each other; and when two or more $R_a$'s are present, one or more sets of adjacent two or more $R_a$'s independently form a substituted or unsubstituted, saturated or unsaturated ring by bonding with.

8. The compound according to claim 1, wherein —Ar$_1$-Ar$_2$ is a group selected from the group consisting of the groups represented by any of the following formulas (ac2) to (a72), (a74) to (a89) and (a91) to (ac93), Ar$_3$-Ar$_4$ is a group selected from the group consisting of the groups represented by any of the following formulas (ac1) to (ac93):

(ac1)

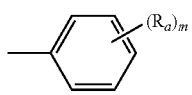

(ac2)

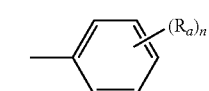

(ac3)

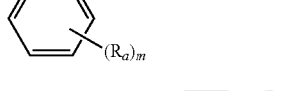

(ac4)

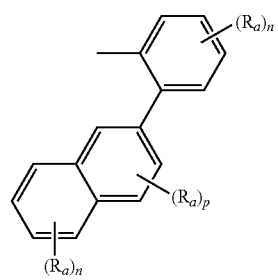

(ac5)

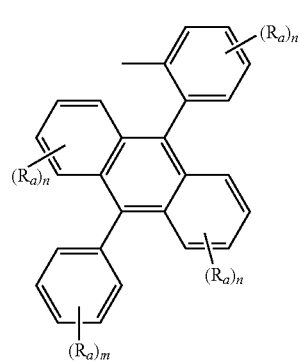

(ac6)

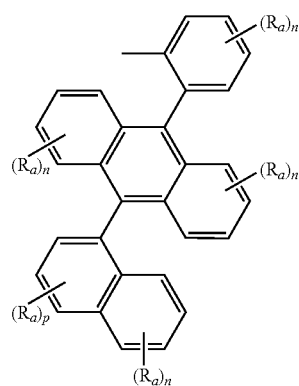

(ac7)

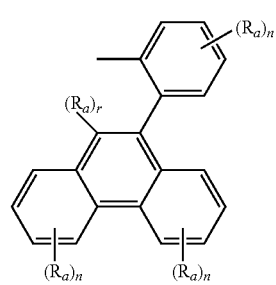

(ac8)

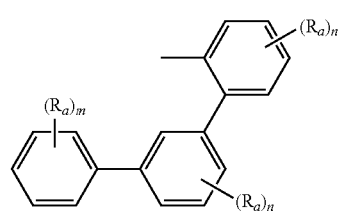

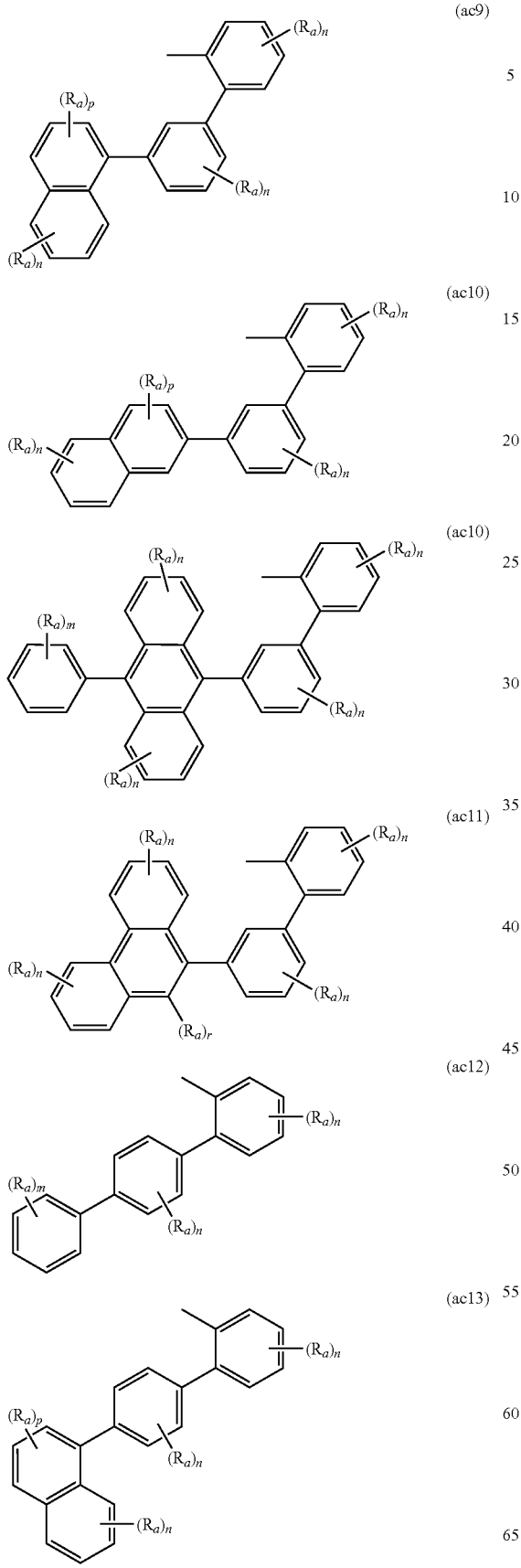
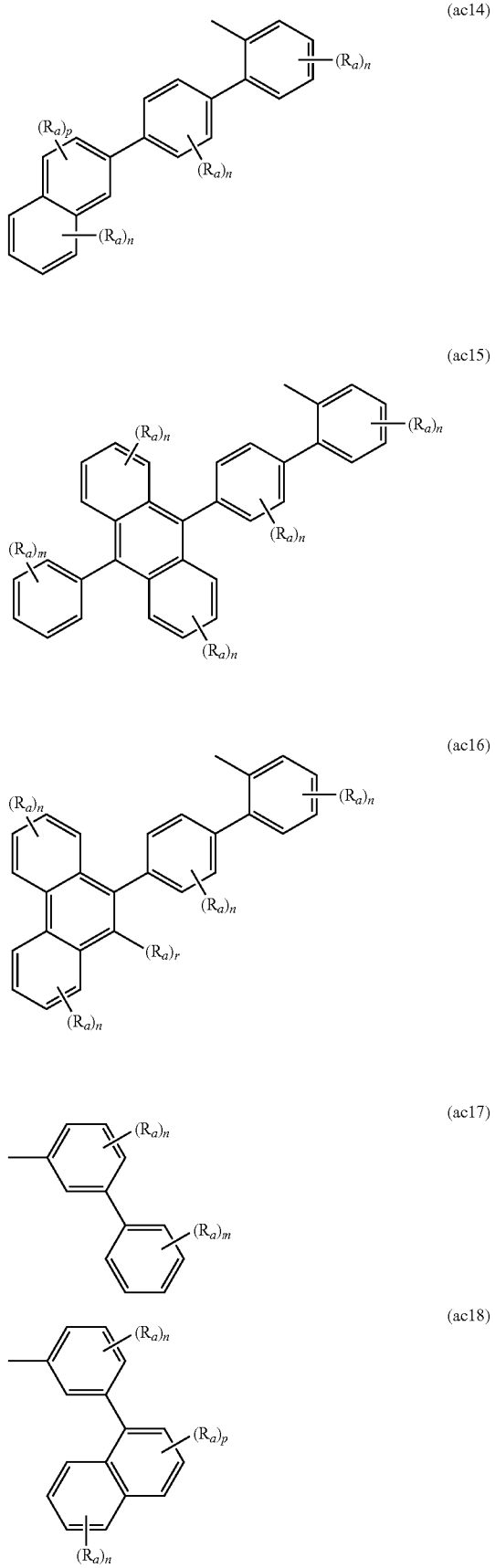

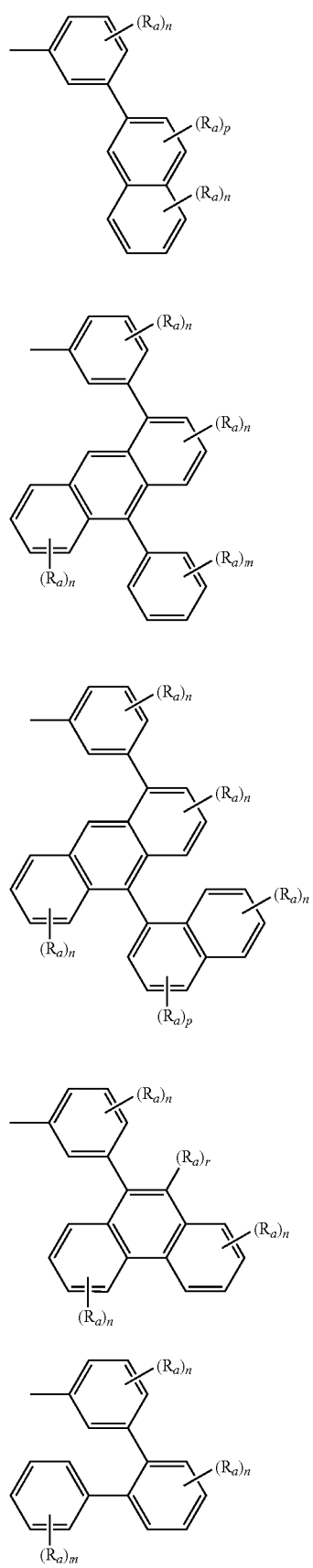
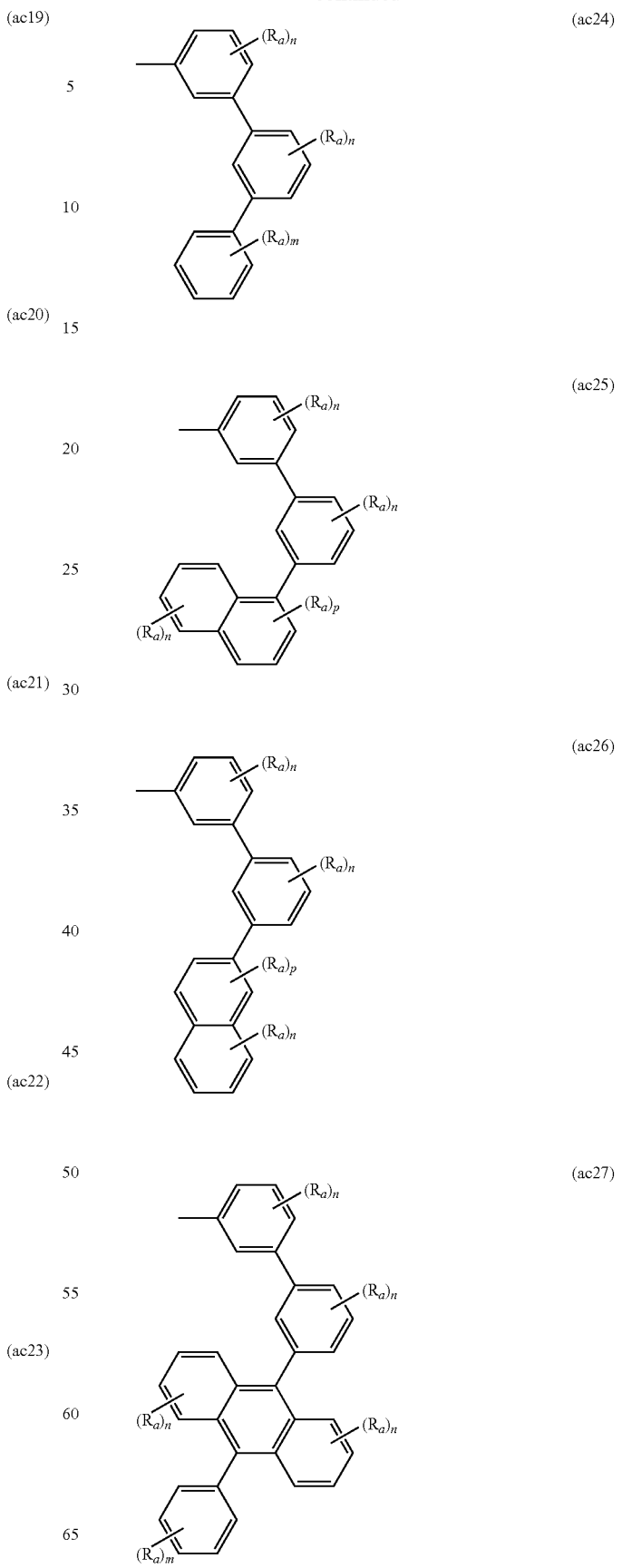

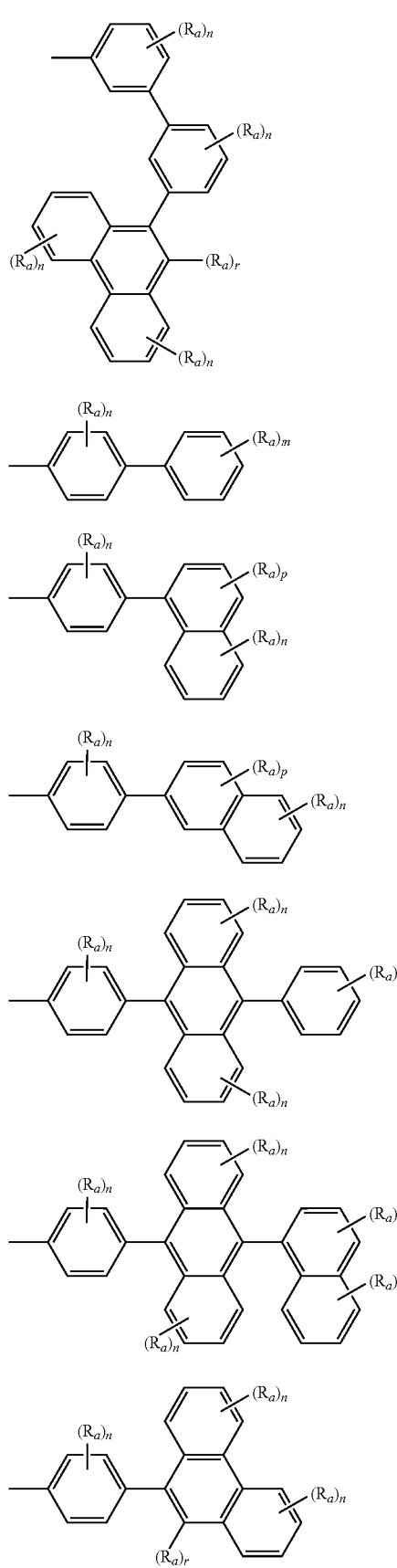
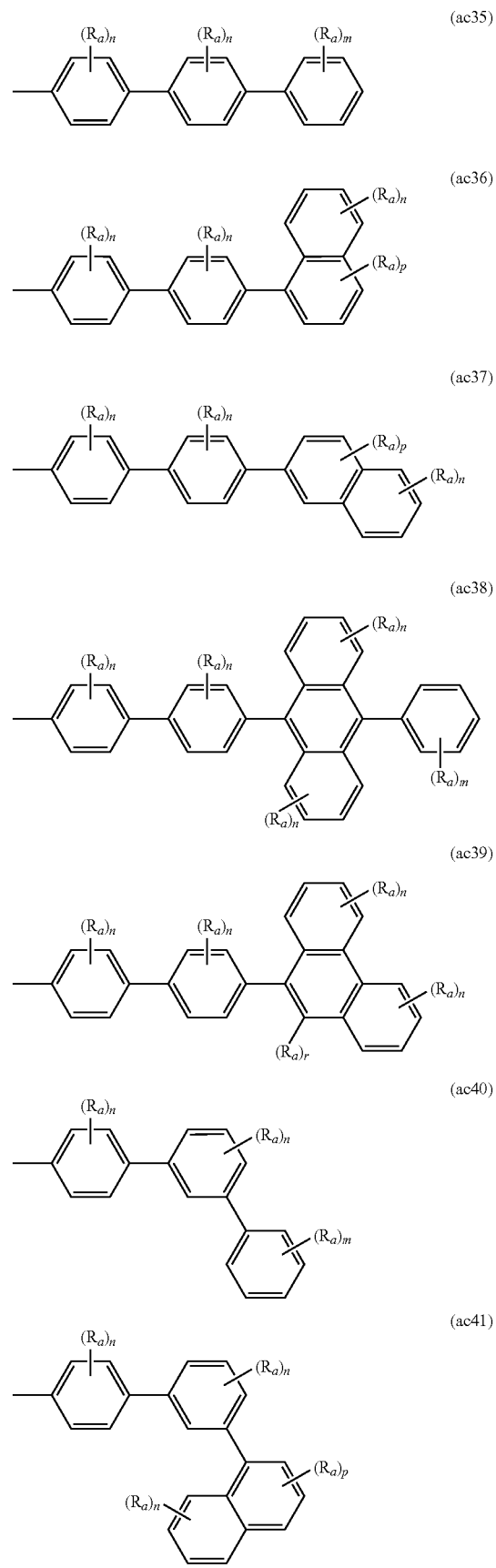

(ac42)
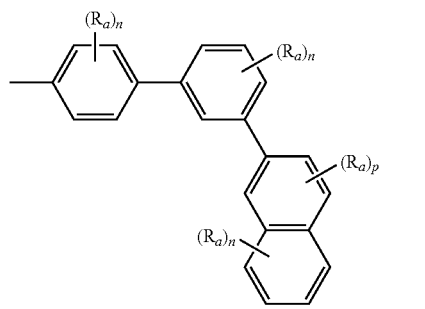
(ac43)
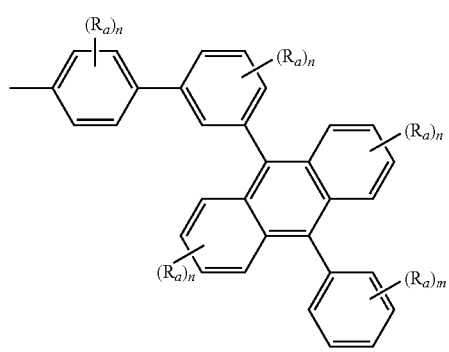
(ac44)
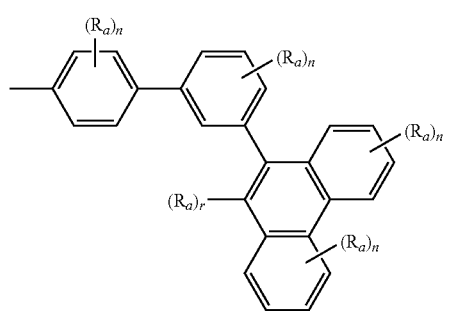
(ac45)
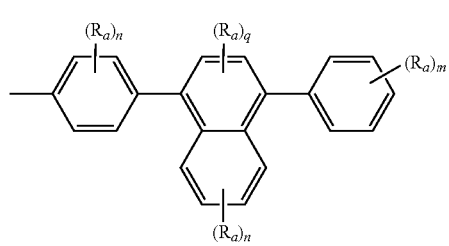
(ac46)
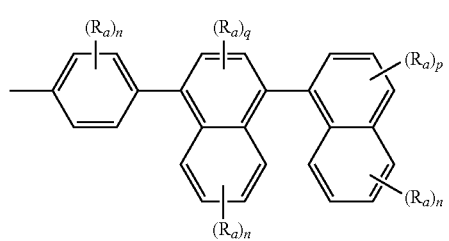
(ac47)
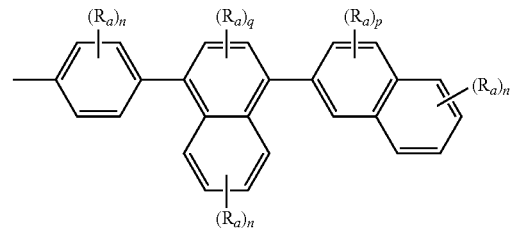
(ac48)
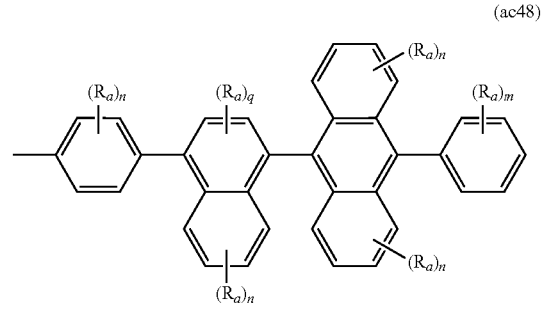
(ac49)
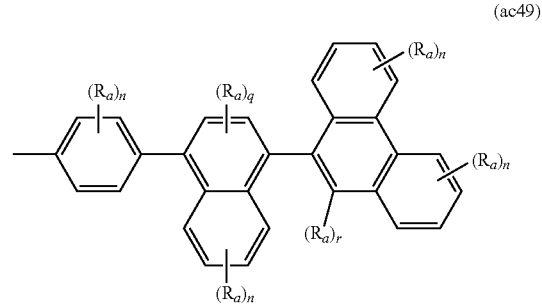
(ac50)
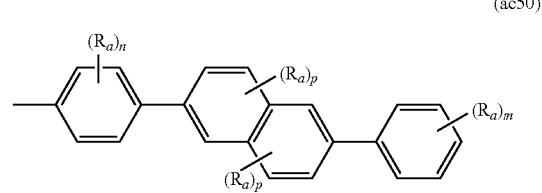
(ac51)
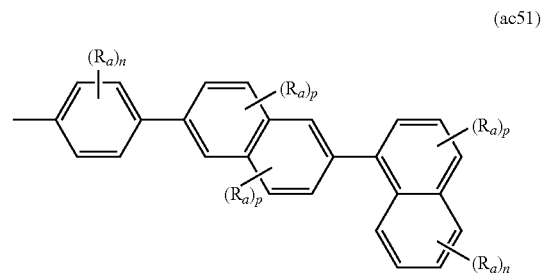
(ac52)
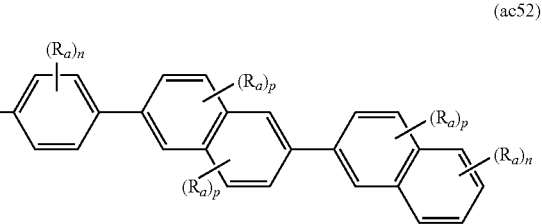

(ac53)
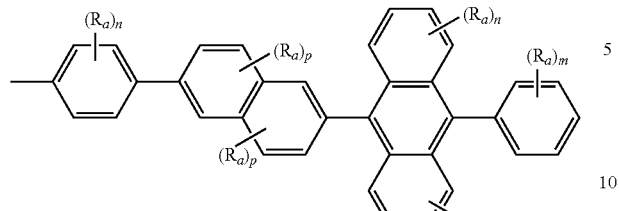
(ac54)
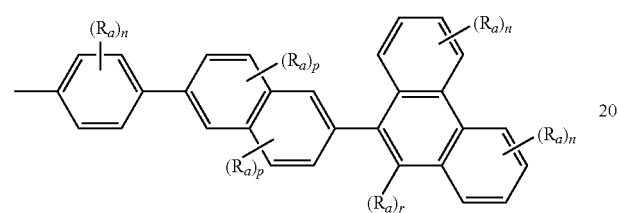
(ac55)
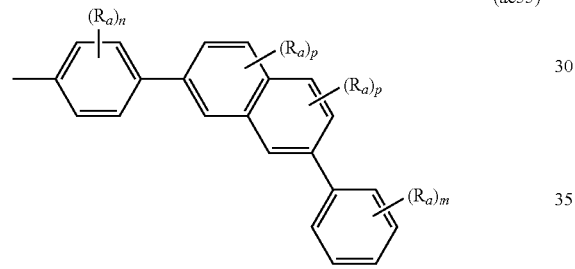
(ac56)
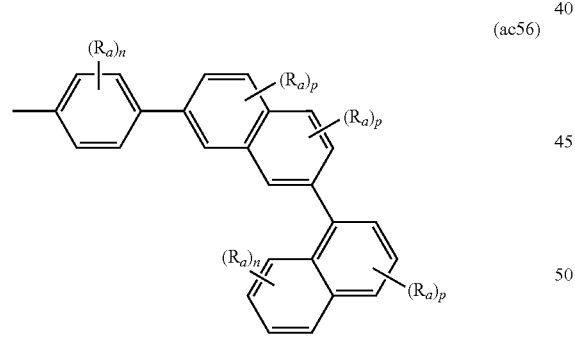
(ac57)
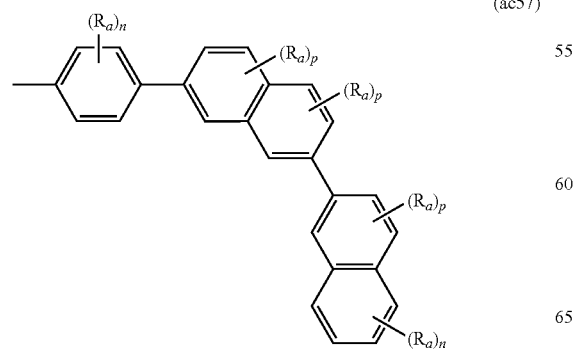
(ac58)
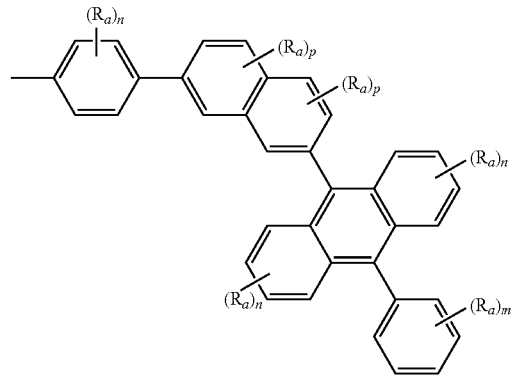
(ac59)
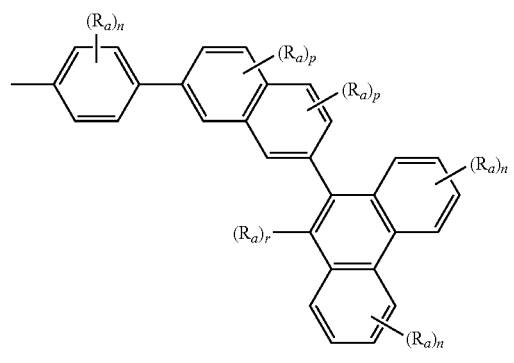
(ac60)
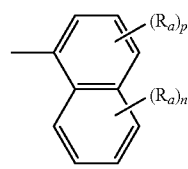
(ac61)
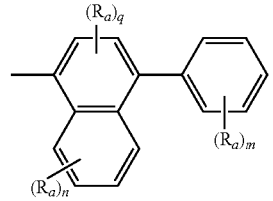
(ac62)
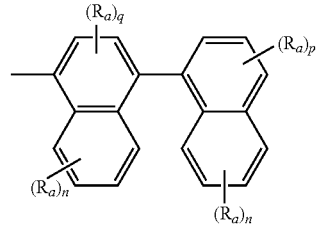
(ac63)
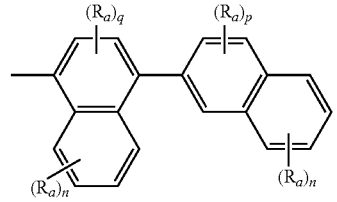

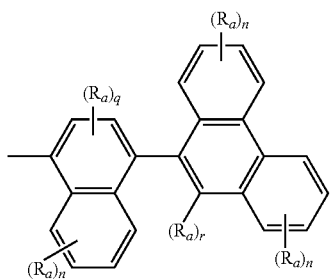
(ac64)
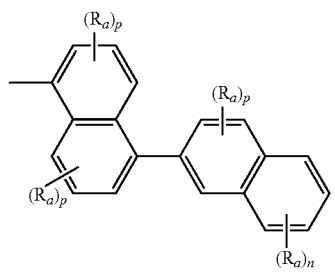
(ac69)
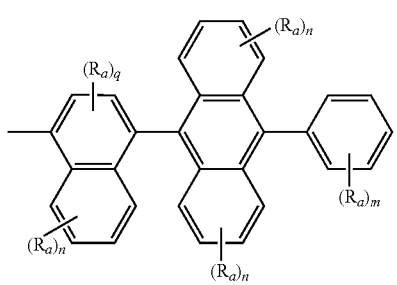
(ac65)
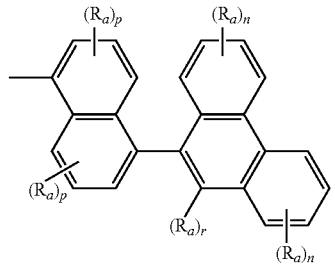
(ac70)
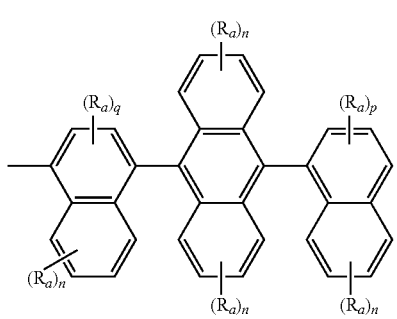
(ac66)
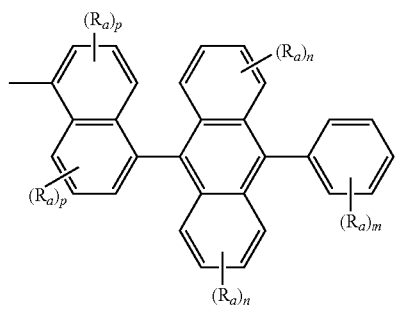
(ac71)
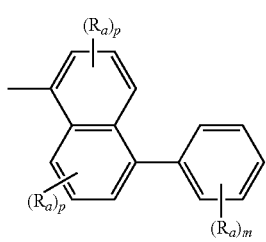
(ac67)
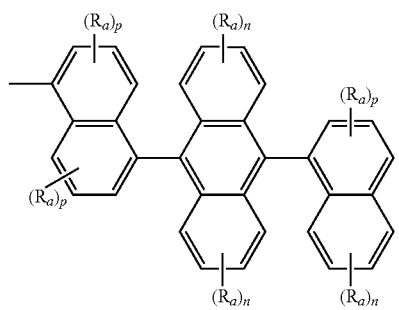
(ac72)
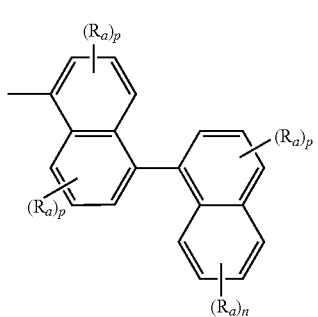
(ac68)
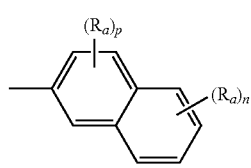
(ac73)
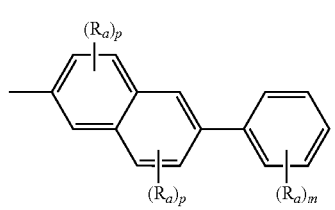
(ac74)

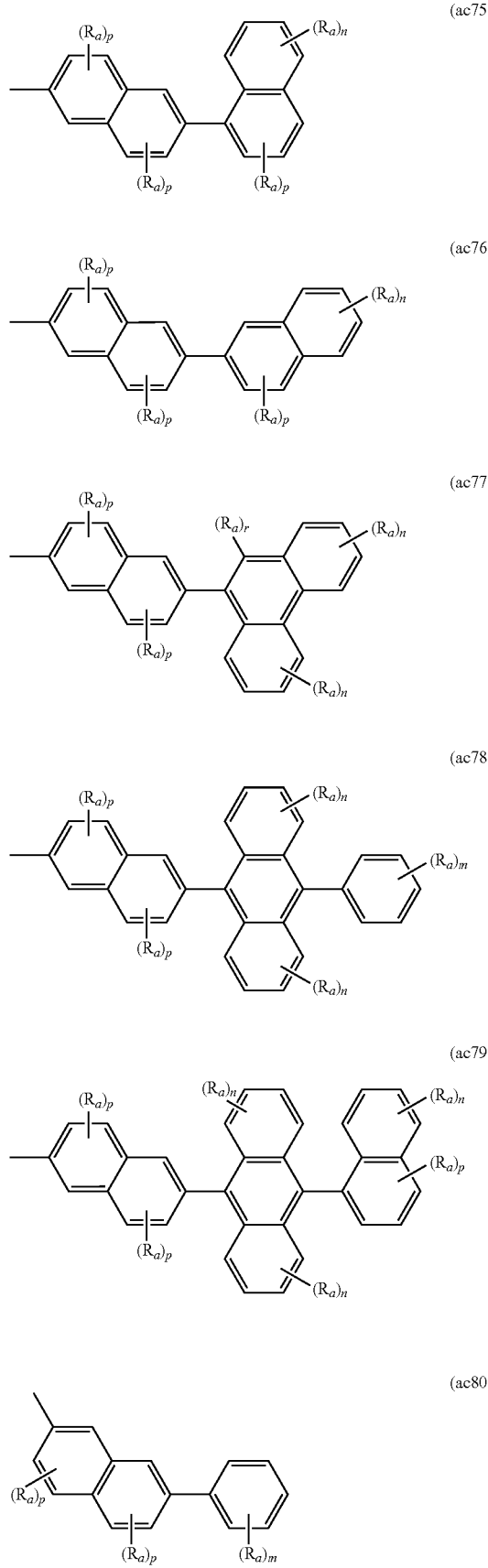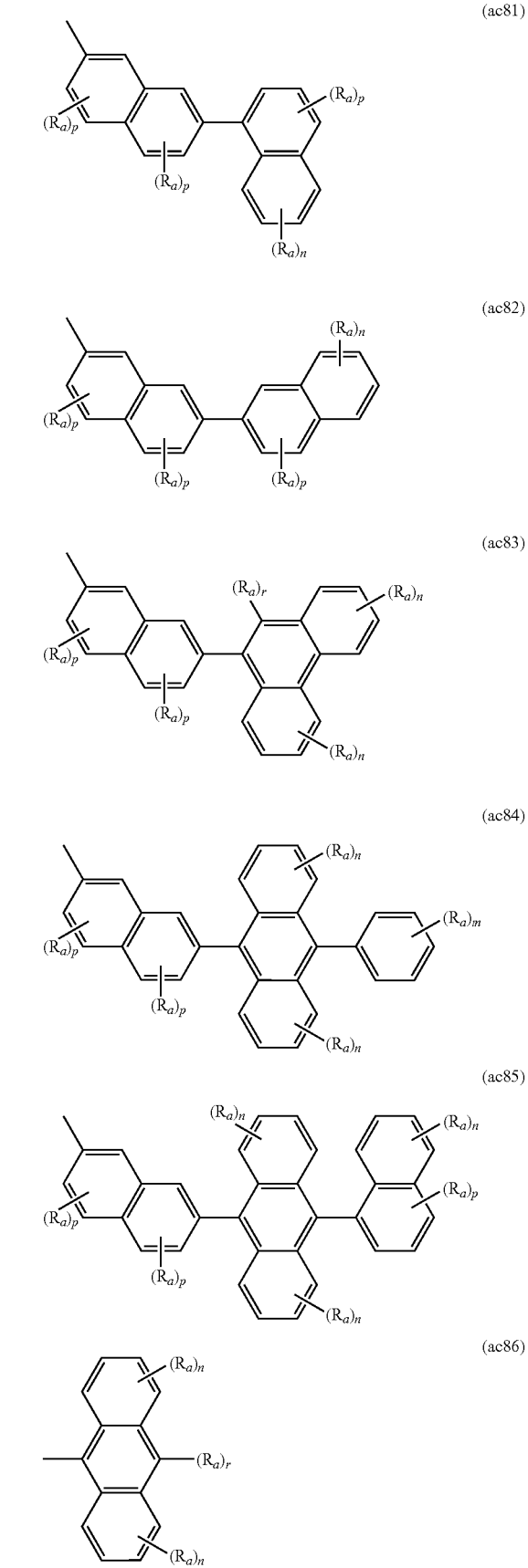

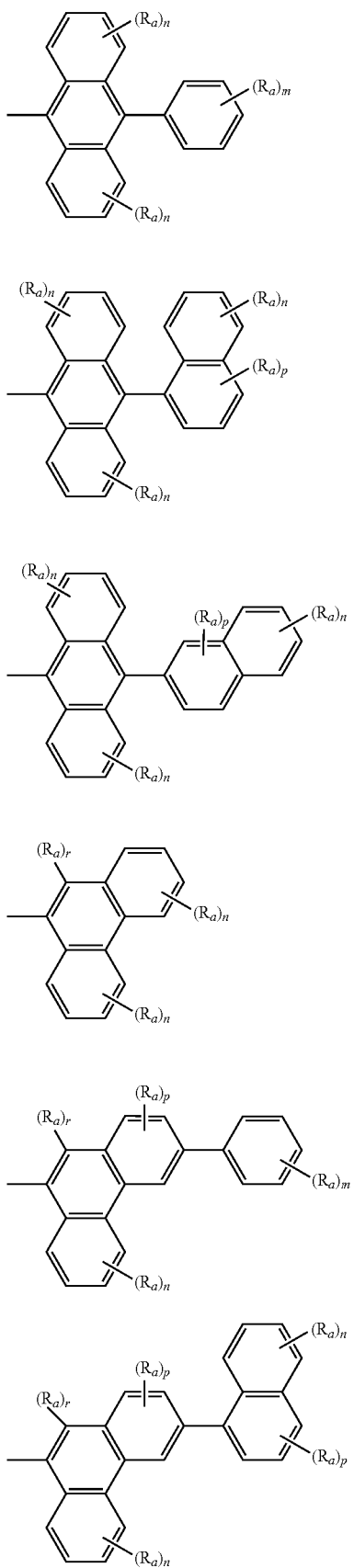
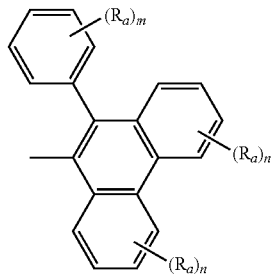

wherein in the formulas (ac1) to (ac93), $R_a$ is a substituted or unsubstituted phenyl group, a substituted or unsubstituted naphthyl group, a substituted or unsubstituted phenanthryl group, a substituted or unsubstituted an anthryl group, a substituted or unsubstituted alkyl group including 1 to 50 carbon atoms, or a substituted or unsubstituted cycloalkyl group including 3 to 50 ring carbon atoms;

each m is an integer of 0 to 5;

each n is an integer of 0 to 4;

each p is an integer of 0 to 3;

each q is an integer of 0 to 2;

each r is an integer of 0 or 1;

when two or more $R_a$'s are present, two or more $R_a$'s may be the same as or different to each other and do not form a ring with each other.

9. The compound according to claim 1, wherein $Ar_2$ and $Ar_4$ are independently an unsubstituted phenyl group, an unsubstituted naphthyl group, an unsubstituted anthryl group, or an unsubstituted phenanthryl group.

10. The compound according to claim 1, wherein $X_1$ is S.

11. The compound according to claim 1, wherein the compound represented by the formula (1) is the compound represented by the following formula (4):

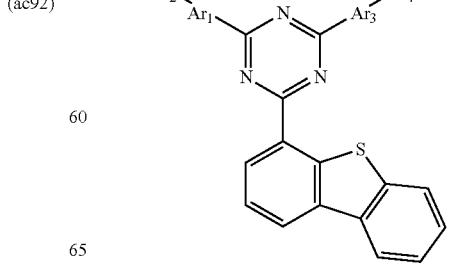

12. The compound according to claim 1, wherein the following compounds are excluded:

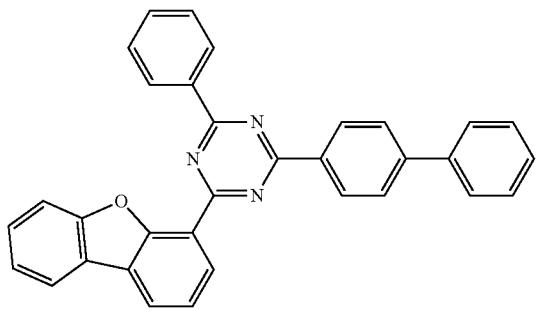

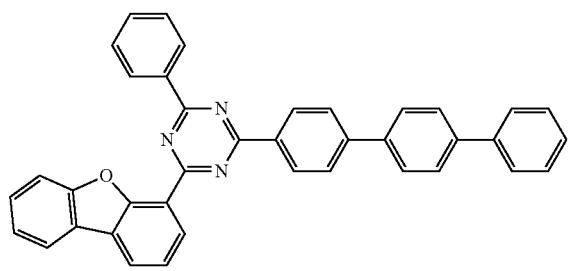

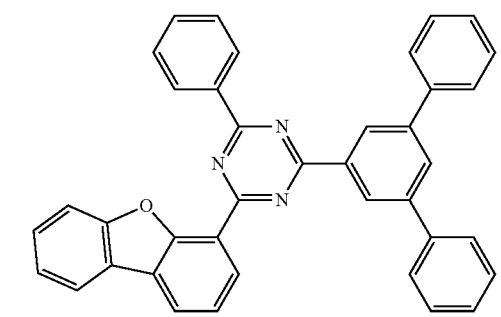

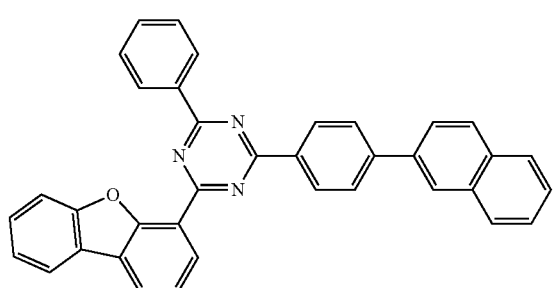

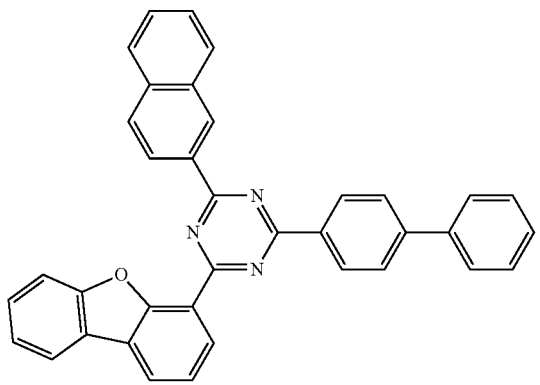

-continued

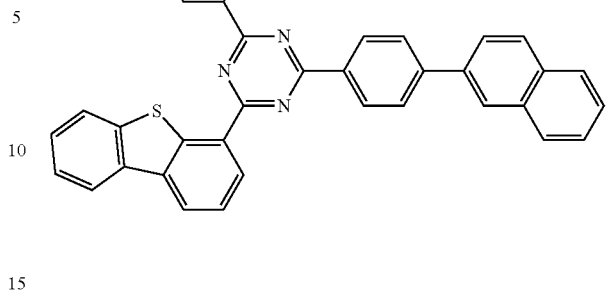

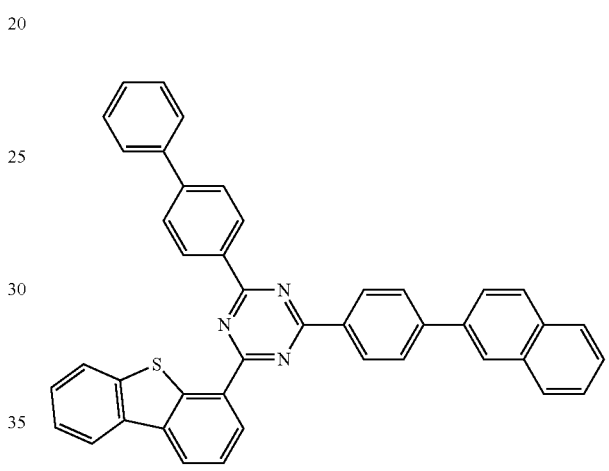

13. The compound according to claim 1, wherein the compound represented by the formula (1) is the compound represented by the following formula (6):

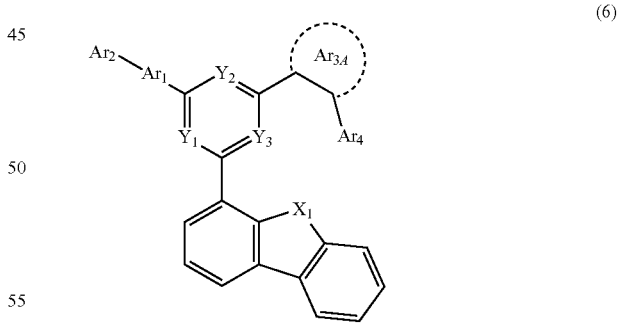

(6)

wherein $Ar_{3A}$ is a phenylene group, a naphthylene group, a phenanthrylene group, or an anthrylene group, that is constituted with at least inclusion of the benzene ring substituted by $Ar_4$ at an ortho-position thereof, and that may be substituted by one or more substituents in addition to $Ar_4$.

14. The compound according to claim 13, wherein the compound represented by the formula (1) is the compound represented by the following formula (6-1):

(6-1)

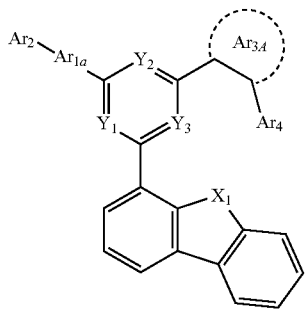

5 wherein $Ar_{1a}$ is a divalent group selected from the following group:

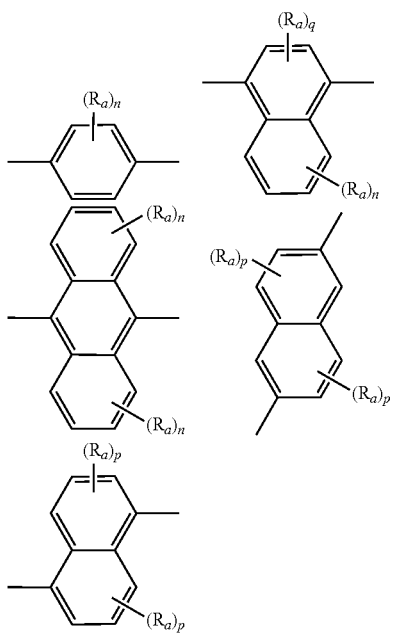

wherein in the formulas, $R_a$ is a substituted or unsubstituted phenyl group, a substituted or unsubstituted naphthyl group, a substituted or unsubstituted phenanthryl group, a substituted or unsubstituted anthryl group, a substituted or unsubstituted alkyl group including 1 to 50 carbon atoms, or a substituted or unsubstituted cycloalkyl group including 3 to 50 ring carbon atoms;

each n is an integer of 0 to 4;

each p is an integer of 0 to 3;

q is an integer of 0 to 2;

when two or more $R_a$'s are present, two or more $R_a$'s may be the same as or different to each other and do not form a ring with each other.

15. The compound according to claim 1, wherein the compound represented by the formula (1) is the compound represented by the following formula (7):

(7)

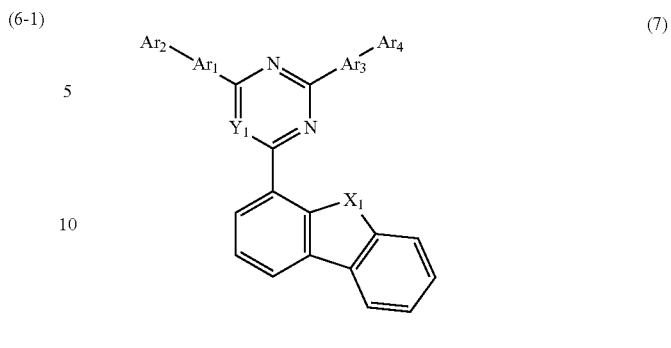

wherein at least one of $Ar_1$ to $Ar_4$ is a substituted or unsubstituted naphthyl group, a substituted or unsubstituted naphthylene group, a substituted or unsubstituted phenanthrenyl group, or a substituted or unsubstituted phenanthrenylene group.

16. The compound according to claim 15, wherein at least one of $Ar_1$ to $Ar_4$ is a substituted or unsubstituted naphthalene ring:

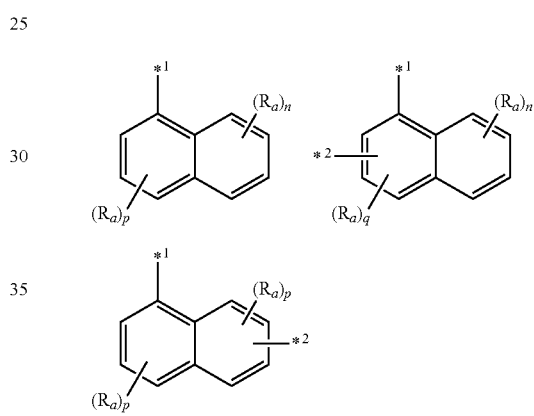

wherein in the formulas, *1 bonds to the nitrogen-containing heterocyclic ring, or $Ar_1$ or $Ar_3$;

*2 bonds to $Ar_2$ or $Ar_4$;

$R_a$ is a substituted or unsubstituted phenyl group, a substituted or unsubstituted naphthyl group, a substituted or unsubstituted phenanthryl group, a substituted or unsubstituted anthryl group, a substituted or unsubstituted alkyl group including 1 to 50 carbon atoms, or a substituted or unsubstituted cycloalkyl group including 3 to 50 ring carbon atoms;

each n is an integer of 0 to 4, respectively;

each p is an integer of 0 to 3, respectively;

q is an integer of 0 to 2;

When two or more $R_a$'s are present, two or more $R_a$'s may be the same as or different to each other and do not form a ring with each other.

17. The compound according to claim 1, wherein the compound represented by the formula (1) is the compound represented by the following formula (8):

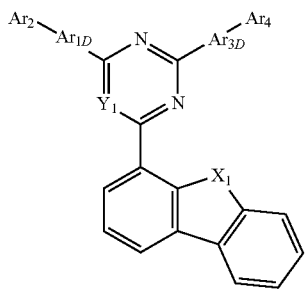
(8)

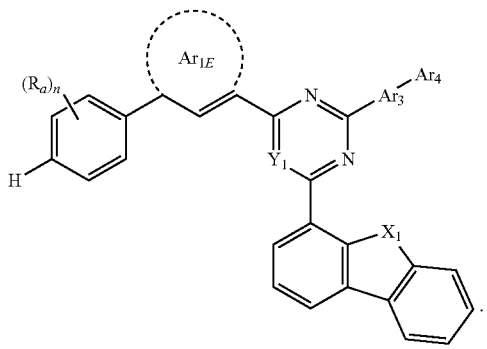
(9)

wherein $Ar_{1D}$ and $Ar_{3D}$ are independently a divalent group selected from the following group consisting of:

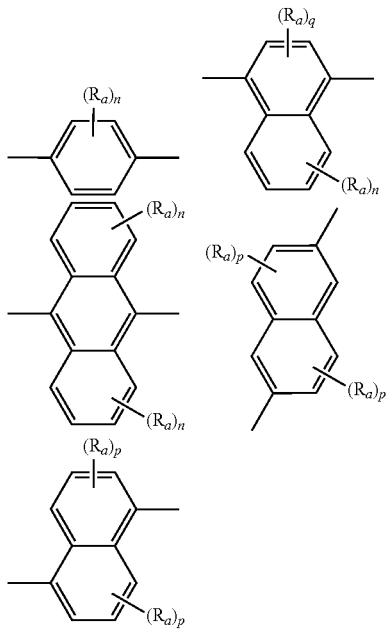

wherein in the formulas, $R_a$ is a substituted or unsubstituted phenyl group, a substituted or unsubstituted naphthyl group, a substituted or unsubstituted phenanthryl group, a substituted or unsubstituted anthryl group, a substituted or unsubstituted alkyl group including 1 to 50 carbon atoms, or a substituted or unsubstituted cycloalkyl group including 3 to 50 ring carbon atoms;

each n is an integer of 0 to 4;

each p is an integer of 0 to 3;

q is an integer of 0 to 2;

When two or more $R_a$'s are present, two or more $R_a$'s may be the same as or different to each other and do not form a ring with each other.

18. The compound according to claim 1, wherein the compound represented by the formula (1) is the compound represented by the following formula (9):

wherein $Ar_{1E}$ is a phenylene group, a naphthylene group, a phenanthrylene group, or an anthrylene group, that is constituted with at least inclusion of the benzene ring substituted by a phenyl group at a meta-position thereof, and that may be substituted by one or more substituents in addition to the phenyl group;

$R_a$ is a substituted or unsubstituted phenyl group;

a substituted or unsubstituted naphthyl group;

a substituted or unsubstituted phenanthryl group, a substituted or unsubstituted anthryl group, a substituted or unsubstituted alkyl group including 1 to 50 carbon atoms; or a substituted or unsubstituted cycloalkyl group including 3 to 50 ring carbon atoms;

n is an integer of 0 to 4;

when two or more $R_a$'s are present, two or more $R_a$'s may be the same as or different to each other and do not form a ring with each other.

19. An electron-transporting material for an organic electroluminescence device, which comprises the compound according to claim 1.

20. An organic electroluminescence device comprising an anode, an organic layer, and a cathode in this order, wherein the organic layer comprises the compound according to claim 1.

21. An organic electroluminescence device comprising an anode, an emitting layer, an electron-transporting region, and a cathode in this order, wherein the electron transporting region comprises the compound according to claim 1.

22. The organic electroluminescence device according to claim 21, wherein the electron-transporting region comprises a first electron-transporting layer, and a second electron-transporting layer, and the emitting layer, the first electron-transporting layer, the second electron-transporting layer and the cathode in this order, and at least one of the first electron-transporting layer and the second electron-transporting layer comprises the compound represented by formula (1).

23. The organic electroluminescence device according to claim 21, wherein, the emitting layer comprises a compound represented by the following formula (11):

(11)

[Structure of formula (11): anthracene core with R13, R12 at top; R14, R11 on upper sides; Ar12—L12 and L11—Ar11 attached at center positions; R15, R18 on lower sides; R16, R17 at bottom]

wherein in the formula (11),
$R_{11}$ to $R_{18}$ are independently a hydrogen atom,
a substituted or unsubstituted alkyl group including 1 to 50 carbon atoms,
a substituted or unsubstituted alkenyl group including 2 to 50 carbon atoms,
a substituted or unsubstituted alkynyl group including 2 to 50 carbon atoms,
a substituted or unsubstituted cycloalkyl group including 3 to 50 ring carbon atoms,
—Si($R_{901}$)($R_{902}$)($R_{903}$),
—O—($R_{904}$),
—S—($R_{905}$),
—N($R_{906}$)($R_{907}$),
a halogen atom, a cyano group, a nitro group,
a substituted or unsubstituted aryl group including 6 to 50 ring carbon atoms,
a substituted or unsubstituted monovalent heterocyclic group including 5 to 50 ring atoms;
$R_{901}$ to $R_{907}$ are independently a hydrogen atom,
a substituted or unsubstituted alkyl group including 1 to 50 carbon atoms,
a substituted or unsubstituted cycloalkyl group including 3 to 50 ring carbon atoms,
a substituted or unsubstituted aryl group including 6 to 50 ring carbon atoms, or
a substituted or unsubstituted monovalent heterocyclic group including 5 to 50 ring atoms;
when two or more of each of $R_{901}$ to $R_{907}$ are present, two or more of each of $R_{901}$ to $R_{907}$ may be the same as or different to each other;
adjacent two or more of $R_{11}$ to $R_{14}$, and adjacent two or more $R_{15}$ to $R_{18}$ do not form a ring by bonding with each other;
$L_{11}$ and $L_{12}$ are independently a single bond,
a substituted or unsubstituted arylene group including 6 to 50 ring carbon atoms, or
a substituted or unsubstituted divalent heterocyclic ring including 5 to 50 ring atoms; and
$Ar_{11}$ and $Ar_{12}$ are independently
a substituted or unsubstituted aryl group including 6 to 50 ring carbon atoms, or
a substituted or unsubstituted monovalent heterocyclic group including 5 to 50 ring atoms.

24. The organic electroluminescence device according to claim 23, wherein the compound represented by the formula (11) is the compound represented by the following formula (12):

(12)

[Structure of formula (12): anthracene core with R13, R12 at top; R14, R11 on upper sides; Ar12a—L12 and L11—Ar11a attached at center positions; R15, R18 on lower sides; R16, R17 at bottom]

wherein at least one of $Ar_{11a}$ and $Ar_{12a}$ is the monovalent group represented by the following formula (20):

(20)

[Structure of formula (20): dibenzofuran core with R24, R28 at top flanking O; R23, R27 on upper sides; R22, R26 on lower sides; R21, R25 at bottom]

wherein in the formula (20),
at least one of $R_{21}$ to $R_{28}$ is bonded with $L_{11}$ or $L_{12}$;
$R_{21}$ to $R_{28}$ that are not bonded with $L_{11}$ or $L_{12}$ are independently
a hydrogen atom,
a substituted or unsubstituted alkyl group including 1 to 50 carbon atoms,
a substituted or unsubstituted alkenyl group including 2 to 50 carbon atoms,
a substituted or unsubstituted alkynyl group including 2 to 50 carbon atoms,
a substituted or unsubstituted cycloalkyl group including 3 to 50 ring carbon atoms,
—Si($R_{901}$)($R_{902}$)($R_{903}$),
—O—($R_{904}$),
—S—($R_{905}$),
—N($R_{906}$)($R_{907}$),
a halogen atom, a cyano group, a nitro group,
a substituted or unsubstituted aryl group including 6 to 50 ring carbon atoms,
a substituted or unsubstituted monovalent heterocyclic group including 5 to 50 ring atoms; and
adjacent two or more of $R_{21}$ to $R_{28}$ that are not bonded with $L_{11}$ or $L_{12}$ do not form a ring by bonding with each other;
$Ar_{11a}$ or $Ar_{12a}$ that is not a monovalent group represented by the formula (20) is
a substituted or unsubstituted aryl group including 6 to 50 ring carbon atoms, or
a substituted or unsubstituted monovalent heterocyclic group including 5 to 50 ring atoms, other than the monovalent group represented by the formula (20).

25. The organic electroluminescence device according to claim 24, wherein the compound represented by the formula (12) is the compound represented by the following formula (12-1):

(12-1)

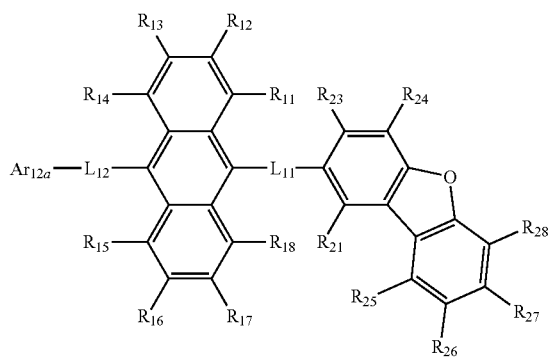

wherein Ar$_{12a}$ is a substituted or unsubstituted aryl group including 6 to 50 ring carbon atoms, or
a substituted or unsubstituted monovalent heterocyclic group including 5 to 50 ring atoms, other than the monovalent group represented by the formula (20);
R$_{21}$ and R$_{23}$ to R$_{28}$ are independently
a hydrogen atom,
a substituted or unsubstituted alkyl group including 1 to 50 carbon atoms,
a substituted or unsubstituted alkenyl group including 2 to 50 carbon atoms
a substituted or unsubstituted alkynyl group including 2 to 50 carbon atoms,
a substituted or unsubstituted cycloalkyl group including 3 to 50 ring carbon atoms,
—Si(R$_{901}$)(R$_{902}$)(R$_{903}$),
—O—(R$_{904}$),
—S—(R$_{905}$),
—N(R$_{906}$)(R$_{907}$),
a halogen atom, a cyano group, a nitro group,
a substituted or unsubstituted aryl group including 6 to 50 ring carbon atoms, and
a substituted or unsubstituted monovalent heterocyclic group including 5 to 50 ring atoms.

26. The organic electroluminescence device according to claim 23, wherein the compound represented by the formula (11) is the compound represented by the following formula (13):

(13)

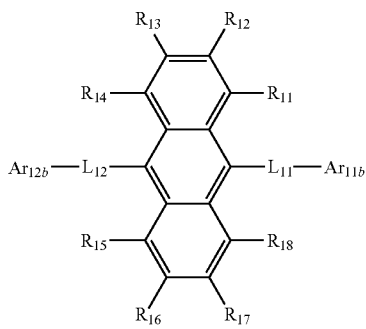

wherein Ar$_{11b}$ and Ar$_{12b}$ are independently a substituted or unsubstituted aryl group including 6 to 50 ring carbon atoms, that is constituted only with a benzene ring.

27. The organic electroluminescence device according to claim 26, wherein the compound represented by the formula (13) is the compound represented by the following formula (13-1):

(13-1)

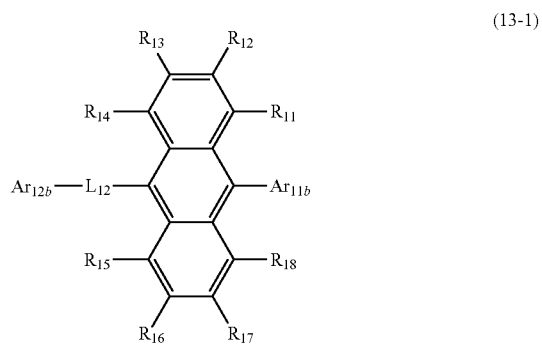

wherein Ar$_{11b}$ and Ar$_{12b}$ are independently a substituted or unsubstituted aryl group including 6 to 50 ring carbon atoms, that are constituted only with a benzene ring.

28. The organic electroluminescence device according to claim 26, wherein
Ar$_{11b}$ and Ar$_{12b}$ are independently
a substituted or unsubstituted phenyl group,
a substituted or unsubstituted naphthyl group,
a substituted or unsubstituted biphenylyl group,
a substituted or unsubstituted terphenylyl group,
a substituted or unsubstituted anthryl group, or
a substituted or unsubstituted phenanthryl group.

29. The organic electroluminescence device according to claim 22, wherein
one or both of the first electron-transporting layer and the second electron-transporting layer further includes one or two or more kinds selected from the group consisting of an alkali metal, an alkaline earth metal, a rare earth metal, an alkali metal oxide, an alkali metal halide, an alkaline earth metal oxide, an alkaline earth metal halide, a rare earth metal oxide, a rare earth metal halide, an organic complex containing an alkali metal, an organic complex containing an alkaline earth metal, and an organic complex containing a rare earth metal.

30. The organic electroluminescence device according to claim 21, comprising a hole-transporting layer disposed between the anode and the emitting layer.

31. An electronic apparatus comprising the organic electroluminescence device according to claim 21.

* * * * *

UNITED STATES PATENT AND TRADEMARK OFFICE
CERTIFICATE OF CORRECTION

PATENT NO. : 11,765,972 B2
APPLICATION NO. : 16/971260
DATED : September 19, 2023
INVENTOR(S) : Yoshinao Shirasaki et al.

Page 1 of 1

It is certified that error appears in the above-identified patent and that said Letters Patent is hereby corrected as shown below:

In the Claims

Column 457, Line 44: replace "$Ar_1$" with --$Ar_4$--

Column 457, Line 66-67: replace "–$Ar_1$-$Ar_2$ is the following group is excluded group is excluded" with -- -$Ar_3$-$Ar_4$ is the following group is excluded--

Column 463, Lines 32-37: replace "; and when two or more Ra's are present, one or more sets of adjacent two or more Ra's independent form a substituted or unsubstituted, saturated or unsaturated ring by bonding with." with --and do not form a ring with each other.--

Column 477, Lines 35-41: the label and formula structure of (ac78) is deleted entirely Column 478, Lines 57-66: the label and formula structure of (ac86) is deleted entirely Column 479, Lines 36-44: the label and formula structure of (ac90) is deleted entirely Column 484, Line 61: replace "When" with --when--

Column 485, Line 61: replace "When" with --when--

Signed and Sealed this
Ninth Day of July, 2024

*Katherine Kelly Vidal*

Katherine Kelly Vidal
*Director of the United States Patent and Trademark Office*